US006902902B2

(12) United States Patent
Unett et al.

(10) Patent No.: US 6,902,902 B2
(45) Date of Patent: Jun. 7, 2005

(54) HUMAN G PROTEIN-COUPLED RECEPTORS AND MODULATORS THEREOF FOR THE TREATMENT OF METABOLIC-RELATED DISORDERS

(75) Inventors: David J. Unett, San Diego, CA (US); Ruoping Chen, San Diego, CA (US); Jeremy G. Richman, San Diego, CA (US); Daniel T. Connolly, Carlsbad, CA (US); Yaron Hakak, San Diego, CA (US); Dominic P. Behan, San Diego, CA (US); Derek T. Chalmers, Cardiff, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 195 days.

(21) Appl. No.: 10/314,048

(22) Filed: Dec. 6, 2002

(65) Prior Publication Data

US 2004/0142377 A1 Jul. 22, 2004

Related U.S. Application Data

(63) Continuation-in-part of application No. 10/096,511, filed on Mar. 12, 2002, now abandoned, which is a continuation of application No. 09/995,543, filed on Nov. 27, 2001, now abandoned.

(60) Provisional application No. 60/399,917, filed on Jul. 29, 2002, provisional application No. 60/410,747, filed on Sep. 13, 2002, and provisional application No. 60/404,761, filed on Aug. 19, 2002.

(51) Int. Cl.[7] ........................ G01N 33/53; C07K 14/00; C07H 21/04

(52) U.S. Cl. ........................ 435/7.1; 435/7.2; 435/7.21; 435/69.1; 435/235.1; 435/320.1; 435/375; 530/300; 530/350; 536/23.1

(58) Field of Search ......................... 435/7.1, 7.2, 7.21, 435/69.1, 235.1, 320.1, 375; 530/300, 350; 536/23.1, 23.5

(56) References Cited

U.S. PATENT DOCUMENTS

| | | | | |
|---|---|---|---|---|
| 5,514,578 | A | 5/1996 | Hogness et al. | 435/240.2 |
| 5,532,157 | A | 7/1996 | Fink | 435/240.2 |
| 5,573,944 | A | 11/1996 | Kirschner et al. | 435/252.3 |
| 5,639,616 | A | 6/1997 | Liao et al. | 435/7.1 |
| 5,750,353 | A | 5/1998 | Kopin et al. | 435/7.21 |
| 5,861,309 | A | 1/1999 | Bard et al. | 135/325 |
| 5,891,720 | A | 4/1999 | Moore et al. | 435/325 |
| 5,955,308 | A | 9/1999 | Bergsma et al. | |
| 2002/0137063 | A1 | 9/2002 | Glucksmann et al. | |
| 2003/0078218 | A1 | 4/2003 | Jaral et al. | |

FOREIGN PATENT DOCUMENTS

| | | |
|---|---|---|
| CA | 2135253 | 5/1996 |
| EP | 0 612 845 A2 | 8/1994 |
| EP | 0 878 542 A2 | 11/1998 |
| EP | 0 892 051 A2 | 1/1999 |
| EP | 1 090 989 A1 | 4/2001 |
| EP | 1 094 076 A1 | 4/2001 |
| GB | 0109028.1 | 5/2001 |
| GB | 0126637.8 | 1/2002 |
| GB | 2 365 868 | 2/2002 |
| WO | WO 96/05302 | 2/1996 |
| WO | WO 97/11159 | 9/1996 |
| WO | WO 97/21731 | 6/1997 |
| WO | WO 98/00552 | 1/1998 |
| WO | WO 98/29439 | 7/1998 |
| WO | WO 98/34948 | 8/1998 |

(Continued)

OTHER PUBLICATIONS

Szapary, et al, "Pharmacological management of high triglycerides and low high–density lipoprotein cholesterol," Curr. Opin. Pharmacol. (2001) 1:113–120.

PCT International Search Report, for International Application PCT/US01/44615, issued Sep. 9, 2002.

Soga T., et al.; "Molecular identification of nicotinic acid receptor"; Academic Press; Biochemical and Biophysical Research Communications 303 (2003) 364–69; 0006–291X/03/$; 2003 Elsevier Science (USA): doi:10.1016/S0006–291X(03)00342–5.

Hosoi, T., et al.; "Identification of a Novel Human Elcosanold Receptor Coupled to Gi/o"; The Journal of Biological Chemistry; vol. 277, No. 35, Issue of Aug. 30, pp. 31465–31465, 2002; The American Society for biochemistry and Molecular Biology, Inc., USA.

Wise, A, et al.; "Molecular identification of high and low affinity receptors for nicotinic acid"; JBC Papers in Press; Published on Jan. 9, 2003 as Manuscript M210695200; The American Socidety for Biochemistry and Molecular Biology, Inc.; 2003.

(Continued)

*Primary Examiner*—Gary Kunz
*Assistant Examiner*—Nirmal S. Basi
(74) *Attorney, Agent, or Firm*—Melody E. Clark; Michael P. Straher; Cozen O'Connor

(57) ABSTRACT

The present invention relates to methods of identifying whether a candidate compound is a modulator of a G protein-coupled receptor (GPCR). In preferred embodiments, the GPCR is human. In other preferred embodiments, the GPCR is coupled to Gi and lowers the level of intracellular cAMP. In other preferred embodiments, the GPCR is expressed endogenously by adipocytes. In further preferred embodiments, the GPCR inhibits intracellular lipolysis. In other further preferred embodiments, the GPCR is a nicotinic acid receptor. The present invention also relates to methods of using a modulator of said GPCR. Preferred modulator is agonist. Agonists of the invention are useful as therapeutic agents for the prevention or treatment of metabolic-related disorders, including dyslipidemia, atherosclerosis, coronary heart disease, stroke, insulin resistance, and type 2 diabetes.

4 Claims, 39 Drawing Sheets

FOREIGN PATENT DOCUMENTS

| | | |
|---|---|---|
| WO | WO 98/38217 | 9/1998 |
| WO | WO 98/46620 | 10/1998 |
| WO | WO 98/46995 | 10/1998 |
| WO | WO 98/56820 A1 | 12/1998 |
| WO | WO 98/56820 | 12/1998 |
| WO | WO 99/06552 | 2/1999 |
| WO | WO 99/32519 | 7/1999 |
| WO | WO 99/48921 | 9/1999 |
| WO | WO 99/52927 | 10/1999 |
| WO | WO 00/14229 | 3/2000 |
| WO | WO 00/22129 | 4/2000 |
| WO | WO 00/22131 | 4/2000 |
| WO | WO 00/49046 | 8/2000 |
| WO | WO 01/07606 A1 | 2/2001 |
| WO | WO 01/09184 A1 | 2/2001 |
| WO | WO 01/12673 A1 | 2/2001 |
| WO | WO 01/14577 A1 | 3/2001 |
| WO | WO 01/16159 A1 | 3/2001 |
| WO | WO 01/31014 A2 | 5/2001 |
| WO | WO 01/36471 A2 | 5/2001 |
| WO | WO 01/36473 A2 | 5/2001 |
| WO | WO01/36476 | 5/2001 |
| WO | WO01/61359 | 5/2001 |
| WO | WO01/73029 | 10/2001 |
| WO | WO01/74904 | 10/2001 |
| WO | WO01/77320 | 10/2001 |
| WO | WO01/87937 | 11/2001 |
| WO | WO01/94385 | 12/2001 |
| WO | WO02/13845 | 2/2002 |
| WO | WO 02/18579 | 3/2002 |
| WO | WO 02/18579 A2 | 3/2002 |
| WO | WO02/18938 | 3/2002 |
| WO | WO 02/072765 A2 | 9/2002 |
| WO | WO 02/064298 A2 | 10/2002 |
| WO | WO 02/083736 A2 | 10/2002 |
| WO | WO02/084298 A3 | 10/2002 |

OTHER PUBLICATIONS

Tunaru, S., et al.; "PUMA–G and HM74 are receptors for nicotinic acid and mediate its anti–lipolytic effect"; Nature Medicine; Advance Online Publication; Feb. 3, 2003, dol:10, 1038/nm824; 2003 Nature Publishing Group; http://www.nature.com/naturemedicine.

Lorenzen, A, et al.; "G protein–coupled receptor for nicotinic acid in mouse macrophages"; Biochemical Pharmacology 64 (2002) 645–648; 0006–2952/02/$; 2002 Elsevier Science Inc.; PII:S0006–2952(02)01220–0.

Lorenzen, A., et al.; "Characterization of a G Protein–Coupled Receptor for Nicotinic Acid"; Mol. Pharmacol. 59:349–357, 2001; 0026–895x/01/5902–349–357$3.00; Molecular Pharmacology; 2001 The American Society for Pharmacology and Experimental Therapeutics; vol. 59, No. 2; 136/882146; Online: http://molpharm.aspetjournals.org.

Jones, C. et al.; Expression and Characterization of a 5–oxo–6E, 8Z, 11Z, 14Z–Eicosatetraenoic Acid Receptor Highly Expressed on Human Eosinophils and Neutrophils; Molar Pharmacology; pp. 471–477; vol. 63, No. 3; The American Society for Pharmacology and Experimental Therapeutics; 2003.

Alla, S.A. et al., "Extracellular domains of the bradykinin B2 receptor involved in ligand binding and agonist sensing defined by anti–peptide antibodies," *J. Biol. Chem.*, 1996, 271, 1748–1755.

Advenier, C. et al., "Effects on the isolated human bronchus of SR 48968, a potent and selective nonpeptide antagonist of the neurokinin A ($NK_2$) receptors," *Am. Rev. Respir. Dis.*, 1992, 146(5, Pt. 1), 1177–1181.

Alexander, W.S. et al., "Point mutations within the dimer interface homology domain of c–MpI induce constitutive receptor activity and tumorigenicity," *Embo J.*, 1995, 14(22), 5569–5578.

Arvanitikis, L. et al., "Human herpesvirus KSHV encodes a constitutively active G–protein–coupled receptor linked to cell proliferation," *Nature*, 1997, 385, 347–349.

Barker, E.L. et al., "Constitutively active 5–hydroxytryptamine$_{2c}$ receptors reveal novel inverse agonist activity of receptor ligands," *J. Biol. Chem.*, 1994, 269(16), 11687–11690.

Baxter, G., "5–$HT_2$ receptors: a family re–united?" *Trends Pharmacol. Sci.*, 1995, 16, 105–110.

Besmer, P. et al., "A new acute transforming feline retrovirus and relationship of its oncogene v–kit with the protein kinase gene family," *Nature*, 1986, 320, 415–421.

Blin, N. et al., "Mapping of single amino acid residues required for selective activation of $G_{q/11}$ by the m3 muscarinic acetylcholine receptor," *J. Biol. Chem.*, 1995, 270, 17741–17748.

Bond, R.A. et al., "Inverse agonists and G–protein–coupled receptors," in *Receptor–Based Drug Design*, Leff, P. (ed.), New York, M. Dekker, 1998, 363–377.

Boone, C. et al., "Mutations that alter the third cytoplasmic loop of the a–factor receptor lead to a constitutive and hypersensitive phenotype," *Proc. Natl. Acad. Sci. USA*, 1993, 90(21), 9921–9925.

Burstein, E.S. et al., "Constitutive activation of chimeric m2/m5 muscarinic receptors and delineation of G–protein coupling selectivity domains," *Biochem. Pharmacol.*, 1996, 51(4), 539–544.

Burstein, E.S. et al., "Amino acid side chains that define muscarinic receptor/G–protein coupling. Studies of the third intracellular loop," *J. Biol. Chem.*, 1996, 271(6), 2882–2885.

Burstein, E.S. et al., "Constitutive activation of muscarinic receptors by the G–protein $G_q$," *FEBS Lett.*, 1995, 363(3), 261–263.

Bylund, D., "International union of pharmacology nomenclature of adrenoceptors," *Pharmacol. Rev.*, 1994, 46, 121–136.

Cheatham, B. et al., "Substitution of the erbB–2 oncoprotein transmembrane domain activates the insulin receptor and modulates the action of insulin–receptor substrate 1," *Proc. Natl. Acad. Sci. USA*, 1993, 90, 7336–7340.

Chen, J. et al., "Tethered Ligand Library for Discovery of Peptide Agonists," *J. Biol. Chem.*, 1995, 270, 23398–23401.

Chen, T.S. et al., "Microbial hydroxylation and glucuronidation of the angiotensin II (AII) receptor antagonist MK 954," *J. Antibiot,* (*Tokyo*), 1993, 46(1), 131–134.

Chen, W. et al., "A colorimetric assay for measuring activation of $G_s$– and $G_q$–coupled signaling pathways," *Anal. Biochem.*, 1995, 226(2), 349–354.

Chidiac, P. et al., "Inverse agonist activity of β–adrenergic antagonists," *J. Pharm. Exp. Ther.*, 1994, 45, 490–499.

Clozel, M. et al., "In vivo pharmacology of Ro 46–2005, the first synthetic nonpeptide endothelin receptor antagonist implications for endothelin physiology," *J. Cardiovas. Pharmacol.*, 1993, *22*(*Suppl. 8*), S377–S379.

Collesi, C. et al., "A splicing variant of the *RON* transcript induces constitutive tyrosine kinase activity and an invasive phenotype," *Mol. Cell. Biol.*, 1996, 16(2), 5518–5526.

Cooper, C.S. et al., "Molecular cloning of a new transforming gene from a chemically transformed human cell line," *Nature*, 1984, 311, 29–33.

De Dios, I. et al., "Effect of L–364,718 (CCK Receptor Antagonist) on Exocrine Pancreatic Secretion of Hydrocortison–Treated Rats," *Pancreas*, 1994, 9(2), 212–218.

Desbois–Mouthon, C. et al., "Deletion of $Asn^{281}$ in the α–subunit of the human insulin receptor causes constitutive activation of the receptor and insulin desensitization," *J. Clin. Endocrinol. Metab.*, 1996, 81(2), 719–727.

Di Renzo, M.F. et al., "Expression of the Met/HGF receptor in normal and neoplastic human tissues," *Oncogene*, 1991, 6(11), 1997–2003.

Di Renzo, M.F. et al., "Overexpression of the c–MET/HGF receptor gene in human thyroid carcinomas," *Oncogene*, 1992, 7, 2549–2553.

Duprez, L. et al., "Germline mutations of the thyrotropin receptor gene cause non–autoimmune autosomal dominant hyperethyroidism," *Nature Genetics*, 1994, 7, 396–401.

Eggerickx, D. et al., "Molecular Cloning of an Orphan G–Protein–Coupled Receptor that Constitutively Activates Adenylate Cyclase," *Biochem. J.*, 1995, 309, 837–843.

Evans, B.E. et al., "Orally Active, Nonpeptide Oxytocin Antagonists," *J. Med. Chem.*, 1992, 35, 3919–3927.

Fu, M. et al., "Functional autoimmune epitope on $\alpha_1$–adrenergic receptors in patients with malignant hypertension," *Lancet*, 1994, 344, 1660–1663.

Furitsu, T. et al., "Identification of Mutations in the Coding Sequence of the Proto–oncogene *c–kit* in a Human Mast Cell Leukemia Cell Line Causing Ligand–independent Activation of *c–kit* Product," *J. Clin. Invest.*, 1993, 92, 1736–1744.

Gellai, M. et al., "Nonpeptide Endothelin Receptor Antagonists V: Prevention and Reversal of Acute Renal Failure in the Rat by SB 209670," *J. Pharm. Exp. Therap.*, 1995, 275(1), 200–206.

Gitter, B. et al., "Pharmacological Characterization of LY303870: A Novel Potent and Selective Nonpeptide Substance P (Neurokinin–1) Receptor Antagonist," *J. Pharm. Exp. Therp.*, 1995, 275(2), 737–744.

Gouilleux–Gruart, V. et al., "STAT–Related Transcription Factors are Constitutively Activated in Peripheral Blood Cells from Acute Leukemia Patients," *Blood*, 1996, 87(5), 1692–1697.

Hansson, J.H. et al., "Hypertension caused by a truncated epithelial sodium channel γ subunit: genetic heterogeneity of Liddle syndrome," *Nat. Genet.*, 1995, 11(1), 76–82.

Hasegawa, H. et al., "Two Isoforms of the Prostaglandin E Receptor EP3 Subtype Different in Agonist–independent Constitutive Activity," *J. Biol. Chem.*, 1996, 271(4), 1857–1860.

Hendler, F. et al., "Human Squamous Cell Lung Cancers Express Increased Epidermal Growth Factor Receptors," *J. Clin. Invest.*, 1984, 74, 647–651.

Herrick–Davis, K. et al., "Constitutively Active 5HT2C Serotonin Receptor Created by Site–Directed Mutagenesis," *Sos. Neurosci.*, Abstract No. 699.18.

Hieble, J., "International union of pharmacology. X. Recommendation for nomenclature of 1–adrenoceptors," *Pharm. Rev.*, 1995, 47, 267–270.

Hill, S., "Distribution, Properties, and Functional Characteristics of Three Classes of Histamine Receptor," *Am. Soc. Pharm. Exp. Therap.*, 1990, 42(1), 45–83.

Högger, P. et al., "Activating and Inactivating Mutations in—and C–terminal i3 Loop Junctions of Muscarinic Acetylcholine Hm1 Receptors," *J. Biol. Chem.*, 1995, 270(13), 7405–7410.

Ikeda, H. et al., "Expression and Functional Role of the Proto–oncogene *c–kit* in Acute Myeloblastic Leukemia Cells," *Blood*, 1991, 78(11), 2962–2968.

Imura, R. et al., "Inhibition by HS–142–I, a novel nonpeptide atrial natriuretic peptide antagonist of microbial origin, of atrial natriuretic peptide–induced relaxation of isolated rabbit sorta through the blockade of guanylyl cyclase–linked receptors," *Mol. Pharm.*, 1992, 42, 982–990.

Jakubik, J. et al., "Constitutive activity of the $M_1$–$M_4$ subtypes of muscarinic receptors in transfected CHO cells and of muscarinic receptors in the heart cells revealed by negative antagonists," *FEBS Letts.*, 1995, 377, 275–279.

Kjelsberg, M.A. et al., "Constitutive activation of the $\alpha_{1B}$–adrenergic receptor by all amino acid substitutions at a single site," *J. Biol. Chem.*, 1992, 267(3), 1430–1433.

Knapp, R. et al., "Molecular biology and pharmacology of cloned opioid receptors," *FASEB J.*, 1995, 9, 516–525.

Kosugi, S. et al., "Characterization of heterogeneous mutations cusing constitutive activation of the luteinizing hormone receptor in familial male precocious puberty," *Human Mol. Genetics*, 1995, 4(2), 183–188.

Kosugi, S. et al., "Identification of Thyroid–Stimulating Antibody–Specific Interaction Sites in the N–Terminal Region of the Thyrotropin Receptor," *Mol. Endocrinology*, 1993, 7, 114–130.

Kraus, M. et al., "Demonstration of ligand–dependent signaling by the *erbB–3* tyrosine kinase and its constitutive activation in human breast tumor cells," *Proc. Natl. Acad. Sci. USA*, 1993, 90, 2900–2904.

Kudlacz, E. et al., "In Vitro and In Vivo Characterization of MDL 105,212A, a Nonpeptide NK–1/NK–2 Tachykinin Receptor Antagonist," *J. Pharm. Exp. Therap.*, 1996, 277(2), 840–851.

Kuriu, A. et al., "Proliferation of Human Myeloid leukemia Cell Line Associated with the Tyrosine–Phosphorylation and Activation of the Proto–oncogene *c–kit* Product," *Blood*, 1991, 78(11), 2834–2840.

Labbé–Jullié, "Effect of the nonpeptide neurotensin antagonist, SR 48692, and two enantiomeric analogs, SR 48527 and SR 49711, on neurotension binding and contractile responses in guinea pig ileum and colon," *J. Pharm. Exp. Therap.*, 1994, 271(1), 267–276.

Latronico, A. et al., "A novel mutation of the luteinizing hormone receptor gene causing male gonadotropin–independent precocious puberty," *J. Clin. Endocrinol. Metabl.*, 1995, 80(8), 2490–2494.

Laue, L. et al., "Genetic heterogeneity of constitutively activating mutations of the human luteinizing hormone receptor in familial male–limited precocious puberty," *Proc. Natl. Acad. Sci USA*, 1995, 92, 1906–1910.

Løvlie, R. et al., "The $Ca^{2+}$ –sensing receptor gene (PCAR1) mutation TI51M in isolated autosomal dominant hypoparathyroidism," *Hum. Genet.* 1996, 98, 129–133.

Lefkowitz, R. et al., "Constitutive activity of receptors coupled to guanine nucleotide regulatory proteins," *Trends Pharmacol. Sci.*, 1993, 14, 303–307.

Libermann, T. et al., "Amplification, enhanced expression and possible rearrangement of EGF receptor gene in primary human brain tumours of glial origin," *Nature*, 1985, 313, 144–147.

Liu, C. et al., "Overexpression of c–met proto–oncogene but not epidermal growth factor receptor or c–erbB–2 in primary human colorectal carcinomas," *Oncogene*, 1992, 7, 181–185.

Liu, J. et al., "Molecular mechanisms involved in muscarinic acetylcholine receptor–mediated G protein activation studied by insertion mutagenesis," *J. Biol. Chem.*, 1996, 271(11), 6172–6178.

Lonardo, F. et al., "The normal erbB–2 product is an arypical receptor–like tyrosine kinase with constitutive activity in the absence of ligand," *New Biologist*, 1990, 2(11), 992–1003.

Maenhaut, F. et al., "RDC8 codes for an adenosine A2 receptor with physiological constitutive activity," *Biochem. Biophys. Res. Comm.*, 1990, 173(3), 1169–1178.

Mann, J. et al., "Increased serotonin$_2$ and β–adrenergic receptor binding in the frontal cortices of suicide victims," *Arch. Gen. Psychiatry*, 1986, 43, 954–959.

Martone, R.L. et al., "Human CRF receptor chimeras: Mapping of ligand binding determinants," 26th Meeting of the Society of Neuroscience, Washington, D.C. Nov. 16–21, 1996, Abstract No. 609.8.

Magnusson, Y. et al., "Autoimmunity in idiopathic dilated cardiomyopathy," *Circulation*, 1994, 89, 2760–2767.

Matus–Leibovitch, N. et al., "Truncation of the thyrotropin–releasing hormone receptor carboxyl tail causes constitutive activity and leads to impaired responsiveness in *Xenopus Oocytes* and AtT20 Cells," *J. Biol. Chem.*, 1995, 270(3), 1041–1047.

Myles, G.M. et al., "Tyrosine 569 in the c–Fms juxtamembrane domain is essential for kinase activity and macrophage colony–stimulating factor–dependent internalization," *Mol. Cell. Biol.*, 1994, 14(7), 4843–4854.

Nanevicz, T. et al., "Thrombin receptor activating mutations," *J. Biol. Chem.*, 1996, 271(2), 702–706.

Natali, P.G. et al., "Expression of the c–Met/HGF receptor in human melanocytic neoplasms: demonstration of the relationship to malignant melanoma tumour progression," *Br. J. Cancer*, 1993, 68, 746–749.

Neilson, K.M. et al., "Constitutive activation of fibroblast growth factor receptor–2 by a point mutation associated with Crouzon syndrome," *J. Biol. Chem.*, 1995, 270(44), 26037–26040.

Oda, S. et al., "Pharmacological profile of HS–142–1, a novel nonpeptide atrial natriuretic peptide (ANP) antagonist of microbial origin. II. Restoration by HS–142–1 of ANP–induced inhibition of aldosterone production in adrenal glomerulosa cells," *J. Pharm. Exp. Ther.*, 1992, 263(1), 241–245.

O'Dowd, B.F. et al., "Site–directed mutagenesis of the cytoplasmic domains of the human β2–adrenergic receptor," *J. Biol. Chem.*, 1988, 263(31), 15985–15992.

Offermanns, S. et al., "G$\alpha_{15}$ and G$\alpha_{16}$ Couple a Wide Variety of Receptors to Phospholipase C," *J. Biol. Chem.*, 1995, 270, 15175–15180.

Palkowitz, A.D. et al., "Structural evolution and Pharmacology of a novel series of triacid angiotensin II receptor antagonists," *J. Med. Chem.*, 1994, 37, 4508–4521.

Parent, J. et al., "Mutations of two adjacent amino acids generate inactive and constitutively active forms of the human platelet–activating factor receptor," *J. Biol. Chem.*, 1996, 271(14), 7949–7955.

Parfitt, A.M. et al., "Hypercalcemia due to constitutive activity of the parathyroid hormone (PTH)/PTH–related peptide receptor: comparison with primary hyperparathyroidism," *J. Clin. Endocr. Metabl.*, 1996, 81, 3584–3588.

Parma, J. et al., "Somatic mutations in the thyrotropin receptor gene cause hyperfunctioning thyroid adenomas," *Nature*, 1993, 365, 649–651.

Pei, G. et al., "A constitutive active mutant β$_2$–adrenergic receptor is constitutively desensitized and phosphorylated," *Proc. Natl. Acad. Sci. USA*, 1994, 91, 2699–2702.

Pendley, C.E. et al., "The gastrin/cholecystokinin–B receptor antagonist L–365,260 reduces basal acid secretion and prevents gastrointestinal damage induced by aspirin, ethanol and cysteamine in the rat," *J. Pharmacol. Exp. Ther.*, 1993, 265(3), 1348–1354.

Peroutka, S., "Serotonin receptor subtypes. Their evolution and clinical relevance," *CNS Drugs*, 1995, *4* (*Suppl. I*), 18–27.

Pettibone, D.J. et al., "Development and pharmacological assessment of novel peptide and nonpeptide oxytocin antagonists," *Regul. Pept.*, 1993, 45, 289–293.

Prat, M.P. et al., "The receptor encoded by the human *c–Met* oncogene is expressed in hepatocytes, epithelial cells and solid tumors," *Int. J. Cancer*, 1991, 49, 323–328.

Prezeua, L. et al., "Changes in the carboxy–terminal domain of metabotropic glutamate receptor 1 by alternate splicing generate receptors with differing agonist–independent activity," *Mol. Pharmacol.*, 1996, 49, 422–429.

Rakovska, A. et al., "Effect of loxiglumide (CR 1505) on CCK–induced contractions and $^3$H–acetylcholine release from guinea–pig gallbaldder," *Neuropeptides*, 1993, 25(5), 271–276.

Ren, Q. et al., "Constitutive active mutants of the $\alpha_2$–adrenergic receptor," *J. Biol. Chem.*, 1993, 268, 16483–16487.

Reynolds, E.E. et al., "Pharmacological characterization of PD 156707, an orally active ET$_A$ receptor antagonist," *J. Pharmacol, Exp. Ther.*, 1995, 273(3), 1410–1417.

Robbins, L.S. et al., "Pigmentation phenotypes of variant extension locus alleles result from point mutations that alter MSH receptor function," *Cell*, 1993, 72, 827–834.

Rong, S. et al., "Met expression and sarcoma tumorigenicity," *Cancer*, 1993, 53(22), 5355–5360.

Samama, P. et al., "A mutation–induced activation state of the β2–adrenergic receptor," *J. Biol. Chem.*, 1993, 268(7), 4625–4636.

Sautel, M. et al., "Neuropeptide Y and the nonpeptide antagonist BIBP 3226 share an overlapping binding site at the human Y1 receptor," *Am. Soc. Pharm. Exp. Ther.*, 1996, 50, 285–292.

Sawutz, D.G. et al., "Pharmacology and structure–activity relationships of the nonpeptide bradykinin receptor antagonist WIN 64338," *Can. J. Physiol. Pharmacol.*, 1995, 73, 805–811.

Scheer, A. et al., "Constitutively active G protein–coupled receptors: potential mechanisms of receptor activation," *J. Rec. Signal Transduct. Res.*, 1997, 17(I–3), 57–73.

Scheer, A. et al., "The activation process of the $\alpha_{1B}$–adrenergic receptor: Potential role of protonation and hydrophobicity of a highly conserved aspartate," *Proc. Natl. Acad. Sci. USA*, 1997, 94, 808–813.

Schwinn, D.A. et al., "Cloning and pharmacological characterization of human Alpha–1 adrenergic receptors: sequence corrections and direct comparison with other species homologues," *J. Pharmacol.*, 1995, 272(I), 134–142.

Schild, L. et al., "A mutation in the epithelial sodium channel cuasing Liddle disease increases channel activity in the *Xenopus Laevls oocyte* expression system," *Proc. Natl. Acad. Sci. USA*, 1995, 92, 5699–5703.

Seeman, P. et al., "Dopamine receptor pharmacology," *Trends Pharmacol. Sci.*, 1994, 15, 264–270.

Seeman, P. et al., "Dopamine D4 receptors elevated in schizophrenia," *Nature*, 1993, 365, 441–445.

Serradeil–Le Gal, C. et al., "Biochemical and pharmacological properties of SR 49059, a new, potent, nonpeptide antagonist of rat and human vasopressin $V_{1a}$ receptors," *J. Clin. Invest.*, 1993, 92, 224–231.

Sharif, M. et al., "Malignant transformation by G protein–coupled hormone receptors," *Mol. Cell. Endocrinology*, 1994, 100, 115–119.

Showers, M.O. et al., "Activation of the erythropoietin receptor by the Friend spleen focus–forming virus gp55 glycoprotein induces constitutive protein tyrosine phosphorylation," *Blood*, 80(12), 3070–3078.

Skinner, R.H. et al., "Direct Measurement of the binding of RAS to neurofibromin using scintillation proximity assay," *Anal. Biochem.*, 1994, 223, 259–265.

Slamon, D.J. et al., "Human breast cancer: correlation of relapse and survival with amplification of the HER–2/neu oncogene," *Science*, 1987, 235, 177–181.

Slamon, D. et al., "Studies of the HER–2/neu proto–oncogene in human breast and ovarian cancer," *Science*, 1989, 244, 707–712.

Salomon, Y. et al., "A highly sensitive adenylate cyclase assay," *Anal. Biochem.*, 1974, 58, 541–548.

Spiegel, A.M., "Defects in G protein–coupled signal transduction in human disease," *Ann. Rev. Physiol.*, 1995, 58, 143–170.

ter Laak, A. et al., "Modelling and mutation studies on the histamine $H_1$–receptor agonist binding site reveal different binding modes for $H_1$–agonists: $Asp^{116}$ (TM3) has a constitutive role in receptor stimulation," *J. Computer–Aided Mol. Design*, 1995, 9, 319–330.

Tiberi, M. et al., "High agonist–independent activity is a distinguishing feature of the dopamine D1B receptor subtype," *J. Biol. Chem.*, 1994, 269(45), 27925–27931.

Tsujimura, T. et al., "Constitutive activation of *c–kit* in FMA3 murine mastocytoma cells caused by deletion of seven amino acids at the juxtamembrane domain," *Blood*, 1996, 87(1), 273–283.

Wang, Z. et al., "Constitutive $\mu$ opioid receptor activation as a regulatory mechanism underlying narcotic tolerance and dependence," *Life Sci.*, 1994, 54(20), 339–350.

Watowich, S.S. et al., "Homodimerization and constitutive activation of the erythropoietin receptor," *Proc. Natl. Acad. Sci USA*, 1992, 89, 2140–2144.

Weber–Nordt, R.M. et al., "Constitutive activation of STAT proteins in primary lymphoid and myeloid leukemia cells and in Epstein–Barr virus (EBV)–related lymphoma cell lines," *Blood*, 1996, 88(3), 809–816.

Webster, M.K. et al., "Constitutive activation of fibroblast growth factor receptor 3 by the transmembrane point mutation found in achondroplasia," *EMBO J.*, 1996, 15, 520–527.

Xu, Y. et al., "Characterization of epidermal growth factor receptor gene expression in malignant and normal human cell lines," *Proc. Natl. Acad. Sci. USA*, 1984, 81, 7308–7312.

Yamada, K. et al., "Substitution of the insulin receptor transmembrane domain with the *c–new/erbB2* transmembrane domain constitutively activates the insulin receptor kinas in vitro," *J. Biol. Chem.*, 1992, 267(18), 12452–12461.

Zhang, S. et al., "Identification of Dynorphins as Endogenous Ligands for an Opioid Receptor–Like Orphan Receptor," *J. Biol. Chem.*, 1995, 270, 22772–22776.

Zhen, Z. et al., "Structural and functional domains critical for constitutive activation of the HGF–receptor (Met)," *Oncogene*, 1994, 9, 1691–1697.

Bergsma, D.J., et al., "Cloning and characterization of a human angiotensin II type I receptor," *Biochem. & Biophy. Res. Comm.*, 1992, XP–002145165, 183(3), 989–995.

Forman, B.M., et al., "Androstane Metabolites Bind to and Deactivate the Nuclear receptor CAR–β", *Nature*, 1998, 395, pp. 612–615.

Gantz, I. et al., "Molecular Cloning of a Novel Melanocortin Receptor," *J. Biol. Chem.*, 1993, 268(11), 8246–8250.

Groblewski, T., et al., "Mutation of $Asn^{111}$ in the third transmembrane domain of the $AT_{1a}$ angiotensin II receptor induces its constitutive activation," *J. Biol. Chem.*, 1997, XP–002145162, 272(3), 1822–1826.

Itoh, H. et al., *Proc. Natl. Acad. Sci. USA*, 1986, vol. 83, pp. 3776.

Kenakin, T., *Life Sciences*, 1988, vol. 43, pp. 1095.

Koike, G., et al., "Human type 2 angiotensin II receptor gene: cloned, mapped to the X chromosome, and its mRNA is expressed in the human lung," *Biochem. And Biophy. Res. Comm.*, 1994, XP–002145166, 203(3), 1842–1850.

Kyaw, H., et al., "Cloning, characterization, and mapping of human homolog of mouse T–cell death–associated gene," *DNA and Cell Biology*, 1998, XP000929737, 17(6), 493–500.

McKee, K. et al., "Cloning and Characterization of Two Human G Protein–coupled Receptor Genes (GPR38 and GPR39) Related to the Growth Hormone Secretagogue and Neurotensin Receptors", *Genomics*, 1997, 17:6, pp. 426–434.

Noda, K., et al., "The active state of the $AT_1$ angiotensin receptor is generated by angiotensin II induction," *Biochem.*, 1996, XP–002145163, 35, 16435–16442.

Pauwels P.J. et al., "Review: Amino Acid Domains Involved in Constitutive Activation of G–Protein–Coupled Receptors", *Molecular Neurobiology*, 1998, 17, pp. 109–135.

Reppert, S.M., et al., "Cloning of a melatonin–related receptor from human pituitary," *FEBS Letts.*, 1996, XP–002145161, 219–2254.

Seifert R et al., "Different Effects of $G_s\alpha$ Splice Variants on $\beta_2$–Adrenoreceptor–mediated Signaling", *Journal of Biological Chem.*, 1998, 273, pp. 5109–5116.

Shyrock, John et al., "Inverse Agonists and Nuetral Antagonists of Recombinant Human $A_1$ Adenosine Receptors Stably Expressed in Chinese Hamster Ovary Cells", *Molecular Pharmacology*, 1998, 53, pp. 886–893.

Suzuki, M. et al., "Regulatable Promoters for Use in Gene Therapy Applications: Modification of the 5'–Flanking Region of the CFTR Gene with Multiple cAMP Response Elements to Support Basal, Low–Level Gene Expression that can be Upregulated by Exogenous Agents that Raise Intracellular Levels of cAMP," *Human Gene Therapy*, 1996, 7, 1883–1893.
Wenzel–Seifert et al., High Constitutive Activity of the Human Formyl Peptide Receptor, *Journal of Biological Chem.*, 1998, 273, pp. 24181–24189.
Abola, A.P., et al., "Omo sapiens chromosome 13 clone RP11–286P8, complete sequence," AC026756 XP–002175912, Apr. 24, 2000, 1–41.
Adams, M.D., et al., "CIT–HSP–2286K19.TF CIT–HSP *Homo sapiens* genomic clone 2286k19, genomic survey sequence," AQ001459, XP–002175783, Aug. 24, 2001, 1 page.
Birren, B., et al., "*Homo sapiens* chromosome 11, clone RP11–589F4," AC027026, XP002175913, Apr. 27, 2000, 1–40.
Birren, B., et al., "*Homo sapiens* clone RP11–15H8, 31 unordered pieces," AC011780, XP002175781, Oct. 18, 1999, 1–46.
Birren, B., et al., "*Homo sapiens* clone RP11–14N15," AC016468, XP002175784, Dec. 1, 1999, 1–38.
Boyer, J.L., et al., "Molecular cloning and expression of an avian G protein–coupled P2Y receptor," *Am. Soc. For Pharmacology & Experimental Therapeutics*, XP–002175907, 1997, 928–934.
Burton, J., et al., "Human DNA sequence from clone RP11–163L4," A1161458, XP002175911, Apr. 16, 2000, 1–39.
Burton, J., "Human DNA sequence from clone RP11–15909," AL136106, XP002175785, Jan. 7, 2000.
Collier, R., "DJ68ON, 3 (G–protein coupled receptors) (fragment)," Accession Nr. Q9NTTO, XP002168498, Jan. 10, 2001, 1 page.
Doe Joint Genome Institute, "*Homo sapiens* chomosome 5 clone CTC–502m5, complete sequence," AC008547, XP002175786, Aug. 4, 1999, 1–30.
Doe Joint Genome Institute, "*Homo sapiens* chomosome 19 clone CTD–3023J11, complete sequence," AC008754, XP002175778, Aug. 4, 1999, 1–18.
Gempscpue, "drosophila melanogaster genome survey sequence TET3 end of BAC # BACRO8K10 of RPCI–98 library from Drosophila melanogaster (fruit fly)," AL065769, XP00217590, 2000.
Hattori, M., et al., "*Homo sapiens* 171, 539 genomic of 11q13," AP000808, XP002175780, Dec. 3, 1999, 1–45.
Heise, C.E., et al., "Characterization of the human cysteinyl leukotriene 2 receptor," *J. Biological Chemistry*, Sep. 29, 2000, 275(39), 30531–30536.
Mahairas, G.G., et al., "Sequence–tagged connectors: A sequence approach to mapping and scanning the human genome," *Proc. Natl. Acad. Sci. USA*, Aug. 1999, 96, 9739–9744.
Marchese, A., et al., "Novel GPCRs and their endogenous ligands: expanding the boundaries of physiology and pharmacology," *TiPS*, Sep. 1999, 20, 370–375.
O'Dowd, B.F., et al., "Discovery of three novel G–protein–coupled receptor genes," *Genomics*, XP–000863786, 1998, 310–313.
Ohono, M., et al., "*Homo sapiens* mRNA for G proteine–coupled receptor C5L2, complete cds," AB038237, XP002175947, May 4, 2000, 1 page.
Stadel, J.M., et al., "Orphan G protein–coupled receptors: a neglected opportunity for pioneer drug discovery," *TiPS*, Nov. 1997, 18, 430–437.
Devlin, et al., "Random peptide libraries: A source of specific protein binding molecules", *Science*, 1990, 249, 404–406.
Nomura, et al., "Molecular cloning of cDNAsencoding a LD78 receptor and putative leukocyte chemotactic peptide receptors", *International Immunology*, 1993, 5(10), 1239–1249.
Stone, N., et al., "*Homo sapiens* chomosome 4, 16 unordered pieces," AC007104, XP002175914, Apr. 23, 1999, 1–52.
Wallis, J., "Human DNA sequence from clone RP5–1160K1," AL355310, XP002175782, May 5, 2000, 1–39.
Waterson, R.H., "*Homo sapiens* chromosome 2 clone RP11–510c1," AC010984, XP002175915, Sep. 29, 1999, 1–50.
Weinshank, R.H., "5–hydroxytryptamine 1B receptor (–HT–1B) (serotonin receptor)," AC 008892, XP002175948, Jul. 15, 1998, 1 page.
Zhao, S., et al., "Use of BAC end sequences from library RPCI–11 for sequence–ready map building," AQ532303, XP002175779, May 18, 1999, 1 page.
Watson, S. et al., *The G–Protein Linked Receptor Facts Book*, Academic Press, 1994, pp. 2–6 and 162–169.
Rudinger, J. et al., *Peptide Hormones*, ed. Parson, J.A., University Park Press, 1993, Baltimore, pp. 1–7.
U.S. Appl. No. 10/484,788, (Claiming priority PCT/GB02/01671).

Tissue Distribution of hRUP38 *versus* hRUP25 *via* RT-PCR

Figure 14A
hRUP25 $G_i$ - Coupled Constitutive Activity in Melanophore
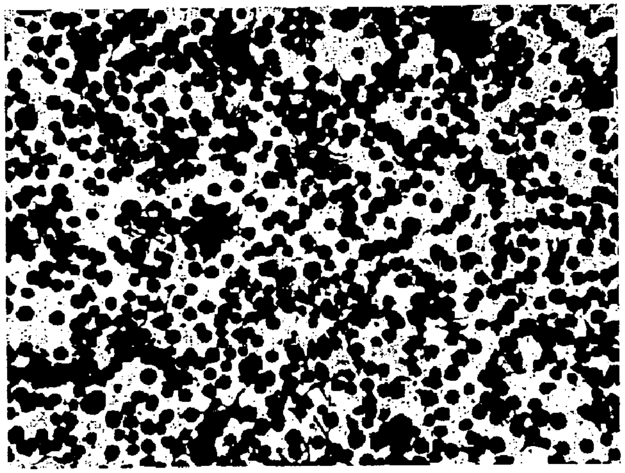
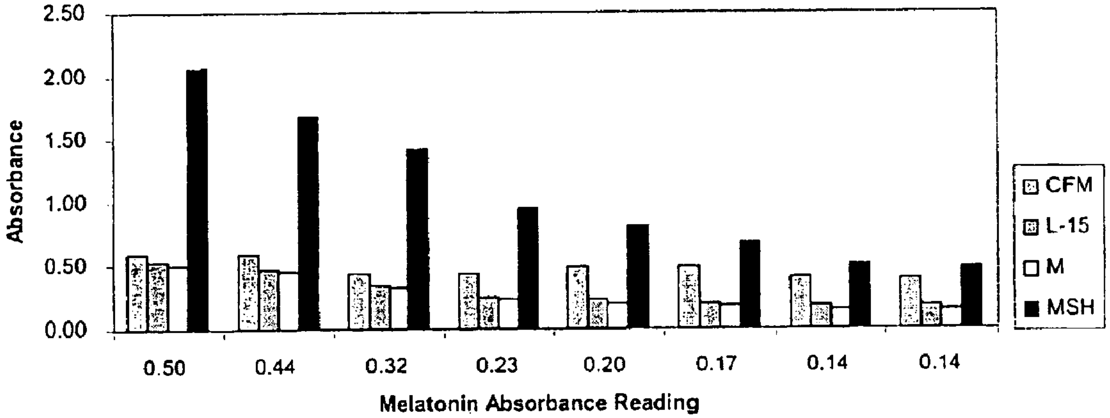

hRUP38 $G_i$ - Coupled Constitutive Activity in Melanophore

Figure 14C
hRUP19 $G_i$ - Coupled Constitutive Activity in Melanophore
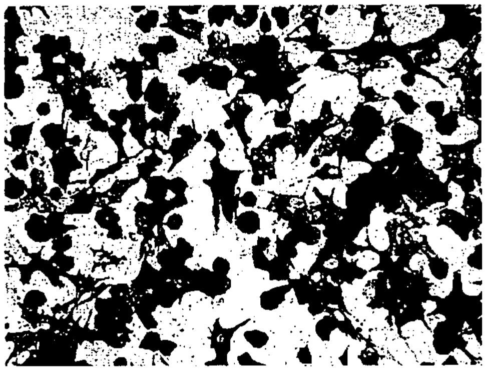
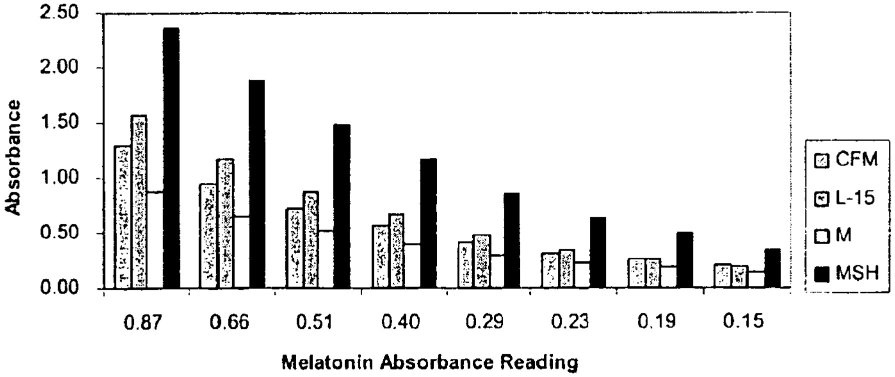

Nicotinic Acid Induced Inositol Phosphate Accumulation in 293 Cells Co-Expressing hRUP25 and GqΔGi

Saturation Binding of [$^3$H]Nicotinic Acid to Membranes from Cells Expressing Either hRUP25, hRUP38, hRUP19 or Vector Alone hRUP25-CHO Stable Clone Identified by Anti-HA Immunofluorescence Staining

Clone #46 Mock

Nicotinic Acid and Nicotine Induced Inhibition of Forskolin Stimulated cAMP

Accumulation in hRUP25-CHO Stable Cell Line #46 hRUP25 and mRUP25 Inhibit TSHR Induced cAMP Accumulation Following Activation by Nicotinic Acid hRUP25 and mRUP25 Bind to Nicotinic Acid Specifically and with High Affinity

Figure 21

The Rank Order of Potency of Compounds on hRUP25 Closely Matches That of the Pharmacologically Defined Nicotinic Acid Receptor

| | | EC 50 (μM) | | | |
|---|---|---|---|---|---|
| Compound | | Adipocytes* | Spleen* | hRUP25† | hRUP25 ($K_d$)‡ |
| Nicotinic acid | 1.42 | 0.703 | 0.04 | 0.14 | |
| Pyridazine-4-carboxylic acid | 3.76 | 3.14 | N.D. | 2.19 | |
| Acipimox | | 10.3 | 6.56 | 2 | 2.68 |
| 3-Pyridine-acetic acid | | 16.4 | 21.8 | 3 | 1.64 |
| Pyrazine-2-carboxylic acid | 26 | 22 | 4 | 4.14 | |
| 5-Methylnicotinic acid | | 30.2 | 30.0 | 7 | 3.58 |
| 5-Methylpyrazine-2-carboxylic acid | | 52.0 | 14.5 | 7 | 7.36 |
| 6-Methylnicotinic acid | | 72.6 | 53.7 | 34 | 21.95 |
| Nicotinic acid-1-oxide | | 80.4 | 73.7 | 120 | 55.25 |
| 2-Hydroxynicotinic acid | | 132 | N.D. | 130 | 145.4 |
| Furane-3-carboxylic acid | 142 | N.D. | 110 | 130.6 | |
| Nicotinamide | >1000 | >1000 | >1000 | 128.2 | |

N.D., not determined.

* From Lorenzen,A. *et. al. Mol.Pharmacol.* 59 (2):349-357, 2001.

† Arena data, inhibition of forskolin-induced cAMP production in hRUP25-CHO stable line #46.

‡ Arena data, [$^3$H]nicotinic acid radioligand binding assay on membranes derived from hRUP25-CHO stable line #46.

Nicotinic Acid and Related Compounds Inhibit Isoproterenol Induced Lipolysis in Rat Epididymal Fat Derived Adipocytes

Nicotinic Acid Dose-Dependent Inhibition of Isoproterenol Induced-Lipolysis in Rat Epididymal Fat Derived Adipocytes Dose-Dependent Inhibition of Isoproterenol Induced Lipolysis in Human Subcutaneous-Derived Primary Adipocytes by Nicotinic Acid and P-3-T

Figure 24
Screening Data for Nicotinic Acid and 1-Isopropyl-1H-Benzotriazole-5-Carboxylic Acid in cAMP Assays
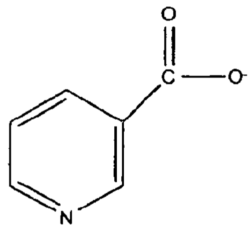
Nicotinic Acid
(MW=123.11g/mole)
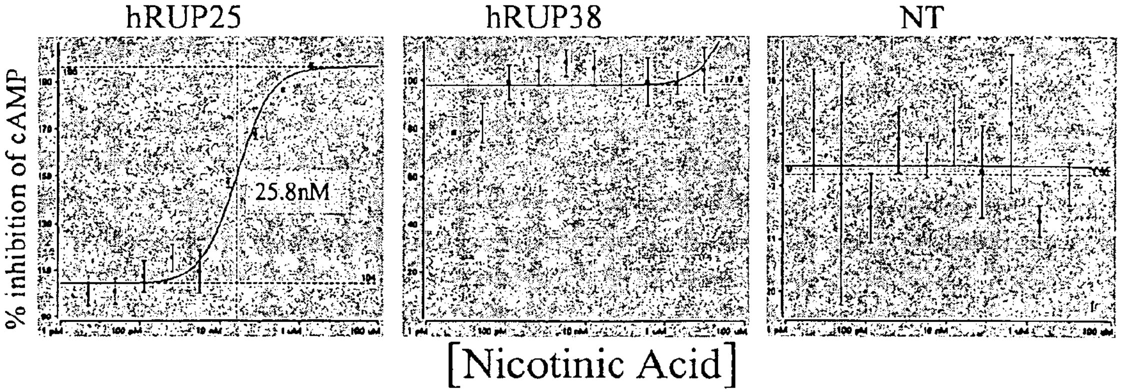
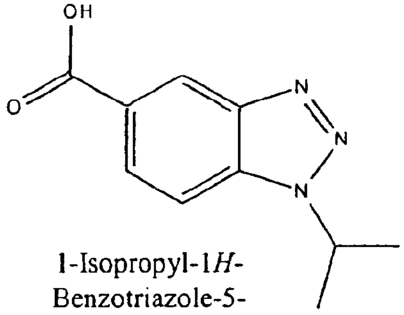
1-Isopropyl-1*H*-Benzotriazole-5-Carboxylic Acid
(MW=205.22g/mole)
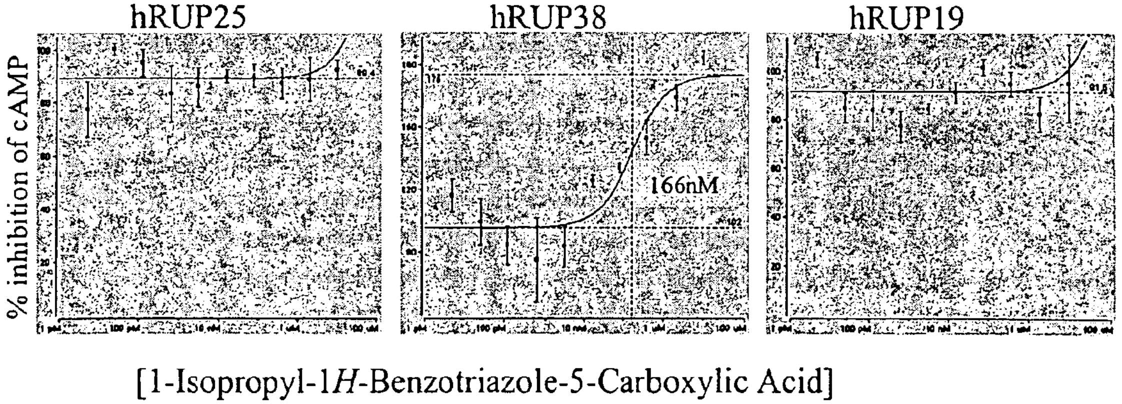

Inhibition of Isoproterenol Stimulated Lipolysis in Human Subcutaneous Adipocytes

Figure 26
Inhibition of Forskolin Stimulated cAMP Accumulation in hRUP38-CHO Stable Cell Line by 3-(5-Bromo-2-Ethoxy-Phenyl)-Acrylic Acid
hRUP38
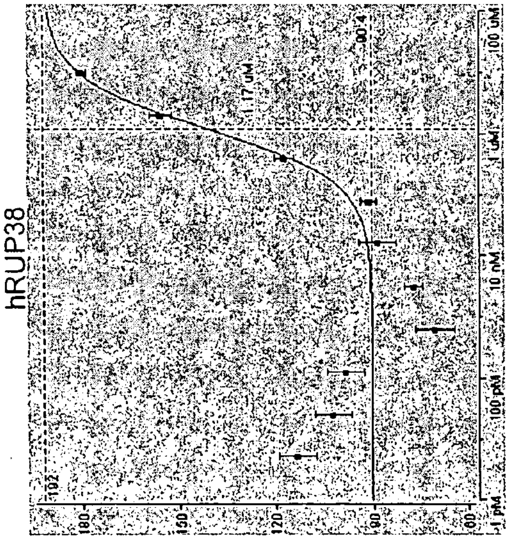
hRUP25
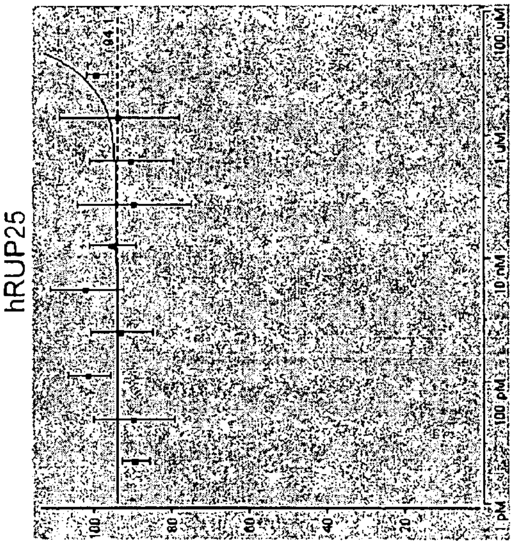
hRUP19
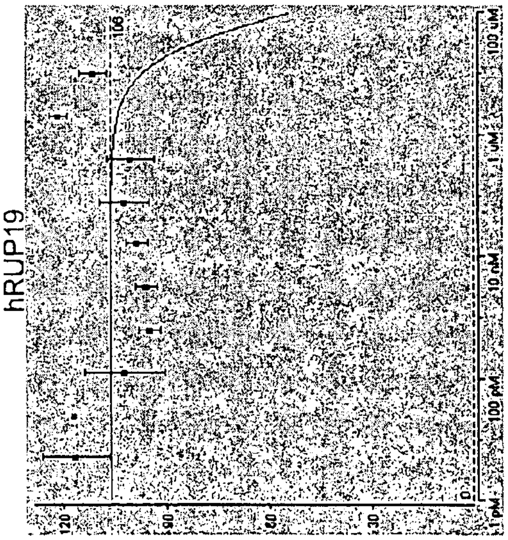

RT-PCR Indicates that hRUP19 is Selectively Expressed in Human Fat Cells

RNA Blot of hRUP19 Expression in Selected Tissues

Strong mammary gland expression probably due to fat cell-specific expression of this receptor.

RUP19 Expression is Induced During Adipocyte Differentiation

CART-Activated hRUP19 Inhibits cAMP Production in Membranes of Transfected 293 Cells

Inhibition of Forskolin Stimulated cAMP Accumulation in hRUP25-CHO Stable Cell Line by (5-Hydroxy-1-methyl-3-propyl-1H-pyrazol-4-yl)-pyridin-3-yl-methanone

Measurement of Plasma Free Fatty Acids (FFA) in Rats Administered Niacin

Cyclase Assay on 293 Cells
TSHR Co-Transfection with hRUP25 S91

SEQUENCE LISTING

```
<160> NUMBER OF SEQ ID NOS: 161

<210> SEQ ID NO 1
<211> LENGTH: 1155
<212> TYPE: DNA
<213> ORGANISM: Homo sapiens

<400> SEQUENCE: 1

atggcagccc agaatggaaa caccagtttc acacccaact ttaatccacc ccaagaccat     60

gcctcctccc tctcctttaa cttcagttat ggtgattatg acctccctat ggatgaggat    120

gaggacatga ccaagacccg gaccttcttc gcagccaaga tcgtcattgg cattgcactg    180

gcaggcatca tgctggtctg cggcatcggt aactttgtct ttatcgctgc cctcacccgc    240

tataagaagt tgcgcaacct caccaatctg ctcattgcca acctggccat ctccgacttc    300

ctggtggcca tcatctgctg ccccttcgag atggactact acgtggtacg gcagctctcc    360

tgggagcatg gccacgtgct ctgtgcctcc gtcaactacc tgcgcaccgt ctccctctac    420

gtctccacca atgccttgct ggccattgcc attgacagat atctcgccat cgttcacccc    480

ttgaaaccac ggatgaatta tcaaacggcc tccttcctga tcgccttggt ctggatggtg    540

tccattctca ttgccatccc atcggcttac tttgcaacag aaacggtcct ctttattgtc    600

aagagccagg agaagatctt ctgtggccag atctggcctg tggatcagca gctctactac    660

aagtcctact tcctcttcat ctttggtgtc gagttcgtgg gccctgtggt caccatgacc    720

ctgtgctatg ccaggatctc ccgggagctc tggttcaagg cagtccctgg gttccagacg    780

gagcagattc gcaagcggct gcgctgccgc aggaagacgg tcctggtgct catgtgcatt    840

ctcacggcct atgtgctgtg ctgggcaccc ttctacggtt tcaccatcgt tcgtgacttc    900

ttccccactg tgttcgtgaa ggaaaagcac tacctcactg ccttctacgt ggtcgagtgc    960

atcgccatga gcaacagcat gatcaacacc gtgtgcttcg tgacggtcaa gaacaacacc   1020

atgaagtact tcaagaagat gatgctgctg cactggcgtc cctcccagcg ggggagcaag   1080

tccagtgctg accttgacct cagaaccaac ggggtgccca ccacagaaga ggtggactgt   1140

atcaggctga agtga                                                     1155

<210> SEQ ID NO 2
<211> LENGTH: 384
<212> TYPE: PRT
<213> ORGANISM: Homo sapiens

<400> SEQUENCE: 2

Met Ala Ala Gln Asn Gly Asn Thr Ser Phe Thr Pro Asn Phe Asn Pro
1               5                   10                  15

Pro Gln Asp His Ala Ser Ser Leu Ser Phe Asn Phe Ser Tyr Gly Asp
            20                  25                  30

Tyr Asp Leu Pro Met Asp Glu Asp Glu Asp Met Thr Lys Thr Arg Thr
        35                  40                  45
```

-continued

```
Phe Phe Ala Ala Lys Ile Val Ile Gly Ile Ala Leu Ala Gly Ile Met
    50                  55                  60

Leu Val Cys Gly Ile Gly Asn Phe Val Phe Ile Ala Ala Leu Thr Arg
65                  70                  75                  80

Tyr Lys Lys Leu Arg Asn Leu Thr Asn Leu Leu Ile Ala Asn Leu Ala
                85                  90                  95

Ile Ser Asp Phe Leu Val Ala Ile Ile Cys Cys Pro Phe Glu Met Asp
            100                 105                 110

Tyr Tyr Val Val Arg Gln Leu Ser Trp Glu His Gly His Val Leu Cys
        115                 120                 125

Ala Ser Val Asn Tyr Leu Arg Thr Val Ser Leu Tyr Val Ser Thr Asn
    130                 135                 140

Ala Leu Leu Ala Ile Ala Ile Asp Arg Tyr Leu Ala Ile Val His Pro
145                 150                 155                 160

Leu Lys Pro Arg Met Asn Tyr Gln Thr Ala Ser Phe Leu Ile Ala Leu
                165                 170                 175

Val Trp Met Val Ser Ile Leu Ile Ala Ile Pro Ser Ala Tyr Phe Ala
            180                 185                 190

Thr Glu Thr Val Leu Phe Ile Val Lys Ser Gln Glu Lys Ile Phe Cys
        195                 200                 205

Gly Gln Ile Trp Pro Val Asp Gln Gln Leu Tyr Tyr Lys Ser Tyr Phe
    210                 215                 220

Leu Phe Ile Phe Gly Val Glu Phe Val Gly Pro Val Val Thr Met Thr
225                 230                 235                 240

Leu Cys Tyr Ala Arg Ile Ser Arg Glu Leu Trp Phe Lys Ala Val Pro
                245                 250                 255

Gly Phe Gln Thr Glu Gln Ile Arg Lys Arg Leu Arg Cys Arg Arg Lys
            260                 265                 270

Thr Val Leu Val Leu Met Cys Ile Leu Thr Ala Tyr Val Leu Cys Trp
        275                 280                 285

Ala Pro Phe Tyr Gly Phe Thr Ile Val Arg Asp Phe Phe Pro Thr Val
    290                 295                 300

Phe Val Lys Glu Lys His Tyr Leu Thr Ala Phe Tyr Val Val Glu Cys
305                 310                 315                 320

Ile Ala Met Ser Asn Ser Met Ile Asn Thr Val Cys Phe Val Thr Val
                325                 330                 335

Lys Asn Asn Thr Met Lys Tyr Phe Lys Lys Met Met Leu Leu His Trp
            340                 345                 350

Arg Pro Ser Gln Arg Gly Ser Lys Ser Ser Ala Asp Leu Asp Leu Arg
        355                 360                 365

Thr Asn Gly Val Pro Thr Thr Glu Glu Val Asp Cys Ile Arg Leu Lys
    370                 375                 380
```

<210> SEQ ID NO 3
<211> LENGTH: 1260
<212> TYPE: DNA
<213> ORGANISM: Homo sapiens

<400> SEQUENCE: 3

```
atgctggcag ctgcctttgc agactctaac tccagcagca tgaatgtgtc ctttgctcac     60

ctccactttg ccggagggta cctgccctct gattcccagg actggagaac catcatcccg    120

gctctcttgg tggctgtctg cctggtgggc ttcgtgggaa acctgtgtgt gattggcatc    180

ctccttcaca atgcttggaa aggaaagcca tccatgatcc actccctgat tctgaatctc    240
```

-continued

```
agcctggctg atctctccct cctgctgttt tctgcaccta tccgagctac ggcgtactcc    300
aaaagtgttt gggatctagg ctggtttgtc tgcaagtcct ctgactggtt tatccacaca    360
tgcatggcag ccaagagcct gacaatcgtt gtggtggcca aagtatgctt catgtatgca    420
agtgacccag ccaagcaagt gagtatccac aactacacca tctggtcagt gctggtggcc    480
atctggactg tggctagcct gttaccccctg ccggaatggt tctttagcac catcaggcat    540
catgaaggtg tggaaatgtg cctcgtggat gtaccagctg tggctgaaga gtttatgtcg    600
atgtttggta agctctaccc actcctggca tttggccttc cattattttt tgccagcttt    660
tatttctgga gagcttatga ccaatgtaaa aaacgaggaa ctaagactca aaatcttaga    720
aaccagatac gctcaaagca agtcacagtg atgctgctga gcattgccat catctctgct    780
ctcttgtggc tccccgaatg ggtagcttgg ctgtgggtat ggcatctgaa ggctgcaggc    840
ccggccccac cacaaggttt catagccctg tctcaagtct tgatgttttc catctcttca    900
gcaaatcctc tcatttttct tgtgatgtcg gaagagttca gggaaggctt gaaaggtgta    960
tggaaatgga tgataaccaa aaaacctcca actgtctcag agtctcagga aacaccagct   1020
ggcaactcag agggtcttcc tgacaaggtt ccatctccag aatccccagc atccatacca   1080
gaaaaagaga aacccagctc tccctcctct ggcaaaggga aaactgagaa ggcagagatt   1140
cccatccttc ctgacgtaga gcagttttgg catgagaggg acacagtccc ttctgtacag   1200
gacaatgacc ctatccccctg ggaacatgaa gatcaagaga caggggaagg tgttaaatag  1260
```

<210> SEQ ID NO 4
<211> LENGTH: 419
<212> TYPE: PRT
<213> ORGANISM: Homo sapiens

<400> SEQUENCE: 4

```
Met Leu Ala Ala Ala Phe Ala Asp Ser Asn Ser Ser Ser Met Asn Val
1               5                   10                  15

Ser Phe Ala His Leu His Phe Ala Gly Gly Tyr Leu Pro Ser Asp Ser
            20                  25                  30

Gln Asp Trp Arg Thr Ile Ile Pro Ala Leu Leu Val Ala Val Cys Leu
        35                  40                  45

Val Gly Phe Val Gly Asn Leu Cys Val Ile Gly Ile Leu Leu His Asn
    50                  55                  60

Ala Trp Lys Gly Lys Pro Ser Met Ile His Ser Leu Ile Leu Asn Leu
65                  70                  75                  80

Ser Leu Ala Asp Leu Ser Leu Leu Leu Phe Ser Ala Pro Ile Arg Ala
                85                  90                  95

Thr Ala Tyr Ser Lys Ser Val Trp Asp Leu Gly Trp Phe Val Cys Lys
            100                 105                 110

Ser Ser Asp Trp Phe Ile His Thr Cys Met Ala Ala Lys Ser Leu Thr
        115                 120                 125

Ile Val Val Val Ala Lys Val Cys Phe Met Tyr Ala Ser Asp Pro Ala
    130                 135                 140

Lys Gln Val Ser Ile His Asn Tyr Thr Ile Trp Ser Val Leu Val Ala
145                 150                 155                 160

Ile Trp Thr Val Ala Ser Leu Leu Pro Leu Pro Glu Trp Phe Phe Ser
                165                 170                 175

Thr Ile Arg His His Glu Gly Val Glu Met Cys Leu Val Asp Val Pro
            180                 185                 190
```

-continued

```
Ala Val Ala Glu Glu Phe Met Ser Met Phe Gly Lys Leu Tyr Pro Leu
        195                 200                 205

Leu Ala Phe Gly Leu Pro Leu Phe Phe Ala Ser Phe Tyr Phe Trp Arg
    210                 215                 220

Ala Tyr Asp Gln Cys Lys Lys Arg Gly Thr Lys Thr Gln Asn Leu Arg
225                 230                 235                 240

Asn Gln Ile Arg Ser Lys Gln Val Thr Val Met Leu Leu Ser Ile Ala
                245                 250                 255

Ile Ile Ser Ala Leu Leu Trp Leu Pro Glu Trp Val Ala Trp Leu Trp
            260                 265                 270

Val Trp His Leu Lys Ala Ala Gly Pro Ala Pro Pro Gln Gly Phe Ile
        275                 280                 285

Ala Leu Ser Gln Val Leu Met Phe Ser Ile Ser Ser Ala Asn Pro Leu
    290                 295                 300

Ile Phe Leu Val Met Ser Glu Glu Phe Arg Glu Gly Leu Lys Gly Val
305                 310                 315                 320

Trp Lys Trp Met Ile Thr Lys Lys Pro Pro Thr Val Ser Glu Ser Gln
                325                 330                 335

Glu Thr Pro Ala Gly Asn Ser Glu Gly Leu Pro Asp Lys Val Pro Ser
            340                 345                 350

Pro Glu Ser Pro Ala Ser Ile Pro Glu Lys Glu Lys Pro Ser Ser Pro
        355                 360                 365

Ser Ser Gly Lys Gly Lys Thr Glu Lys Ala Glu Ile Pro Ile Leu Pro
    370                 375                 380

Asp Val Glu Gln Phe Trp His Glu Arg Asp Thr Val Pro Ser Val Gln
385                 390                 395                 400

Asp Asn Asp Pro Ile Pro Trp Glu His Glu Asp Gln Glu Thr Gly Glu
                405                 410                 415

Gly Val Lys
```

<210> SEQ ID NO 5
<211> LENGTH: 1014
<212> TYPE: DNA
<213> ORGANISM: Homo sapiens

<400> SEQUENCE: 5

```
atggggaacg attctgtcag ctacgagtat ggggattaca gcgacctctc ggaccgccct     60

gtggactgcc tggatggcgc ctgcctggcc atcgacccgc tgcgcgtggc cccgctccca    120

ctgtatgccg ccatcttcct ggtgggggtg ccgggcaatg ccatggtggc ctgggtggct    180

gggaaggtgg cccgccggag ggtgggtgcc acctggttgc tccacctggc cgtggcggat    240

ttgctgtgct gtttgtctct gcccatcctg gcagtgccca ttgcccgtgg aggccactgg    300

ccgtatggtg cagtgggctg tcgggcgctg ccctccatca tcctgctgac catgtatgcc    360

agcgtcctgc tcctggcagc tctcagtgcc gacctctgct tcctggctct cgggcctgcc    420

tggtggtcta cggttcagcg ggcgtgcggg gtgcaggtgg cctgtggggc agcctggaca    480

ctggccttgc tgctcaccgt gccctccgcc atctaccgcc ggctgcacca ggagcacttc    540

ccagcccggc tgcagtgtgt ggtggactac ggcggctcct ccagcaccga gaatgcggtg    600

actgccatcc ggtttctttt tggcttcctg gggcccctgg tggccgtggc cagctgccac    660

agtgccctcc tgtgctgggc agcccgacgc tgccggccgc tgggcacagc cattgtggtg    720

gggtttttg tctgctgggc accctaccac ctgctggggc tggtgctcac tgtggcggcc    780

ccgaactccg cactcctggc cagggccctg cgggctgaac ccctcatcgt gggccttgcc    840
```

-continued

```
ctcgctcaca gctgcctcaa tcccatgctc ttcctgtatt ttgggagggc tcaactccgc    900

cggtcactgc cagctgcctg tcactgggcc ctgagggagt cccagggcca ggacgaaagt    960

gtggacagca agaaatccac cagccatgac ctggtctcgg agatggaggt gtag         1014


<210> SEQ ID NO 6
<211> LENGTH: 337
<212> TYPE: PRT
<213> ORGANISM: Homo sapiens

<400> SEQUENCE: 6

Met Gly Asn Asp Ser Val Ser Tyr Glu Tyr Gly Asp Tyr Ser Asp Leu
1               5                   10                  15

Ser Asp Arg Pro Val Asp Cys Leu Asp Gly Ala Cys Leu Ala Ile Asp
            20                  25                  30

Pro Leu Arg Val Ala Pro Leu Pro Leu Tyr Ala Ala Ile Phe Leu Val
        35                  40                  45

Gly Val Pro Gly Asn Ala Met Val Ala Trp Val Ala Gly Lys Val Ala
    50                  55                  60

Arg Arg Arg Val Gly Ala Thr Trp Leu Leu His Leu Ala Val Ala Asp
65                  70                  75                  80

Leu Leu Cys Cys Leu Ser Leu Pro Ile Leu Ala Val Pro Ile Ala Arg
                85                  90                  95

Gly Gly His Trp Pro Tyr Gly Ala Val Gly Cys Arg Ala Leu Pro Ser
            100                 105                 110

Ile Ile Leu Leu Thr Met Tyr Ala Ser Val Leu Leu Leu Ala Ala Leu
        115                 120                 125

Ser Ala Asp Leu Cys Phe Leu Ala Leu Gly Pro Ala Trp Trp Ser Thr
    130                 135                 140

Val Gln Arg Ala Cys Gly Val Gln Val Ala Cys Gly Ala Ala Trp Thr
145                 150                 155                 160

Leu Ala Leu Leu Leu Thr Val Pro Ser Ala Ile Tyr Arg Arg Leu His
                165                 170                 175

Gln Glu His Phe Pro Ala Arg Leu Gln Cys Val Val Asp Tyr Gly Gly
            180                 185                 190

Ser Ser Ser Thr Glu Asn Ala Val Thr Ala Ile Arg Phe Leu Phe Gly
        195                 200                 205

Phe Leu Gly Pro Leu Val Ala Val Ala Ser Cys His Ser Ala Leu Leu
    210                 215                 220

Cys Trp Ala Ala Arg Arg Cys Arg Pro Leu Gly Thr Ala Ile Val Val
225                 230                 235                 240

Gly Phe Phe Val Cys Trp Ala Pro Tyr His Leu Leu Gly Leu Val Leu
                245                 250                 255

Thr Val Ala Ala Pro Asn Ser Ala Leu Leu Ala Arg Ala Leu Arg Ala
            260                 265                 270

Glu Pro Leu Ile Val Gly Leu Ala Leu Ala His Ser Cys Leu Asn Pro
        275                 280                 285

Met Leu Phe Leu Tyr Phe Gly Arg Ala Gln Leu Arg Arg Ser Leu Pro
    290                 295                 300

Ala Ala Cys His Trp Ala Leu Arg Glu Ser Gln Gly Gln Asp Glu Ser
305                 310                 315                 320

Val Asp Ser Lys Lys Ser Thr Ser His Asp Leu Val Ser Glu Met Glu
                325                 330                 335

Val
```

-continued

<210> SEQ ID NO 7
<211> LENGTH: 1272
<212> TYPE: DNA
<213> ORGANISM: Homo sapiens

<400> SEQUENCE: 7

```
atgttgtgtc accgtggtgg ccagctgata gtgccaatca tcccactttg ccctgagcac     60
tcctgcaggg gtagaagact ccagaacctt ctctcaggcc catggcccaa gcagcccatg    120
gaacttcata acctgagctc tccatctccc tctctctcct cctctgttct ccctccctcc    180
ttctctccct caccctcctc tgctccctct gcctttacca ctgtgggggg gtcctctgga    240
gggccctgcc accccacctc ttcctcgctg gtgtctgcct tcctggcacc aatcctggcc    300
ctggagtttg tcctgggcct ggtggggaac agtttggccc tcttcatctt ctgcatccac    360
acgcggccct ggacctccaa cacggtgttc ctggtcagcc tggtggccgc tgacttcctc    420
ctgatcagca acctgcccct ccgcgtggac tactacctcc tccatgagac ctggcgcttt    480
ggggctgctg cctgcaaagt caacctcttc atgctgtcca ccaaccgcac ggccagcgtt    540
gtcttcctca cagccatcgc actcaaccgc tacctgaagg tggtgcagcc ccaccacgtg    600
ctgagccgtg cttccgtggg ggcagctgcc cgggtggccg ggggactctg ggtgggcatc    660
ctgctcctca acgggcacct gctcctgagc accttctccg gcccctcctg cctcagctac    720
agggtgggca cgaagccctc ggcctcgctc cgctggcacc aggcactgta cctgctggag    780
ttcttcctgc cactggcgct catcctcttt gctattgtga gcattgggct caccatccgg    840
aaccgtggtc tgggcgggca ggcaggcccg cagagggcca tgcgtgtgct ggccatggtg    900
gtggccgtct acaccatctg cttcttgccc agcatcatct ttggcatggc ttccatggtg    960
gctttctggc tgtccgcctg ccgatccctg gacctctgca cacagctctt ccatggctcc   1020
ctggccttca cctacctcaa cagtgtcctg gaccccgtgc tctactgctt ctctagcccc   1080
aacttcctcc accagagccg ggccttgctg ggcctcacgc ggggccggca gggcccagtg   1140
agcgacgaga gctcctacca accctccagg cagtggcgct accgggaggc ctctaggaag   1200
gcggaggcca tagggaagct gaaagtgcag ggcgaggtct ctctggaaaa ggaaggctcc   1260
tcccagggct ga                                                       1272
```

<210> SEQ ID NO 8
<211> LENGTH: 423
<212> TYPE: PRT
<213> ORGANISM: Homo sapiens

<400> SEQUENCE: 8

```
Met Leu Cys His Arg Gly Gly Gln Leu Ile Val Pro Ile Ile Pro Leu
1               5                   10                  15

Cys Pro Glu His Ser Cys Arg Gly Arg Arg Leu Gln Asn Leu Leu Ser
            20                  25                  30

Gly Pro Trp Pro Lys Gln Pro Met Glu Leu His Asn Leu Ser Ser Pro
        35                  40                  45

Ser Pro Ser Leu Ser Ser Ser Val Leu Pro Pro Ser Phe Ser Pro Ser
    50                  55                  60

Pro Ser Ser Ala Pro Ser Ala Phe Thr Thr Val Gly Gly Ser Ser Gly
65                  70                  75                  80

Gly Pro Cys His Pro Thr Ser Ser Ser Leu Val Ser Ala Phe Leu Ala
                85                  90                  95

Pro Ile Leu Ala Leu Glu Phe Val Leu Gly Leu Val Gly Asn Ser Leu
            100                 105                 110
```

-continued

```
Ala Leu Phe Ile Phe Cys Ile His Thr Arg Pro Trp Thr Ser Asn Thr
        115                 120                 125

Val Phe Leu Val Ser Leu Val Ala Ala Asp Phe Leu Leu Ile Ser Asn
    130                 135                 140

Leu Pro Leu Arg Val Asp Tyr Tyr Leu Leu His Glu Thr Trp Arg Phe
145                 150                 155                 160

Gly Ala Ala Ala Cys Lys Val Asn Leu Phe Met Leu Ser Thr Asn Arg
                165                 170                 175

Thr Ala Ser Val Val Phe Leu Thr Ala Ile Ala Leu Asn Arg Tyr Leu
            180                 185                 190

Lys Val Val Gln Pro His His Val Leu Ser Arg Ala Ser Val Gly Ala
        195                 200                 205

Ala Ala Arg Val Ala Gly Gly Leu Trp Val Gly Ile Leu Leu Leu Asn
    210                 215                 220

Gly His Leu Leu Leu Ser Thr Phe Ser Gly Pro Ser Cys Leu Ser Tyr
225                 230                 235                 240

Arg Val Gly Thr Lys Pro Ser Ala Ser Leu Arg Trp His Gln Ala Leu
                245                 250                 255

Tyr Leu Leu Glu Phe Phe Leu Pro Leu Ala Leu Ile Leu Phe Ala Ile
            260                 265                 270

Val Ser Ile Gly Leu Thr Ile Arg Asn Arg Gly Leu Gly Gly Gln Ala
        275                 280                 285

Gly Pro Gln Arg Ala Met Arg Val Leu Ala Met Val Val Ala Val Tyr
    290                 295                 300

Thr Ile Cys Phe Leu Pro Ser Ile Ile Phe Gly Met Ala Ser Met Val
305                 310                 315                 320

Ala Phe Trp Leu Ser Ala Cys Arg Ser Leu Asp Leu Cys Thr Gln Leu
                325                 330                 335

Phe His Gly Ser Leu Ala Phe Thr Tyr Leu Asn Ser Val Leu Asp Pro
            340                 345                 350

Val Leu Tyr Cys Phe Ser Ser Pro Asn Phe Leu His Gln Ser Arg Ala
        355                 360                 365

Leu Leu Gly Leu Thr Arg Gly Arg Gln Gly Pro Val Ser Asp Glu Ser
    370                 375                 380

Ser Tyr Gln Pro Ser Arg Gln Trp Arg Tyr Arg Glu Ala Ser Arg Lys
385                 390                 395                 400

Ala Glu Ala Ile Gly Lys Leu Lys Val Gln Gly Glu Val Ser Leu Glu
                405                 410                 415

Lys Glu Gly Ser Ser Gln Gly
            420
```

<210> SEQ ID NO 9
<211> LENGTH: 966
<212> TYPE: DNA
<213> ORGANISM: Homo sapiens

<400> SEQUENCE: 9

```
atgaaccaga ctttgaatag cagtgggacc gtggagtcag ccctaaacta ttccagaggg     60

agcacagtgc acacggccta cctggtgctg agctccctgg ccatgttcac ctgcctgtgc    120

gggatggcag gcaacagcat ggtgatctgg ctgctgggct ttcgaatgca caggaacccc    180

ttctgcatct atatcctcaa cctggcggca gccgacctcc tcttcctctt cagcatggct    240

tccacgctca gcctggaaac ccagcccctg gtcaatacca ctgacaaggt ccacgagctg    300

atgaagagac tgatgtactt tgcctacaca gtgggcctga gcctgctgac ggccatcagc    360
```

-continued

```
acccagcgct gtctctctgt cctcttccct atctggttca agtgtcaccg gcccaggcac    420

ctgtcagcct gggtgtgtgg cctgctgtgg acactctgtc tcctgatgaa cgggttgacc    480

tcttccttct gcagcaagtt cttgaaattc aatgaagatc ggtgcttcag ggtggacatg    540

gtccaggccg ccctcatcat gggggtctta accccagtga tgactctgtc cagcctgacc    600

ctctttgtct gggtgcggag gagctcccag cagtggcggc ggcagcccac acggctgttc    660

gtggtggtcc tggcctctgt cctggtgttc ctcatctgtt ccctgcctct gagcatctac    720

tggtttgtgc tctactggtt gagcctgccg cccgagatgc aggtcctgtg cttcagcttg    780

tcacgcctct cctcgtccgt aagcagcagc gccaaccccg tcatctactt cctggtgggc    840

agccggagga gccacaggct gcccaccagg tccctgggga ctgtgctcca acaggcgctt    900

cgcgaggagc ccgagctgga aggtggggag acgcccaccg tgggcaccaa tgagatgggg    960

gcttga                                                               966
```

<210> SEQ ID NO 10
<211> LENGTH: 321
<212> TYPE: PRT
<213> ORGANISM: Homo sapiens

<400> SEQUENCE: 10

```
Met Asn Gln Thr Leu Asn Ser Ser Gly Thr Val Glu Ser Ala Leu Asn
1               5                   10                  15

Tyr Ser Arg Gly Ser Thr Val His Thr Ala Tyr Leu Val Leu Ser Ser
            20                  25                  30

Leu Ala Met Phe Thr Cys Leu Cys Gly Met Ala Gly Asn Ser Met Val
        35                  40                  45

Ile Trp Leu Leu Gly Phe Arg Met His Arg Asn Pro Phe Cys Ile Tyr
    50                  55                  60

Ile Leu Asn Leu Ala Ala Ala Asp Leu Leu Phe Leu Phe Ser Met Ala
65                  70                  75                  80

Ser Thr Leu Ser Leu Glu Thr Gln Pro Leu Val Asn Thr Thr Asp Lys
                85                  90                  95

Val His Glu Leu Met Lys Arg Leu Met Tyr Phe Ala Tyr Thr Val Gly
            100                 105                 110

Leu Ser Leu Leu Thr Ala Ile Ser Thr Gln Arg Cys Leu Ser Val Leu
        115                 120                 125

Phe Pro Ile Trp Phe Lys Cys His Arg Pro Arg His Leu Ser Ala Trp
    130                 135                 140

Val Cys Gly Leu Leu Trp Thr Leu Cys Leu Leu Met Asn Gly Leu Thr
145                 150                 155                 160

Ser Ser Phe Cys Ser Lys Phe Leu Lys Phe Asn Glu Asp Arg Cys Phe
                165                 170                 175

Arg Val Asp Met Val Gln Ala Ala Leu Ile Met Gly Val Leu Thr Pro
            180                 185                 190

Val Met Thr Leu Ser Ser Leu Thr Leu Phe Val Trp Val Arg Arg Ser
        195                 200                 205

Ser Gln Gln Trp Arg Arg Gln Pro Thr Arg Leu Phe Val Val Val Leu
    210                 215                 220

Ala Ser Val Leu Val Phe Leu Ile Cys Ser Leu Pro Leu Ser Ile Tyr
225                 230                 235                 240

Trp Phe Val Leu Tyr Trp Leu Ser Leu Pro Pro Glu Met Gln Val Leu
                245                 250                 255
```

-continued

```
Cys Phe Ser Leu Ser Arg Leu Ser Ser Ser Val Ser Ser Ser Ala Asn
            260                 265                 270

Pro Val Ile Tyr Phe Leu Val Gly Ser Arg Arg Ser His Arg Leu Pro
        275                 280                 285

Thr Arg Ser Leu Gly Thr Val Leu Gln Gln Ala Leu Arg Glu Glu Pro
    290                 295                 300

Glu Leu Glu Gly Gly Glu Thr Pro Thr Val Gly Thr Asn Glu Met Gly
305                 310                 315                 320

Ala


<210> SEQ ID NO 11
<211> LENGTH: 1356
<212> TYPE: DNA
<213> ORGANISM: Homo sapiens

<400> SEQUENCE: 11

atggagtcct cacccatccc ccagtcatca gggaactctt ccactttggg gagggtccct     60

caaaccccag gtccctctac tgccagtggg gtcccggagg tggggctacg ggatgttgct    120

tcggaatctg tggccctctt cttcatgctc ctgctggact tgactgctgt ggctggcaat    180

gccgctgtga tggccgtgat cgccaagacg cctgccctcc gaaaatttgt cttcgtcttc    240

cacctctgcc tggtggacct gctggctgcc ctgaccctca tgcccctggc catgctctcc    300

agctctgccc tctttgacca cgccctcttt ggggaggtgg cctgccgcct ctacttgttt    360

ctgagcgtgt gctttgtcag cctggccatc ctctcggtgt cagccatcaa tgtggagcgc    420

tactattacg tagtccaccc catgcgctac gaggtgcgca tgacgctggg gctggtggcc    480

tctgtgctgg tgggtgtgtg ggtgaaggcc ttggccatgg cttctgtgcc agtgttggga    540

agggtctcct gggaggaagg agctcccagt gtcccccag gctgttcact ccagtggagc     600

cacagtgcct actgccagct tttgtggtg gtctttgctg tcctttactt tctgttgccc     660

ctgctcctca tacttgtggt ctactgcagc atgttccgag tggcccgcgt ggctgccatg    720

cagcacgggc cgctgcccac gtggatggag acaccccggc aacgctccga atctctcagc    780

agccgctcca cgatggtcac cagctcgggg gccccccaga ccaccccaca ccggacgttt    840

gggggaggga aagcagcagt ggttctcctg gctgtggggg gacagttcct gctctgttgg    900

ttgccctact tctctttcca cctctatgtt gccctgagtg ctcagcccat ttcaactggg    960

caggtggaga gtgtggtcac ctggattggc tacttttgct tcacttccaa ccctttcttc   1020

tatggatgtc tcaaccggca gatccggggg gagctcagca agcagtttgt ctgcttcttc   1080

aagccagctc cagaggagga gctgaggctg cctagccggg agggctccat tgaggagaac   1140

ttcctgcagt tccttcaggg gactggctgt ccttctgagt cctgggtttc ccgaccccta   1200

cccagcccca agcaggagcc acctgctgtt gactttcgaa tcccaggcca gatagctgag   1260

gagacctctg agttcctgga gcagcaactc accagcgaca tcatcatgtc agacagctac   1320

ctccgtcctg ccgcctcacc ccggctggag tcatga                              1356


<210> SEQ ID NO 12
<211> LENGTH: 451
<212> TYPE: PRT
<213> ORGANISM: Homo sapiens

<400> SEQUENCE: 12

Met Glu Ser Ser Pro Ile Pro Gln Ser Ser Gly Asn Ser Ser Thr Leu
1               5                   10                  15
```

-continued

```
Gly Arg Val Pro Gln Thr Pro Gly Pro Ser Thr Ala Ser Gly Val Pro
            20                  25                  30

Glu Val Gly Leu Arg Asp Val Ala Ser Glu Ser Val Ala Leu Phe Phe
        35                  40                  45

Met Leu Leu Leu Asp Leu Thr Ala Val Ala Gly Asn Ala Ala Val Met
    50                  55                  60

Ala Val Ile Ala Lys Thr Pro Ala Leu Arg Lys Phe Val Phe Val Phe
65                  70                  75                  80

His Leu Cys Leu Val Asp Leu Leu Ala Ala Leu Thr Leu Met Pro Leu
                85                  90                  95

Ala Met Leu Ser Ser Ser Ala Leu Phe Asp His Ala Leu Phe Gly Glu
            100                 105                 110

Val Ala Cys Arg Leu Tyr Leu Phe Leu Ser Val Cys Phe Val Ser Leu
        115                 120                 125

Ala Ile Leu Ser Val Ser Ala Ile Asn Val Glu Arg Tyr Tyr Tyr Val
    130                 135                 140

Val His Pro Met Arg Tyr Glu Val Arg Met Thr Leu Gly Leu Val Ala
145                 150                 155                 160

Ser Val Leu Val Gly Val Trp Val Lys Ala Leu Ala Met Ala Ser Val
                165                 170                 175

Pro Val Leu Gly Arg Val Ser Trp Glu Glu Gly Ala Pro Ser Val Pro
            180                 185                 190

Pro Gly Cys Ser Leu Gln Trp Ser His Ser Ala Tyr Cys Gln Leu Phe
        195                 200                 205

Val Val Val Phe Ala Val Leu Tyr Phe Leu Leu Pro Leu Leu Leu Ile
    210                 215                 220

Leu Val Val Tyr Cys Ser Met Phe Arg Val Ala Arg Val Ala Ala Met
225                 230                 235                 240

Gln His Gly Pro Leu Pro Thr Trp Met Glu Thr Pro Arg Gln Arg Ser
                245                 250                 255

Glu Ser Leu Ser Ser Arg Ser Thr Met Val Thr Ser Ser Gly Ala Pro
            260                 265                 270

Gln Thr Thr Pro His Arg Thr Phe Gly Gly Gly Lys Ala Ala Val Val
        275                 280                 285

Leu Leu Ala Val Gly Gly Gln Phe Leu Leu Cys Trp Leu Pro Tyr Phe
    290                 295                 300

Ser Phe His Leu Tyr Val Ala Leu Ser Ala Gln Pro Ile Ser Thr Gly
305                 310                 315                 320

Gln Val Glu Ser Val Val Thr Trp Ile Gly Tyr Phe Cys Phe Thr Ser
                325                 330                 335

Asn Pro Phe Phe Tyr Gly Cys Leu Asn Arg Gln Ile Arg Gly Glu Leu
            340                 345                 350

Ser Lys Gln Phe Val Cys Phe Phe Lys Pro Ala Pro Glu Glu Glu Leu
        355                 360                 365

Arg Leu Pro Ser Arg Glu Gly Ser Ile Glu Glu Asn Phe Leu Gln Phe
    370                 375                 380

Leu Gln Gly Thr Gly Cys Pro Ser Glu Ser Trp Val Ser Arg Pro Leu
385                 390                 395                 400

Pro Ser Pro Lys Gln Glu Pro Pro Ala Val Asp Phe Arg Ile Pro Gly
                405                 410                 415

Gln Ile Ala Glu Glu Thr Ser Glu Phe Leu Glu Gln Gln Leu Thr Ser
            420                 425                 430
```

-continued

```
Asp Ile Ile Met Ser Asp Ser Tyr Leu Arg Pro Ala Ala Ser Pro Arg
        435                 440                 445

Leu Glu Ser
    450


<210> SEQ ID NO 13
<211> LENGTH: 1041
<212> TYPE: DNA
<213> ORGANISM: Homo sapiens

<400> SEQUENCE: 13

atggagagaa aatttatgtc cttgcaacca tccatctccg tatcagaaat ggaaccaaat      60

ggcaccttca gcaataacaa cagcaggaac tgcacaattg aaaacttcaa gagagaattt     120

ttcccaattg tatatctgat aatatttttc tggggagtct tgggaaatgg gttgtccata     180

tatgttttcc tgcagcctta taagaagtcc acatctgtga acgttttcat gctaaatctg     240

gccatttcag atctcctgtt cataagcacg cttcccttca gggctgacta ttatcttaga     300

ggctccaatt ggatatttgg agacctggcc tgcaggatta tgtcttattc cttgtatgtc     360

aacatgtaca gcagtattta tttcctgacc gtgctgagtg ttgtgcgttt cctggcaatg     420

gttcacccct ttcggcttct gcatgtcacc agcatcagga gtgcctggat cctctgtggg     480

atcatatgga tccttatcat ggcttcctca ataatgctcc tggacagtgg ctctgagcag     540

aacggcagtg tcacatcatg cttagagctg aatctctata aaattgctaa gctgcagacc     600

atgaactata ttgccttggt ggtgggctgc ctgctgccat tttcacact cagcatctgt      660

tatctgctga tcattcgggt tctgttaaaa gtggaggtcc cagaatcggg gctgcgggtt     720

tctcacagga aggcactgac caccatcatc atcaccttga tcatcttctt cttgtgtttc     780

ctgccctatc acacactgag gaccgtccac ttgacgacat ggaaagtggg tttatgcaaa     840

gacagactgc ataaagcttt ggttatcaca ctggccttgg cagcagccaa tgcctgcttc     900

aatcctctgc tctattactt tgctggggag aattttaagg acagactaaa gtctgcactc     960

agaaaaggcc atccacagaa ggcaaagaca aagtgtgttt tccctgttag tgtgtggttg    1020

agaaaggaaa caagagtata a                                              1041


<210> SEQ ID NO 14
<211> LENGTH: 346
<212> TYPE: PRT
<213> ORGANISM: Homo sapiens

<400> SEQUENCE: 14

Met Glu Arg Lys Phe Met Ser Leu Gln Pro Ser Ile Ser Val Ser Glu
1               5                   10                  15

Met Glu Pro Asn Gly Thr Phe Ser Asn Asn Asn Ser Arg Asn Cys Thr
            20                  25                  30

Ile Glu Asn Phe Lys Arg Glu Phe Phe Pro Ile Val Tyr Leu Ile Ile
        35                  40                  45

Phe Phe Trp Gly Val Leu Gly Asn Gly Leu Ser Ile Tyr Val Phe Leu
    50                  55                  60

Gln Pro Tyr Lys Lys Ser Thr Ser Val Asn Val Phe Met Leu Asn Leu
65                  70                  75                  80

Ala Ile Ser Asp Leu Leu Phe Ile Ser Thr Leu Pro Phe Arg Ala Asp
                85                  90                  95

Tyr Tyr Leu Arg Gly Ser Asn Trp Ile Phe Gly Asp Leu Ala Cys Arg
            100                 105                 110
```

-continued

```
Ile Met Ser Tyr Ser Leu Tyr Val Asn Met Tyr Ser Ser Ile Tyr Phe
        115                 120                 125

Leu Thr Val Leu Ser Val Val Arg Phe Leu Ala Met Val His Pro Phe
    130                 135                 140

Arg Leu Leu His Val Thr Ser Ile Arg Ser Ala Trp Ile Leu Cys Gly
145                 150                 155                 160

Ile Ile Trp Ile Leu Ile Met Ala Ser Ser Ile Met Leu Leu Asp Ser
                165                 170                 175

Gly Ser Glu Gln Asn Gly Ser Val Thr Ser Cys Leu Glu Leu Asn Leu
            180                 185                 190

Tyr Lys Ile Ala Lys Leu Gln Thr Met Asn Tyr Ile Ala Leu Val Val
        195                 200                 205

Gly Cys Leu Leu Pro Phe Phe Thr Leu Ser Ile Cys Tyr Leu Leu Ile
    210                 215                 220

Ile Arg Val Leu Leu Lys Val Glu Val Pro Glu Ser Gly Leu Arg Val
225                 230                 235                 240

Ser His Arg Lys Ala Leu Thr Thr Ile Ile Ile Thr Leu Ile Ile Phe
                245                 250                 255

Phe Leu Cys Phe Leu Pro Tyr His Thr Leu Arg Thr Val His Leu Thr
            260                 265                 270

Thr Trp Lys Val Gly Leu Cys Lys Asp Arg Leu His Lys Ala Leu Val
        275                 280                 285

Ile Thr Leu Ala Leu Ala Ala Ala Asn Ala Cys Phe Asn Pro Leu Leu
    290                 295                 300

Tyr Tyr Phe Ala Gly Glu Asn Phe Lys Asp Arg Leu Lys Ser Ala Leu
305                 310                 315                 320

Arg Lys Gly His Pro Gln Lys Ala Lys Thr Lys Cys Val Phe Pro Val
                325                 330                 335

Ser Val Trp Leu Arg Lys Glu Thr Arg Val
            340                 345
```

<210> SEQ ID NO 15
<211> LENGTH: 1527
<212> TYPE: DNA
<213> ORGANISM: Homo sapiens

<400> SEQUENCE: 15

```
atgacgtcca cctgcaccaa cagcacgcgc gagagtaaca gcagccacac gtgcatgccc      60

ctctccaaaa tgcccatcag cctggcccac ggcatcatcc gctcaaccgt gctggttatc     120

ttcctcgccg cctctttcgt cggcaacata gtgctggcgc tagtgttgca gcgcaagccg     180

cagctgctgc aggtgaccaa ccgttttatc tttaacctcc tcgtcaccga cctgctgcag     240

atttcgctcg tggccccctg ggtggtggcc acctctgtgc ctctcttctg gcccctcaac     300

agccacttct gcacggccct ggttagcctc acccacctgt tcgccttcgc cagcgtcaac     360

accattgtcg tggtgtcagt ggatcgctac ttgtccatca tccaccctct ctcctacccg     420

tccaagatga cccagcgccg cggttacctg ctcctctatg gcacctggat tgtggccatc     480

ctgcagagca ctcctccact ctacggctgg ggccaggctg cctttgatga gcgcaatgct     540

ctctgctcca tgatctgggg ggccagcccc agctacacta ttctcagcgt ggtgtccttc     600

atcgtcattc cactgattgt catgattgcc tgctactccg tggtgttctg tgcagcccgg     660

aggcagcatg ctctgctgta caatgtcaag agacacagct tggaagtgcg agtcaaggac     720

tgtgtggaga atgaggatga agagggagca gagaagaagg aggagttcca ggatgagagt     780
```

-continued

```
gagtttcgcc gccagcatga aggtgaggtc aaggccaagg agggcagaat ggaagccaag    840

gacggcagcc tgaaggccaa ggaaggaagc acggggacca gtgagagtag tgtagaggcc    900

aggggcagcg aggaggtcag agagagcagc acggtggcca gcgacggcag catggagggt    960

aaggaaggca gcaccaaagt tgaggagaac agcatgaagg cagacaaggg tcgcacagag   1020

gtcaaccagt gcagcattga cttgggtgaa gatgacatgg agtttggtga agacgacatc   1080

aatttcagtg aggatgacgt cgaggcagtg aacatcccgg agagcctccc acccagtcgt   1140

cgtaacagca acagcaaccc tcctctgccc aggtgctacc agtgcaaagc tgctaaagtg   1200

atcttcatca tcattttctc ctatgtgcta tccctggggc cctactgctt tttagcagtc   1260

ctggccgtgt gggtggatgt cgaaacccag gtaccccagt gggtgatcac cataatcatc   1320

tggcttttct tcctgcagtg ctgcatccac ccctatgtct atggctacat gcacaagacc   1380

attaagaagg aaatccagga catgctgaag aagttcttct gcaaggaaaa gcccccgaaa   1440

gaagatagcc acccagacct gcccggaaca gagggtggga ctgaaggcaa gattgtccct   1500

tcctacgatt ctgctacttt tccttga                                       1527
```

```
<210> SEQ ID NO 16
<211> LENGTH: 508
<212> TYPE: PRT
<213> ORGANISM: Homo sapiens

<400> SEQUENCE: 16

Met Thr Ser Thr Cys Thr Asn Ser Thr Arg Glu Ser Asn Ser Ser His
1               5                   10                  15

Thr Cys Met Pro Leu Ser Lys Met Pro Ile Ser Leu Ala His Gly Ile
            20                  25                  30

Ile Arg Ser Thr Val Leu Val Ile Phe Leu Ala Ala Ser Phe Val Gly
        35                  40                  45

Asn Ile Val Leu Ala Leu Val Leu Gln Arg Lys Pro Gln Leu Leu Gln
    50                  55                  60

Val Thr Asn Arg Phe Ile Phe Asn Leu Leu Val Thr Asp Leu Leu Gln
65                  70                  75                  80

Ile Ser Leu Val Ala Pro Trp Val Val Ala Thr Ser Val Pro Leu Phe
                85                  90                  95

Trp Pro Leu Asn Ser His Phe Cys Thr Ala Leu Val Ser Leu Thr His
            100                 105                 110

Leu Phe Ala Phe Ala Ser Val Asn Thr Ile Val Val Val Ser Val Asp
        115                 120                 125

Arg Tyr Leu Ser Ile Ile His Pro Leu Ser Tyr Pro Ser Lys Met Thr
    130                 135                 140

Gln Arg Arg Gly Tyr Leu Leu Leu Tyr Gly Thr Trp Ile Val Ala Ile
145                 150                 155                 160

Leu Gln Ser Thr Pro Pro Leu Tyr Gly Trp Gly Gln Ala Ala Phe Asp
                165                 170                 175

Glu Arg Asn Ala Leu Cys Ser Met Ile Trp Gly Ala Ser Pro Ser Tyr
            180                 185                 190

Thr Ile Leu Ser Val Val Ser Phe Ile Val Ile Pro Leu Ile Val Met
        195                 200                 205

Ile Ala Cys Tyr Ser Val Val Phe Cys Ala Ala Arg Arg Gln His Ala
    210                 215                 220

Leu Leu Tyr Asn Val Lys Arg His Ser Leu Glu Val Arg Val Lys Asp
225                 230                 235                 240
```

-continued

```
Cys Val Glu Asn Glu Asp Glu Glu Gly Ala Glu Lys Lys Glu Glu Phe
                245                 250                 255

Gln Asp Glu Ser Glu Phe Arg Arg Gln His Glu Gly Glu Val Lys Ala
            260                 265                 270

Lys Glu Gly Arg Met Glu Ala Lys Asp Gly Ser Leu Lys Ala Lys Glu
        275                 280                 285

Gly Ser Thr Gly Thr Ser Glu Ser Ser Val Glu Ala Arg Gly Ser Glu
    290                 295                 300

Glu Val Arg Glu Ser Ser Thr Val Ala Ser Asp Gly Ser Met Glu Gly
305                 310                 315                 320

Lys Glu Gly Ser Thr Lys Val Glu Glu Asn Ser Met Lys Ala Asp Lys
                325                 330                 335

Gly Arg Thr Glu Val Asn Gln Cys Ser Ile Asp Leu Gly Glu Asp Asp
            340                 345                 350

Met Glu Phe Gly Glu Asp Asp Ile Asn Phe Ser Glu Asp Asp Val Glu
        355                 360                 365

Ala Val Asn Ile Pro Glu Ser Leu Pro Pro Ser Arg Arg Asn Ser Asn
    370                 375                 380

Ser Asn Pro Pro Leu Pro Arg Cys Tyr Gln Cys Lys Ala Ala Lys Val
385                 390                 395                 400

Ile Phe Ile Ile Ile Phe Ser Tyr Val Leu Ser Leu Gly Pro Tyr Cys
                405                 410                 415

Phe Leu Ala Val Leu Ala Val Trp Val Asp Val Glu Thr Gln Val Pro
            420                 425                 430

Gln Trp Val Ile Thr Ile Ile Ile Trp Leu Phe Phe Leu Gln Cys Cys
        435                 440                 445

Ile His Pro Tyr Val Tyr Gly Tyr Met His Lys Thr Ile Lys Lys Glu
    450                 455                 460

Ile Gln Asp Met Leu Lys Lys Phe Phe Cys Lys Glu Lys Pro Pro Lys
465                 470                 475                 480

Glu Asp Ser His Pro Asp Leu Pro Gly Thr Glu Gly Gly Thr Glu Gly
                485                 490                 495

Lys Ile Val Pro Ser Tyr Asp Ser Ala Thr Phe Pro
            500                 505


<210> SEQ ID NO 17
<211> LENGTH: 1068
<212> TYPE: DNA
<213> ORGANISM: Homo sapiens

<400> SEQUENCE: 17

atgcccttga cggacggcat ttcttcattt gaggacctct tggctaacaa tatcctcaga     60

atatttgtct gggttatagc tttcattacc tgctttggaa atctttttgt cattggcatg    120

agatctttca ttaaagctga aaatacaact cacgctatgt ccatcaaaat cctttgttgc    180

gctgattgcc tgatgggtgt ttacttgttc tttgttggca ttttcgatat aaaataccga    240

gggcagtatc agaagtatgc cttgctgtgg atggagagcg tgcagtgccg cctcatgggg    300

ttcctggcca tgctgtccac cgaagtctct gttctgctac tgacctactt gactttggag    360

aagttcctgg tcattgtctt ccccttcagt aacattcgac ctggaaaacg gcagacctca    420

gtcatcctca tttgcatctg gatggcggga tttttaatag ctgtaattcc attttggaat    480

aaggattatt ttggaaactt ttatgggaaa aatggagtat gtttcccact ttattatgac    540

caaacagaag atattggaag caaagggtat tctcttggaa ttttcctagg tgtgaacttg    600
```

-continued

```
ctggcttttc tcatcattgt gttttcctat attactatgt tctgttccat tcaaaaaacc    660

gccttgcaga ccacagaagt aaggaattgt tttggaagag aggtggctgt tgcaaatcgt    720

ttcttttta tagtgttctc tgatgccatc tgctggattc ctgtatttgt agttaaaatc    780

ctttccctct tccgggtgga aataccagac acaatgactt cctggatagt gattttttc    840

cttccagtta acagtgcttt gaatccaatc ctctatactc tcacaaccaa cttttttaag    900

gacaagttga aacagctgct gcacaaacat cagaggaaat caattttcaa aattaaaaaa    960

aaaagtttat ctacatccat tgtgtggata gaggactcct cttccctgaa acttggggtt   1020

ttgaacaaaa taacacttgg agacagtata atgaaaccag tttcctag                1068
```

```
<210> SEQ ID NO 18
<211> LENGTH: 355
<212> TYPE: PRT
<213> ORGANISM: Homo sapiens

<400> SEQUENCE: 18

Met Pro Leu Thr Asp Gly Ile Ser Ser Phe Glu Asp Leu Leu Ala Asn
1               5                   10                  15

Asn Ile Leu Arg Ile Phe Val Trp Val Ile Ala Phe Ile Thr Cys Phe
            20                  25                  30

Gly Asn Leu Phe Val Ile Gly Met Arg Ser Phe Ile Lys Ala Glu Asn
        35                  40                  45

Thr Thr His Ala Met Ser Ile Lys Ile Leu Cys Cys Ala Asp Cys Leu
    50                  55                  60

Met Gly Val Tyr Leu Phe Phe Val Gly Ile Phe Asp Ile Lys Tyr Arg
65                  70                  75                  80

Gly Gln Tyr Gln Lys Tyr Ala Leu Leu Trp Met Glu Ser Val Gln Cys
                85                  90                  95

Arg Leu Met Gly Phe Leu Ala Met Leu Ser Thr Glu Val Ser Val Leu
            100                 105                 110

Leu Leu Thr Tyr Leu Thr Leu Glu Lys Phe Leu Val Ile Val Phe Pro
        115                 120                 125

Phe Ser Asn Ile Arg Pro Gly Lys Arg Gln Thr Ser Val Ile Leu Ile
    130                 135                 140

Cys Ile Trp Met Ala Gly Phe Leu Ile Ala Val Ile Pro Phe Trp Asn
145                 150                 155                 160

Lys Asp Tyr Phe Gly Asn Phe Tyr Gly Lys Asn Gly Val Cys Phe Pro
                165                 170                 175

Leu Tyr Tyr Asp Gln Thr Glu Asp Ile Gly Ser Lys Gly Tyr Ser Leu
            180                 185                 190

Gly Ile Phe Leu Gly Val Asn Leu Leu Ala Phe Leu Ile Ile Val Phe
        195                 200                 205

Ser Tyr Ile Thr Met Phe Cys Ser Ile Gln Lys Thr Ala Leu Gln Thr
    210                 215                 220

Thr Glu Val Arg Asn Cys Phe Gly Arg Glu Val Ala Val Ala Asn Arg
225                 230                 235                 240

Phe Phe Phe Ile Val Phe Ser Asp Ala Ile Cys Trp Ile Pro Val Phe
                245                 250                 255

Val Val Lys Ile Leu Ser Leu Phe Arg Val Glu Ile Pro Asp Thr Met
            260                 265                 270

Thr Ser Trp Ile Val Ile Phe Phe Leu Pro Val Asn Ser Ala Leu Asn
        275                 280                 285
```

-continued

```
Pro Ile Leu Tyr Thr Leu Thr Thr Asn Phe Phe Lys Asp Lys Leu Lys
    290                 295                 300

Gln Leu Leu His Lys His Gln Arg Lys Ser Ile Phe Lys Ile Lys Lys
305                 310                 315                 320

Lys Ser Leu Ser Thr Ser Ile Val Trp Ile Glu Asp Ser Ser Ser Leu
                325                 330                 335

Lys Leu Gly Val Leu Asn Lys Ile Thr Leu Gly Asp Ser Ile Met Lys
            340                 345                 350

Pro Val Ser
        355


<210> SEQ ID NO 19
<211> LENGTH: 969
<212> TYPE: DNA
<213> ORGANISM: Homo sapiens

<400> SEQUENCE: 19

atggatccaa ccatctcaac cttggacaca gaactgacac caatcaacgg aactgaggag      60

actctttgct acaagcagac cttgagcctc acggtgctga cgtgcatcgt ttcccttgtc     120

gggctgacag gaaacgcagt tgtgctctgg ctcctgggct gccgcatgcg caggaacgcc     180

ttctccatct acatcctcaa cttggccgca gcagacttcc tcttcctcag cggccgcctt     240

atatattccc tgttaagctt catcagtatc ccccatacca tctctaaaat cctctatcct     300

gtgatgatgt tttcctactt tgcaggcctg agctttctga gtgccgtgag caccgagcgc     360

tgcctgtccg tcctgtggcc catctggtac cgctgccacc gccccacaca cctgtcagcg     420

gtggtgtgtg tcctgctctg ggccctgtcc ctgctgcgga gcatcctgga gtggatgtta     480

tgtggcttcc tgttcagtgg tgctgattct gcttggtgtc aaacatcaga tttcatcaca     540

gtcgcgtggc tgattttttt atgtgtggtt ctctgtgggt ccagcctggt cctgctgatc     600

aggattctct gtggatcccg gaagataccg ctgaccaggc tgtacgtgac catcctgctc     660

acagtactgg tcttcctcct ctgtggcctg ccctttggca ttcagttttt cctatttta     720

tggatccacg tggacaggga agtcttattt tgtcatgttc atctagtttc tattttcctg     780

tccgctctta acagcagtgc caaccccatc atttacttct tcgtgggctc ctttaggcag     840

cgtcaaaata ggcagaacct gaagctggtt ctccagaggg ctctgcagga cgcgtctgag     900

gtggatgaag gtggagggca gcttcctgag gaaatcctgg agctgtcggg aagcagattg     960

gagcagtga                                                             969


<210> SEQ ID NO 20
<211> LENGTH: 322
<212> TYPE: PRT
<213> ORGANISM: Homo sapiens

<400> SEQUENCE: 20

Met Asp Pro Thr Ile Ser Thr Leu Asp Thr Glu Leu Thr Pro Ile Asn
1               5                   10                  15

Gly Thr Glu Glu Thr Leu Cys Tyr Lys Gln Thr Leu Ser Leu Thr Val
            20                  25                  30

Leu Thr Cys Ile Val Ser Leu Val Gly Leu Thr Gly Asn Ala Val Val
        35                  40                  45

Leu Trp Leu Leu Gly Cys Arg Met Arg Arg Asn Ala Phe Ser Ile Tyr
    50                  55                  60

Ile Leu Asn Leu Ala Ala Ala Asp Phe Leu Phe Leu Ser Gly Arg Leu
65                  70                  75                  80
```

-continued

```
Ile Tyr Ser Leu Leu Ser Phe Ile Ser Ile Pro His Thr Ile Ser Lys
                85                  90                  95

Ile Leu Tyr Pro Val Met Met Phe Ser Tyr Phe Ala Gly Leu Ser Phe
            100                 105                 110

Leu Ser Ala Val Ser Thr Glu Arg Cys Leu Ser Val Leu Trp Pro Ile
        115                 120                 125

Trp Tyr Arg Cys His Arg Pro Thr His Leu Ser Ala Val Val Cys Val
    130                 135                 140

Leu Leu Trp Ala Leu Ser Leu Leu Arg Ser Ile Leu Glu Trp Met Leu
145                 150                 155                 160

Cys Gly Phe Leu Phe Ser Gly Ala Asp Ser Ala Trp Cys Gln Thr Ser
                165                 170                 175

Asp Phe Ile Thr Val Ala Trp Leu Ile Phe Leu Cys Val Val Leu Cys
            180                 185                 190

Gly Ser Ser Leu Val Leu Leu Ile Arg Ile Leu Cys Gly Ser Arg Lys
        195                 200                 205

Ile Pro Leu Thr Arg Leu Tyr Val Thr Ile Leu Leu Thr Val Leu Val
    210                 215                 220

Phe Leu Leu Cys Gly Leu Pro Phe Gly Ile Gln Phe Phe Leu Phe Leu
225                 230                 235                 240

Trp Ile His Val Asp Arg Glu Val Leu Phe Cys His Val His Leu Val
                245                 250                 255

Ser Ile Phe Leu Ser Ala Leu Asn Ser Ser Ala Asn Pro Ile Ile Tyr
            260                 265                 270

Phe Phe Val Gly Ser Phe Arg Gln Arg Gln Asn Arg Gln Asn Leu Lys
        275                 280                 285

Leu Val Leu Gln Arg Ala Leu Gln Asp Ala Ser Glu Val Asp Glu Gly
    290                 295                 300

Gly Gly Gln Leu Pro Glu Glu Ile Leu Glu Leu Ser Gly Ser Arg Leu
305                 310                 315                 320

Glu Gln
```

<210> SEQ ID NO 21
<211> LENGTH: 1305
<212> TYPE: DNA
<213> ORGANISM: Homo sapiens

<400> SEQUENCE: 21

```
atggaggatc tctttagccc ctcaattctg ccgccggcgc ccaacatttc cgtgcccatc     60

ttgctgggct ggggtctcaa cctgaccttg gggcaaggag cccctgcctc tgggccgccc    120

agccgccgcg tccgcctggt gttcctgggg gtcatcctgg tggtggcggt ggcaggcaac    180

accacagtgc tgtgccgcct gtgcggcggc ggcgggccct gggcgggccc caagcgtcgc    240

aagatggact tcctgctggt gcagctggcc ctggcggacc tgtacgcgtg cgggggcacg    300

gcgctgtcac agctggcctg ggaactgctg ggcgagcccc gcgcggccac gggggacctg    360

gcgtgccgct tcctgcagct gctgcaggca tccgggcggg gcgcctcggc ccacctcgtg    420

gtgctcatcg ccctcgagcg ccggcgcgcg gtgcgtcttc cgcacggccg gccgctgccc    480

gcgcgtgccc tcgccgccct gggctggctg ctggcactgc tgctggcgct gcccccggcc    540

ttcgtggtgc gcggggactc cccctcgccg ctgccgccgc cgccgccgcc aacgtccctg    600

cagccaggcg cgcccccggc cgcccgcgcc tggccggggg agcgtcgctg ccacgggatc    660

ttcgcgcccc tgccgcgctg gcacctgcag gtctacgcgt tctacgaggc cgtcgcgggc    720
```

-continued

```
ttcgtcgcgc ctgttacggt cctgggcgtc gcttgcggcc acctactctc cgtctggtgg    780

cggcaccggc cgcaggcccc cgcggctgca gcgccctggt cggcgagccc aggtcgagcc    840

cctgcgccca gcgcgctgcc ccgcgccaag gtgcagagcc tgaagatgag cctgctgctg    900

gcgctgctgt tcgtgggctg cgagctgccc tactttgccg cccggctggc ggccgcgtgg    960

tcgtccgggc ccgcgggaga ctgggaggga gagggcctgt cggcggcgct gcgcgtggtg   1020

gcgatggcca acagcgctct caatcccttc gtctacctct tcttccaggc gggcgactgc   1080

cggctccggc gacagctgcg gaagcggctg ggctctctgt gctgcgcgcc gcagggaggc   1140

gcggaggacg aggaggggcc ccggggccac caggcgctct accgccaacg ctggccccac   1200

cctcattatc accatgctcg gcgggaaccg ctggacgagg gcggcttgcg cccaccccct   1260

ccgcgcccca gacccctgcc ttgctcctgc gaaagtgcct tctag                   1305


<210> SEQ ID NO 22
<211> LENGTH: 434
<212> TYPE: PRT
<213> ORGANISM: Homo sapiens

<400> SEQUENCE: 22

Met Glu Asp Leu Phe Ser Pro Ser Ile Leu Pro Pro Ala Pro Asn Ile
1               5                   10                  15

Ser Val Pro Ile Leu Leu Gly Trp Gly Leu Asn Leu Thr Leu Gly Gln
            20                  25                  30

Gly Ala Pro Ala Ser Gly Pro Pro Ser Arg Arg Val Arg Leu Val Phe
        35                  40                  45

Leu Gly Val Ile Leu Val Val Ala Val Ala Gly Asn Thr Thr Val Leu
    50                  55                  60

Cys Arg Leu Cys Gly Gly Gly Gly Pro Trp Ala Gly Pro Lys Arg Arg
65                  70                  75                  80

Lys Met Asp Phe Leu Leu Val Gln Leu Ala Leu Ala Asp Leu Tyr Ala
                85                  90                  95

Cys Gly Gly Thr Ala Leu Ser Gln Leu Ala Trp Glu Leu Leu Gly Glu
            100                 105                 110

Pro Arg Ala Ala Thr Gly Asp Leu Ala Cys Arg Phe Leu Gln Leu Leu
        115                 120                 125

Gln Ala Ser Gly Arg Gly Ala Ser Ala His Leu Val Val Leu Ile Ala
    130                 135                 140

Leu Glu Arg Arg Arg Ala Val Arg Leu Pro His Gly Arg Pro Leu Pro
145                 150                 155                 160

Ala Arg Ala Leu Ala Ala Leu Gly Trp Leu Leu Ala Leu Leu Leu Ala
                165                 170                 175

Leu Pro Pro Ala Phe Val Val Arg Gly Asp Ser Pro Ser Pro Leu Pro
            180                 185                 190

Pro Pro Pro Pro Pro Thr Ser Leu Gln Pro Gly Ala Pro Pro Ala Ala
        195                 200                 205

Arg Ala Trp Pro Gly Glu Arg Arg Cys His Gly Ile Phe Ala Pro Leu
    210                 215                 220

Pro Arg Trp His Leu Gln Val Tyr Ala Phe Tyr Glu Ala Val Ala Gly
225                 230                 235                 240

Phe Val Ala Pro Val Thr Val Leu Gly Val Ala Cys Gly His Leu Leu
                245                 250                 255

Ser Val Trp Trp Arg His Arg Pro Gln Ala Pro Ala Ala Ala Ala Pro
            260                 265                 270
```

-continued

```
Trp Ser Ala Ser Pro Gly Arg Ala Pro Ala Pro Ser Ala Leu Pro Arg
        275                 280                 285

Ala Lys Val Gln Ser Leu Lys Met Ser Leu Leu Leu Ala Leu Leu Phe
    290                 295                 300

Val Gly Cys Glu Leu Pro Tyr Phe Ala Ala Arg Leu Ala Ala Ala Trp
305                 310                 315                 320

Ser Ser Gly Pro Ala Gly Asp Trp Glu Gly Glu Gly Leu Ser Ala Ala
                325                 330                 335

Leu Arg Val Val Ala Met Ala Asn Ser Ala Leu Asn Pro Phe Val Tyr
            340                 345                 350

Leu Phe Phe Gln Ala Gly Asp Cys Arg Leu Arg Arg Gln Leu Arg Lys
        355                 360                 365

Arg Leu Gly Ser Leu Cys Cys Ala Pro Gln Gly Gly Ala Glu Asp Glu
    370                 375                 380

Glu Gly Pro Arg Gly His Gln Ala Leu Tyr Arg Gln Arg Trp Pro His
385                 390                 395                 400

Pro His Tyr His His Ala Arg Arg Glu Pro Leu Asp Glu Gly Gly Leu
                405                 410                 415

Arg Pro Pro Pro Pro Arg Pro Arg Pro Leu Pro Cys Ser Cys Glu Ser
            420                 425                 430

Ala Phe


<210> SEQ ID NO 23
<211> LENGTH: 1041
<212> TYPE: DNA
<213> ORGANISM: Homo sapiens

<400> SEQUENCE: 23

atgtacaacg ggtcgtgctg ccgcatcgag ggggacacca tctcccaggt gatgccgccg      60

ctgctcattg tggcctttgt gctgggcgca ctaggcaatg gggtcgccct gtgtggtttc     120

tgcttccaca tgaagacctg gaagcccagc actgtttacc ttttcaattt ggccgtggct     180

gatttcctcc ttatgatctg cctgcctttt cggacagact attacctcag acgtagacac     240

tgggcttttg ggacattccc ctgccgagtg ggctcttca cgttggccat gaacagggcc     300

gggagcatcg tgttccttac ggtggtggct gcggacaggt atttcaaagt ggtccacccc     360

caccacgcgg tgaacactat ctccacccgg gtggcggctg gcatcgtctg caccctgtgg     420

gccctggtca tcctgggaac agtgtatctt ttgctggaga accatctctg cgtgcaagag     480

acggccgtct cctgtgagag cttcatcatg gagtcggcca atggctggca tgacatcatg     540

ttccagctgg agttctttat gcccctcggc atcatcttat tttgctcctt caagattgtt     600

tggagcctga ggcggaggca gcagctggcc agacaggctc ggatgaagaa ggcgacccgg     660

ttcatcatgg tggtggcaat tgtgttcatc acatgctacc tgcccagcgt gtctgctaga     720

ctctatttcc tctggacggt gccctcgagt gcctgcgatc cctctgtcca tggggccctg     780

cacataaccc tcagcttcac ctacatgaac agcatgctgg atcccctggt gtattatttt     840

tcaagcccct cctttcccaa attctacaac aagctcaaaa tctgcagtct gaaacccaag     900

cagccaggac actcaaaaac acaaaggccg gaagagatgc caatttcgaa cctcggtcgc     960

aggagttgca tcagtgtggc aaatagtttc caaagccagt ctgatgggca atgggatccc    1020

cacattgttg agtggcactg a                                              1041
```

-continued

<210> SEQ ID NO 24
<211> LENGTH: 346
<212> TYPE: PRT
<213> ORGANISM: Homo sapiens

<400> SEQUENCE: 24

```
Met Tyr Asn Gly Ser Cys Cys Arg Ile Glu Gly Asp Thr Ile Ser Gln
1               5                   10                  15

Val Met Pro Pro Leu Leu Ile Val Ala Phe Val Leu Gly Ala Leu Gly
            20                  25                  30

Asn Gly Val Ala Leu Cys Gly Phe Cys Phe His Met Lys Thr Trp Lys
        35                  40                  45

Pro Ser Thr Val Tyr Leu Phe Asn Leu Ala Val Ala Asp Phe Leu Leu
    50                  55                  60

Met Ile Cys Leu Pro Phe Arg Thr Asp Tyr Tyr Leu Arg Arg Arg His
65                  70                  75                  80

Trp Ala Phe Gly Asp Ile Pro Cys Arg Val Gly Leu Phe Thr Leu Ala
                85                  90                  95

Met Asn Arg Ala Gly Ser Ile Val Phe Leu Thr Val Val Ala Ala Asp
            100                 105                 110

Arg Tyr Phe Lys Val Val His Pro His His Ala Val Asn Thr Ile Ser
        115                 120                 125

Thr Arg Val Ala Ala Gly Ile Val Cys Thr Leu Trp Ala Leu Val Ile
    130                 135                 140

Leu Gly Thr Val Tyr Leu Leu Leu Glu Asn His Leu Cys Val Gln Glu
145                 150                 155                 160

Thr Ala Val Ser Cys Glu Ser Phe Ile Met Glu Ser Ala Asn Gly Trp
                165                 170                 175

His Asp Ile Met Phe Gln Leu Glu Phe Phe Met Pro Leu Gly Ile Ile
            180                 185                 190

Leu Phe Cys Ser Phe Lys Ile Val Trp Ser Leu Arg Arg Arg Gln Gln
        195                 200                 205

Leu Ala Arg Gln Ala Arg Met Lys Lys Ala Thr Arg Phe Ile Met Val
    210                 215                 220

Val Ala Ile Val Phe Ile Thr Cys Tyr Leu Pro Ser Val Ser Ala Arg
225                 230                 235                 240

Leu Tyr Phe Leu Trp Thr Val Pro Ser Ser Ala Cys Asp Pro Ser Val
                245                 250                 255

His Gly Ala Leu His Ile Thr Leu Ser Phe Thr Tyr Met Asn Ser Met
            260                 265                 270

Leu Asp Pro Leu Val Tyr Tyr Phe Ser Ser Pro Ser Phe Pro Lys Phe
        275                 280                 285

Tyr Asn Lys Leu Lys Ile Cys Ser Leu Lys Pro Lys Gln Pro Gly His
    290                 295                 300

Ser Lys Thr Gln Arg Pro Glu Glu Met Pro Ile Ser Asn Leu Gly Arg
305                 310                 315                 320

Arg Ser Cys Ile Ser Val Ala Asn Ser Phe Gln Ser Gln Ser Asp Gly
                325                 330                 335

Gln Trp Asp Pro His Ile Val Glu Trp His
            340                 345
```

<210> SEQ ID NO 25
<211> LENGTH: 1011
<212> TYPE: DNA
<213> ORGANISM: Homo sapiens -continued

<400> SEQUENCE: 25

```
atgaacaaca atacaacatg tattcaacca tctatgatct cttccatggc tttaccaatc     60
atttacatcc tcctttgtat tgttggtgtt tttggaaaca ctctctctca atggatattt    120
ttaacaaaaa taggtaaaaa aacatcaacg cacatctacc tgtcacacct tgtgactgca    180
aacttacttg tgtgcagtgc catgcctttc atgagtatct atttcctgaa aggtttccaa    240
tgggaatatc aatctgctca atgcagagtg gtcaattttc tgggaactct atccatgcat    300
gcaagtatgt ttgtcagtct cttaatttta agttggattg ccataagccg ctatgctacc    360
ttaatgcaaa aggattcctc gcaagagact acttcatgct atgagaaaat attttatggc    420
catttactga aaaaatttcg ccagcccaac tttgctagaa aactatgcat ttacatatgg    480
ggagttgtac tgggcataat cattccagtt accgtatact actcagtcat agaggctaca    540
gaaggagaag agagcctatg ctacaatcgg cagatggaac taggagccat gatctctcag    600
attgcaggtc tcattggaac cacatttatt ggattttcct ttttagtagt actaacatca    660
tactactctt ttgtaagcca tctgagaaaa ataagaacct gtacgtccat tatggagaaa    720
gatttgactt acagttctgt gaaaagacat cttttggtca tccagattct actaatagtt    780
tgcttccttc cttatagtat ttttaaaccc attttttatg ttctacacca aagagataac    840
tgtcagcaat tgaattattt aatagaaaca aaaaacattc tcacctgtct tgcttcggcc    900
agaagtagca cagaccccat tatatttctt ttattagata aaacattcaa gaagacacta    960
tataatctct ttacaaagtc taattcagca catatgcaat catatggttg a            1011
```

<210> SEQ ID NO 26
<211> LENGTH: 336
<212> TYPE: PRT
<213> ORGANISM: Homo sapiens

<400> SEQUENCE: 26

```
Met Asn Asn Asn Thr Thr Cys Ile Gln Pro Ser Met Ile Ser Ser Met
1               5                   10                  15

Ala Leu Pro Ile Ile Tyr Ile Leu Leu Cys Ile Val Gly Val Phe Gly
            20                  25                  30

Asn Thr Leu Ser Gln Trp Ile Phe Leu Thr Lys Ile Gly Lys Lys Thr
        35                  40                  45

Ser Thr His Ile Tyr Leu Ser His Leu Val Thr Ala Asn Leu Leu Val
    50                  55                  60

Cys Ser Ala Met Pro Phe Met Ser Ile Tyr Phe Leu Lys Gly Phe Gln
65                  70                  75                  80

Trp Glu Tyr Gln Ser Ala Gln Cys Arg Val Val Asn Phe Leu Gly Thr
                85                  90                  95

Leu Ser Met His Ala Ser Met Phe Val Ser Leu Leu Ile Leu Ser Trp
            100                 105                 110

Ile Ala Ile Ser Arg Tyr Ala Thr Leu Met Gln Lys Asp Ser Ser Gln
        115                 120                 125

Glu Thr Thr Ser Cys Tyr Glu Lys Ile Phe Tyr Gly His Leu Leu Lys
    130                 135                 140

Lys Phe Arg Gln Pro Asn Phe Ala Arg Lys Leu Cys Ile Tyr Ile Trp
145                 150                 155                 160

Gly Val Val Leu Gly Ile Ile Ile Pro Val Thr Val Tyr Tyr Ser Val
                165                 170                 175

Ile Glu Ala Thr Glu Gly Glu Glu Ser Leu Cys Tyr Asn Arg Gln Met
            180                 185                 190
```

-continued

```
Glu Leu Gly Ala Met Ile Ser Gln Ile Ala Gly Leu Ile Gly Thr Thr
        195                 200                 205

Phe Ile Gly Phe Ser Phe Leu Val Val Leu Thr Ser Tyr Tyr Ser Phe
    210                 215                 220

Val Ser His Leu Arg Lys Ile Arg Thr Cys Thr Ser Ile Met Glu Lys
225                 230                 235                 240

Asp Leu Thr Tyr Ser Ser Val Lys Arg His Leu Leu Val Ile Gln Ile
                245                 250                 255

Leu Leu Ile Val Cys Phe Leu Pro Tyr Ser Ile Phe Lys Pro Ile Phe
            260                 265                 270

Tyr Val Leu His Gln Arg Asp Asn Cys Gln Gln Leu Asn Tyr Leu Ile
        275                 280                 285

Glu Thr Lys Asn Ile Leu Thr Cys Leu Ala Ser Ala Arg Ser Ser Thr
    290                 295                 300

Asp Pro Ile Ile Phe Leu Leu Leu Asp Lys Thr Phe Lys Lys Thr Leu
305                 310                 315                 320

Tyr Asn Leu Phe Thr Lys Ser Asn Ser Ala His Met Gln Ser Tyr Gly
                325                 330                 335
```

<210> SEQ ID NO 27
<211> LENGTH: 1014
<212> TYPE: DNA
<213> ORGANISM: Homo sapiens

<400> SEQUENCE: 27

```
atgaatgagc cactagacta tttagcaaat gcttctgatt tccccgatta tgcagctgct      60

tttggaaatt gcactgatga aaacatccca ctcaagatgc actacctccc tgttatttat     120

ggcattatct tcctcgtggg atttccaggc aatgcagtag tgatatccac ttacattttc     180

aaaatgagac cttggaagag cagcaccatc attatgctga acctggcctg cacagatctg     240

ctgtatctga ccagcctccc cttcctgatt cactactatg ccagtggcga aaactggatc     300

tttggagatt tcatgtgtaa gtttatccgc ttcagcttcc atttcaacct gtatagcagc     360

atcctcttcc tcacctgttt cagcatcttc cgctactgtg tgatcattca cccaatgagc     420

tgcttttcca ttcacaaaac tcgatgtgca gttgtagcct gtgctgtggt gtggatcatt     480

tcactggtag ctgtcattcc gatgaccttc ttgatcacat caaccaacag gaccaacaga     540

tcagcctgtc tcgacctcac cagttcggat gaactcaata ctattaagtg gtacaacctg     600

attttgactg caactacttt ctgcctcccc ttggtgatag tgacactttg ctataccacg     660

attatccaca ctctgaccca tggactgcaa actgacagct gccttaagca gaaagcacga     720

aggctaacca ttctgctact ccttgcattt tacgtatgtt ttttaccctt ccatatcttg     780

agggtcattc ggatcgaatc tcgcctgctt tcaatcagtt gttccattga gaatcagatc     840

catgaagctt acatcgtttc tagaccatta gctgctctga acacctttgg taacctgtta     900

ctatatgtgg tggtcagcga caactttcag caggctgtct gctcaacagt gagatgcaaa     960

gtaagcggga accttgagca agcaaagaaa attagttact caaacaaccc ttga          1014
```

<210> SEQ ID NO 28
<211> LENGTH: 337
<212> TYPE: PRT
<213> ORGANISM: Homo sapiens

<400> SEQUENCE: 28

```
Met Asn Glu Pro Leu Asp Tyr Leu Ala Asn Ala Ser Asp Phe Pro Asp
1               5                   10                  15
```

-continued

```
Tyr Ala Ala Ala Phe Gly Asn Cys Thr Asp Glu Asn Ile Pro Leu Lys
            20                  25                  30

Met His Tyr Leu Pro Val Ile Tyr Gly Ile Ile Phe Leu Val Gly Phe
        35                  40                  45

Pro Gly Asn Ala Val Val Ile Ser Thr Tyr Ile Phe Lys Met Arg Pro
    50                  55                  60

Trp Lys Ser Ser Thr Ile Ile Met Leu Asn Leu Ala Cys Thr Asp Leu
65                  70                  75                  80

Leu Tyr Leu Thr Ser Leu Pro Phe Leu Ile His Tyr Tyr Ala Ser Gly
                85                  90                  95

Glu Asn Trp Ile Phe Gly Asp Phe Met Cys Lys Phe Ile Arg Phe Ser
            100                 105                 110

Phe His Phe Asn Leu Tyr Ser Ser Ile Leu Phe Leu Thr Cys Phe Ser
        115                 120                 125

Ile Phe Arg Tyr Cys Val Ile Ile His Pro Met Ser Cys Phe Ser Ile
    130                 135                 140

His Lys Thr Arg Cys Ala Val Val Ala Cys Ala Val Val Trp Ile Ile
145                 150                 155                 160

Ser Leu Val Ala Val Ile Pro Met Thr Phe Leu Ile Thr Ser Thr Asn
                165                 170                 175

Arg Thr Asn Arg Ser Ala Cys Leu Asp Leu Thr Ser Ser Asp Glu Leu
            180                 185                 190

Asn Thr Ile Lys Trp Tyr Asn Leu Ile Leu Thr Ala Thr Thr Phe Cys
        195                 200                 205

Leu Pro Leu Val Ile Val Thr Leu Cys Tyr Thr Thr Ile Ile His Thr
    210                 215                 220

Leu Thr His Gly Leu Gln Thr Asp Ser Cys Leu Lys Gln Lys Ala Arg
225                 230                 235                 240

Arg Leu Thr Ile Leu Leu Leu Leu Ala Phe Tyr Val Cys Phe Leu Pro
                245                 250                 255

Phe His Ile Leu Arg Val Ile Arg Ile Glu Ser Arg Leu Leu Ser Ile
            260                 265                 270

Ser Cys Ser Ile Glu Asn Gln Ile His Glu Ala Tyr Ile Val Ser Arg
        275                 280                 285

Pro Leu Ala Ala Leu Asn Thr Phe Gly Asn Leu Leu Leu Tyr Val Val
    290                 295                 300

Val Ser Asp Asn Phe Gln Gln Ala Val Cys Ser Thr Val Arg Cys Lys
305                 310                 315                 320

Val Ser Gly Asn Leu Glu Gln Ala Lys Lys Ile Ser Tyr Ser Asn Asn
                325                 330                 335

Pro


<210> SEQ ID NO 29
<211> LENGTH: 993
<212> TYPE: DNA
<213> ORGANISM: Homo sapiens

<400> SEQUENCE: 29

atggatccaa ccaccccggc ctggggaaca gaaagtacaa cagtgaatgg aaatgaccaa     60

gcccttcttc tgctttgtgg caaggagacc ctgatcccgg tcttcctgat ccttttcatt    120

gccctggtcg ggctggtagg aaacgggttt gtgctctggc tcctgggctt ccgcatgcgc    180

aggaacgcct tctctgtcta cgtcctcagc ctggccgggg ccgacttcct cttcctctgc    240

ttccagatta taaattgcct ggtgtacctc agtaacttct tctgttccat ctccatcaat    300
```

-continued

```
ttccctagct tcttcaccac tgtgatgacc tgtgcctacc ttgcaggcct gagcatgctg    360

agcaccgtca gcaccgagcg ctgcctgtcc gtcctgtggc ccatctggta tcgctgccgc    420

cgccccagac acctgtcagc ggtcgtgtgt gtcctgctct gggccctgtc cctactgctg    480

agcatcttgg aagggaagtt ctgtggcttc ttatttagtg atggtgactc tggttggtgt    540

cagacatttg atttcatcac tgcagcgtgg ctgatttttt tattcatggt tctctgtggg    600

tccagtctgg ccctgctggt caggatcctc tgtggctcca ggggtctgcc actgaccagg    660

ctgtacctga ccatcctgct cacagtgctg gtgttcctcc tctgcggcct gccctttggc    720

attcagtggt tcctaatatt atggatctgg aaggattctg atgtcttatt ttgtcatatt    780

catccagttt cagttgtcct gtcatctctt aacagcagtg ccaaccccat catttacttc    840

ttcgtgggct cttttaggaa gcagtggcgg ctgcagcagc cgatcctcaa gctggctctc    900

cagagggctc tgcaggacat tgctgaggtg gatcacagtg aaggatgctt ccgtcagggc    960

accccggaga tgtcgagaag cagtctggtg tag                                 993


<210> SEQ ID NO 30
<211> LENGTH: 330
<212> TYPE: PRT
<213> ORGANISM: Homo sapiens

<400> SEQUENCE: 30

Met Asp Pro Thr Thr Pro Ala Trp Gly Thr Glu Ser Thr Thr Val Asn
1               5                   10                  15

Gly Asn Asp Gln Ala Leu Leu Leu Leu Cys Gly Lys Glu Thr Leu Ile
            20                  25                  30

Pro Val Phe Leu Ile Leu Phe Ile Ala Leu Val Gly Leu Val Gly Asn
        35                  40                  45

Gly Phe Val Leu Trp Leu Leu Gly Phe Arg Met Arg Arg Asn Ala Phe
    50                  55                  60

Ser Val Tyr Val Leu Ser Leu Ala Gly Ala Asp Phe Leu Phe Leu Cys
65                  70                  75                  80

Phe Gln Ile Ile Asn Cys Leu Val Tyr Leu Ser Asn Phe Phe Cys Ser
                85                  90                  95

Ile Ser Ile Asn Phe Pro Ser Phe Phe Thr Thr Val Met Thr Cys Ala
            100                 105                 110

Tyr Leu Ala Gly Leu Ser Met Leu Ser Thr Val Ser Thr Glu Arg Cys
        115                 120                 125

Leu Ser Val Leu Trp Pro Ile Trp Tyr Arg Cys Arg Arg Pro Arg His
    130                 135                 140

Leu Ser Ala Val Val Cys Val Leu Leu Trp Ala Leu Ser Leu Leu Leu
145                 150                 155                 160

Ser Ile Leu Glu Gly Lys Phe Cys Gly Phe Leu Phe Ser Asp Gly Asp
                165                 170                 175

Ser Gly Trp Cys Gln Thr Phe Asp Phe Ile Thr Ala Ala Trp Leu Ile
            180                 185                 190

Phe Leu Phe Met Val Leu Cys Gly Ser Ser Leu Ala Leu Leu Val Arg
        195                 200                 205

Ile Leu Cys Gly Ser Arg Gly Leu Pro Leu Thr Arg Leu Tyr Leu Thr
    210                 215                 220

Ile Leu Leu Thr Val Leu Val Phe Leu Leu Cys Gly Leu Pro Phe Gly
225                 230                 235                 240

Ile Gln Trp Phe Leu Ile Leu Trp Ile Trp Lys Asp Ser Asp Val Leu
                245                 250                 255
```

-continued

```
Phe Cys His Ile His Pro Val Ser Val Val Leu Ser Ser Leu Asn Ser
            260                 265                 270

Ser Ala Asn Pro Ile Ile Tyr Phe Phe Val Gly Ser Phe Arg Lys Gln
        275                 280                 285

Trp Arg Leu Gln Gln Pro Ile Leu Lys Leu Ala Leu Gln Arg Ala Leu
    290                 295                 300

Gln Asp Ile Ala Glu Val Asp His Ser Glu Gly Cys Phe Arg Gln Gly
305                 310                 315                 320

Thr Pro Glu Met Ser Arg Ser Ser Leu Val
                325                 330


<210> SEQ ID NO 31
<211> LENGTH: 1092
<212> TYPE: DNA
<213> ORGANISM: Homo sapiens

<400> SEQUENCE: 31

atgggccccg gcgaggcgct gctggcgggt ctcctggtga tggtactggc cgtggcgctg      60

ctatccaacg cactggtgct gctttgttgc gcctacagcg ctgagctccg cactcgagcc     120

tcaggcgtcc tcctggtgaa tctgtcgctg ggccacctgc tgctggcggc gctggacatg     180

cccttcacgc tgctcggtgt gatgcgcggg cggacaccgt cggcgcccgg cgcatgccaa     240

gtcattggct tcctggacac cttcctggcg tccaacgcgg cgctgagcgt ggcggcgctg     300

agcgcagacc agtggctggc agtgggcttc ccactgcgct acgccggacg cctgcgaccg     360

cgctatgccg gcctgctgct gggctgtgcc tggggacagt cgctggcctt ctcaggcgct     420

gcacttggct gctcgtggct tggctacagc agcgccttcg cgtcctgttc gctgcgcctg     480

ccgcccgagc ctgagcgtcc gcgcttcgca gccttcaccg ccacgctcca tgccgtgggc     540

ttcgtgctgc cgctggcggt gctctgcctc acctcgctcc aggtgcaccg ggtggcacgc     600

agccactgcc agcgcatgga caccgtcacc atgaaggcgc tcgcgctgct cgccgacctg     660

caccccagtg tgcggcagcg ctgcctcatc cagcagaagc ggcgccgcca ccgcgccacc     720

aggaagattg gcattgctat tgcgaccttc ctcatctgct ttgccccgta tgtcatgacc     780

aggctggcgg agctcgtgcc cttcgtcacc gtgaacgccc agtggggcat cctcagcaag     840

tgcctgacct acagcaaggc ggtggccgac ccgttcacgt actctctgct ccgccggccg     900

ttccgccaag tcctggccgg catggtgcac cggctgctga agagaacccc gcgcccagca     960

tccacccatg acagctctct ggatgtggcc ggcatggtgc accagctgct gaagagaacc    1020

ccgcgcccag cgtccaccca caacggctct gtggacacag agaatgattc ctgcctgcag    1080

cagacacact ga                                                        1092


<210> SEQ ID NO 32
<211> LENGTH: 363
<212> TYPE: PRT
<213> ORGANISM: Homo sapiens

<400> SEQUENCE: 32

Met Gly Pro Gly Glu Ala Leu Leu Ala Gly Leu Leu Val Met Val Leu
1               5                   10                  15

Ala Val Ala Leu Leu Ser Asn Ala Leu Val Leu Leu Cys Cys Ala Tyr
            20                  25                  30

Ser Ala Glu Leu Arg Thr Arg Ala Ser Gly Val Leu Leu Val Asn Leu
        35                  40                  45
```

-continued

```
Ser Leu Gly His Leu Leu Leu Ala Ala Leu Asp Met Pro Phe Thr Leu
    50                  55                  60

Leu Gly Val Met Arg Gly Arg Thr Pro Ser Ala Pro Gly Ala Cys Gln
65                  70                  75                  80

Val Ile Gly Phe Leu Asp Thr Phe Leu Ala Ser Asn Ala Ala Leu Ser
                85                  90                  95

Val Ala Ala Leu Ser Ala Asp Gln Trp Leu Ala Val Gly Phe Pro Leu
            100                 105                 110

Arg Tyr Ala Gly Arg Leu Arg Pro Arg Tyr Ala Gly Leu Leu Leu Gly
        115                 120                 125

Cys Ala Trp Gly Gln Ser Leu Ala Phe Ser Gly Ala Ala Leu Gly Cys
    130                 135                 140

Ser Trp Leu Gly Tyr Ser Ser Ala Phe Ala Ser Cys Ser Leu Arg Leu
145                 150                 155                 160

Pro Pro Glu Pro Glu Arg Pro Arg Phe Ala Ala Phe Thr Ala Thr Leu
                165                 170                 175

His Ala Val Gly Phe Val Leu Pro Leu Ala Val Leu Cys Leu Thr Ser
            180                 185                 190

Leu Gln Val His Arg Val Ala Arg Ser His Cys Gln Arg Met Asp Thr
        195                 200                 205

Val Thr Met Lys Ala Leu Ala Leu Leu Ala Asp Leu His Pro Ser Val
    210                 215                 220

Arg Gln Arg Cys Leu Ile Gln Gln Lys Arg Arg Arg His Arg Ala Thr
225                 230                 235                 240

Arg Lys Ile Gly Ile Ala Ile Ala Thr Phe Leu Ile Cys Phe Ala Pro
                245                 250                 255

Tyr Val Met Thr Arg Leu Ala Glu Leu Val Pro Phe Val Thr Val Asn
            260                 265                 270

Ala Gln Trp Gly Ile Leu Ser Lys Cys Leu Thr Tyr Ser Lys Ala Val
        275                 280                 285

Ala Asp Pro Phe Thr Tyr Ser Leu Leu Arg Arg Pro Phe Arg Gln Val
    290                 295                 300

Leu Ala Gly Met Val His Arg Leu Leu Lys Arg Thr Pro Arg Pro Ala
305                 310                 315                 320

Ser Thr His Asp Ser Ser Leu Asp Val Ala Gly Met Val His Gln Leu
                325                 330                 335

Leu Lys Arg Thr Pro Arg Pro Ala Ser Thr His Asn Gly Ser Val Asp
            340                 345                 350

Thr Glu Asn Asp Ser Cys Leu Gln Gln Thr His
        355                 360


<210> SEQ ID NO 33
<211> LENGTH: 1125
<212> TYPE: DNA
<213> ORGANISM: Homo sapiens

<400> SEQUENCE: 33

atgcccacac tcaatacttc tgcctctcca cccacattct tctgggccaa tgcctccgga      60

ggcagtgtgc tgagtgctga tgatgctccg atgcctgtca aattcctagc cctgaggctc     120

atggttgccc tggcctatgg gcttgtgggg gccattggct tgctgggaaa tttggcggtg     180

ctgtgggtac tgagtaactg tgcccggaga gcccctggcc caccttcaga caccttcgtc     240

ttcaacctgg ctctggcgga cctgggactg gcactcactc tcccctttg ggcagccgag     300

tcggcactgg actttcactg gcccttcgga ggtgccctct gcaagatggt tctgacggcc     360
```

-continued

```
actgtcctca acgtctatgc cagcatcttc ctcatcacag cgctgagcgt tgctcgctac    420

tgggtggtgg ccatggctgc ggggccaggc acccacctct cactcttctg ggcccgaata    480

gccaccctgg cagtgtgggc ggcggctgcc ctggtgacgg tgcccacagc tgtcttcggg    540

gtggagggtg aggtgtgtgg tgtgcgcctt tgcctgctgc gtttccccag caggtactgg    600

ctgggggcct accagctgca gagggtggtg ctggctttca tggtgccctt gggcgtcatc    660

accaccagct acctgctgct gctggccttc ctgcagcggc ggcaacggcg gcggcaggac    720

agcagggtcg tggcccgctc tgtccgcatc ctggtggctt ccttcttcct ctgctggttt    780

cccaaccatg tggtcactct ctggggtgtc ctggtgaagt ttgacctggt gccctggaac    840

agtactttct atactatcca gacgtatgtc ttccctgtca ctacttgctt ggcacacagc    900

aatagctgcc tcaaccctgt gctgtactgt ctcctgaggc gggagccccg gcaggctctg    960

gcaggcacct tcagggatct gcggtcgagg ctgtggcccc agggcggagg ctgggtgcaa   1020

caggtggccc taaagcaggt aggcaggcgg tgggtcgcaa gcaacccccg ggagagccgc   1080

ccttctaccc tgctcaccaa cctggacaga gggacacccg ggtga                   1125
```

<210> SEQ ID NO 34
<211> LENGTH: 374
<212> TYPE: PRT
<213> ORGANISM: Homo sapiens

<400> SEQUENCE: 34

```
Met Pro Thr Leu Asn Thr Ser Ala Ser Pro Pro Thr Phe Phe Trp Ala
1               5                   10                  15

Asn Ala Ser Gly Gly Ser Val Leu Ser Ala Asp Asp Ala Pro Met Pro
            20                  25                  30

Val Lys Phe Leu Ala Leu Arg Leu Met Val Ala Leu Ala Tyr Gly Leu
        35                  40                  45

Val Gly Ala Ile Gly Leu Leu Gly Asn Leu Ala Val Leu Trp Val Leu
    50                  55                  60

Ser Asn Cys Ala Arg Arg Ala Pro Gly Pro Pro Ser Asp Thr Phe Val
65                  70                  75                  80

Phe Asn Leu Ala Leu Ala Asp Leu Gly Leu Ala Leu Thr Leu Pro Phe
                85                  90                  95

Trp Ala Ala Glu Ser Ala Leu Asp Phe His Trp Pro Phe Gly Gly Ala
            100                 105                 110

Leu Cys Lys Met Val Leu Thr Ala Thr Val Leu Asn Val Tyr Ala Ser
        115                 120                 125

Ile Phe Leu Ile Thr Ala Leu Ser Val Ala Arg Tyr Trp Val Val Ala
    130                 135                 140

Met Ala Ala Gly Pro Gly Thr His Leu Ser Leu Phe Trp Ala Arg Ile
145                 150                 155                 160

Ala Thr Leu Ala Val Trp Ala Ala Ala Ala Leu Val Thr Val Pro Thr
                165                 170                 175

Ala Val Phe Gly Val Glu Gly Glu Val Cys Gly Val Arg Leu Cys Leu
            180                 185                 190

Leu Arg Phe Pro Ser Arg Tyr Trp Leu Gly Ala Tyr Gln Leu Gln Arg
        195                 200                 205

Val Val Leu Ala Phe Met Val Pro Leu Gly Val Ile Thr Thr Ser Tyr
    210                 215                 220

Leu Leu Leu Leu Ala Phe Leu Gln Arg Arg Gln Arg Arg Arg Gln Asp
225                 230                 235                 240
```

-continued

```
Ser Arg Val Val Ala Arg Ser Val Arg Ile Leu Val Ala Ser Phe Phe
                245                 250                 255

Leu Cys Trp Phe Pro Asn His Val Val Thr Leu Trp Gly Val Leu Val
            260                 265                 270

Lys Phe Asp Leu Val Pro Trp Asn Ser Thr Phe Tyr Thr Ile Gln Thr
        275                 280                 285

Tyr Val Phe Pro Val Thr Thr Cys Leu Ala His Ser Asn Ser Cys Leu
    290                 295                 300

Asn Pro Val Leu Tyr Cys Leu Leu Arg Arg Glu Pro Arg Gln Ala Leu
305                 310                 315                 320

Ala Gly Thr Phe Arg Asp Leu Arg Ser Arg Leu Trp Pro Gln Gly Gly
                325                 330                 335

Gly Trp Val Gln Gln Val Ala Leu Lys Gln Val Gly Arg Arg Trp Val
            340                 345                 350

Ala Ser Asn Pro Arg Glu Ser Arg Pro Ser Thr Leu Leu Thr Asn Leu
        355                 360                 365

Asp Arg Gly Thr Pro Gly
    370
```

<210> SEQ ID NO 35
<211> LENGTH: 1092
<212> TYPE: DNA
<213> ORGANISM: Homo sapiens

<400> SEQUENCE: 35

```
atgaatcggc accatctgca ggatcacttt ctggaaatag acaagaagaa ctgctgtgtg     60

ttccgagatg acttcattgt caaggtgttg ccgccggtgt tggggctgga gtttatcttc    120

gggcttctgg gcaatggcct tgccctgtgg attttctgtt tccacctcaa gtcctggaaa    180

tccagccgga ttttcctgtt caacctggca gtggctgact ttctactgat catctgcctg    240

cccttcctga tggacaacta tgtgaggcgt tgggactgga agtttgggga catcccttgc    300

cggctgatgc tcttcatgtt ggctatgaac cgccagggca gcatcatctt cctcacggtg    360

gtggcggtag acaggtattt ccgggtggtc catccccacc acgccctgaa caagatctcc    420

aatcggacag cagccatcat ctcttgcctt ctgtggggca tcactattgg cctgacagtc    480

cacctcctga agaagaagat gccgatccag aatggcggtg caaatttgtg cagcagcttc    540

agcatctgcc ataccttcca gtggcacgaa gccatgttcc tcctggagtt cttcctgccc    600

ctgggcatca tcctgttctg ctcagccaga attatctgga gcctgcggca gagacaaatg    660

gaccggcatg ccaagatcaa gagagccatc accttcatca tggtggtggc catcgtcttt    720

gtcatctgct tccttcccag cgtggttgtg cggatccgca tcttctggct cctgcacact    780

tcgggcacgc agaattgtga agtgtaccgc tcggtggacc tggcgttctt tatcactctc    840

agcttcacct acatgaacag catgctggac cccgtggtgt actacttctc cagcccatcc    900

tttcccaact tcttctccac tttgatcaac cgctgcctcc agaggaagat gacaggtgag    960

ccagataata accgcagcac gagcgtcgag ctcacagggg accccaacaa aaccagaggc   1020

gctccagagg cgttaatggc caactccggt gagccatgga gcccctctta tctgggccca   1080

acctctcctt aa                                                       1092
```

<210> SEQ ID NO 36
<211> LENGTH: 363
<212> TYPE: PRT
<213> ORGANISM: Homo sapiens -continued

<400> SEQUENCE: 36

```
Met Asn Arg His His Leu Gln Asp His Phe Leu Glu Ile Asp Lys Lys
1               5                   10                  15

Asn Cys Cys Val Phe Arg Asp Asp Phe Ile Val Lys Val Leu Pro Pro
            20                  25                  30

Val Leu Gly Leu Glu Phe Ile Phe Gly Leu Leu Gly Asn Gly Leu Ala
        35                  40                  45

Leu Trp Ile Phe Cys Phe His Leu Lys Ser Trp Lys Ser Ser Arg Ile
    50                  55                  60

Phe Leu Phe Asn Leu Ala Val Ala Asp Phe Leu Leu Ile Ile Cys Leu
65                  70                  75                  80

Pro Phe Leu Met Asp Asn Tyr Val Arg Arg Trp Asp Trp Lys Phe Gly
                85                  90                  95

Asp Ile Pro Cys Arg Leu Met Leu Phe Met Leu Ala Met Asn Arg Gln
            100                 105                 110

Gly Ser Ile Ile Phe Leu Thr Val Val Ala Val Asp Arg Tyr Phe Arg
        115                 120                 125

Val Val His Pro His His Ala Leu Asn Lys Ile Ser Asn Arg Thr Ala
    130                 135                 140

Ala Ile Ile Ser Cys Leu Leu Trp Gly Ile Thr Ile Gly Leu Thr Val
145                 150                 155                 160

His Leu Leu Lys Lys Lys Met Pro Ile Gln Asn Gly Gly Ala Asn Leu
                165                 170                 175

Cys Ser Ser Phe Ser Ile Cys His Thr Phe Gln Trp His Glu Ala Met
            180                 185                 190

Phe Leu Leu Glu Phe Phe Leu Pro Leu Gly Ile Ile Leu Phe Cys Ser
        195                 200                 205

Ala Arg Ile Ile Trp Ser Leu Arg Gln Arg Gln Met Asp Arg His Ala
    210                 215                 220

Lys Ile Lys Arg Ala Ile Thr Phe Ile Met Val Val Ala Ile Val Phe
225                 230                 235                 240

Val Ile Cys Phe Leu Pro Ser Val Val Val Arg Ile Arg Ile Phe Trp
                245                 250                 255

Leu Leu His Thr Ser Gly Thr Gln Asn Cys Glu Val Tyr Arg Ser Val
            260                 265                 270

Asp Leu Ala Phe Phe Ile Thr Leu Ser Phe Thr Tyr Met Asn Ser Met
        275                 280                 285

Leu Asp Pro Val Val Tyr Tyr Phe Ser Ser Pro Ser Phe Pro Asn Phe
    290                 295                 300

Phe Ser Thr Leu Ile Asn Arg Cys Leu Gln Arg Lys Met Thr Gly Glu
305                 310                 315                 320

Pro Asp Asn Asn Arg Ser Thr Ser Val Glu Leu Thr Gly Asp Pro Asn
                325                 330                 335

Lys Thr Arg Gly Ala Pro Glu Ala Leu Met Ala Asn Ser Gly Glu Pro
            340                 345                 350

Trp Ser Pro Ser Tyr Leu Gly Pro Thr Ser Pro
        355                 360
```

<210> SEQ ID NO 37
<211> LENGTH: 1044
<212> TYPE: DNA
<213> ORGANISM: Homo sapiens -continued

<400> SEQUENCE: 37

```
atgggggatg agctggcacc ttgccctgtg ggcactacag cttggccggc cctgatccag     60
ctcatcagca agacaccctg catgccccaa gcagccagca acacttcctt gggcctgggg    120
gacctcaggg tgcccagctc catgctgtac tggcttttcc ttccctcaag cctgctggct    180
gcagccacac tggctgtcag ccccctgctg ctggtgacca tcctgcggaa ccaacggctg    240
cgacaggagc cccactacct gctcccggct aacatcctgc tctcagacct ggcctacatt    300
ctcctccaca tgctcatctc ctccagcagc ctgggtggct gggagctggg ccgcatggcc    360
tgtggcattc tcactgatgc tgtcttcgcc gcctgcacca gcaccatcct gtccttcacc    420
gccattgtgc tgcacaccta cctggcagtc atccatccac tgcgctacct ctccttcatg    480
tcccatgggg ctgcctggaa ggcagtggcc ctcatctggc tggtggcctg ctgcttcccc    540
acattcctta tttggctcag caagtggcag gatgcccagc tggaggagca aggagcttca    600
tacatcctac caccaagcat gggcacccag ccgggatgtg gcctcctggt cattgttacc    660
tacacctcca ttctgtgcgt tctgttcctc tgcacagctc tcattgccaa ctgtttctgg    720
aggatctatg cagaggccaa gacttcaggc atctgggggc agggctattc ccgggccagg    780
ggcaccctgc tgatccactc agtgctgatc acattgtacg tgagcacagg ggtggtgttc    840
tccctggaca tggtgctgac caggtaccac cacattgact ctgggactca cacatggctc    900
ctggcagcta acagtgaggt actcatgatg cttccccgtg ccatgctccc atacctgtac    960
ctgctccgct accggcagct gttgggcatg gtccggggcc acctcccatc caggaggcac   1020
caggccatct ttaccatttc ctag                                          1044
```

<210> SEQ ID NO 38
<211> LENGTH: 347
<212> TYPE: PRT
<213> ORGANISM: Homo sapiens

<400> SEQUENCE: 38

```
Met Gly Asp Glu Leu Ala Pro Cys Pro Val Gly Thr Thr Ala Trp Pro
1               5                   10                  15

Ala Leu Ile Gln Leu Ile Ser Lys Thr Pro Cys Met Pro Gln Ala Ala
            20                  25                  30

Ser Asn Thr Ser Leu Gly Leu Gly Asp Leu Arg Val Pro Ser Ser Met
        35                  40                  45

Leu Tyr Trp Leu Phe Leu Pro Ser Ser Leu Leu Ala Ala Ala Thr Leu
    50                  55                  60

Ala Val Ser Pro Leu Leu Leu Val Thr Ile Leu Arg Asn Gln Arg Leu
65                  70                  75                  80

Arg Gln Glu Pro His Tyr Leu Leu Pro Ala Asn Ile Leu Leu Ser Asp
                85                  90                  95

Leu Ala Tyr Ile Leu Leu His Met Leu Ile Ser Ser Ser Ser Leu Gly
            100                 105                 110

Gly Trp Glu Leu Gly Arg Met Ala Cys Gly Ile Leu Thr Asp Ala Val
        115                 120                 125

Phe Ala Ala Cys Thr Ser Thr Ile Leu Ser Phe Thr Ala Ile Val Leu
    130                 135                 140

His Thr Tyr Leu Ala Val Ile His Pro Leu Arg Tyr Leu Ser Phe Met
145                 150                 155                 160

Ser His Gly Ala Ala Trp Lys Ala Val Ala Leu Ile Trp Leu Val Ala
                165                 170                 175
```

-continued

```
Cys Cys Phe Pro Thr Phe Leu Ile Trp Leu Ser Lys Trp Gln Asp Ala
            180                 185                 190

Gln Leu Glu Glu Gln Gly Ala Ser Tyr Ile Leu Pro Pro Ser Met Gly
        195                 200                 205

Thr Gln Pro Gly Cys Gly Leu Leu Val Ile Val Thr Tyr Thr Ser Ile
    210                 215                 220

Leu Cys Val Leu Phe Leu Cys Thr Ala Leu Ile Ala Asn Cys Phe Trp
225                 230                 235                 240

Arg Ile Tyr Ala Glu Ala Lys Thr Ser Gly Ile Trp Gly Gln Gly Tyr
                245                 250                 255

Ser Arg Ala Arg Gly Thr Leu Leu Ile His Ser Val Leu Ile Thr Leu
            260                 265                 270

Tyr Val Ser Thr Gly Val Val Phe Ser Leu Asp Met Val Leu Thr Arg
        275                 280                 285

Tyr His His Ile Asp Ser Gly Thr His Thr Trp Leu Leu Ala Ala Asn
    290                 295                 300

Ser Glu Val Leu Met Met Leu Pro Arg Ala Met Leu Pro Tyr Leu Tyr
305                 310                 315                 320

Leu Leu Arg Tyr Arg Gln Leu Leu Gly Met Val Arg Gly His Leu Pro
                325                 330                 335

Ser Arg Arg His Gln Ala Ile Phe Thr Ile Ser
            340                 345
```

<210> SEQ ID NO 39
<211> LENGTH: 1023
<212> TYPE: DNA
<213> ORGANISM: Homo sapiens

<400> SEQUENCE: 39

```
atgaatccat ttcatgcatc ttgttggaac acctctgccg aacttttaaa caaatcctgg      60

aataaagagt ttgcttatca aactgccagt gtggtagata cagtcatcct cccttccatg     120

attgggatta tctgttcaac agggctggtt ggcaacatcc tcattgtatt cactataata     180

agatccagga aaaaaacagt ccctgacatc tatatctgca acctggctgt ggctgatttg     240

gtccacatag ttggaatgcc ttttcttatt caccaatggg cccgaggggg agagtgggtg     300

tttgggggc ctctctgcac catcatcaca tccctggata cttgtaacca atttgcctgt     360

agtgccatca tgactgtaat gagtgtggac aggtactttg ccctcgtcca accatttcga     420

ctgacacgtt ggagaacaag gtacaagacc atccggatca atttgggcct ttgggcagct     480

tcctttatcc tggcattgcc tgtctgggtc tactcgaagg tcatcaaatt taaagacggt     540

gttgagagtt gtgcttttga tttgacatcc cctgacgatg tactctggta tacactttat     600

ttgacgataa caactttttt tttccctcta cccttgattt tggtgtgcta tattttaatt     660

ttatgctata cttgggagat gtatcaacag aataaggatg ccagatgctg caatcccagt     720

gtaccaaaac agagagtgat gaagttgaca aagatggtgc tggtgctggt ggtagtcttt     780

atcctgagtg ctgcccctta tcatgtgata caactggtga acttacagat ggaacagccc     840

acactggcct tctatgtggg ttattacctc tccatctgtc tcagctatgc cagcagcagc     900

attaaccctt ttctctacat cctgctgagt ggaaatttcc agaaacgtct gcctcaaatc     960

caaagaagag cgactgagaa ggaaatcaac aatatgggaa acactctgaa atcacacttt    1020

tag                                                                  1023
```

-continued

<210> SEQ ID NO 40
<211> LENGTH: 340
<212> TYPE: PRT
<213> ORGANISM: Homo sapiens

<400> SEQUENCE: 40

```
Met Asn Pro Phe His Ala Ser Cys Trp Asn Thr Ser Ala Glu Leu Leu
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
        35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Arg Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Val Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Val Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ser Ile Asn Pro Phe
    290                 295                 300

Leu Tyr Ile Leu Leu Ser Gly Asn Phe Gln Lys Arg Leu Pro Gln Ile
305                 310                 315                 320

Gln Arg Arg Ala Thr Glu Lys Glu Ile Asn Asn Met Gly Asn Thr Leu
                325                 330                 335

Lys Ser His Phe
            340
```

<210> SEQ ID NO 41
<211> LENGTH: 24
<212> TYPE: DNA
<213> ORGANISM: Artificial Sequence -continued
<220> FEATURE:
<223> OTHER INFORMATION: Novel Sequence
<220> FEATURE:
<221> NAME/KEY: misc_feature
<223> OTHER INFORMATION: Novel Sequence

<400> SEQUENCE: 41
cttgcagaca tcaccatggc agcc 24

<210> SEQ ID NO 42
<211> LENGTH: 24
<212> TYPE: DNA
<213> ORGANISM: Artificial Sequence
<220> FEATURE:
<223> OTHER INFORMATION: Novel Sequence

<400> SEQUENCE: 42
gtgatgctct gagtactgga ctgg 24

<210> SEQ ID NO 43
<211> LENGTH: 20
<212> TYPE: DNA
<213> ORGANISM: Artificial Sequence
<220> FEATURE:
<223> OTHER INFORMATION: Novel Sequence

<400> SEQUENCE: 43
gaagctgtga agagtgatgc 20

<210> SEQ ID NO 44
<211> LENGTH: 24
<212> TYPE: DNA
<213> ORGANISM: Artificial Sequence
<220> FEATURE:
<223> OTHER INFORMATION: Novel Sequence

<400> SEQUENCE: 44
gtcagcaata ttgataagca gcag 24

<210> SEQ ID NO 45
<211> LENGTH: 27
<212> TYPE: DNA
<213> ORGANISM: Artificial Sequence
<220> FEATURE:
<223> OTHER INFORMATION: Novel Sequence

<400> SEQUENCE: 45
ccatggggaa cgattctgtc agctacg 27

<210> SEQ ID NO 46
<211> LENGTH: 24
<212> TYPE: DNA
<213> ORGANISM: Artificial Sequence
<220> FEATURE:
<223> OTHER INFORMATION: Novel Sequence

<400> SEQUENCE: 46
gctatgcctg aagccagtct tgtg 24

<210> SEQ ID NO 47
<211> LENGTH: 26
<212> TYPE: DNA
<213> ORGANISM: Artificial Sequence
<220> FEATURE:
<223> OTHER INFORMATION: Novel Sequence -continued

<400> SEQUENCE: 47
ccaggatgtt gtgtcaccgt ggtggc 26

<210> SEQ ID NO 48
<211> LENGTH: 26
<212> TYPE: DNA
<213> ORGANISM: Artificial Sequence
<220> FEATURE:
<223> OTHER INFORMATION: Novel Sequence

<400> SEQUENCE: 48
cacagcgctg cagccctgca gctggc 26

<210> SEQ ID NO 49
<211> LENGTH: 26
<212> TYPE: DNA
<213> ORGANISM: Artificial Sequence
<220> FEATURE:
<223> OTHER INFORMATION: Novel Sequence

<400> SEQUENCE: 49
cttcctctcg tagggatgaa ccagac 26

<210> SEQ ID NO 50
<211> LENGTH: 26
<212> TYPE: DNA
<213> ORGANISM: Artificial Sequence
<220> FEATURE:
<223> OTHER INFORMATION: Novel Sequence

<400> SEQUENCE: 50
ctcgcacagg tgggaagcac ctgtgg 26

<210> SEQ ID NO 51
<211> LENGTH: 23
<212> TYPE: DNA
<213> ORGANISM: Artificial Sequence
<220> FEATURE:
<223> OTHER INFORMATION: Novel Sequence

<400> SEQUENCE: 51
gcctgtgaca ggaggtaccc tgg 23

<210> SEQ ID NO 52
<211> LENGTH: 25
<212> TYPE: DNA
<213> ORGANISM: Artificial Sequence
<220> FEATURE:
<223> OTHER INFORMATION: Novel Sequence

<400> SEQUENCE: 52
catatccctc cgagtgtcca gcggc 25

<210> SEQ ID NO 53
<211> LENGTH: 31
<212> TYPE: DNA
<213> ORGANISM: Artificial Sequence
<220> FEATURE:
<223> OTHER INFORMATION: Novel Sequence

<400> SEQUENCE: 53
gcatggagag aaaatttatg tccttgcaac c 31

-continued

<210> SEQ ID NO 54
<211> LENGTH: 27
<212> TYPE: DNA
<213> ORGANISM: Artificial Sequence
<220> FEATURE:
<223> OTHER INFORMATION: Novel Sequence
<220> FEATURE:
<221> NAME/KEY: misc_feature
<223> OTHER INFORMATION: Novel Sequence

<400> SEQUENCE: 54
caagaacagg tctcatctaa gagctcc 27

<210> SEQ ID NO 55
<211> LENGTH: 26
<212> TYPE: DNA
<213> ORGANISM: Artificial Sequence
<220> FEATURE:
<223> OTHER INFORMATION: Novel Sequence

<400> SEQUENCE: 55
gctgttgcca tgacgtccac ctgcac 26

<210> SEQ ID NO 56
<211> LENGTH: 26
<212> TYPE: DNA
<213> ORGANISM: Artificial Sequence
<220> FEATURE:
<223> OTHER INFORMATION: Novel Sequence

<400> SEQUENCE: 56
ggacagttca aggtttgcct tagaac 26

<210> SEQ ID NO 57
<211> LENGTH: 23
<212> TYPE: DNA
<213> ORGANISM: Artificial Sequence
<220> FEATURE:
<223> OTHER INFORMATION: Novel Sequence

<400> SEQUENCE: 57
ctttcgatac tgctcctatg ctc 23

<210> SEQ ID NO 58
<211> LENGTH: 26
<212> TYPE: DNA
<213> ORGANISM: Artificial Sequence
<220> FEATURE:
<223> OTHER INFORMATION: Novel Sequence

<400> SEQUENCE: 58
gtagtccact gaaagtccag tgatcc 26

<210> SEQ ID NO 59
<211> LENGTH: 26
<212> TYPE: DNA
<213> ORGANISM: Artificial Sequence
<220> FEATURE:
<223> OTHER INFORMATION: Novel Sequence

<400> SEQUENCE: 59
tttctgagca tggatccaac catctc 26

<210> SEQ ID NO 60
<211> LENGTH: 25
<212> TYPE: DNA
<213> ORGANISM: Artificial Sequence -continued
<220> FEATURE:
<223> OTHER INFORMATION: Novel Sequence

<400> SEQUENCE: 60
ctgtctgaca gggcagaggc tcttc 25

<210> SEQ ID NO 61
<211> LENGTH: 28
<212> TYPE: DNA
<213> ORGANISM: Artificial Sequence
<220> FEATURE:
<223> OTHER INFORMATION: Novel Sequence

<400> SEQUENCE: 61
ggaactcgta tagacccagc gtcgctcc 28

<210> SEQ ID NO 62
<211> LENGTH: 28
<212> TYPE: DNA
<213> ORGANISM: Artificial Sequence
<220> FEATURE:
<223> OTHER INFORMATION: Novel Sequence

<400> SEQUENCE: 62
ggaggttgcg ccttagcgac agatgacc 28

<210> SEQ ID NO 63
<211> LENGTH: 22
<212> TYPE: DNA
<213> ORGANISM: Artificial Sequence
<220> FEATURE:
<223> OTHER INFORMATION: Novel Sequence

<400> SEQUENCE: 63
ctgcacccgg acacttgctc tg 22

<210> SEQ ID NO 64
<211> LENGTH: 25
<212> TYPE: DNA
<213> ORGANISM: Artificial Sequence
<220> FEATURE:
<223> OTHER INFORMATION: Novel Sequence

<400> SEQUENCE: 64
gtctgcttgt tcagtgccac tcaac 25

<210> SEQ ID NO 65
<211> LENGTH: 26
<212> TYPE: DNA
<213> ORGANISM: Artificial Sequence
<220> FEATURE:
<223> OTHER INFORMATION: Novel Sequence

<400> SEQUENCE: 65
tatctgcaat tctattctag ctcctg 26

<210> SEQ ID NO 66
<211> LENGTH: 26
<212> TYPE: DNA
<213> ORGANISM: Artificial Sequence
<220> FEATURE:
<223> OTHER INFORMATION: Novel Sequence

<400> SEQUENCE: 66
tgtccctaat aaagtcacat gaatgc 26

-continued

<210> SEQ ID NO 67
<211> LENGTH: 23
<212> TYPE: DNA
<213> ORGANISM: Artificial Sequence
<220> FEATURE:
<223> OTHER INFORMATION: Novel Sequence

<400> SEQUENCE: 67
ggagacaacc atgaatgagc cac 23

<210> SEQ ID NO 68
<211> LENGTH: 24
<212> TYPE: DNA
<213> ORGANISM: Artificial Sequence
<220> FEATURE:
<223> OTHER INFORMATION: Novel Sequence

<400> SEQUENCE: 68
tatttcaagg gttgtttgag taac 24

<210> SEQ ID NO 69
<211> LENGTH: 27
<212> TYPE: DNA
<213> ORGANISM: Artificial Sequence
<220> FEATURE:
<223> OTHER INFORMATION: Novel Sequence

<400> SEQUENCE: 69
ggcaccagtg gaggttttct gagcatg 27

<210> SEQ ID NO 70
<211> LENGTH: 27
<212> TYPE: DNA
<213> ORGANISM: Artificial Sequence
<220> FEATURE:
<223> OTHER INFORMATION: Novel Sequence

<400> SEQUENCE: 70
ctgatggaag tagaggctgt ccatctc 27

<210> SEQ ID NO 71
<211> LENGTH: 23
<212> TYPE: DNA
<213> ORGANISM: Artificial Sequence
<220> FEATURE:
<223> OTHER INFORMATION: Novel Sequence

<400> SEQUENCE: 71
cctggcgagc cgctagcgcc atg 23

<210> SEQ ID NO 72
<211> LENGTH: 23
<212> TYPE: DNA
<213> ORGANISM: Artificial Sequence
<220> FEATURE:
<223> OTHER INFORMATION: Novel Sequence

<400> SEQUENCE: 72
atgagccctg ccaggccctc agt 23

<210> SEQ ID NO 73
<211> LENGTH: 27
<212> TYPE: DNA
<213> ORGANISM: Artificial Sequence
<220> FEATURE:
<223> OTHER INFORMATION: Novel Sequence -continued

<400> SEQUENCE: 73
ctgcgatgcc cacactcaat acttctg 27

<210> SEQ ID NO 74
<211> LENGTH: 27
<212> TYPE: DNA
<213> ORGANISM: Artificial Sequence
<220> FEATURE:
<223> OTHER INFORMATION: Novel Sequence

<400> SEQUENCE: 74
aaggatccta cacttggtgg atctcag 27

<210> SEQ ID NO 75
<211> LENGTH: 22
<212> TYPE: DNA
<213> ORGANISM: Artificial Sequence
<220> FEATURE:
<223> OTHER INFORMATION: Novel Sequence

<400> SEQUENCE: 75
gctggagcat tcactaggcg ag 22

<210> SEQ ID NO 76
<211> LENGTH: 24
<212> TYPE: DNA
<213> ORGANISM: Artificial Sequence
<220> FEATURE:
<223> OTHER INFORMATION: Novel Sequence

<400> SEQUENCE: 76
agatcctggt tcttggtgac aatg 24

<210> SEQ ID NO 77
<211> LENGTH: 24
<212> TYPE: DNA
<213> ORGANISM: Artificial Sequence
<220> FEATURE:
<223> OTHER INFORMATION: Novel Sequence

<400> SEQUENCE: 77
agccatccct gccaggaagc atgg 24

<210> SEQ ID NO 78
<211> LENGTH: 27
<212> TYPE: DNA
<213> ORGANISM: Artificial Sequence
<220> FEATURE:
<223> OTHER INFORMATION: Novel Sequence

<400> SEQUENCE: 78
ccagactgtg gactcaagaa ctctagg 27

<210> SEQ ID NO 79
<211> LENGTH: 28
<212> TYPE: DNA
<213> ORGANISM: Artificial Sequence
<220> FEATURE:
<223> OTHER INFORMATION: Novel Sequence

<400> SEQUENCE: 79
agtccacgaa caatgaatcc atttcatg 28

-continued

<210> SEQ ID NO 80
<211> LENGTH: 25
<212> TYPE: DNA
<213> ORGANISM: Artificial Sequence
<220> FEATURE:
<223> OTHER INFORMATION: Novel Sequence

<400> SEQUENCE: 80
atcatgtcta gactcatggt gatcc 25

<210> SEQ ID NO 81
<211> LENGTH: 30
<212> TYPE: DNA
<213> ORGANISM: Artificial Sequence
<220> FEATURE:
<223> OTHER INFORMATION: Novel Sequence

<400> SEQUENCE: 81
ggggagggaa agcaaaggtg gtcctcctgg 30

<210> SEQ ID NO 82
<211> LENGTH: 30
<212> TYPE: DNA
<213> ORGANISM: Artificial Sequence
<220> FEATURE:
<223> OTHER INFORMATION: Novel Sequence

<400> SEQUENCE: 82
ccaggagaac cacctttgct ttccctcccc 30

<210> SEQ ID NO 83
<211> LENGTH: 1356
<212> TYPE: DNA
<213> ORGANISM: Homo sapiens

<400> SEQUENCE: 83
atggagtcct cacccatccc ccagtcatca gggaactctt ccactttggg gagggtccct 60
caaaccccag gtccctctac tgccagtggg gtcccggagg tggggctacg ggatgttgct 120
tcggaatctg tggccctctt cttcatgctc ctgctggact tgactgctgt ggctggcaat 180
gccgctgtga tggccgtgat cgccaagacg cctgccctcc gaaaatttgt cttcgtcttc 240
cacctctgcc tggtggacct gctggctgcc ctgaccctca tgcccctggc catgctctcc 300
agctctgccc tctttgacca cgccctcttt ggggaggtgg cctgccgcct ctacttgttt 360
ctgagcgtgt gctttgtcag cctggccatc ctctcggtgt cagccatcaa tgtggagcgc 420
tactattacg tagtccaccc catgcgctac gaggtgcgca tgacgctggg gctggtggcc 480
tctgtgctgg tgggtgtgtg ggtgaaggcc ttggccatgg cttctgtgcc agtgttggga 540
agggtctcct gggaggaagg agctcccagt gtcccccag gctgttcact ccagtggagc 600
cacagtgcct actgccagct tttgtggtg gtctttgctg tcctttactt tctgttgccc 660
ctgctcctca tacttgtggt ctactgcagc atgttccgag tggcccgcgt ggctgccatg 720
cagcacgggc cgctgcccac gtggatggag acaccccggc aacgctccga atctctcagc 780
agccgctcca cgatggtcac cagctcgggg gccccccaga ccaccccaca ccggacgttt 840
gggggaggga aagcaaaggt ggttctcctg gctgtggggg gacagttcct gctctgttgg 900
ttgccctact tctctttcca cctctatgtt gccctgagtg ctcagcccat ttcaactggg 960
caggtggaga gtgtggtcac ctggattggc tacttttgct tcacttccaa ccctttcttc 1020
tatggatgtc tcaaccggca gatccggggg gagctcagca agcagtttgt ctgcttcttc 1080

-continued

```
aagccagctc cagaggagga gctgaggctg cctagccggg agggctccat tgaggagaac   1140

ttcctgcagt tccttcaggg gactggctgt ccttctgagt cctgggtttc ccgaccccta   1200

cccagcccca agcaggagcc acctgctgtt gactttcgaa tcccaggcca gatagctgag   1260

gagacctctg agttcctgga gcagcaactc accagcgaca tcatcatgtc agacagctac   1320

ctccgtcctg ccgcctcacc ccggctggag tcatga                             1356


<210> SEQ ID NO 84
<211> LENGTH: 451
<212> TYPE: PRT
<213> ORGANISM: Homo sapiens

<400> SEQUENCE: 84

Met Glu Ser Ser Pro Ile Pro Gln Ser Ser Gly Asn Ser Ser Thr Leu
1               5                   10                  15

Gly Arg Val Pro Gln Thr Pro Gly Pro Ser Thr Ala Ser Gly Val Pro
            20                  25                  30

Glu Val Gly Leu Arg Asp Val Ala Ser Glu Ser Val Ala Leu Phe Phe
        35                  40                  45

Met Leu Leu Leu Asp Leu Thr Ala Val Ala Gly Asn Ala Ala Val Met
    50                  55                  60

Ala Val Ile Ala Lys Thr Pro Ala Leu Arg Lys Phe Val Phe Val Phe
65                  70                  75                  80

His Leu Cys Leu Val Asp Leu Leu Ala Ala Leu Thr Leu Met Pro Leu
                85                  90                  95

Ala Met Leu Ser Ser Ser Ala Leu Phe Asp His Ala Leu Phe Gly Glu
            100                 105                 110

Val Ala Cys Arg Leu Tyr Leu Phe Leu Ser Val Cys Phe Val Ser Leu
        115                 120                 125

Ala Ile Leu Ser Val Ser Ala Ile Asn Val Glu Arg Tyr Tyr Tyr Val
    130                 135                 140

Val His Pro Met Arg Tyr Glu Val Arg Met Thr Leu Gly Leu Val Ala
145                 150                 155                 160

Ser Val Leu Val Gly Val Trp Val Lys Ala Leu Ala Met Ala Ser Val
                165                 170                 175

Pro Val Leu Gly Arg Val Ser Trp Glu Glu Gly Ala Pro Ser Val Pro
            180                 185                 190

Pro Gly Cys Ser Leu Gln Trp Ser His Ser Ala Tyr Cys Gln Leu Phe
        195                 200                 205

Val Val Val Phe Ala Val Leu Tyr Phe Leu Leu Pro Leu Leu Leu Ile
    210                 215                 220

Leu Val Val Tyr Cys Ser Met Phe Arg Val Ala Arg Val Ala Ala Met
225                 230                 235                 240

Gln His Gly Pro Leu Pro Thr Trp Met Glu Thr Pro Arg Gln Arg Ser
                245                 250                 255

Glu Ser Leu Ser Ser Arg Ser Thr Met Val Thr Ser Ser Gly Ala Pro
            260                 265                 270

Gln Thr Thr Pro His Arg Thr Phe Gly Gly Gly Lys Ala Lys Val Val
        275                 280                 285

Leu Leu Ala Val Gly Gly Gln Phe Leu Leu Cys Trp Leu Pro Tyr Phe
    290                 295                 300

Ser Phe His Leu Tyr Val Ala Leu Ser Ala Gln Pro Ile Ser Thr Gly
305                 310                 315                 320
```

-continued

```
Gln Val Glu Ser Val Val Thr Trp Ile Gly Tyr Phe Cys Phe Thr Ser
                325                 330                 335

Asn Pro Phe Phe Tyr Gly Cys Leu Asn Arg Gln Ile Arg Gly Glu Leu
            340                 345                 350

Ser Lys Gln Phe Val Cys Phe Phe Lys Pro Ala Pro Glu Glu Glu Leu
        355                 360                 365

Arg Leu Pro Ser Arg Glu Gly Ser Ile Glu Glu Asn Phe Leu Gln Phe
    370                 375                 380

Leu Gln Gly Thr Gly Cys Pro Ser Glu Ser Trp Val Ser Arg Pro Leu
385                 390                 395                 400

Pro Ser Pro Lys Gln Glu Pro Pro Ala Val Asp Phe Arg Ile Pro Gly
                405                 410                 415

Gln Ile Ala Glu Glu Thr Ser Glu Phe Leu Glu Gln Gln Leu Thr Ser
            420                 425                 430

Asp Ile Ile Met Ser Asp Ser Tyr Leu Arg Pro Ala Ala Ser Pro Arg
        435                 440                 445

Leu Glu Ser
    450


<210> SEQ ID NO 85
<211> LENGTH: 28
<212> TYPE: DNA
<213> ORGANISM: Homo sapiens

<400> SEQUENCE: 85

caggaaggca aagaccacca tcatcatc                                          28


<210> SEQ ID NO 86
<211> LENGTH: 28
<212> TYPE: DNA
<213> ORGANISM: Homo sapiens

<400> SEQUENCE: 86

gatgatgatg gtggtctttg ccttcctg                                          28


<210> SEQ ID NO 87
<211> LENGTH: 1041
<212> TYPE: DNA
<213> ORGANISM: Homo sapiens

<400> SEQUENCE: 87

atggagagaa aatttatgtc cttgcaacca tccatctccg tatcagaaat ggaaccaaat      60

ggcaccttca gcaataacaa cagcaggaac tgcacaattg aaaacttcaa gagagaattt     120

ttcccaattg tatatctgat aatatttttc tggggagtct tgggaaatgg gttgtccata     180

tatgttttcc tgcagcctta taagaagtcc acatctgtga acgttttcat gctaaatctg     240

gccatttcag atctcctgtt cataagcacg cttcccttca gggctgacta ttatcttaga     300

ggctccaatt ggatatttgg agacctggcc tgcaggatta tgtcttattc cttgtatgtc     360

aacatgtaca gcagtattta tttcctgacc gtgctgagtg ttgtgcgttt cctggcaatg     420

gttcacccct ttcggcttct gcatgtcacc agcatcagga gtgcctggat cctctgtggg     480

atcatatgga tccttatcat ggcttcctca ataatgctcc tggacagtgg ctctgagcag     540

aacggcagtg tcacatcatg cttagagctg aatctctata aaattgctaa gctgcagacc     600

atgaactata ttgccttggt ggtgggctgc ctgctgccat ttttcacact cagcatctgt     660

tatctgctga tcattcgggt tctgttaaaa gtggaggtcc cagaatcggg gctgcgggtt     720
```

-continued

```
tctcacagga aggcaaagac caccatcatc atcaccttga tcatcttctt cttgtgtttc    780

ctgccctatc acacactgag gaccgtccac ttgacgacat ggaaagtggg tttatgcaaa    840

gacagactgc ataaagcttt ggttatcaca ctggccttgg cagcagccaa tgcctgcttc    900

aatcctctgc tctattactt tgctggggag aattttaagg acagactaaa gtctgcactc    960

agaaaaggcc atccacagaa ggcaaagaca aagtgtgttt tccctgttag tgtgtggttg   1020

agaaaggaaa caagagtata a                                              1041


<210> SEQ ID NO 88
<211> LENGTH: 346
<212> TYPE: PRT
<213> ORGANISM: Homo sapiens

<400> SEQUENCE: 88

Met Glu Arg Lys Phe Met Ser Leu Gln Pro Ser Ile Ser Val Ser Glu
1               5                   10                  15

Met Glu Pro Asn Gly Thr Phe Ser Asn Asn Asn Ser Arg Asn Cys Thr
            20                  25                  30

Ile Glu Asn Phe Lys Arg Glu Phe Phe Pro Ile Val Tyr Leu Ile Ile
        35                  40                  45

Phe Phe Trp Gly Val Leu Gly Asn Gly Leu Ser Ile Tyr Val Phe Leu
    50                  55                  60

Gln Pro Tyr Lys Lys Ser Thr Ser Val Asn Val Phe Met Leu Asn Leu
65                  70                  75                  80

Ala Ile Ser Asp Leu Leu Phe Ile Ser Thr Leu Pro Phe Arg Ala Asp
                85                  90                  95

Tyr Tyr Leu Arg Gly Ser Asn Trp Ile Phe Gly Asp Leu Ala Cys Arg
            100                 105                 110

Ile Met Ser Tyr Ser Leu Tyr Val Asn Met Tyr Ser Ser Ile Tyr Phe
        115                 120                 125

Leu Thr Val Leu Ser Val Val Arg Phe Leu Ala Met Val His Pro Phe
    130                 135                 140

Arg Leu Leu His Val Thr Ser Ile Arg Ser Ala Trp Ile Leu Cys Gly
145                 150                 155                 160

Ile Ile Trp Ile Leu Ile Met Ala Ser Ser Ile Met Leu Leu Asp Ser
                165                 170                 175

Gly Ser Glu Gln Asn Gly Ser Val Thr Ser Cys Leu Glu Leu Asn Leu
            180                 185                 190

Tyr Lys Ile Ala Lys Leu Gln Thr Met Asn Tyr Ile Ala Leu Val Val
        195                 200                 205

Gly Cys Leu Leu Pro Phe Phe Thr Leu Ser Ile Cys Tyr Leu Leu Ile
    210                 215                 220

Ile Arg Val Leu Leu Lys Val Glu Val Pro Glu Ser Gly Leu Arg Val
225                 230                 235                 240

Ser His Arg Lys Ala Lys Thr Thr Ile Ile Ile Thr Leu Ile Ile Phe
                245                 250                 255

Phe Leu Cys Phe Leu Pro Tyr His Thr Leu Arg Thr Val His Leu Thr
            260                 265                 270

Thr Trp Lys Val Gly Leu Cys Lys Asp Arg Leu His Lys Ala Leu Val
        275                 280                 285

Ile Thr Leu Ala Leu Ala Ala Ala Asn Ala Cys Phe Asn Pro Leu Leu
    290                 295                 300

Tyr Tyr Phe Ala Gly Glu Asn Phe Lys Asp Arg Leu Lys Ser Ala Leu
305                 310                 315                 320
```

-continued

```
Arg Lys Gly His Pro Gln Lys Ala Lys Thr Lys Cys Val Phe Pro Val
                325                 330                 335

Ser Val Trp Leu Arg Lys Glu Thr Arg Val
            340                 345
```

<210> SEQ ID NO 89
<211> LENGTH: 28
<212> TYPE: DNA
<213> ORGANISM: Artificial Sequence
<220> FEATURE:
<223> OTHER INFORMATION: Novel Sequence

<400> SEQUENCE: 89

```
ccagtgcaaa gctaagaaag tgatcttc                                          28
```

<210> SEQ ID NO 90
<211> LENGTH: 28
<212> TYPE: DNA
<213> ORGANISM: Artificial Sequence
<220> FEATURE:
<223> OTHER INFORMATION: Novel Sequence
<220> FEATURE:
<221> NAME/KEY: misc_feature
<223> OTHER INFORMATION: Novel Sequence

<400> SEQUENCE: 90

```
gaagatcact ttcttagctt tgcactgg                                          28
```

<210> SEQ ID NO 91
<211> LENGTH: 1527
<212> TYPE: DNA
<213> ORGANISM: Homo sapiens

<400> SEQUENCE: 91

```
atgacgtcca cctgcaccaa cagcacgcgc gagagtaaca gcagccacac gtgcatgccc      60

ctctccaaaa tgcccatcag cctggcccac ggcatcatcc gctcaaccgt gctggttatc     120

ttcctcgccg cctctttcgt cggcaacata gtgctggcgc tagtgttgca gcgcaagccg     180

cagctgctgc aggtgaccaa ccgttttatc tttaacctcc tcgtcaccga cctgctgcag     240

atttcgctcg tggccccctg ggtggtggcc acctctgtgc ctctcttctg gcccctcaac     300

agccacttct gcacggccct ggttagcctc acccacctgt tcgccttcgc cagcgtcaac     360

accattgtcg tggtgtcagt ggatcgctac ttgtccatca tccaccctct ctcctacccg     420

tccaagatga cccagcgccg cggttacctg ctcctctatg gcacctggat tgtggccatc     480

ctgcagagca ctcctccact ctacggctgg ggccaggctg cctttgatga gcgcaatgct     540

ctctgctcca tgatctgggg ggccagcccc agctacacta ttctcagcgt ggtgtccttc     600

atcgtcattc cactgattgt catgattgcc tgctactccg tggtgttctg tgcagcccgg     660

aggcagcatg ctctgctgta caatgtcaag agacacagct tggaagtgcg agtcaaggac     720

tgtgtggaga atgaggatga agagggagca gagaagaagg aggagttcca ggatgagagt     780

gagtttcgcc gccagcatga aggtgaggtc aaggccaagg agggcagaat ggaagccaag     840

gacggcagcc tgaaggccaa ggaaggaagc acggggacca gtgagagtag tgtagaggcc     900

aggggcagcg aggaggtcag agagagcagc acggtggcca gcgacggcag catggagggt     960

aaggaaggca gcaccaaagt tgaggagaac agcatgaagg cagacaaggg tcgcacagag    1020

gtcaaccagt gcagcattga cttgggtgaa gatgacatgg agtttggtga agacgacatc    1080

aatttcagtg aggatgacgt cgaggcagtg aacatcccgg agagcctccc acccagtcgt    1140
```

-continued

```
cgtaacagca acagcaaccc tcctctgccc aggtgctacc agtgcaaagc taagaaagtg   1200

atcttcatca tcattttctc ctatgtgcta tccctggggc cctactgctt tttagcagtc   1260

ctggccgtgt gggtggatgt cgaaacccag gtaccccagt gggtgatcac cataatcatc   1320

tggcttttct tcctgcagtg ctgcatccac ccctatgtct atggctacat gcacaagacc   1380

attaagaagg aaatccagga catgctgaag aagttcttct gcaaggaaaa gcccccgaaa   1440

gaagatagcc acccagacct gcccggaaca gagggtggga ctgaaggcaa gattgtccct   1500

tcctacgatt ctgctacttt tccttga                                       1527
```

<210> SEQ ID NO 92
<211> LENGTH: 508
<212> TYPE: PRT
<213> ORGANISM: Homo sapiens

<400> SEQUENCE: 92

```
Met Thr Ser Thr Cys Thr Asn Ser Thr Arg Glu Ser Asn Ser Ser His
1               5                   10                  15

Thr Cys Met Pro Leu Ser Lys Met Pro Ile Ser Leu Ala His Gly Ile
            20                  25                  30

Ile Arg Ser Thr Val Leu Val Ile Phe Leu Ala Ala Ser Phe Val Gly
        35                  40                  45

Asn Ile Val Leu Ala Leu Val Leu Gln Arg Lys Pro Gln Leu Leu Gln
    50                  55                  60

Val Thr Asn Arg Phe Ile Phe Asn Leu Leu Val Thr Asp Leu Leu Gln
65                  70                  75                  80

Ile Ser Leu Val Ala Pro Trp Val Val Ala Thr Ser Val Pro Leu Phe
                85                  90                  95

Trp Pro Leu Asn Ser His Phe Cys Thr Ala Leu Val Ser Leu Thr His
            100                 105                 110

Leu Phe Ala Phe Ala Ser Val Asn Thr Ile Val Val Val Ser Val Asp
        115                 120                 125

Arg Tyr Leu Ser Ile Ile His Pro Leu Ser Tyr Pro Ser Lys Met Thr
    130                 135                 140

Gln Arg Arg Gly Tyr Leu Leu Leu Tyr Gly Thr Trp Ile Val Ala Ile
145                 150                 155                 160

Leu Gln Ser Thr Pro Pro Leu Tyr Gly Trp Gly Gln Ala Ala Phe Asp
                165                 170                 175

Glu Arg Asn Ala Leu Cys Ser Met Ile Trp Gly Ala Ser Pro Ser Tyr
            180                 185                 190

Thr Ile Leu Ser Val Val Ser Phe Ile Val Ile Pro Leu Ile Val Met
        195                 200                 205

Ile Ala Cys Tyr Ser Val Val Phe Cys Ala Ala Arg Arg Gln His Ala
    210                 215                 220

Leu Leu Tyr Asn Val Lys Arg His Ser Leu Glu Val Arg Val Lys Asp
225                 230                 235                 240

Cys Val Glu Asn Glu Asp Glu Glu Gly Ala Glu Lys Lys Glu Glu Phe
                245                 250                 255

Gln Asp Glu Ser Glu Phe Arg Arg Gln His Glu Gly Glu Val Lys Ala
            260                 265                 270

Lys Glu Gly Arg Met Glu Ala Lys Asp Gly Ser Leu Lys Ala Lys Glu
        275                 280                 285

Gly Ser Thr Gly Thr Ser Glu Ser Ser Val Glu Ala Arg Gly Ser Glu
    290                 295                 300
```

-continued

```
Glu Val Arg Glu Ser Ser Thr Val Ala Ser Asp Gly Ser Met Glu Gly
305                 310                 315                 320

Lys Glu Gly Ser Thr Lys Val Glu Glu Asn Ser Met Lys Ala Asp Lys
                325                 330                 335

Gly Arg Thr Glu Val Asn Gln Cys Ser Ile Asp Leu Gly Glu Asp Asp
            340                 345                 350

Met Glu Phe Gly Glu Asp Asp Ile Asn Phe Ser Glu Asp Asp Val Glu
        355                 360                 365

Ala Val Asn Ile Pro Glu Ser Leu Pro Pro Ser Arg Arg Asn Ser Asn
    370                 375                 380

Ser Asn Pro Pro Leu Pro Arg Cys Tyr Gln Cys Lys Ala Lys Lys Val
385                 390                 395                 400

Ile Phe Ile Ile Ile Phe Ser Tyr Val Leu Ser Leu Gly Pro Tyr Cys
                405                 410                 415

Phe Leu Ala Val Leu Ala Val Trp Val Asp Val Glu Thr Gln Val Pro
            420                 425                 430

Gln Trp Val Ile Thr Ile Ile Ile Trp Leu Phe Phe Leu Gln Cys Cys
        435                 440                 445

Ile His Pro Tyr Val Tyr Gly Tyr Met His Lys Thr Ile Lys Lys Glu
    450                 455                 460

Ile Gln Asp Met Leu Lys Lys Phe Phe Cys Lys Glu Lys Pro Pro Lys
465                 470                 475                 480

Glu Asp Ser His Pro Asp Leu Pro Gly Thr Glu Gly Gly Thr Glu Gly
                485                 490                 495

Lys Ile Val Pro Ser Tyr Asp Ser Ala Thr Phe Pro
            500                 505
```

<210> SEQ ID NO 93
<211> LENGTH: 29
<212> TYPE: DNA
<213> ORGANISM: Artificial Sequence
<220> FEATURE:
<223> OTHER INFORMATION: Novel Sequence

<400> SEQUENCE: 93
gccgccaccg cgccaagagg aagattggc 29

<210> SEQ ID NO 94
<211> LENGTH: 29
<212> TYPE: DNA
<213> ORGANISM: Artificial Sequence
<220> FEATURE:
<223> OTHER INFORMATION: Novel Sequence

<400> SEQUENCE: 94
gccaatcttc ctcttggcgc ggtggcggc 29

<210> SEQ ID NO 95
<211> LENGTH: 1092
<212> TYPE: DNA
<213> ORGANISM: Homo sapiens

<400> SEQUENCE: 95
atgggccccg gcgaggcgct gctggcgggt ctcctggtga tggtactggc cgtggcgctg 60
ctatccaacg cactggtgct gctttgttgc gcctacagcg ctgagctccg cactcgagcc 120
tcaggcgtcc tcctggtgaa tctgtcgctg ggccacctgc tgctggcggc gctggacatg 180
cccttcacgc tgctcggtgt gatgcgcggg cggacaccgt cggcgcccgg cgcatgccaa 240

-continued

```
gtcattggct tcctggacac cttcctggcg tccaacgcgg cgctgagcgt ggcggcgctg    300

agcgcagacc agtggctggc agtgggcttc ccactgcgct acgccggacg cctgcgaccg    360

cgctatgccg gcctgctgct gggctgtgcc tggggacagt cgctggcctt ctcaggcgct    420

gcacttggct gctcgtggct tggctacagc agcgccttcg cgtcctgttc gctgcgcctg    480

ccgcccgagc ctgagcgtcc gcgcttcgca gccttcaccg ccacgctcca tgccgtgggc    540

ttcgtgctgc cgctggcggt gctctgcctc acctcgctcc aggtgcaccg ggtggcacgc    600

agccactgcc agcgcatgga caccgtcacc atgaaggcgc tcgcgctgct cgccgacctg    660

caccccagtg tgcggcagcg ctgcctcatc cagcagaagc ggcgccgcca ccgcgccacc    720

aggaagattg gcattgctat tgcgaccttc ctcatctgct ttgccccgta tgtcatgacc    780

aggctggcgg agctcgtgcc cttcgtcacc gtgaacgccc agaagggcat cctcagcaag    840

tgcctgacct acagcaaggc ggtggccgac ccgttcacgt actctctgct ccgccggccg    900

ttccgccaag tcctggccgg catggtgcac cggctgctga agagaacccc gcgcccagca    960

tccacccatg acagctctct ggatgtggcc ggcatggtgc accagctgct gaagagaacc   1020

ccgcgcccag cgtccaccca caacggctct gtggacacag agaatgattc ctgcctgcag   1080

cagacacact ga                                                       1092
```

<210> SEQ ID NO 96
<211> LENGTH: 363
<212> TYPE: PRT
<213> ORGANISM: Homo sapiens

<400> SEQUENCE: 96

```
Met Gly Pro Gly Glu Ala Leu Leu Ala Gly Leu Leu Val Met Val Leu
1               5                   10                  15

Ala Val Ala Leu Leu Ser Asn Ala Leu Val Leu Leu Cys Cys Ala Tyr
            20                  25                  30

Ser Ala Glu Leu Arg Thr Arg Ala Ser Gly Val Leu Leu Val Asn Leu
        35                  40                  45

Ser Leu Gly His Leu Leu Leu Ala Ala Leu Asp Met Pro Phe Thr Leu
    50                  55                  60

Leu Gly Val Met Arg Gly Arg Thr Pro Ser Ala Pro Gly Ala Cys Gln
65                  70                  75                  80

Val Ile Gly Phe Leu Asp Thr Phe Leu Ala Ser Asn Ala Ala Leu Ser
                85                  90                  95

Val Ala Ala Leu Ser Ala Asp Gln Trp Leu Ala Val Gly Phe Pro Leu
            100                 105                 110

Arg Tyr Ala Gly Arg Leu Arg Pro Arg Tyr Ala Gly Leu Leu Leu Gly
        115                 120                 125

Cys Ala Trp Gly Gln Ser Leu Ala Phe Ser Gly Ala Ala Leu Gly Cys
    130                 135                 140

Ser Trp Leu Gly Tyr Ser Ser Ala Phe Ala Ser Cys Ser Leu Arg Leu
145                 150                 155                 160

Pro Pro Glu Pro Glu Arg Pro Arg Phe Ala Ala Phe Thr Ala Thr Leu
                165                 170                 175

His Ala Val Gly Phe Val Leu Pro Leu Ala Val Leu Cys Leu Thr Ser
            180                 185                 190

Leu Gln Val His Arg Val Ala Arg Ser His Cys Gln Arg Met Asp Thr
        195                 200                 205

Val Thr Met Lys Ala Leu Ala Leu Leu Ala Asp Leu His Pro Ser Val
    210                 215                 220
```

-continued

```
Arg Gln Arg Cys Leu Ile Gln Gln Lys Arg Arg Arg His Arg Ala Thr
225                 230                 235                 240

Arg Lys Ile Gly Ile Ala Ile Ala Thr Phe Leu Ile Cys Phe Ala Pro
                245                 250                 255

Tyr Val Met Thr Arg Leu Ala Glu Leu Val Pro Phe Val Thr Val Asn
            260                 265                 270

Ala Gln Lys Gly Ile Leu Ser Lys Cys Leu Thr Tyr Ser Lys Ala Val
        275                 280                 285

Ala Asp Pro Phe Thr Tyr Ser Leu Leu Arg Arg Pro Phe Arg Gln Val
    290                 295                 300

Leu Ala Gly Met Val His Arg Leu Leu Lys Arg Thr Pro Arg Pro Ala
305                 310                 315                 320

Ser Thr His Asp Ser Ser Leu Asp Val Ala Gly Met Val His Gln Leu
                325                 330                 335

Leu Lys Arg Thr Pro Arg Pro Ala Ser Thr His Asn Gly Ser Val Asp
            340                 345                 350

Thr Glu Asn Asp Ser Cys Leu Gln Gln Thr His
        355                 360
```

<210> SEQ ID NO 97
<211> LENGTH: 34
<212> TYPE: DNA
<213> ORGANISM: Artificial Sequence
<220> FEATURE:
<223> OTHER INFORMATION: Novel Sequence

<400> SEQUENCE: 97
gatctctaga atggagtcct cacccatccc ccag 34

<210> SEQ ID NO 98
<211> LENGTH: 36
<212> TYPE: DNA
<213> ORGANISM: Artificial Sequence
<220> FEATURE:
<223> OTHER INFORMATION: Novel Sequence

<400> SEQUENCE: 98
gatcgatatc cgtgactcca gccggggtga ggcggc 36

<210> SEQ ID NO 99
<211> LENGTH: 2610
<212> TYPE: DNA
<213> ORGANISM: Homo sapiens and Rat

<400> SEQUENCE: 99

```
atggagtcct cacccatccc ccagtcatca gggaactctt ccactttggg gagggtccct     60

caaaccccag gtccctctac tgccagtggg gtcccggagg tggggctacg ggatgttgct    120

tcggaatctg tggccctctt cttcatgctc ctgctggact tgactgctgt ggctggcaat    180

gccgctgtga tggccgtgat cgccaagacg cctgccctcc gaaaatttgt cttcgtcttc    240

cacctctgcc tggtggacct gctggctgcc ctgaccctca tgcccctggc catgctctcc    300

agctctgccc tctttgacca cgccctcttt ggggaggtgg cctgccgcct ctacttgttt    360

ctgagcgtgt gctttgtcag cctggccatc ctctcggtgt cagccatcaa tgtggagcgc    420

tactattacg tagtccaccc catgcgctac gaggtgcgca tgacgctggg gctggtggcc    480

tctgtgctgg tgggtgtgtg ggtgaaggcc ttggccatgg cttctgtgcc agtgttggga    540

agggtctcct gggaggaagg agctcccagt gtcccccag gctgttcact ccagtggagc    600
```

-continued

```
cacagtgcct actgccagct ttttgtggtg gtctttgctg tcctttactt tctgttgccc    660
ctgctcctca tacttgtggt ctactgcagc atgttccgag tggcccgcgt ggctgccatg    720
cagcacgggc cgctgcccac gtggatggag acaccccggc aacgctccga atctctcagc    780
agccgctcca cgatggtcac cagctcgggg gccccccaga ccaccccaca ccggacgttt    840
gggggaggga aagcagcagt ggttctcctg gctgtggggg gacagttcct gctctgttgg    900
ttgccctact tctctttcca cctctatgtt gccctgagtg ctcagcccat ttcaactggg    960
caggtggaga gtgtggtcac ctggattggc tacttttgct tcacttccaa ccctttcttc   1020
tatggatgtc tcaaccggca gatccggggg gagctcagca agcagtttgt ctgcttcttc   1080
aagccagctc cagaggagga gctgaggctg cctagccggg agggctccat tgaggagaac   1140
ttcctgcagt tccttcaggg gactggctgt ccttctgagt cctgggtttc ccgacccta    1200
cccagcccca agcaggagcc acctgctgtt gactttcgaa tcccaggcca gatagctgag   1260
gagacctctg agttcctgga gcagcaactc accagcgaca tcatcatgtc agacagctac   1320
ctccgtcctg ccgcctcacc ccggctggag tcagcgatat ctgcagaatt ccaccacact   1380
ggactagtgg atccgagctc ggtaccaagc ttgggctgca ggtcgatggg ctgcctcggc   1440
aacagtaaga ccgaggacca gcgcaacgag gagaaggcgc agcgcgaggc caacaaaaag   1500
atcgagaagc agctgcagaa ggacaagcag gtctaccggg ccacgcaccg cctgctgctg   1560
ctgggtgctg gagagtctgg caaaagcacc attgtgaagc agatgaggat cctacatgtt   1620
aatgggttta acggagaggg cggcgaagag gacccgcagg ctgcaaggag caacagcgat   1680
ggtgagaagg ccaccaaagt gcaggacatc aaaaacaacc tgaaggaggc cattgaaacc   1740
attgtggccg ccatgagcaa cctggtgccc cccgtggagc tggccaaccc tgagaaccag   1800
ttcagagtgg actacattct gagcgtgatg aacgtgccaa actttgactt cccacctgaa   1860
ttctatgagc atgccaaggc tctgtgggag gatgagggag ttcgtgcctg ctacgagcgc   1920
tccaacgagt accagctgat cgactgtgcc cagtacttcc tggacaagat tgatgtgatc   1980
aagcaggccg actacgtgcc aagtgaccag gacctgcttc gctgccgcgt cctgacctct   2040
ggaatctttg agaccaagtt ccaggtggac aaagtcaact tccacatgtt cgatgtgggc   2100
ggccagcgcg atgaacgccg caagtggatc cagtgcttca atgatgtgac tgccatcatc   2160
ttcgtggtgg ccagcagcag ctacaacatg gtcatccggg aggacaacca gaccaaccgt   2220
ctgcaggagg ctctgaacct cttcaagagc atctggaaca acagatggct gcgtaccatc   2280
tctgtgatcc tcttcctcaa caagcaagat ctgcttgctg agaaggtcct cgctgggaaa   2340
tcgaagattg aggactactt tccagagttc gctcgctaca ccactcctga ggatgcgact   2400
cccgagcccg gagaggaccc acgcgtgacc cgggccaagt acttcatccg ggatgagttt   2460
ctgagaatca gcactgctag tggagatgga cgtcactact gctaccctca ctttacctgc   2520
gccgtggaca ctgagaacat ccgccgtgtc ttcaacgact gccgtgacat catccagcgc   2580
atgcatcttc gccaatacga gctgctctaa                                    2610
```

<210> SEQ ID NO 100
<211> LENGTH: 869
<212> TYPE: PRT
<213> ORGANISM: Homo sapiens and Rat

<400> SEQUENCE: 100

```
Met Glu Ser Ser Pro Ile Pro Gln Ser Ser Gly Asn Ser Ser Thr Leu
1               5                   10                  15
```

-continued

```
Gly Arg Val Pro Gln Thr Pro Gly Pro Ser Thr Ala Ser Gly Val Pro
            20                  25                  30

Glu Val Gly Leu Arg Asp Val Ala Ser Glu Ser Val Ala Leu Phe Phe
        35                  40                  45

Met Leu Leu Leu Asp Leu Thr Ala Val Ala Gly Asn Ala Ala Val Met
    50                  55                  60

Ala Val Ile Ala Lys Thr Pro Ala Leu Arg Lys Phe Val Phe Val Phe
65                  70                  75                  80

His Leu Cys Leu Val Asp Leu Leu Ala Ala Leu Thr Leu Met Pro Leu
                85                  90                  95

Ala Met Leu Ser Ser Ser Ala Leu Phe Asp His Ala Leu Phe Gly Glu
            100                 105                 110

Val Ala Cys Arg Leu Tyr Leu Phe Leu Ser Val Cys Phe Val Ser Leu
        115                 120                 125

Ala Ile Leu Ser Val Ser Ala Ile Asn Val Glu Arg Tyr Tyr Tyr Val
    130                 135                 140

Val His Pro Met Arg Tyr Glu Val Arg Met Thr Leu Gly Leu Val Ala
145                 150                 155                 160

Ser Val Leu Val Gly Val Trp Val Lys Ala Leu Ala Met Ala Ser Val
                165                 170                 175

Pro Val Leu Gly Arg Val Ser Trp Glu Glu Gly Ala Pro Ser Val Pro
            180                 185                 190

Pro Gly Cys Ser Leu Gln Trp Ser His Ser Ala Tyr Cys Gln Leu Phe
        195                 200                 205

Val Val Val Phe Ala Val Leu Tyr Phe Leu Leu Pro Leu Leu Leu Ile
    210                 215                 220

Leu Val Val Tyr Cys Ser Met Phe Arg Val Ala Arg Val Ala Ala Met
225                 230                 235                 240

Gln His Gly Pro Leu Pro Thr Trp Met Glu Thr Pro Arg Gln Arg Ser
                245                 250                 255

Glu Ser Leu Ser Ser Arg Ser Thr Met Val Thr Ser Ser Gly Ala Pro
            260                 265                 270

Gln Thr Thr Pro His Arg Thr Phe Gly Gly Gly Lys Ala Ala Val Val
        275                 280                 285

Leu Leu Ala Val Gly Gly Gln Phe Leu Leu Cys Trp Leu Pro Tyr Phe
    290                 295                 300

Ser Phe His Leu Tyr Val Ala Leu Ser Ala Gln Pro Ile Ser Thr Gly
305                 310                 315                 320

Gln Val Glu Ser Val Val Thr Trp Ile Gly Tyr Phe Cys Phe Thr Ser
                325                 330                 335

Asn Pro Phe Phe Tyr Gly Cys Leu Asn Arg Gln Ile Arg Gly Glu Leu
            340                 345                 350

Ser Lys Gln Phe Val Cys Phe Phe Lys Pro Ala Pro Glu Glu Glu Leu
        355                 360                 365

Arg Leu Pro Ser Arg Glu Gly Ser Ile Glu Glu Asn Phe Leu Gln Phe
    370                 375                 380

Leu Gln Gly Thr Gly Cys Pro Ser Glu Ser Trp Val Ser Arg Pro Leu
385                 390                 395                 400

Pro Ser Pro Lys Gln Glu Pro Pro Ala Val Asp Phe Arg Ile Pro Gly
                405                 410                 415

Gln Ile Ala Glu Glu Thr Ser Glu Phe Leu Glu Gln Gln Leu Thr Ser
            420                 425                 430
```

-continued

```
Asp Ile Ile Met Ser Asp Ser Tyr Leu Arg Pro Ala Ala Ser Pro Arg
        435                 440                 445

Leu Glu Ser Ala Ile Ser Ala Glu Phe His His Thr Gly Leu Val Asp
    450                 455                 460

Pro Ser Ser Val Pro Ser Leu Gly Cys Arg Ser Met Gly Cys Leu Gly
465                 470                 475                 480

Asn Ser Lys Thr Glu Asp Gln Arg Asn Glu Glu Lys Ala Gln Arg Glu
                485                 490                 495

Ala Asn Lys Lys Ile Glu Lys Gln Leu Gln Lys Asp Lys Gln Val Tyr
            500                 505                 510

Arg Ala Thr His Arg Leu Leu Leu Leu Gly Ala Gly Glu Ser Gly Lys
        515                 520                 525

Ser Thr Ile Val Lys Gln Met Arg Ile Leu His Val Asn Gly Phe Asn
    530                 535                 540

Gly Glu Gly Gly Glu Glu Asp Pro Gln Ala Ala Arg Ser Asn Ser Asp
545                 550                 555                 560

Gly Glu Lys Ala Thr Lys Val Gln Asp Ile Lys Asn Asn Leu Lys Glu
                565                 570                 575

Ala Ile Glu Thr Ile Val Ala Ala Met Ser Asn Leu Val Pro Pro Val
            580                 585                 590

Glu Leu Ala Asn Pro Glu Asn Gln Phe Arg Val Asp Tyr Ile Leu Ser
        595                 600                 605

Val Met Asn Val Pro Asn Phe Asp Phe Pro Pro Glu Phe Tyr Glu His
    610                 615                 620

Ala Lys Ala Leu Trp Glu Asp Glu Gly Val Arg Ala Cys Tyr Glu Arg
625                 630                 635                 640

Ser Asn Glu Tyr Gln Leu Ile Asp Cys Ala Gln Tyr Phe Leu Asp Lys
                645                 650                 655

Ile Asp Val Ile Lys Gln Ala Asp Tyr Val Pro Ser Asp Gln Asp Leu
            660                 665                 670

Leu Arg Cys Arg Val Leu Thr Ser Gly Ile Phe Glu Thr Lys Phe Gln
        675                 680                 685

Val Asp Lys Val Asn Phe His Met Phe Asp Val Gly Gly Gln Arg Asp
    690                 695                 700

Glu Arg Arg Lys Trp Ile Gln Cys Phe Asn Asp Val Thr Ala Ile Ile
705                 710                 715                 720

Phe Val Val Ala Ser Ser Ser Tyr Asn Met Val Ile Arg Glu Asp Asn
                725                 730                 735

Gln Thr Asn Arg Leu Gln Glu Ala Leu Asn Leu Phe Lys Ser Ile Trp
            740                 745                 750

Asn Asn Arg Trp Leu Arg Thr Ile Ser Val Ile Leu Phe Leu Asn Lys
        755                 760                 765

Gln Asp Leu Leu Ala Glu Lys Val Leu Ala Gly Lys Ser Lys Ile Glu
    770                 775                 780

Asp Tyr Phe Pro Glu Phe Ala Arg Tyr Thr Thr Pro Glu Asp Ala Thr
785                 790                 795                 800

Pro Glu Pro Gly Glu Asp Pro Arg Val Thr Arg Ala Lys Tyr Phe Ile
                805                 810                 815

Arg Asp Glu Phe Leu Arg Ile Ser Thr Ala Ser Gly Asp Gly Arg His
            820                 825                 830

Tyr Cys Tyr Pro His Phe Thr Cys Ala Val Asp Thr Glu Asn Ile Arg
        835                 840                 845
```

-continued

```
Arg Val Phe Asn Asp Cys Arg Asp Ile Ile Gln Arg Met His Leu Arg
    850                 855                 860

Gln Tyr Glu Leu Leu
865


<210> SEQ ID NO 101
<211> LENGTH: 30
<212> TYPE: DNA
<213> ORGANISM: Artificial Sequence
<220> FEATURE:
<223> OTHER INFORMATION: Novel Sequence

<400> SEQUENCE: 101

tctagaatga cgtccacctg caccaacagc                                    30


<210> SEQ ID NO 102
<211> LENGTH: 34
<212> TYPE: DNA
<213> ORGANISM: Artificial Sequence
<220> FEATURE:
<223> OTHER INFORMATION: Novel Sequence

<400> SEQUENCE: 102

gatatcgcag gaaaagtagc agaatcgtag gaag                               34


<210> SEQ ID NO 103
<211> LENGTH: 2781
<212> TYPE: DNA
<213> ORGANISM: Homo Sapiens and Rat

<400> SEQUENCE: 103

atgacgtcca cctgcaccaa cagcacgcgc gagagtaaca gcagccacac gtgcatgccc     60

ctctccaaaa tgcccatcag cctggcccac ggcatcatcc gctcaaccgt gctggttatc    120

ttcctcgccg cctctttcgt cggcaacata gtgctggcgc tagtgttgca gcgcaagccg    180

cagctgctgc aggtgaccaa ccgttttatc tttaacctcc tcgtcaccga cctgctgcag    240

atttcgctcg tggccccctg ggtggtggcc acctctgtgc ctctcttctg gcccctcaac    300

agccacttct gcacggccct ggttagcctc acccacctgt tcgccttcgc cagcgtcaac    360

accattgtcg tggtgtcagt ggatcgctac ttgtccatca tccaccctct ctcctacccg    420

tccaagatga cccagcgccg cggttacctg ctcctctatg gcacctggat tgtggccatc    480

ctgcagagca ctcctccact ctacggctgg ggccaggctg cctttgatga gcgcaatgct    540

ctctgctcca tgatctgggg ggccagcccc agctacacta ttctcagcgt ggtgtccttc    600

atcgtcattc cactgattgt catgattgcc tgctactccg tggtgttctg tgcagcccgg    660

aggcagcatg ctctgctgta caatgtcaag agacacagct tggaagtgcg agtcaaggac    720

tgtgtggaga atgaggatga agagggagca gagaagaagg aggagttcca ggatgagagt    780

gagtttcgcc gccagcatga aggtgaggtc aaggccaagg agggcagaat ggaagccaag    840

gacggcagcc tgaaggccaa ggaaggaagc acggggacca gtgagagtag tgtagaggcc    900

aggggcagcg aggaggtcag agagagcagc acggtggcca gcgacggcag catggagggt    960

aaggaaggca gcaccaaagt tgaggagaac agcatgaagg cagacaaggg tcgcacagag   1020

gtcaaccagt gcagcattga cttgggtgaa gatgacatgg agtttggtga agacgacatc   1080

aatttcagtg aggatgacgt cgaggcagtg aacatcccgg agagcctccc acccagtcgt   1140

cgtaacagca acagcaaccc tcctctgccc aggtgctacc agtgcaaagc tgctaaagtg   1200

atcttcatca tcattttctc ctatgtgcta tccctggggc cctactgctt tttagcagtc   1260
```

-continued

```
ctggccgtgt gggtggatgt cgaaacccag gtaccccagt gggtgatcac cataatcatc   1320

tggcttttct tcctgcagtg ctgcatccac ccctatgtct atggctacat gcacaagacc   1380

attaagaagg aaatccagga catgctgaag aagttcttct gcaaggaaaa gcccccgaaa   1440

gaagatagcc acccagacct gcccggaaca gagggtggga ctgaaggcaa gattgtccct   1500

tcctacgatt ctgctacttt tcctgcgata tctgcagaat tccaccacac tggactagtg   1560

gatccgagct cggtaccaag cttgggctgc aggtcgatgg gctgcctcgg caacagtaag   1620

accgaggacc agcgcaacga ggagaaggcg cagcgcgagg ccaacaaaaa gatcgagaag   1680

cagctgcaga aggacaagca ggtctaccgg gccacgcacc gcctgctgct gctgggtgct   1740

ggagagtctg gcaaaagcac cattgtgaag cagatgagga tcctacatgt taatgggttt   1800

aacggagagg gcggcgaaga ggacccgcag gctgcaagga gcaacagcga tggtgagaag   1860

gccaccaaag tgcaggacat caaaaacaac ctgaaggagg ccattgaaac cattgtggcc   1920

gccatgagca acctggtgcc ccccgtggag ctggccaacc ctgagaacca gttcagagtg   1980

gactacattc tgagcgtgat gaacgtgcca aactttgact tcccacctga attctatgag   2040

catgccaagg ctctgtggga ggatgaggga gttcgtgcct gctacgagcg ctccaacgag   2100

taccagctga tcgactgtgc ccagtacttc ctggacaaga ttgatgtgat caagcaggcc   2160

gactacgtgc caagtgacca ggacctgctt cgctgccgcg tcctgacctc tggaatcttt   2220

gagaccaagt tccaggtgga caaagtcaac ttccacatgt tcgatgtggg cggccagcgc   2280

gatgaacgcc gcaagtggat ccagtgcttc aatgatgtga ctgccatcat cttcgtggtg   2340

gccagcagca gctacaacat ggtcatccgg gaggacaacc agaccaaccg tctgcaggag   2400

gctctgaacc tcttcaagag catctggaac aacagatggc tgcgtaccat ctctgtgatc   2460

ctcttcctca acaagcaaga tctgcttgct gagaaggtcc tcgctgggaa atcgaagatt   2520

gaggactact ttccagagtt cgctcgctac accactcctg aggatgcgac tcccgagccc   2580

ggagaggacc cacgcgtgac ccgggccaag tacttcatcc gggatgagtt tctgagaatc   2640

agcactgcta gtggagatgg acgtcactac tgctaccctc actttacctg cgccgtggac   2700

actgagaaca tccgccgtgt cttcaacgac tgccgtgaca tcatccagcg catgcatctt   2760

cgccaatacg agctgctcta a                                             2781
```

<210> SEQ ID NO 104
<211> LENGTH: 926
<212> TYPE: PRT
<213> ORGANISM: Homo sapiens and Rat

<400> SEQUENCE: 104

```
Met Thr Ser Thr Cys Thr Asn Ser Thr Arg Glu Ser Asn Ser Ser His
1               5                   10                  15

Thr Cys Met Pro Leu Ser Lys Met Pro Ile Ser Leu Ala His Gly Ile
            20                  25                  30

Ile Arg Ser Thr Val Leu Val Ile Phe Leu Ala Ala Ser Phe Val Gly
        35                  40                  45

Asn Ile Val Leu Ala Leu Val Leu Gln Arg Lys Pro Gln Leu Leu Gln
    50                  55                  60

Val Thr Asn Arg Phe Ile Phe Asn Leu Leu Val Thr Asp Leu Leu Gln
65                  70                  75                  80

Ile Ser Leu Val Ala Pro Trp Val Val Ala Thr Ser Val Pro Leu Phe
                85                  90                  95
```

-continued

```
Trp Pro Leu Asn Ser His Phe Cys Thr Ala Leu Val Ser Leu Thr His
            100                 105                 110

Leu Phe Ala Phe Ala Ser Val Asn Thr Ile Val Val Val Ser Val Asp
        115                 120                 125

Arg Tyr Leu Ser Ile Ile His Pro Leu Ser Tyr Pro Ser Lys Met Thr
    130                 135                 140

Gln Arg Arg Gly Tyr Leu Leu Leu Tyr Gly Thr Trp Ile Val Ala Ile
145                 150                 155                 160

Leu Gln Ser Thr Pro Pro Leu Tyr Gly Trp Gly Gln Ala Ala Phe Asp
                165                 170                 175

Glu Arg Asn Ala Leu Cys Ser Met Ile Trp Gly Ala Ser Pro Ser Tyr
            180                 185                 190

Thr Ile Leu Ser Val Val Ser Phe Ile Val Ile Pro Leu Ile Val Met
        195                 200                 205

Ile Ala Cys Tyr Ser Val Val Phe Cys Ala Ala Arg Arg Gln His Ala
    210                 215                 220

Leu Leu Tyr Asn Val Lys Arg His Ser Leu Glu Val Arg Val Lys Asp
225                 230                 235                 240

Cys Val Glu Asn Glu Asp Glu Glu Gly Ala Glu Lys Lys Glu Glu Phe
                245                 250                 255

Gln Asp Glu Ser Glu Phe Arg Arg Gln His Glu Gly Glu Val Lys Ala
            260                 265                 270

Lys Glu Gly Arg Met Glu Ala Lys Asp Gly Ser Leu Lys Ala Lys Glu
        275                 280                 285

Gly Ser Thr Gly Thr Ser Glu Ser Ser Val Glu Ala Arg Gly Ser Glu
    290                 295                 300

Glu Val Arg Glu Ser Ser Thr Val Ala Ser Asp Gly Ser Met Glu Gly
305                 310                 315                 320

Lys Glu Gly Ser Thr Lys Val Glu Glu Asn Ser Met Lys Ala Asp Lys
                325                 330                 335

Gly Arg Thr Glu Val Asn Gln Cys Ser Ile Asp Leu Gly Glu Asp Asp
            340                 345                 350

Met Glu Phe Gly Glu Asp Asp Ile Asn Phe Ser Glu Asp Asp Val Glu
        355                 360                 365

Ala Val Asn Ile Pro Glu Ser Leu Pro Pro Ser Arg Arg Asn Ser Asn
    370                 375                 380

Ser Asn Pro Pro Leu Pro Arg Cys Tyr Gln Cys Lys Ala Ala Lys Val
385                 390                 395                 400

Ile Phe Ile Ile Ile Phe Ser Tyr Val Leu Ser Leu Gly Pro Tyr Cys
                405                 410                 415

Phe Leu Ala Val Leu Ala Val Trp Val Asp Val Glu Thr Gln Val Pro
            420                 425                 430

Gln Trp Val Ile Thr Ile Ile Ile Trp Leu Phe Phe Leu Gln Cys Cys
        435                 440                 445

Ile His Pro Tyr Val Tyr Gly Tyr Met His Lys Thr Ile Lys Lys Glu
    450                 455                 460

Ile Gln Asp Met Leu Lys Lys Phe Phe Cys Lys Glu Lys Pro Pro Lys
465                 470                 475                 480

Glu Asp Ser His Pro Asp Leu Pro Gly Thr Glu Gly Gly Thr Glu Gly
                485                 490                 495

Lys Ile Val Pro Ser Tyr Asp Ser Ala Thr Phe Pro Ala Ile Ser Ala
            500                 505                 510
```

-continued

```
Glu Phe His His Thr Gly Leu Val Asp Pro Ser Ser Val Pro Ser Leu
        515                 520                 525

Gly Cys Arg Ser Met Gly Cys Leu Gly Asn Ser Lys Thr Glu Asp Gln
    530                 535                 540

Arg Asn Glu Glu Lys Ala Gln Arg Glu Ala Asn Lys Lys Ile Glu Lys
545                 550                 555                 560

Gln Leu Gln Lys Asp Lys Gln Val Tyr Arg Ala Thr His Arg Leu Leu
                565                 570                 575

Leu Leu Gly Ala Gly Glu Ser Gly Lys Ser Thr Ile Val Lys Gln Met
            580                 585                 590

Arg Ile Leu His Val Asn Gly Phe Asn Gly Glu Gly Gly Glu Glu Asp
        595                 600                 605

Pro Gln Ala Ala Arg Ser Asn Ser Asp Gly Glu Lys Ala Thr Lys Val
    610                 615                 620

Gln Asp Ile Lys Asn Asn Leu Lys Glu Ala Ile Glu Thr Ile Val Ala
625                 630                 635                 640

Ala Met Ser Asn Leu Val Pro Pro Val Glu Leu Ala Asn Pro Glu Asn
                645                 650                 655

Gln Phe Arg Val Asp Tyr Ile Leu Ser Val Met Asn Val Pro Asn Phe
            660                 665                 670

Asp Phe Pro Pro Glu Phe Tyr Glu His Ala Lys Ala Leu Trp Glu Asp
        675                 680                 685

Glu Gly Val Arg Ala Cys Tyr Glu Arg Ser Asn Glu Tyr Gln Leu Ile
    690                 695                 700

Asp Cys Ala Gln Tyr Phe Leu Asp Lys Ile Asp Val Ile Lys Gln Ala
705                 710                 715                 720

Asp Tyr Val Pro Ser Asp Gln Asp Leu Leu Arg Cys Arg Val Leu Thr
                725                 730                 735

Ser Gly Ile Phe Glu Thr Lys Phe Gln Val Asp Lys Val Asn Phe His
            740                 745                 750

Met Phe Asp Val Gly Gly Gln Arg Asp Glu Arg Arg Lys Trp Ile Gln
        755                 760                 765

Cys Phe Asn Asp Val Thr Ala Ile Ile Phe Val Val Ala Ser Ser Ser
    770                 775                 780

Tyr Asn Met Val Ile Arg Glu Asp Asn Gln Thr Asn Arg Leu Gln Glu
785                 790                 795                 800

Ala Leu Asn Leu Phe Lys Ser Ile Trp Asn Asn Arg Trp Leu Arg Thr
                805                 810                 815

Ile Ser Val Ile Leu Phe Leu Asn Lys Gln Asp Leu Leu Ala Glu Lys
            820                 825                 830

Val Leu Ala Gly Lys Ser Lys Ile Glu Asp Tyr Phe Pro Glu Phe Ala
        835                 840                 845

Arg Tyr Thr Thr Pro Glu Asp Ala Thr Pro Glu Pro Gly Glu Asp Pro
    850                 855                 860

Arg Val Thr Arg Ala Lys Tyr Phe Ile Arg Asp Glu Phe Leu Arg Ile
865                 870                 875                 880

Ser Thr Ala Ser Gly Asp Gly Arg His Tyr Cys Tyr Pro His Phe Thr
                885                 890                 895

Cys Ala Val Asp Thr Glu Asn Ile Arg Arg Val Phe Asn Asp Cys Arg
            900                 905                 910

Asp Ile Ile Gln Arg Met His Leu Arg Gln Tyr Glu Leu Leu
        915                 920                 925
```

-continued

<210> SEQ ID NO 105
<211> LENGTH: 23
<212> TYPE: DNA
<213> ORGANISM: Artificial Sequence
<220> FEATURE:
<223> OTHER INFORMATION: Novel Sequence

<400> SEQUENCE: 105
catgtatgcc agcgtcctgc tcc 23

<210> SEQ ID NO 106
<211> LENGTH: 24
<212> TYPE: DNA
<213> ORGANISM: Artificial Sequence
<220> FEATURE:
<223> OTHER INFORMATION: Novel Sequence

<400> SEQUENCE: 106
gctatgcctg aagccagtct tgtg 24

<210> SEQ ID NO 107
<211> LENGTH: 25
<212> TYPE: DNA
<213> ORGANISM: Artificial Sequence
<220> FEATURE:
<223> OTHER INFORMATION: Novel Sequence

<400> SEQUENCE: 107
gcacctgctc ctgagcacct tctcc 25

<210> SEQ ID NO 108
<211> LENGTH: 26
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 108
cacagcgctg cagccctgca gctggc 26

<210> SEQ ID NO 109
<211> LENGTH: 24
<212> TYPE: DNA
<213> ORGANISM: Artificial Sequence
<220> FEATURE:
<223> OTHER INFORMATION: Novel Sequence

<400> SEQUENCE: 109
ccagtgatga ctctgtccag cctg 24

<210> SEQ ID NO 110
<211> LENGTH: 24
<212> TYPE: DNA
<213> ORGANISM: Artificial Sequence
<220> FEATURE: 4925:<220
<223> OTHER INFORMATION: 4926:><223> Novel Sequence

<400> SEQUENCE: 110
cagacacttg gcagggacga ggtg 24

<210> SEQ ID NO 111
<211> LENGTH: 26
<212> TYPE: DNA
<213> ORGANISM: Artificial Sequence
<220> FEATURE:
<223> OTHER INFORMATION: Novel Sequence -continued

<400> SEQUENCE: 111
cttgtggtct actgcagcat gttccg 26

<210> SEQ ID NO 112
<211> LENGTH: 25
<212> TYPE: DNA
<213> ORGANISM: Artificial Sequence
<220> FEATURE:
<223> OTHER INFORMATION: Novel Sequence

<400> SEQUENCE: 112
catatccctc cgagtgtcca gcggc 25

<210> SEQ ID NO 113
<211> LENGTH: 24
<212> TYPE: DNA
<213> ORGANISM: Artificial Sequence
<220> FEATURE:
<223> OTHER INFORMATION: Novel Sequence

<400> SEQUENCE: 113
atggatcctt atcatggctt cctc 24

<210> SEQ ID NO 114
<211> LENGTH: 27
<212> TYPE: DNA
<213> ORGANISM: Artificial Sequence
<220> FEATURE:
<223> OTHER INFORMATION: Novel Sequence

<400> SEQUENCE: 114
caagaacagg tctcatctaa gagctcc 27

<210> SEQ ID NO 115
<211> LENGTH: 26
<212> TYPE: DNA
<213> ORGANISM: Artificial Sequence
<220> FEATURE:
<223> OTHER INFORMATION: Novel Sequence

<400> SEQUENCE: 115
ctctgatgcc atctgctgga ttcctg 26

<210> SEQ ID NO 116
<211> LENGTH: 26
<212> TYPE: DNA
<213> ORGANISM: Artificial Sequence
<220> FEATURE:
<223> OTHER INFORMATION: Novel Sequence

<400> SEQUENCE: 116
gtagtccact gaaagtccag tgatcc 26

<210> SEQ ID NO 117
<211> LENGTH: 24
<212> TYPE: DNA
<213> ORGANISM: Artificial Sequence
<220> FEATURE:
<223> OTHER INFORMATION: Novel Sequence

<400> SEQUENCE: 117
tggtggcgat ggccaacagc gctc 24

-continued

<210> SEQ ID NO 118
<211> LENGTH: 24
<212> TYPE: DNA
<213> ORGANISM: Artificial Sequence
<220> FEATURE:
<223> OTHER INFORMATION: Novel Sequence

<400> SEQUENCE: 118
gttgcgcctt agcgacagat gacc 24

<210> SEQ ID NO 119
<211> LENGTH: 23
<212> TYPE: DNA
<213> ORGANISM: Artificial Sequence
<220> FEATURE:
<223> OTHER INFORMATION: Novel Sequence

<400> SEQUENCE: 119
tcaacctgta tagcagcatc ctc 23

<210> SEQ ID NO 120
<211> LENGTH: 23
<212> TYPE: DNA
<213> ORGANISM: Artificial Sequence
<220> FEATURE:
<223> OTHER INFORMATION: Novel Sequence

<400> SEQUENCE: 120
aaggagtagc agaatggtta gcc 23

<210> SEQ ID NO 121
<211> LENGTH: 24
<212> TYPE: DNA
<213> ORGANISM: Artificial Sequence
<220> FEATURE:
<223> OTHER INFORMATION: Novel Sequence

<400> SEQUENCE: 121
gacacctgtc agcggtcgtg tgtg 24

<210> SEQ ID NO 122
<211> LENGTH: 27
<212> TYPE: DNA
<213> ORGANISM: Artificial Sequence
<220> FEATURE:
<223> OTHER INFORMATION: Novel Sequence

<400> SEQUENCE: 122
ctgatggaag tagaggctgt ccatctc 27

<210> SEQ ID NO 123
<211> LENGTH: 24
<212> TYPE: DNA
<213> ORGANISM: Artificial Sequence
<220> FEATURE:
<223> OTHER INFORMATION: Novel Sequence

<400> SEQUENCE: 123
gcgctgagcg cagaccagtg gctg 24

<210> SEQ ID NO 124
<211> LENGTH: 24
<212> TYPE: DNA
<213> ORGANISM: Artificial Sequence
<220> FEATURE:
<223> OTHER INFORMATION: Novel Sequence -continued

<400> SEQUENCE: 124
cacggtgacg aagggcacga gctc 24

<210> SEQ ID NO 125
<211> LENGTH: 24
<212> TYPE: DNA
<213> ORGANISM: Artificial Sequence
<220> FEATURE:
<223> OTHER INFORMATION: Novel Sequence

<400> SEQUENCE: 125
agccatccct gccaggaagc atgg 24

<210> SEQ ID NO 126
<211> LENGTH: 25
<212> TYPE: DNA
<213> ORGANISM: Artificial Sequence
<220> FEATURE:
<223> OTHER INFORMATION: Novel Sequence

<400> SEQUENCE: 126
ccaggtaggt gtgcagcaca atggc 25

<210> SEQ ID NO 127
<211> LENGTH: 25
<212> TYPE: DNA
<213> ORGANISM: Artificial Sequence
<220> FEATURE:
<223> OTHER INFORMATION: Novel Sequence

<400> SEQUENCE: 127
ctgttcaaca gggctggttg gcaac 25

<210> SEQ ID NO 128
<211> LENGTH: 25
<212> TYPE: DNA
<213> ORGANISM: Artificial Sequence
<220> FEATURE:
<223> OTHER INFORMATION: Novel Sequence

<400> SEQUENCE: 128
atcatgtcta gactcatggt gatcc 25

<210> SEQ ID NO 129
<211> LENGTH: 6
<212> TYPE: PRT
<213> ORGANISM: Artificial Sequence
<220> FEATURE:
<223> OTHER INFORMATION: Novel Sequence

<400> SEQUENCE: 129

Thr Leu Glu Ser Ile Met
1 5

<210> SEQ ID NO 130
<211> LENGTH: 5
<212> TYPE: PRT
<213> ORGANISM: Artificial Sequence
<220> FEATURE:
<223> OTHER INFORMATION: Novel Sequence

<400> SEQUENCE: 130

Glu Tyr Asn Leu Val
1 5

-continued

<210> SEQ ID NO 131
<211> LENGTH: 5
<212> TYPE: PRT
<213> ORGANISM: Artificial Sequence
<220> FEATURE:
<223> OTHER INFORMATION: Novel Sequence

<400> SEQUENCE: 131

Asp Cys Gly Leu Phe
1               5

<210> SEQ ID NO 132
<211> LENGTH: 36
<212> TYPE: PRT
<213> ORGANISM: Artificial Sequence
<220> FEATURE:
<223> OTHER INFORMATION: Novel Sequence

<400> SEQUENCE: 132

Gly Ala Thr Cys Ala Ala Gly Cys Thr Thr Cys Cys Ala Thr Gly Gly
1               5                   10                  15

Cys Gly Thr Gly Cys Thr Gly Cys Cys Thr Gly Ala Gly Cys Gly Ala
            20                  25                  30

Gly Gly Ala Gly
        35

<210> SEQ ID NO 133
<211> LENGTH: 53
<212> TYPE: PRT
<213> ORGANISM: Artificial Sequence
<220> FEATURE:
<223> OTHER INFORMATION: Novel Sequence

<400> SEQUENCE: 133

Gly Ala Thr Cys Gly Gly Ala Thr Cys Cys Thr Thr Ala Gly Ala Ala
1               5                   10                  15

Cys Ala Gly Gly Cys Cys Gly Cys Ala Gly Thr Cys Cys Thr Thr Cys
            20                  25                  30

Ala Gly Gly Thr Thr Cys Ala Gly Cys Thr Gly Cys Ala Gly Gly Ala
        35                  40                  45

Thr Gly Gly Thr Gly
    50

<210> SEQ ID NO 134
<211> LENGTH: 1164
<212> TYPE: DNA
<213> ORGANISM: Homo Sapien

<400> SEQUENCE: 134
atgaatcggc accatctgca ggatcacttt ctggaaatag acaagaagaa ctgctgtgtg     60
ttccgagatg acttcattgc caaggtgttg ccgccggtgt tggggctgga gtttatcttt    120
gggcttctgg gcaatggcct tgccctgtgg attttctgtt tccacctcaa gtcctggaaa    180
tccagccgga ttttcctgtt caacctggca gtagctgact ttctactgat catctgcctg    240
ccgttcgtga tggactacta tgtgcggcgt tcagactgga actttgggga catcccttgc    300
cggctggtgc tcttcatgtt tgccatgaac cgccagggca gcatcatctt cctcacggtg    360
gtggcggtag acaggtattt ccgggtggtc catccccacc acgccctgaa caagatctcc    420
aattggacag cagccatcat ctcttgcctt ctgtggggca tcactgttgg cctaacagtc    480
cacctcctga agaagaagtt gctgatccag aatggccctg caaatgtgtg catcagcttc    540

-continued

```
agcatctgcc ataccttccg gtggcacgaa gctatgttcc tcctggagtt cctcctgccc    600

ctgggcatca tcctgttctg ctcagccaga attatctgga gcctgcggca gagacaaatg    660

gaccggcatg ccaagatcaa gagagccatc accttcatca tggtggtggc catcgtcttt    720

gtcatctgct tccttcccag cgtggttgtg cggatccgca tcttctggct cctgcacact    780

tcgggcacgc agaattgtga agtgtaccgc tcggtggacc tggcgttctt tatcactctc    840

agcttcacct acatgaacag catgctggac cccgtggtgt actacttctc cagcccatcc    900

tttcccaact tcttctccac tttgatcaac cgctgcctcc agaggaagat gacaggtgag    960

ccagataata accgcagcac gagcgtcgag ctcacagggg accccaacaa aaccagaggc   1020

gctccagagg cgttaatggc caactccggt gagccatgga gcccctctta tctgggccca   1080

acctcaaata accattccaa gaagggacat tgtcaccaag aaccagcatc tctggagaaa   1140

cagttgggct gttgcatcga gtaa                                          1164
```

```
<210> SEQ ID NO 135
<211> LENGTH: 387
<212> TYPE: PRT
<213> ORGANISM: Homo sapiens

<400> SEQUENCE: 135

Met Asn Arg His His Leu Gln Asp His Phe Leu Glu Ile Asp Lys Lys
1               5                   10                  15

Asn Cys Cys Val Phe Arg Asp Asp Phe Ile Ala Lys Val Leu Pro Pro
            20                  25                  30

Val Leu Gly Leu Glu Phe Ile Phe Gly Leu Leu Gly Asn Gly Leu Ala
        35                  40                  45

Leu Trp Ile Phe Cys Phe His Leu Lys Ser Trp Lys Ser Ser Arg Ile
    50                  55                  60

Phe Leu Phe Asn Leu Ala Val Ala Asp Phe Leu Leu Ile Ile Cys Leu
65                  70                  75                  80

Pro Phe Val Met Asp Tyr Tyr Val Arg Arg Ser Asp Trp Asn Phe Gly
                85                  90                  95

Asp Ile Pro Cys Arg Leu Val Leu Phe Met Phe Ala Met Asn Arg Gln
            100                 105                 110

Gly Ser Ile Ile Phe Leu Thr Val Val Ala Val Asp Arg Tyr Phe Arg
        115                 120                 125

Val Val His Pro His His Ala Leu Asn Lys Ile Ser Asn Trp Thr Ala
    130                 135                 140

Ala Ile Ile Ser Cys Leu Leu Trp Gly Ile Thr Val Gly Leu Thr Val
145                 150                 155                 160

His Leu Leu Lys Lys Lys Leu Leu Ile Gln Asn Gly Pro Ala Asn Val
                165                 170                 175

Cys Ile Ser Phe Ser Ile Cys His Thr Phe Arg Trp His Glu Ala Met
            180                 185                 190

Phe Leu Leu Glu Phe Leu Leu Pro Leu Gly Ile Ile Leu Phe Cys Ser
        195                 200                 205

Ala Arg Ile Ile Trp Ser Leu Arg Gln Arg Gln Met Asp Arg His Ala
    210                 215                 220

Lys Ile Lys Arg Ala Ile Thr Phe Ile Met Val Val Ala Ile Val Phe
225                 230                 235                 240

Val Ile Cys Phe Leu Pro Ser Val Val Val Arg Ile Arg Ile Phe Trp
                245                 250                 255
```

-continued

```
Leu Leu His Thr Ser Gly Thr Gln Asn Cys Glu Val Tyr Arg Ser Val
            260                 265                 270

Asp Leu Ala Phe Phe Ile Thr Leu Ser Phe Thr Tyr Met Asn Ser Met
        275                 280                 285

Leu Asp Pro Val Val Tyr Tyr Phe Ser Ser Pro Ser Phe Pro Asn Phe
    290                 295                 300

Phe Ser Thr Leu Ile Asn Arg Cys Leu Gln Arg Lys Met Thr Gly Glu
305                 310                 315                 320

Pro Asp Asn Asn Arg Ser Thr Ser Val Glu Leu Thr Gly Asp Pro Asn
                325                 330                 335

Lys Thr Arg Gly Ala Pro Glu Ala Leu Met Ala Asn Ser Gly Glu Pro
            340                 345                 350

Trp Ser Pro Ser Tyr Leu Gly Pro Thr Ser Asn Asn His Ser Lys Lys
        355                 360                 365

Gly His Cys His Gln Glu Pro Ala Ser Leu Glu Lys Gln Leu Gly Cys
    370                 375                 380

Cys Ile Glu
385


<210> SEQ ID NO 136
<211> LENGTH: 1083
<212> TYPE: DNA
<213> ORGANISM: Mouse

<400> SEQUENCE: 136

atgagcaagt cagaccattt tctagtgata aacggcaaga actgctgtgt gttccgagat      60

gaaaacatcg ccaaggtctt gccaccggtg ttggggctgg aatttgtgtt cggactcctg     120

ggcaatggcc ttgccttgtg gattttctgt ttccacctca agtcctggaa atccagccgg     180

atttcttgt  tcaacttggc cgtggctgac tttctcctga tcatctgcct gccgttcctg     240

acggacaact atgtccataa ctgggactgg aggttcggag gcatcccttg ccgtgtgatg     300

ctcttcatgt tggctatgaa ccgacagggc agcatcatct tcctcaccgt ggtggctgtg     360

gaccgctact tccgggtggt ccatccacac cacttcttga acaagatctc caaccggacg     420

gcggccatca tttcttgctt cttgtggggt ctcaccatcg gcctgactgt ccacctcctc     480

tatacaaaca tgatgaccaa aaatggcgag gcatatctgt gtagcagctt cagcatctgt     540

tacaacttca ggtggcacga tgctatgttc ctcttggaat tcttcttgcc cctggccatc     600

atcttgttct gctcaggcag gatcatctgg agcctgaggc agagacagat ggacagacat     660

gccaagatca agagggccat caacttcatc atggtggtgg ctattgtatt catcatttgc     720

ttcctaccca gtgtggctgt gcgcatccgc atcttctggc ttctctacaa atataacgta     780

cgcaactgtg acatctactc ctcggtggac ctggctttct ttaccaccct tagctttacc     840

tacatgaaca gcatgctgga ccctgtggtc tactatttct ccagcccatc tttccccaac     900

ttcttctcca cgtgtatcaa ccgctgcctt cgaaagaaaa cattgggtga acccgataat     960

aaccgaagca ctagtgtgga gctcacgggg gaccccagca caaccagaag tattccaggg    1020

gcgctaatgg ctgaccccag tgagccaggc agcccccctt atctggcttc cacatctcgt    1080

taa                                                                  1083


<210> SEQ ID NO 137
<211> LENGTH: 360
<212> TYPE: PRT
<213> ORGANISM: Mouse
```

-continued

<400> SEQUENCE: 137

```
Met Ser Lys Ser Asp His Phe Leu Val Ile Asn Gly Lys Asn Cys Cys
1               5                   10                  15

Val Phe Arg Asp Glu Asn Ile Ala Lys Val Leu Pro Pro Val Leu Gly
            20                  25                  30

Leu Glu Phe Val Phe Gly Leu Leu Gly Asn Gly Leu Ala Leu Trp Ile
        35                  40                  45

Phe Cys Phe His Leu Lys Ser Trp Lys Ser Ser Arg Ile Phe Leu Phe
    50                  55                  60

Asn Leu Ala Val Ala Asp Phe Leu Leu Ile Ile Cys Leu Pro Phe Leu
65                  70                  75                  80

Thr Asp Asn Tyr Val His Asn Trp Asp Trp Arg Phe Gly Gly Ile Pro
                85                  90                  95

Cys Arg Val Met Leu Phe Met Leu Ala Met Asn Arg Gln Gly Ser Ile
            100                 105                 110

Ile Phe Leu Thr Val Val Ala Val Asp Arg Tyr Phe Arg Val Val His
        115                 120                 125

Pro His His Phe Leu Asn Lys Ile Ser Asn Arg Thr Ala Ala Ile Ile
    130                 135                 140

Ser Cys Phe Leu Trp Gly Leu Thr Ile Gly Leu Thr Val His Leu Leu
145                 150                 155                 160

Tyr Thr Asn Met Met Thr Lys Asn Gly Glu Ala Tyr Leu Cys Ser Ser
                165                 170                 175

Phe Ser Ile Cys Tyr Asn Phe Arg Trp His Asp Ala Met Phe Leu Leu
            180                 185                 190

Glu Phe Phe Leu Pro Leu Ala Ile Ile Leu Phe Cys Ser Gly Arg Ile
        195                 200                 205

Ile Trp Ser Leu Arg Gln Arg Gln Met Asp Arg His Ala Lys Ile Lys
    210                 215                 220

Arg Ala Ile Asn Phe Ile Met Val Val Ala Ile Val Phe Ile Ile Cys
225                 230                 235                 240

Phe Leu Pro Ser Val Ala Val Arg Ile Arg Ile Phe Trp Leu Leu Tyr
                245                 250                 255

Lys Tyr Asn Val Arg Asn Cys Asp Ile Tyr Ser Ser Val Asp Leu Ala
            260                 265                 270

Phe Phe Thr Thr Leu Ser Phe Thr Tyr Met Asn Ser Met Leu Asp Pro
        275                 280                 285

Val Val Tyr Tyr Phe Ser Ser Pro Ser Phe Pro Asn Phe Phe Ser Thr
    290                 295                 300

Cys Ile Asn Arg Cys Leu Arg Lys Lys Thr Leu Gly Glu Pro Asp Asn
305                 310                 315                 320

Asn Arg Ser Thr Ser Val Glu Leu Thr Gly Asp Pro Ser Thr Thr Arg
                325                 330                 335

Ser Ile Pro Gly Ala Leu Met Ala Asp Pro Ser Glu Pro Gly Ser Pro
            340                 345                 350

Pro Tyr Leu Ala Ser Thr Ser Arg
        355                 360
```

<210> SEQ ID NO 138
<211> LENGTH: 1086
<212> TYPE: DNA
<213> ORGANISM: Rat

-continued

<400> SEQUENCE: 138

```
atgagcaagt cagaccattt tctagtgata aacggcaaga actgctgtgt gttccgagat     60
gaaaacatcg ccaaggtcct gccgccggtg ttggggctgg agtttgtgtt tggactcctg    120
ggtaatggcc ttgccttgtg gatcttctgt ttccatctca aatcctggaa atccagccgg    180
attttcttgt tcaacctggc cgtggctgac tttctcctga tcatttgctt gccgttcttg    240
acggacaact atgtccagaa ctgggactgg aggttcggga gcatcccctg ccgcgtgatg    300
ctcttcatgt tggccatgaa ccgacagggc agcatcatct tcctcacggt ggtggctgtg    360
gacaggtact tcagggtggt ccacccgcac cacttcctga acaagatctc caaccggacg    420
gcggccatca tctcttgctt cctgtggggc atcaccatcg ggcctggaca gtccaccttc    480
ctctacacgg acatgatgac ccgaaacggc gatgcaaacc tgtgcagcag ttttagcatc    540
tgctacactt tcaggtggca cgatgcaatg ttcctcttgg aattcttcct gcccctgggc    600
atcatcctgt tctgctctgg caggatcatt tggagcctaa ggcagagaca gatggacagg    660
cacgtcaaga tcaagagggc catcaacttc atcatggtgg ttgccattgt gtttgtcatc    720
tgcttcctgc ccagtgtggc cgtgaggatc cgcatcttct ggctcctcta caaacacaac    780
gtgaggaact gtgacatcta ctcctctgtg gacttggcct tcttcaccac ccttagcttt    840
acctacatga acagcatgct cgacccggtg gtctactatt tctccagccc atctttcccc    900
aacttcttct ccacgtgcat caaccgttgc cttcgaagga aaaccttggg cgaaccagat    960
aataaccgga gcacgagtgt ggagctcacg gggacccca gcacaatcag aagtattcca   1020
ggggcattaa tgactgaccc cagtgagcca ggcagccccc cttatctggc ttccacatct   1080
cgttaa                                                              1086
```

<210> SEQ ID NO 139
<211> LENGTH: 361
<212> TYPE: PRT
<213> ORGANISM: Rat

<400> SEQUENCE: 139

```
Met Ser Lys Ser Asp His Phe Leu Val Ile Asn Gly Lys Asn Cys Cys
1               5                   10                  15

Val Phe Arg Asp Glu Asn Ile Ala Lys Val Leu Pro Pro Val Leu Gly
            20                  25                  30

Leu Glu Phe Val Phe Gly Leu Leu Gly Asn Gly Leu Ala Leu Trp Ile
        35                  40                  45

Phe Cys Phe His Leu Lys Ser Trp Lys Ser Ser Arg Ile Phe Leu Phe
    50                  55                  60

Asn Leu Ala Val Ala Asp Phe Leu Leu Ile Ile Cys Leu Pro Phe Leu
65                  70                  75                  80

Thr Asp Asn Tyr Val Gln Asn Trp Asp Trp Arg Phe Gly Ser Ile Pro
                85                  90                  95

Cys Arg Val Met Leu Phe Met Leu Ala Met Asn Arg Gln Gly Ser Ile
            100                 105                 110

Ile Phe Leu Thr Val Val Ala Val Asp Arg Tyr Phe Arg Val Val His
        115                 120                 125

Pro His His Phe Leu Asn Lys Ile Ser Asn Arg Thr Ala Ala Ile Ile
    130                 135                 140

Ser Cys Phe Leu Trp Gly Ile Thr Ile Gly Pro Gly Gln Ser Thr Phe
145                 150                 155                 160
```

-continued

```
Leu Tyr Thr Asp Met Met Thr Arg Asn Gly Asp Ala Asn Leu Cys Ser
                165                 170                 175

Ser Phe Ser Ile Cys Tyr Thr Phe Arg Trp His Asp Ala Met Phe Leu
            180                 185                 190

Leu Glu Phe Phe Leu Pro Leu Gly Ile Ile Leu Phe Cys Ser Gly Arg
        195                 200                 205

Ile Ile Trp Ser Leu Arg Gln Arg Gln Met Asp Arg His Val Lys Ile
    210                 215                 220

Lys Arg Ala Ile Asn Phe Ile Met Val Val Ala Ile Val Phe Val Ile
225                 230                 235                 240

Cys Phe Leu Pro Ser Val Ala Val Arg Ile Arg Ile Phe Trp Leu Leu
                245                 250                 255

Tyr Lys His Asn Val Arg Asn Cys Asp Ile Tyr Ser Ser Val Asp Leu
            260                 265                 270

Ala Phe Phe Thr Thr Leu Ser Phe Thr Tyr Met Asn Ser Met Leu Asp
        275                 280                 285

Pro Val Val Tyr Tyr Phe Ser Ser Pro Ser Phe Pro Asn Phe Phe Ser
    290                 295                 300

Thr Cys Ile Asn Arg Cys Leu Arg Arg Lys Thr Leu Gly Glu Pro Asp
305                 310                 315                 320

Asn Asn Arg Ser Thr Ser Val Glu Leu Thr Gly Asp Pro Ser Thr Ile
                325                 330                 335

Arg Ser Ile Pro Gly Ala Leu Met Thr Asp Pro Ser Glu Pro Gly Ser
            340                 345                 350

Pro Pro Tyr Leu Ala Ser Thr Ser Arg
        355                 360
```

<210> SEQ ID NO 140
<211> LENGTH: 30
<212> TYPE: DNA
<213> ORGANISM: Artificial
<220> FEATURE:
<223> OTHER INFORMATION: Novel Sequence

<400> SEQUENCE: 140
atgagcaagt cagaccattt tctagtgata 30

<210> SEQ ID NO 141
<211> LENGTH: 25
<212> TYPE: DNA
<213> ORGANISM: Artificial
<220> FEATURE:
<223> OTHER INFORMATION: Novel Sequence

<400> SEQUENCE: 141
ttatctggct tccacatctc gttaa 25

<210> SEQ ID NO 142
<211> LENGTH: 30
<212> TYPE: DNA
<213> ORGANISM: Artificial
<220> FEATURE:
<223> OTHER INFORMATION: Novel Sequence

<400> SEQUENCE: 142
atgagcaagt cagaccattt tctagtgata 30

-continued

<210> SEQ ID NO 143
<211> LENGTH: 25
<212> TYPE: DNA
<213> ORGANISM: Artificial
<220> FEATURE:
<223> OTHER INFORMATION: Novel Sequence

<400> SEQUENCE: 143
ttatctggct tccacatctc gttaa 25

<210> SEQ ID NO 144
<211> LENGTH: 27
<212> TYPE: DNA
<213> ORGANISM: Artificial
<220> FEATURE:
<223> OTHER INFORMATION: Novel Sequence

<400> SEQUENCE: 144
ctgatggaca actatgtgag gcgttgg 27

<210> SEQ ID NO 145
<211> LENGTH: 27
<212> TYPE: DNA
<213> ORGANISM: Artificial
<220> FEATURE:
<223> OTHER INFORMATION: Novel Sequence

<400> SEQUENCE: 145
gctgaagctg ctgcacaaat ttgcacc 27

<210> SEQ ID NO 146
<211> LENGTH: 19
<212> TYPE: DNA
<213> ORGANISM: Artificial
<220> FEATURE:
<223> OTHER INFORMATION: Novel Sequence

<400> SEQUENCE: 146
ctactatgtg cggcgttca 19

<210> SEQ ID NO 147
<211> LENGTH: 21
<212> TYPE: DNA
<213> ORGANISM: Artificial
<220> FEATURE:
<223> OTHER INFORMATION: Novel Sequence

<400> SEQUENCE: 147
cccttcttgg aatggttatt t 21

<210> SEQ ID NO 148
<211> LENGTH: 20
<212> TYPE: DNA
<213> ORGANISM: Artificial
<220> FEATURE:
<223> OTHER INFORMATION: Novel Sequence

<400> SEQUENCE: 148
gcactcatga atcggcacca 20

<210> SEQ ID NO 149
<211> LENGTH: 20
<212> TYPE: DNA
<213> ORGANISM: Artificial
<220> FEATURE:
<223> OTHER INFORMATION: Novel Sequence -continued

<400> SEQUENCE: 149
cagtgacatt actcgatgca 20

<210> SEQ ID NO 150
<211> LENGTH: 1032
<212> TYPE: DNA
<213> ORGANISM: Mouse

<400> SEQUENCE: 150
atggacaacg ggtcgtgctg tctcatcgag ggggagccca tctcccaagt gatgcctcct 60
ctactcatcc tggtcttcgt gcttggcgcc ctgggcaacg gcatagccct gtgcggcttc 120
tgctttcaca tgaagacctg gaagtcaagc actatttacc ttttcaactt ggctgtggcc 180
gattttctcc tcatgatctg cttacccctt cggacagact actacctcag acgcagacac 240
tggatttttg gagatatcgc ctgtcgcctg gtcctcttca agctggccat gaatagggcc 300
gggagcattg tcttcctcac tgtggtggct gtggataggt atttcaaagt ggtccacccc 360
caccatatgg tgaatgccat ctccaaccgg actgccgccg ccaccgcctg tgtcctctgg 420
actttggtca tcttggggac tgtgtatctt ctgatggaga gtcacctgtg tgtgcagggg 480
acactgtcgt cctgtgagag cttcatcatg gagtcagcca acgggtggca cgatgtcatg 540
ttccagctgg agttcttcct gcccctgaca atcatcttgt tctgctcggt caacgttgtt 600
tggagcctga gacggaggca gcagctgacc agacaggctc ggatgaggag ggccacccgg 660
ttcatcatgg tggtggcttc tgtgttcatc acgtgttacc tgcccagcgt gctggctagg 720
ctctacttcc tctggacggt gcccactagt gcctgtgacc cctctgtcca cacagccctc 780
cacgtcaccc tgagcttcac ctacctgaac agtatgctgg atccccttgt atattacttc 840
tcaagcccct cgctccccaa attctacacc aagctcacaa tctgcagcct gaagcccaaa 900
cgcccaggac gcacgaagac gcggaggtca gaagagatgc caatttcgaa cctctgcagt 960
aagagctcca tcgatggggc aaatcgttcc cagaggccat ctgacgggca gtgggatctc 1020
caagtgtgtt ga 1032

<210> SEQ ID NO 151
<211> LENGTH: 343
<212> TYPE: PRT
<213> ORGANISM: Mouse

<400> SEQUENCE: 151

Met Asp Asn Gly Ser Cys Cys Leu Ile Glu Gly Glu Pro Ile Ser Gln
1 5 10 15

Val Met Pro Pro Leu Leu Ile Leu Val Phe Val Leu Gly Ala Leu Gly
20 25 30

Asn Gly Ile Ala Leu Cys Gly Phe Cys Phe His Met Lys Thr Trp Lys
35 40 45

Ser Ser Thr Ile Tyr Leu Phe Asn Leu Ala Val Ala Asp Phe Leu Leu
50 55 60

Met Ile Cys Leu Pro Leu Arg Thr Asp Tyr Tyr Leu Arg Arg Arg His
65 70 75 80

Trp Ile Phe Gly Asp Ile Ala Cys Arg Leu Val Leu Phe Lys Leu Ala
85 90 95

Met Asn Arg Ala Gly Ser Ile Val Phe Leu Thr Val Val Ala Val Asp
100 105 110

Arg Tyr Phe Lys Val Val His Pro His His Met Val Asn Ala Ile Ser
115 120 125

-continued

```
Asn Arg Thr Ala Ala Ala Thr Ala Cys Val Leu Trp Thr Leu Val Ile
    130                 135                 140

Leu Gly Thr Val Tyr Leu Leu Met Glu Ser His Leu Cys Val Gln Gly
145                 150                 155                 160

Thr Leu Ser Ser Cys Glu Ser Phe Ile Met Glu Ser Ala Asn Gly Trp
                165                 170                 175

His Asp Val Met Phe Gln Leu Glu Phe Phe Leu Pro Leu Thr Ile Ile
            180                 185                 190

Leu Phe Cys Ser Val Asn Val Val Trp Ser Leu Arg Arg Arg Gln Gln
        195                 200                 205

Leu Thr Arg Gln Ala Arg Met Arg Arg Ala Thr Arg Phe Ile Met Val
    210                 215                 220

Val Ala Ser Val Phe Ile Thr Cys Tyr Leu Pro Ser Val Leu Ala Arg
225                 230                 235                 240

Leu Tyr Phe Leu Trp Thr Val Pro Thr Ser Ala Cys Asp Pro Ser Val
                245                 250                 255

His Thr Ala Leu His Val Thr Leu Ser Phe Thr Tyr Leu Asn Ser Met
            260                 265                 270

Leu Asp Pro Leu Val Tyr Tyr Phe Ser Ser Pro Ser Leu Pro Lys Phe
        275                 280                 285

Tyr Thr Lys Leu Thr Ile Cys Ser Leu Lys Pro Lys Arg Pro Gly Arg
    290                 295                 300

Thr Lys Thr Arg Arg Ser Glu Glu Met Pro Ile Ser Asn Leu Cys Ser
305                 310                 315                 320

Lys Ser Ser Ile Asp Gly Ala Asn Arg Ser Gln Arg Pro Ser Asp Gly
                325                 330                 335

Gln Trp Asp Leu Gln Val Cys
            340
```

<210> SEQ ID NO 152
<211> LENGTH: 24
<212> TYPE: DNA
<213> ORGANISM: Artificial
<220> FEATURE:
<223> OTHER INFORMATION: Novel Sequence

<400> SEQUENCE: 152
ggccgtggct gatttcctcc ttat 24

<210> SEQ ID NO 153
<211> LENGTH: 22
<212> TYPE: DNA
<213> ORGANISM: Artificial
<220> FEATURE:
<223> OTHER INFORMATION: Novel Sequence

<400> SEQUENCE: 153
aaccgggtcg ccttcttcat cc 22

<210> SEQ ID NO 154
<211> LENGTH: 23
<212> TYPE: DNA
<213> ORGANISM: Artificial
<220> FEATURE:
<223> OTHER INFORMATION: Novel Sequence

<400> SEQUENCE: 154
actgtggtgg ctgtggatag gta 23

-continued

<210> SEQ ID NO 155
<211> LENGTH: 24
<212> TYPE: DNA
<213> ORGANISM: Artificial
<220> FEATURE:
<223> OTHER INFORMATION: Novel Sequence

<400> SEQUENCE: 155
gcagattgtg agcttggcgt agaa 24

<210> SEQ ID NO 156
<211> LENGTH: 1056
<212> TYPE: DNA
<213> ORGANISM: Rat

<400> SEQUENCE: 156
atgctcttcc tctctccgag tgctatggac aacgggtcgt gctgtctcat cgagggggaa 60
cccatcaccc aggtaatgcc acctttactc atcctggcct tcctgcttgg agccctgggc 120
aacggcctag ccctgtgtgg tttctgcttt cacatgaaga cctggaagtc gagcactatt 180 tacctttca acttggctgt agccgatttt ctcctcatga tctgcctacc ccttcggaca 240
gactactacc tcagacgtag gcattggatt ttgggggata ttccctgccg cctggtcctc 300
ttcatgctgg ccatgaatag ggccggaagc attgtcttcc tcactgtggt ggccgtggac 360
aggtatttca aagtggtcca cccccaccat atggtgaacg ccatctccaa tcggactgca 420
gctgccatcg tctgtgtcct ctggactttg gtcatcttgg ggactgtgta tcttctgatg 480
gagagtcacc tgtgtgtgcg gggggatggtg tcatcttgtg agagcttcat catggagtca 540
gccaacgggt ggcacgatat catgttccag ctggagttct tcctgcccct gaccatcatc 600
ttgttctgct ccttcaaagt tgtttggagc ctgagacaga ggcaacagct gaccagacag 660
gctcggatga ggagggccac ccggttcatc atggtggtgg cttccgtgtt catcacgtgt 720
tacctgccca gcgtgttggc gaggctctac ttcctctgga cggtgccctc cagtgcttgt 780
gacccctctg tccacatagc tctccatgtc accctgagtc tcacctacct gaacagcatg 840
ctggaccctc ttgtgtacta cttttcaagc cctcgttcc ccaaattcta cgccaagctc 900
aaaatccgca gcttgaaacc cagacgccca ggacgctcgc aggcacggag gtcggaagag 960
atgccaattt cgaatctctg tcgtaagagt tccaccgatg tggtaaatag ttcccagagg 1020
ccgtctgacg ggcagtgggg tctccaagtg tgttga 1056

<210> SEQ ID NO 157
<211> LENGTH: 351
<212> TYPE: PRT
<213> ORGANISM: Rat

<400> SEQUENCE: 157

Met Leu Phe Leu Ser Pro Ser Ala Met Asp Asn Gly Ser Cys Cys Leu
1 5 10 15

Ile Glu Gly Glu Pro Ile Thr Gln Val Met Pro Pro Leu Leu Ile Leu
20 25 30

Ala Phe Leu Leu Gly Ala Leu Gly Asn Gly Leu Ala Leu Cys Gly Phe
35 40 45

Cys Phe His Met Lys Thr Trp Lys Ser Ser Thr Ile Tyr Leu Phe Asn
50 55 60

Leu Ala Val Ala Asp Phe Leu Leu Met Ile Cys Leu Pro Leu Arg Thr
65 70 75 80

-continued

```
Asp Tyr Tyr Leu Arg Arg Arg His Trp Ile Leu Gly Asp Ile Pro Cys
                85                  90                  95

Arg Leu Val Leu Phe Met Leu Ala Met Asn Arg Ala Gly Ser Ile Val
            100                 105                 110

Phe Leu Thr Val Val Ala Val Asp Arg Tyr Phe Lys Val Val His Pro
        115                 120                 125

His His Met Val Asn Ala Ile Ser Asn Arg Thr Ala Ala Ala Ile Val
    130                 135                 140

Cys Val Leu Trp Thr Leu Val Ile Leu Gly Thr Val Tyr Leu Leu Met
145                 150                 155                 160

Glu Ser His Leu Cys Val Arg Gly Met Val Ser Ser Cys Glu Ser Phe
                165                 170                 175

Ile Met Glu Ser Ala Asn Gly Trp His Asp Ile Met Phe Gln Leu Glu
            180                 185                 190

Phe Phe Leu Pro Leu Thr Ile Ile Leu Phe Cys Ser Phe Lys Val Val
        195                 200                 205

Trp Ser Leu Arg Gln Arg Gln Gln Leu Thr Arg Gln Ala Arg Met Arg
    210                 215                 220

Arg Ala Thr Arg Phe Ile Met Val Val Ala Ser Val Phe Ile Thr Cys
225                 230                 235                 240

Tyr Leu Pro Ser Val Leu Ala Arg Leu Tyr Phe Leu Trp Thr Val Pro
                245                 250                 255

Ser Ser Ala Cys Asp Pro Ser Val His Ile Ala Leu His Val Thr Leu
            260                 265                 270

Ser Leu Thr Tyr Leu Asn Ser Met Leu Asp Pro Leu Val Tyr Tyr Phe
        275                 280                 285

Ser Ser Pro Ser Phe Pro Lys Phe Tyr Ala Lys Leu Lys Ile Arg Ser
    290                 295                 300

Leu Lys Pro Arg Arg Pro Gly Arg Ser Gln Ala Arg Arg Ser Glu Glu
305                 310                 315                 320

Met Pro Ile Ser Asn Leu Cys Arg Lys Ser Ser Thr Asp Val Val Asn
                325                 330                 335

Ser Ser Gln Arg Pro Ser Asp Gly Gln Trp Gly Leu Gln Val Cys
            340                 345                 350
```

<210> SEQ ID NO 158
<211> LENGTH: 1092
<212> TYPE: DNA
<213> ORGANISM: Homo sapiens

<400> SEQUENCE: 158

```
atgaatcggc accatctgca ggatcacttt ctggaaatag acaagaagaa ctgctgtgtg      60

ttccgagatg acttcattgt caaggtgttg ccgccggtgt tggggctgga gtttatcttc     120

gggcttctgg gcaatggcct tgccctgtgg attttctgtt tccacctcaa gtcctggaaa     180

tccagccgga ttttcctgtt caacctggca gtggctgact ttctactgat catctgcctg     240

cccttcctga tggacaacta tgtgaggcgt tgggactgga agtttgggga catcccttgc     300

cggctgatgc tcttcatgtt ggctatgaac cgccagggca gcatcatctt cctcacggtg     360

gtggcggtag acaggtattt ccgggtggtc catccccacc acgccctgaa caagatctcc     420

aatcggacag cagccatcat ctcttgcctt ctgtggggca tcactattgg cctgacagtc     480

cacctcctga agaagaagat gccgatccag aatggcggtg caaatttgtg cagcagcttc     540

agcatctgcc ataccttcca gtggcacgaa gccatgttcc tcctggagtt cttcctgccc     600
```

-continued

```
ctgggcatca tcctgttctg ctcagccaga attatctgga gcctgcggca gagacaaatg    660

gaccggcatg ccaagatcaa gagagccatc accttcatca tggtggtggc catcgtcttt    720

gtcatctgct tccttcccag cgtggttgtg cggatccgca tcttctggct cctgcacact    780

tcgggcacgc agaattgtga agtgtaccgc tcggtggacc tggcgttctt tatcactctc    840

agcttcacct acatgaacag catgctggac cccgtggtgt actacttctc cagcccatcc    900

tttcccaact tcttctccac tttgatcaac cgctgcctcc agaggaagat gacaggtgag    960

ccagataata accgcagcac gagcgtcgag ctcacagggg accccaacaa aaccagaggc   1020

gctccagagg cgttaatggc caactccggt gagccatgga gcccctctta tctgggccca   1080

acctctcctt aa                                                       1092
```

<210> SEQ ID NO 159
<211> LENGTH: 363
<212> TYPE: PRT
<213> ORGANISM: Homo sapiens

<400> SEQUENCE: 159

```
Met Asn Arg His His Leu Gln Asp His Phe Leu Glu Ile Asp Lys Lys
1               5                   10                  15

Asn Cys Cys Val Phe Arg Asp Asp Phe Ile Val Lys Val Leu Pro Pro
            20                  25                  30

Val Leu Gly Leu Glu Phe Ile Phe Gly Leu Leu Gly Asn Gly Leu Ala
        35                  40                  45

Leu Trp Ile Phe Cys Phe His Leu Lys Ser Trp Lys Ser Ser Arg Ile
    50                  55                  60

Phe Leu Phe Asn Leu Ala Val Ala Asp Phe Leu Leu Ile Ile Cys Leu
65                  70                  75                  80

Pro Phe Leu Met Asp Asn Tyr Val Arg Arg Ser Asp Trp Lys Phe Gly
                85                  90                  95

Asp Ile Pro Cys Arg Leu Met Leu Phe Met Leu Ala Met Asn Arg Gln
            100                 105                 110

Gly Ser Ile Ile Phe Leu Thr Val Val Ala Val Asp Arg Tyr Phe Arg
        115                 120                 125

Val Val His Pro His His Ala Leu Asn Lys Ile Ser Asn Arg Thr Ala
    130                 135                 140

Ala Ile Ile Ser Cys Leu Leu Trp Gly Ile Thr Ile Gly Leu Thr Val
145                 150                 155                 160

His Leu Leu Lys Lys Lys Met Pro Ile Gln Asn Gly Gly Ala Asn Leu
                165                 170                 175

Cys Ser Ser Phe Ser Ile Cys His Thr Phe Gln Trp His Glu Ala Met
            180                 185                 190

Phe Leu Leu Glu Phe Phe Leu Pro Leu Gly Ile Ile Leu Phe Cys Ser
        195                 200                 205

Ala Arg Ile Ile Trp Ser Leu Arg Gln Arg Gln Met Asp Arg His Ala
    210                 215                 220

Lys Ile Lys Arg Ala Ile Thr Phe Ile Met Val Val Ala Ile Val Phe
225                 230                 235                 240

Val Ile Cys Phe Leu Pro Ser Val Val Val Arg Ile Arg Ile Phe Trp
                245                 250                 255

Leu Leu His Thr Ser Gly Thr Gln Asn Cys Glu Val Tyr Arg Ser Val
            260                 265                 270

Asp Leu Ala Phe Phe Ile Thr Leu Ser Phe Thr Tyr Met Asn Ser Met
        275                 280                 285
```

-continued

```
Leu Asp Pro Val Val Tyr Tyr Phe Ser Ser Pro Ser Phe Pro Asn Phe
    290                 295                 300

Phe Ser Thr Leu Ile Asn Arg Cys Leu Gln Arg Lys Met Thr Gly Glu
305                 310                 315                 320

Pro Asp Asn Asn Arg Ser Thr Ser Val Glu Leu Thr Gly Asp Pro Asn
                325                 330                 335

Lys Thr Arg Gly Ala Pro Glu Ala Leu Met Ala Asn Ser Gly Glu Pro
            340                 345                 350

Trp Ser Pro Ser Tyr Leu Gly Pro Thr Ser Pro
        355                 360


<210> SEQ ID NO 160
<211> LENGTH: 29
<212> TYPE: DNA
<213> ORGANISM: Artificial
<220> FEATURE:
<223> OTHER INFORMATION: Novel Sequence

<400> SEQUENCE: 160

ctatgtgagg cgttcagact ggaagtttg                                        29


<210> SEQ ID NO 161
<211> LENGTH: 29
<212> TYPE: DNA
<213> ORGANISM: Artificial
<220> FEATURE:
<223> OTHER INFORMATION: Novel Sequence

<400> SEQUENCE: 161

caaacttcca gtctgaacgc ctcacatag                                        29
```

HUMAN G PROTEIN-COUPLED RECEPTORS AND MODULATORS THEREOF FOR THE TREATMENT OF METABOLIC-RELATED DISORDERS

This application is a continuation-in-part of U.S. Utility patent application Ser. No. 10/096,511, filed Mar. 12, 2002 now abandoned and which is a continuation of U.S. application Ser. No. 09/995,543, filed Nov. 27, 2001 (now abandoned); and U.S. Provisional Patent Applications: Ser. No. 60/399,917, filed Jul. 29, 2002, Ser. No. 60/404,761, filed Aug. 19, 2002 and Ser. No. 60/410,747, filed Sep. 13, 2002; the disclosure of each of which is hereby incorporated by reference in its entirety.

FIELD OF THE INVENTION

The present invention relates to methods of identifying whether a candidate compound is a modulator of a G protein-coupled receptor (GPCR). In preferred embodiments, the GPCR is human. In other preferred embodiments, the GPCR is coupled to Gi and lowers the level of intracellular cAMP. In other preferred embodiments, the GPCR is expressed endogenously by adipocytes. In further preferred embodiments, the GPCR inhibits intracellular lipolysis. In other further preferred embodiments, the GPCR is a nicotinic acid receptor. The present invention also relates to methods of using a modulator of said GPCR. Preferred modulator is agonist. Agonists of the invention are useful as therapeutic agents for the prevention or treatment of metabolic-related disorders, including dyslipidemia, atherosclerosis, coronary heart disease, stroke, insulin resistance and type 2 diabetes.

BACKGROUND OF THE INVENTION

A. Nicotinic Acid as an Antilipolytic Agent

Atherosclerosis and stroke are the numbers one and number three leading causes of death of both men and women in the United States. [See, e.g., Nature Medicine, Special Focus on Atherosclerosis, (2002) 8:1209–1262; the disclosure of which is hereby incorporated by reference in its entirely.] Type 2 diabetes is a public health problem that is serious, widespread and increasing [Brownlee M, Nature (2001) 414:813–20 and references therein; Zimmet P et al., Nature (2001) 414:782–7 and references therein; Saltiel A R et al., Nature (2001) 414:799–806 and references therein; the disclosure of each of which is hereby incorporated by reference in its entirety]. Elevated levels of low density lipoprotein (LDL) cholesterol or low levels of high density lipoprotein (HDL) cholesterol are, independently, risk factors for atherosclerosis and associated cardiovascular pathologies. In addition, high levels of plasma free fatty acids are associated with insulin resistance and type 2 diabetes. One strategy for decreasing LDL-cholesterol, increasing HDL-cholesterol, and decreasing plasma free fatty acids is to inhibit lipolysis in adipose tissue. This approach involves regulation of hormone sensitive lipase, which is the rate-limiting enzyme in lipolysis. Lipolytic agents increase cellular levels of cAMP, which leads to activation of hormone sensitive lipase within adipocytes. Agents that lower intracellular cAMP levels, by contrast, would be antilipolytic.

It is also worth noting in passing that an increase in cellular levels of cAMP down-regulates the secretion of adiponectin from adipocytes [Delporte, M L et al. *Biochem J* (2002) 367:677–85; the disclosure of which is incorporated by reference in its entirety]. Reduced levels of plasma adiponectin have been associated with metabolic-related disorders, including atherosclerosis, coronary heart disease, stroke, insulin resistance and type 2 diabetes [Matsuda, M et al. J Biol Chem (2002) 277:37487–91 and reviewed therein; the disclosure of which is hereby incorporated by reference in its entirety]. [Also see: Yamauchi T et al., Nat Med (2002) 8:1288–95; and Tomas E et al., Proc Natl Acad Sci USA (2002) November 27; the disclosure of each of which is hereby incorporated by reference in its entirety.] Globular adiponectin protected ob/ob mice from diabetes and apoE deficient mice from atherosclerosis [Yamauchi, T et al. J Biol Chem (2002) November; the disclosure of which is hereby incorporated by reference in its entirety]. [Also see Okamoto, Y et al. Circulation (2002) 26:2767–70; the disclosure of which is hereby incorporated by reference in its entirety.] There is evidence that the regulation of human serum adiponectin levels through modulation of adipocyte intracellular cAMP level is independent of adipocyte lipolysis [Staiger H et al., Horm Metab Res (2002) 34:601–3; the disclosure of which is hereby incorporated by reference in its entirety].

Nicotinic acid (niacin, pyridine-3-carboxylic acid) is a water-soluble vitamin required by the human body for health, growth and reproduction; a part of the Vitamin B complex. Nicotinic acid is also one of the oldest used drugs for the treatment of dyslipidemia. It is a valuable drug in that it favorably affects virtually all of the lipid parameters listed above [Goodman and Gilman's Pharmacological Basis of Therapeutics, editors Harmon J G and Limbird L E, Chapter 36, Mahley R W and Bersot T P (2001) pages 971–1002]. The benefits of nicotinic acid in the treatment or prevention of atherosclerotic cardiovascular disease have been documented in six major clinical trials [Guyton J R (1998) Am J Cardiol 82:18U–23U]. Structure and synthesis of analogs or derivatives of nicotinic acid are discussed throughout the Merck Index, An Encyclopedia of Chemicals, Drugs, and Biologicals, Tenth Edition (1983), which is incorporated herein by reference in its entirety.

Nicotinic acid and currently existing analogs thereof inhibit the production and release of free fatty acids from adipose tissue, likely via an inhibition of adenylyl cyclase, a decrease in intracellular cAMP levels, and a concomitant decrease in hormone sensitive lipase activity. Agonists that down-regulate hormone sensitive lipase activity leading to a decrease in plasma free fatty acid levels are likely to have therapeutic value. The consequence of decreasing plasma free fatty acids is two-fold. First, it will ultimately lower LDL-cholesterol and raise HDL-cholesterol levels, independent risk factors, thereby reducing the risk of mortality due to cardiovascular incidence subsequent to atheroma formation. Second, it will provide an increase in insulin sensitivity in individuals with insulin resistance or type 2 diabetes. Unfortunately, the use of nicotinic acid as a therapeutic is partially limited by a number of associated, adverse side-effects. These include flushing, free fatty acid rebound, and liver toxicity.

Agonists of antilipolytic GPCRs having limited tissue distribution beyond adipose may be especially valuable in view of the diminished opportunity for potentially undesirable side-effects.

The rational development of novel, nicotinic acid receptor agonists that have fewer side-effects is an area of active investigation, but to date it has been hindered by the inability to molecularly identify the nicotinic acid receptor. Recent work suggests that nicotinic acid may act through a specific GPCR [Lorenzen A, et al. (2001) Molecular Pharmacology 59:349–357 and reviewed therein; the disclosure of which is hereby incorporated by reference in its entirety]. Furthermore, it is important to consider that other receptors of the same class may exist on the surface of adipocytes and similarly decrease hormone sensitive lipase activity through a reduction in the level of intracellular cAMP but without the elicitation of adverse effects such as flushing, thereby representing promising novel therapeutic targets.

B. G Protein-Coupled Receptors

Although a number of receptor classes exist in humans, by far the most abundant and therapeutically relevant is represented by the G protein-coupled receptor (GPCR) class. It is estimated that there are some 30,00040,000 genes within the human genome, and of these, approximately 2% are estimated to code for GPCRs. Receptors, including GPCRs, for which the endogenous ligand has been identified, are referred to as "known" receptors, while receptors for which the endogenous ligand has not been identified are referred to as "orphan" receptors.

GPCRs represent an important area for the development of pharmaceutical products: from approximately 20 of the 100 known GPCRs, approximately 60% of all prescription pharmaceuticals have been developed. For example, in 1999, of the top 100 brand name prescription drugs, the following drugs interact with GPCRs (the primary diseases and/or disorders treated related to the drug is indicated in parentheses):

| | | |
|---|---|---|
| Claritin ® (allergies) | Prozac ® (depression) | Vasotec ® (hypertension) |
| Paxil ® (depression) | Zoloft ® (depression) | Zyprexa ® (psychotic disorder) |
| Cozaar ® (hypertension) | Imitrex ® (migraine) | Zantac ® (reflux) |
| Propulsid ® (reflux disease) | Risperdal ® (schizophrenia) | Serevent ® (asthma) |
| Pepcid ® (reflux) | Gaster ® (ulcers) | Atrovent ® (bronchospasm) |
| Effexor ® (depression) | Depakote ® (epilepsy) | Cardura ® (prostatic ypertrophy) |
| Allegra ® (allergies) | Lupron ® (prostate cancer) | Zoladex ® (prostate cancer) |
| Diprivan ® (anesthesia) | BuSpar ® (anxiety) | Ventolin ® (bronchospasm) |
| Hytrin ® (hypertension) | Wellbutrin ® (depression) | Zyrtec ® (rhinitis) |
| Plavix ® (MI/stroke) | Toprol-XL ® (hypertension) | Tenormin ® (angina) |
| Xalatan ® (glaucoma) | Singulair ® (asthma) | Diovan ® (hypertension) |
| Hamal ® (prostatic hyperplasia) | | |
| (Med Ad News 1999 Data). | | |

GPCRs share a common structural motif, having seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when a ligand binds with the receptor (often referred to as "activation" of the receptor), there is a change in the conformation of the receptor that facilitates coupling between the intracellular region and an intracellular "G-protein." It has been reported that GPCRs are "promiscuous" with respect to G proteins, i.e., that a GPCR can interact with more than one G protein. See, Kenakin, T., 43 *Life Sciences* 1095 (1988). Although other G proteins exist, currently, Gq, Gs, Gi, Gz and Go are G proteins that have been identified. Ligand-activated GPCR coupling with the G-protein initiates a signaling cascade process (referred to as "signal transduction"). Under normal conditions, signal transduction ultimately results in cellular activation or cellular inhibition. Although not wishing to be bound to theory, it is thought that the IC-3 loop as well as the carboxy terminus of the receptor interact with the G protein.

Gi-coupled GPCRs lower intracellular cAMP levels. The Melanophore technology (see infra) is useful for identifying Gi-coupled GPCRs.

Under physiological conditions, GPCRs exist in the cell membrane in equilibrium between two different conformations: an "inactive" state and an "active" state. A receptor in an inactive state is unable to link to the intracellular signaling transduction pathway to initiate signal transduction leading to a biological response. Changing the receptor conformation to the active state allows linkage to the transduction pathway (via the G-protein) and produces a biological response.

A receptor may be stabilized in an active state by a ligand or a compound such as a drug. Recent discoveries, including but not exclusively limited to modifications to the amino acid sequence of the receptor, provide means other than ligands or drugs to promote and stabilize the receptor in the active state conformation. These means effectively stabilize the receptor in an active state by simulating the effect of a ligand binding to the receptor. Stabilization by such ligand-independent means is termed "constitutive receptor activation."

SUMMARY OF THE INVENTION

RUP25, RUP38, RUP19 and RUP11 belong to a subfamily of human GPCRs on the basis of homology at the nucleotide level. See, Tables B and C, infra. Polynucleotide sequence and polypeptide sequence for human (h), rat (r), or mouse (m) RUP25, RUP38, RUP19, or RUP11 is provided in the Sequence Listing (also see, Tables E and F infra for corresponding SEQ. ID. NOs.).

Agonist engagement of Gi-coupled GPCRs is known to lead to lowered levels of intracellular cAMP. Lower levels of cAMP in adipocytes lead to diminished hormone sensitive lipase activity. (See, supra.) The present invention is based in part on the discovery by Applicant that GPCRs RUP25, RUP38, and RUP19 are coupled to Gi and expressed endogenously by adipocytes. RUP38 and RUP19 are further shown by Applicant to have limited tissue distribution beyond adipose. RUP11 is also disclosed to be coupled to Gi.

Applicant discloses herein that RUP25 is a nicotinic acid and an antilipolytic GPCR. Applicant further discloses that RUP38 and RUP19 are antilipolytic GPCRs. RUP11 is also disclosed to be antilipolytic. The present invention is directed in part to methods of identifying whether a candidate compound is a modulator of RUP25, RUP38, RUP19 or RUP11. The present invention also relates to methods of using said modulator of RUP25, RUP38, RUP19 or RUP11. Preferred said modulator is an agonist. Agonists of RUP25, RUP38, RUP19 or RUP11 are useful as therapeutic agents for the prevention or treatment of metabolic-related disorders, including dyslipidemia, atherosclerosis, coronary heart disease, stroke, insulin resistance, and type 2 diabetes.

Nicotinic acid is disclosed by Applicant to be an agonist for RUP25 but not for RUP38 or RUP19. (−)-Nicotine is also disclosed to be an agonist for RUP25. Exposure of cells expressing RUP25 to nicotinic acid is shown by Applicant to lower the level of intracellular cAMP. Exposure of isolated rat epididymal adipocyte RUP25 to nicotinic acid is shown by Applicant to inhibit lipolysis. Exposure of RUP25 within adipocyte primary cultures derived from human subcutaneous fat to nicotinic acid is shown by Applicant also to inhibit lipolysis. In vivo administration of nicotinic acid to rats is shown by Applicant to lower plasma free fatty acids (FFA).

Applicant has identified (5-Hydroxy-1-methyl-3-propyl-1H-pyrazol-4-yl)-pyridin-3-yl-methanone to be an agonist for RUP25 but not for RUP38. Exposure of cells expressing RUP25 to (5-hydroxy-1-methyl-3-propyl-1H-pyrazol-4-yl)-pyridin-3-yl-methanone is shown by Applicant to lower the level of intracellular cAMP.

Applicant has identified 1-Isopropyl-1H-benzotriazole-5-carboxylic acid to be an agonist for hRUP38 but not for RUP25. Exposure of cells expressing RUP38 to 1-Isopropyl-1H-benzotriazole-5-carboxylic acid is shown by Applicant to lower the level of intracellular cAMP. Exposure of RUP38 within adipocyte primary cultures derived from human subcutaneous fat to 1-Isopropyl-1H-benzotriazole-5-carboxylic acid is shown by Applicant to inhibit lipolysis.

Applicant has identified 3-(5-Bromo-2-ethoxy-phenyl)-acrylic acid to also be an agonist for RUP38 but not for either RUP25 or RUP19. Exposure of cells expressing RUP38 to 3-(5-Bromo-2-ethoxy-phenyl)-acrylic acid is shown by Applicant to lower the level of intracellular cAMP.

Applicant, supra, provides direct in vitro evidence for RUP25 and RUP38 being antilipolytic and direct in vivo evidence in the rat for RUP25 being antilipolytic. Applicant also notes illustrative clinical evidence that nicotinic acid receptor is antilipolytic. Said evidence is consistent with the disclosure by Applicant in the present application that RUP25 is a nicotinic acid and an antilipolytic GPCR. Said evidence is consistent with the disclosure by Applicant in the present application that RUP38 and RUP19 are antilipolytic GPCRs. Said evidence is consistent with the disclosure by Applicant in the present application that RUP11 is an antilipolytic GPCR.

RUP38, RUP19 and RUP11 are further disclosed herein as being antilipolytic GPCRs responsive to agonists other than nicotinic acid. The failure of nicotinic acid to serve as an agonist for RUP38, RUP19 or RUP11 indicates that RUP38, RUP19 and RUP11 represent novel antilipolytic pathways not engaged by conventional nicotinic acid therapy.

See, Table M (Example 24) for a brief Summary and other additional Examples, infra.

In a first aspect, the invention features a method of identifying whether a candidate compound is a modulator of a nicotinic acid GPCR, said receptor comprising an amino acid sequence selected from the group consisting of:

(a) SEQ. ID. NO.:36 (hRUP25);

(b) SEQ. ID. NO.:137 (mRUP25); and (c) SEQ. ID. NO.:139 (rRUP25);

or an allelic variant, a biologically active mutant, or a biologically active fragment of said amino acid sequence;

comprising the steps of:

(a') contacting the candidate compound with the receptor;

(b') determining whether the receptor functionality is modulated;

wherein a change in receptor functionality is indicative of the candidate compound being a modulator of a nicotinic acid GPCR.

In some embodiments, said nicotinic acid GPCR is endogenous.

In some preferred embodiments, said nicotinic acid GPCR is recombinant.

Preferred said identified modulator binds to said GPCR.

In some embodiments, said contacting is carried out in the presence of a known ligand of the GPCR. In some embodiments, said known ligand is an agonist of the GPCR. In some embodiments, said agonist is nicotinic acid or an analog or derivative thereof. In some embodiments, said agonist is (−)-nicotine or an analog or derivative thereof.

The invention also relates to a method of identifying whether a candidate compound is a modulator of lipolysis, comprising the steps of:

(a) contacting the candidate compound with a GPCR comprising an amino acid sequence selected from the group consisting of:

(i) SEQ. ID. NO.:36 (hRUP25);

(ii) SEQ. ID. NO.:137 (mRUP25); and (iii) SEQ. ID. NO.:139 (rRUP25);

or an allelic variant, a biologically active mutant, or a biologically active fragment of said amino acid sequence; and (b) determining whether the receptor functionality is modulated;

wherein a change in receptor functionality is indicative of the candidate compound being a modulator of lipolysis.

In some embodiments, said GPCR is endogenous.

In some preferred embodiments, said GPCR is recombinant.

Preferred said identified modulator binds to said GPCR.

In some embodiments, said contacting is carried out in the presence of a known ligand of the GPCR. In some embodiments, said known ligand is an agonist of the GPCR. In some embodiments, said agonist is nicotinic acid or an analog or derivative thereof. In some embodiments, said agonist is (−)-nicotine or an analog or derivative thereof.

The invention also relates to a method of determining whether a candidate compound is a modulator of a nicotinic acid GPCR, comprising the steps of:

(a) culturing nicotinic acid GPCR-expressing host cells under conditions that would allow expression of a recombinant nicotinic acid GPCR, said host cells being transfected with a polynucleotide encoding said recombinant nicotinic acid GPCR comprising an amino acid sequence selected from the group consisting of:

(i) SEQ. ID. NO.:36 (hRUP25);
(ii) SEQ. ID. NO.:137 (mRUP25); and
(iii) SEQ. ID. NO.:139 (rRUP25);
or an allelic variant, a biologically active mutant, or a biologically active fragment of said amino acid sequence;
(b) contacting the nicotinic acid GPCR-expressing host cells of step (a) with the candidate compound;
(c) contacting control host cells with the candidate compound of step (b), wherein said control host cells do not express recombinant nicotinic acid GPCR protein;
(d) measuring the modulating effect of the candidate compound which interacts with the recombinant nicotinic acid GPCR from the host cells of step (a) and control host cells of step (c); and
(e) comparing the modulating effect of the test compound on the host cells and control host cells.

The invention also relates to a method of determining whether a candidate compound is a modulator of a nicotinic acid GPCR, comprising the steps of:

(a) culturing nicotinic acid GPCR-expressing host cells under conditions that would allow expression of a recombinant nicotinic acid GPCR, said host cells being transfected with a polynucleotide encoding said recombinant nicotinic acid GPCR comprising an amino acid sequence selected from the group consisting of:
(i) SEQ. ID. NO.:36 (hRUP25);
(ii) SEQ. ID. NO.:137 (mRUP25); and
(iii) SEQ. ID. NO.:139 (rRUP25);
or an allelic valiant, a biologically active mutant, or a biologically active fragment of said amino acid sequence;
(b) contacting a first population of nicotinic acid GPCR-expressing cells of step (a) with a known ligand of said nicotinic receptor GPCR;
(c) contacting a second population of nicotinic acid GPCR-expressing cells of step (a) with the candidate compound and with the known nicotinic acid GPCR ligand;
(d) contacting control host cells with the candidate compound of step (c), wherein said control host cells do not express recombinant nicotinic acid GPCR protein;
(e) measuring the modulating effect of the candidate compound, which interacts with recombinant nicotinic acid GPCR, in the presence and absence of the known nicotinic acid GPCR ligand, from the cells of step (b), step (c) and step (d); and
(f) comparing the modulating effect of the candidate compound as determined from step (b), step (c) and step (d).

In some embodiments, said ligand is an agonist of said nicotinic acid GPCR. In a particular embodiment, said agonist is nicotinic acid or an analog or derivative thereof. In other particular embodiment, said agonist is (−)-nicotine or an analog or derivative thereof.

The invention also relates to a method of determining whether a candidate compound is a modulator of a nicotinic acid GPCR, comprising the steps of:

(a) culturing nicotinic acid GPCR-expressing host cells under conditions that would allow expression of a recombinant nicotinic acid GPCR, said host cells being transfected with a polynucleotide encoding said recombinant nicotinic acid GPCR comprising an amino acid sequence selected from the group consisting of:
(i) SEQ. ID. NO.:36 (hRUP25);
(ii) SEQ. ID. NO.:137 (mRUP25); and
(iii) SEQ. ID. NO.:139 (rRUP25);
or an allelic variant, a biologically active mutant, or a biologically active fragment of said amino acid sequence;
(b) contacting a first population of the nicotinic acid GPCR-expressing host cells of step (a) with the candidate compound;
(c) not contacting a second population of the nicotinic acid GPCR-expressing cells of step (a) with the candidate compound of step (b);
(d) contacting control host cells to the candidate compound of step (b), wherein said control host cells do not express recombinant nicotinic acid GPCR protein;
(e) measuring the modulating effect of the candidate compound, which interacts with recombinant nicotinic acid GPCR protein, from the cells of step (b) and step (c) and from the cells of step (d); and
(f) comparing the modulating effect of the candidate compound as determined from step (b) and step (c) and from step (d).

In some embodiments, the nicotinic acid GPCR has an amino acid sequence selected from the group consisting of: SEQ. ID. NO.:36 (hRUP25);
(a) SEQ. ID. NO.:137 (mRUP25); and
(b) SEQ. ID. NO.:139 (rRUP25);
or an allelic variant, a biologically active mutant, or a biologically active fragment of said amino acid sequence.

In some embodiments, the nicotinic acid GPCR comprises a biologically active fragment of said amino acid sequence.

In some embodiments, said biologically active mutant is CART or EFA. In preferred embodiments, said CART mutant has the amino acid sequence of SEQ. ID. NO.:36 further substituted at amino acid position 230 with lysine in place of isoleucine. In preferred embodiments, said EFA mutant has the amino acid sequence of SEQ. ID. NO.:159.

In preferred embodiments, said G protein is Gi.

In other preferred embodiments, said determining is through the use of a Melanophore assay.

In other preferred embodiments, said determining is through the measurement of the level of a second messenger selected from the group consisting of cyclic AMP (cAMP), cyclic GMP (cGMP), inositol triphosphate ($IP_3$), diacylglycerol (DAG), and $Ca^{2+}$. In further preferred embodiments, said second messenger is cAMP. In more preferred embodiments, the level of the cAMP is reduced. In some embodiments, said measurement of cAMP is carried out with membrane comprising said GPCR.

In other preferred embodiments, said determining is through the measurement of an activity up-regulated or down-regulated by a reduction in intracellular cAMP level. In further preferred embodiments, said down-regulated activity is intracellular lipolysis. In other further preferred embodiments, said down-regulated activity is hormone sensitive lipase activity. In other further preferred embodiments, said up-regulated activity is adiponectin secretion.

In other preferred embodiments, said determining is through CRE-reporter assay. In preferred embodiments, said reporter is luciferase. In some embodiments, said reporter is β-galactosidase.

In other embodiments, said recombinant host cell further comprises promiscuous G alpha 15/16 or chimeric Gq/Gi alpha subunit and said determining is through measurement of intracellular $Ca^{2+}$. In preferred embodiments, said $Ca^{2+}$ measurement is carried out by FLIPR.

In other embodiments, said recombinant host cell further comprises promiscuous G alpha 15/16 or chimeric Gq/Gi alpha subunit and said determining is through measurement of intracellular $IP_3$.

In other preferred embodiments, said determining is through the measurement of GTPγS binding to membrane comprising said GPCR. In further preferred embodiments, said GTPγS is labeled with [$^{35}$S].

In other preferred embodiments, said method further comprises the step of comparing the modulation of the receptor caused by the candidate compound to a second modulation of the receptor caused by contacting the receptor with a known modulator of the receptor. In some preferred embodiments, said known modulator is an agonist. In some preferred embodiments, said agonist is nicotinic acid or an analog or derivative therof. In some preferred embodiments, said agonist is (−)-nicotine or an analog or derivative thereof.

In a second aspect, the invention features a modulator of a nicotinic acid GPCR identified according to the method of the first aspect, provided that the modulator is not identical to a compound having a formula selected from the group consisting of:

a)

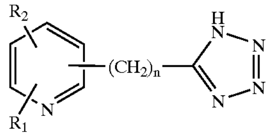

wherein:

$R_1$ is selected from the group consisting of halogen, hydroxyl, acetylamino, amino, alkoxy, carboalkoxy, alkylthio, monoalkylamino, dialkylamino, N-alkylcarbamyl, N,N-dialkylcarbamyl, alkylsulfonyl, said alkyl groups containing from 1 to 4 carbons, trifluoromethyl, trifluoromethoxy, trifluoromethylthio, methoxymethyl, carboxy, carbamyl, alkanoyloxy containing up to 4 carbon atoms, phenyl, p-chlorophenyl, p-methylphenyl and p-aminophenyl;

$R_2$ is selected from the group consisting of halogen, alkannoyloxy containing from 1–4 carbon atoms, carboalkoxy containing from 2 to 5 carbon atoms, carbamyl, N-alkyl carbamyl and N,N-dialkylcarbamyl wherein said alkyl groups contain from 1–4 carbon atoms and trifluoromethyl;

n is a whole number from 0 to 4; and

N-oxides thereof;

b)

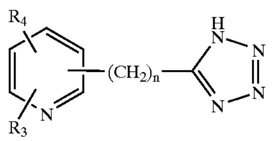

$R_3$ and $R_4$ are hydrogen, alkyl containing from 1 to 4 carbon atoms or cycloalkyl containing from 3 to 7 carbon atoms;

n is a whole number from 0 to 4; and

N-oxides thereof;

c)

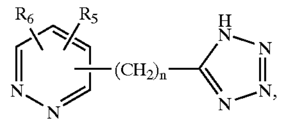

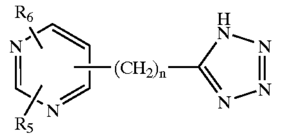

or

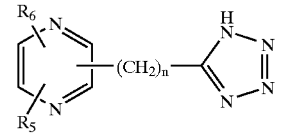

wherein:

$R_5$ and $R_6$ are each selected from the group consisting of H, halogen, hydroxyl, amino, alkyloxy, alkylthio, monoalkylamino, dialkylamino, N-alkylcarbamyl, N,N-dialkylcarbamyl, alkylsulfoxy, alkylsulfony, said alkyl groups containing from 1 to 4 carbons, trifluoromethyl, trifluoromethoxy, trifluoromethylthio, carboxy, carbamyl, alkanoyloxy containing up to 4 carbon atoms, phenyl, p-chlorophenyl, p-methylphenyl and p-aminophenyl;

n is a whole number from 0 to 4; and

N-oxides thereof;

d)

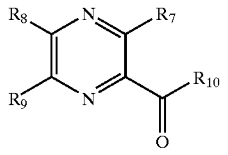

wherein:

at least one of $R_7$, $R_8$ and $R_9$ is $C_{1-6}$ alkyl and the others are hydrogen atoms; $R_{10}$ is hydroxy or $C_{1-6}$ alkoxy, or a salt of the compounds wherein $R_4$ is hydroxy with a pharmaceutically acceptable base; and a 4-N-oxide thereof. The position of the N-oxide is designated by the following numbering and a structure for a 4-N-oxide has the following structure:

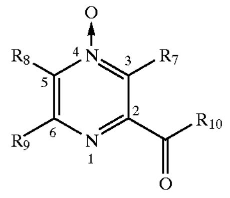

One particular 4-N-oxide is 5-Methylpyrazine-2-carboxylic acid-4-oxide (Acipimox™) and has the structure:

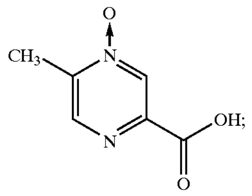

e)

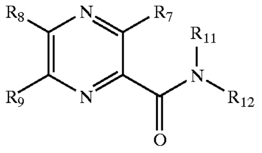

wherein:

at least one of $R_7$, $R_8$ and $R_9$ is $C_{1-6}$ alkyl and the others are hydrogen atoms; each of $R_{11}$ and $R_{12}$, which may be the same or different, is hydrogen or $C_{1-6}$ alkyl; and a 4-N-oxide thereof; the position of the N-oxide is the same as described above herein;

(f)

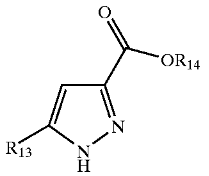

wherein:

at least one of $R_{13}$ represents an alkyl group of 7–11 carbon atoms and $R_{14}$ represents H or a lower alkyl group of up to two carbon atoms, and a pharmaceutically acceptable carrier;

(g) Pyrazine-2-carboxylic acid amide and has the structure:

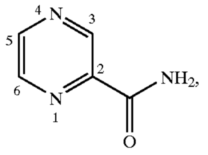

5-chloro-pyrazine-2-carboxylic acid amide and has the structure:

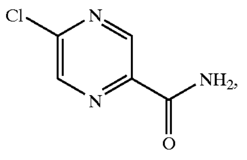

5-amino-pyrazine-2-carboxylic acid amide and has the structure:

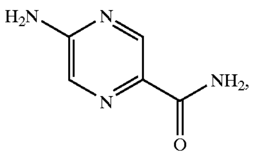

5-benzyl-pyrazine-2-carboxylic acid amide and has the structure:

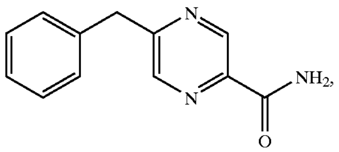

6-chloro-pyrazine-2-carboxylic acid amide and has the structure:

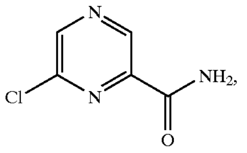

6-methoxy-pyrazine-2-carboxylic acid amide and has the structure:

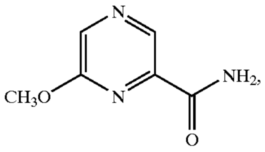

3-chloro-pyrazine-2-carboxylic acid amide and has the structure:

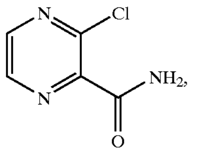

3-methoxy-pyrazine-2-carboxylic acid amide and has the structure:

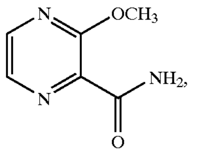

pyrazine-2-carboxylic acid ethylamide and has the structure:

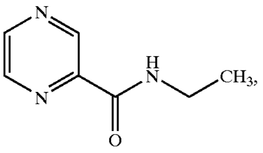

morpholin-4-yl-pyrazine-2-ylmethanone and has the structure:

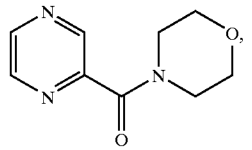

5-methyl-pyrazine-2-carboxylic acid (6-methyl-pyrazin-2-yl)-amide and has the structure:

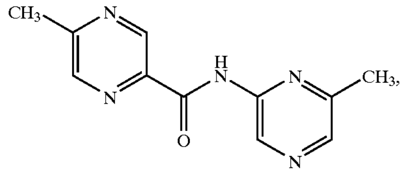

5-methyl-pyrazine-2-carboxylic acid (5-methyl-pyrazin-2-yl)-amide and has the structure:

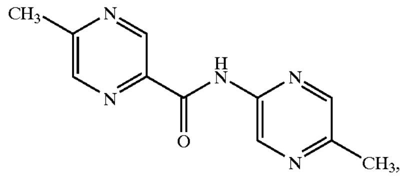

5-methyl-pyrazine-2-carboxylic acid (3-methyl-pyrazin-2-yl)-amide and has the structure:

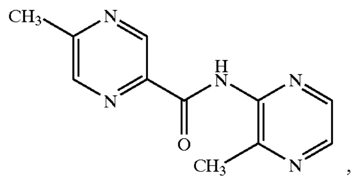

(5-methyl-pyrazin-2-yl)-morpholin4-yl-methanone and has the structure:

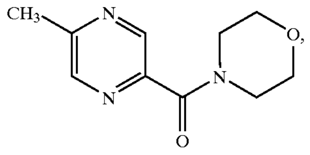

5-methyl-pyrazine-2-carboxylic acid hydroxyamide and has the structure:

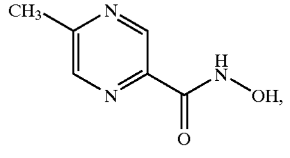

pyrazine-2-carboxylic acid and has the structure:

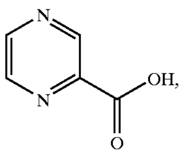

5-amino-pyrazine-2-carboxylic acid and has the structure:

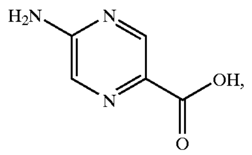

5-benzyl-pyrazine-2-carboxylic acid and has the structure:

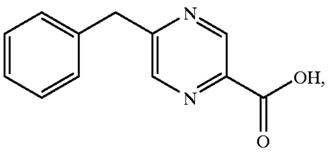

6-chloro-pyrazine-2-carboxylic acid and has the structure:

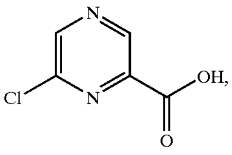

6-methoxy-pyrazine-2-carboxylic acid and has the structure:

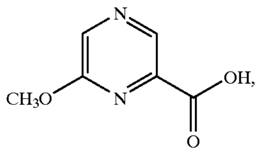

3-hydroxy-pyrazine-2-carboxylic acid and has the structure:

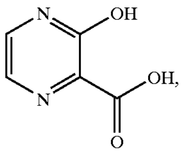

5-methyl-pyrazine-2-carboxylic acid 2-hydroxy-ethyl ester and has the structure:

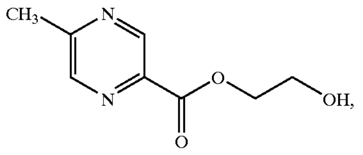

5-methyl-pyrazine-2-carboxylic acid allyl ester and has the structure:

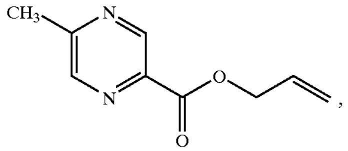

5-methyl-pyrazine-2-carboxylic acid phenyl ester and has the structure:

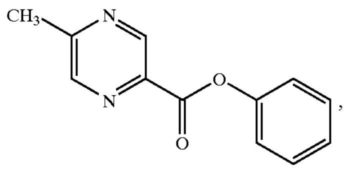

5-methyl-pyrazine-2-carboxylic acid ethoxycarbonylmethyl ester and has the structure:

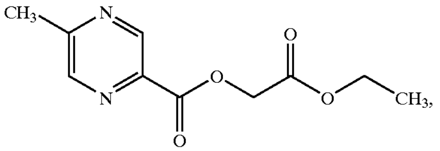

pyrazine-2-carboxylic acid methyl ester and has the structure:

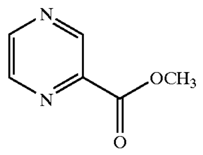

and 2-methyl-5-(1H-tetrazol-5-yl)-pyrazine and has the structure:

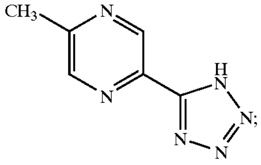

and 4-N-oxides thereof as described above herein;

(h) 5-(3-(5-Methyl)isoxazolyl)tetrazole and has the structure:

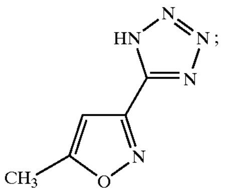

(i) 5-(5-(3-Methyl)isoxazolyl)tetrazole and has the structure:

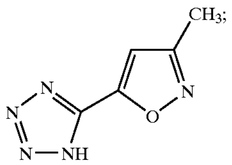

(j) 5-(3-Quinolyl)tetrazole and has the structure:

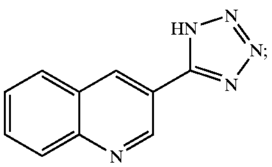

(k) Nicotinic acid and has the structure:

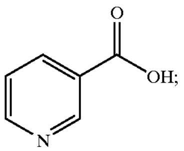

(l) Pyridazine-4-carboxylic acid and has the structure:

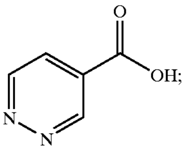

(m) 3-Pyridine acetic acid and has the structure:

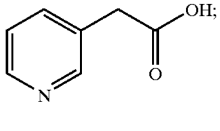

(n) 5-Methylnicotinic acid and has the structure:

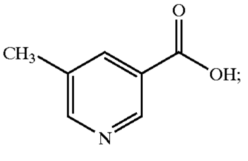

(o) 6-Methylnicotinic acid and has the structure:

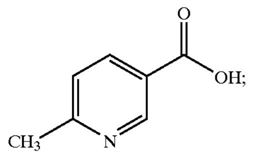

(p) Nicotinic acid-1-oxide and has the structure:

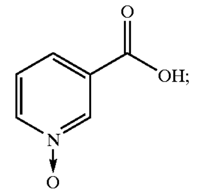

(q) 2-Hydroxynicotinic acid and has the structure:

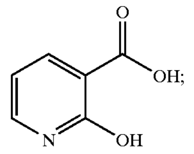

(r) Furane-3-carboxylic acid and has the structure:

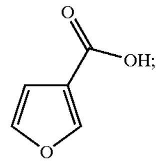

(s) 5-Methylpyrazole-3-carboxylic acid and has the structure:

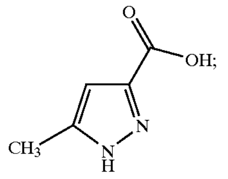

and (t) 3-Methylisoxazole-5-carboxylic acid and has the structure:

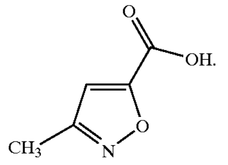

In preferred embodiments, said modulator is selected from the group consisting of agonist, partial agonist, inverse agonist and antagonist. More preferably, said modulator is an agonist. In some embodiments, said modulator is a partial agonist.

In some embodiments, said modulator is an agonist with an $EC_{50}$ of less than 1000 μM in GTPγS binding assay carried out with membrane from stably transfected CHO cells expressing recombinant hRUP25 polypeptide having the amino acid sequence of SEQ. ID. NO.:36. In some embodiments, said modulator is an agonist with an $EC_{50}$ of less than 900 μM in said assay. In some embodiments, said modulator is an agonist with an $EC_{50}$ of less than 800 μM in said assay. In some embodiments, said modulator is an agonist with an $EC_{50}$ of less than 700 μM in said assay. In some embodiments, said modulator is an agonist with an $EC_{50}$ of less than 600 μM in said assay. In some embodiments, said modulator is an agonist with an $EC_{50}$ of less than 550 μM in said assay. In some embodiments, said modulator is an agonist with an $EC_{50}$ of less than 500 μM in said assay. In some embodiments, said modulator is an agonist with an $EC_{50}$ of less than 450 μM in said assay. In some embodiments, said modulator is an agonist with an $EC_{50}$ of less than 400 μM in said assay. In some embodiments, said modulator is an agonist with an $EC_{50}$ of less than 350 μM in said assay. In some embodiments, said modulator is an agonist with an $EC_{50}$ of less than 300 μM in said assay. In some embodiments, said modulator is an agonist with an $EC_{50}$ of less than 250 μM in said assay. In some embodiments, said modulator is an agonist with an $EC_{50}$ of less than 200 μM in said assay. In some embodiments, said modulator is an agonist with an $EC_{50}$ of less than 150 μM in said assay. In some embodiments, said modulator is an agonist with an $EC_{50}$ of less than 100 μM in said assay. In some preferred embodiments, said modulator is an agonist with an $EC_{50}$ in said assay of less than a value selected from the interval of 600 μM to 1000 μM.

In some embodiments, said modulator is selective for the GPCR.

In some embodiments, said modulator is antilipolytic.

In some embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In highly less preferred embodiments, said modulator is an antibody or derivative thereof.

In a third aspect, the invention features the method of the first aspect, wherein said candidate compound is an agonist of hRUP38 GPCR comprising the amino acid sequence of SEQ. ID. NO.:135 and wherein said method further comprises the step of comparing the modulation of hRUP25 GPCR comprising the amino acid sequence of SEQ. ID. NO.:36 caused by said agonist to a second modulation of hRUP25 GPCR comprising a variant of said amino acid sequence caused by contacting the variant hRUP25 GPCR with said agonist.

In preferred embodiments, said variant amino acid sequence is identical to the amino acid sequence of SEQ. ID. NO.:36, further comprising a single amino acid substitution selected from the group consisting of:

(a) A for V at amino acid position 27 of SEQ. ID. NO.:36;

(b) V for L at amino acid position 83 of SEQ. ID. NO.:36;

(c) Y for N at amino acid position 86 of SEQ. ID. NO.:36;

(d) S for W at amino acid position 91 of SEQ. ID. NO.:36;

(e) N for K at amino acid position 94 of SEQ. ID. NO.:36;

(f) V for M at amino acid position 103 of SEQ. ID. NO.:36;

(g) F for L at amino acid position 107 of SEQ. ID. NO.:36;

(h) W for R at amino acid position 142 of SEQ. ID. NO.:36;

(i) V for I at amino acid position 156 of SEQ. ID. NO.:36;

(j) L for M at amino acid position 167 of SEQ. ID. NO.:36;

(k) L for P at amino acid position 168 of SEQ. ID. NO.:36;

(l) P for G at amino acid position 173 of SEQ. ID. NO.:36;

(m) V for L at amino acid position 176 of SEQ. ID. NO.:36;

(n) I for S at amino acid position 178 of SEQ. ID. NO.:36;

(o) R for Q at amino acid position 187 of SEQ. ID. NO.:36;

(p) L for F at amino acid position 198 of SEQ. ID. NO.:36; and (q) N for P at amino acid position 363 of SEQ. ID. NO.:36.

In particularly preferred embodiments, said method is used to identify whether said substituted amino acid additionally found at the identical position within SEQ. ID. NO.:135 is necessary for modulation of said hRUP38 GPCR by said agonist, comprising the steps of:

(a) determining the level of modulation of said hRUP25 GPCR by said agonist; and (b) determining the level of modulation of said variant hRUP25 GPCR by said agonist;

wherein if said level of modulation for (b) is greater than said level of modulation for (a), then said substituted amino acid is necessary for modulation of said hRUP38 GPCR by said agonist.

In a fourth aspect, the invention features a method of modulating the activity of a nicotinic acid GPCR, said receptor comprising an amino acid sequence selected from the group consisting of:

(a) SEQ. ID. NO.:36 (hRUP25);

(b) SEQ. ID. NO.:137 (mRUP25); and (c) SEQ. ID. NO.:139 (rRUP25);

or an allelic variant, a biologically active mutant, or a biologically active fragment of said amino acid sequence; comprising the step of contacting the receptor with the modulator of the second aspect.

In some embodiments, the nicotinic acid GPCR has an amino acid sequence selected from the group consisting of:

(a) SEQ. ID. NO.:36 (hRUP25);

(b) SEQ. ID. NO.:137 (mRUP25); and (c) SEQ. ID. NO.:139 (rRUP25);

or an allelic variant, a biologically active mutant, or a biologically active fragment of said amino acid sequence.

In some embodiments, the nicotinic acid GPCR comprises an active fragment of said amino acid sequence.

In some embodiments, the nicotinic acid GPCR is endogenous.

In some embodiments, the nicotinic acid GPCR is recombinant.

In some embodiments, said biologically active mutant is CART or EFA. In preferred embodiments, said CART mutant has the amino acid sequence of SEQ. ID. NO.:36 further substituted at amino acid position 230 with lysine in place of isoleucine. In preferred embodiments, said EFA mutant has the amino acid sequence of SEQ. ID. NO.:159.

In preferred embodiments, said G protein is Gi.

In some preferred embodiments, said modulator is an agonist.

In preferred embodiments, said modulator is selective for the GPCR.

In other preferred embodiments, said contacting comprises administration of the modulator to a membrane comprising the receptor.

In other preferred embodiments, said contacting comprises administration of the modulator to a cell or tissue comprising the receptor.

In other preferred embodiments, said contacting comprises administration of the modulator to an individual comprising the receptor. In more preferred embodiments, said individual is a mammal. In other more preferred embodiments, said mammal is a horse, cow, sheep, pig, cat, dog, rabbit, mouse, rat, non-human primate or human. Yet more preferred is mouse, rat or human. Most preferred is human.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP25 polypeptide having the amino acid sequence of SEQ. ID. NO.:36. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said administration is oral.

In preferred embodiments, said modulator is an agonist and said individual is in need of prevention of or treatment for a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In other embodiments, said modulator is an inverse agonist and said metabolic-related disorder relates to a low level of plasma free fatty acids.

In other preferred embodiments, said modulator is an agonist and said individual is in need of a change in lipid metabolism selected from the group consisting of:

(a) a decrease in the level of plasma triglycerides;

(b) a decrease in the level of plasma free fatty acids;

(c) a decrease in the level of plasma cholesterol;

(d) a decrease in the level of LDL-cholesterol;

(e) an increase in the level of HDL-cholesterol;

(f) a decrease in the total cholesterol/HDL-cholesterol ratio; and (g) an increase in the level of plasma adiponectin.

In other preferred embodiments, said needed change in lipid metabolism is a decrease in the postprandial increase in plasma free fatty acids due to a high fat meal or an inhibition of the progression from impaired glucose tolerance to insulin resistance.

In some embodiments, the modulator is an inverse agonist and the needed change in lipid metabolism is an increase in the level of plasma free fatty acids.

In other preferred embodiments, said modulator is an agonist and said individual is a mouse genetically predisposed to a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure.

In further preferred embodiments, said metabolic-related disorder is hyperlipidemia.

In further preferred embodiments, said method is used to identify whether said agonist has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering said agonist to the mouse; and (b') determining whether the disorder is prevented, delayed, or made less severe on administering said agonist compared to not administering said agonist;

wherein said determination is indicative of said agonist having therapeutic efficacy.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In other preferred embodiments, said modulator is an agonist and said individual is a rat genetically predisposed to a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In further preferred embodiments, said metabolic-related disorder is hyperlipidemia.

In further preferred embodiments, said method is used to identify whether said agonist has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering said agonist to the rat; and (b') determining whether the disorder is prevented, delayed, or made less severe on administering said agonist compared to not administering said agonist;

wherein said determination is indicative of said agonist having therapeutic efficacy.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In a fifth aspect, the invention features a method of preventing or treating a disorder of lipid metabolism in an individual comprising contacting a therapeutically effective amount of the modulator of the second aspect with a nicotinic acid GPCR, said receptor comprising an amino acid sequence selected from the group consisting of:

(a) SEQ. ID. NO.:36 (hRUP25);

(b) SEQ. ID. NO.:137 (mRUP25); and (c) SEQ. ID. NO.:139 (rRUP25);

or an allelic variant or biologically active fragment of said amino acid sequence.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP25 polypeptide having the amino acid sequence of SEQ. ID. NO.:36. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said contacting comprises oral administration of said modulator to said individual.

In preferred embodiment, said modulator is an agonist and said disorder of lipid metabolism is selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/EDL-cholesterol ratio; and (g) reduced level of plasma adiponectin.

In a sixth aspect, the invention features a method of preventing or treating a metabolic-related disorder in an individual comprising contacting a therapeutically effective amount of the modulator of the second aspect with a nicotinic acid GPCR, said receptor comprising an amino acid sequence selected from the group consisting of:

(a) SEQ. ID. NO.:36 (hRUP25);

(b) SEQ. ID. NO.:137 (mRUP25); and (c) SEQ. ID. NO.:139 (rRUP25);

or an allelic variant or biologically active fragment of said amino acid sequence.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP25 polypeptide having the amino acid sequence of SEQ. ID. NO.:36. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said contacting comprises oral administration of said modulator to said individual.

In preferred embodiment, said modulator is an agonist and said metabolic-related disorder is selected from the group consisting of:

(a) dyslipidemia;

(b) atherosclerosis;

(c) coronary heart disease;

(d) stroke;

(e) insulin resistance; and (f) type 2 diabetes.

In a seventh aspect, the invention features a method of preparing a composition which comprises identifying a modulator of a nicotinic acid GPCR and then admixing a carrier and the modulator, wherein the modulator is identifiable by the method of the first aspect and provided that the modulator is not identical to a compound having a formula selected from the group consisting of:

a)

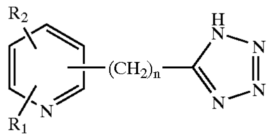

wherein:

$R_1$ is selected from the group consisting of halogen, hydroxyl, acetylamino, amino, alkoxy, carboalkoxy, alkylthio, monoalkylamino, dialkylamino, N-alkylcarbamyl, N,N-dialkylcarbamyl, alkylsulfonyl, said alkyl groups containing from 1 to 4 carbons, trifluoromethyl, trifluoromethoxy, trifluoromethylthio, methoxymethyl, carboxy, carbamyl, alkanoyloxy containing up to 4 carbon atoms, phenyl, p-chlorophenyl, p-methylphenyl and p-aminophenyl;

$R_2$ is selected from the group consisting of halogen, alkannoyloxy containing from 1–4 carbon atoms, carboalkoxy containing from 2 to 5 carbon atoms, carbamyl, N-alkyl carbamyl and N,N-dialkylcarbamyl wherein said alkyl groups contain from 1–4 carbon atoms and trifluoromethyl;

n is a whole number from 0 to 4; and

N-oxides thereof;

b)

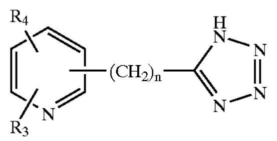

$R_3$ and $R_4$ are hydrogen, alkyl containing from 1 to 4 carbon atoms or cycloalkyl containing from 3 to 7 carbon atoms;

n is a whole number from 0 to 4; and

N-oxides thereof;

c)

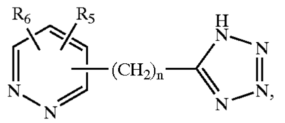

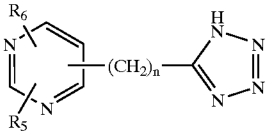

or

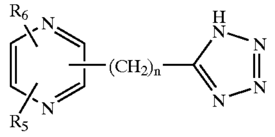

wherein:

$R_5$ and $R_6$ are each selected from the group consisting of H, halogen, hydroxyl, amino, alkyloxy, alkylthio, monoalkylamino, dialkylamino, N-alkylcarbamyl, N,N-dialkylcarbamyl, alkylsulfoxy, alkylsulfony, said alkyl groups containing from 1 to 4 carbons, trifluoromethyl, trifluoromethoxy, trifluoromethylthio, carboxy, carbamyl, alkanoyloxy containing up to 4 carbon atoms, phenyl, p-chlorophenyl, p-methylphenyl and p-aminophenyl;

n is a whole number from 0 to 4; and

N-oxides thereof;

d)

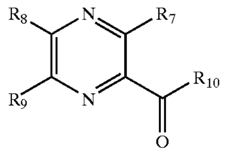

wherein:

at least one of $R_7$, $R_8$ and $R_9$ is $C_{1-6}$ alkyl and the others are hydrogen atoms; $R_{10}$ is hydroxy or $C_{1-6}$ alkoxy, or a salt of the compounds wherein $R_4$ is hydroxy with a pharmaceutically acceptable base; and a 4-N-oxide thereof. The position of the N-oxide is designated by the following numbering and a structure for a 4-N-oxide has the following structure:

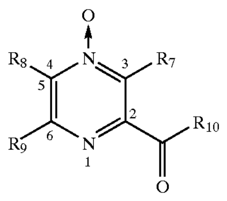

One particular 4-N-oxide is 5-Methylpyrazine-2-carboxylic acid-4-oxide (Acipimox™) and has the structure:

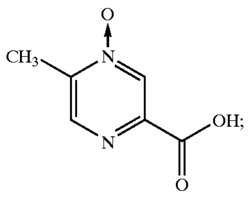

e)

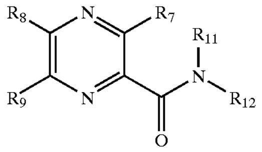

wherein:

at least one of $R_7$, $R_8$ and $R_9$ is $C_{1-6}$ alkyl and the others are hydrogen atoms; each of $R_{11}$ and $R_{12}$, which may be the same or different, is hydrogen or $C_{1-6}$ alkyl; and a 4-N-oxide thereof; the position of the N-oxide is the same as described above herein;

f)

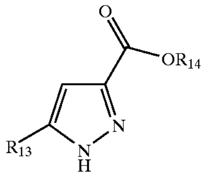

wherein:

at least one of $R_{13}$ represents an alkyl group of 7–11 carbon atoms and $R_{14}$ represents H or a lower alkyl group of up to two carbon atoms, and a pharmaceutically acceptable carrier;

(g) Pyrazine-2-carboxylic acid amide and has the structure:

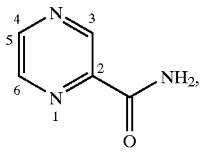

5-chloro-pyrazine-2-carboxylic acid amide and has the structure:

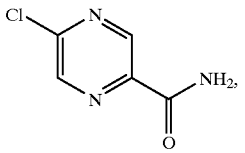

5-amino-pyrazine-2-carboxylic acid amide and has the structure:

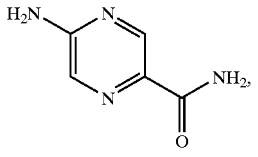

5-benzyl-pyrazine-2-carboxylic acid amide and has the structure:

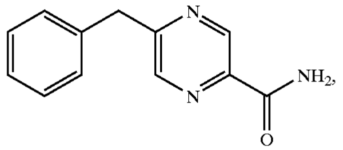

6-chloro-pyrazine-2-carboxylic acid amide and has the structure:

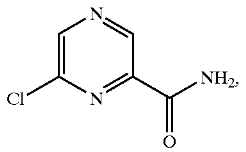

6-methoxy-pyrazine-2-carboxylic acid amide and has the structure:

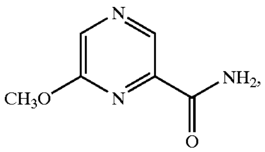

3-chloro-pyrazine-2-carboxylic acid amide and has the structure:

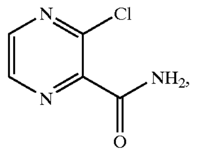

3-methoxy-pyrazine-2-carboxylic acid amide and has the structure:

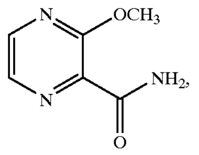

pyrazine-2-carboxylic acid ethylamide and has the structure:

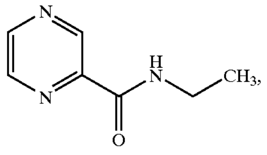

morpholin-4-yl-pyrazine-2-ylmethanone and has the structure:

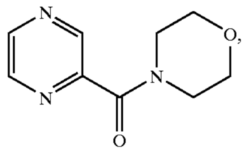

5-methyl-pyrazine-2-carboxylic acid (6-methyl-pyrazin-2-yl)-amide and has the structure:

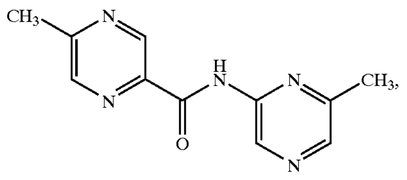

5-methyl-pyrazine-2-carboxylic acid (5-methyl-pyrazin-2-yl)-amide and has the structure:

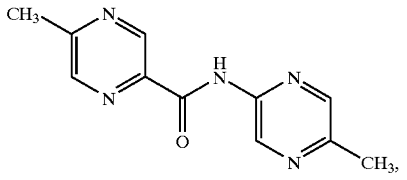

5-methyl-pyrazine-2-carboxylic acid (3-methyl-pyrazin-2-yl)-amide and has the structure:

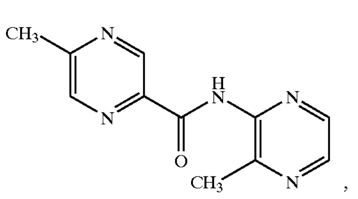

(5-methyl-pyrazin-2-yl)-morpholin-4-yl-methanone and has the structure:

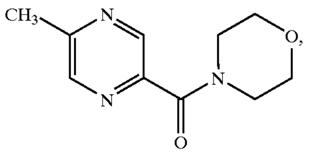

5-methyl-pyrazine-2-carboxylic acid hydroxyamide and has the structure:

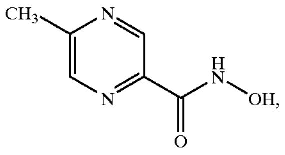

pyrazine-2-carboxylic acid and has the structure:

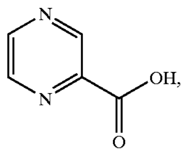

5-amino-pyrazine-2-carboxylic acid and has the structure:

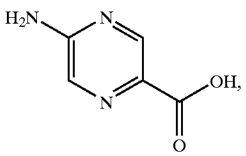

5-benzyl-pyrazine-2-carboxylic acid and has the structure:

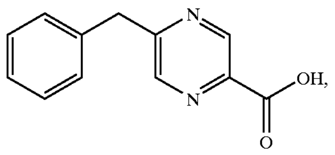

6-chloro-pyrazine-2-carboxylic acid and has the structure:

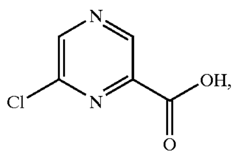

6-methoxy-pyrazine-2-carboxylic acid and has the structure:

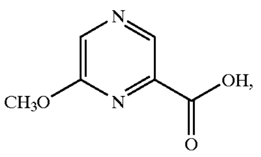

3-hydroxy-pyrazine-2-carboxylic acid and has the structure:

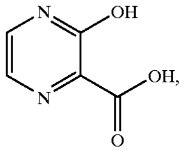

5-methyl-pyrazine-2-carboxylic acid 2-hydroxy-ethyl ester and has the structure:

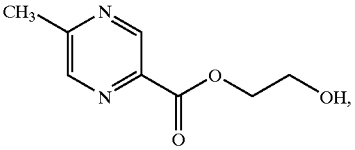

5-methyl-pyrazine-2-carboxylic acid allyl ester and has the structure:

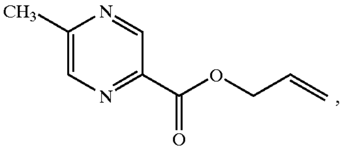

5-methyl-pyrazine-2-carboxylic acid phenyl ester and has the structure:

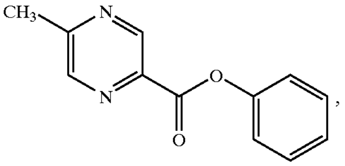

5-methyl-pyrazine-2-carboxylic acid ethoxycarbonylmethyl ester and has the structure:

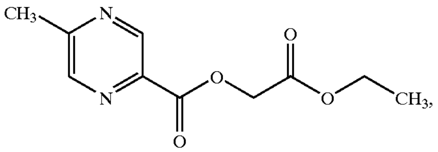

pyrazine-2-carboxylic acid methyl ester and has the structure:

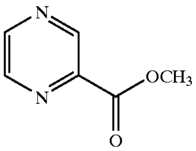

and 2-methyl-5-(1H-tetrazol-5-yl)-pyrazine and has the structure:

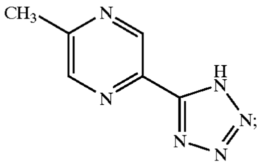

and 4-N-oxides thereof as described above herein;

(h) 5-(3-(5-Methyl)isoxazolyl)tetrazole and has the structure:

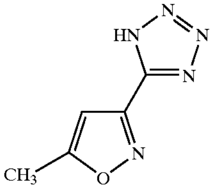

;

(i) 5-(5-(3-Methyl)isoxazolyl)tetrazole and has the structure:

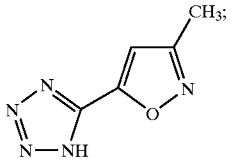

(j) 5-(3-Quinolyl)tetrazole and has the structure:

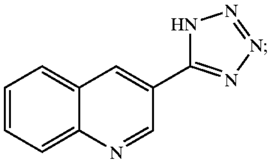

(k) Nicotinic acid and has the structure:

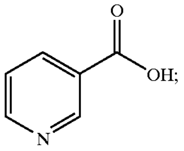

(l) Pyridazine-4-carboxylic acid and has the structure:

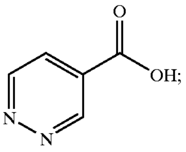

(m) 3-Pyridine acetic acid and has the structure:

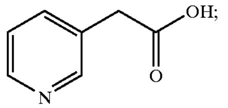

(n) 5-Methylnicotinic acid and has the structure:

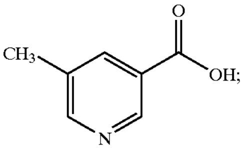

(o) 6-Methylnicotinic acid and has the structure:

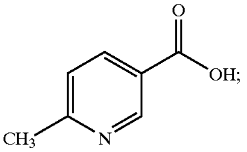

(p) Nicotinic acid-I-oxide and has the structure:

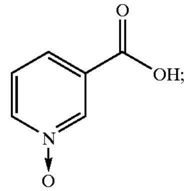

(q) 2-Hydroxynicotinic acid and has the structure:

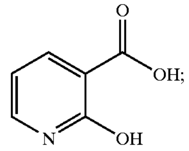

(r) Furane-3-carboxylic acid and has the structure:

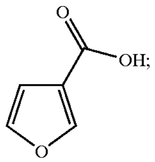

(s) 5-Methylpyrazole-3-carboxylic acid and has the structure:

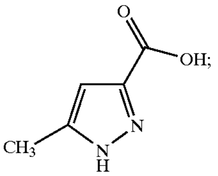

and t) 3-Methylisoxazole-5-carboxylic acid and has the structure:

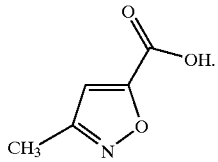

In preferred embodiments, said modulator is selected from the group consisting of agonist, partial agonist, inverse agonist and antagonist. More preferably, said modulator is an agonist. In some embodiments, said modulator is a partial agonist.

In some embodiments, said modulator is an agonist with an $EC_{50}$ of less than 1000 μM in GTPγS binding assay carried out with membrane from stably transfected CHO cells expressing recombinant hRUP25 polypeptide having the amino acid sequence of SEQ. ID. NO.:36. In some embodiments, said modulator is an agonist with an $EC_{50}$ of less than 900 μM in said assay. In some embodiments, said modulator is an agonist with an $EC_{50}$ of less than 800 μM in said assay. In some embodiments, said modulator is an agonist with an $EC_{50}$ of less than 700 μM in said assay. In some embodiments, said modulator is an agonist with an $EC_{50}$ of less than 600 μM in said assay. In some embodiments, said modulator is an agonist with an $EC_{50}$ of less than 550 μM in said assay. In some embodiments, said modulator is an agonist with an $EC_{50}$ of less than 500 μM in said assay. In some embodiments, said modulator is an agonist with an $EC_{50}$ of less than 450 μM in said assay. In some embodiments, said modulator is an agonist with an $EC_{50}$ of less than 400 μM in said assay. In some embodiments, said modulator is an agonist with an $EC_{50}$ of less than 350 μM in said assay. In some embodiments, said modulator is an agonist with an $EC_{50}$ of less than 300 μM in said assay. In some embodiments, said modulator is an agonist with an $EC_{50}$ of less than 250 μM in said assay. In some embodiments, said modulator is an agonist with an $EC_{50}$ of less than 200 μM in said assay. In some embodiments, said modulator is an agonist with an $EC_{50}$ of less than 150 μM in said assay. In some embodiments, said modulator is an agonist with an $EC_{50}$ of less than 100 μM in said assay. In some preferred embodiments, said modulator is an agonist with an $EC_{50}$ in said assay of less than a value selected from the interval of 600 μM to 1000 μM.

In some embodiments, said modulator is selective for the GPCR.

In some embodiments, said modulator is antilipolytic.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to either intraperitoneal or intravenous administration. In some preferred embodiments, said oral bioavailability is at least 1%, at least 5%, at least 10%, or at least 15% relative to either intraperitoneal or intravenous administration.

In an eighth aspect, the invention features a pharmaceutical or physiologically acceptable composition comprising, consisting essentially of or consisting of the modulator of the second aspect. In preferred embodiments, said modulator is an agonist.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 μM in GTPγS binding assay carried out with membrane from stably transfected CHO cells expressing recombinant hRUP25 polypeptide having the amino acid sequence of SEQ. ID. NO.:36. In some embodiments, said modulator is an agonist with an $EC_{50}$ of less than 900 μM in said assay. In some embodiments, said modulator is an agonist with an $EC_{50}$ of less than 800 μM in said assay. In some embodiments, said modulator is an agonist with an $EC_{50}$ of less than 700 μM in said assay. In some embodiments, said modulator is an agonist with an $EC_{50}$ of less than 600 μM in said assay. In some embodiments, said modulator is an agonist with an $EC_{50}$ of less than 550 μM in said assay. In some embodiments, said modulator is an agonist with an $EC_{50}$ of less than 500 μM in said assay. In some embodiments, said modulator is an agonist with an $EC_{50}$ of less than 450 μM in said assay. In some embodiments, said modulator is an agonist with an $EC_{50}$ of less than 400 μM in said assay. In some embodiments, said modulator is an agonist with an $EC_{50}$ of less than 350 μM in said assay. In some embodiments, said modulator is an agonist with an $EC_{50}$ of less than 300 μM in said assay. In some embodiments, said modulator is an agonist with an $EC_{50}$ of less than 250 μM in said assay. In some embodiments, said modulator is an agonist with an $EC_{50}$ of less than 200 μM in said assay. In some embodiments, said modulator is an agonist with an $EC_{50}$ of less than 150 μM in said assay. In some embodiments, said modulator is an agonist with an $EC_{50}$ of less than 100 μM in said assay. In some preferred embodiments, said modulator is an agonist with an $EC_{50}$ in said assay of less than a value selected from the interval of 600 μM to 1000 μM.

In a ninth aspect, the invention features a method of changing lipid metabolism comprising providing or administering to an individual in need of said change said pharmaceutical or physiologically acceptable composition of the eighth aspect, said needed change in lipid metabolism selected from the group consisting of:

(a) a decrease in the level of plasma triglycerides;

(b) a decrease in the level of plasma free fatty acids;

(c) a decrease in the level of plasma cholesterol;

(d) a decrease in the level of LDL-cholesterol;

(e) an increase in the level of HDL-cholesterol;

(f) a decrease in the total cholesterol/HDL-cholesterol ratio; and (g) an increase in the level of plasma adiponectin.

In preferred embodiments, a therapeutically effective amount of said pharmaceutical or physiologically acceptable composition is provided or administered to said individual.

In some preferred embodiments, said providing or administering of said pharmaceutical or physiologically acceptable composition is oral.

In other preferred embodiments, said needed change in lipid metabolism is a decrease in the prostprandial increase in plasma free fatty acids due to a high fat meal or an inhibition of the progression from impaired glucose tolerance to insulin resistance.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In a tenth aspect, the invention features a method of preventing or treating a metabolic-related disorder comprising providing or administering to an individual in need of said treatment said pharmaceutical or physiologically acceptable composition of the eighth aspect, said metabolic-related disorder selected from the group consisting of:

(a) dyslipidemia;

(b) atherosclerosis;

(c) coronary heart disease;

(d) stroke;

(e) insulin resistance; and (f) type 2 diabetes.

In preferred embodiments, a therapeutically effective amount of said pharmaceutical or physiologically acceptable composition is provided or administered to said individual.

In some preferred embodiments, said providing or administering of said pharmaceutical or physiologically acceptable composition is oral.

In other preferred embodiments, said metabolic-related disorder is selected from the group consisting of obesity, impaired glucose tolerance, atheromatous disease, hypertension, stroke, Syndrome X, and heart disease. Heart disease includes, but is not limited to, cardiac insufficiency, coronary insufficiency, and high blood pressure. In other preferred embodiments, said metabolic-related disorder is hyperlipidemia.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In an eleventh aspect, the invention features a method of using the modulator of the second aspect for the preparation of a medicament for the treatment of a disorder in lipid metabolism in an individual.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP25 polypeptide having the amino acid sequence of SEQ. ID. NO.:36. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said-modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said treatment comprises oral administration of said medicament to said individual.

In preferred embodiments, said modulator is an agonist and said disorder in lipid metabolism is selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin.

In other preferred embodiments, said disorder in lipid metabolism is an elevated postprandial increase in plasma free fatty acids due to a high fat meal or a progression from impaired glucose tolerance to insulin resistance.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In a twelfth aspect, the invention features a method of using the modulator of the second aspect for the preparation of a medicament for the treatment of a metabolic-related disorder in an individual.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP25 polypeptide having the amino acid sequence of SEQ. ID. NO.:36. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said treatment comprises oral administration of said medicament to said individual.

In preferred embodiments, said modulator is an agonist and said metabolic-related disorder is selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In a thirteenth aspect, the invention features a method of identifying whether a candidate compound binds to a nicotinic acid GPCR, said receptor comprising an amino acid sequence selected from the group consisting of:

(a) SEQ. ID. NO.:36 (hRUP25);

(b) SEQ. ID. NO.:137 (mRUP25); and (c) SEQ. ID. NO.:139 (rRUP25);

or an allelic variant or a biologically active fragment of said amino acid sequence;

comprising the steps of:

(a') contacting the receptor with a labeled reference compound known to bind to the GPCR in the presence or absence of the candidate compound; and (b') determining whether the binding of said labeled reference compound to the receptor is inhibited in the presence of the candidate compound;

wherein said inhibition is indicative of the candidate compound binding to a nicotinic acid GPCR.

In some embodiments, the nicotinic acid GPCR comprises a biologically active fragment of said amino acid sequence.

In some embodiments, the nicotinic acid GPCR is endogenous.

In preferred embodiments, the nicotinic acid GPCR is recombinant.

In preferred embodiments, said G protein is Gi.

In some preferred embodiments, said reference compound is nicotinic acid.

In some preferred embodiments, said reference compound is (−)-nicotine.

In some preferred embodiments, said reference compound is the modulator of the second aspect.

In other embodiments, said reference compound is an antibody specific for the GPCR, or a derivative thereof.

In preferred embodiments, said reference compound comprises a label selected from the group consisting of:

(a) radioisotope;

(b) enzyme; and (c) fluorophore.

In some preferred embodiments, said label is $^3H$.

In other embodiments, said method further comprises the step of comparing the level of inhibition of binding of a labeled first reference compound by the candidate compound to a second level of inhibition of binding of said labeled first reference compound by a second reference compound known to bind to the GPCR.

In a fourteenth aspect, the invention features a method of making a mouse genetically predisposed to a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the step of knocking out the gene encoding the nicotinic acid mRUP25 GPCR polypeptide of SEQ. ID. NO.:137.

In some preferred embodiments, said knocking out the gene encoding the nicotinic acid mRUP25 GPCR polypeptide pf SEQ. ID. NO.:137 is essentially restricted to adipocytes.

In a fifteenth aspect, the invention features the knockout mouse according to the method of the fourteenth aspect.

In a sixteenth aspect, the invention features a method of using the knockout mouse of the fifteenth aspect to identify whether a candidate compound has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering the compound to the mouse; and (b') determining whether the disorder is prevented, delayed, or made less severe on administering the compound compared to not administering the compound; wherein said determination is indicative of the compound having therapeutic efficacy.

In a seventeenth aspect, the invention features a method of making a rat genetically predisposed to a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the step of knocking out the gene encoding the nicotinic acid rRUP25 GPCR polypeptide of SEQ. ID. NO.:139.

In some preferred embodiments, said knocking out the gene encoding the nicotinic acid rRUP25 GPCR polypeptide pf SEQ. ID. NO.:139 is essentially restricted to adipocytes.

In an eighteenth aspect, the invention features the knockout rat according to the method of the seventeenth aspect.

In a nineteenth aspect, the invention features a method of using the knockout rat of the eighteenth aspect to identify whether a candidate compound has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering the compound to the rat; and (b') determining whether the disorder is prevented, delayed, or made less severe on administering the compound compared to not administering the compound; wherein said determination is indicative of the compound having therapeutic efficacy.

In a twentieth aspect, the invention features an isolated, purified or recombinant RUP25 polynucleotide selected from the group consisting of:

(a) a polynucleotide comprising a contiguous span of at least 75 nucleotides of SEQ.ID. NO.:35, SEQ. ID. NO.:136 or SEQ. ID. NO.:138, or an allelic variant of said polynucleotide;

(b) a polynucleotide comprising a contiguous span of at least 150 nucleotides of SEQ. ID. NO.:35, SEQ. ID. NO.:136 or SEQ. ID. NO.:138, or an allelic variant of said polynucleotide;

(c) a polynucleotide comprising a contiguous span of at least 250 nucleotides of SEQ. ID. NO.:35, SEQ. ID. NO.:136 or SEQ. ID. NO.:138, or an allelic variant of said polynucleotide;

(d) a polynucleotide comprising a contiguous span of at least 350 nucleotides of SEQ. ID. NO.:35, SEQ. ID. NO.:136 or SEQ. ID. NO.:138, or an allelic variant of said polynucleotide;

(e) a polynucleotide comprising a contiguous span of at least 500 nucleotides of SEQ. ID. NO.:35, SEQ. ID. NO.:136 or SEQ. ID. NO.:138, or an allelic variant of said polynucleotide;

(f) a polynucleotide comprising a contiguous span of at least 750 nucleotides of SEQ. ID. NOs.:35, SEQ. ID. NO.:136 or SEQ. ID. NO.:138, or an allelic variant of said polynucleotide;

(g) a polynucleotide comprising a contiguous span of at least 1000 nucleotides of SEQ. ID. NO.:35, SEQ. ID. NO.:136 or SEQ. ID. NO.:138, or an allelic variant of said polynucleotide;

(h) a polynucleotide encoding a polypeptide comprising a contiguous span of at least 20 amino acids of SEQ. ID. NO.:36, SEQ. ID. NO:137 or SEQ. ID. NO.:139 or an allelic variant of said polypeptide;

(i) a polynucleotide encoding a polypeptide comprising a contiguous span of at least 30 amino acids of SEQ. ID. NO.:36, SEQ. ID. NO.:137 or SEQ. ID. NO.:139 or an allelic variant of said polypeptide;

(j) a polynucleotide encoding a polypeptide comprising a contiguous span of at least 40 amino acids of SEQ. ID. NO.:36, SEQ. ID. NO.:137 or SEQ. ID. NO.:139 or an allelic variant of said polypeptide;

(k) a polynucleotide encoding a polypeptide comprising a contiguous span of at least 50 amino acids of SEQ. ID. NO.:36, SEQ. ID. NO.:137 or SEQ. ID. NO.:139 or an allelic variant of said polypeptide;

(l) a polynucleotide encoding a polypeptide comprising a contiguous span of at least 75 amino acids of SEQ. ID. NO.:36, SEQ. ID. NO.:137 or SEQ. ID. NO.:139 or an allelic variant of said polypeptide;

(m) a polynucleotide encoding a polypeptide comprising a contiguous span of at least 100 amino acids of SEQ. ID. NO.:36, SEQ. ID. NO.:137 or SEQ. ID. NO.:139 or an allelic variant of said polypeptide;

(n) a polynucleotide encoding a polypeptide comprising a contiguous span of at least 150 amino acids of SEQ. ID. NO.:36, SEQ. ID. NO.:137 or SEQ. ID. NO.:139 or an allelic variant of said polypeptide;

(o) a polynucleotide encoding a polypeptide comprising a contiguous span of at least 200 amino acids of SEQ. ID. NO.:36, SEQ. ID. NO.:137 or SEQ. ID. NO.:139 or an allelic variant of said polypeptide;

(p) a polynucleotide encoding a polypeptide comprising a contiguous span of at least 250 amino acids of SEQ. ID. NO.:36, SEQ. ID. NO.:137 or SEQ. ID. NO.:139 or an allelic variant of said polypeptide; and (q) a polynucleotide encoding a polypeptide comprising a contiguous span of at least 300 amino acids of SEQ.ID. NO.:36, SEQ. ID. NO.:137 or SEQ. ID. NO.:139 or an allelic variant of said polypeptide.

The invention also relates to an isolated, purified or recombinant RUP25 polynucleotide wherein said polynucleotide is selected from the group consisting of:

(a) a polynucleotide comprising a nucleotide sequence selected from the group consisting of SEQ. ID. NO.:35, SEQ. ID. NO.:136 and SEQ. ID. NO.:138 or an allelic variant of said polynucleotide;

(b) a polynucleotide selected from the group consisting of the polynucleotide of SEQ. ID. NO. :35, the polynucleotide of SEQ. ID. NO.:136 and the polynucleotide of SEQ. ID. NO.:138, or an allelic variant of said polynucleotide;

(c) a polynucleotide comprising a nucleotide sequence encoding a polypeptide having an amino acid sequence selected from the group consisting of SEQ. ID. NO.:36, SEQ. ID. NO.:137 and SEQ. ID. NO.:139 or an allelic variant of said polypeptide; and (d) a polynucleotide encoding a polypeptide having an amino acid sequence selected from the group consisting of SEQ. ID. NO.:36, SEQ. ID. NO.:137 and SEQ. ID. NO.:139 or an allelic variant of said polypeptide.

In preferred embodiments, said isolated, purified or recombinant polynucleotide comprises at least 8 contiguous nucleotides of a polynucleotide of the present invention. In other preferred embodiments, said isolated, purified or recombinant polynucleotide comprises at least 10, 12, 15, 18, 20, 25, 28, 30, 35, 40, 50, 75, 100, 150, 200, 300, 400, 500, 600, 700, 800, 900 or 1000 contiguous nucleotides of a polynucleotide of the present invention. Preferably said polynucleotide encodes full-length RUP25 polypeptide or a biologically active fragment thereof.

The polynucleotides of the present invention include genomic polynucleotides comprising RUP25 polynucleotides of the invention.

The present invention also relates to a polynucleotide encoding a fusion protein, wherein said fusion protein comprises an RUP25 polypeptide of the invention fused to a heterologous polypeptide. In a preferred embodiment, said polypeptide of the invention is constitutively active and said heterologous polypeptide is a G protein. In other embodiments, said heterologous polypeptide provides an antigenic epitope. In a preferred embodiment, said heterologous polypeptide provides a hemaglutinin (HA) antigenic epitope. Methods relating to a polynucleotide encoding a fusion protein are well known to those of ordinary skill in the art.

The polynucleotides of the present invention also include variant polynucleotides at least 60%, 70%, 80%, 90%, 95%, 96%, 97%, 98% or 99% identical to an RUP25 polynucleotide of the invention. In a particularly preferred embodiments, polynucleotide sequence homologies are evaluated using the Basic Local Alignment Search Tool ("BLAST"), which is well known in the art [See, e.g., Karlin and Altschul, Proc Natl Acad Sci USA (1990) 87:2264–8; Altschul et al., J Mol Biol (1990) 215:403–410; Altschul et al., Nature Genetics (1993) 3:266–72; and Altschul et al., Nucleic Acids Res (1997) 25:3389–3402; the disclosures of which are incorporated by reference in their entirety].

In further preferred embodiments, the invention features the complement of said polynucleotide.

In a twenty-first aspect, the invention features an isolated, purified or recombinant RUP25 polypeptide selected from the group consisting of:

(a) a polypeptide comprising a contiguous span of at least 20 amino acids of SEQ. ID. NO.:36, SEQ. ID. NO.:137 or SEQ. ID. NO.:139;

(b) a polypeptide comprising a contiguous span of at least 30 amino acids of SEQ. ID. NO.:36, SEQ. ID. NO.:137 or SEQ. ID. NO.:139;

(c) a polypeptide comprising a contiguous span of at least 40 amino acids of SEQ. ID. NO.:36, SEQ. ID. NO.:137 or SEQ. ID. NO.:139;

(d) a polypeptide comprising a contiguous span of at least 50 amino acids of SEQ. ID. NO.:36, SEQ. ID. NO.:137 or SEQ. ID. NO.:139;

(e) a polypeptide comprising a contiguous span of at least 75 amino acids of SEQ. ID. NO.:36, SEQ. ID. NO.:137 or SEQ. ID. NO.:139;

(f) a polypeptide comprising a contiguous span of at least 100 amino acids of SEQ. ID. NO.:36, SEQ. ID. NO.:137 or SEQ. ID. NO.:139;

(g) a polypeptide comprising a contiguous span of at least 150 amino acids of SEQ. ID. NO.:36, SEQ. ID. NO.:137 or SEQ. ID. NO.:139;

(h) a polypeptide comprising a contiguous span of at least 200 amino acids of SEQ. ID. NO.:36, SEQ. ID. NO.:137 or SEQ. ID. NO.:139;

(i) a polypeptide comprising a contiguous span of at least 250 amino acids of SEQ. ID. NO.:36, SEQ. ID. NO.:137 or SEQ. ID. NO.:139; and (j) a polypeptide comprising a contiguous span of at least 300 amino acids of SEQ. ID. NO.:36, SEQ. ID. NO.:137 or SEQ. ID. NO.:139;

or an allelic variant of said polypeptide.

The invention also relates to an isolated, purified or recombinant RUP25 polypeptide wherein said polypeptide is selected from the group consisting of:

(a) a polypeptide comprising an amino acid sequence selected from the group consisting of SEQ. ID. NO.:36, SEQ. ID. NO.:137 and SEQ. ID. NO.:139; and (b) a polypeptide selected from the group consisting of the polypeptide of SEQ. ID. NO.:36, the polypeptide of SEQ. ID. NO:137 and the polypeptide of SEQ. ID. NO.:139;

or an allelic variant, a biologically active mutant, or a biologically active fragment of said polypeptide.

In preferred embodiments, said isolated, purified or recombinant polypeptide comprises at least 6 contiguous amino acids of an RUP25 polypeptide of the invention. In further embodiments, said isolated, purified or recombinant polypeptide comprises at least 10, 12, 15, 20, 25, 30, 35, 40, 50, 60, 75, 100, 125, 150, 175, 200, 225, 250, 275 or 300 contiguous amino acids of a polypeptide of the present invention. Preferably, said polypeptide is full-length RUP25 polypeptide or an active fragment thereof.

The present invention also relates to a fusion protein, wherein said fusion protein comprises an RUP25 polypeptide of the invention fused to a heterologous polypeptide. In a preferred embodiment, said polypeptide of the invention is constitutively active and said heterologous polypeptide is a G protein. In other preferred embodiments, said heterologous polypeptide provides an antigenic epitope. In particularly preferred embodiment, said heterologous polypeptide provides a hemaglutinin (HA) antigenic epitope. Methods relating to a fusion protein are well known to those of ordinary skill in the art.

The polypeptides of the present invention also include variant polypeptides at least 80%, 85%, 90%, 91%, 92%, 93%, 94%, 95%, 96%, 97%, 98% or 99% identical to an RUP25 polypeptide of the invention. In a particularly preferred embodiments, polypeptide sequence homologies are evaluated using the Basic Local Alignment Search Tool ("BLAST"), which is well known in the art [See, e.g., Karlin and Altschul, Proc Natl Acad Sci USA (1990) 87:2264–8; Altschul et al., J Mol Biol (1990) 215:403–410; Altschul et al., Nature Genetics (1993) 3:266–72; and Altschul et al., Nucleic Acids Res (1997) 25:3389–3402; the disclosures of which are incorporated by reference in their entirety].

In an twenty-second aspect, the invention features a composition comprising, consisting essentially of, or consisting of the RUP25 polypeptide of the twenty-first aspect.

In a twenty-third aspect, the invention features a recombinant vector, said vector comprising, consisting essentially of, or consisting of the polynucleotide of the twentieth aspect. In some preferred embodiments, said vector is a targeting vector used in a method of inactivating a gene encoding a nicotinic acid GPCR of the invention. In other preferred embodiments, said vector is used in a method of transient or stable transfection.

In particularly preferred embodiment, said vector is an expression vector for the expression of a nicotinic acid GPCR in a recombinant host cell wherein said expression vector comprises, consists essentially of, or consists of the polynucleotide of the twentieth aspect.

Although a variety of expression vectors are available to those in the art, for purposes of utilization for both the endogenous and non-endogenous human, mouse and rat GPCRs, it is most preferred that the vector utilized be pCMV. In some alternative embodiments as relates to said human, mouse and rat nicotinic acid GPCRs, it is preferred that the vector utilized be an adenoviral expression vector.

In a twenty-fourth aspect, the invention features a prokaryotic or eukaryotic host cell comprising, consisting essentially of, or consisting of the recombinant vector of the twenty-third aspect. In some preferred embodiments, said host cell is a eukaryotic embryonic stem cell wherein said vector of the twenty-third aspect has been used in a method to inactivate a gene encoding a nicotinic acid GPCR of the invention within said cell. In some other preferred embodiments, said host cell is a eukaryotic embryonic somatic cell wherein said vector of the twenty-third aspect has been used in a method to inactivate a gene encoding a nicotinic acid GPCR of the invention within said cell. In other preferred embodiments, said host cell is prokaryotic and has been transformed using the vector of the twenty-third aspect. In further preferred embodiments, said host cell is eukaryotic and has been transiently transfected using the vector of the twenty-third aspect. In other further preferred embodiments, said host cell is eukaryotic and has been stably transfected using the vector of the twenty-third aspect.

In particularly preferred embodiment, said host cell expresses a recombinant nicotinic acid GPCR wherein said host cell comprises, consists essentially of, or consists of the expression vector of the twenty-third aspect.

A further embodiment includes a prokaryotic or eukaryotic host cell recombinant for the polynucleotide of the twentieth aspect.

In some embodiments the host cell is eukaryotic, more preferably, mammalian, and more preferably selected from the group consisting of 293, 293T, CHO, and COS-7 cells. In other embodiments, the host cell is eukaryotic, more preferably melanophore.

In a twenty-fifth aspect, the invention features a process for the expression of a nicotinic acid GPCR in a recombinant host cell comprising the steps of:

(a) transfecting the expression vector of the twenty-third aspect into a suitable host cell; and (b) culturing the host cells under conditions which allow expression of the nicotinic acid GPCR protein from the expression vectors.

In a twenty-sixth aspect, the invention features an antibody that specifically binds to the polypeptide of the twenty-first aspect. In some preferred embodiments, the antibody is monoclonal. In some embodiments, the antibody is polyclonal.

In a twenty-seventh aspect, the invention features a method of binding the polypeptide of the twenty-first aspect to the antibody of the twenty-sixth aspect, comprising contacting said antibody with said polypeptide under conditions in which said antibody can specifically bind to said polypeptide.

In a twenty-eighth aspect, the invention features a method of detecting a nicotinic acid GPCR polypeptide in a biological sample obtained from an individual comprising the steps of:

(a) obtaining said biological sample from said individual;

(b) contacting said biological sample with the antibody of the twenty-sixth aspect; and (c) detecting the presence or absence of binding of said antibody to said biological sample;

wherein a detection of said binding is indicative of the receptor polypeptide being expressed in said biological sample.

In preferred embodiments, said detecting is through the use of an enzyme-labeled secondary reagent. In other preferred embodiments, said detecting is through the use of a fluorophore-labeled secondary reagent. In other preferred embodiments, said detecting is through the use of a radioisotope-labeled secondary reagent. In other embodiments, the antibody is directly labeled with enzyme, fluorophore or radioisotope.

In other preferred embodiments, said biological sample is taken from adipose, skin or blood.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In further embodiments, said individual has a disorder of lipid metabolism selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin.

In other preferred embodiments, said disorder in lipid metabolism is an elevated postprandial increase in plasma free fatty acids due to a high fat meal or a progression from impaired glucose tolerance to insulin resistance.

In further embodiments, said individual has a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodimens, said metabolic-related disorder is hyperlipidemia.

In other embodiments, said method further comprises the step of comparing the level of detection of said binding for a first individual to the level of detection of said binding for a second individual.

In a twenty-ninth aspect, the invention features a method of detecting expression of a gene encoding a nicotinic acid GPCR in a biological sample obtained from an individual comprising the steps of:

(a) obtaining said biological sample from said individual;

(b) contacting said biological sample with the complementary polynucleotide of the twentieth aspect, optionally labeled, under conditions permissive for hybridization; and (c) detecting the presence or absence of said hybridization between said complementary polynucleotide and an RNA species within said sample;

wherein a detection of said hybridization is indicative of expression of said GPCR gene in said biological sample.

In preferred embodiments, the biological sample is taken from adipose, skin or blood.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In preferred embodiments, said individual has a disorder of lipid metabolism selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin.

In other preferred embodiments, said disorder in lipid metabolism is an elevated postprandial increase in plasma free fatty acids due to a high fat meal or a progression from impaired glucose tolerance to insulin resistance.

In other preferred embodiments, said individual has a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In other embodiments, said method further comprises the step of comparing the level of detection of said hybridization for a first individual to the level of detection of said hybridization for a second individual.

In some preferred embodiments, said complementary polynucleotide is a primer and said hybridization is detected by detecting the presence of an amplification product comprising the sequence of said primer. In more preferred embodiments, said method is RT-PCR.

In a thirtieth aspect, the invention features a GPCR Fusion Protein construct comprising a constitutively active GPCR and a G protein, said receptor comprising an amino acid sequence selected from the group consisting of:

(a) SEQ. ID. NO.:36 (hRUP25);

(b) SEQ. ID. NO.:137 (mRUP25); and (c) SEQ. ID. NO.:139 (rRUP25);

or an allelic variant or a biologically active fragment of said amino acid sequence.

The invention also relates to a GPCR Fusion Protein construct wherein the isoleucine at amino acid position 230 of SEQ. ID. NO.:36 is substituted by lysine.

In a thirty-first aspect, the invention features a method of binding a known ligand of RUP25 nicotinic acid GPCR to a polypeptide selected from the group consisting of:

(a) a polypeptide comprising a contiguous span of at least 6 amino acids of SEQ. ID. NO.:36, SEQ. ID. NO.:137 or SEQ. ID. NO.:139;

(b) a polypeptide comprising a contiguous span of at least 10 amino acids of SEQ. ID. NO.:36, SEQ. ID. NO.:137 or SEQ. ID. NO.:139;

(c) a polypeptide comprising a contiguous span of at least 15 amino acids of SEQ. ID. NO.:36, SEQ. ID. NO.:137 or SEQ. ID. NO.:139;

(d) a polypeptide comprising a contiguous span of at least 20 amino acids of SEQ. ID. NO.:36, SEQ. ID. NO.:137 or SEQ. ID. NO.:139;

(e) a polypeptide comprising a contiguous span of at least 25 amino acids of SEQ. ID. NO.:36, SEQ. ID. NO.:137 or SEQ. ID. NO.:139;

(f) a polypeptide comprising a contiguous span of at least 30 amino acids of SEQ. ID. NO.:36, SEQ. ID. NO.:137 or SEQ. ID. NO.:139;

(g) a polypeptide comprising a contiguous span of at least 35 amino acids of SEQ. ID. NO.:36, SEQ. ID. NO.:137 or SEQ. ID. NO.:139;

(h) a polypeptide comprising a contiguous span of at least 40 amino acids of SEQ. ID. NO.:36, SEQ. ID. NO.:137 or SEQ. ID. NO.:139;

(i) a polypeptide comprising a contiguous span of at least 45 amino acids of SEQ. ID. NO.:36, SEQ. ID. NO.:137 or SEQ. ID. NO.:139; and (j) a polypeptide comprising a contiguous span of at least 50 amino acids of SEQ. ID. NO.:36, SEQ. ID. NO.:137 or SEQ. ID. NO.:139;

or an allelic variant of said polypeptide;

comprising the step of contacting said known ligand with said polypeptide under conditions which allow said binding to occur.

In some embodiments, said known ligand is a modulator of the nicotinic acid GPCR. In some embodiments, said known ligand is an agonist of the nicotinic acid GPCR. In other embodiments, said agonist is nicotinic acid or an analog or derivative thereof. In other embodiments, said agonist is (−)-nicotine or an analog or derivative thereof. In some embodiments, said known ligand is the modulator of the second aspect. In some embodiments, said known ligand is an antibody specific for the GPCR, or a derivative thereof.

In other preferred embodiments, said method is used to identify whether a candidate compound inhibits said binding of said known ligand to said polypeptide, comprising the steps of:

(a) contacting said polypeptide with said known ligand, optionally labeled, in the presence or absence of said candidate compound;

(b) detecting the complex between said known ligand and said polypeptide; and (c) determining whether less of said complex is formed in the presence of the compound than in the absence of the compound;

wherein said determination is indicative of the candidate compound being an inhibitor of said binding of said known ligand to said polypeptide.

In some embodiments, said known ligand is a known modulator of the nicotinic acid GPCR. In some embodiments, said known ligand is a modulator of the nicotinic acid GPCR. In some embodiments, said known ligand is an agonist of the nicotinic acid GPCR. In embodiments, said agonist is nicotinic acid or an analog or derivative thereof. In other embodiments, said agonist is (−)-nicotine or an analog or derivative thereof. In some embodiments, said known ligand is the modulator of the second aspect. In some embodiments, said known ligand is an antibody specific for the GPCR, or a derivative thereof.

In other preferred embodiments, said method is used to identify whether a candidate compound is an inhibitor of said binding of said known ligand to said polypeptide, comprising the steps of:

(a) contacting said polypeptide with said known ligand, optionally labeled, in the presence separately of a plurality of concentrations of said candidate compound for a time sufficient to allow equilibration of binding;

(b) measuring unbound ligand and bound ligand; and (c) determining $K_i$ for the candidate compound;

wherein a $K_i$ value of less than 50 uM is indicative of the candidate compound being an inhibitor of said binding of said known ligand to said polypeptide. Preferably said $K_i$ value is less than 25 μM, 10 μM, 5 μM, 1 μM, 750 nM, 500 nM, 400 nM, 300 nM, 250 nM, 200 nM, 150 nM, 100 nM, 90 nM, 80 nM, 70 nM, 60 nM, 50 nM, 40 nM, 30 nM, 20 nM or 10 nM. In preferred embodiments, $K_i$ determination is made through nonlinear curve fitting with the program SCTFIT [De Lean et al. (1982) Mol Pharmacol 21:5–16; cited in Lorenzen et al. (2001) Mol Pharmacol 59:349–357, the disclosures of which are incorporated by reference herein in their entireties].

In some embodiments, said known ligand is a modulator of the nicotinic acid GPCR. In some embodiments, said known ligand is an agonist of the nicotinic acid GPCR. In other embodiments, said agonist is nicotinic acid or an analog or derivative thereof. In other embodiments, said agonist is (−)-nicotine or an analog or derivative thereof. In some embodiments, said known ligand is the modulator of the second aspect. In some embodiments, said known ligand is an antibody specific for the GPCR, or a derivative thereof.

In a thirty-second aspect, the invention features a method of binding an optionally labeled affinity reagent specific for a nicotinic acid GPCR to said receptor in a biological sample, said receptor comprising an amino acid sequence selected from the group consisting of:

(a) SEQ. ID. NO.:36 (hRUP25);

(b) SEQ. ID. NO.:137 (mRUP25); and (c) SEQ. ID. NO.:139 (rRUP25);

or an allelic variant, a biologically active mutant, or a biologically active fragment of said amino acid sequence, comprising the steps of:

(a') obtaining said biological sample;

(b') contacting the affinity reagent with said receptor in said biological sample; and (c') detecting the complex of said affinity reagent with said receptor.

In some embodiments, the nicotinic acid GPCR has an amino acid sequence selected from the group consisting of:

(a) SEQ. ID. NO.:36 (hRUP25);

(b) SEQ. ID. NO.:137 (mRUP25); and (c) SEQ. ID. NO.:139 (rRUP25);

or an allelic variant, a biologically active mutant, or a biologically active fragment of said amino acid sequence.

In some embodiments, the nicotinic acid GPCR comprises an active fragment of said amino acid sequence.

In some embodiments, the nicotinic acid GPCR is endogenous.

In some embodiments, the nicotinic acid GPCR is recombinant.

In some embodiments, said biologically active mutant is CART or EFA. In preferred embodiments, said CART mutant has the amino acid sequence of SEQ. ID. NO.:36 further substituted at amino acid position 230 with lysine in place of isoleucine. In preferred embodiments, said EFA mutant has the amino acid sequence of SEQ. ID. NO.:159.

In preferred embodiments, said G protein is Gi.

In some embodiments, said affinity reagent is a modulator of the GPCR. In some embodiments, said affinity reagent is an agonist of the GPCR. In some embodiments, said affinity reagent is nicotinic acid or an analog or derivative thereof. In some embodiments, said affinity reagent is (−)-nicotine or an analog or derivative thereof. In some embodiments, said affinity reagent is the modulator of the second aspect. In some embodiments, said known ligand is an antibody specific for the GPCR, or a derivative thereof.

In further preferred embodiments, said affinity reagent comprises a label selected from the group consisting of:

(a) radioisotope;

(b) enzyme; and (c) fluorophore.

In preferred embodiments, said radioisotope is $^3H$.

In a thirty-third aspect, the invention features the method of the thirty-second aspect further comprising the step of comparing the level of detection of said complex in a first biological sample to a second level of detection of said complex in a second biological sample.

In a thirty-fourth aspect, the invention features the method of the thirty-third aspect wherein the relationship between said first and second biological samples is selected from the group consisting of:

(a) said second biological sample is a replicate of said first biological sample;

(b) said first biological sample was obtained prior to an experimental intervention whereas said second biological sample was obtained after the experimental intervention, from the same individual;

(c) said second biological sample was obtained at a different time point after an experimental intervention than was said first biological sample, from the same individual;

(d) said second biological sample corresponds to a different subcellular compartment than does said first biological sample;

(e) said second biological sample represents a different cell type than does said first biological sample;

(f) said second biological sample corresponds to a different tissue than does said first biological sample;

(g) said second biological sample was obtained from a different individual than was said first biological sample;

(h) said second biological sample was obtained at a different point in time than was said first biological sample, from the same individual;

(i) said first biological samples was obtained from a normal individual, whereas said second biological sample was obtained from an individual having a metabolic-related disorder;

(j) said first biological sample was obtained from a normal individual, whereas said second biological sample was obtained from an individual having a disorder in lipid metabolism;

(k) said first biological sample was obtained before a therapeutic intervention whereas said second biological sample was obtained after the therapeutic intervention, from the same individual;

(l) said second biological sample was obtained at a different time point after therapeutic intervention than was said first biological sample, from the same individual; and (m) said first biological sample was not exposed to a compound, whereas said second biological sample was exposed to said compound.

In a thirty-fifth aspect, the invention features a method of identifying whether a candidate compound is a modulator of an antilipolytic GPCR, said receptor comprising the amino acid sequence of SEQ. ID. NO.:135 (hRUP38);

or an allelic variant, a biologically active mutant, or a biologically active fragment of said amino acid sequence; comprising the steps of:

(a) contacting the candidate compound with the receptor;

(b) determining whether the receptor functionality is modulated;

wherein a change in receptor functionality is indicative of the candidate compound being a modulator of an antilipolytic GPCR.

In some embodiments, said antilipolytic GPCR is endogenous.

In some preferred embodiments, said antilipolytic GPCR is recombinant.

Preferred said identified modulator binds to said GPCR.

In some embodiments, said contacting is carried out in the presence of a known ligand of the GPCR. In some embodiments, said known ligand is an agonist of the GPCR.

The invention also relates to a method of identifying whether a candidate compound is a modulator of lipolysis, comprising the steps of:

(a) contacting the candidate compound with a GPCR comprising the amino acid sequence of SEQ. ID. NO.:135 (hRUP38);

or an allelic variant, a biologically active mutant, or a biologically active fragment of said amino acid sequence; and (b) determining whether the receptor functionality is modulated;

wherein a change in receptor functionality is indicative of the candidate compound being a modulator of lipolysis.

In some embodiments, said GPCR is endogenous.

In some preferred embodiments, said GPCR is recombinant.

Preferred said identified modulator binds to said GPCR.

In some embodiments, said contacting is carried out in the presence of a known ligand of the GPCR. In some embodiments, said known ligand is an agonist of the GPCR.

The invention also relates to a method of determining whether a candidate compound is a modulator of an antilipolytic GPCR, comprising the steps of:

(a) culturing antilipolytic GPCR-expressing host cells under conditions that would allow expression of a recombinant antilipolytic GPCR, said host cells being transfected with a polynucleotide encoding said recombinant antilipolytic GPCR comprising the amino acid sequence of SEQ. ID. NO.:135 (hRUP38); or an allelic variant, a biologically active mutant, or a biologically active fragment of said amino acid sequence;

(b) contacting the antilipolytic GPCR-expressing host cells of step (a) with the candidate compound;

(c) contacting control host cells with the candidate compound of step (b), wherein said control host cells do not express recombinant antilipolytic GPCR protein;

(d) measuring the modulating effect of the candidate compound which interacts with the recombinant antilipolytic GPCR from the host cells of step (a) and control host cells of step (c); and (e) comparing the modulating effect of the test compound on the host cells and control host cells.

The invention also relates to a method of determining whether a candidate compound is a modulator of an antilipolytic GPCR, comprising the steps of:

(a) culturing antilipolytic GPCR-expressing host cells under conditions that would allow expression of a recombinant antilipolytic GPCR, said host cells being transfected with a polynucleotide encoding said recombinant antilipolytic GPCR comprising the amino acid sequence of SEQ. ID. NO.:135 (hRUP38); or an allelic variant, a-biologically active mutant, or a biologically active fragment of said amino acid sequence;

(b) contacting a first population of antilipolytic GPCR-expressing cells of step (a) with a known ligand of said antilipolytic GPCR;

(c) contacting a second population of antilipolytic GPCR-expressing cells of step (a) with the candidate compound and with the known antilipolytic GPCR ligand;

(d) contacting control host cells with the candidate compound of step (c), wherein said control host cells do not express recombinant antilipolytic GPCR protein;

(e) measuring the modulating effect of the candidate compound, which interacts with recombinant antilipolytic GPCR, in the presence and absence of the known antilipolytic GPCR ligand, from the cells of step (b), step (c) and step (d); and (f) comparing the modulating effect of the candidate compound as determined from step (b), step (c) and step (d).

In some embodiments, said known ligand is an agonist of the GPCR.

The invention also relates to a method of determining whether a candidate compound is a modulator of an antilipolytic GPCR, comprising the steps of:

(a) culturing antilipolytic GPCR-expressing host cells under conditions that would allow expression of a recombinant antilipolytic GPCR, said host cells being transfected with a polynucleotide encoding said recombinant antilipolytic GPCR comprising the amino acid sequence of SEQ. ID. NO.:135 (hRUP38); or an allelic variant, a biologically active mutant, or a biologically active fragment of said amino acid sequence;

(b) contacting a first population of the antilipolytic GPCR-expressing host cells of step (a) with the candidate compound;

(c) not contacting a second population of the antilipolytic GPCR-expressing cells of step (a) with the candidate compound of step (b);

(d) contacting control host cells to the candidate compound of step (b), wherein said control host cells do not express recombinant antilipolytic GPCR protein;

(e) measuring the modulating effect of the candidate compound, which interacts with recombinant antilipolytic GPCR protein, from the cells of step (b) and step (c) and from the cells of step (d); and (f) comparing the modulating effect of the candidate compound as determined from step (b) and step (c) and from step (d).

In some embodiments, the antilipolytic GPCR has the amino acid sequence of SEQ. ID. NO.:135 (hRUP38); or an allelic variant, a biologically active mutant, or a biologically active fragment of said amino acid sequence.

In some embodiments, the antilipolytic GPCR comprises a biologically active fragment of said amino acid sequence.

In some embodiments, said biologically active mutant is CART or EFA. In preferred embodiments, said CART mutant has the amino acid sequence of SEQ. ID. NO.:135 further substituted at amino acid position 230 with lysine in place of isoleucine.

In preferred embodiments, said G protein is Gi.

In other preferred embodiments, said determining is through the use of a Melanophore assay.

In other preferred embodiments, said determining is through the measurement of the level of a second messenger selected from the group consisting of cyclic AMP (cAMP), cyclic GMP (cGMP), inositol triphosphate ($IP_3$), diacylglycerol (DAG), and $Ca^{2+}$. In further preferred embodiments, said second messenger is cAMP. In more preferred embodiments, the level of the cAMP is reduced. In some embodiments, said measurement of cAMP is carried out with membrane comprising said GPCR.

In other preferred embodiments, said determining is through the measurement of an activity up-regulated or down-regulated by a reduction in intracellular cAMP level. In further preferred embodiments, said down-regulated activity is intracellular lipolysis. In other further preferred embodiments, said down-regulated activity is hormone sensitive lipase activity. In other further preferred embodiments, said up-regulated activity is adiponectin secretion.

In other preferred embodiments, said determining is through CRE-reporter assay. In preferred embodiments, said reporter is luciferase. In some embodiments, said reporter is β-galactosidase.

In other embodiments, said recombinant host cell further comprises promiscuous G alpha 15/16 or chimeric Gq/Gi alpha subunit and said determining is through measurement of intracellular $Ca^{2+}$. In preferred embodiments, said $Ca^{2+}$ measurement is carried out by FLIPR.

In other embodiments, said recombinant host cell further comprises promiscuous G alpha 15/16 or chimeric Gq/Gi alpha subunit and said determining is through measurement of intracellular $IP_3$.

In other preferred embodiments, said determining is through the measurement of GTPγS binding to membrane comprising said GPCR. In further preferred embodiments, said GTPγS is labeled with [$^{35}$S].

In other preferred embodiments, said method further comprises the step of comparing the modulation of the receptor caused by the candidate compound to a second modulation of the receptor caused by contacting the receptor with a known modulator of the receptor. In some preferred embodiments, said known modulator is an agonist.

In a thirty-sixth aspect, the invention features a modulator of an antilipolytic GPCR identified according to the method of the thirty-fifth aspect.

In some preferred embodiments, said modulator is selected from the group consisting of agonist, partial agonist, inverse agonist and antagonist. More preferably, said modulator is an agonist. In some embodiments, said modulator is a partial agonist.

In some embodiments, said modulator is an agonist with an $EC_{50}$ of less than 1000 $\mu$M in GTPγS binding assay carried out with membrane from stably transfected CHO cells expressing recombinant hRUP38 polypeptide having the amino acid sequence of SEQ. ID. NO.:135. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some embodiments, said modulator is selective for the GPCR.

In some embodiments, said modulator is antilipolytic.

In some embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some preferred embodiments, said oral bioavailability is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some preferred embodiments, said oral bioavailability is at least 1%, at least 5%, at least 10%, or at least 15% relative to intravenous administration.

In highly less preferred embodiments, said modulator is an antibody or derivative thereof.

In a thirty-seventh aspect, the invention features the method of the thirty-fifth aspect, wherein said-candidate compound is an agonist of hRUP25 GPCR comprising the amino acid sequence of SEQ. ID. NO.:36 and wherein said method further comprises the step of comparing the modulation of hRUP38 GPCR comprising the amino acid sequence of SEQ. ID. NO.:135 caused by said agonist to a second modulation of hRUP38 GPCR comprising a variant of said amino acid sequence caused by contacting the variant hRUP38 GPCR with said agonist.

In preferred embodiments, said variant amino acid sequence is identical to hRUP38 polypeptide of SEQ. ID. NO.:135, further comprising a single amino acid substitution selected from the group consisting of:

(a) V for A at amino acid position 27 of SEQ. ID. NO.:135;

(b) L for V at amino acid position 83 of SEQ. ID. NO.:135;

(c) N for Y at amino acid position 86 of SEQ. ID. NO.:135;

(d) W for S at amino acid position 91 of SEQ. ID. NO.:135;

(e) K for N at amino acid position 94 of SEQ. ID. NO.:135;

(f) M for V at amino acid position 103 of SEQ. ID. NO.:135;

(g) L for F at amino acid position 107 of SEQ. ID. NO.:135;

(h) R for W at amino acid position 142 of SEQ. ID. NO.:135;

(i) I for V at amino acid position 156 of SEQ. ID. NO.:135;

(j) M for L at amino acid position 167 of SEQ. ID. NO.:135;

(k) P for L at amino acid position 168 of SEQ. ID. NO.:135;

(l) G for P at amino acid position 173 of SEQ. ID. NO.:135;

(m) L for V at amino acid position 176 of SEQ. ID. NO.:135;

(n) S for I at amino acid position 178 of SEQ. ID. NO.:135;

(o) Q for R at amino acid position 187 of SEQ. ID. NO.:135;

(p) F for L at amino acid position 198 of SEQ. ID. NO.:135; and (q) P for N at amino acid position 363 of SEQ. ID. NO.:135.

In particularly preferred embodiments, said method is used to identify whether said substituted amino acid additionally found at the identical position within SEQ. ID. NO.:36 is necessary for modulation of said hRUP25 GPCR by said agonist, comprising the steps of:

(a) determining the level of modulation of said hRUP38 GPCR by said agonist; and (b) determining the level of modulation of said variant hRUP38 GPCR by said agonist;

wherein if said level of modulation for (b) is greater than said level of modulation for (a), then said substituted amino acid is necessary for modulation of said hRUP25 GPCR by said agonist.

In a thirty-eighth aspect, the invention features a method of modulating the activity of an antilipolytic GPCR, said receptor comprising the amino acid sequence of SEQ. ID. NO.:135 (hRUP38); or an allelic variant, a biologically active mutant, or a biologically active fragment of said amino acid sequence;

comprising the step of contacting the receptor with the modulator of the thirty-sixth aspect.

In some embodiments, the antilipolytic GPCR has the amino acid sequence of SEQ. ID. NO.:135 (hRUP38); or an allelic variant, a biologically active mutant, or a biologically active fragment of said amino acid sequence.

In some embodiments, the antilipolytic GPCR comprises an active fragment of said amino acid sequence.

In some embodiments, the antilipolytic GPCR is endogenous.

In some embodiments, the antilipolytic GPCR is recombinant.

In some embodiments, said biologically active mutant is CART or EFA. In preferred embodiments, said CART mutant has the amino acid sequence of SEQ. ID. NO.:135 further substituted at amino acid position 230 with lysine in place of isoleucine.

In preferred embodiments, said G protein is Gi.

In some preferred embodiments, said modulator is an agonist.

In preferred embodiments, said modulator is selective for the GPCR.

In other preferred embodiments, said contacting comprises administration of the modulator to a membrane comprising the receptor.

In other preferred embodiments, said contacting comprises administration of the modulator to a cell or tissue comprising the receptor.

In other preferred embodiments, said contacting comprises administration of the modulator to an individual comprising the receptor. In more preferred embodiments, said individual is a mammal. In other more preferred embodiments, said mammal is a horse, cow, sheep, pig, cat, dog, rabbit, mouse, rat, non-human primate or human. Yet more preferred is mouse, rat or human. Most preferred is human.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP38 polypeptide having the amino acid sequence of SEQ. ID. NO.:135. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said administration is oral.

In preferred embodiments, said modulator is an agonist and said individual is in need of prevention of or treatment for a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In other embodiments, said modulator is an inverse agonist and said metabolic-related disorder relates to a low level of plasma free fatty acids.

In other preferred embodiments, said modulator is an agonist and said individual is in need of a change in lipid metabolism selected from the group consisting of:

(a) a decrease in the level of plasma triglycerides;

(b) a decrease in the level of plasma free fatty acids;

(c) a decrease in the level of plasma cholesterol;

(d) a decrease in the level of LDL-cholesterol;

(e) an increase in the level of HDL-cholesterol;

(f) a decrease in the total cholesterol/HDL-cholesterol ratio; and (g) an increase in the level of plasma adiponectin.

In other preferred embodiments, said needed change in lipid metabolism is a decrease in the postprandial increase in plasma free fatty acids due to a high fat meal or an inhibition of the progression from impaired glucose tolerance to insulin resistance.

In some embodiments, the modulator is an inverse agonist and the needed change in lipid metabolism is an increase in the level of plasma free fatty acids.

In other preferred embodiments, said modulator is an agonist and said individual is a mouse genetically predisposed to a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure.

In further preferred embodiments, said metabolic-related disorder is hyperlipidemia.

In further preferred embodiments, said method is used to identify whether said agonist has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering said agonist to the mouse; and (b') determining whether the disorder is prevented, delayed, or made less severe on administering said agonist compared to not administering said agonist;

wherein said determination is indicative of said agonist having therapeutic efficacy.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In other preferred embodiments, said modulator is an agonist and said individual is a rat genetically predisposed to a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In further preferred embodiments, said metabolic-related disorder is hyperlipidemia.

In further preferred embodiments, said method is used to identify whether said agonist has-therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering said agonist to the rat; and (b') determining whether the disorder is prevented, delayed, or made less severe on administering said agonist compared to not administering said agonist;

wherein said determination is indicative of said agonist having therapeutic efficacy.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In a thirty-ninth aspect, the invention features a method of preventing or treating a disorder of lipid metabolism in an individual comprising contacting a therapeutically effective amount of the modulator of the thirty-sixth aspect with an antilipolytic GPCR, said receptor comprising the amino acid sequence of SEQ. ID. NO.:135 (hRUP38); or an allelic variant or biologically active fragment of said amino acid sequence.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP38 polypeptide having the amino acid sequence of SEQ. ID. NO:135. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said contacting comprises oral administration of said modulator to said individual.

In preferred embodiment, said modulator is an agonist and said disorder of lipid metabolism is selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin.

In a fortieth aspect, the invention features a method of preventing or treating a metabolic-related disorder in an individual comprising contacting a therapeutically effective amount of the modulator of the thirty-sixth aspect with an antilipolytic GPCR, said receptor comprising the amino acid sequence of SEQ. ID. NO.:135 (hRUP38);

or an allelic variant or biologically active fragment of said amino acid sequence.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP38 polypeptide having the amino acid sequence of SEQ. ID. NO.:135. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said contacting comprises oral administration of said modulator to said individual.

In preferred embodiment, said modulator is an agonist and said metabolic-related disorder is selected from the group consisting of:

(a) dyslipidemia;

(b) atherosclerosis;

(c) coronary heart disease;

(d) stroke;

(e) insulin resistance; and (f) type 2 diabetes.

In a forty-first aspect, the invention features a method of preparing a composition which comprises identifying a modulator of an antilipolytic GPCR and then admixing a carrier and the modulator -wherein the modulator is identifiable by the method of the thirty-fifth aspect.

In some preferred embodiments, said modulator is selected from the group consisting of agonist, partial agonist, inverse agonist and antagonist. More preferably, said modulator is an agonist. In some embodiments, said modulator is a partial agonist.

In some embodiments, said modulator is an agonist with an $EC_{50}$ of less than 1000 $\mu$M in GTPγS binding assay carried out with membrane from stably transfected CHO cells expressing recombinant hRUP38 polypeptide having the amino acid sequence of SEQ. ID. NO.:135. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some embodiments, said modulator is selective for the GPCR.

In some embodiments, said modulator is antilipolytic.

In some embodiments, said modulator is orally bioavailable. In some embodiments, said oral bioavailability is at least 1%, at least 5%, at least 10%, at least 15%, at least 20%, at least 25%, at least 30%, at least 35%,-at least 40%, or at least 45% relative to either intraperitoneal or intravenous administration. In some preferred embodiments, said oral bioavailability is at least 1%, at least 5%, at least 10%, or at least 15% relative to either intraperitoneal or intravenous administration.

In a forty-second aspect, the invention features a pharmaceutical or physiologically acceptable composition comprising, consisting essentially of, or consisting of the modulator of the thirty-sixth aspect. In preferred embodiments, said modulator is an agonist.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP38 polypeptide having the amino acid sequence of SEQ. ID. NO.:135. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In a forty-third aspect, the invention features a method of changing lipid metabolism comprising providing or administering to an individual in need of said change said pharmaceutical or physiologically acceptable composition of the forty-second aspect, said needed change in lipid metabolism selected from the group consisting of:

(a) a decrease in the level of plasma triglycerides;

(b) a decrease in the level of plasma free fatty acids;

(c) a decrease in the level of plasma cholesterol;

(d) a decrease in the level of LDL-cholesterol;

(e) an increase in the level of HDL-cholesterol;

(f) a decrease in the total cholesterol/HDL-cholesterol ratio; and (g) an increase in the level of plasma adiponectin.

In preferred embodiments, a therapeutically effective amount of said pharmaceutical or physiologically acceptable composition is provided or administered to said individual.

In some preferred embodiments, said providing or administering of said pharmaceutical or physiologically acceptable composition is oral.

In other preferred embodiments, said needed change in lipid metabolism is a decrease in the postprandial increase in plasma free fatty acids due to a high fat meal or an inhibition of the progression from impaired glucose tolerance to insulin resistance.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In a forty-fourth aspect, the invention features a method of preventing or treating a metabolic-related disorder comprising providing or administering to an individual in need of said treatment said pharmaceutical or physiologically acceptable composition of the forty-second aspect, said metabolic-related disorder selected from the group consisting of:

(a) dyslipidemia;

(b) atherosclerosis;

(c)coronary heart disease;

(d) stroke;

(e) insulin resistance; and (f) type 2 diabetes.

In preferred embodiments, a therapeutically effective amount of said pharmaceutical or physiologically acceptable composition is provided or administered to said individual.

In some preferred embodiments, said providing or administering of said pharmaceutical or physiologically acceptable composition is oral.

In other preferred embodiments, said metabolic-related disorder is selected from the group consisting of obesity, impaired glucose tolerance, atheromatous disease, hypertension, stroke, Syndrome X, and heart disease. Heart disease includes, but is not limited to, cardiac insufficiency, coronary insufficiency, and high blood pressure. In other preferred embodiments, said metabolic-related disorder is hyperlipidemia.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In an forty-fifth aspect, the invention features a method of using the modulator of the thirty-sixth aspect for the preparation of a medicament for the treatment of a disorder in lipid metabolism in an individual.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is anti-lipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP38 polypeptide having the amino acid sequence of SEQ. ID. NO.:135. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said treatment comprises oral administration, of said medicament to said individual.

In preferred embodiments, said modulator is an agonist and said disorder in lipid metabolism is selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) reduced total cholesterol/HDL-cholesterol ratio; and (g) reduced level of plasma adiponectin.

In other preferred embodiments, said disorder in lipid metabolism is an elevated postprandial increase in plasma free fatty acids due to a high fat meal or a progression from impaired glucose tolerance to insulin resistance.

In preferred embodiments, said individual is a mammal. In more preferred embodiments said mammal is a horse, cow, sheep, pig, cat, dog, rabbit, mouse, rat, non-human primate or human. Yet more preferred is mouse, rat or human. Most preferred is human.

In a forty-sixth aspect, the invention features a method of using the modulator of the thirty-sixth aspect for the preparation of a medicament for the treatment of a metabolic-related disorder in an individual.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is anti-lipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP38 polypeptide having the amino acid sequence of SEQ. ID. NO.:135. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said treatment comprises oral administration of said medicament to said individual.

In preferred embodiments, said modulator is an agonist and said metabolic-related disorder is selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In a forty-seventh aspect, the invention features a method of identifying whether a candidate compound is binds to an antilipolytic GPCR, said receptor comprising the amino acid sequence of SEQ. ID. NO.:135 (hRUP38); or an allelic variant or a biologically active fragment of said amino acid sequence;

comprising the steps of:

(a) contacting the receptor with a labeled reference compound known to bind to the GPCR in the presence or absence of the candidate compound; and (b) determining whether the binding of said labeled reference compound to the receptor is inhibited in the presence of the candidate compound;

wherein said inhibition is indicative of the candidate compound binding to an antilipolytic GPCR.

In some embodiments, the antilipolytic GPCR comprises a biologically active fragment of said amino acid sequence.

In some embodiments, the antilipolytic GPCR is endogenous.

In some embodiments, the antilipolytic GPCR is recombinant.

In preferred embodiments, said G protein is Gi.

In some preferred embodiments, said reference compound is the modulator of the thirty-sixth aspect.

In other embodiments, said reference compound is an antibody specific for the GPCR, or a derivative thereof.

In preferred embodiments, said reference compound comprises a label selected from the group consisting of:

(a) radioisotope;

(b) enzyme; and (c) fluorophore.

In some preferred embodiments, said label is $^3$H.

In other embodiments, said method further comprises the step of comparing the level of inhibition of binding of a labeled first reference compound by the candidate compound to a second level of inhibition of binding of said labeled first reference compound by a second reference compound known to bind to the GPCR.

In a forty-eighth aspect, the invention features a method of making a transgenic mouse, comprising the step of engineering said mouse to carry as part of its own genetic material the gene encoding the human antilipolytic GPCR polypeptide of SEQ. ID. NO.:135 (hRUP38).

In some preferred embodiments, expression of said gene is placed under the control of an essentially adipocyte specific promoter.

In a forty-ninth aspect, the invention features the transgenic mouse according to the method of the forty-eighth aspect.

In a fiftieth aspect, the invention features a method of using the transgenic mouse of the forty-ninth aspect to identify whether an agonist of said human receptor has therapeutic efficacy for the treatment of a disorder of lipid metabolism selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin;

comprising the steps of:

(a') administering or not administering the agonist to the mouse; and (b') determining whether on administering the agonist there is a change selected from the group consisting of:

(i) a decrease in the level of plasma triglycerides;

(ii) a decrease in the level of plasma free fatty acids;

(iii) a decrease in the level of plasma cholesterol;

(iv) a decrease in the level of LDL-cholesterol;

(v) an increase in the level of HDL-cholesterol;

(vi) a decrease in the total cholesterol/HDL-cholesterol ratio; and (vii) an increase in the level of plasma adiponectin;

wherein said change is indicative of the agonist having therapeutic efficacy.

In a fifty-first aspect, the invention features a method of using the transgenic mouse of the forty-ninth aspect to identify whether an agonist of said human receptor has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering the agonist to the mouse; and (b') determining whether on administering the agonist there is a change selected from the group consisting of:

(i) a decrease in the level of plasma triglycerides;

(ii) a decrease in the level of plasma free fatty acids;

(iii) a decrease in the level of plasma cholesterol;

(iv) a decrease in the level of LDL-cholesterol;

(v) an increase in the level of HDL-cholesterol;

(vi) a decrease in the total cholesterol/HDL-cholesterol ratio; and (vii) an increase in the level of plasma adiponectin;

wherein said change is indicative of the agonist having therapeutic efficacy.

In a fifty-second aspect, the invention features a method of making a transgenic rat, comprising the step of engineering said rat to carry as part of its own genetic material the gene encoding the human antilipolytic GPCR polypeptide of SEQ. ID. NO.:135 (hRUP38).

In some preferred embodiments, expression of said gene is placed under the control of an essentially adipocyte specific promoter.

In a fifty-third aspect, the invention features the transgenic rat according to the method of the fifty-second aspect.

In a fifty-fourth aspect, the invention features a method of using the transgenic rat of the fifty-third aspect to identify whether an agonist of said human receptor has therapeutic efficacy for the treatment of a disorder of lipid metabolism selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin;

comprising the steps of:

(a') administering or not administering the agonist to the rat; and (b') determining whether on administering the agonist there is a change selected from the group consisting of:

(i) a decrease in the level of plasma triglycerides;

(ii) a decrease in the level of plasma free fatty acids;

(iii) a decrease in the level of plasma cholesterol;

(iv) a decrease in the level of LDL-cholesterol;

(v) an increase in the level of HDL-cholesterol;

(vi) a decrease in the total cholesterol/HDL-cholesterol ratio; and (vii) an increase in the level of plasma adiponectin;

wherein said change is indicative of the agonist having therapeutic efficacy.

In a fifty-fifth aspect, the invention features a method of using the transgenic rat of the fifty-third aspect to identify whether an agonist of said human receptor has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering the agonist to the rat; and (b') determining whether on administering the agonist there is a change selected from the group consisting of:

(i) a decrease in the level of plasma triglycerides;

(ii) a decrease in the level of plasma free fatty acids;

(iii) a decrease in the level of plasma cholesterol;

(iv) a decrease in the level of LDL-cholesterol;

(v) an increase in the level of HDL-cholesterol;

(vi) a decrease in the total cholesterol/HDL-cholesterol ratio; and (vii) an increase in the level of plasma adiponectin;

wherein said change is indicative of the agonist having therapeutic efficacy.

In a fifty-sixth aspect, the invention features an isolated, purified or recombinant RUP38 polynucleotide selected from the group consisting of:

(a) a polynucleotide comprising a contiguous span of at least 75 nucleotides of SEQ.ID. NO.:134, or an allelic variant of said polynucleotide;

(b) a polynucleotide comprising a contiguous span of at least 150 nucleotides of SEQ. ID. NO.:134, or an allelic variant of said polynucleotide;

(c) a polynucleotide comprising a contiguous span of at least 250 nucleotides of SEQ. ID. NO.:134, or an allelic variant of said polynucleotide;

(d) a polynucleotide comprising a contiguous span of at least 350 nucleotides of SEQ. ID. NO.:134, or an allelic variant of said polynucleotide;

(e) a polynucleotide comprising a contiguous span of at least 500 nucleotides of SEQ. ID. NO.:134, or an allelic variant of said polynucleotide;

(f) a polynucleotide comprising a contiguous span of at least 750 nucleotides of SEQ. ID. NOs.:134, or an allelic variant of said polynucleotide;

(g) a polynucleotide comprising a contiguous span of at least 1000 nucleotides of SEQ. ID. NO.:134, or an allelic variant of said polynucleotide;

(h) a polynucleotide encoding a polypeptide comprising a contiguous span of at least 20 amino acids of SEQ. ID. NO.:135 or an allelic variant of said polypeptide;

(i) a polynucleotide encoding a polypeptide comprising a contiguous span of at least 30 amino acids of SEQ. ID. NO.:135, or an allelic variant of said polypeptide;

(j) a polynucleotide encoding a polypeptide comprising a contiguous span of at least 40 amino acids of SEQ. ID. NO.:135, or an allelic variant of said polypeptide;

(k) a polynucleotide encoding a polypeptide comprising a contiguous span of at least 50 amino acids of SEQ. ID. NO.:135 or an allelic variant of said polypeptide;

(l) a polynucleotide encoding a polypeptide comprising a contiguous span of at least 75 amino acids of SEQ. ID. NO.:135 or an allelic variant of said polypeptide;

(m) a polynucleotide encoding a polypeptide comprising a contiguous span of at least 100 amino acids of SEQ. ID. NO.:135 or an allelic variant of said polypeptide;

(n) a polynucleotide encoding a polypeptide comprising a contiguous span of at least 150 amino acids of SEQ. ID. NO.:135 or an allelic variant of said polypeptide;

(o) a polynucleotide encoding a polypeptide comprising a contiguous span of at least 200 amino acids of SEQ. ID. NO.:135 or an allelic variant of said polypeptide;

(p) a polynucleotide encoding a polypeptide comprising a contiguous span of at least 250 amino acids of SEQ. ID. NO.:135 or an allelic variant of said polypeptide; and (q) a polynucleotide encoding a polypeptide comprising a contiguous span of at least 300 amino acids of SEQ.ID. NO.:135 or an allelic variant of said polypeptide.

The invention also relates to an isolated, purified or recombinant RUP25 polynucleotide wherein said polynucleotide is selected from the group consisting of:

(a) a polynucleotide comprising the nucleotide sequence of SEQ. ID. NO.:134 or an allelic variant of said nucleotide sequence;

(b) the polynucleotide of SEQ. ID. NO.:134, or an allelic variant of said polynucleotide;

(c) a polynucleotide comprising a nucleotide sequence encoding a polypeptide having the amino acid sequence of SEQ. ID. NO.:135 or an allelic variant of said amino acid sequence; and (d) a polynucleotide encoding a polypeptide having the amino acid sequence of SEQ. ID. NO.:135, or an allelic variant of said polypeptide.

In preferred embodiments, said isolated, purified or recombinant polynucleotide comprises at least 8 contiguous nucleotides of a polynucleotide of the present invention. In other preferred embodiments, said isolated, purified or recombinant polynucleotide comprises at least 10, 12, 15, 18, 20, 25, 28, 30, 35, 40, 50, 75, 100, 150, 200, 300, 400, 500, 600, 700, 800, 900 or 1000 contiguous nucleotides of a polynucleotide of the present invention. Preferably said polynucleotide encodes full-length RUP38 polypeptide or a biologically active fragment thereof.

The polynucleotides of the present invention include genomic polynucleotides comprising RUP38 polynucleotides of the invention.

The present invention also relates to a polynucleotide encoding a fusion protein, wherein said fusion protein comprises an RUP38 polypeptide of the invention fused to a heterologous polypeptide. In a preferred embodiment, said polypeptide of the invention is constitutively active and said heterologous polypeptide is a G protein. In other embodiments, said heterologous polypeptide provides an antigenic epitope. In a preferred embodiment, said heterologous polypeptide provides a hemaglutinin (HA) antigenic epitope. Methods relating to a polynucleotide encoding a fusion protein are well known to those of ordinary skill in the art.

The polynucleotides of the present invention also include variant polynucleotides at least 60%, 70%, 80%, 90%, 95%, 96%, 97%, 98% or 99% identical to an RUP38 polynucleotide of the invention. In a particularly preferred embodiments, polynucleotide sequence homologies are evaluated using the Basic Local Alignment Search Tool ("BLAST"), which is well known in the art [See, e.g., Karlin and Altschul, Proc Natl Acad Sci USA (1990) 87:2264–8; Altschul et al., J Mol Biol (1990) 215:403–410; Altschul et al., Nature Genetics (1993) 3:266–72; and Altschul et al., Nucleic Acids Res (1997) 25:3389–3402; the disclosures of which are incorporated by reference in their entirety].

In further preferred embodiments, the invention features the complement of said polynucleotide.

In a fifty-seventh aspect, the invention features an isolated, purified or recombinant RUP38 polypeptide selected from the group consisting of:

(a) a polypeptide comprising a contiguous span of at least 20 amino acids of SEQ. ID. NO.:135 or an allelic variant of said contiguous span of amino acids;

(b) a polypeptide comprising a contiguous span of at least 30 amino acids of SEQ. ID. NO.:135 or an allelic variant of said contiguous span of amino acids;

(c) a polypeptide comprising a contiguous span of at least 40 amino acids of SEQ. ID. NO.:135 or an allelic variant of said contiguous span of amino acids;

(d) a polypeptide comprising a contiguous span of at least 50 amino acids of SEQ. ID. NO.:135 or an allelic variant of said contiguous span of amino acids;

(e) a polypeptide comprising a contiguous span of at least 75 amino acids of SEQ. ID. NO.:135 or an allelic variant of said contiguous span of amino acids;

(f) a polypeptide comprising a contiguous span of at least 100 amino acids of SEQ. ID. NO.:135 or an allelic variant of said contiguous span of amino acids;

(g) a polypeptide comprising a contiguous span of at least 150 amino acids of SEQ. ID. NO.:135 or an allelic variant of said contiguous span of amino acids;

(h) a polypeptide comprising a contiguous span of at least 200 amino acids of SEQ. ID. NO.:135 or an allelic variant of said contiguous span of amino acids;

(i) a polypeptide comprising a contiguous span of at least 250 amino acids of SEQ. ID. NO.:135 or an allelic variant of said contiguous span of amino acids; and (j) a polypeptide comprising a contiguous span of at least 300 amino acids of SEQ. ID. NO.:135 or an allelic variant of said contiguous span of amino acids.

The invention also relates to an isolated, purified or recombinant RUP38 polypeptide wherein said polypeptide is selected from the group consisting of:

(a) a polypeptide comprising the amino acid sequence of SEQ. ID. NO.:135 or an allelic variant or a biologically active mutant of said amino acid sequence; and (b) the polypeptide having the amino acid sequence of SEQ. ID. NO.:135 or an allelic variant or a biologically active mutant of said amino acid sequence;

or a biologically active fragment of said polypeptide.

In preferred embodiments, said isolated, purified or recombinant polypeptide comprises at least 6 contiguous amino acids of an RUP38 polypeptide of the invention. In further embodiments, said isolated, purified or recombinant polypeptide comprises at least 10, 12, 15, 20, 25, 30, 35, 40, 50, 60, 75, 100, 125, 150, 175, 200, 225, 250, 275 or 300 contiguous amino acids of a polypeptide of the present invention. Preferably, said polypeptide is full-length RUP38 polypeptide or an active fragment thereof.

The present invention also relates to a fusion protein, wherein said fusion protein comprises an RUP38 polypeptide of the invention fused to a heterologous polypeptide. In a preferred embodiment, said polypeptide of the invention is constitutively active and said heterologous polypeptide is a G protein. In other preferred embodiments, said heterologous polypeptide provides an antigenic epitope. In particularly preferred embodiment, said heterologous polypeptide provides a hemaglutinin (HA) antigenic epitope. Methods relating to a fusion protein are well known to those of ordinary skill in the art.

The polypeptides of the present invention also include variant polypeptides at least 80%, 85%, 90%, 91%, 92%, 93%, 94%, 95%, 96%, 97%, 98% or 99% identical to an RUP38 polypeptide of the invention. In a particularly preferred embodiments, polypeptide sequence homologies are evaluated using the Basic Local Alignment Search Tool ("BLAST"), which is well known in the art [See, e.g., Karlin and Altschul, Proc Natl Acad Sci USA (1990) 87:2264–8; Altschul et al., J Mol Biol (1990) 215:403–410; Altschul et al., Nature Genetics (1993) 3;266–72; and Altschul et al., Nucleic Acids Res (1997) 25:3389–3402; the disclosures of which are incorporated by reference in their entirety].

In an fifty-eighth aspect, the invention features a composition comprising, consisting essentially of, or consisting of the RUP38 polypeptide of the fifty-seventh aspect.

In a fifty-ninth aspect, the invention features a recombinant vector, said vector comprising, consisting essentially of, or consisting of the polynucleotide of the fifty-sixth aspect. In some embodiments, said vector is a targeting vector used in a method of inactivating a gene encoding an antilipolytic GPCR of the invention. In some preferred embodiments, said vector is used in a method of transient or stable transfection. In other preferred embodiments, said vector is used in a method of transgenic expression of an antilipolytic GPCR.

In particularly preferred embodiment, said vector is an expression vector for the expression of a an antilipolytic GPCR in a recombinant host cell wherein said expression vector comprises, consists essentially of, or consists of the polynucleotide of the fifty-sixth aspect. Although a variety of expression vectors are available to those in the art, for purposes of utilization for both the endogenous and non-endogenous human, mouse and rat GPCRs, it is most preferred that the vector utilized be pCMV. In some alternative embodiments as relates to said human, mouse and rat antilipolytic GPCRs, it is preferred that the vector utilized be an adenoviral expression vector.

In a sixtieth aspect, the invention features a prokaryotic or eukaryotic host cell comprising, consisting essentially of, or consisting of the recombinant vector of the fifty-ninth aspect. In some embodiments, said host cell is a eukaryotic embryonic stem cell wherein said vector of the fifty-ninth aspect has been used in a method to inactivate a gene encoding an antilipolytic GPCR of the invention within said cell. In some embodiments, said host cell is a eukaryotic embryonic somatic cell wherein said vector of the fifty-ninth aspect has been used in a method to inactivate a gene encoding an antilipolytic GPCR of the invention within said cell. In some preferred embodiments, said host cell is derived from a mouse or rat made transgenic for a human RUP38 antilipolytic GPCR of the invention. In some preferred embodiments, said host cell is prokaryotic and has been transformed using the vector of the fifty-ninth aspect. In further preferred embodiments, said host cell is eukaryotic and has been transiently transfected using the vector of the fifty-ninth aspect. In other further preferred embodiments, said host cell is eukaryotic and has been stably transfected using the vector of the fifty-ninth aspect.

In particularly preferred embodiment, said host cell expresses a recombinant antilipolytic GPCR wherein said host cell comprises, consists essentially of, or consists of the expression vector of the fifty-ninth aspect.

A further embodiment includes a prokaryotic or eukaryotic host cell recombinant for the polynucleotide of the fifty-sixth aspect.

In some embodiments the host cell is eukaryotic, more preferably, mammalian, and more preferably selected from the group consisting of 293, 293T, CHO, and COS-7 cells. In other embodiments, the host cell is eukaryotic, more preferably melanophore.

In a sixty-first aspect, the invention features a process for the expression of a antilipolytic GPCR in a recombinant host cell comprising the steps of:

(a) transfecting the expression vector of the fifty-ninth aspect into a suitable host cell; and (b) culturing the host cells under conditions which allow expression of the antilipolytic GPCR protein from the expression vectors.

In a sixty-second aspect, the invention features an antibody that specifically binds to the polypeptide of the fifty-seventh aspect. In some preferred embodiments, the antibody is monoclonal. In some embodiments, the antibody is polyclonal.

In a sixty-third aspect, the invention features a method of binding the polypeptide of the fifty-seventh aspect to the antibody of the sixty-second aspect, comprising contacting said antibody with said polypeptide under conditions in which said antibody can specifically bind to said polypeptide.

In a sixty-fourth aspect, the invention features a method of detecting an antilipolytic GPCR polypeptide in a biological sample obtained from an individual comprising the steps of:

(a) obtaining said biological sample from said individual;

(b) contacting said biological sample with the antibody of the sixty-second aspect; and (c) detecting the presence or absence of binding of said antibody to said biological sample;

wherein a detection of said binding is indicative of the receptor polypeptide being expressed in said biological sample.

In preferred embodiments, said detecting is through the use of an enzyme-labeled secondary reagent. In other preferred embodiments, said detecting is through the use of a fluorophore-labeled secondary reagent. In other preferred embodiments, said detecting is through the use of a radioisotope-labeled secondary reagent. In other embodiments, the antibody is directly labeled with enzyme, fluorophore or radioisotope.

In other preferred embodiments, said biological sample is taken from adipose, skin or blood.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In further embodiments, said individual has a disorder of lipid metabolism selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin.

In other preferred embodiments, said disorder in lipid metabolism is an elevated postprandial increase in plasma free fatty acids due to a high fat meal or a progression from impaired glucose tolerance to insulin resistance.

In further embodiments, said individual has a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodimens, said metabolic-related disorder is hyperlipidemia.

In other embodiments, said method further comprises the step of comparing the level of detection of said binding for a first individual to the level of detection of said binding for a second individual.

In a sixty-fifth aspect, the invention features a method of detecting expression of a gene encoding an antilipolytic GPCR in a biological sample obtained from an individual comprising the steps of:

(a) obtaining said biological sample from said individual;

(b) contacting said biological sample with the complementary polynucleotide of the fifty-sixth aspect, optionally labeled, under conditions permissive for hybridization; and (c) detecting the presence or absence of said hybridization between said complementary polynucleotide and an RNA species within said sample;

wherein a detection of said hybridization is indicative of expression of said GPCR gene in said biological sample.

In preferred embodiments, the biological sample is taken from adipose, skin or blood.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In preferred embodiments, said individual has a disorder of lipid metabolism selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin.

In other preferred embodiments, said disorder in lipid metabolism is an elevated postprandial increase in plasma free fatty acids due to a high fat meal or a progression from impaired glucose tolerance to insulin resistance.

In other preferred embodiments, said individual has a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In other embodiments, said method further comprises the step of comparing the level of detection of said hybridization for a first individual to the level of detection of said hybridization for a second individual.

In some preferred embodiments, said complementary polynucleotide is a primer and said hybridization is detected by detecting the presence of an amplification product comprising the sequence of said primer. In more preferred embodiments, said method is RT-PCR.

In a sixty-sixth aspect, the invention features a GPCR Fusion Protein construct comprising a constitutively active GPCR and a G protein, said receptor comprising the amino acid sequence of SEQ. ID. NO.:135 (hRUP38) or an allelic variant or a biologically active fragment of said amino acid sequence.

The invention also relates to a GPCR Fusion Protein construct wherein the isoleucine at amino acid position 230 of SEQ. ID. NO.:135 is substituted by lysine.

In a sixty-seventh aspect, the invention features a method of binding a known ligand of RUP38 antilipolytic GPCR to a polypeptide selected from the group consisting of:

(a) a polypeptide comprising a contiguous span of at least 6 amino acids of SEQ. ID. NO.:135;

(b) a polypeptide comprising a contiguous span of at least 10 amino acids of SEQ. ID. NO.:135;

(c) a polypeptide comprising a contiguous span of at least 15 amino acids of SEQ. ID. NO.:135;

(d) a polypeptide comprising a contiguous span of at least 20 amino acids of SEQ. ID. NO.:135;

(e) a polypeptide comprising a contiguous span of at least 25 amino acids of SEQ. ID. NO.:135;

(f) a polypeptide comprising a contiguous span of at least 30 amino acids of SEQ. ID. NO.:135;

(g) a polypeptide comprising a contiguous span of at least 35 amino acids of SEQ. ID. NO.:135;

(h) a polypeptide comprising a contiguous span of at least 40 amino acids of SEQ. ID. NO.:135;

(i) a polypeptide comprising a contiguous span of at least 45 amino acids of SEQ. ID. NO.:135; and (j) a polypeptide comprising a contiguous span of at least 50 amino acids of SEQ. ID. NO.:135; or an allelic variant of said polypeptide;

comprising the step of contacting said known ligand with said polypeptide under conditions which allow said binding to occur.

In some embodiments, said known ligand is a modulator of the antilipolytic GPCR. In some embodiments, said known modulator is an agonist of the antilipolytic GPCR. In some embodiments, said known ligand is the modulator of the thirty-sixth aspect. In some embodiments, said known ligand is an antibody specific for the GPCR, or a derivative thereof.

In other preferred embodiments, said method is used to identify whether a candidate compound inhibits said binding of said known ligand to said polypeptide, comprising the steps of:

(a) contacting said polypeptide with said known ligand, optionally labeled, in the presence or absence of said candidate compound;

(b) detecting the complex between said known ligand and said polypeptide; and (c) determining whether less of said complex is formed in the presence of the compound than in the absence of the compound;

wherein said determination is indicative of the candidate compound being an inhibitor of said binding of said known ligand to said polypeptide.

In some embodiments, said known ligand is a modulator of the antilipolytic GPCR. In some embodiments, said known modulator is an agonist. In some embodiments, said known ligand is the modulator of the thirty-sixth aspect. In some embodiments, said known ligand is an antibody specific for the GPCR, or a derivative thereof.

In other preferred embodiments, said method is used to identify whether a candidate compound is an inhibitor of said binding of said known ligand to said polypeptide, comprising the steps of:

(a) contacting said polypeptide with said known ligand, optionally labeled, in the presence separately of a plurality of concentrations of said candidate compound for a time sufficient to allow equilibration of binding;

(b) measuring unbound ligand and bound ligand; and (c) determining $K_i$ for the candidate compound;

wherein a $K_i$ value of less than 50 uM is indicative of the candidate compound being an inhibitor of said binding of said known ligand to said polypeptide. Preferably said $K_i$ value is less than 25 $\mu$M, 10 $\mu$M, 5 $\mu$M, 1 $\mu$M, 750 nM, 500 nM, 400 nM, 300 nM, 250 nM, 200 nM, 150 nM, 100 nM, 90 nM, 80 nM, 70 nM, 60 nM, 50 nM, 40 nM, 30 nM, 20 nM or 10 nM. In preferred embodiments, $K_i$ determination is made through nonlinear curve fitting with the program SCTFIT [De Lean et al. (1982) Mol Pharmacol 21:5–16; cited in Lorenzen et al. (2001) Mol Pharmacol 59:349–357, the disclosures of which are incorporated by reference herein in their entireties].

In some embodiments, said known ligand is a modulator of the antilipolytic GPCR. In some embodiments, said known modulator is an agonist. In some embodiments, said known ligand is the modulator of the thirty-sixth aspect. In some embodiments, said known ligand is an antibody specific for the GPCR, or a derivative thereof.

In a sixty-eighth aspect, the invention features a method of binding an optionally labeled affinity reagent specific for an antilipolytic GPCR to said receptor in a biological sample, said receptor comprising the amino acid sequence of SEQ. ID. NO.:135 (hRUP38); or an allelic variant, a biologically active mutant, or a biologically active fragment of said amino acid sequence, comprising the steps of:

(a) obtaining said biological sample;

(b) contacting the affinity reagent with said receptor in said biological sample; and (c) detecting the complex of said affinity reagent with said receptor.

In some embodiments, the antilipolytic GPCR has the amino acid sequence of SEQ. ID. NO.: 135 (hRUP38); or an allelic variant, a biologically active mutant, or a biologically active fragment of said amino acid sequence.

In some embodiments, the antilipolytic GPCR comprises a biologically active fragment of said amino acid sequence.

In some embodiments, the antilipolytic GPCR is endogenous.

In some embodiments, the antilipolytic GPCR is recombinant.

In some embodiments, said biologically active mutant is CART or EFA. In preferred embodiments, said CART mutant has the amino acid sequence of SEQ. ID. NO.:135 further substituted at amino acid position 230 with lysine in place of isoleucine.

In preferred embodiments, said G protein is Gi.

In some embodiments, said affinity reagent is a modulator of the GPCR. In some embodiments, said affinity reagent is an agonist of the GPCR. In some embodiments, said affinity reagent is the modulator of the thirty-sixth aspect. In some embodiments, said affinity reagent is an antibody specific for the GPCR, or a derivative thereof.

In further preferred embodiments, said affinity reagent comprises a label selected from the group consisting of:

(a) radioisotope;

(b) enzyme; and (c) fluorophore.

In preferred embodiments, said radioisotope is $^3$H.

In a sixty-ninth aspect, the invention features the method of the sixty-eighth aspect further comprising the step of comparing the level of detection of said complex in a first biological sample to a second level of detection of said complex in a second biological sample.

In a seventieth aspect, the invention features the method of the sixty-ninth aspect wherein the relationship between said first and second biological samples is selected from the group consisting of:

(a) said second biological sample is a replicate of said first biological sample;

(b) said first biological sample was obtained prior to an experimental intervention whereas said second biological sample was obtained after the experimental intervention, from the same individual;

(c) said second biological sample was obtained at a different time point after an experimental intervention than was said first biological sample, from the same individual;

(d) said second biological sample corresponds to a different subcellular compartment than does said first biological sample;

(e) said second biological sample represents a different cell type than does said first biological sample;

(f) said second biological sample corresponds to a different tissue than does said first biological sample;

(g) said second biological sample was obtained from a different individual than was said first biological sample;

(h) said second biological sample was obtained at a different point in time than was said first biological sample, from the same individual;

(i) said first biological samples was obtained from a normal individual, whereas said second biological sample was obtained from an individual having a metabolic-related disorder;

(j) said first biological sample was obtained from a normal individual, whereas said second biological sample was obtained from an individual having a disorder in lipid metabolism;

(k) said first biological sample was obtained before a therapeutic intervention whereas said second biological sample was obtained after the therapeutic intervention, from the same individual;

(l) said second biological sample was obtained at a different time point after therapeutic intervention than was said first biological sample, from the same individual; and (m) said first biological sample was not exposed to a compound, whereas said second biological sample was exposed to said compound.

In a seventy-first aspect, the invention features a method of identifying whether a candidate compound is a modulator of an antilipolytic GPCR, said receptor comprising an amino acid sequence selected from the group consisting of:

(a) SEQ. ID. NO.:24 (hRUP19);

(b) SEQ. ID. NO.:151 (mRUP19); and (c) SEQ. ID. NO.:157 (rRUP19);

or an allelic variant, a biologically active mutant, or a biologically active fragment of said amino acid sequence;

comprising the steps of:

(a') contacting the candidate compound with the receptor;

(b') determining whether the receptor functionality is modulated;

wherein a change in receptor functionality is indicative of the candidate compound being a modulator of an antilipolytic GPCR.

In some embodiments, said antilipolytic GPCR is endogenous.

In some preferred embodiments, said antilipolytic GPCR is recombinant.

Preferred said identified modulator binds to said GPCR.

In some embodiments, said contacting is carried out in the presence of a known ligand of the GPCR. In some embodiments, said known ligand is an agonist of the GPCR.

The invention also relates to a method of identifying whether a candidate compound is a modulator of lipolysis, comprising the steps of:

(a) contacting the candidate compound with a GPCR comprising an amino acid sequence selected from the group consisting of:
  (i) SEQ. ID. NO.:24 (hRUP19);
  (ii) SEQ. ID. NO.:151 (mRUP19); and
  (iii) SEQ. ID. NO.:157 (rRUP19);
  or an allelic variant, a biologically active mutant, or a biologically active fragment of said amino acid sequence; and
(b) determining whether the receptor functionality is modulated;

wherein a change in receptor functionality is indicative of the candidate compound being a modulator of lipolysis.

In some embodiments, said GPCR is endogenous.

In some preferred embodiments, said GPCR is recombinant.

Preferred said identified modulator binds to said GPCR.

In some embodiments, said contacting is carried out in the presence of a known ligand of the GPCR. In some embodiments, said known ligand is an agonist of the GPCR.

The invention also relates to a method of determining whether a candidate compound is a modulator of an antilipolytic GPCR, comprising the steps of:

(a) culturing antilipolytic GPCR-expressing host cells under conditions that would allow expression of a recombinant antilipolytic GPCR, said host cells being transfected with a polynucleotide encoding said recombinant antilipolytic GPCR comprising an amino acid sequence selected from the group consisting of:
  (i) SEQ. ID. NO.:24 (hRUP19);
  (ii) SEQ. ID. NO.:151 (mRUP19); and
  (iii) SEQ. ID. NO.:157 (rRUP19);
  or an allelic variant, a biologically active mutant, or a biologically active fragment of said amino acid sequence;
(b) contacting the antilipolytic GPCR-expressing host cells of step (a) with the candidate compound;
(c) contacting control host cells with the candidate compound of step (b), wherein said control host cells do not express recombinant antilipolytic GPCR protein;
(d) measuring the modulating effect of the candidate compound which interacts with the recombinant antilipolytic GPCR from the host cells of step (a) and control host cells of step (c); and
(e) comparing the modulating effect of the test compound on the host cells and control host cells.

The invention also relates to a method of determining whether a candidate compound is a modulator of an antilipolytic GPCR, comprising the steps of:

(a) culturing antilipolytic GPCR-expressing host cells under conditions that would allow expression of a recombinant antilipolytic GPCR, said host cells being transfected with a polynucleotide encoding said recombinant antilipolytic GPCR comprising an amino acid sequence selected from the group consisting of:
  (i) SEQ. ID. NO.:24 (hRUP19);
  (ii) SEQ. ID. NO.:151 (mRUP19); and
  (iii) SEQ. ID. NO.:157 (rRUP19);
  or an allelic variant, a biologically active mutant, or a biologically active fragment of said amino acid sequence;
(b) contacting a first population of antilipolytic GPCR-expressing cells of step (a) with a known ligand of said antilipolytic GPCR;
(c) contacting a second population of antilipolytic GPCR-expressing cells of step (a) with the candidate compound and with the known antilipolytic GPCR ligand;
(d) contacting control host cells with the candidate compound of step (c), wherein said control host cells do not express recombinant antilipolytic GPCR protein;
(e) measuring the modulating effect of the candidate compound, which interacts with recombinant antilipolytic GPCR, in the presence and absence of the known antilipolytic GPCR ligand, from the cells of step (b), step (c) and step (d); and
(f) comparing the modulating effect of the candidate compound as determined from step (b), step (c) and step (d).

In some embodiments, said ligand is an agonist of the GPCR.

The invention also relates to a method of determining whether a candidate compound is a modulator of an antilipolytic GPCR, comprising the steps of:

(a) culturing antilipolytic GPCR-expressing host cells under conditions that would allow expression of a recombinant antilipolytic GPCR, said host cells being transfected with a polynucleotide encoding said recombinant antilipolytic GPCR comprising an amino acid sequence selected from the group consisting of:
  (i) SEQ. ID. NO.:24 (hRUP19);
  (ii) SEQ. ID. NO.:151 (mRUP19); and
  (iii) SEQ. ID. NO.:157 (rRUP19);
  or an allelic variant, a biologically active mutant, or a biologically active fragment of said amino acid sequence;
(b) contacting a first population of the antilipolytic GPCR-expressing host cells of step (a) with the candidate compound;
(c) not contacting a second population of the antilipolytic GPCR-expressing cells of step (a) with the candidate compound of step (b);
(d) contacting control host cells to the candidate compound of step (b), wherein said control host cells do not express recombinant antilipolytic GPCR protein;
(e) measuring the modulating effect of the candidate compound, which interacts with recombinant antilipolytic GPCR protein, from the cells of step (b) and step (c) and from the cells of step (d); and
(f) comparing the modulating effect of the candidate compound as determined from step (b) and step (c) and from step (d).

In some embodiments, the antilipolytic GPCR has an amino acid sequence selected from the group consisting of:

(a) SEQ. ID. NO.:24 (hRUP19);
(b) SEQ. ID. NO.:151 (mRUP19); and
(c) SEQ. ID. NO.:157 (rRUP19);
or an allelic variant, a biologically active mutant, or a biologically active fragment of said amino acid sequence.

In some embodiments, the antilipolytic GPCR comprises a biologically active fragment of said amino acid sequence.

In some embodiments, said biologically active mutant is CART or EFA. In preferred embodiments, said CART mutant has the amino acid sequence of SEQ. ID. NO.:24 further substituted at amino acid position 219 with lysine in place of threonine.

In preferred embodiments, said G protein is Gi.

In other preferred embodiments, said determining is through the use of a Melanophore assay.

In other preferred embodiments, said determining is through the measurement of the level of a second messenger selected from the group consisting of cyclic AMP (cAMP), cyclic GMP (cGMP), inositol triphosphate ($IP_3$), diacylglycerol (DAG), and $Ca^{2+}$. In further preferred embodiments, said second messenger is cAMP. In more preferred embodiments, the level of the cAMP is reduced. In some embodiments, said measurement of cAMP is carried out with membrane comprising said GPCR.

In other preferred embodiments, said determining is through the measurement of an activity up-regulated or down-regulated by a reduction in intracellular cAMP level. In further preferred embodiments, said down-regulated activity is intracellular lipolysis. In other further preferred embodiments, said down-regulated activity is hormone sensitive lipase activity. In other further preferred embodiments, said up-regulated activity is adiponectin secretion.

In other preferred embodiments, said determining is through CRE-reporter assay. In preferred embodiments, said reporter is luciferase. In some embodiments, said reporter is β-galactosidase.

In other preferred embodiments, said recombinant host cell further comprises promiscuous G alpha 15/16 or chimeric Gq/Gi alpha subunit and said determining is through measurement of intracellular $Ca^{2+}$. In preferred embodiments, said $Ca^{2+}$ measurement is carried out by FLIPR.

In other preferred embodiments, said recombinant host cell further comprises promiscuous G alpha 15/16 or chimeric Gq/Gi alpha subunit and said determining is through measurement of intracellular $IP_3$.

In other preferred embodiments, said determining is through the measurement of GTPγS binding to membrane comprising said GPCR. In further preferred embodiments, said GTPγS is labeled with $[^{35}S]$.

In other preferred embodiments, said method further comprises the step of comparing the modulation of the receptor caused by the candidate compound to a second modulation of the receptor caused by contacting the receptor with a known modulator of the receptor. In some preferred embodiments, said known modulator is an agonist.

In a seventy-second aspect, the invention features a modulator of an antilipolytic GPCR identified according to the method of the seventy-first aspect.

In some preferred embodiments, said modulator is selected from the group consisting of agonist, partial agonist, inverse agonist and antagonist. More preferably, said modulator is an agonist. In some embodiments, said modulator is a partial agonist.

In some embodiments, said modulator is an agonist with an $EC_{50}$ of less than 1000 μM in GTPγS binding assay carried out with membrane from stably transfected CHO cells expressing recombinant hRUP19 polypeptide having the amino acid sequence of SEQ. ID. NO.:24. In some embodiments, said modulator is an agonist with an $EC_{50}$ of less than 900 μM in said assay. In some embodiments, said modulator is an agonist with an $EC_{50}$ of less than 800 μM in said assay. In some embodiments, said modulator is an agonist with an $EC_{50}$ of less than 700 μM in said assay. In some embodiments, said modulator is an agonist with an $EC_{50}$ of less than 600 μM in said assay. In some embodiments, said modulator is an agonist with an $EC_{50}$ of less than 550 μM in said assay. In some embodiments, said modulator is an agonist with an $EC_{50}$ of less than 500 μM in said assay. In some embodiments, said modulator is an agonist with an $EC_{50}$ of less than 450 μM in said assay. In some embodiments, said modulator is an agonist with an $EC_{50}$ of less than 400 μM in said assay. In some embodiments, said modulator is an agonist with an $EC_{50}$ of less than 350 μM in said assay. In some embodiments, said modulator is an agonist with an $EC_{50}$ of less than 300 μM in said assay. In some embodiments, said modulator is an agonist with an $EC_{50}$ of less than 250 μM in said assay. In some embodiments, said modulator is an agonist with an $EC_{50}$ of less than 200 μM in said assay. In some embodiments, said modulator is an agonist with an $EC_{50}$ of less than 150 μM in said assay. In some embodiments, said modulator is an agonist with an $EC_{50}$ of less than 100 μM in said assay. In some preferred embodiments, said modulator is an agonist with an $EC_{50}$ in said assay of less than a value selected from the interval of 600 μM to 1000 μM.

In some embodiments, said modulator is selective for the GPCR.

In some embodiments, said modulator is antilipolytic.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some preferred embodiments, said oral bioavailability is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some preferred embodiments, said oral bioavailability is at least 1%, at least 5%, at least 10%, or at least 15% relative to intravenous administration.

In highly less preferred embodiments, said modulator is an antibody or derivative thereof.

In a seventy-third aspect, the invention features a method of modulating the activity of an antilipolytic GPCR, said receptor comprising an amino acid sequence selected from the group consisting of:

(a) SEQ. ID. NO.:24 (hRUP19);

(b) SEQ. ID. NO.:151 (mRUP19); and (c) SEQ. ID. NO.:157 (rRUP19);

or an allelic variant, a biologically active mutant, or a biologically active fragment of said amino acid sequence; comprising the step of contacting the receptor with the modulator of the seventy-second aspect.

In some embodiments, the antilipolytic GPCR has an amino acid sequence selected from the group consisting of:

(a) SEQ. ID. NO.:24 (hRUP19);

(b) SEQ. ID. NO.:151 (mRUP19); and (c) SEQ. ID. NO.:157 (rRUP19);

or an allelic variant, a biologically active mutant, or a biologically active fragment of said amino acid sequence.

In some embodiments, the antilipolytic GPCR comprises an active fragment of said amino acid sequence.

In some embodiments, the antilipolytic GPCR is recombinant.

In some embodiments, the antilipolytic GPCR is endogenous.

In some embodiments, said biologically active mutant is CART or EFA. In preferred embodiments, said CART mutant has the amino acid sequence of SEQ. ID. NO.:24 further substituted at amino acid position 219 with lysine in place of threonine.

In preferred embodiments, said G protein is Gi.

In some preferred embodiments, said modulator is an agonist.

In preferred embodiments, said modulator is selective for the GPCR.

In other preferred embodiments, said contacting comprises administration of the modulator to a membrane comprising the receptor.

In other preferred embodiments, said contacting comprises administration of the modulator to a cell or tissue comprising the receptor.

In other preferred embodiments, said contacting comprises administration of the modulator to an individual comprising the receptor. In more preferred embodiments, said individual is a mammal. In other more preferred embodiments, said mammal is a horse, cow, sheep, pig, cat, dog, rabbit, mouse, rat, non-human primate or human. Yet more preferred is mouse, rat or human. Most preferred is human.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP19 polypeptide having the amino acid sequence of SEQ. ID. NO.:24. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said administration is oral.

In preferred embodiments, said modulator is an agonist and said individual is in need of prevention of or treatment for a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In other embodiments, said modulator is an inverse agonist and said metabolic-related disorder relates to a low level of plasma free fatty acids.

In other preferred embodiments, said modulator is an agonist and said individual is in need of a change in lipid metabolism selected from the group consisting of:

(a) a decrease in the level of plasma triglycerides;

(b) a decrease in the level of plasma free fatty acids;

(c) a decrease in the level of plasma cholesterol;

(d) a decrease in the level of LDL-cholesterol;

(e) an increase in the level of HDL-cholesterol;

(f) a decrease in the total cholesterol/HDL-cholesterol ratio; and (g) an increase in the level of plasma adiponectin.

In other preferred embodiments, said needed change in lipid metabolism is a decrease in the postprandial increase in plasma free fatty acids due to a high fat meal or an inhibition of the progression from impaired glucose tolerance to insulin resistance.

In some embodiments, the modulator is an inverse agonist and the needed change in lipid metabolism is an increase in the level of plasma free fatty acids.

In other preferred embodiments, said modulator is an agonist and said individual is a mouse genetically predisposed to a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure.

In further preferred embodiments, said metabolic-related disorder is hyperlipidemia.

In further preferred embodiments, said method is used to identify whether said agonist has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering said agonist to the mouse; and (b') determining whether the disorder is prevented, delayed, or made less severe on administering said agonist compared to not administering said agonist; wherein said determination is indicative of said agonist having therapeutic efficacy.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In other preferred embodiments, said modulator is an agonist and said individual is a rat genetically predisposed to a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In further preferred embodiments, said metabolic-related disorder is hyperlipidemia.

In further preferred embodiments, said method is used to identify whether said agonist has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering said agonist to the rat; and (b') determining whether the disorder is prevented, delayed, or made less severe on administering said agonist compared to not administering said agonist; wherein said determination is indicative of said agonist having therapeutic efficacy.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In a seventy-fourth aspect, the invention features a method of preventing or treating a disorder of lipid metabolism in an individual comprising contacting a therapeutically effective amount of the modulator of the seventy-second aspect with an antilipolytic GPCR, said receptor comprising an amino acid sequence selected from the group consisting of:

(a) SEQ. ID. NO.:24 (hRUP19);

(b) SEQ. ID. NO.:151 (mRUP19); and (c) SEQ. ID. NO.:157 (rRUP19);

or an allelic variant or biologically active fragment of said amino acid sequence.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP19 polypeptide having the amino acid sequence of SEQ. ID. NO.:24. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 μM in said assay. In some preferred embodiments, said modulator is an agonist with an $EC_{50}$ in said assay of less than a value selected from the interval of 600 μM to 1000 μM.

In some preferred embodiments, said contacting comprises oral administration of said modulator to said individual.

In preferred embodiment, said modulator is an agonist and said disorder of lipid metabolism is selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin.

In a seventy-fifth aspect, the invention features a method of preventing or treating a metabolic-related disorder in an individual comprising contacting a therapeutically effective amount of the modulator of the seventy-second aspect with an antilipolytic GPCR, said receptor comprising an amino acid sequence selected from the group consisting of:

(a) SEQ. ID. NO.:24 (hRUP19);

(b) SEQ. ID. NO.:151 (mRUP19); and (c) SEQ. ID. NO.:157 (rRUP19);

or an allelic variant or biologically active fragment of said amino acid sequence.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 μM in GTPγS binding assay carried out with membrane from stably transfected CHO cells expressing recombinant hRUP19 polypeptide having the amino acid sequence of SEQ. ID. NO.:24. In some embodiments, said modulator is an agonist with an $EC_{50}$ of less than 900 μM in said assay. In some embodiments, said modulator is an agonist with an $EC_{50}$ of less than 800 μM in said assay. In some embodiments, said modulator is an agonist with an $EC_{50}$ of less than 700 μM in said assay. In some embodiments, said modulator is an agonist with an $EC_{50}$ of less than 600 μM in said assay. In some embodiments, said modulator is an agonist with an $EC_{50}$ of less than 550 μM in said assay. In some embodiments, said modulator is an agonist with an $EC_{50}$ of less than 500 μM in said assay. In some embodiments, said modulator is an agonist with an $EC_{50}$ of less than 450 μM in said assay. In some embodiments, said modulator is an agonist with an $EC_{50}$ of less than 400 μM in said assay. In some embodiments, said modulator is an agonist with an $EC_{50}$ of less than 350 μM in said assay. In some embodiments, said modulator is an agonist with an $EC_{50}$ of less than 300 μM in said assay. In some embodiments, said modulator is an agonist with an $EC_{50}$ of less than 250 μM in said assay. In some embodiments, said modulator is an agonist with an $EC_{50}$ of less than 200 μM in said assay. In some embodiments, said modulator is an agonist with an $EC_{50}$ of less than 150 μM in said assay. In some embodiments, said modulator is an agonist with an $EC_{50}$ of less than 100 μM in said assay. In some preferred embodiments, said modulator is an agonist with an $EC_{50}$ in said assay of less than a value selected from the interval of 600 μM to 1000 μM.

In some preferred embodiments, said contacting comprises oral administration of said modulator to said individual.

In preferred embodiment, said modulator is an agonist and said metabolic-related disorder is selected from the group consisting of:

(a) dyslipidemia;

(b) atherosclerosis;

(c) coronary heart disease;

(d) stroke;

(e) insulin resistance; and (f) type 2 diabetes.

In a seventy-sixth aspect, the invention features a method of preparing a composition which comprises identifying a modulator of a antilipolytic GPCR and then admixing a carrier and the modulator, wherein the modulator is identifiable by the method of the seventy-first aspect.

In some preferred embodiments, said modulator is selected from the group consisting of agonist, partial agonist, inverse agonist and antagonist. More preferably, said modulator is an agonist. In some embodiments, said modulator is a partial agonist.

In some embodiments, said modulator is an agonist with an $EC_{50}$ of less than 1000 μM in GTPγS binding assay carried out with membrane from stably transfected CHO cells expressing recombinant hRUP19 polypeptide having the amino acid sequence of SEQ. ID. NO.:24. In some embodiments, said modulator is an agonist with an $EC_{50}$ of less than 900 μM in said assay. In some embodiments, said modulator is an agonist with an $EC_{50}$ of less than 800 μM in said assay. In some embodiments, said modulator is an agonist with an $EC_{50}$ of less than 700 μM in said assay. In some embodiments, said modulator is an agonist with an $EC_{50}$ of less than 600 μM in said assay. In some embodiments, said modulator is an agonist with an $EC_{50}$ of less than 550 μM in said assay. In some embodiments, said modulator is an agonist with an $EC_{50}$ of less than 500 μM in said assay. In some embodiments, said modulator is an agonist with an $EC_{50}$ of less than 450 μM in said assay. In some embodiments, said modulator is an agonist with an $EC_{50}$ of less than 400 μM in said assay. In some embodiments, said modulator is an agonist with an $EC_{50}$ of less than 350 μM in said assay. In some embodiments, said modulator is an agonist with an $EC_{50}$ of less than 300 μM in said assay. In some embodiments, said modulator is an agonist with an $EC_{50}$ of less than 250 μM in said assay. In some embodiments, said modulator is an agonist with an $EC_{50}$ of less than 200 μM in said assay. In some embodiments, said modulator is an agonist with an $EC_{50}$ of less than 150 μM in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some embodiments, said modulator is selective for the GPCR.

In some embodiments, said modulator is antilipolytic.

In some embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to either intraperitoneal or intravenous administration. In some preferred embodiments, said oral bioavailability is at least 1%, at least 5%, at least 10%, or at least 15% relative to either intraperitoneal or intravenous administration.

In an seventy-seventh aspect, the invention features a pharmaceutical or physiologically acceptable composition comprising, consisting essentially of, or consisting of the modulator of the seventy-second aspect. In preferred embodiments, said modulator is an agonist.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP19 polypeptide having the amino acid sequence of SEQ. ID. NO.:24. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In a seventy-eighth aspect, the invention features a method of changing lipid metabolism comprising providing or administering to an individual in need of said change said pharmaceutical or physiologically acceptable composition of the seventy-seventh aspect, said needed change in lipid metabolism selected from the group consisting of:

(a) a decrease in the level of plasma triglycerides;

(b) a decrease in the level of plasma free fatty acids;

(c) a decrease in the level of plasma cholesterol;

(d) a decrease in the level of LDL-cholesterol;

(e) an increase in the level of HDL-cholesterol;

(f) a decrease in the total cholesterol/HDL-cholesterol ratio; and (g) an increase in the level of plasma adiponectin.

In preferred embodiments, a therapeutically effective amount of said pharmaceutical or physiologically acceptable composition is provided or administered to said individual.

In some preferred embodiments, said providing or administering of said pharmaceutical or physiologically acceptable composition is oral.

In other preferred embodiments, said needed change in lipid metabolism is a decrease in the postprandial increase in plasma free fatty acids due to a high fat meal or an inhibition of the progression from impaired glucose tolerance to insulin resistance.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In a seventy-ninth aspect, the invention features a method of preventing or treating a metabolic-related disorder comprising providing or administering to an individual in need of said treatment said pharmaceutical or physiologically acceptable composition of the seventy-seventh aspect, said metabolic-related disorder selected from the group consisting of:

(a) dyslipidemia;

(b) atherosclerosis;

(c) coronary heart disease;

(d) stroke;

(e) insulin resistance; and (f) type 2 diabetes.

In preferred embodiments, a therapeutically effective amount of said pharmaceutical or physiologically acceptable composition is provided or administered to said individual.

In some preferred embodiments, said providing or administering of said pharmaceutical or physiologically acceptable composition is oral.

In other preferred embodiments, said metabolic-related disorder is selected from the group consisting of obesity, impaired glucose tolerance, atheromatous disease, hypertension, stroke, Syndrome X, and heart disease. Heart disease includes, but is not limited to, cardiac insufficiency, coronary insufficiency, and high blood pressure. In other preferred embodiments, said metabolic-related disorder is hyperlipidemia.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In an eightieth aspect, the invention features a method of using the modulator of the seventy-second aspect for the preparation of a medicament for the treatment of a disorder in lipid metabolism in an individual.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP19 polypeptide having the amino acid sequence of SEQ. ID. NO.:24. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said treatment comprises oral administration of said medicament to said individual.

In preferred embodiments, said modulator is an agonist and said disorder in lipid metabolism is selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin.

In other preferred embodiments, said disorder in lipid metabolism is an elevated postprandial increase in plasma free fatty acids due to a high fat meal or a progression from impaired glucose tolerance to insulin resistance.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In an eighty-first aspect, the invention features a method of using the modulator of the seventy-second aspect for the preparation of a medicament for the treatment of a metabolic-related disorder in an individual.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP19 polypeptide having the amino acid sequence of SEQ. ID. NO.:24. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said treatment comprises oral administration of said medicament to said individual.

In preferred embodiments, said modulator is an agonist and said metabolic-related disorder is selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In an eighty-second aspect, the invention features a method of identifying whether a candidate compound binds to an antilipolytic GPCR, said receptor comprising an amino acid sequence selected from the group consisting of:

(a) SEQ. ID. NO.:24 (hRUP19);

(b) SEQ. ID. NO.:151 (mRUP19); and (c) SEQ. ID. NO.:157 (rRUP19);

or an allelic variant or a biologically active fragment of said amino acid sequence;

comprising the steps of:

(a') contacting the receptor with a labeled reference compound known to bind to the GPCR in the presence or absence of the candidate compound; and (b') determining whether the binding of said labeled reference compound to the receptor is inhibited in the presence of the candidate compound;

wherein said inhibition is indicative of the candidate compound binding to an antilipolytic GPCR.

In some embodiments, the antilipolytic GPCR comprises a biologically active fragment of said amino acid sequence.

In some embodiments, the antilipolytic GPCR is endogenous.

In some embodiments, the antilipolytic GPCR is recombinant.

In preferred embodiments, said G protein is Gi.

In some preferred embodiments, said reference compound is the modulator of the seventy-second aspect.

In other embodiments, said reference compound is an antibody specific for the GPCR, or a derivative thereof.

In preferred embodiments, said reference compound comprises a label selected from the group consisting of:

(a) radioisotope;

(b) enzyme; and (c) fluorophore.

In some preferred embodiments, said label is $^{3}H$.

In other embodiments, said method further comprises the step of comparing the level of inhibition of binding of a labeled first reference compound by the candidate compound to a second level of inhibition of binding of said labeled first reference compound by a second reference compound known to bind to the GPCR.

In an eighty-third aspect, the invention features a method of making a mouse genetically predisposed to a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the step of knocking out the gene encoding the antilipolytic mRUP19 GPCR polypeptide of SEQ. ID. NO.:151.

In some preferred embodiments, said knocking out the gene encoding the antilipolytic mRUP19 GPCR polypeptide of SEQ. ID. NO.:151 is essentially restricted to adipocytes.

In an eighty-fourth aspect, the invention features the knockout mouse according to the method of the eighty-third aspect.

In an eighty-fifth aspect, the invention features a method of using the knockout mouse of the eighty-fourth aspect to identify whether a candidate compound has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering the compound to the mouse; and (b') determining whether the disorder is prevented, delayed, or made less severe on administering the compound compared to not administering the compound;

wherein said determination is indicative of the compound having therapeutic efficacy.

In an eighty-sixth aspect, the invention features a method of making a rat genetically predisposed to a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the step of knocking out the gene encoding the antilipolytic rRUP19 GPCR polypeptide of SEQ. ID. NO.:157.

In some preferred embodiments, said knocking out the gene encoding the antilipolytic rRUP19 GPCR polypeptide of SEQ. ID. NO.:157 is essentially restricted to adipocytes.

In an eighty-seventh aspect, the invention features the knockout rat according to the method of the eighty-sixth aspect.

In an eighty-eighth aspect, the invention features a method of using the knockout rat of the eighty-seventh aspect to identify whether a candidate compound has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering the compound to the rat; and (b') determining whether the disorder is prevented, delayed, or made less severe on administering the compound compared to not administering the compound;

wherein said determination is indicative of the compound having therapeutic efficacy.

In an eighty-ninth aspect, the invention features an isolated, purified or recombinant RUP19 polynucleotide selected from the group consisting of:

(a) a polynucleotide comprising a contiguous span of at least 75 nucleotides of SEQ.ID. NO.:23, SEQ. ID. NO.:150 or SEQ. ID. NO.:156, or an allelic variant of said polynucleotide;

(b) a polynucleotide comprising a contiguous span of at least 150 nucleotides of SEQ. ID. NO.:23, SEQ. ID. NO.:150 or SEQ. ID. NO.:156, or an allelic variant of said polynucleotide;

(c) a polynucleotide comprising a contiguous span of at least 250 nucleotides of SEQ. ID. NO.:23, SEQ. ID. NO.:150 or SEQ. ID. NO.:156, or an allelic variant of said polynucleotide;

(d) a polynucleotide comprising a contiguous span of at least 350 nucleotides of SEQ. ID. NO.:23, SEQ. ID. NO.:150 or SEQ. ID. NO.:156, or an allelic variant of said polynucleotide;

(e) a polynucleotide comprising a contiguous span of at least 500 nucleotides of SEQ. ID. NO.:23, SEQ. ID. NO.:150 or SEQ. ID. NO.:156, or an allelic variant of said polynucleotide;

(f) a polynucleotide comprising a contiguous span of at least 750 nucleotides of SEQ. ID. NOs.:23, SEQ. ID. NO.:150 or 156, or an allelic variant of said polynucleotide;

(g) a polynucleotide comprising a contiguous span of at least 1000 nucleotides of SEQ. ID. NO.:23, SEQ. ID. NO.:150 or SEQ. ID. NO.:156, or an allelic variant of said polynucleotide;

(h) a polynucleotide encoding a polypeptide comprising a contiguous span of at least 20 amino acids of SEQ. ID. NO.:24, SEQ. ID. NO:151 or SEQ. ID. NO.:157 or an allelic variant of said polypeptide;

(i) a polynucleotide encoding a polypeptide comprising a contiguous span of at least 30 amino acids of SEQ. ID. NO.:24, SEQ. ID. NO.:151 or SEQ. ID. NO.:157 or an allelic variant of said polypeptide;

(j) a polynucleotide encoding a polypeptide comprising a contiguous span of at least 40 amino acids of SEQ. ID. NO.:24, SEQ. ID. NO.:151 or SEQ. ID. NO.:157 or an allelic variant of said polypeptide;

(k) a polynucleotide encoding a polypeptide comprising a contiguous span of at least 50 amino acids of SEQ. ID. NO.:24, SEQ. ID. NO.:151 or SEQ. ID. NO.:157 or an allelic variant of said polypeptide;

(l) a polynucleotide encoding a polypeptide comprising a contiguous span of at least 75 amino acids of SEQ. ID. NO.:24, SEQ. ID. NO.:151 or SEQ. ID. NO.:157 or an allelic variant of said polypeptide;

(m) a polynucleotide encoding a polypeptide comprising a contiguous span of at least 100 amino acids of SEQ. ID. NO.:24, SEQ. ID. NO.:151 or SEQ. ID. NO.:157 or an allelic variant of said polypeptide;

(n) a polynucleotide encoding a polypeptide comprising a contiguous span of at least 150 amino acids of SEQ. ID. NO.:24, SEQ. ID. NO.:151 or SEQ. ID. NO.:157 or an allelic variant of said polypeptide;

(o) a polynucleotide encoding a polypeptide comprising a contiguous span of at least 200 amino acids of SEQ. ID. NO.:24, SEQ. ID. NO.:151 or SEQ. ID. NO.:157 or an allelic variant of said polypeptide;

(p) a polynucleotide encoding a polypeptide comprising a contiguous span of at least 250 amino acids of SEQ. ID. NO.:24, SEQ. ID. NO.:151 or SEQ. ID. NO.:157 or an allelic variant of said polypeptide; and (q) a polynucleotide encoding a polypeptide comprising a contiguous span of at least 300 amino acids of SEQ.ID. NO.:24, SEQ. ID. NO.:151 or SEQ. ID. NO.:157 or an allelic variant of said polypeptide.

The invention also relates to an isolated, purified or recombinant RUP19 polynucleotide wherein said polynucleotide is selected from the group consisting of:

(a) a polynucleotide comprising a nucleotide sequence selected from the group consisting of SEQ. ID. NO.:23, SEQ. ID. NO.:150 and SEQ. ID. NO.:156 or an allelic variant of said polynucleotide;

(b) a polynucleotide selected from the group consisting of the polynucleotide of SEQ. ID. NO.:23, the polynucleotide of SEQ. ID. NO.:150 and the polynucleotide of SEQ. ID. NO.:156, or an allelic variant of said polynucleotide;

(c) a polynucleotide comprising a nucleotide sequence encoding a polypeptide having an amino acid sequence selected from the group consisting of SEQ. ID. NO.:24, SEQ. ID. NO.:151 and SEQ. ID. NO.:157 or an allelic variant of said polypeptide; and (d) a polynucleotide encoding a polypeptide having an amino acid sequence selected from the group consisting of SEQ. ID. NO.:24, SEQ. ID. NO.:151 and SEQ. ID. NO.:157 or an allelic variant of said polypeptide.

In preferred embodiments, said isolated, purified or recombinant polynucleotide comprises at least 8 contiguous nucleotides of a polynucleotide of the present invention. In other preferred embodiments, said isolated, purified or recombinant polynucleotide comprises at least 10, 12, 15, 18, 20, 25, 28, 30, 35, 40, 50, 75, 100, 150, 200, 300, 400, 500, 600, 700, 800, 900 or 1000 contiguous nucleotides of a polynucleotide of the present invention. Preferably said polynucleotide encodes full-length RUP19 polypeptide or a biologically active fragment thereof.

The polynucleotides of the present invention include genomic polynucleotides comprising RUP19 polynucleotides of the invention.

The present invention also relates to a polynucleotide encoding a fusion protein, wherein said fusion protein comprises an RUP19 polypeptide of the invention fused to a heterologous polypeptide. In a preferred embodiment, said polypeptide of the invention is constitutively active and said heterologous polypeptide is a G protein. In other embodiments, said heterologous polypeptide provides an antigenic epitope. In a preferred embodiment, said heterologous polypeptide provides a hemaglutinin (HA) antigenic epitope. Methods relating to a polynucleotide encoding a fusion protein are well known to those of ordinary skill in the art.

The polynucleotides of the present invention also include variant polynucleotides at least 60%, 70%, 80%, 90%, 95%, 96%, 97%, 98% or 99% identical to an RUP19 polynucleotide of the invention. In a particularly preferred embodiments, polynucleotide sequence homologies are evaluated using the Basic Local Alignment Search Tool ("BLAST"), which is well known in the art [See, e.g., Karlin and Altschul, Proc Natl Acad Sci USA (1990) 87:2264–8; Altschul et al., J Mol Biol (1990) 215:403–410; Altschul et al., Nature Genetics (1993) 3:266–72; and Altschul et al., Nucleic Acids Res (1997) 25:3389–3402; the disclosures of which are incorporated by reference in their entirety].

In further preferred embodiments, the invention features the complement of said polynucleotide.

In a ninetieth aspect, the invention features an isolated, purified or recombinant RUP19 polypeptide selected from the group consisting of:

(a) a polypeptide comprising a contiguous span of at least 20 amino acids of SEQ. ID. NO.:24, SEQ. ID. NO.:151 or SEQ. ID. NO.:157;

(b) a polypeptide comprising a contiguous span of at least 30 amino acids of SEQ. ID. NO.:24, SEQ. ID. NO.:151 or SEQ. ID. NO.:157;

(c) a polypeptide comprising a contiguous span of at least 40 amino acids of SEQ. ID. NO.:24, SEQ. ID. NO.:151 or SEQ. ID. NO.:157;

(d) a polypeptide comprising a contiguous span of at least 50 amino acids of SEQ. ID. NO.:24, SEQ. ID. NO.:151 or SEQ. ID. NO.:157;

(e) a polypeptide comprising a contiguous span of at least 75 amino acids of SEQ. ID. NO.:24, SEQ. ID. NO.:151 or SEQ. ID. NO.:157;

(f) a polypeptide comprising a contiguous span of at least 100 amino acids of SEQ. ID. NO.:24, SEQ. ID. NO.:151 or SEQ. ID. NO.:157;

(g) a polypeptide comprising a contiguous span of at least 150 amino acids of SEQ. ID. NO.:24, SEQ. ID. NO.:151 or SEQ. ID. NO.:157;

(h) a polypeptide comprising a contiguous span of at least 200 amino acids of SEQ. ID. NO.:24, SEQ. ID. NO.:151 or SEQ. ID. NO.:157;

(i) a polypeptide comprising a contiguous span of at least 250 amino acids of SEQ. ID. NO.:24, SEQ. ID. NO.:151 or SEQ. ID. NO.:157; and (j) a polypeptide comprising a contiguous span of at least 300 amino acids of SEQ. ID. NO.:24, SEQ. ID. NO.:151 or SEQ. ID. NO.:157;

or an allelic variant of said polypeptide.

The invention also relates to an isolated, purified or recombinant RUP19 polypeptide wherein said polypeptide is selected from the group consisting of:

(a) a polypeptide comprising an amino acid sequence selected from the group consisting of SEQ. ID. NO.:24, SEQ. ID. NO.:151 and SEQ. ID. NO.:157; and (b) a polypeptide selected from the group consisting of the polypeptide of SEQ. ID. NO.:24, the polypeptide of SEQ. ID. NO:151 and the polypeptide of SEQ. ID. NO.:157;

or an allelic variant, a biologically active mutant, or a biologically active fragment of said polypeptide.

In preferred embodiments, said isolated, purified or recombinant polypeptide comprises at least 6 contiguous amino acids of an RUP19 polypeptide of the invention. In further embodiments, said isolated, purified or recombinant polypeptide comprises at least 10, 12, 15, 20, 25, 30, 35, 40, 50, 60, 75, 100, 125, 150, 175, 200, 225, 250, 275 or 300 contiguous amino acids of a polypeptide of the present invention. Preferably, said polypeptide is full-length RUP19 polypeptide or an active fragment thereof.

The present invention also relates to a fusion protein, wherein said fusion protein comprises an RUP19 polypeptide of the invention fused to a heterologous polypeptide. In a preferred embodiment, said polypeptide of the invention is constitutively active and said heterologous polypeptide is a G protein. In other preferred embodiments, said heterologous polypeptide provides an antigenic epitope. In particularly preferred embodiment, said heterologous polypeptide provides a hemaglutinin (HA) antigenic epitope. Methods relating to a fusion protein are well known to those of ordinary skill in the art.

The polypeptides of the present invention also include variant polypeptides at least 80%, 85%, 90%, 91%, 92%, 93%, 94%, 95%, 96%, 97%, 98% or 99% identical to an RUP19 polypeptide of the invention. In a particularly preferred embodiments, polypeptide sequence homologies are evaluated using the Basic Local Alignment Search Tool ("BLAST"), which is well known in the art [See, e.g., Karlin and Altschul, Proc Natl Acad Sci USA (1990) 87:2264–8; Altschul et al., J Mol Biol (1990) 215:403–410; Altschul et al., Nature Genetics (1993) 3:266–72; and Altschul et al., Nucleic Acids Res (1997) 25:3389–3402; the disclosures of which are incorporated by reference in their entirety].

In an ninety-first aspect, the invention features a composition comprising, consisting essentially of, or consisting of the RUP19 polypeptide of the ninetieth aspect.

In a ninety-second aspect, the invention features a recombinant vector, said vector comprising, consisting essentially of, or consisting of the polynucleotide of the eighty-ninth aspect. In preferred embodiments, said vector is a targeting vector used in a method of inactivating a gene encoding an antilipolytic GPCR of the invention. In other preferred embodiments, said vector is used in a method of transient or stable transfection.

In particularly preferred embodiment, said vector is an expression vector for the expression of a antilipolytic GPCR in a recombinant host cell wherein said expression vector comprises, consists essentially of, or consists of the polynucleotide of the eighty-ninth aspect.

Although a variety of expression vectors are available to those in the art, for purposes of utilization for both the endogenous and non-endogenous human, mouse and rat GPCRs, it is most preferred that the vector utilized be pCMV. In some alternative embodiments as relates to said human, mouse and rat antilipolytic GPCRs, it is preferred that the vector utilized be an adenoviral expression vector.

In a ninety-third aspect, the invention features a prokaryotic or eukaryotic host cell comprising, consisting essentially of, or consisting of the recombinant vector of the ninety-second aspect. In some preferred embodiments, said host cell is a eukaryotic embryonic stem cell wherein said vector of the ninety-second aspect has been used in a method to inactivate a gene encoding an antilipolytic GPCR of the invention within said cell. In some other preferred embodiments, said host cell is a eukaryotic embryonic somatic cell wherein said vector of the ninety-second aspect has been used in a method to inactivate a gene encoding an antilipolytic GPCR of the invention within said cell. In other preferred embodiments, said host cell is prokaryotic and has been transformed using the vector of the ninety-second aspect. In further preferred embodiments, said host cell is eukaryotic and has been transiently transfected using the vector of the ninety-second aspect. In other further preferred embodiments, said host cell is eukaryotic and has been stably transfected using the vector of the ninety-second aspect.

In particularly preferred embodiment, said host cell expresses a recombinant antilipolytic GPCR wherein said host cell comprises, consists essentially of, or consists of the expression vector of the ninety-second aspect.

A further embodiment includes a prokaryotic or eukaryotic host cell recombinant for the polynucleotide of the eighty-ninth aspect.

In some embodiments the host cell is eukaryotic, more preferably, mammalian, and more preferably selected from the group consisting of 293, 293T, CHO, and COS-7 cells. In other embodiments, the host cell is eukaryotic, more preferably melanophore.

In a ninety-fourth aspect, the invention features a process for the expression of an antilipolytic GPCR in a recombinant host cell comprising the steps of:

(a) transfecting the expression vector of the ninety-second aspect into a suitable host cell; and (b) culturing the host cells under conditions which allow expression of the antilipolytic GPCR protein from the expression vectors.

In a ninety-fifth aspect, the invention features an antibody that specifically binds to the polypeptide of the ninetieth aspect. In some preferred embodiments, the antibody is monoclonal. In some embodiments, the antibody is polyclonal.

In a ninety-sixth aspect, the invention features a method of binding the polypeptide of the ninetieth aspect to the antibody of the ninety-fifth aspect, comprising contacting said antibody with said polypeptide under conditions in which said antibody can specifically bind to said polypeptide.

In a ninety-seventh aspect, the invention features a method of detecting an antilipolytic GPCR polypeptide in a biological sample obtained from an individual comprising the steps of:

(a) obtaining said biological sample from said individual;

(b) contacting said biological sample with the antibody of the ninety-fifth aspect; and (c) detecting the presence or absence of binding of said antibody to said biological sample;

wherein a detection of said binding is indicative of the receptor polypeptide being expressed in said biological sample.

In preferred embodiments, said detecting is through the use of an enzyme-labeled secondary reagent. In other preferred embodiments, said detecting is through the use of a fluorophore-labeled secondary reagent. In other preferred embodiments, said detecting is through the use of a radioisotope-labeled secondary reagent. In other embodiments, the antibody is directly labeled with enzyme, fluorophore or radioisotope.

In other preferred embodiments, said biological sample is taken from adipose, skin or blood.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In further embodiments, said individual has a disorder of lipid metabolism selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin.

In other preferred embodiments, said disorder in lipid metabolism is an elevated postprandial increase in plasma free fatty acids due to a high fat meal or a progression from impaired glucose tolerance to insulin resistance.

In further embodiments, said individual has a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodimens, said metabolic-related disorder is hyperlipidemia.

In other embodiments, said method further comprises the step of comparing the level of detection of said binding for a first individual to the level of detection of said binding for a second individual.

In a ninety-eighth aspect, the invention features a method of detecting expression of a gene encoding antilipolytic GPCR in a biological sample obtained from an individual comprising the steps of:

(a) obtaining said biological sample from said individual;

(b) contacting said biological sample with the complementary polynucleotide of the eighty-ninth aspect, optionally labeled, under conditions permissive for hybridization; and (c) detecting the presence or absence of said hybridization between said complementary polynucleotide and an RNA species within said sample;

wherein a detection of said hybridization is indicative of expression of said GPCR gene in said biological sample.

Methods of labeling a nucleic acid probe are well known to those of ordinary skill in the art.

In preferred embodiments, the biological sample is taken from adipose, skin or blood.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In preferred embodiments, said individual has a disorder of lipid metabolism selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin.

In other preferred embodiments, said disorder in lipid metabolism is an elevated postprandial increase in plasma free fatty acids due to a high fat meal or a progression from impaired glucose tolerance to insulin resistance.

In other preferred embodiments, said individual has a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In other embodiments, said method further comprises the step of comparing the level of detection of said hybridization for a first individual to the level of detection of said hybridization for a second individual.

In some preferred embodiments, said complementary polynucleotide is a primer and said hybridization is detected by detecting the presence of an amplification product comprising the sequence of said primer. In more preferred embodiments, said method is RT-PCR.

In a ninety-ninth aspect, the invention features a GPCR Fusion Protein construct comprising a constitutively active GPCR and a G protein, said receptor comprising an amino acid sequence selected from the group consisting of:

(a) SEQ. ID. NO.:24 (hRUP19);

(b) SEQ. ID. NO.:151 (mRUP19); and (c) SEQ. ID. NO.:157 (rRUP19);

or an allelic variant or a biologically active fragment of said amino acid sequence.

The invention also relates to a GPCR Fusion Protein construct wherein the threonine at amino acid position 219 of SEQ. ID. NO.:24 is substituted by lysine.

In a one hundredth aspect, the invention features a method of binding a known ligand of RUP19 antilipolytic GPCR to a polypeptide selected from the group consisting of:

(a) a polypeptide comprising a contiguous span of at least 6 amino acids of SEQ. ID. NO.:24, SEQ. ID. NO.:151 or SEQ. ID. NO.:157;

(b) a polypeptide comprising a contiguous span of at least 10 amino acids of SEQ. ID. NO.:24, SEQ. ID. NO.:151 or SEQ. ID. NO.:157;

(c) a polypeptide comprising a contiguous span of at least 15 amino acids of SEQ. ID. NO.:24, SEQ. ID. NO.:151 or SEQ. ID. NO.:157;

(d) a polypeptide comprising a contiguous span of at least 20 amino acids of SEQ. ID. NO.:24, SEQ. ID. NO.:151 or SEQ. ID. NO.:157;

(e) a polypeptide comprising a contiguous span of at least 25 amino acids of SEQ. ID. NO.:24, SEQ. ID. NO.:151 or SEQ. ID. NO.:157;

(f) a polypeptide comprising a contiguous span of at least 30 amino acids of SEQ. ID. NO.:24, SEQ. ID. NO.:151 or SEQ. ID. NO.:157;

(g) a polypeptide comprising a contiguous span of at least 35 amino acids of SEQ. ID. NO.:24, SEQ. ID. NO.:151 or SEQ. ID. NO.:157;

(h) a polypeptide comprising a contiguous span of at least 40 amino acids of SEQ. ID. NO.:24, SEQ. ID. NO.:151 or SEQ. ID. NO.:157;

(i) a polypeptide comprising a contiguous span of at least 45 amino acids of SEQ. ID. NO.:24, SEQ. ID. NO.:151 or SEQ. ID. NO.:157; and (j) a polypeptide comprising a contiguous span of at least 50 amino acids of SEQ. ID. NO.:24, SEQ. ID. NO.:151 or SEQ. ID. NO.:157;

or an allelic variant of said polypeptide;

comprising the step of contacting said known ligand with said polypeptide under conditions which allow said binding to occur.

In a some embodiments, said known ligand is a modulator of the GPCR. In some embodiments, said known ligand is an agonist of the GPCR. In some embodiments, said known ligand is the modulator of the seventy-second aspect. In some embodiments, said known ligand is an antibody specific for the GPCR, or a derivative thereof.

In other preferred embodiments, said method is used to identify whether a candidate compound inhibits said binding of said known ligand to said polypeptide, comprising the steps of:

(a) contacting said polypeptide with said known ligand, optionally labeled, in the presence or absence of said candidate compound;

(b) detecting the complex between said known ligand and said polypeptide; and (c) determining whether less of said complex is formed in the presence of the compound than in the absence of the compound;

wherein said determination is indicative of the candidate compound being an inhibitor of said binding of said known ligand to said polypeptide.

In a some embodiments, said known ligand is a modulator of the GPCR. In some embodiments, said known ligand is an agonist of the GPCR. In some embodiments, said known ligand is the modulator of the seventy-second aspect. In some embodiments, said known ligand is an antibody specific for the GPCR, or a derivative thereof.

In other preferred embodiments, said method is used to identify whether a candidate compound is an inhibitor of said binding of said known ligand to said polypeptide, comprising the steps of:

(a) contacting said polypeptide with said known ligand, optionally labeled, in the presence separately of a plurality of concentrations of said candidate compound for a time sufficient to allow equilibration of binding;

(b) measuring unbound ligand and bound ligand; and (c) determining $K_i$ for the candidate compound;

wherein a $K_i$ value of less than 50 uM is indicative of the candidate compound being an inhibitor of said binding of said known ligand to said polypeptide. Preferably said $K_i$ value is less than 25 μM, 10 μM, 5 μM, 1 μM, 750 nM, 500 nM, 400 nM, 300 nM, 250 nM, 200 nM, 150 nM, 100 nM, 90 nM, 80 nM, 70 nM, 60 nM, 50 nM, 40 nM, 30 nM, 20 nM or 10 nM. In preferred embodiments, $K_i$ determination is made through nonlinear curve fitting with the program SCTFIT [De Lean et al. (1982) Mol Pharmacol 21:5–16; cited in Lorenzen et al. (2001) Mol Pharmacol 59:349–357, the disclosures of which are incorporated by reference herein in their entireties].

In a some embodiments, said known ligand is a modulator of the GPCR. In some embodiments, said known ligand is an agonist of the GPCR. In some embodiments, said known ligand is the modulator of the seventy-second aspect. In some embodiments, said known ligand is an antibody specific for the GPCR, or a derivative thereof.

In a one hundred first aspect, the invention features a method of binding an optionally labeled affinity reagent specific for an antilipolytic GPCR to said receptor in a biological sample, said receptor comprising an amino acid sequence selected from the group consisting of:

(a) SEQ. ID. NO.:24 (hRUP19);

(b) SEQ. ID. NO.:151 (mRUP19); and (c) SEQ. ID. NO.:157 (rRUP19);

or an allelic variant, a biologically active mutant, or a biologically active fragment of said amino acid sequence, comprising the steps of:

(a') obtaining said biological sample;

(b') contacting the affinity reagent with said receptor in said biological sample; and (c') detecting the complex of said affinity reagent with said receptor.

In some embodiments, the antilipolytic GPCR has an amino acid sequence selected from the group consisting of:

(a) SEQ. ID. NO.:24 (hRUP19);

(b) SEQ. ID. NO.:151 (mRUP19); and (c) SEQ. ID. NO.:157 (rRUP19);

or an allelic variant, a biologically active mutant, or a biologically active fragment of said amino acid sequence.

In some embodiments, the antilipolytic GPCR comprises an active fragment of said amino acid sequence.

In some embodiments, the antilipolytic GPCR is endogenous.

In some embodiments, the antilipolytic GPCR is recombinant.

In some embodiments, said biologically active mutant is CART or EFA. In preferred embodiments, said CART mutant has the amino acid sequence of SEQ. ID. NO.:24 further substituted at amino acid position 219 with lysine in place of threonine.

In preferred embodiments, said G protein is Gi.

In a some embodiments, said affinity reagent is a modulator of the GPCR. In some embodiments, said affinity reagent is an agonist of the GPCR. In some embodiments, said affinity reagent is the modulator of the seventy-second aspect. In some embodiments, said affinity reagent is an antibody specific for the GPCR, or a derivative thereof.

In further preferred embodiments, said affinity reagent comprises a label selected from the group consisting of:

(a) radioisotope;

(b) enzyme; and (c) fluorophore.

In preferred embodiments, said radioisotope is $^{3}H$.

In a one hundred second aspect, the invention features the method of the one hundred first aspect further comprising the step of comparing the level of detection of said complex in a first biological sample to a second level of detection of said complex in a second biological sample.

In a one hundred third aspect, the invention features the method of the one hundred second aspect wherein the relationship between said first and second biological samples is selected from the group consisting of:

(a) said second biological sample is a replicate of said first biological sample;

(b) said first biological sample was obtained prior to an experimental intervention whereas said second biological sample was obtained after the experimental intervention, from the same individual;

(c) said second biological sample was obtained at a different time point after an experimental intervention than was said first biological sample, from the same individual;

(d) said second biological sample corresponds to a different subcellular compartment than does said first biological sample;

(e) said second biological sample represents a different cell type than does said first biological sample;

(f) said second biological sample corresponds to a different tissue than does said first biological sample;

(g) said second biological sample was obtained from a different individual than was said first biological sample;

(h) said second biological sample was obtained at a different point in time than was said first biological sample, from the same individual;

(i) said first biological samples was obtained from a normal individual, whereas said second biological sample was obtained from an individual having a metabolic-related disorder;

(j) said first biological sample was obtained from a normal individual, whereas said second biological sample was obtained from an individual having a disorder in lipid metabolism;

(k) said first biological sample was obtained before a therapeutic intervention whereas said second biological sample was obtained after the therapeutic intervention, from the same individual;

(l) said second biological sample was obtained at a different time point after therapeutic intervention than was said first biological sample, from the same individual; and (m) said first biological sample was not exposed to a compound, whereas said second biological sample was exposed to said compound.

In a one hundred fourth aspect, the invention features a method of identifying whether a candidate compound is a modulator of an antilipolytic GPCR, said receptor comprising the amino acid sequence of SEQ. ID. NO.:8 (hRUP11); or an allelic variant, a biologically active mutant, or a biologically active fragment of said amino acid sequence; comprising the steps of:

(a) contacting the candidate compound with the receptor;

(b) determining whether the receptor functionality is modulated;

wherein a change in receptor functionality is indicative of the candidate compound being a modulator of an antilipolytic GPCR.

In some embodiments, said antilipolytic GPCR is endogenous.

In some preferred embodiments, said antilipolytic GPCR is recombinant.

Preferred said identified modulator binds to said GPCR.

In some embodiments, said contacting is carried out in the presence of a known ligand of the GPCR. In some embodiments, said known ligand is an agonist of the GPCR.

The invention also relates to a method of identifying whether a candidate compound is a modulator of lipolysis, comprising the steps of:

(a) contacting the candidate compound with a GPCR comprising the amino acid sequence of SEQ. ID. NO.:8 (hRUP11);

or an allelic variant, a biologically active mutant, or a biologically active fragment of said amino acid sequence; and (b) determining whether the receptor functionality is modulated;

wherein a change in receptor functionality is indicative of the candidate compound being a modulator of lipolysis.

In some embodiments, said GPCR is endogenous.

In some preferred embodiments, said GPCR is recombinant.

Preferred said identified modulator binds to said GPCR.

In some embodiments, said contacting is carried out in the presence of a known ligand of the GPCR. In some embodiments, said known ligand is an agonist of the GPCR.

The invention also relates to a method of determining whether a candidate compound is a modulator of an antilipolytic GPCR, comprising the steps of:

(a) culturing antilipolytic GPCR-expressing host cells under conditions that would allow expression of a recombinant antilipolytic GPCR, said host cells being transfected with a polynucleotide encoding said recombinant antilipolytic GPCR comprising the amino acid sequence of SEQ. ID. NO.:8 (hRUP11); or an allelic variant, a biologically active mutant, or a biologically active fragment of said amino acid sequence;

(b) contacting the antilipolytic GPCR-expressing host cells of step (a) with the candidate compound;

(c) contacting control host cells with the candidate compound of step (b), wherein said control host cells do not express recombinant antilipolytic GPCR protein;

(d) measuring the modulating effect of the candidate compound which interacts with the recombinant antilipolytic GPCR from the host cells of step (a) and control host cells of step (c); and (e) comparing the modulating effect of the test compound on the host cells and control host cells.

The invention also relates to a method of determining whether a candidate compound is a modulator of an antilipolytic GPCR, comprising the steps of:

(a) culturing antilipolytic GPCR-expressing host cells under conditions that would allow expression of a recombinant antilipolytic GPCR, said host cells being transfected with a polynucleotide encoding said recombinant antilipolytic GPCR comprising the amino acid sequence of SEQ. ID. NO.:8 (hRUP11); or an allelic variant, a biologically active mutant, or a biologically active fragment of said amino acid sequence;

(b) contacting a first population of antilipolytic GPCR-expressing cells of step (a) with a known ligand of said antilipolytic GPCR;

(c) contacting a second population of antilipolytic GPCR-expressing cells of step (a) with the candidate compound and with the known antilipolytic GPCR ligand;

(d) contacting control host cells with the candidate compound of step (c), wherein said control host cells do not express recombinant antilipolytic GPCR protein;

(e) measuring the modulating effect of the candidate compound, which interacts with recombinant antilipolytic GPCR, in the presence and absence of the known antilipolytic GPCR ligand, from the cells of step (b), step (c) and step (d); and (f) comparing the modulating effect of the candidate compound as determined from step (b), step (c) and step (d).

In some embodiments, said known ligand is an agonist of the GPCR.

The invention also relates to a method of determining whether a candidate compound is a modulator of an antilipolytic GPCR, comprising the steps of:

(a) culturing antilipolytic GPCR-expressing host cells under conditions that would allow expression of a recombinant antilipolytic GPCR, said host cells being transfected with a polynucleotide encoding said recombinant antilipolytic GPCR comprising the amino acid sequence of SEQ. ID. NO.:8 (hRUP11); or an allelic variant, a biologically active mutant, or a biologically active fragment of said amino acid sequence;

(b) contacting a first population of the antilipolytic GPCR-expressing host cells of step (a) with the candidate compound;

(c) not contacting a second population of the antilipolytic GPCR-expressing cells of step (a) with the candidate compound of step (b);

(d) contacting control host cells to the candidate compound of step (b), wherein said control host cells do not express recombinant antilipolytic GPCR protein;

(e) measuring the modulating effect of the candidate compound, which interacts with recombinant antilipolytic GPCR protein, from the cells of step (b) and step (c) and from the cells of step (d); and (f) comparing the modulating effect of the candidate compound as determined from step (b) and step (c) and from step (d).

In some embodiments, the antilipolytic GPCR has the amino acid sequence of SEQ. ID. NO.:8 (hRUP11); or an allelic variant, a biologically active mutant, or a biologically active fragment of said amino acid sequence.

In some embodiments, the antilipolytic GPCR comprises a biologically active fragment of said amino acid sequence.

In some embodiments, said biologically active mutant is CART or EFA. In preferred embodiments, said CART mutant has the amino acid sequence of SEQ. ID. NO.:8 further substituted at amino acid position 294 with lysine in place of methionine.

In preferred embodiments, said G protein is Gi.

In other preferred embodiments, said determining is through the use of a Melanophore assay.

In other preferred embodiments, said determining is through the measurement of the level of a second messenger selected from the group consisting of cyclic AMP (cAMP), cyclic GMP (cGMP), inositol triphosphate ($IP_3$), diacylglycerol (DAG), and $Ca^{2+}$. In further preferred embodiments, said second messenger is cAMP. In more preferred embodiments, the level of the cAMP is reduced. In some embodiments, said measurement of cAMP is carried out with membrane comprising said GPCR.

In other preferred embodiments, said determining is through the measurement of an activity up-regulated or down-regulated by a reduction in intracellular cAMP level. In further preferred embodiments, said down-regulated activity is intracellular lipolysis. In other further preferred embodiments, said down-regulated activity is hormone sensitive lipase activity. In other further preferred embodiments, said up-regulated activity is adiponectin secretion.

In other preferred embodiments, said determining is through CRE-reporter assay. In preferred embodiments, said reporter is luciferase. In some embodiments, said reporter is β-galactosidase.

In other preferred embodiments, said recombinant host cell further comprises promiscuous G alpha 15/16 or chimeric Gq/Gi alpha subunit and said determining is through measurement of intracellular $Ca^{2+}$. In preferred embodiments, said $Ca^{2+}$ measurement is carried out by FLIPR.

In other preferred embodiments, said recombinant host cell further comprises promiscuous G alpha 15/16 or chimeric Gq/Gi alpha subunit and said determining is through measurement of intracellular $IP_3$.

In other preferred embodiments, said determining is through the measurement of GTPγS binding to membrane comprising said GPCR. In further preferred embodiments, said GTPγS is labeled with [$^{35}S$].

In other preferred embodiments, said method further comprises the step of comparing the modulation of the receptor caused by the candidate compound to a second modulation of the receptor caused by contacting the receptor with a known modulator of the receptor. In some preferred embodiments, said known modulator is an agonist.

In a one hundred fifth aspect, the invention features a modulator of an antilipolytic GPCR identified according to the method of the one hundred fourth aspect.

In some preferred embodiments, said modulator is selected from the group consisting of agonist, partial agonist, inverse agonist and antagonist. More preferably, said modulator is an agonist. In some embodiments, said modulator is a partial agonist.

In some embodiments, said modulator is an agonist with an $EC_{50}$ of less than 1000 $\mu$M in GTPγS binding assay carried out with membrane from stably transfected CHO cells expressing recombinant hRUP11 polypeptide having the amino acid sequence of SEQ. ID. NO.:8. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some embodiments, said modulator is selective for the GPCR.

In some embodiments, said modulator is antilipolytic.

In some embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some preferred embodiments, said oral bioavailability is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some preferred embodiments, said oral bioavailability is at least 1%, at least 5%, at least 10%, or at least 15% relative to intravenous administration.

In highly less preferred embodiments, said modulator is an antibody or derivative thereof.

In a one hundred sixth aspect, the invention features a method of modulating the activity of an antilipolytic GPCR, said receptor comprising the amino acid sequence of SEQ. ID. NO.:8 (hRUP11); or an allelic variant, a biologically active mutant, or a biologically active fragment of said amino acid sequence;

comprising the step of contacting the receptor with the modulator of the one hundred fifth aspect.

In some embodiments, the antilipolytic GPCR has the amino acid sequence of SEQ. ID. NO.:8 (hRUP11); or an allelic variant, a biologically active mutant, or a biologically active fragment of said amino acid sequence.

In some embodiments, the antilipolytic GPCR comprises an active fragment of said amino acid sequence.

In some embodiments, the antilipolytic GPCR is endogenous.

In some embodiments, the antilipolytic GPCR is recombinant.

In some embodiments, said biologically active mutant is CART or EFA. In preferred embodiments, said CART mutant has the amino acid sequence of SEQ. ID. NO.:8 further substituted at amino acid position 294 with lysine in place of methionine.

In preferred embodiments, said G protein is Gi.

In some preferred embodiments, said modulator is an agonist.

In preferred embodiments, said modulator is selective for the GPCR.

In other preferred embodiments, said contacting comprises administration of the modulator to a membrane comprising the receptor.

In other preferred embodiments, said contacting comprises administration of the modulator to a cell or tissue comprising the receptor.

In other preferred embodiments, said contacting comprises administration of the modulator to an individual comprising the receptor. In more preferred embodiments, said individual is a mammal. In other more preferred embodiments, said mammal is a horse, cow, sheep, pig, cat, dog, rabbit, mouse, rat, non-human primate or human. Yet more preferred is mouse, rat or human. Most preferred is human.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is anti-lipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP11 polypeptide having the amino acid sequence of SEQ. ID. NO.:8. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said administration is oral.

In preferred embodiments, said modulator is an agonist and said individual is in need of prevention of or treatment for a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In other embodiments, said modulator is an inverse agonist and said metabolic-related disorder relates to a low level of plasma free fatty acids.

In other preferred embodiments, said modulator is an agonist and said individual is in need of a change in lipid metabolism selected from the group consisting of:

(a) a decrease in the level of plasma triglycerides;

(b) a decrease in the level of plasma free fatty acids;

(c) a decrease in the level of plasma cholesterol;

(d) a decrease in the level of LDL-cholesterol;

(e) an increase in the level of HDL-cholesterol;

(f) a decrease in the total cholesterol/HDL-cholesterol ratio; and (g) an increase in the level of plasma adiponectin.

In other preferred embodiments, said needed change in lipid metabolism is a decrease in the postprandial increase in plasma free fatty acids due to a high fat meal or an inhibition of the progression from impaired glucose tolerance to insulin resistance.

In some embodiments, the modulator is an inverse agonist and the needed change in lipid metabolism is an increase in the level of plasma free fatty acids.

In other preferred embodiments, said modulator is an agonist and said individual is a mouse genetically predisposed to a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure.

In further preferred embodiments, said metabolic-related disorder is hyperlipidemia.

In further preferred embodiments, said method is used to identify whether said agonist has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering said agonist to the mouse; and (b') determining whether the disorder is prevented, delayed, or made less severe on administering said agonist compared to not administering said agonist;

wherein said determination is indicative of said agonist having therapeutic efficacy.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In other preferred embodiments, said modulator is an agonist and said individual is a rat genetically predisposed to a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In further preferred embodiments, said metabolic-related disorder is hyperlipidemia.

In further preferred embodiments, said method is used to identify whether said agonist has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering said agonist to the rat; and (b') determining whether the disorder is prevented, delayed, or made less severe on administering said agonist compared to not administering said agonist;

wherein said determination is indicative of said agonist having therapeutic efficacy.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In a one hundred seventh aspect, the invention features a method of preventing or treating a disorder of lipid metabolism in an individual comprising contacting a therapeutically effective amount of the modulator of the one hundred fifth aspect with an antilipolytic GPCR, said receptor comprising the amino acid sequence of SEQ. ID. NO.:8 (hRUP11); or an allelic variant or biologically active fragment of said amino acid sequence.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP11 polypeptide having the amino acid sequence of SEQ. ID. NO.:8. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said contacting comprises oral administration of said modulator to said individual.

In preferred embodiment, said modulator is an agonist and said disorder of lipid metabolism is selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin.

In a one hundred eighth aspect, the invention features a method of preventing or treating a metabolic-related disorder in an individual comprising contacting a therapeutically effective amount of the modulator of the one hundred fifth aspect with an antilipolytic GPCR, said receptor comprising the amino acid sequence of SEQ. ID. NO.:8 (hRUP11); or an allelic variant or biologically active fragment of said amino acid sequence.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP11 polypeptide having the amino acid sequence of SEQ. ID. NO.:8. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said contacting comprises oral administration of said modulator to said individual.

In preferred embodiment, said modulator is an agonist and said metabolic-related disorder is selected from the group consisting of:

(a) dyslipidemia;

(b) atherosclerosis;

(c) coronary heart disease;

(d) stroke;

(e) insulin resistance; and (f) type 2 diabetes.

In a one hundred ninth aspect, the invention features a method of preparing a composition which comprises identifying a modulator of an antilipolytic GPCR and then admixing a carrier and the modulator, wherein the modulator is identifiable by the method of the one hundred fourth aspect.

In some preferred embodiments, said modulator is selected from the group consisting of agonist, partial agonist, inverse agonist and antagonist. More preferably, said modulator is an agonist. In some embodiments, said modulator is a partial agonist.

In some embodiments, said modulator is an agonist with an $EC_{50}$ of less than 1000 $\mu$M in GTPγS binding assay carried out with membrane from stably transfected CHO cells expressing recombinant hRUP11 polypeptide having the amino acid sequence of SEQ. ID. NO.:8. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some embodiments, said modulator is selective for the GPCR.

In some embodiments, said modulator is antilipolytic.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to either intraperitoneal or intravenous administration. In some preferred embodiments, said oral bioavailability is at least 1%, at least 5%, at least 10%, or at least 15% relative to either intraperitoneal or intravenous administration.

In an one hundred tenth aspect, the invention features a pharmaceutical or physiologically acceptable composition comprising, consisting essentially of, or consisting of the modulator of the one hundred fifth aspect. In preferred embodiments, said modulator is an agonist.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP11 polypeptide having the amino acid sequence of SEQ. ID. NO.:8. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In a one hundred eleventh aspect, the invention features a method of changing lipid metabolism comprising providing or administering to an individual in need of said change said pharmaceutical or physiologically acceptable composition of the one hundred tenth aspect, said needed change in lipid metabolism selected from the group consisting of:

(a) a decrease in the level of plasma triglycerides;

(b) a decrease in the level of plasma free fatty acids;

(c) a decrease in the level of plasma cholesterol;

(d) a decrease in the level of LDL-cholesterol;

(e) an increase in the level of HDL-cholesterol;

(f) a decrease in the total cholesterol/HDL-cholesterol ratio; and (g) an increase in the level of plasma adiponectin.

In preferred embodiments, a therapeutically effect amount of said pharmaceutical or physiologically acceptable composition is provided or administered to said individual.

In some preferred embodiments, said providing or administering of said pharmaceutical or physiologically acceptable composition is oral.

In other preferred embodiments, said needed change in lipid metabolism is a decrease in the postprandial increase in plasma free fatty acids due to a high fat meal or an inhibition of the progression from impaired glucose tolerance to insulin resistance.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In a one hundred twelfth aspect, the invention features a method of preventing or treating a metabolic-related disorder comprising providing or administering to an individual in need of said treatment said pharmaceutical or physiologically acceptable composition of the one hundred tenth aspect, said metabolic-related disorder selected from the group consisting of:

(a) dyslipidemia;

(b) atherosclerosis;

(c) coronary heart disease;

(d) stroke;

(e) insulin resistance; and (f) type 2 diabetes.

In preferred embodiments, a therapeutically effect amount of said pharmaceutical or physiologically acceptable composition is provided or administered to said individual.

In some preferred embodiments, said providing or administering of said pharmaceutical or physiologically acceptable composition is oral.

In other preferred embodiments, said metabolic-related disorder is selected from the group consisting of obesity, impaired glucose tolerance, atheromatous disease, hypertension, stroke, Syndrome X, and heart disease. Heart disease includes, but is not limited to, cardiac insufficiency, coronary insufficiency, and high blood pressure. In other preferred embodiments, said metabolic-related disorder is hyperlipidemia.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In an one hundred thirteenth aspect, the invention features a method of using the modulator of the one hundred fifth aspect for the preparation of a medicament for the treatment of a disorder in lipid metabolism in an individual.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP11 polypeptide having the amino acid sequence of SEQ. ID. NO.:8. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said treatment comprises oral administration of said medicament to said individual.

In preferred embodiments, said modulator is an agonist and said disorder in lipid metabolism is selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin.

In other preferred embodiments, said disorder in lipid metabolism is an elevated postprandial increase in plasma free fatty acids due to a high fat meal or a progression from impaired glucose tolerance to insulin resistance.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In a one hundred fourteenth aspect, the invention features a method of using the modulator of the one hundred fifth aspect for the preparation of a medicament for the treatment of a metabolic-related disorder in an individual.

In some preferred embodiments, said modulator is selective for the GPCR.

In some preferred embodiments, said modulator is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 1%, at least 5%, at least 10%, or at least 15% relative to intraperitoneal administration. In some embodiments, said oral bioavailability is at least 1%, at least 5%, at least 10%, at least 15%, at least 20%, at least 25%, at least 30%, at least 35%, at least 40%, or at least 45% relative to intravenous administration. In some embodiments, said oral bioavailablity is at least 1%, at least 5%, at least 10%, or at least 15% relative to intravenous administration.

In some preferred embodiments, said modulator is antilipolytic.

In some preferred embodiments, said modulator is an agonist.

In some preferred embodiments, said modulator is an agonist with an $EC_{50}$ of less than 1000 $\mu$M in GTPγS binding assay carried out with membrane from stably transfected CHO cells expressing recombinant hRUP11 polypeptide having the amino acid sequence of SEQ. ID. NO.:8. In some embodiments, said modulator is an agonist with an $EC_{50}$ of less than 900 $\mu$M in said assay. In some embodiments, said modulator is an agonist with an $EC_{50}$ of less than 800 $\mu$M in said assay. In some embodiments, said modulator is an agonist with an $EC_{50}$ of less than 700 $\mu$M in said assay. In some embodiments, said modulator is an agonist with an $EC_{50}$ of less than 600 $\mu$M in said assay. In some embodiments, said modulator is an agonist with an $EC_{50}$ of less than 550 $\mu$M in said assay. In some embodiments, said modulator is an agonist with an $EC_{50}$ of less than 500 $\mu$M in said assay. In some embodiments, said modulator is an agonist with an $EC_{50}$ of less than 450 $\mu$M in said assay. In some embodiments, said modulator is an agonist with an $EC_{50}$ of less than 400 $\mu$M in said assay. In some embodiments, said modulator is an agonist with an $EC_{50}$ of less than 350 $\mu$M in said assay. In some embodiments, said modulator is an agonist with an $EC_{50}$ of less than 300 $\mu$M in said assay. In some embodiments, said modulator is an agonist with an $EC_{50}$ of less than 250 $\mu$M in said assay. In some embodiments, said modulator is an agonist with an $EC_{50}$ of less than 200 $\mu$M in said assay. In some embodiments, said modulator is an agonist with an $EC_{50}$ of less than 150 $\mu$M in said assay. In some embodiments, said modulator is an agonist with an $EC_{50}$ of less than 100 $\mu$M in said assay. In some preferred embodiments, said modulator is an agonist with an $EC_{50}$ in said assay of less than a value selected from the interval of 600 $\mu$M to 1000 $\mu$M.

In some preferred embodiments, said treatment comprises oral administration of said medicament to said individual.

In preferred embodiments, said modulator is an agonist and said metabolic-related disorder is selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In a one hundred fifteenth aspect, the invention features a method of identifying whether a candidate compound binds to an antilipolytic GPCR, said receptor comprising the amino acid sequence of SEQ. ID. NO.:8 (hRUP11); or an allelic variant or a biologically active fragment of said amino acid sequence;

comprising the steps of:

(a) contacting the receptor with a labeled reference compound known to bind to the GPCR in the presence or absence of the candidate compound; and (b) determining whether the binding of said labeled reference compound to the receptor is inhibited in the presence of the candidate compound;

wherein said inhibition is indicative of the candidate compound binding to an antilipolytic GPCR.

In some embodiments, the antilipolytic acid GPCR comprises a biologically active fragment of said amino acid sequence.

In some embodiments, the antilipolytic GPCR is endogenous.

In some embodiments, the antilipolytic GPCR is recombinant.

In preferred embodiments, said G protein is Gi.

In some preferred embodiments, said reference compound is the modulator of the one hundred fifth aspect.

In other embodiments, said reference compound is an antibody specific for the GPCR, or a derivative thereof.

In preferred embodiments, said reference compound comprises a label selected from the group consisting of:

(a) radioisotope;

(b) enzyme; and (c) fluorophore.

In some preferred embodiments, said label is $^3H$.

In other embodiments, said method further comprises the step of comparing the level of inhibition of binding of a labeled first reference compound by the candidate compound to a second level of inhibition of binding of said labeled first reference compound by a second reference compound known to bind to the GPCR.

In a one hundred sixteenth aspect, the invention features a method of making a transgenic mouse, comprising the step of engineering said mouse to carry as part of its own genetic material the gene encoding the human antilipolytic GPCR polypeptide of SEQ. ID. NO. :8 (hRUP11).

In some preferred embodiments, expression of said gene is placed under the control of an essentially adipocyte specific promoter.

In a one hundred seventeenth aspect, the invention features the transgenic mouse according to the method of the one hundred sixteenth aspect.

In a one hundred eighteenth aspect, the invention features a method of using the transgenic mouse of the one hundred seventeenth aspect to identify whether an agonist of said human receptor has therapeutic efficacy for the treatment of a disorder of lipid metabolism selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin;

comprising the steps of:

(a') administering or not administering the agonist to the mouse; and (b') determining whether on administering the agonist there is a change selected from the group consisting of:
 (i) a decrease in the level of plasma triglycerides;
 (ii) a decrease in the level of plasma free fatty acids;
 (iii) a decrease in the level of plasma cholesterol;
 (iv) a decrease in the level of LDL-cholesterol;
 (v) an increase in the level of HDL-cholesterol;
 (vi) a decrease in the total cholesterol/HDL-cholesterol ratio; and
 (vii) an increase in the level of plasma adiponectin;

wherein said change is indicative of the agonist having therapeutic efficacy.

In a one hundred nineteenth aspect, the invention features a method of using the transgenic mouse of the one hundred seventeenth aspect to identify whether an agonist of said human receptor has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering the agonist to the mouse; and (b') determining whether on administering the agonist there is a change selected from the group consisting of:
 (i) a decrease in the level of plasma triglycerides;
 (ii) a decrease in the level of plasma free fatty acids;
 (iii) a decrease in the level of plasma cholesterol;
 (iv) a decrease in the level of LDL-cholesterol;
 (v) an increase in the level of HDL-cholesterol;
 (vi) a decrease in the total cholesterol/HDL-cholesterol ratio; and
 (vii) an increase in the level of plasma adiponectin;

wherein said change is indicative of the agonist having therapeutic efficacy.

In a one hundred twentieth aspect, the invention features a method of making a transgenic rat, comprising the step of engineering said rat to carry as part of its own genetic material the gene encoding the human antilipolytic GPCR polypeptide of SEQ. ID. NO.:8 (hRUP11).

In some preferred embodiments, expression of said gene is placed under the control of an essentially adipocyte specific promoter.

In a one hundred twenty-first aspect, the invention features the transgenic rat according to the method of the one hundred twentieth aspect.

In a one hundred twenty-second aspect, the invention features a method of using the transgenic rat of the one hundred twenty-first aspect to identify whether an agonist of said human receptor has therapeutic efficacy for the treatment of a disorder of lipid metabolism selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin;

comprising the steps of:

(a') administering or not administering the agonist to the rat; and (b') determining whether on administering the agonist there is a change selected from the group consisting of:
 (i) a decrease in the level of plasma triglycerides;
 (ii) a decrease in the level of plasma free fatty acids;
 (iii) a decrease in the level of plasma cholesterol;
 (iv) a decrease in the level of LDL-cholesterol;
 (v) an increase in the level of HDL-cholesterol;
 (vi) a decrease in the total cholesterol/HDL-cholesterol ratio; and
 (vii) an increase in the level of plasma adiponectin;

wherein said change is indicative of the agonist having therapeutic efficacy.

In a one hundred twenty-third aspect, the invention features a method of using the transgenic rat of the one hundred twenty-first aspect to identify whether an agonist of said human receptor has therapeutic efficacy for the treatment of a metabolic-related disorder selected from the group consisting of:

(a) dyslipidemia;

(b) atherosclerosis;

(c) coronary heart disease;

(d) stroke;

(e) insulin resistance; and (f) type 2 diabetes;

comprising the steps of:

(a') administering or not administering the agonist to the rat; and (b') determining whether on administering the agonist there is a change selected from the group consisting of:

(i) a decrease in the level of plasma triglycerides;

(ii) a decrease in the level of plasma free fatty acids;

(iii) a decrease in the level of plasma cholesterol;

(iv) a decrease in the level of LDL-cholesterol;

(v) an increase in the level of HDL-cholesterol;

(vi) a decrease in the total cholesterol/HDL-cholesterol ratio; and (vii) an increase in the level of plasma adiponectin;

wherein said change is indicative of the agonist having therapeutic efficacy.

In a one hundred twenty-fourth aspect, the invention features an isolated, purified or recombinant RUP11 polynucleotide selected from the group consisting of:

(a) a polynucleotide comprising a contiguous span of at least 75 nucleotides of SEQ. ID. NO.:7, or an allelic variant of said polynucleotide;

(b) a polynucleotide comprising a contiguous span of at least 150 nucleotides of SEQ. ID. NO.:7, or an allelic variant of said polynucleotide;

(c) a polynucleotide comprising a contiguous span of at least 250 nucleotides of SEQ. ID. NO.:7, or an allelic variant of said polynucleotide;

(d) a polynucleotide comprising a contiguous span of at least 350 nucleotides of SEQ. ID. NO.:7, or an allelic variant of said polynucleotide;

(e) a polynucleotide comprising a contiguous span of at least 500 nucleotides of SEQ. ID. NO.:7, or an allelic variant of said polynucleotide;

(f) a polynucleotide comprising a contiguous span of at least 750 nucleotides of SEQ. ID. NOs.:7, or an allelic variant of said polynucleotide;

(g) a polynucleotide comprising a contiguous span of at least 1000 nucleotides of SEQ. ID. NO.:7, or an allelic variant of said polynucleotide;

(h) a polynucleotide encoding a polypeptide comprising a contiguous span of at least 20 amino acids of SEQ. ID. NO.:8 or an allelic variant of said polypeptide;

(i) a polynucleotide encoding a polypeptide comprising a contiguous span of at least 30 amino acids of SEQ. ID. NO.:8, or an allelic variant of said polypeptide;

(j) a polynucleotide encoding a polypeptide comprising a contiguous span of at least 40 amino acids of SEQ. ID. NO.:8, or an allelic variant of said polypeptide;

(k) a polynucleotide encoding a polypeptide comprising a contiguous span of at least 50 amino acids of SEQ. ID. NO.:8, or an allelic variant of said polypeptide;

(l) a polynucleotide encoding a polypeptide comprising a contiguous span of at least 75 amino acids of SEQ. ID. NO.:8, or an allelic variant of said polypeptide;

(m) a polynucleotide encoding a polypeptide comprising a contiguous span of at least 100 amino acids of SEQ. ID. NO.:8, or an allelic variant of said polypeptide;

(n) a polynucleotide encoding a polypeptide comprising a contiguous span of at least 150 amino acids of SEQ. ID. NO.:8, or an allelic variant of said polypeptide;

(o) a polynucleotide encoding a polypeptide comprising a contiguous span of at least 200 amino acids of SEQ. ID. NO.:8, or an allelic variant of said polypeptide;

(p) a polynucleotide encoding a polypeptide comprising a contiguous span of at least 250 amino acids of SEQ. ID. NO.:8, or an allelic variant of said polypeptide; and (q) a polynucleotide encoding a polypeptide comprising a contiguous span of at least 300 amino acids of SEQ.ID. NO.:8, or an allelic variant of said polypeptide.

The invention also relates to an isolated, purified or recombinant RUP11 polynucleotide wherein said polynucleotide is selected from the group consisting of:

(a) a polynucleotide comprising the nucleotide sequence of SEQ. ID. NO.:7 or an allelic variant of said nucleotide sequence;

(b) the polynucleotide of SEQ. ID. NO.:7, or an allelic variant of said polynucleotide;

(c) a polynucleotide comprising a nucleotide sequence encoding a polypeptide having the amino acid sequence of SEQ. ID. NO.:8 or an allelic variant of said amino acid sequence; and (d) a polynucleotide encoding a polypeptide having the amino acid sequence of SEQ. ID. NO.:8, or an allelic variant of said polypeptide.

In preferred embodiments, said isolated, purified or recombinant polynucleotide comprises at least 8 contiguous nucleotides of a polynucleotide of the present invention. In other preferred embodiments, said isolated, purified or recombinant polynucleotide comprises at least 10, 12, 15, 18, 20, 25, 28, 30, 35, 40, 50, 75, 100, 150, 200, 300, 400, 500, 600, 700, 800, 900 or 1000 contiguous nucleotides of a polynucleotide of the present invention. Preferably said polynucleotide encodes full-length RUP11 polypeptide or a biologically active fragment thereof.

The polynucleotides of the present invention include genomic polynucleotides comprising RUP11 polynucleotides of the invention.

The present invention also relates to a polynucleotide encoding a fusion protein, wherein said fusion protein comprises an RUP11 polypeptide of the invention fused to a heterologous polypeptide. In a preferred embodiment, said polypeptide of the invention is constitutively active and said heterologous polypeptide is a G protein. In other embodiments, said heterologous polypeptide provides an antigenic epitope. In a preferred embodiment, said heterologous polypeptide provides a hemaglutinin (HA) antigenic epitope. Methods relating to a polynucleotide encoding a fusion protein are well known to those of ordinary skill in the art.

The polynucleotides of the present invention also include variant polynucleotides at least 60%, 70%, 80%, 90%, 95%, 96%, 97%, 98% or 99% identical to an RUP11 polynucleotide of the invention. In a particularly preferred embodiments, polynucleotide sequence homologies are evaluated using the Basic Local Alignment Search Tool ("BLAST"), which is well known in the art [See, e.g., Karlin and Altschul, Proc Natl Acad Sci USA (1990) 87:2264–8; Altschul et al., J Mol Biol (1990) 215:403–410; Altschul et al., Nature Genetics (1993) 3:266–72; and Altschul et al., Nucleic Acids Res (1997) 25:3389–3402; the disclosures of which are incorporated by reference in their entirety].

In further preferred embodiments, the invention features the complement of said polynucleotide.

In a one hundred twenty-fifth aspect, the invention features an isolated, purified or recombinant RUP11 polypeptide selected from the group consisting of:

(a) a polypeptide comprising a contiguous span of at least 20 amino acids of SEQ. ID. NO.:8 or an allelic variant of said contiguous span of amino acids;

(b) a polypeptide comprising a contiguous span of at least 30 amino acids of SEQ. ID. NO.:8 or an allelic variant of said contiguous span of amino acids;

(c) a polypeptide comprising a contiguous span of at least 40 amino acids of SEQ. ID. NO.:8 or an allelic variant of said contiguous span of amino acids;

(d) a polypeptide comprising a contiguous span of at least 50 amino acids of SEQ. ID. NO.:8 or an allelic variant of said contiguous span of amino acids;

(e) a polypeptide comprising a contiguous span of at least 75 amino acids of SEQ. ID. NO.:8 or an allelic variant of said contiguous span of amino acids;

(f) a polypeptide comprising a contiguous span of at least 100 amino acids of SEQ. ID. NO.:8 or an allelic variant of said contiguous span of amino acids;

(g) a polypeptide comprising a contiguous span of at least 150 amino acids of SEQ. ID. NO.:8 or an allelic variant of said contiguous span of amino acids;

(h) a polypeptide comprising a contiguous span of at least 200 amino acids of SEQ. ID. NO.:8 or an allelic variant of said contiguous span of amino acids;

(i) a polypeptide comprising a contiguous span of at least 250 amino acids of SEQ. ID. NO.:8 or an allelic variant of said contiguous span of amino acids; and (j) a polypeptide comprising a contiguous span of at least 300 amino acids of SEQ. ID. NO.:8 or an allelic variant of said contiguous span of amino acids.

The invention also relates to an isolated, purified or recombinant RUP11 polypeptide wherein said polypeptide is selected from the group consisting of:

(a) a polypeptide comprising the amino acid sequence of SEQ. ID. NO.:8 or an allelic variant or a biologically active mutant of of said amino acid sequence; and (b) the polypeptide having the amino acid sequence of SEQ. ID. NO.:8 or an allelic variant or a biologically active mutant of said amino acid sequence;

or a biologically active fragment of said polypeptide.

In preferred embodiments, said isolated, purified or recombinant polypeptide comprises at least 6 contiguous amino acids of an RUP11 polypeptide of the invention. In further embodiments, said isolated, purified or recombinant polypeptide comprises at least 10, 12, 15, 20, 25, 30, 35, 40, 50, 60, 75, 100, 125, 150, 175, 200, 225, 250, 275 or 300 contiguous amino acids of a polypeptide of the present invention. Preferably, said polypeptide is full-length RUP11 polypeptide or an active fragment thereof.

The present invention also relates to a fusion protein, wherein said fusion protein comprises an RUP11 polypeptide of the invention fused to a heterologous polypeptide. In a preferred embodiment, said polypeptide of the invention is constitutively active and said heterologous polypeptide is a G protein. In other preferred embodiments, said heterologous polypeptide provides an antigenic epitope. In particularly preferred embodiment, said heterologous polypeptide provides a hemaglutinin (HA) antigenic epitope. Methods relating to a fusion protein are well known to those of ordinary skill in the art.

The polypeptides of the present invention also include variant polypeptides at least 80%, 85%, 90%, 91%, 92%, 93%, 94%, 95%, 96%, 97%, 98% or 99% identical to an RUP11 polypeptide of the invention. In a particularly preferred embodiments, polypeptide sequence homologies are evaluated using the Basic Local Alignment Search Tool ("BLAST"), which is well known in the art [See, e.g., Karlin and Altschul, Proc Natl Acad Sci USA (1990) 87:2264–8; Altschul et al., J Mol Biol (1990) 215:403–410; Altschul et al., Nature Genetics (1993) 3:266–72; and Altschul et al., Nucleic Acids Res (1997) 25:3389–3402; the disclosures of which are incorporated by reference in their entirety].

In an one hundred twenty-sixth aspect, the invention features a composition comprising, consisting essentially of, or consisting of the RUP11 polypeptide of the one hundred twenty-fifth aspect.

In a one hundred twenty-seventh aspect, the invention features a recombinant vector, said vector comprising, consisting essentially of, or consisting of the polynucleotide of the one hundred twenty-fourth aspect. In some embodiments, said vector is a targeting vector used in a method of inactivating a gene encoding an antilipolytic GPCR of the invention. In some preferred embodiments, said vector is used in a method of transient or stable transfection. In other preferred embodiments, said vector is used in a method of transgenic expression.

In particularly preferred embodiment, said vector is an expression vector for the expression of a an antilipolytic GPCR in a recombinant host cell wherein said expression vector comprises, consists essentially of, or consists of the polynucleotide of the one hundred twenty-fourth aspect.

Although a variety of expression vectors are available to those in the art, for purposes of utilization for both the endogenous and non-endogenous human, mouse and rat GPCRs, it is most preferred that the vector utilized be pCMV. In some alternative embodiments as relates to said human, mouse and rat antilipolytic GPCRs, it is preferred that the vector utilized be an adenoviral expression vector.

In a one hundred twenty-eighth aspect, the invention features a prokaryotic or eukaryotic host cell comprising, consisting essentially of, or consisting of the recombinant vector of the one hundred twenty-seventh aspect. In some embodiments, said host cell is a eukaryotic embryonic stem cell wherein said vector of the one hundred twenty-seventh aspect has been used in a method to inactivate a gene encoding an antilipolytic GPCR of the invention within said cell. In some embodiments, said host cell is a eukaryotic embryonic somatic cell wherein said vector of the one hundred twenty-seventh aspect has been used in a method to inactivate a gene encoding an antilipolytic GPCR of the invention within said cell. In some preferred embodiments, said host cell is derived from a mouse or rat made transgenic for a human RUP11 antilipolytic GPCR of the invention. In other preferred embodiments, said host cell is prokaryotic and has been transformed using the vector of the one hundred twenty-seventh aspect. In further preferred embodiments, said host cell is eukaryotic and has been transiently transfected using the vector of the one hundred twenty-seventh aspect. In other further preferred embodiments, said host cell is eukaryotic and has been stably transfected using the vector of the one hundred twenty-seventh aspect.

In particularly preferred embodiment, said host cell expresses a recombinant antilipolytic GPCR wherein said host cell comprises, consists essentially of, or consists of the expression vector of the one hundred twenty-seventh aspect.

A further embodiment includes a prokaryotic or eukaryotic host cell recombinant for the polynucleotide of the one hundred twenty-fourth aspect.

In some embodiments the host cell is eukaryotic, more preferably, mammalian, and more preferably selected from the group consisting of 293, 293T, CHO, and COS-7 cells. In other embodiments, the host cell is eukaryotic, more preferably melanophore.

In a one hundred twenty-ninth aspect, the invention features a process for the expression of a antilipolytic GPCR in a recombinant host cell comprising the steps of:

(a) transfecting the expression vector of the one hundred twenty-seventh aspect into a suitable host cell; and (b) culturing the host cells under conditions which allow expression of the antilipolytic GPCR protein from the expression vectors.

In a one hundred thirtieth aspect, the invention features an antibody that specifically binds to the polypeptide of the one hundred twenty-fifth aspect. In some preferred embodiments, the antibody is monoclonal. In some embodiments, the antibody is polyclonal.

In a one hundred thirty-first aspect, the invention features a method of binding the polypeptide of the one hundred twenty-fifth aspect to the antibody of the one hundred thirtieth aspect, comprising contacting said antibody with said polypeptide under conditions in which said antibody can specifically bind to said polypeptide.

In a one hundred thirty-second aspect, the invention features a method of detecting an antilipolytic GPCR polypeptide in a biological sample obtained from an individual comprising the steps of:

(a) obtaining said biological sample from said individual;

(b) contacting said biological sample with the antibody of the one hundred thirtieth aspect; and (c) detecting the presence or absence of binding of said antibody to said biological sample;

wherein a detection of said binding is indicative of the receptor polypeptide being expressed in said biological sample.

In preferred embodiments, said detecting is through the use of an enzyme-labeled secondary reagent. In other preferred embodiments, said detecting is through the use of a fluorophore-labeled secondary reagent. In other preferred embodiments, said detecting is through the use of a radioisotope-labeled secondary reagent. In other embodiments, the antibody is directly labeled with enzyme, fluorophore or radioisotope.

In other preferred embodiments, said biological sample is taken from adipose, skin or blood.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In further embodiments, said individual has a disorder of lipid metabolism selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin.

In other preferred embodiments, said disorder in lipid metabolism is an elevated postprandial increase in plasma free fatty acids due to a high fat meal or a progression from impaired glucose tolerance to insulin resistance.

In further embodiments, said individual has a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodimens, said metabolic-related disorder is hyperlipidemia.

In other embodiments, said method further comprises the step of comparing the level of detection of said binding for a first individual to the level of detection of said binding for a second individual.

In a one hundred thirty-third aspect, the invention features a method of detecting expression of a gene encoding an antilipolytic GPCR in a biological sample obtained from an individual comprising the steps of:

(a) obtaining said biological sample from said individual;

(b) contacting said biological sample with the complementary polynucleotide of the one hundred twenty-fourth aspect, optionally labeled, under conditions permissive for hybridization; and (c) detecting the presence or absence of said hybridization between said complementary polynucleotide and an RNA species within said sample;

wherein a detection of said hybridization is indicative of expression of said GPCR gene in said biological sample.

In preferred embodiments, the biological sample is taken from adipose, skin or blood.

In preferred embodiments, said individual is a mammal. In more preferred embodiments, said mammal is a horse, cow, sheep, pig, cat, dog, rabbit, mouse, rat, non-human primate or human. Yet more preferred is mouse, rat or human. Most preferred is human.

In preferred embodiments, said individual has a disorder of lipid metabolism selected from the group consisting of:

(a) elevated level of plasma triglycerides;

(b) elevated level of plasma free fatty acids;

(c) elevated level of plasma cholesterol;

(d) elevated level of LDL-cholesterol;

(e) reduced level of HDL-cholesterol;

(f) elevated total cholesterol/HDL-cholesterol ratio; and (g) reduced level of plasma adiponectin.

In other preferred embodiments, said disorder in lipid metabolism is an elevated postprandial increase in plasma free fatty acids due to a high fat meal or a progression from impaired glucose tolerance to insulin resistance.

In other preferred embodiments, said individual has a metabolic-related disorder selected from the group consisting of:

(a) dyslipidemia;

(b) atherosclerosis;

(c) coronary heart disease;

(d) stroke;

(e) insulin resistance; and (f) type 2 diabetes.

In other preferred embodiments, said metabolic-related disorder is selected from the group consisting of obesity, impaired glucose tolerance, atheromatous disease, hypertension, Syndrome X, and heart disease. Heart disease includes, but is not limited to, cardiac insufficiency, coronary insufficiency, and high blood pressure. In other preferred embodiments, said metabolic-related disorder is hyperlipidemia.

In other embodiments, said method further comprises the step of comparing the level of detection of said hybridization for a first individual to the level of detection of said hybridization for a second individual.

In some preferred embodiments, said complementary polynucleotide is a primer and said hybridization is detected by detecting the presence of an amplification product comprising the sequence of said primer. In more preferred embodiments, said method is RT-PCR.

In a one hundred thirty-fourth aspect, the invention features a GPCR Fusion Protein construct comprising a constitutively active GPCR and a G protein, said receptor comprising the amino acid sequence of SEQ. ID. NO.:8 (hRUP11) or an allelic variant or a biologically active fragment of said amino acid sequence.

The invention also relates to a GPCR Fusion Protein construct wherein the methionine at amino acid position 294 of SEQ. ID. NO.:8 is substituted by lysine.

In a one hundred thirty-fifth aspect, the invention features a method of binding a known ligand of RUP11 antilipolytic GPCR to a polypeptide selected from the group consisting of:

(a) a polypeptide comprising a contiguous span of at least 6 amino acids of SEQ. ID. NO.:8;

(b) a polypeptide comprising a contiguous span of at least 10 amino acids of SEQ. ID. NO.:8;

(c) a polypeptide comprising a contiguous span of at least 15 amino acids of SEQ. ID. NO.:8;

(d) a polypeptide comprising a contiguous span of at least 20 amino acids of SEQ. ID. NO.:8;

(e) a polypeptide comprising a contiguous span of at least 25 amino acids of SEQ. ID. NO.:8;

(f) a polypeptide comprising a contiguous span of at least 30 amino acids of SEQ. ID. NO.:8;

(g) a polypeptide comprising a contiguous span of at least 35 amino acids of SEQ. ID. NO.:8;

(h) a polypeptide comprising a contiguous span of at least 40 amino acids of SEQ. ID. NO.:8;

(i) a polypeptide comprising a contiguous span of at least 45 amino acids of SEQ. ID. NO.:8; and (j) a polypeptide comprising a contiguous span of at least 50 amino acids of SEQ. ID. NO.:8; or an allelic variant of said polypeptide;

comprising the step of contacting said known ligand with said polypeptide under conditions which allow said binding to occur.

In some embodiments, said known ligand is a modulator of the GPCR. In some embodiments, said known ligand is an agonist of the GPCR. In some embodiments, said known ligand is the modulator of the one hundred fifth aspect. In some embodiments, said known ligand is an antibody specific for the GPCR, or a derivative thereof.

In other preferred embodiments, said method is used to identify whether a candidate compound inhibits said binding of said known ligand to said polypeptide, comprising the steps of:

(a) contacting said polypeptide with said known ligand, optionally labeled, in the presence or absence of said candidate compound;

(b) detecting the complex between said known ligand and said polypeptide; and (c) determining whether less of said complex is formed in the presence of the compound than in the absence of the compound;

wherein said determination is indicative of the candidate compound being an inhibitor of said binding of said known ligand to said polypeptide.

In some embodiments, said known ligand is a modulator of the GPCR. In some embodiments, said known ligand is an agonist of the GPCR. In some embodiments, said known ligand is the modulator of the one hundred fifth aspect. In some embodiments, said known ligand is an antibody specific for the GPCR, or a derivative thereof.

In other preferred embodiments, said method is used to identify whether a candidate compound is an inhibitor of said binding of said known ligand to said polypeptide, comprising the steps of:

(a) contacting said polypeptide with said known ligand, optionally labeled, in the presence separately of a plurality of concentrations of said candidate compound for a time sufficient to allow equilibration of binding;

(b) measuring unbound ligand and bound ligand; and (c) determining $K_i$ for the candidate compound;

wherein a $K_i$ value of less than 50 uM is indicative of the candidate compound being an inhibitor of said binding of said known ligand to said polypeptide. Preferably said $K_i$ value is less than 25 μM, 10 μM, 5 μM, 1 μM, 750 nM, 500 nM, 400 nM, 300 nM, 250 nM, 200 nM, 150 nM, 100 nM, 90 nM, 80 nM, 70 nM, 60 nM, 50 nM, 40 nM, 30 nM, 20 nM or 10 nM. In preferred embodiments, $K_i$ determination is made through nonlinear curve fitting with the program SCTFIT [De Lean et al. (1982) Mol Pharmacol 21:5–16; cited in Lorenzen et al. (2001) Mol Pharmacol 59:349–357, the disclosures of which are incorporated by reference herein in their entireties].

In some embodiments, said known ligand is a modulator of the GPCR. In some embodiments, said known ligand is an agonist of the GPCR. In some embodiments, said known ligand is the modulator of the one hundred fifth aspect. In some embodiments, said known ligand is an antibody specific for the GPCR, or a derivative thereof.

In a one hundred thirty-six aspect, the invention features a method of binding an optionally labeled affinity reagent specific for an antilipolytic GPCR to said receptor in a biological sample, said receptor comprising the amino acid sequence of SEQ. ID. NO.:8 (hRUP11); or an allelic variant, a biologically active mutant, or a biologically active fragment of said amino acid sequence, comprising the steps of:

(a) obtaining said biological sample;

(b) contacting the affinity reagent with said receptor in said biological sample; and (c) detecting the complex of said affinity reagent with said receptor.

In some embodiments, the antilipolytic GPCR has the amino acid sequence of SEQ. ID. NO.:8 (hRUP11); or an allelic variant, a biologically active mutant, or a biologically active fragment of said amino acid sequence.

In some embodiments, the antilipolytic GPCR comprises a biologically active fragment of said amino acid sequence.

In some embodiments, the antilipolytic GPCR is endogenous.

In some embodiments, the antilipolytic GPCR is recombinant.

In some embodiments, said biologically active mutant is CART or EFA. In preferred embodiments, said CART mutant has the amino acid sequence of SEQ. ID. NO.:8 further substituted at amino acid position 294 with lysine in place of methionine.

In preferred embodiments, said G protein is Gi.

In some embodiments, said affinity reagent is a modulator of the GPCR. In some embodiments, said affinity reagent is an agonist of the GPCR. In some embodiments, said affinity reagent is the modulator of the one hundred fifth aspect. In some embodiments, said affinity reagent is an antibody specific for the GPCR, or a derivative thereof.

In further preferred embodiments, said affinity reagent comprises a label selected from the group consisting of:

(a) radioisotope;

(b) enzyme; and (c) fluorophore.

In preferred embodiments, said radioisotope is $^3H$.

In a one hundred thirty-seventh aspect, the invention features the method of the one hundred thirty-sixth aspect further comprising the step of comparing the level of detection of said complex in a first biological sample to a second level of detection of said complex in a second biological sample.

In a one hundred thirty-eighth aspect, the invention features the method of the one hundred thirty-seventh aspect wherein the relationship between said first and second biological samples is selected from the group consisting of:

(a) said second biological sample is a replicate of said first biological sample;

(b) said first biological sample was obtained prior to an experimental intervention whereas said second biological sample was obtained after the experimental intervention, from the same individual;

(c) said second biological sample was obtained at a different time point after an experimental intervention than was said first biological sample, from the same individual;

(d) said second biological sample corresponds to a different subcellular compartment than does said first biological sample;

(e) said second biological sample represents a different cell type than does said first biological sample;

(f) said second biological sample corresponds to a different tissue than does said first biological sample;

(g) said second biological sample was obtained from a different individual than was said first biological sample;

(h) said second biological sample was obtained at a different point in time than was said first biological sample, from the same individual;

(i) said first biological samples was obtained from a normal individual, whereas said second biological sample was obtained from an individual having a metabolic-related disorder;

(j) said first biological sample was obtained from a normal individual, whereas said second biological sample was obtained from an individual having a disorder in lipid metabolism;

(k) said first biological sample was obtained before a therapeutic intervention whereas said second biological sample was obtained after the therapeutic intervention, from the same individual;

(l) said second biological sample was obtained at a different time point after therapeutic intervention than was said first biological sample, from the same individual; and (m) said first biological sample was not exposed to a compound, whereas said second biological sample was exposed to said compound.

In a one hundred thirty-ninth aspect, the invention features an isolated EFA-hRUP25 polynucleotide selected from the group consisting of:

(a) a polynucleotide comprising the nucleotide sequence of SEQ. ID. NO.:158;

(b) a polynucleotide having the nucleotide sequence of SEQ. ID. NO.:158;

(c) a polynucleotide comprising a polynucleotide encoding the polypeptide having the amino acid sequence of SEQ. ID. NO.:159 or a biologically active fragment of said polypeptide; and (d) a polynucleotide encoding the polypeptide having the amino acid sequence of SEQ. ID. NO.:159 or a biologically active fragment of said polypeptide.

In a one hundred fortieth aspect, the invention features an isolated EFA-hRUP25 polypeptide selected from the group consisting of:

(a) a polypeptide comprising the amino acid sequence of SEQ. ID. NO.:159, or a biologically active fragment of said polypeptide; and (b) a polypeptide having the amino acid sequence of SEQ. ID. NO.:159, or a biologically active fragment of said polypeptide.

In an one hundred forty-first aspect, the invention features a composition comprising, consisting essentially of, or consisting of the EFA-hRUP25 polypeptide of the one hundred fortieth aspect.

In a one hundred forty-second aspect, the invention features a recombinant vector comprising the polynucleotide of the one hundred thirty-ninth aspect. In some preferred embodiments, said vector is used in a method of transient or stable transfection.

In particularly preferred embodiment, said vector is an expression vector for the expression of an EFA-hRUP25 nicotinic acid GPCR in a recombinant host cell wherein said expression vector comprises, consists essentially of, or consists of the polynucleotide of the one hundred thirty-ninth aspect.

Although a variety of expression vectors are available to those in the art, it is most preferred that the vector utilized be pCMV. In some alternative embodiments as relates to EFA-hRUP25 nicotinic acid GPCR, it is preferred that the vector utilized be an adenoviral expression vector.

In a one hundred forty-third aspect, the invention features a prokaryotic or eukaryotic host cell comprising, consisting essentially of, or consisting of the recombinant vector of the one hundred forty-second aspect. In some embodiments, said host cell is prokaryotic and has been transformed using the vector of the one hundred forty-second aspect. In some embodiments, said host cell is eukaryotic and has been transiently transfected using the vector of the one hundred forty-second aspect. In some preferred embodiments, said host cell is eukaryotic and has been stably transfected using the vector of the one hundred forty-second aspect.

In particularly preferred embodiment, said host cell expresses a recombinant EFA-hRUP25 nicotinic acid GPCR wherein said host cell comprises, consists essentially of, or consists of the expression vector of the one hundred forty-second aspect.

A further embodiment includes a prokaryotic or eukaryotic host cell recombinant for the polynucleotide of the one hundred thirty-ninth aspect.

In some embodiments the host cell is eukaryotic, more preferably, mammalian, and more preferably selected from the group consisting of 293, 293T, CHO, and COS-7 cells. In other embodiments; the Host Cell is eukaryotic, more preferably melanophore.

In a one hundred forty-fourth aspect, the invention features a process for the expression of an EFA-hRUP25 nicotinic acid GPCR in a recombinant host cell comprising the steps of:

(a) transfecting the expression vector of the one hundred forty-second aspect into a suitable host cell; and (b) culturing the host cells under conditions which allow expression of the EFA-hRUP25 nicotinic acid GPCR protein from the expression vectors.

In a one hundred forty-fifth aspect, the invention features a method of making an EFA mutant of an endogenous GPCR polypeptide having constitutive activity, comprising the steps of:

(a) introducing 1, 2, 3, 4, or 5 substitutions, insertions, or deletions into the amino acid sequence of the endogenous GPCR polypeptide;

(b) measuring the activity of the mutant GPCR of (a) in the absence of agonist and in the presence of a known agonist;

(c) measuring the activity of the endogenous GPCR in the absence of agonist and in the presence of said known agonist; and (d) comparing (b) and (c);

wherein a determination that the agonist screening window of (b) is at least 20% greater than that of (c) identifies the mutant resulting from (a) to be an EFA mutant of the endogenous GPCR.

In some embodiments, said number of substitutions, insertions, or deletions is 1.

In some embodiments, said number of substitutions, insertions, or deletions is 1 or 2.

In some embodiments, said number of substitutions, insertions, or deletions is 1, 2 or 3.

In some embodiments, said number of substitutions, insertions, or deletions is 1, 2, 3 or 4.

In more preferred embodiments, said number of substitutions, insertions, or deletions is 1, 2, 3, 4 or 5.

Applicant reserves the right to exclude any one or more candidate compounds from any of the embodiments of the invention. Applicant also reserves the right to exclude any one or more modulators from any of the embodiments of the invention, including but not limited to nicotinic acid or any analog or derivative thereof. Applicant further reserves the right to exclude any polynucleotide or polypeptide from any of the embodiments of the invention. Applicant additionally reserves the right to exclude any metabolic-related disorder or any disorder of lipid metabolism from any of the embodiments of the invention.

Throughout this application, various publications, patents and published patent applications are cited. The disclosures of these publications, patents and published patent applications referenced in this application are hereby incorporated by reference in their entirety into the present disclosure. Citation herein by Applicant of a publication, patent, or published patent application is not an admission by Applicant of said publication, patent, or published patent application as prior art.

Modifications and extension of the disclosed inventions that are within the purview of the skilled artisan are encompassed within the above disclosure and the claims that follow.

BRIEF DESCRIPTION OF THE DRAWINGS

FIG. 1 depicts second messenger $IP_3$ production from endogenous version hRUP12 ("hRUP12") as compared with the control ("CMV").

FIG. 2 depicts the results of a second messenger cell-based cyclic AMP assay providing comparative results for constitutive signaling of endogenous hRUP13 ("hRUP13") and a control vector ("CMV").

FIG. 3 depicts the signal measured comparing CMV, endogenous hRUP13 ("hRUP13 wt") and non-endogenous, constitutively activated hRUP13 ("hRUP13 (A268K)"), utilizing 8×CRE-Luc reporter plasmid.

FIG. 4 depicts the results of a [$^{35}$S]GTPγS assay providing comparative results for constitutive signaling by hRUP13:Gs Fusion Protein ("hRUP13-Gs") and a control vector ("CMV").

FIG. 5 depicts the signal measured comparing CMV, endogenous hRUP14 ("hRUP14 wt") and non-endogenous, constitutively activated hRUP13 ("hRUP14 (L246K"), utilizing 8×CRE-Luc reporter plasmid.

FIG. 6 depicts the signal measured comparing CMV, endogenous hRUP15 ("hRUP15 wt") and non-endogenous, constitutively activated hRUP15 ("hRUP15 (A398K"), utilizing 8×CRE-Luc reporter plasmid.

FIG. 7 depicts the results of a second messenger cell-based cyclic AMP assay providing comparative results for constitutive signaling of endogenous hRUP15 ("hRUP15 wt"), non-endogenous, constitutively activated version of hRUP15 ("hRUP15(A398K)") and a control vector ("CMV").

FIG. 8 depicts the results of a [$^{35}$S]GTPγS assay providing comparative results for constitutive signaling by hRUP15:Gs Fusion Protein ("hRUP15-Gs") and a control vector ("CMV").

FIG. 9 depicts second messenger $IP_3$ production from endogenous version hRUP17 ("hRUP17") as compared with the control ("CMV").

FIG. 10 depicts messenger $IP_3$ production from endogenous version hRUP21 ("hRUP21") as compared with the control ("CMV").

FIG. 11 depicts the signal measured comparing CMV, endogenous hRUP23 ("hRUP23 wt") and non-endogenous, constitutively activated hRUP23 ("hRUP23 (W275K)"), utilizing 8×CRE-Luc reporter plasmid.

FIG. 12 depicts results from a primary screen of several candidate compounds against hRUP13; results for "Compound A" are provided in well A2 and "Compound "B" are provided in well G9.

FIGS. 13A and 13B are histograms representing relative expression levels of hRUP25 (FIG. 13A) and hRUP38 (FIG. 13B) detected in different human tissues via DNA microarray. The horizontal axis displays the different tissues, identified in vertical text above the bar. The vertical axis indicates level of expression of either hRUP25 (FIG. 13A) or hRUP38 (FIG. 13B). In FIG. 13A and FIG. 13B, note the high level of expression in primary adipocytes of hRUP25 and hRUP38, respectively (the signal toward the left of each of the histograms corresponding to primary adipocytes is identified by a vertical arrow above the bar, for ease of reference).

FIG. 13C is a photograph of an ethidium bromide stained gel illustrating the relative expression of hRUP25 and hRUP38 as detected by RT-PCR using cDNA derived from a number of human tissues as template. Note the controls of the far right three lanes.

FIGS. 14A–C. FIGS. 14A, 14B and 14C depict melanophores transfected with DNA plasmids expressing hRUP25 (FIG. 14A), hRUP38 (FIG. 14B) and hRUP19 (FIG. 14C) without treatment. These cells are pigment-aggregated because hRUP25 (FIG. 14A), hRUP38 (FIG. 14B) and hRUP19 (FIG. 14C) are Gi-coupled receptors having a high basal level of activity, and therefore driving the aggregation to a measurable level in the absence of a ligand. hRUP11 is also a Gi-coupled receptor having a high basal level of activity (not shown).

FIGS. 15A and 15B illustrate the dose-dependant, nicotinic acid induced aggregation response of melanophores transfected with increasing amounts of plasmid DNA encoding hRUP25 (FIG. 15A). Cells transfected with 10 $\mu$g of plasmid DNA encoding hRUP25, respond to nicotinic acid with an $EC_{50}$ of about 54 nM.

As negative controls, FIG. 15B depicts melanophores transfected with either salmon sperm DNA (Mock) or plasmid DNA encoding the $\alpha_{2A}$AR. As is evident there is no aggregation response in these cells upon nicotinic acid treatment at doses up to 10 $\mu$M.

FIG. 16 illustrates the nicotinic acid induced-inositol phosphates (IPs) accumulation in HEK293 cells co-expressing hRUP25 and the chimeric G$\alpha$q-subunit in which the last five amino acids have been replaced with the corresponding amino acids of G$\alpha$i (Gq$\Delta$Gi). This construct has been shown to convert the signaling of a Gi-coupled receptor to the Gq pathway (i.e. accumulation of inositol phosphates) in response to receptor activation. Cells transfected with Gq$\Delta$Gi plus either empty plasmid or the constitutively activated $\alpha_{2A}$AR ($\alpha_{2A}$K) are non-responsive to nicotinic acid and served as controls for the IP assay. Cells transfected with Gq$\Delta$Gi plus either hRUP19 or hRUP38 are also unresponsive to nicotinic acid, indicating that nicotinic acid is not an agonist for either hRUP19 or hRUP38.

FIG. 17 shows the results from saturation binding of [$^3$H]nicotinic acid to membranes from cells expressing either hRUP25, hRUP38, hRUP19 or vector alone [CHO(—)]. Note that only hRUP25 binds nicotinic acid in a specific and high-affinity manner.

FIG. 18A is a set of immunofluorescent photomicrographs illustrating the expression of hemaglutinin (HA)-tagged hRUP25 in a stably transfected line of CHO cells (top; clone #46). No significant labeling is detected in mock stably-transfected CHO cells (Mock). The lower panels identify the nuclear (DAPI) staining of cells in the same field.

FIG. 18B illustrates nicotinic acid and (−)-nicotine induced-inhibition of forskolin stimulated cAMP accumulation in hRUP25-CHO cell stable line #46 (described in preceding paragraph). The $EC_{50}$ for nicotinic acid is 23.6 nM and that for (−)-nicotine is 9.8 $\mu$M.

FIG. 19 indicates that, in response to nicotinic acid, both hRUP25 and the mouse ortholog mRUP25 can inhibit TSHR stimulated cAMP production (in the presence and absence of TSH).

FIG. 20 shows the saturation binding curves of [$^3$H]nicotinic acid ([$^3$H]NA) to membranes prepared from HEK293 cells transiently expressing either hRUP25 or mRUP25. Note the significant binding of [$^3$H]NA relative to either that found in membranes derived from mock transfected cells or in the presence of an excess of non-labeled nicotinic acid (200 $\mu$M).

FIG. 21. FIG. 21 is a table comparing the rank order of potency of various compounds on hRUP25 and the pharmacologically defined nicotinic acid receptor. The potencies at hRUP25 derived both by a functional analysis measuring the inhibition of forskolin induced cAMP production and competitive radioligand binding assays, closely match the order of potencies of the pharmacologically defined nicotinic acid receptor.

FIG. 22A depicts nicotinic acid and related compounds inhibiting isoproterenol induced lipolysis in rat epididymal fat derived adipocytes at a concentration of 10 $\mu$M. P-3-T represents 3-tetrazole-5-pyridine.

FIG. 22B illustrates a nicotinic acid dose-dependent inhibition of isoproterenol induced-lipolysis in rat epididymal fat derived adipocytes. Note the rightward shift in the dose-response curves with increasing concentrations of nicotinic acid.

FIG. 23 illustrates the ability of both nicotinic acid and the related compound P-3-T (3-tetrazole-5-pyridine) to inhibit isoproterenol induced lipolysis in adipocyte primary cultures derived from human subcutaneous fat in a dose-dependant manner. The $EC_{50}$ value for nicotinic acid and P-3-T were 716 nM and 218 nM respectively.

FIG. 24. FIG. 24 presents screening data via adenylyl cyclase assay for hRUP38. Note that nicotinic acid does not activate inhibition of forskolin stimulated cAMP in hRUP38-expressing CHO cells whereas 1-Isopropyl-1H-benzotriazole-5-carboxylic acid does. 1-Isopropyl-1H-benzotriazole-5-carboxylic acid has no effect on CHO cells expressing either hRUP25 or hRUP19. The $EC_{50}$ for nicotinic acid is 25.8 nM and that for 1-Isopropyl-1H-benzotriazole-5-carboxylic acid is 166 nM. NT indicates not tested. (Also see the legend to FIG. 18A above for details directed to stable CHO transfectants.) Also see Example 30, infra.

FIG. 25 illustrates the ability of 1-Isopropyl-1H-benzotriazole-5-carboxylic acid to inhibit isoproterenol stimulated lipolysis in adipocyte primary cultures derived from human subcutaneous fat in a dose-dependant manner comparable to that of nicotinic acid.

FIG. 26. FIG. 26 presents screening data via adenylyl cyclase assay for hRUP38. The horizontal axis indicates the concentration of 3-(5-Bromo-2-ethoxy-phenyl)-acrylic acid. The vertical axis indicates "% inhibition of cAMP". Note that a value of 100% on the vertical axis corresponds to the cAMP level of forskolin stimulated cells in the absence of 3-(5-Bromo-2-ethoxy-phenyl)-acrylic acid, whereas a value of 200% on the vertical axis corresponds to the cAMP level of unstimulated cells in the absence of 3-(5-Bromo-2-ethoxy-phenyl)-acrylic acid. Note that 3-(5-Bromo-2-ethoxy-phenyl)-acrylic acid activates inhibition of forskolin stimulated cAMP in hRUP38-expressing CHO cells but has no effect on CHO cells expressing either hRUP25 or hRUP19. The $EC_{50}$ for 3-(5-Bromo-2-ethoxy-phenyl)-acrylic acid is 1.17 $\mu$M. (Also see the legend to FIG. 18A above for details directed to stable CHO transfectants.)

FIG. 27 presents an RT-PCR analysis of hRUP19 expression using a panel of human tissues. The analysis indicates that hRUP19 is selectively expressed in fat cells. Low expression is also evident in testis, placenta, kidney and spleen.

FIG. 28 presents a Northern blot analysis of hRUP19 expression using a panel of human tissues. The analysis indicates that hRUP19 is strongly expressed in mammary gland, probably due to fat cell-specific expression of hRUP19. Ad, adrenal gland; Bl, bladder, BM, bone marrow; Br, brain (whole); LN, lymph node; MG, mammary gland; Pr, prostate; Sp, spinal cord; St, stomach; Thyr, thyroid; Trch, trachea; Ut, uterus.

FIG. 29 presents an analysis of RUP19 expression as a function of adipocyte differentiation. RT-PCR and Northern blot analysis of mRUP19 expression by mouse 3T3 pre-adipocytes and differentiated 3T3 adipocytes was carried out. The analysis indicates that RUP19 expression is induced during adipocyte differentiation. Pre-diff 3T3-L1, mouse 3T3 pre-adipocytes; Post-diff 3T3-L1, differentiated 3T3 adipocytes; β-TC-6, a mouse insulin-producing cell line; NIT-1, a mouse insulin-producing cell line.

FIG. 30 presents a CART analysis of signal transduction by hRUP19. The analysis indicates that CART-activated hRUP19 inhibits cAMP production in membranes of transfected 293 cells.

FIG. 31 presents screening data via adenylyl cyclase assay for hRUP25. The horizontal axis indicates the concentration of (5-hydroxy-1-methyl-3-propyl-1H-pyrazol-4-yl)-pyridin-3-yl-methanone. The vertical axis indicates "% inhibition of cAMP". Note that a value of 100% on the vertical axis corresponds to the cAMP level of forskolin stimulated cells in the absence of (5-hydroxy-1-methyl-3-propyl-1H-pyrazol-4-yl)-pyridin-3-yl-methanone, whereas a value of 200% on the vertical axis corresponds to the cAMP level of unstimulated cells in the absence of (5-hydroxy-1-methyl-3-propyl-1H-pyrazol-4-yl)-pyridin-3-yl-methanone. Note that (5-hydroxy-1-methyl -3-propyl-1H-pyrazol-4-yl)-pyridin-3-yl-methanone activates inhibition of forskolin stimulated cAMP in hRUP25-expressing CHO cells and has an $EC_{50}$ of 352 nM. (5-Hydroxy-1-methyl-3-propyl-1H-pyrazol-4-yl)-pyridin-3-yl-methanone has no activity on hRUP38-expressing CHO cells up to a concentration of at least 100 μM (not shown). Also see Example 29, infra.

FIG. 32 presents a time-course analysis of plasma free fatty acids (FFA) concentration in rats administered either vehicle or niacin [NA] at 15 mg/kg, 30 mg/kg, or 45 mg/kg. Also see Example 31, infra.

FIG. 33 presents an analysis of the agonist screening window for EFA-hRUP25 GPCR polypeptide of SEQ. ID. NO.:159 ["hRUP25-S91"] relative to that for endogenous hRUP25 GPCR polypeptide of SEQ. ID. NO.:36 ["hRUP25 wt"]. Samples were set up in triplicate. HEK293 cells were transfected with pCMV vector alone ["CMV"], with TSHR alone ["CMV+TSHR"], or were co-transfected with TSHR and either a2AK (a constitutively activated lysine mutant of alpha2A adrenergic receptor) ["a2AK"] or endogenous hRUP25 ["hRUP25 wt"] or EFA-hRUP25 ["hRUP25-S91"]. Niacin ["Ni"] was taken as a known agonist of hRUP25. UK14,304 ["UK"] was taken as a known agonist of a2AK, a positive control for the assay. The level of intracellular cAMP was determined for each sample. Also see Example 32, infra, for more details.

DETAILED DESCRIPTION

Definitions

Figure 1:
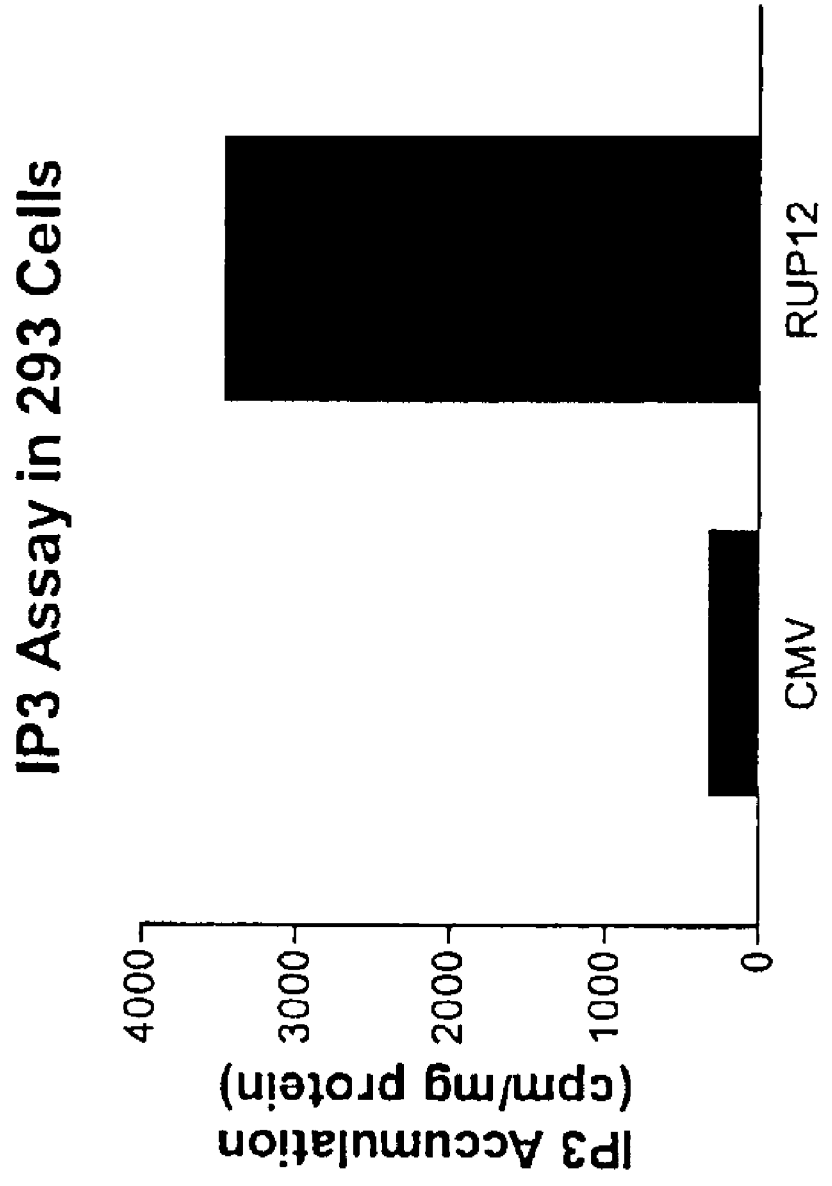
FIG. 1.

The scientific literature that has evolved around receptors has adopted a number of terms to refer to ligands having various effects on receptors. For clarity and consistency, the following definitions will be used throughout this patent document. To the extent that these definitions conflict with other definitions for these terms, the following definitions shall control:

ADIPONECTIN. ADIPONECTIN is a plasma protein secreted by adipocytes and comprised of an N-terminally disposed collagen-like region and a C-terminal globular region. Reduced levels of plasma ADIPONECTIN have been associated with a number of metabolic-related disorders, including atherosclerosis, coronary heart disease, stroke, insulin resistance and type 2 diabetes. The serum ADIPONECTIN level for women has been reported to be higher than that for men, for example 13.5 μg $ml^{-1}$ versus 7.2 μg $ml^{-1}$ in one study [Yamamoto Y et al., Clin Sci (Lond) (2002) 103:137–42; the disclosure of which is hereby incorporated by reference in its entirety].

AFFINITY REAGENTS shall mean compounds that specifically and measurably bind to a target molecule. Preferably the target molecule is a GPCR.

AGONISTS shall mean materials (e.g., ligands, candidate compounds) that activate an intracellular response when they bind to the receptor. In some embodiments, AGONISTS are those materials not previously known to activate the intracellular response when they bind to the receptor (e.g. to enhance GTPγS binding to membranes or to lower intracellular cAMP level). In some embodiments, AGONISTS are those materials not previously known to inhibit lipolysis when they bind to the receptor.

ALLELIC VARIANT. See VARIANT.

ALLOSTERIC MODULATORS shall mean materials (e.g., ligands, candidate compounds) that affect the functional activity of the receptor but which do not inhibit the endogenous ligand from binding to the receptor. Allosteric modulators include inverse agonists, partial agonists and agonists.

AMINO ACID ABBREVIATIONS used herein are set out in Table A:

TABLE A

| | | |
|---|---|---|
| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

ANTAGONISTS shall mean materials (e.g., ligands, candidate compounds) that competitively bind to the receptor at the same site as the agonists but which do not activate an intracellular response, and can thereby inhibit the intracellular responses elicited by agonists. ANTAGONISTS do not diminish the baseline intracellular response in the absence of an agonist. In some embodiments, ANTAGONISTS are those materials not previously known to compete with an agonist to inhibit the cellular response when they bind to the receptor, e.g. wherein the cellular response is GTPγS binding to membranes or to the lowering of intracellular cAMP level.

ANTIBODIES are intended herein to encompass monoclonal antibodies and polyclonal antibodies. ANTIBODIES are further intended to encompass IgG, IgA, IgD, IgE, and IgM. ANTIBODIES include whole antibodies, including single-chain whole antibodies, and antigen binding fragments thereof, including Fab, Fab', F(ab)2 and F(ab')2. ANTIBODIES may be from any animal origin. Preferably, ANTIBODIES are human, murine, rabbit, goat, guinea pig, hamster, camel, donkey, sheep, horse or chicken. Preferably ANTIBODIES have binding affinities with a dissociation constant or Kd value less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{31}$ $^{10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M and $10^{-15}$M. ANTIBODIES of the present invention may be prepared by any suitable method known in the art.

ATHEROSCLEROSIS is intended herein to encompass disorders of large and medium-sized arteries that result in the progressive accumulation within the intima of smooth muscle cells and lipids. Atherosclerosis is the primary cause of heart disease and stroke.

BIOLOGICALLY ACTIVE FRAGMENT is interchangeable herein with ACTIVE FRAGMENT and shall mean a fragment of full-length polypeptide or full-length amino acid sequence retaining part or all of the functionality of said full-length polypeptide or full-length amino acid sequence. In particular embodiment, a GPCR comprising an active fragment of a full-length GPCR polypeptide or full-length GPCR amino acid sequence retains part or all of the functionality of said GPCR comprising said full-length polypeptide or said full-length amino acid sequence. Said GPCR functionality is understood to include but not intended to be limited to ligand binding, G protein coupling, and ligand-facilitated coupling to G protein. By way of illustration and not limitation, BIOLOGICALLY ACTIVE FRAGMENT is intended herein to encompass full-length GPCR polypeptide absent the N-terminal methionine.

3-(5-BROMO-2-ETHOXY-PHENYL)-ACRYLIC ACID shall be understood herein to have the formula:

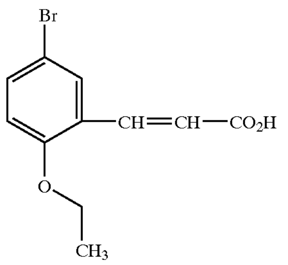

and to encompass the E isomer, the Z isomer, and mixtures of E and Z isomers.

CANDIDATE COMPOUND shall mean a molecule (for example, and not limitation, a chemical compound) that is amenable to a screening technique. Preferably, the phrase "candidate compound" does not include compounds which were publicly known to be compounds selected from the group consisting of inverse agonist, agonist or antagonist to a receptor, as previously determined by an indirect identification process ("indirectly identified compound"); more preferably, not including an indirectly identified compound which has previously been determined to have therapeutic efficacy in at least one mammal; and, most preferably, not including an indirectly identified compound which has previously been determined to have therapeutic utility in humans.

CHOLESTEROL. Generally, the total cholesterol/HDL-cholesterol (i.e., TC/HDL) ratio represents a useful predictor as to the risk of an individual in developing a more serious condition, such as an HDL-related condition, such as but not limited to atherosclerosis and complications therefrom. The classification of plasma lipid levels is shown in Chart A:

CHART A

| CLASSIFICATION OF PLASMA LIPID LEVELS | | |
|---|---|---|
| TOTAL CHOLESTEROL | <200 mg/dl | Desirable |
| | 200–239 mg/dl | Borderline High |
| | >240 mg/dl | High |
| HDL-CHOLESTEROL | <40 mg/dl | Low (Men) |
| | <50 mg/dl | Low (Women) |
| | >60 mg/dl | High |

From: 2001 National Cholesterol Education Program Guidelines

Accordingly, the recommended total cholesterol/HDL-C (i.e., TC/HDL) ratio indicates that a ratio of less than or equal to 3.5 is ideal and a ratio of greater than 4.5 is considered an increased "at risk." The value of determining the TC/HDL ratio is clearly evident in the circumstance where an individual presents with "normal" LDL and total cholesterol but possesses low HDL-cholesterol. Based on LDL and total cholesterol the individual may not qualify for treatment however, factor in the HDL-cholesterol level then a more accurate risk assessment may be obtained. Thus, if the individual's level of HDL-cholesterol is such that the ratio is greater than 4.5 then therapeutic or preventive intervention may be warranted. A physician or care provider may determine the need of prevention or treatment based on a TC/HDL ratio; for example, a TC/HDL ratio of 2.5 or greater, 3.0 or greater, 3.5 or greater, 4.0 or greater, 4.5 or greater, 5.0 or greater, or a TC/HDL ratio of 5.5 or greater.

CODON shall mean a grouping of three nucleotides (or equivalents to nucleotides) which generally comprise a nucleoside [adenosine (A), guanosine (G), cytidine (C), uridine (U) and thymidine (T)] coupled to a phosphate group and which, when translated, encodes an amino acid.

COMPOSITION means a material comprising at least one component; a "pharmaceutical composition" is an example of a composition.

COMPOUND EFFICACY shall mean a measurement of the ability of a compound to inhibit or stimulate receptor functionality; i.e. the ability to activate/inhibit a signal transduction pathway, in contrast to receptor binding affinity. Exemplary means of detecting compound efficacy are disclosed in the Example section of this patent document.

COMPRISING, CONSISTING ESSENTIALLY OF, and CONSISTING OF are defined herein according to their standard meaning. A defined meaning set forth in the M.P.E.P. controls over a defined meaning in the art and a defined meaning set forth in controlling Federal Circuit case law controls over a meaning set forth in the M.P.E.P.

CONSTITUTIVELY ACTIVE RECEPTOR shall mean a receptor stabilized in an active state by means other than through binding of the receptor to its ligand or a chemical equivalent thereof. A CONSTITUTIVELY ACTIVE RECEPTOR may be endogenous or non-endogenous.

CONSTITUTIVELY ACTIVATED RECEPTOR shall mean an endogenous receptor that has been modified so as to be constitutively active. CART is an acronym for Constitutively Activated Receptor Technology and when used herein prefixing or suffixing a GPCR, shall be understood to identify said prefixed or suffixed GPCR as a CONSTIFUTIVELY ACTIVATED RECEPTOR.

CONSTITUTIVE RECEPTOR ACTIVATION shall mean activation of a receptor in the absence of binding to its ligand or a chemical equivalent thereof.

CONTACT or CONTACTING shall mean bringing at least two moieties together, whether in an in vitro system or an in vivo system.

CORONARY HEART DISEASE is intended herein to encompass disorders comprising a narrowing of the small blood vessels that supply blood and oxygen to the heart. CORONARY HEART DISEASE usually results from the build up of fatty material and plaque. As the coronary arteries narrow, the flow of blood to the heart can slow or stop. CORONARY HEART DISEASE can cause chest pain (stable angina), shortness of breath, heart attack, or other symptoms. CORONARY HEART DISEASE is intended herein to include coronary artery disease, the most common type of heart disease. Coronary artery disease results from atherosclerosis.

DECREASE is used to refer to a reduction in a measurable quantity and is used synonymously with the terms "reduce", "diminish", "lower", and "lessen".

DIABETES as used herein is intended to encompass the usual diagnosis of DIABETES made from any of the methods including, but not limited to, the following list: symptoms of diabetes (e.g., polyuria, polydipsia, polyphagia) plus casual plasma glucose levels of greater than or equal to 200 mg/dl, wherein casual plasma glucose is defined any time of the day regardless of the timing of meal or drink consumption; 8 hour fasting plasma glucose levels of less than or equal to 126 mg/dl; and plasma glucose levels of greater than or equal to 200 mg/dl 2 hours following oral administration of 75 g anhydrous glucose dissolved in water.

DIRECTLY IDENTIFYING or DIRECTLY IDENTIFIED, in relationship to the phrase "candidate compound", shall mean the screening of a candidate compound against a constitutively activated receptor, preferably a constitutively activated orphan receptor, and most preferably against a constitutively activated G protein-coupled cell surface orphan receptor, and assessing the compound efficacy of such compound. This phrase is, under no circumstances, to be interpreted or understood to be encompassed by or to encompass the phrase "indirectly identifying" or "indirectly identified."

DISORDERS OF LIPID METABOLISM are intended herein to include, but not be limited to, dyslipidemia.

DYSLIPIDEMIA is intended herein to encompass disorders comprising any one of elevated level of plasma free fatty acids, elevated level of plasma cholesterol, elevated level of LDL-cholesterol, reduced level of HDL-cholesterol, elevated ratio of total cholesterol to HDL-cholesterol, and elevated level of plasma triglycerides.

EFA-GPCR shall mean a mutant GPCR polypeptide that consists of 1, 2, 3, 4, or 5 amino acid substitutions, deletions, or insertions relative to the amino acid sequence of an endogenous GPCR polypeptide having constitutive activity, wherein the agonist screening window of the mutant GPCR is expanded by greater than 20%, greater than 25%, greater than 30%, greater than 31%, greater than 32%, greater than 33%, greater than 34%, greater than 35%, greater than 36%, greater than 37%, greater than 38%, greater than 39%, or greater than 40% relative to that of said endogenous GPCR.

ENDOGENOUS shall mean a material that a mammal naturally produces. ENDOGENOUS in reference to, for example and not limitation, the term "receptor," shall mean that which is naturally produced by a mammal (for example, and not limitation, a human) or a virus. ENDOGENOUS shall be understood to encompass allelic variants of a gene as well as the allelic polypeptide variants so encoded. By contrast, the term NON-ENDOGENOUS in this context shall mean that which is not naturally produced by a mammal (for example, and not limitation, a human) or a virus. For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not limitation, in a screening approach, the endogenous or non-endogenous receptor may be in reference to an in vitro screening system. As a further example and not limitation, where the genome of a mammal has been manipulated to include a non-endogenous constitutively activated receptor, screening of a candidate compound by means of an in vivo system is viable.

EXPRESSION VECTOR is defined herein as a DNA sequence that is required for the transcription of cloned DNA and the translation of the transcribed mRNAs in an appropriate host cell recombinant for said EXPRESSION VECTOR. An appropriately constructed EXPRESSION VECTOR should contain an origin of replication for autonomous replication in host cells, selectable markers, a limited number of useful restriction enzyme sites, a potential for high copy number, and active promoters. By way of illustration and not limitation, pCMV is an expression vector.

G PROTEIN COUPLED RECEPTOR FUSION PROTEIN and GPCR FUSION PROTEIN, in the context of the invention disclosed herein, each mean a non-endogenous protein comprising an endogenous, constitutively activate GPCR or a non-endogenous, constitutively activated GPCR fused to at least one G protein, most preferably the alpha (α) subunit of such G protein (this being the subunit that binds GTP), with the G protein preferably being of the same type as the G protein that naturally couples with endogenous orphan GPCR. For example, and not limitation, in an endogenous state, if the G protein "$G_s\alpha$" is the predominate G protein that couples with the GPCR, a GPCR Fusion Protein based upon the specific GPCR would be a non-endogenous protein comprising the GPCR fused to $G_s\alpha$; in some circumstances, as will be set forth below, a non-predominant G protein can be fused to the GPCR. The G protein can be fused directly to the C-terminus of the constitutively active GPCR or there may be spacers between the two.

HOST CELL shall mean a cell capable of having a Plasmid and/or Vector incorporated therein. In the case of a prokaryotic Host Cell, a Plasmid is typically replicated as a autonomous molecule as the Host Cell replicates (generally, the Plasmid is thereafter isolated for introduction into a eukaryotic Host Cell); in the case of a eukaryotic Host Cell, a Plasmid may be integrated into the cellular DNA of the Host Cell such that when the eukaryotic Host Cell replicates, the Plasmid replicates. In some embodiments the Host Cell is eukaryotic, more preferably, mammalian, and more preferably selected from the group consisting of 293, 293T, CHO, and COS-7 cells. In other embodiments, the Host Cell is eukaryotic, more preferably melanophore.

(5-HYDROXY-1-METHYL-3-PROPYL-1H-PYRAZOL-4-YL)-PYRIDIN-3-YL-METHANONE shall be understood herein to have the formula:

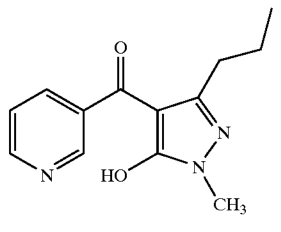

IN NEED OF PREVENTION OR TREATMENT as used herein refers to a judgement made by a caregiver (e.g. physician, nurse, nurse practitioner, etc. in the case of humans; veterinarian in the case of animals, including non-human mammals) that an individual or animal requires or will benefit from treatment. This judgement is made based on a variety of factors that are in the realm of a caregiver's expertise, but that include the knowledge that the individual or animal is ill, or will be ill, as the result of a condition that is treatable by the compounds of the invention.

INDIRECTLY IDENTIFYING or INDIRECTLY IDENTIFIED means the traditional approach to the drug discovery process involving identification of an endogenous ligand specific for an endogenous receptor, screening of candidate compounds against the receptor for determination of those which interfere and/or compete with the ligand-receptor interaction, and assessing the efficacy of the compound for affecting at least one second messenger pathway associated with the activated receptor.

INDIVIDUAL as used herein refers to any animal, including mammals, preferably mice, rats, other rodents, rabbits, dogs, cats, swine, cattle, sheep, horses, or primates, and most preferably humans.

INHIBIT or INHIBITING, in relationship to the term "response" shall mean that a response is decreased or prevented in the presence of a compound as opposed to in the absence of the compound.

INSULIN RESISTANCE as used herein is intended to encompass the usual diagnosis of insulin resistance made by any of a number of methods, including but not restricted to: the intravenous glucose tolerance test or measurement of the fasting insulin level. It is well known that there is an excellent correlation between the height of the fasting insulin level and the degree of insulin resistance. Therefore, one could use elevated fasting insulin levels as a surrogate marker for insulin resistance for the purpose of identifying which normal glucose tolerance (NGT) individuals have insulin resistance. A diagnosis of insulin resistance can also be made using the euglycemic glucose clamp test.

INVERSE AGONISTS shall mean materials (e.g., ligand, candidate compound) that bind either to the endogenous form or to the constitutively activated form of the receptor so as to reduce the baseline intracellular response of the receptor observed in the absence of agonists.

ISOLATED shall mean that the material is removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such a polynucleotide could be part of a vector and/or such a polynucleotide or polypeptide could be part of a composition, and still be isolated in that the vector or composition is not part of its natural environment.

1-ISOPROPYL-1H-BENZOTRIAZOLE-5-CARBOXYLIC ACID shall be understood herein to have the formula:

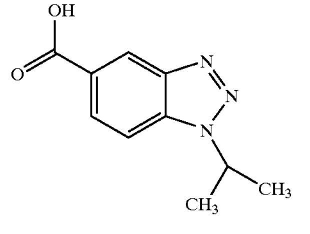

KNOCKOUT MOUSE/RAT is intended herein to encompass a mouse or rat that has been manipulated by recombinant means such that a single gene of choice has been inactivated or "knocked-out" in a manner that leaves all other genes unaffected.

KNOWN RECEPTOR shall mean an endogenous receptor for which the endogenous ligand specific for that receptor has been identified.

LIGAND shall mean a molecule specific for a naturally occurring receptor.

METABOLIC-RELATED DISORDERS are intended herein to include, but not be limited to, dyslipidemia, atherosclerosis, coronary heart disease, stroke, insulin resistance and type 2 diabetes.

As used herein, the terms MODULATE or MODIFY are meant to refer to an increase or decrease in the amount, quality, or effect of a particular activity, function or molecule.

MUTANT or MUTATION in reference to an endogenous receptor's nucleic acid and/or aminacicid sequence shall mean a specified change or changes to such endogenous sequences such that a mutated form of an endogenous non-constitutively activated receptor evidences constitutive activation of the receptor. In terms of equivalents to specific sequences, a subsequent mutated form of a human receptor is considered to be equivalent to a first mutation of the human receptor if (a) the level of constitutive activation of the subsequent mutated form of a human receptor is substantially the same as that evidenced by the first mutation of the receptor; and (b) the percent sequence (amino acid and/or nucleic acid) homology between the subsequent mutated form of the receptor and the first mutation of the receptor is at least 80%, at least 85%, at least 90%, at least 92%, at least 94%, at least 95%, at least 96%, at least 97%, at least 98%, and most preferably at least 99%. In some embodiments, owing to the fact that some preferred cassettes disclosed herein for achieving constitutive activation include a single amino acid and/or codon change between the endogenous and the non-endogenous forms of the GPCR, it is preferred that the percent sequence homology should be at least 98%.

(−)-NICOTINE shall be understood herein to have the formula:

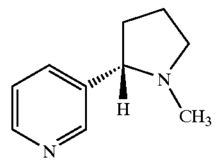

NICOTINIC ACID shall be understood herein to have the formula:

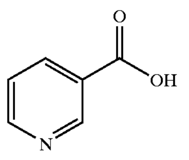

As used herein, the term NICOTINIC ACID ANALOG OR DERIVATIVE is meant to molecules which bind to nicotinic acid receptors and have substantially similar effects on the receptor. Such analogs and derivatives are well-known to those skilled in the art and include, but are not limited to, Acipimox™ and niacinamide.

NON-ORPHAN RECEPTOR shall mean an endogenous naturally occurring molecule specific for an identified ligand wherein the binding of a ligand to a receptor activates an intracellular signaling pathway.

ORPHAN RECEPTOR shall mean an endogenous receptor for which the ligand specific for that receptor has not been identified or is not known.

PARTIAL AGONISTS shall mean materials (e.g., ligands, candidate compounds) that activate the intracellular response when they bind to the receptor to a lesser degree/extent than do full agonists.

PHARMACEUTICAL COMPOSITION shall mean a composition comprising at least one active ingredient, whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome based upon the needs of the artisan.

PLASMID shall mean the combination of a Vector and cDNA. Generally, a Plasmid is introduced into a Host Cell for the purposes of replication and/or expression of the cDNA as a protein.

POLYNUCLEOTIDES shall mean RNA, DNA, or RNA/DNA hybrid sequences of more than one nucleotide in either single chain or duplex form. The polynucleotides of the invention may be prepared by any known method, including synthetic, recombinant, ex vivo generation, or a combination thereof, as well as utilizing any purification methods known in the art.

POLYPEPTIDE shall refer to a polymer of amino acids without regard to the length of the polymer. Thus, peptides, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term POLYPEPTIDE.

PRIMER is used herein to denote a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

PURIFIED is used herein to describe a polynucleotide or polynucleotide vector of the invention that has been separated from other compounds including, but not limited to, other nucleic acids, carbohydrates, lipids and proteins (such as the enzymes used in the synthesis of the polynucleotide). A polynucleotide is substantially pure when at least about 50%, 60%, 75%, or 90% of a sample contains a single polynucleotide sequence. A substantially pure polynucleotide typically comprises about 50, 60, 70, 80, 90, 95, 99% weight/weight of a nucleic acid sample. Polynucleotide purity or homogeneity may be indicated by a number of means well known in the art, such as agarose or polyacrylamide gel electrophoresis of a sample, followed by visualizing a single polynucleotide band upon staining the gel.

Similarly, the term PURIFIED is used herein to describe a polypeptide of the invention that has been separated from other compounds including, but not limited to, nucleic acids, lipids, carbohydrates and other proteins. In some preferred embodiments, a polypeptide is substantially pure when at least about 50%, 60%, 75%, 85%, 90%, 95%, 96%, 97%, 98%, 99%, or 99.5% of the polypeptide molecules of a sample have a single amino acid sequence. In some preferred embodiments, a substantially pure polypeptide typically comprises about 50%, 60%, 70%, 80%, 90%, 95%, 96%, 97%, 98%, 99% or 99.5% weight/weight of a protein sample. Polypeptide purity or homogeneity is indicated by a number of methods well known in the art, such as agarose or polyacrylamide gel electrophoresis of a sample, followed by visualizing a single polypeptide band upon staining the gel.

Further, as used herein, the term PURIFIED does not require absolute purity; rather, it is intended as a relative definition. Purification of starting material or natural material to at least one order of magnitude, preferably two or three orders, and more preferably four or five orders of magnitude is expressly contemplated.

RECEPTOR FUNCTIONALITY shall refer to the normal operation of a receptor to receive a stimulus and moderate an effect in the cell, including, but not limited to regulating gene transcription, regulating the influx or efflux of ions, effecting a catalytic reaction, and/or modulating activity through G-proteins.

SECOND MESSENGER shall mean an intracellular response produced as a result of receptor activation. A second messenger can include, for example, inositol triphosphate ($IP_3$), diacylglycerol (DAG), cyclic AMP (cAMP), cyclic GMP (cGMP), and $Ca^{2+}$. Second messenger response can be measured for a determination of receptor activation. In addition, second messenger response can be measured for the direct identification of candidate compounds, including for example, inverse agonists, partial agonists, agonists, and antagonists.

SIGNAL TO NOISE RATIO shall mean the signal generated in response to activation, amplification, or stimulation wherein the signal is above the background noise or the basal level in response to non-activation, non-amplification, or non-stimulation.

SPACER shall mean a translated number of amino acids that are located after the last codon or last amino acid of a gene, for example a GPCR of interest, but before the start codon or beginning regions of the G protein of interest, wherein the translated number amino acids are placed in-frame with the beginnings regions of the G protein of interest. The number of translated amino acids can be one, two, three, four, etc., and up to twelve.

STIMULATE or STIMULATING, in relationship to the term "response" shall mean that a response is increased in the presence of a compound as opposed to in the absence of the compound.

STROKE is a cardiovascular disease that affects the blood vessels supplying blood to the brain and is intended herein to include cerebral thrombosis, the most common type of STROKE. Cerebral thrombosis occurs when a blood clot (thrombus) forms and blocks blood flow in an artery bringing blood to part of the brain. Blood clots usually form in arteries damaged by atherosclerosis.

SUBJECT shall mean primates, including but not limited to humans and baboons, as well as pet animals such as dogs and cats, laboratory animals such as rats and mice, and farm animals such as horses, sheep, and cows.

SUBSTANTIALLY shall refer to a result which is within 40% of a control result, preferably within 35%, more preferably within 30%, more preferably within 25%, more preferably within 20%, more preferably within 15%, more preferably within 10%, more preferably within 5%, more preferably within 2%,and most preferably within 1% of a control result. For example, in the context of receptor functionality, a test receptor may exhibit substantially similar results to a control receptor if the transduced signal, measured using a method taught herein or similar method known to the art-skilled, is within 40% of the signal produced by a control signal.

TRANSGENIC MOUSE/RAT shall be intended herein to encompass a mouse or rat that has been engineered through recombinant means to carry a foreign gene, or transgene, of choice as part of its own genetic material.

VARIANT as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. A typical variant of a polypeptide differs in amino acid sequence from another, reference polypeptide. A variant and reference polypeptide may differe in amino acid sequence by one or more substitutions, additions, deletions in any combination. A variant of a polynucleotide or polypeptide may be a naturally occurring one such as an ALLELIC VARIANT, or it may be a variant that is not known to occur naturally. Non-naturally occurring variants of polynucleotides and polypeptides may be made by mutagenesis techniques or by direct synthesis.

VECTOR in reference to cDNA shall mean a circular DNA capable of incorporating at least one cDNA and capable of incorporation into a Host Cell.

The order of the following sections is set forth for presentational efficiency and is not intended, nor should be construed, as a limitation on the disclosure or the claims to follow.

A. Introduction

The traditional study of receptors has always proceeded from the a priori assumption (historically based) that the endogenous ligand must first be identified before discovery could proceed to find antagonists and other molecules that could affect the receptor. Even in cases where an antagonist might have been known first, the search immediately extended to looking for the endogenous ligand. This mode of thinking has persisted in receptor research even after the discovery of constitutively activated receptors. What has not been heretofore recognized is that it is the active state of the receptor that is most useful for discovering agonists, partial agonists, and inverse agonists of the receptor. For those diseases which result from an overly active receptor or an under-active receptor, what is desired in a therapeutic drug is a compound which acts to diminish the active state of a receptor or enhance the activity of the receptor, respectively, not necessarily a drug which is an antagonist to the endogenous ligand. This is because a compound that reduces or enhances the activity of the active receptor state need not bind at the same site as the endogenous ligand. Thus, as taught by the present invention, in some preferred embodiments, a search for therapeutic compounds should start by screening compounds against the ligand-independent active state.

B. Identification of Human GPCRs

The efforts of the Human Genome project has led to the identification of a plethora of information regarding nucleic acid sequences located within the human genome; it has been the case in this endeavor that genetic sequence information has been made available without an understanding or recognition as to whether or not any particular genomic sequence does or may contain open-reading frame information that translate human proteins. Several methods of identifying nucleic acid sequences within the human genome are within the purview of those having ordinary skill in the art. For example, and not limitation, a variety of human GPCRs, disclosed herein, were discovered by reviewing the GenBank™ database. Table B, below, lists several endogenous GPCRs that we have discovered, along with other GPCRs that are homologous to the disclosed GPCR.

TABLE B

| Disclosed Human Orphan GPCRs | Accession Number Identified | Open Reading Frame (Base Pairs) | Reference To Homologous GPCR | Per Cent Homology To Designated GPCR |
|---|---|---|---|---|
| hRUP8 | AL121755 | 1,152bp | NPY2R | 27% |
| hRUP9 | AC0113375 | 1,260bp | GAL2R | 22% |
| hRUP10 | AC008745 | 1,014bp | C5aR | 40% |
| hRUP11 | AC013396 | 1,272bp | HM74 | 36% |
| hRUP12 | AP000808 | 966bp | Mas1 | 34% |
| hRUP13 | AC011780 | 1,356bp | Fish GPRX-ORYLA | 43% |
| hRUP14 | AL137118 | 1,041bp | CysLTIR | 35% |
| hRUP15 | AL016468 | 1,527bp | RE2 | 30% |
| hRUP16 | AL136106 | 1,068bp | GLR101 | 37% |
| hRUP17 | AC023078 | 969bp | Mas1 | 37% |
| hRUP18 | AC008547 | 1,305bp | Oxytocin | 31% |
| hRUP19 | AC026331 | 1,041bp | HM74 | 52% |
| hRUP20 | AL161458 | 1,011bp | GPR34 | 25% |
| hRUP21 | AC026756 | 1,014bp | P2Y1R | 37% |
| hRUP22 | AC027026 | 993bp | hRUP17 | 67% |
| | | | Mas1 | 37% |
| hRUP23 | AC007104 | 1,092bp | Rat GPR26 | 31% |
| hRUP24 | AL355388 | 1,125bp | SALPR | 44% |
| hRUP25 | AC026331 | 1,092bp | HM74 | 95% |
| hRUP26 | AC023040 | 1,044bp | Rabbit 5HT1D | 27% |
| hRUP27 | AC027643 | 1,020bp | MCH | 38% |
| hRUP38 | AC026331 | 1,164bp | HM74 | 100% |

Such receptors are disclosed, for example, in application Ser. No. 09/714,008, filed Nov. 16, 2000, which is incorporated by reference in its entirety.

Receptor homology is useful in terms of gaining an appreciation of a role of the receptors within the human body. As the patent document progresses, techniques for mutating these receptors to establish non-endogenous, constitutively activated versions of these receptors will be discussed.

The techniques disclosed herein have also been applied to other human, orphan GPCRs known to the art, as will be apparent as the patent document progresses.

C. Identification of the Mouse (m) and Rat (r) Orthologs of Human (h) RUP25 and Identification of the Mouse (m) and Rat (r) Orthologs of Human (h) RUP19

TABLE C

| Disclosed Mouse (m) or Rat (r) RUP25 | Accession Number Identified | Open Reading Frame (Base Pairs) | Reference To Orthologous Human GPCR | Per Cent Homology To Designated GPCR |
|---|---|---|---|---|
| mRUP25 | AJ300199 | 1,083bp | hRUP25 | 83% |
| rRUP25 | None | 1,086bp | hRUP25 | 71% |
| mRUP19 | XM_144529 | 1,032bp | hRUP19 | 81% |
| rRUP19 | None | 1,056bp | hRUP19 | 83% |

D. Receptor Screening

Screening candidate compounds against a non-endogenous, constitutively activated version of the GPCRs disclosed herein allows for the direct identification of candidate compounds which act at the cell surface receptor, without requiring use, or, in some embodiments, of the knowledge of the identity of the receptor's endogenous ligand. Using routine and often commercially available techniques, one can determine areas within the body where the endogenous version of human GPCRs disclosed herein is expressed and/or over-expressed. The expression location of a receptor in a specific tissue provides a scientist with the ability to assign a physiological functional role of the receptor. It is also possible using these techniques to determine related disease/disorder states which are associated with the expression and/or over-expression of the receptor; such an approach is disclosed in this patent document. Furthermore, expression of a receptor in diseased organs can assist one in determining the magnitude of the clinical relevance of the receptor.

Constitutive activation of the GPCRs disclosed herein is based upon the distance from the proline residue at which is presumed to be located within TM6 of the GPCR; this algorithmic technique is disclosed in co-pending and commonly assigned patent document PCT Application Number PCT/US99/23938, published as WO 00/22129 on Apr. 20, 2000, which, along with the other patent documents listed herein, is incorporated herein by reference in its entirety. The algorithmic technique is not predicated upon traditional sequence "alignment" but rather a specified distance from the aforementioned TM6 proline residue (or, of course, endogenous constitutive substitution for such proline residue). By mutating the amino acid residue located 16 amino acid residues from this residue (presumably located in the IC3 region of the receptor) to, preferably, a lysine residue, constitutive activation of the receptor may be obtained. Other amino acid residues may be useful in the mutation at this position to achieve this objective and will be discussed in detail, below.

E. Disease/Disorder Identification and/or Selection

As will be set forth in greater detail below, inverse agonists and agonists to the non-endogenous, constitutively activated GPCR can be identified by the methodologies of this invention. Such inverse agonists and agonists are good candidates as lead compounds in drug discovery programs for treating diseases and/or disorders related to this receptor. Because of the ability to directly identify inverse agonists and agonists to the GPCR, thereby allowing for the development of pharmaceutical compositions, a search for diseases and disorders associated with the GPCR is relevant. The expression location of a receptor in a specific tissue provides a scientist with the ability to assign a physiological function to the receptor. For example, scanning both diseased and normal tissue samples for the presence of the GPCR now becomes more than an academic exercise or one which might be pursued along the path of identifying an endogenous ligand to the specific GPCR. Tissue scans can be conducted across a broad range of healthy and diseased tissues. Such tissue scans provide a potential first step in associating a specific receptor with a disease and/or disorder. Furthermore, expression of a receptor in diseased organs can assist one in determining the magnitude of the clinical relevance of the receptor.

The DNA sequence of the GPCR can be used to make a probe/primer. In some preferred embodiments the DNA sequence is used to make a probe for (a) dot-blot analysis against tissue-mRNA, and/or (b) RT-PCR identification of the expression of the receptor in tissue samples. The presence of a receptor in a tissue source, or a diseased tissue, or the presence of the receptor at elevated concentrations in diseased tissue compared to a normal tissue, can be used to correlate location to function and indicate the receptor's physiological role/function and create a treatment regimen, including but not limited to, a disease associated with that function/role. Receptors can also be localized to regions of organs by this technique. Based on the known or assumed roles/functions of the specific tissues to which the receptor is localized, the putative physiological function of the receptor can be deduced. For example and not limitation, proteins located/expressed in areas of the thalamus are associated with sensorimotor processing and arousal (see, Goodman & Gilman's, *The Pharmacological Basis of Therapeutics, 9$^{th}$* Edition, page 465 (1996)). Proteins expressed in the hippocampus or in Schwann cells are associated with learning and memory, and myelination of peripheral nerves, respectively (see, Kandel, E. et al., *Essentials of Neural Science and Behavior* pages 657, 680 and 28, respectively (1995)).

F. Screening of Candidate Compounds

1. Generic GPCR Screening Assay Techniques

When a G protein receptor becomes constitutively active, it binds to a G protein (e.g., Gq, Gs, Gi, Gz, Go) and stimulates the binding of GTP to the G protein. The G protein then acts as a GTPase and slowly hydrolyzes the GTP to GDP, whereby the receptor, under normal conditions, becomes deactivated. However, constitutively activated receptors continue to exchange GDP to GTP. A non-hydrolyzable analog of GTP, [$^{35}$S]GTPγS, can be used to monitor enhanced binding to membranes which express constitutively activated receptors. It is reported that [$^{35}$S]GTPγS can be used to monitor G protein coupling to membranes in the absence and presence of ligand. An example of this monitoring, among other examples well-known and available to those in the art, was reported by Traynor and Nahorski in 1995. The preferred use of this assay system is for initial screening of candidate compounds because the system is generically applicable to all G protein-coupled receptors regardless of the particular G protein that interacts with the intracellular domain of the receptor.

2. Specific GPCR Screening Assay Techniques

Once candidate compounds are identified using the "generic" G protein-coupled receptor assay (i.e., an assay to select compounds that are agonists or inverse agonists), in some embodiments further screening to confirm that the compounds have interacted at the receptor site is preferred. For example, a compound identified by the "generic" assay may not bind to the receptor, but may instead merely "uncouple" the G protein from the intracellular domain.

a. Gs, Gz and Gi.

Gs stimulates the enzyme adenylyl cyclase. Gi (and Gz and Go), on the other hand, inhibit adenylyl cyclase. Adenylyl cyclase catalyzes the conversion of ATP to cAMP; thus, constitutively activated GPCRs that couple the Gs protein are associated with increased cellular levels of cAMP. On the other hand, constitutively activated GPCRs that couple Gi (or Gz, Go) protein are associated with decreased cellular levels of cAMP. See, generally, "Indirect Mechanisms of Synaptic Transmission," Chpt. 8, *From Neuron To Brain* (3$^{rd}$ Ed.) Nichols, J. G. et al eds. Sinauer Associates, Inc. (1992). Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; in some embodiments a preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) that then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, a constitutively activated Gs-linked receptor causes the accumulation of cAMP that then activates the gene and expression of the reporter protein. The reporter protein such as β-galactosidase or luciferase can then be detected using standard biochemical assays (Chen et al. 1995).

b. Go and Gq.

Gq and Go are associated with activation of the enzyme phospholipase C, which in turn hydrolyzes the phospholipid $PIP_2$, releasing two intracellular messengers: diacycloglycerol (DAG) and inistol 1,4,5-triphoisphate ($IP_3$). Increased accumulation of $IP_3$ is associated with activation of Gq- and Go-associated receptors. See, generally, "Indirect Mechanisms of Synaptic Transmission," Chpt. 8, *From Neuron To Brain* ($3^{rd}$ Ed.) Nichols, J. G. et al eds. Sinauer Associates, Inc. (1992). Assays that detect IP3 accumulation can be utilized to determine if a candidate compound is, e.g., an inverse agonist to a Gq- or Go-associated receptor (i.e., such a compound would decrease the levels of $IP_3$). Gq-associated receptors can also been examined using an AP1 reporter assay in that Gq-dependent phospholipase C causes activation of genes containing AP1 elements; thus, activated Gq-associated receptors will evidence an increase in the expression of such genes, whereby inverse agonists thereto will evidence a decrease in such expression, and agonists will evidence an increase in such expression. Commercially available assays for such detection are available.

3. GPCR Fusion Protein

The use of an endogenous, constitutively activated GPCR or a non-endogenous, constitutively activated GPCR, for use in screening of candidate compounds for the direct identification of inverse agonists or agonists provides an interesting screening challenge in that, by definition, the receptor is active even in the absence of an endogenous ligand bound thereto. Thus, in order to differentiate between, e.g., the non-endogenous receptor in the presence of a candidate compound and the non-endogenous receptor in the absence of that compound, with an aim of such a differentiation to allow for an understanding as to whether such compound may be an inverse agonist or agonist or have no affect on such a receptor, in some embodiments it is preferred that an approach be utilized that can enhance such differentiation. In some embodiments, a preferred approach is the use of a GPCR Fusion Protein.

Generally, once it is determined that a non-endogenous GPCR has been constitutively activated using the assay techniques set forth above (as well as others known to the art-skilled), it is possible to determine the predominant G protein that couples with the endogenous GPCR. Coupling of the G protein to the GPCR provides a signaling pathway that can be assessed. In some embodiments it is preferred that screening take place using a mammalian expression system, such a system will be expected to have endogenous G protein therein. Thus, by definition, in such a system, the non-endogenous, constitutively activated GPCR will continuously signal. In some embodiments it is preferred that this signal be enhanced such that in the presence of, e.g., an inverse agonist to the receptor, it is more likely that it will be able to more readily differentiate, particularly in the context of screening, between the receptor when it is contacted with the inverse agonist.

The GPCR Fusion Protein is intended to enhance the efficacy of G protein coupling with the non-endogenous GPCR. The GPCR Fusion Protein is preferred for screening with either an endogenous, constitutively active GPCR or a non-endogenous, constitutively activated GPCR because such an approach increases the signal that is generated in such screening techniques. This is important in facilitating a significant "signal to noise" ratio; such a significant ratio is preferred for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. Important criteria in the construction of such a GPCR Fusion Protein construct include but are not limited to, that the endogenous GPCR sequence and the G protein sequence both be in-frame (preferably, the sequence for the endogenous GPCR is upstream of the G protein sequence), and that the "stop" codon of the GPCR be deleted or replaced such that upon expression of the GPCR, the G protein can also be expressed. Other embodiments include constructs wherein the endogenous GPCR sequence and the G protein sequence are not in-frame and/or the "stop" codon is not deleted or replaced. The GPCR can be linked directly to the G protein, or there can be spacer residues between the two (preferably, no more than about 12, although this number can be readily ascertained by one of ordinary skill in the art). Based upon convenience it is preferred to use a spacer. In some embodiments it is preferred, that the G protein that couples to the non-endogenous GPCR will have been identified prior to the creation of the GPCR Fusion Protein construct. Because there are only a few G proteins that have been identified, it is preferred that a construct comprising the sequence of the G protein (i.e., a universal G protein construct, see Example 5(a) below) be available for insertion of an endogenous GPCR sequence therein; this provides for further efficiency in the context of large-scale screening of a variety of different endogenous GPCRs having different sequences.

As noted above, constitutively activated GPCRs that couple to Gi, Gz and Go are expected to inhibit the formation of cAMP making assays based upon these types of GPCRs challenging (i.e., the cAMP signal decreases upon activation thus making the direct identification of, e.g., inverse agonists (which would further decrease this signal), challenging. As will be disclosed herein, it has been ascertained that for these types of receptors, it is possible to create a GPCR Fusion Protein that is not based upon the GPCR's endogenous G protein, in an effort to establish a viable cyclase-based assay. Thus, for example, an endogenous Gi coupled receptor can be fused to a Gs protein—such a fusion construct, upon expression, "drives" or "forces" the endogenous GPCR to couple with, e.g., Gs rather than the "natural" Gi protein, such that a cyclase-based assay can be established. Thus, for Gi, Gz and Go coupled receptors, in some embodiments it is preferred that when a GPCR Fusion Protein is used and the assay is based upon detection of adenylyl cyclase activity, that the fusion construct be established with Gs (or an equivalent G protein that stimulates the formation of the enzyme adenylyl cyclase).

TABLE D

| G protein | Effect of cAMP Production upon Activation of GPCR (i.e., constitutive activation or agonist binding) | Effect of $IP_3$ Accumulation upon Activation of GPCR (i.e., constitutive activation or agonist binding) | Effect of cAMP Production upon contact with an Inverse Agonist | Effect on $IP_3$ Accumulation upon contact with an Inverse Agonist |
|---|---|---|---|---|
| Gs | Increase | N/A | Decrease | N/A |
| Gi | Decrease | N/A | Increase | N/A |
| Gz | Decrease | N/A | Increase | N/A |
| Go | Decrease | Increase | Increase | Decrease |
| Gq | N/A | Increase | N/A | Decrease |

Equally effective is a G Protein Fusion construct that utilizes a Gq Protein fused with a Gs, Gi, Gz or Go Protein.

In some embodiments a preferred fusion construct can be accomplished with a Gq Protein wherein the first six (6) amino acids of the G-protein α-subunit ("Gαq") is deleted and the last five (5) amino acids at the C-terminal end of Gαq is replaced with the corresponding amino acids of the Gα of the G protein of interest. For example, a fusion construct can have a Gq (6 amino acid deletion) fused with a Gi Protein, resulting in a "Gq/Gi Fusion Construct". This fusion construct will forces the endogenous Gi coupled receptor to couple to its non-endogenous G protein, Gq, such that the second messenger, for example, inositol triphosphate or diacylgycerol, can be measured in lieu of cAMP production.

4. Co-transfection of a Target Gi Coupled GPCR with a Signal-Enhancer Gs Coupled GPCR (cAMP Based Assays)

A Gi coupled receptor is known to inhibit adenylyl cyclase, and, therefore, decreases the level of cAMP production, which can make the assessment of cAMP levels challenging. In some preferred embodiments, an effective technique in measuring the decrease in production of cAMP as an indication of constitutive activation of a receptor that predominantly couples Gi upon activation can be accomplished by co-transfecting a signal enhancer, e.g., a non-endogenous, constitutively activated receptor that predominantly couples with Gs upon activation (e.g., TSHR-A623I, disclosed below), with the Gi linked GPCR. As is apparent, constitutive activation of a Gs coupled receptor can be determined based upon an increase in production of cAMP. Constitutive activation of a Gi coupled receptor leads to a decrease in production cAMP. Thus, the co-transfection approach is intended to advantageously exploit these "opposite" affects. For example, co-transfection of a non-endogenous, constitutively activated Gs coupled receptor (the "signal enhancer") with the endogenous Gi coupled receptor (the "target receptor") provides a baseline cAMP signal (i.e., although the Gi coupled receptor will decrease cAMP levels, this "decrease" will be relative to the substantial increase in cAMP levels established by constitutively activated Gs coupled signal enhancer). By then co-transfecting the signal enhancer with a constitutively activated version of the target receptor, cAMP would be expected to further decrease (relative to base line) due to the increased functional activity of the Gi target (i.e., which decreases cAMP).

Screening of candidate compounds using a cAMP based assay can then be accomplished, with two 'changes' relative to the use of the endogenous receptor/G-protein fusion: first, relative to the Gi coupled target receptor, "opposite" effects will result, i.e., an inverse agonist of the Gi coupled target receptor will increase the measured cAMP signal, while an agonist of the Gi coupled target receptor will decrease this signal; second, as would be apparent, candidate compounds that are directly identified using this approach should be assessed independently to ensure that these do not target the signal enhancing receptor (this can be done prior to or after screening against the co-transfected receptors).

G. Medicinal Chemistry

Candidate Compounds

Any molecule known in the art can be tested for its ability to modulate (increase or decrease) the activity of a GPCR of the present invention. For identifying a compound that modulates activity, candidate compounds can be directly provided to a cell expressing the receptor.

This embodiment of the invention is well suited to screen chemical libraries for molecules which modulate, e.g., inhibit, antagonize, or agonize, the amount of, or activity of, a receptor. The chemical libraries can be peptide libraries, peptidomimetic libraries, chemically synthesized libraries, recombinant, e.g., phage display libraries, and in vitro translation-based libraries, other non-peptide synthetic organic libraries, etc. This embodiment of the invention is also well suited to screen endogenous candidate compounds comprising biological materials, including but not limited to plasma and tissue extracts, and to screen libraries of endogenous compounds known to have biological activity.

In some embodiments direct identification of candidate compounds is conducted in conjunction with compounds generated via combinatorial chemistry techniques, whereby thousands of compounds are randomly prepared for such analysis. The candidate compound may be a member of a chemical library. This may comprise any convenient number of individual members, for example tens to hundreds to thousand to millions of suitable compounds, for example peptides, peptoids and other oligomeric compounds (cyclic or linear), and template-based smaller molecules, for example benzodiazepines, hydantoins, biaryls, carbocyclic and polycyclic compounds (e.g., naphthalenes, phenothiazines, acridines, steroids etc.), carbohydrate and amino acid derivatives, dihydropyridines, benzhydryls and heterocycles (e.g., trizines, indoles, thiazolidines etc.). The numbers quoted and the types of compounds listed are illustrative, but not limiting. Preferred chemical libraries comprise chemical compounds of low molecular weight and potential therapeutic agents.

Exemplary chemical libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compound's composition. Also, in one example, a single plate position may have from 1–20 chemicals that can be screened by administration to a well containing the interactions of interest. Thus, if modulation is detected, smaller and smaller pools of interacting pairs can be assayed for the modulation activity. By such methods, many candidate molecules can be screened.

Many diversity libraries suitable for use are known in the art and can be used to provide compounds to be tested according to the present invention. Alternatively, libraries can be constructed using standard methods. Further, more general, structurally constrained, organic diversity (e.g., nonpeptide) libraries, can also be used. By way of example, a benzodiazepine library (see e.g., Bunin et al., 1994, Proc. Natl. Acad. Sci. USA 91:4708–4712) may be used.

In another embodiment of the present invention, combinatorial chemistry can be used to identify modulators of the GPCRs of the present invention. Combinatorial chemistry is capable of creating libraries containing hundreds of thousands of compounds, many of which may be structurally similar. While high throughput screening programs are capable of screening these vast libraries for affinity for known targets, new approaches have been developed that achieve libraries of smaller dimension but which provide maximum chemical diversity. (See e.g., Matter, 1997, Journal of Medicinal Chemistry 40:1219–1229).

One method of combinatorial chemistry, affinity fingerprinting, has previously been used to test a discrete library of small molecules for binding affinities for a defined panel of proteins. The fingerprints obtained by the screen are used to predict the affinity of the individual library members for other proteins or receptors of interest (in the instant invention, the receptors of the present invention). The fingerprints are compared with fingerprints obtained from other compounds known to react with the protein of interest to predict whether the library compound might similarly react. For example, rather than testing every ligand in a large library for interaction with a complex or protein component, only those ligands having a fingerprint similar to other compounds known to have that activity could be tested. (See, e.g., Kauvar et al., 1995, Chemistry and Biology 2:107–118; Kauvar, 1995, Affinity fingerprinting, Pharmaceutical Manufacturing International. 8:25–28; and Kauvar, Toxic-Chemical Detection by Pattern Recognition in New Frontiers in Agrochemical Immunoassay, D. Kurtz. L. Stanker and J. H. Skerritt. Editors, 1995, AOAC: Washington, D.C., 305–312).

In some preferred embodiments, the candidate compound is an hydroxypyrazole derivative. In some preferred embodiments, the candidate compound is a benzotriazole carboxylic acid or ester derivative.

Candidate Compounds Identified as Modulators

Generally, the results of such screening will be compounds having unique core structures; thereafter, these compounds may be subjected to additional chemical modification around a preferred core structure(s) to further enhance the medicinal properties thereof. Such techniques are known to those in the art and will not be addressed in detail in this patent document.

H. Pharmaceutical Compositions

The invention provides methods of treatment (and prevention) by administration to an individual in need of said treatment (or prevention) a therapeutically effect amount of a modulator of the invention [also see, e.g., PCT Application Number PCT/IB02/01461 published as WO 02/066505 on 29 Aug. 2002; the disclosure of each of which is hereby incorporated by reference in its entirety]. In a preferred aspect, the modulator is substantially purified. The individual is preferably an animal including, but not limited to animals such as cows, pigs, horses, chickens, cats, dogs, rabbits, rats, mice, etc., and is preferably a mammal, and most preferably human.

Modulators of the invention can be administered to non-human animals [see Examples, infra] and/or humans, alone or in pharmaceutical or physiologically acceptable compositions where they are mixed with suitable carriers or excipient(s) using techniques well known to those in the art. Suitable pharmaceutically-acceptable carriers are available to those in the art; for example, see Remington's Pharmaceutical Sciences, $16^{th}$ Edition, 1980, Mack Publishing Co., (Oslo et al., eds.).

The pharmaceutical or physiologically acceptable composition is then provided at therapeutically effect dose. A therapeutically effective dose refers to that amount of a modulator sufficient to result in prevention or amelioration of symptoms or physiological status of metabolic-related disorders or disorders of lipid metabolism as determined illustratively and not by limitation by the methods described herein.

It is expressly considered that the modulators of the invention may be provided alone or in combination with other pharmaceutically or physiologically acceptable compounds. Other compounds for the treatment of disorders of the invention are currently well known in the art. One aspect of the invention encompasses the use according to embodiments disclosed herein further comprising one or more agents selected from the group consisting of α-glucosidase inhibitor, aldose reductase inhibitor, biguanide, HMG-CoA reductase inhibitor, squalene synthesis inhibitor, fibrate, LDL catabolism enhancer, angiotensin converting enzyme inhibitor, insulin secretion enhancer and thiazolidinedione. In some embodiments the agent is a α-glucosidase inhibitor. In some embodiments the α-glucosidase inhibitor is acarbose, voglibose or miglitol. In some embodiments the α-glucosidase inhibitor is voglibose. In some embodiments the agent is an aldose reductase inhibitor. In some embodiments the aldose reductase inhibitor is tolurestat; epalrestat; imirestat; zenarestat; zopolrestat; or sorbinil. In some embodiments the agent is a biguanide. In some embodiments the biguanide is phenformin, metformin or buformin. In some embodiments the biguanide is metformin. In some embodiments the agent is a HMG-CoA reductase inhibitor. In some embodiments the HMG-CoA reductase inhibitor is rosuvastatin, pravastatin, simvastatin, lovastatin, atorvastatin, fluvastatin or cerivastatin. In some embodiments the agent is a fibrate. In some embodiments the fibrate is bezafibrate, beclobrate, binifibrate, ciplofibrate, clinofibrate, clofibrate, clofibric acid, etofibrate, fenofibrate, gemfibrozil, nicofibrate, pirifibrate, ronifibrate, simfibrate, or theofibrate. In some embodiments the agent is an angiotensin converting enzyme inhibitor. In some embodiments the angiotensin converting enzyme inhibitor is captopril, enalapril, alacepril, delapril; ramipril, lisinopril, imidapril, benazepril, ceronapril, cilazapril, enalaprilat, fosinopril, moveltopril, perindopril, quinapril, spirapril, temocapril or trandolapril. In some embodiments the agent is an insulin secretion enhancer. In some embodiments the insulin secretion enhancer is tolbutamide; chlorpropamide; tolazamide; acetohexamide; glycopyramide; glibenclamide; gliclazide; 1-butyl-3-metanilylurea; carbutamide; glibonuride; glipizide; gliquidone; glisoxepid; glybuthiazole; glibuzole; glyhexamide; glymidine; glypinamide; phenbutamide; tolcyclamide, glimepiride, nateglinide, or mitiglinide. In some embodiments the agent is a thiazolidinedione. In some embodiments the thiazolidinedione is rosiglitazone or pioglitazone. In some embodiments the thiazolidinedione is rosiglitazone. In some embodiments, the agent is human adiponectin or a fragment thereof comprising the globular domain.

In some embodiments the metabolic disorder is selected from the group consisting of dyslipidemia, atherosclerosis, coronary heart disease, insulin resistance, obesity, impaired glucose tolerance, atheromatous disease, hypertension, stroke, Syndrome X, heart disease and type 2 diabetes. In some embodiments the metabolic disorder is selected from the group consisting of dyslipidemia, atherosclerosis, coronary heart disease, stroke, insulin resistance and type 2 diabetes. In some embodiments, the disorder of lipid metabolism is selected from the group consisting of elevated level of plasma triglycerides, elevated level of plasma free fatty acids, elevated level of plasma cholesterol, elevated level of LDL-cholesterol, reduced level of HDL-cholesterol, elevated total cholesterol/HDL-cholesterol ratio, and reduced level of plasm adiponectin.

Routes of Administration

Suitable routes of administration include oral, nasal, rectal, transmucosal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. Other particularly preferred routes of administration are aerosol and depot formulation. Sustained release formulations, particularly depot, of the invented medicaments are expressly contemplated.

Composition/Formulation

Pharmaceutical or physiologically acceptable compositions and medicaments for use in accordance with the present invention may be formulated in a conventional manner using one or more physiologically acceptable carriers comprising excipients and auxiliaries. Proper formulation is dependent upon the route of administration chosen.

Certain of the medicaments described herein will include a pharmaceutically or physiologically acceptable carrier and at least one modulator of the invention. For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the barrier to be permeated are used in the formulation. Such penetrants are generally known in the art.

Pharmaceutical or physiologically acceptable preparations that can be taken orally include push-fit capsules made of gelatin, as well as soft, sealed captulse made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liqid paraffin, or lliquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs for a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for ue in an inhaler or insufflator, may be forumulated containing a powder mix of the compound and a suitable powder base such as lactose or starch.

The compounds may be formulated for parenteral administration by injection, e.g., by bolus injection or continuous infusion. Formulations for injection may be presented in unit dosage for, e.g., in ampoules or in muti-dose containers, with an added preservative. The compositions may take such forms as suspension, solutions or emulsions in aqueous vehicles, and may contain formulatory agents such as suspending, stabilizing and/or dispersing agents.

Pharmaceutical or physiologically acceptable formulations for parenteral administration include aqueous solutions of the active compounds in water-soluble form. Aqueous suspension may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In a particular embodiment, the compounds can be delivered via a controlled release system. In one embodiment, a pump may be used (Langer, supra; Sefton, 1987, CRC Crit. Ref. Biomed. Eng. 14:201–240; Buchwald et al., 1980, Surgery 88:507–516; Saudek et al., 1989, N. Engl. J. Med. 321:574–579). In another embodiment, polymeric materials can be used (Medical Applications of Controlled Release, Langer and Wise, eds., CRC Press, Boca Raton, Fla., 1974; Controlled Drug Bioavailability, Drug Product Design and Performance, Smolen and Ball, eds., Wiley, N.Y., 1984; Ranger and Peppas, 1983, Macromol. Sci. Rev. Macromol. Chem. 23:61; Levy et al., 1985, Science 228:190–192; During et al., 1989, Ann. Neurol. 25:351–356; Howard et al., 1989, J. Neurosurg. 71:858–863). Other controlled release systems are discussed in the review by Langer (1990, Science 249:1527–1533).

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for modulator stabilization may be employed.

The pharmaceutical or physiologically acceptable compositions also may comprise suitable solid or gel phase carriers or excipients. Examples of such carriers or escipients include but are not limited to calcium carbonate, calcium phosphate, various sugars, starches, cellulos derivatives, gelatin, and polymers such as polyethylene glycols.

Effective Dosage

Pharmaceutical or physiologically acceptable compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is wll within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes or encompasses a concentration point or range shown to antilipolytic in an in vitro system. [See Examples, infra, for in vitro assays and in vivo animal models.] Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the $LD_{50}$ (the dose lethal to 50% of the test population) and the $ED_{50}$ (the dose therapeutically effective in 50% of the test population). The dose ratio between toxic and therapeutic effects is the therapeutic index and it can be expressed as the ratio between $LD_{50}$ and $ED_{50}$. Compounds that exhibit high therapeutic indices are preferred.

The data obtained from these cell culture assays and animal studies can be used in formulating a range of dosage for use in humans. The dosage of such compounds lies preferably within a range of circulating concentrations that include the $ED_{50}$, with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1).

Dosage amount and interval may be adjusted individually to provide plasma levels of the active compound which are sufficient to prevent or treat a disorder of the invention, depending on the particular situation. Dosages necessary to achieve these effects will depend on individual characteristics and route of administration.

Dosage intervals can also be determined using the value for the minimum effective concentration. Compounds should be administered using a regimen that maintains plasma levels above the minimum effective concentration for 10–90% of the time, preferably between 30–99%, and most preferably between 50–90%. In cases of local administration or selective uptake, the effective local concentration of the drug may not be related to plasma concentration.

The amount of composition administered will, of course, be dependent on the subject being treated, on the subject's weight, the severity of the affliction, the manner of administration, and the judgement of the prescribing physician.

A preferred dosage range for the amount of a modulator of the invention, which can be administered on a daily or regular basis to achieve desired results, including but not limited to reduction of the level of plasma triglycerides, reduction of the level of plasma free fatty acids, elevation of the level of HDL-cholesterol, reduction of the level of LDL-cholesterol, reduction of the level of plasma cholesterol, reduction of the total cholesterol/HDL-cholesterol ratio, or elevation of the level of plasma adiponectin, is 0.1–100 mg/kg body mass. Other preferred dosage range is 0.1–30 mg/kg body mass. Other preferred dosage range is 0.1–10 mg/kg body mass. Other preferred dosage range is 0.1–3.0 mg/kg body mass. Of course, these daily dosages can be delivered or administered in small amounts periodically during the course of a day. It is noted that these dosage ranges are only preferred ranges and are not meant to be limiting to the invention.

I. Methods of Treatment

The invention is drawn inter alia to methods of preventing or treating disorders of lipid metabolism and metabolic-related disorders comprising providing an individual in need of such treatment with a modulator of the invention. Preferably the modulator is provided to the individual in a pharmaceutical composition that is preferably taken orally. Preferably the individual is a mammal, and most preferably a human. In preferred embodiments, the disorder of lipid metabolism is selected from the group consisting of elevated level of triglycerides, elevated level of plasma free fatty acids, elevated level of plasma cholesterol, elevated level of LDL-cholesterol, reduced level of HDL-cholesterol, elevated total cholesterol/HDL-cholesterol ratio, and reduced level of plasma adiponectin. In preferred embodiments, the metabolic-related disorder is selected from the group consisting of dyslipidemia, atherosclerosis, coronary heart disease, stroke, insulin resistance, and type 2 diabetes. Other metabolic-related disorders to be treated by modulators of the invention include obesity, impaired glucose tolerance, atheromatous disease, hypertension, Syndrome X, and heart disease. Heart disease includes, but is not limited to, cardiac insufficiency, coronary insufficiency, and high blood pressure. Other metabolic-related disorder to be treated by modulators of the invention is hyperlipidemia. In other embodiments, the invention provides for a method of using a modulator of the invention as an inhibitor of the progression from impaired glucose tolerance to insulin resistance.

The invention also features methods of preventing or treating disorders of lipid metabolism or metabolic-related disorders comprising providing an individual in need of such treatment with a modulator identified by assays of the invention. Preferably, the modulator is provided to the individual in a pharmaceutical composition that is preferably taken orally. Preferably the individual is a mammal, and most preferably a human. In preferred embodiments, the disorder of lipid metabolism is selected from the group consisting of elevated level of triglycerides, elevated level of plasma free fatty acids, elevated level of plasma cholesterol, elevated level of LDL-cholesterol, reduced level of HDL-cholesterol, elevated total cholesterol/HDL-cholesterol ratio, and reduced level of plasma adiponectin. In preferred embodiments, the metabolic-related disorder is selected from the group consisting of dyslipidemia, atherosclerosis, coronary heart disease, stroke, insulin resistance, and type 2 diabetes. Other metabolic-related disorders to be treated by modulators of the invention include obesity, impaired glucose tolerance, atheromatous disease, hypertension, Syndrome X, and heart disease. Heart disease includes, but is not limited to, cardiac insufficiency, coronary insufficiency, and high blood pressure. Other metabolic-related disorder to be treated by modulators of the invention is hyperlipidemia. In other embodiments, the invention provides for a method of using a modulator of the invention as an inhibitor of the progression from impaired glucose tolerance to insulin resistance.

J. Other Utility

Although a preferred use of the non-endogenous versions of the GPCRs disclosed herein may be for the direct identification of candidate compounds as inverse agonists or agonists (preferably for use as pharmaceutical agents), other uses of these versions of GPCRs exist. For example, in vitro and in vivo systems incorporating GPCRs can be utilized to further elucidate and understand the roles these receptors play in the human condition, both normal and diseased, as well as understanding the role of constitutive activation as it applies to understanding the signaling cascade. In some embodiments it is preferred that the endogenous receptors be "orphan receptors", i.e., the endogenous ligand for the receptor has not been identified. In some embodiments, therefore, the modified, non-endogenous GPCRs can be used to understand the role of endogenous receptors in the human body before the endogenous ligand has been identified. Such receptors can be used to further elucidate known receptors and the pathways through which they transduce a signal. The present methods may also be useful in developing treatment regimens for diseases and disorders associated with the tissues in which the receptors are localized. Examples of such diseases and disorders and tissues in which the receptors are localized are set forth supra and infra.

Agents that modulate (i.e., increase, decrease, or block) nicotinic acid receptor functionality may be identified by contacting a candidate compound with a nicotinic acid receptor and determining the effect of the candidate compound on nicotinic acid receptor functionality. The selectivity of a compound that modulates the functionality of the nicotinic acid receptor can be evaluated by comparing its effects on the nicotinic acid receptor to its effects on other receptors. Following identification of compounds that modulate nicotinic acid receptor functionality, such candidate compounds may be further tested in other assays including, but not limited to, in vivo models, in order to confirm or quantitate their activity. Modulators of nicotinic acid receptor functionality will be therapeutically useful in treatment of diseases and physiological conditions in which normal or aberrant nicotinic acid receptor functionality is involved.

Agents that modulate (i.e., increase, decrease, or block) antilipolytic receptor functionality may be identified by contacting a candidate compound with an antilipolytic receptor and determining the effect of the candidate compound on antilipolytic receptor functionality. The selectivity of a compound that modulates the functionality of an antilipolytic receptor can be evaluated by comparing its effects on the antilipolytic receptor to its effects on other receptors. Following identification of compounds that modulate antilipolytic receptor functionality, such candidate compounds may be further tested in other assays including, but not limited to, in vivo models, in order to confirm or quantitate their activity. Modulators of antilipolytic receptor functionality will be therapeutically useful in treatment of diseases and physiological conditions in which normal or aberrant antilipolytic receptor functionality is involved.

Other uses of the disclosed receptors and methods will become apparent to those in the art based upon, inter alia, a review of this patent document.

EXAMPLES

The following examples are presented for purposes of elucidation, and not limitation, of the present invention. While specific nucleic acid and amino acid sequences are disclosed herein, those of ordinary skill in the art are credited with the ability to make minor modifications to these sequences while achieving the same or substantially similar results reported below. The traditional approach to application or understanding of sequence cassettes from one sequence to another (e.g. from rat receptor to human receptor or from human receptor A to human receptor B) is generally predicated upon sequence alignment techniques whereby the sequences are aligned in an effort to determine areas of commonality. The mutational approach disclosed herein does not rely upon this approach but is instead based upon an algorithmic approach and a positional distance from a conserved proline residue located within the TM6 region of human GPCRs. Once this approach is secured, those in the art are credited with the ability to make minor modifications thereto to achieve substantially the same results (i.e., constitutive activation) disclosed herein. Such modified approaches are considered within the purview of this disclosure.

The following Examples are provided for illustrative purposes and not as a means of limitation. One of ordinary skill in the art would be able to design equivalent assays and methods based on the disclosure herein, all of which form part of the present invention.

Although a variety of expression vectors are available to those in the art, for purposes of utilization for both the endogenous and non-endogenous human, mouse and rat GPCRs, it is most preferred that the vector utilized be pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351. In some alternative embodiments as relates to said human, mouse and rat GPCRs, it is preferred that the vector utilized be an adenoviral expression vector.

Recombinant DNA techniques relating to the subject matter of the present invention and well known to those of ordinary skill in the art can be found, e.g, in Maniatis T et al., *Molecular Cloning: A Laboratory Manual* (1989) Cold Spring Harbor Laboratory; U.S. Pat. No. 6,399,373; and PCT Application Number PCT/IB02/01461 published as WO 02/066505 on 29 Aug. 2002; the disclosure of each of which is hereby incorporated by reference in its entirety.

Example 1

A. Endogenous Human GPCRs

Identification of Human GPCRs

The disclosed endogenous human GPCRs were identified based upon a review of the GenBank™ database information. While searching the database, the following cDNA clones were identified as evidenced below (Table E).

TABLE E

| Disclosed Human Orphan GPCRs | Accession Number Identified | Complete DNA Sequence (Base Pairs) | Open Reading Frame (Base Pairs) | Nucleic Acid SEQ. ID. NO. | Amino Acid SEQ. ID. NO. |
|---|---|---|---|---|---|
| hRUP8 | AL121755 | 147,566bp | 1,152bp | 1 | 2 |
| hRUP9 | AC0113375 | 143,181bp | 1,260bp | 3 | 4 |
| hRUP10 | AC008745 | 94,194bp | 1,014bp | 5 | 6 |
| hRUP11 | AC013396 | 155,086bp | 1,272bp | 7 | 8 |
| hRUP12 | AP000808 | 177,764bp | 966bp | 9 | 10 |
| hRUP13 | AC011780 | 167,819bp | 1,356bp | 11 | 12 |
| hRUP14 | AL137118 | 168,297bp | 1,041bp | 13 | 14 |
| hRUP15 | AL016468 | 138,828bp | 1,527bp | 15 | 16 |
| hRUP16 | AL136106 | 208,042bp | 1,068bp | 17 | 18 |
| hRUP17 | AC023078 | 161,735bp | 969bp | 19 | 20 |
| hRUP18 | AC008547 | 117,304bp | 1,305bp | 21 | 22 |
| hRUP19 | AC026331 | 145,183bp | 1,041bp | 23 | 24 |
| hRUP20 | AL161458 | 163,511bp | 1,011bp | 25 | 26 |
| hRUP21 | AC026756 | 156,534bp | 1,014bp | 27 | 28 |
| hRUP22 | AC027026 | 151,811bp | 993bp | 29 | 30 |
| hRUP23 | AC007104 | 200,000bp | 1,092bp | 31 | 32 |
| hRUP24 | AL355388 | 190,538bp | 1,125bp | 33 | 34 |
| hRUP25 | AC026331 | 145,183bp | 1,092bp | 35 | 36 |
| hRUP26 | AC023040 | 178,508bp | 1,044bp | 37 | 38 |
| hRUP27 | AC027643 | 158,700bp | 1,020bp | 39 | 40 |
| hRUP38 | AC026331 | 145,183bp | 1,164bp | 134 | 135 |

1. Full Length Cloning a. hRUP8 (Seq. Id. Nos. 1 & 2)

The disclosed human HRUP8 was identified based upon the use of EST database (dbEST) information. While searching the dbEST, a cDNA clone with accession number AL121755 was identified to encode a novel GPCR. The following PCR primers were used for RT-PCR with human testis Marathon-Ready cDNA (Clontech) as templates:

```
5'-CTTGCAGACATCACCATGGCAGCC-3'  (SEQ. ID. NO.:41; sense)

and

5'-GTGATGCTCTGAGTACTGGACTGG-3'. (SEQ. ID. NO.:42; antisense)
```

PCR was performed using Advantage cDNA polymerase (Clontech; manufacturing instructions will be followed) in 50ul reaction by the following cycles: 94° C. for 30 sec; 94° C. for 10 sec; 65° C. for 20 sec, 72° C. for 1.5 min, and 72° C. for 7 min. Cycles 2 through 4 were repeated 35 times.

A 1.2 kb PCR fragment was isolated and cloned into the pCRII-TOPO vector (Invitrogen) and sequenced using the ABI Big Dye Terminator kit (P.E. Biosystem). See, SEQ. ID. NO.:1. The putative amino acid sequence for hRUP8 is set forth in SEQ. ID. NO.:2.

b. hRUP9 (Seq. Id. Nos. 3 & 4)

The disclosed human hRUP9 was identified based upon the use of GeneBank database information. While searching the database, a cDNA clone with Accession Number AC011375 was identified as a human genomic sequence from chromosome 5. The full length hRUP9 was cloned by PCR using primers:

```
5'-GAAGCTGTGAAGAGTGATGC-3',     (SEQ. ID. NO.:43; sense)

5'-GTCAGCAATATTGATAAGCAGCAG-3'  (SEQ. ID. NO.:44; antisense)
```

and human genomic DNA (Promega) as a template. Taq Plus Precision polymerase (Stratagene) was used for the amplification in a 100 $\mu$l reaction with 5% DMSO by the following cycle with step 2 to step 4 repeated 35 times: 94° C. for 1 minute; 94° C. for 30 seconds; 56° C. for 30 seconds; 72° C. for 2 minutes; 72° C. for 5 minutes.

A 1.3 Kb PCR fragment was isolated and cloned into the pCRII-TOPO vector (Invitrogen) from 1% agarose gel and completely sequenced using the ABI Big Dye Terminator kit (P.E. Biosystems). See, SEQ.ID.NO.:3. The putative amino acid sequence for hRUP8 is set forth in SEQ.ID.NO.:4. The sequence of hRUP9 clones isolated from human genomic DNA matched with the sequence obtained from data base.

c. hRUP10 (Seq. Id. Nos. 5 & 6)

The disclosed human hRUP10 was identified based upon the use of GenBank database information. While searching the database, a cDNA clone with accession number AC008754 was identified as a human genomic sequence from chromosome 19. The full length hRUP10 was cloned by RT-PCR using primers:

```
5'-CCATGGGGAACGATTCTGTCAGCTACG-3'  (SEQ. ID. NO.:45; sense)

and

5'-GCTATGCCTGAAGCCAGTCTTGTG-3'     (SEQ. ID. NO.:46; antisense)
```

and human leukocyte Marathon-Ready cDNA (Clontech) as a template. Advantage cDNA polymerase (Clontech) was used for the amplification in a 50 $\mu$l reaction by the following cycle with step 2 to step 4 repeated 35 times: 94° C. for 30 seconds; 94° C. for 10 seconds; 62° C. for 20 seconds; 72° C. for 1.5 minutes; 72° C. for 7 minutes. A 1.0 Kb PCR fragment was isolated and cloned into the pCRII-TOPO vector (Invitrogen) and completely sequenced using the ABI Big Dye Terminator kit (P.E. Biosystems). The nucleic acid sequence of the novel human receptor hRUP10 is set forth in SEQ.ID.NO.:5 and the putative amino acid sequence thereof is set forth in SEQ.ID.NO.:6.

d. hRUP11 (Seq. Id. Nos. 7 & 8)

The disclosed human hRUP11 was identified based upon the use of GenBank database information. While searching the database, a cDNA clone with accession number AC013396 was identified as a human genomic sequence from chromosome 2.

The full length hRUP11 was cloned by PCR using primers:

```
5'-CCAGGATGTTGTGTCACCGTGGTGGC-3',  (SEQ. ID. NO.:47; sense)

5'-CACAGCGCTGCAGCCCTGCAGCTGGC-3'   (SEQ. ID. NO.:48; antisense)
```

and human genonic DNA (Clontech) as a template. TaqPlus Precision DNA polymerase (Stratagene) was used for the amplification in a 50 μl reaction by the following cycle with step 2 to step 4 repeated 35 times: 94° C. for 3 minutes; 94° C. for 20 seconds; 67° C. for 20 seconds; 72° C. for 1.5 minutes; 72° C. for 7 minutes. A 1.3 Kb PCR fragment was isolated and cloned into the pCRII-TOPO vector (Invitrogen) and completely sequenced using the ABI Big Dye Terminator kit (P.E. Biosystems). The nucleic acid sequence of the novel human receptor hRUP11 is set forth in SEQ.ID.NO.:7 and the putative amino acid sequence thereof is set forth in SEQ.ID.NO.:8.

e. hRUP12 (Seq. Id. Nos. 9 & 10)

The disclosed human HRUP12 was identified based upon the use of GenBank database. While searching the database, a cDNA clone with accession number AP000808 was identified to encode a new GPCR, having significant homology with rat RTA and human mas1 oncogene GPCRs. The full length hRUP12 was cloned by PCR using primers:

```
5'-CTTCCTCTCGTAGGGATGAACCAGAC-3' (SEQ. ID. NO.:49; sense)

5'-CTCGCACAGGTGGGAAGCACCTGTGG-3' (SEQ. ID. NO.:50; antisense)
```

and human genomic DNA (Clontech) as template. TaqPlus Precision DNA polymerase (Stratagene) was used for the amplification by the following cycle with step 2 to step 4 repeated 35 times: 94° C. for 3 min; 94° C. for 20 sec; 65° C. for 20sec; 72° C. for 2 min and 72° C. for 7 min. A 1.0 kb PCR fragment was isolated and cloned into the pCRII-TOPO vector (Invitrogen) and sequenced using the ABI Big Dye Terminator kit (P.E. Biosystems) (see, SEQ.ID.NO.:9 for nucleic acid sequence and SEQ.ID.NO.:10 for deduced amino acid sequence).

f. hRUP13 (Seq. Id. Nos. 11 & 12)

The disclosed human HRUP13 was identified based upon the use of GenBank database. While searching the database, a cDNA clone with accession number AC011780 was identified to encode a new GPCR, having significant homology with GPCR fish GPRX-ORYLA. The full length hRUP13 was cloned by PCR using primers:

```
5'-GCCTGTGACAGGAGGTACCCTGG-3'   (SEQ. ID. NO.:51; sense)

5'-CATATCCCTCCGAGTGTCCAGCGGC-3' (SEQ. ID. NO.:52; antisense)
```

and human genomic DNA (Clontech) as template. TaqPlus Precision DNA polymerase (Stratagene) was used for the amplification by the following cycle with step 2 to step 4 repeated 35 times: 94° C. for 3 min; 94° C. for 20 sec; 65° C. for 20sec; 72° C. for 2 min and 72° C. for 7 min. A 1.35 kb PCR fragment was isolated and cloned into the pCRII-TOPO vector (Invitrogen) and completely sequenced using the ABI Big Dye Terminator kit (P.E. Biosystems) (see, SEQ.ID.NO.:11 for nucleic acid sequence and SEQ.ID.NO.:12 for deduced amino acid sequence).

g. hRUP14 (Seq. Id. Nos. 13 & 14)

The disclosed human hRUP14 was identified based upon the use of the GenBank database information. While searching the database, a cDNA clone with Accession Number AL137118 was identified as a human genomic sequence from chromosome 13. The full length hRUP14 was cloned by PCR using primers:

```
5'-GCATGGAGAGAAAATTTATGTCCTTGCAACC-3' (SEQ. ID. NO.:53; sense)

5'-CAAGAACAGGTCTCATCTAAGAGCTCC-3'     (SEQ. ID. NO.:54; antisense)
```

and human genomic DNA (Promega) as a template. Taq Plus Precision polymerase (Stratagene) and 5% DMSO were used for the amplification by the following cycle with step 2 and step 3 repeated 35 times: 94° C. for 3 minute; 94° C. for 20 seconds; 58° C. for 2 minutes; 72° C. for 10 minutes.

A 1.1 Kb PCR fragment was isolated and cloned into the pCRII-TOPO vector (Invitrogen) and completely sequenced using the ABI Big Dye Terminator kit (P.E. Biosystems) (see, SEQ.ID.NO.:13 for nucleic acid sequence and SEQ.ID.NO.:14 for deduced amino acid sequence). The sequence of hRUP14 clones isolated from human genomic DNA matched with the sequence obtained from database.

h. hRUP15 (Seq. Id. Nos. 15 & 16)

The disclosed human hRUP15 was identified based upon the use of the GenBank database information. While searching the database, a cDNA clone with Accession Number AC016468 was identified as a human genomic sequence. The full length hRUP15 was cloned by PCR using primers:

```
5'-GCTGTTGCCATGACGTCCACCTGCAC-3' (SEQ. ID. NO.:55; sense)

5'-GGACAGTTCAAGGTTTGCCTTAGAAC-3' (SEQ. ID. NO.:56; antisense)
```

and human genomic DNA (Promega) as a template. Taq Plus Precision polymerase (Stratagene) was used for the amplification by the following cycle with step 2 to 4 repeated 35 times: 94° C. for 3 minute; 94° C. for 20 seconds; 65° C. for 20 seconds; 72° C. for 2 minutes and 72° C. for 7 minutes.

A 1.5 Kb PCR fragment was isolated and cloned into the pCRII-TOPO vector (Invitrogen) and completely sequenced using the ABI Big Dye Terminator kit (P.E. Biosystems). See, SEQ.ID.NO.:15 for nucleic acid sequence and SEQ.ID.NO.:16 for deduced amino acid sequence. The sequence of hRUP15 clones isolated from human genomic DNA matched with the sequence obtained from database.

i. hRUP16 (Seq. Id. Nos. 17 & 18)

The disclosed human hRUP16 was identified based upon the use of the GenBank database information. While searching the database, a cDNA clone with Accession Number AL136106 was identified as a human genomic sequence from chromosome 13. The full length hRUP16 was cloned by PCR using primers:

```
5'-CTTTCGATACTGCTCCTATGCTC-3',    (SEQ. ID. NO.:57; sense, 5' of initiation codon)

5'-GTAGTCCACTGAAAGTCCAGTGATCC-3' (SEQ. ID. NO.:58; antisense, 3' of stop codon)
```

and human skeletal muscle Marathon-Ready cDNA (Clontech) as template. Advantage cDNA polymerase (Clontech) was used for the amplification in a 50ul reaction by the following cycle with step 2 to 4 repeated 35 times: 94° C. for 30 seconds; 94° C. for 5 seconds; 69° C. for 15 seconds; 72° C. for 1 minute and 72° C. for 5 minutes.

A 1.1 Kb PCR fragment was isolated and cloned into the pCRII-TOPO vector (Invitrogen) and completely sequenced using the T7 Sequenase kit (Amersham). See, SEQ.ID.NO.:17 for nucleic acid sequence and SEQ.ID.NO.:18 for deduced amino acid sequence. The sequence of hRUP16 clones matched with four unordered segments of AL136106, indicating that the hRUP16 cDNA is composed of 4 exons.

j. hRUP17 (Seq. Id. Nos. 19 & 20)

The disclosed human hRUP17 was identified based upon the use of the GenBank database information. While searching the database, a cDNA clone with Accession Number AC023078 was identified as a human genomic sequence from chromosome 11. The full length hRUP17 was cloned by PCR using primers:

5'-TTTCTGAGCATGGATCCAACCATCTC-3' (SEQ. ID. NO.:59; sense, containing initiation codon)

5'-CTGTCTGACAGGGCAGAGGCTCTTC-3' (SEQ. ID. NO.:60; antisense, 3' of stop codon)

and human genomic DNA (Promega) as template. Advantage cDNA polymerase mix (Clontech) was used for the amplification in a 100 μl reaction with 5% DMSO by the following cycle with step 2 to 4 repeated 30 times: 94° C. for 1 min; 94° C. for 15 sec; 67° C. for 20 sec; 72° C. for 1 min and 30 sec; and 72° C. for 5 min.

A 970 bp PCR fragment was isolated from a 1% agarose gel and cloned into the pCRII-TOPO vector (Invitrogen) and completely sequenced using the ABI Big Dye Termiantor Kit (P.E. Biosystems). See, SEQ.ID.NO.:19 for nucleic acid sequence and SEQ.ID.NO.:20 for deduced amino acid sequence.

k. hRUP18 (Seq. Id. Nos. 21 & 22)

The disclosed human hRUP18 was identified based upon the use of the GenBank database information. While searching the database, a cDNA clone with Accession Number AC008547 was identified as a human genomic sequence from chromosome 5. The full length hRUP 18 was cloned by PCR using primers:

5'-GGAACTCGTATAGACCCAGCGTCGCTCC-3', (SEQ. ID. NO.:61; sense, 5' of the initiation codon)

5'GGAGGTTGCGCCTTAGCGACAGATGACC-3' (SEQ. ID. NO.:62; antisense, 3' of stop codon)

and human genomic DNA (Promega) as template. TaqPlus precision DNA polymerase (Stratagene) was used for the amplification in a 100 μl reaction with 5% DMSO by the following cycle with step 2 to 4 repeated 35 times: 95° C. for 5 min; 95° C. for 30 sec; 65° C. for 30 sec; 72° C. for 2 min; and 72° C. for 5 min.

A 1.3 kb PCR fragment was isolated from a 1% agarose gel and cloned into the pCRII-TOPO vector (Invitrogen) and completely sequenced using the ABI Big Dye Termiantor Kit (P.E. Biosystems). See, SEQ.ID.NO.:21 for nucleic acid sequence and SEQ.ID.NO.:22 for deduced amino acid sequence.

l. hRUP19 (Seq. Id. Nos. 23 & 24)

The disclosed human hRUP19 was identified based upon the use of the GenBank database information. While searching the database, a cDNA clone with Accession Number AC026331 was identified as a human genomic sequence from chromosome 12. The full length hRUP19 was cloned by PCR using primers:

5'-CTGCACCCGGACACTTGCTCTG-3', (SEQ. ID. NO.:63; sense, 5' of initiation codon)

5'-GTCTGCTTGTTCAGTGCCACTCAAC-3' (SEQ. ID. NO.:64; antisense, containing the stop codon)

and human genomic DNA (Promega) as template. TaqPlus Precision DNA polymerase (Stratagene) was used for the amplification with 5% DMSO by the following cycle with step 2 to 4 repeated 35 times: 94° C. for 1 min; 94° C. for 15 sec; 70° C. for 20 sec; 72° C. for 1 min and 30 sec; and 72° C. for 5 min.

A 1.1 kp PCR fragment was isolated from a 1% agarose gel and cloned into the pCRII-TOPO vector (Invitrogen) and completely sequenced using the ABI Big Dye Terminator Kit (P.E. Biosystems). See, SEQ.ID.NO.:23 for nucleic acid sequence and SEQ.ID.NO.:24 for deduced amino acid sequence.

m. hRUP20 (Seq. Id. Nos. 25 & 26)

The disclosed human hRUP20 was identified based upon the use of the GenBank database information. While searching the database, a cDNA clone with Accession Number AL161458 was identified as a human genomic sequence from chromosome 1. The full length hRUP20 was cloned by PCR using primers:

```
5'-TATCTGCAATTCTATTCTAGCTCCTG-3',  (SEQ. ID. NO.:65; sense, 5' of initiation codon)

5'-TGTCCCTAATAAAGTCACATGAATGC-3'   (SEQ. ID. NO.:66; antisense, 3' of stop codon)
```

and human genomic DNA (Promega) as template. Advantage cDNA polymerase mix (Clontech) was used for the amplification with 5% DMSO by the following cycle with step 2 to 4 repeated 35 times: 94° C. for 1 min; 94° C. for 15 sec; 60° C. for 20 sec; 72° C. for 1 min and 30 sec; and 72° C. for 5 min.

A 1.0 kp PCR fragment was isolated from a 1% agarose gel and cloned into the pCRII-TOPO vector (Invitrogen) and completely sequenced using the ABI Big Dye Terminator Kit (P.E. Biosystems). See, SEQ.ID.NO.:25 for nucleic acid sequence and SEQ.ID.NO.:26 for deduced amino acid sequence.

n. hRUP21 (Seq. Id. Nos. 27 & 28)

The disclosed human hRUP21 was identified based upon the use of the GenBank database information. While searching the database, a cDNA clone with Accession Number AC026756 was identified as a human genomic sequence from chromosome 13. The full length hRUP21 was cloned by PCR using primers:

```
5'-GGAGACAACCATGAATGAGCCAC-3'   (SEQ. ID. NO.:67; sense)

5'-TATTTCAAGGGTTGTTTGAGTAAC-3'  (SEQ. ID. NO.:68; antisense)
```

and human genomic DNA (Promega) as template. Taq Plus Precision polymerase (Stratagene) was used for the amplification in a 100 μl a reaction with 5% DMSO by the following cycle with step 2 to 4 repeated 30 times: 94° C. for 1 min; 94° C. for 15 sec; 55° C. for 20 sec; 72° C. for 1 min and 30 sec; and 72° C. for 5 min.

A 1,014 bp PCR fragment was isolated from a 1% agarose gel and cloned into the pCRII-TOPO vector (Invitrogen) and completely sequenced using the ABI Big Dye Terminator Kit (P.E. Biosystems). See, SEQ.ID.NO.:27 for nucleic acid sequence and SEQ.ID.NO.:28 for deduced amino acid sequence.

o. hRUP22 (Seq. Id. Nos. 29 & 30)

The disclosed human hRUP22 was identified based upon the use of the GenBank database information. While searching the database, a cDNA clone with Accession Number AC027026 was identified as a human genomic sequence from chromosome 11. The full length hRUP22 was cloned by PCR using primers:

```
5'-GGCACCAGTGGAGGTTTTCTGAGCATG-3'  (SEQ. ID. NO.:69; sense, containing initiation codon)

5'-CTGATGGAAGTAGAGGCTGTCCATCTC-3'  (SEQ. ID. NO.:70; antisense, 3' of stop codon)
```

and human genomic DNA (Promega) as template. TaqPlus Precision DNA polymerase (Stratagene) was used for the amplification in a 100 μl reaction with 5% DMSO by the following cycle with step 2 to 4 repeated 30 times: 94° C., 1 minutes 94° C., 15 seconds 55° C., 20 seconds 72° C., 1.5 minute 72° C. 5 minutes.

A 970 bp PCR fragment was isolated from a 1% agarose gel and cloned into the pCRII-TOPO vector (Invitrogen) and completely sequenced using the ABI Big Dye Terminator Kit (P.E. Biosystems). See, SEQ.ID.NO.:29 for nucleic acid sequence and SEQ.ID.NO.:30 for deduced amino acid sequence.

p. hRUP23 (Seq. Id. Nos. 31 & 32)

The disclosed human hRUP23 was identified based upon the use of the GenBank database information. While searching the database, a cDNA clone with Accession Number AC007104 was identified as a human genomic sequence from chromosome 4. The full length hRUP23 was cloned by PCR using primers:

```
5'-CCTGGCGAGCCGCTAGCGCCATG-3', (SEQ. ID. NO.:71; sense, ATG as the initiation codon)

5'-ATGAGCCCTGCCAGGCCCTCAGT-3'  (SEQ. ID. NO.:72; antisense, TCA as the stop codon)
```

and human placenta Marathon-Ready cDNA (Clontech) as template. Advantage cDNA polymerase (Clontech) was used for the amplification in a 50 ul reaction by the following cycle with step 2 to 4 repeated 35 times: 95° C. for 30 sec; 95° C. for 15 sec; 66° C. for 20 sec; 72° C. for 1 min and 20 sec; and 72° C. for 5 min.

A 1.0 kb PCR fragment was isolated and cloned into the pCRII-TOPO vector (Invitrogen) and completely sequenced using the ABI Big Dye Terminator Kit (P.E. Biosystems). See, SEQ.ID.NO.:31 for nucleic acid sequence and SEQ.ID.NO.:32 for deduced amino acid sequence.

q. hRUP24 (Seq. Id. Nos. 33 & 34)

The disclosed human hRUP24 was identified based upon the use of the GenBank database information. While searching the database, a cDNA clone with Accession Number AL355388 was identified as a human genomic sequence from chromosome 1. The full length hRUP24 was cloned by PCR using primers:

```
5'-CTGCGATGCCCACACTCAATACTTCTG-3', (SEQ. ID. NO.:73; sense, 5' of initiation codon)

5'-AAGGATCCTACACTTGGTGGATCTCAG-3'  (SEQ. ID. NO.:74; antisense, 3' of stop codon)
```

- and human genomic DNA (Promega) as template. Advantage cDNA polymerase mix (Clontech) was used for the amplification with 5% DMSO by the following cycle with step 2 to 4 repeated 35 times: 94° C. for 1 minute; 94° C. for 15 seconds; 56° C. for 20 seconds 72° C. for 1 minute 30 seconds and 72° C. for 5 minutes.

A 1.2 kb PCR fragment was isolated from a 1% agarose gel and cloned into the pCRII-TOPO vector (Invitrogen) and completely sequenced using the ABI Big Dye Terminator Kit (P.E. Biosystems). See, SEQ.ID.NO.:33 for nucleic acid sequence and SEQ.ID.NO.:34 for deduced amino acid sequence.

r. hRUP25 (Seq. Id. Nos. 35 & 36)

The disclosed human hRUP25 was identified based upon the use of the GenBank database information. While searching the database, a cDNA clone with Accession Number AC026331 was identified as a human genomic sequence from chromosome 12. The full length hRUP25 was cloned by PCR using primers:

```
5'-GCTGGAGCATTCACTAGGCGAG-3',   (SEQ. ID. NO.:75; sense, 5' of initiation codon)

5'-AGATCCTGGTTCTTGGTGACAATG-3'  (SEQ. ID. NO.:76; antisense, 3' of stop codon)
```

- and human genomic DNA (Promega) as template. Advantage cDNA polymerase mix (Clontech) was used for the amplification with 5% DMSO by the following cycle with step 2 to 4 repeated 35 times: 94° C. for 1 minute; 94° C. for 15 seconds; 56° C. for 20 seconds 72° C. for 1 minute 30 seconds and 72° C. for 5 minutes.

A 1.2 kb PCR fragment was isolated from a 1% agarose gel and cloned into the pCRII-TOPO vector (Invitrogen) and completely sequenced using the ABI Big Dye Terminator Kit (P.E. Biosystems). See, SEQ.ID.NO.:35 for nucleic acid sequence and SEQ.ID.NO.:36 for deduced amino acid sequence.

s. hRUP26 (Seq. Id. Nos. 37 & 38)

The disclosed human hRUP26 was identified based upon the use of GenBank database information. While searching the database, a cDNA clone with Accession Number AC023040 was identified as a human genomic sequence from chromosome 2. The full length hRUP26 was cloned by RT-PCR using hRUP26 specific primers:

5'-AGCCATCCCTGCCAGGAAGCATGG-3' (SEQ. ID. NO.:77; sense, containing initiation codon)

5'-CCAGACTGTGGACTCAAGAACTCTAGG-3' (SEQ. ID. NO.:78; antisense, containing stop codon)

and human pancreas Marathon-Ready cDNA (Clontech) as template. Advantage cDNA polymerase mix (Clontech) was used for the amplification in a 100 $\mu l$ reaction with 5% DMSO by the following cycle with step 2 to 4 repeated 35 times: 94° C. for 5 minute; 95° C. for 30 seconds; 65° C. for 30 seconds 72° C. for 2 minute and 72° C. for 5 minutes.

A 1.1 kb PCR fragment was isolated from 1% agarose gel and cloned into the pCRII-TOPO vector (Invitrogen) and completely sequenced using the ABI Big Dye Terminator Kit (P.E. Biosystems). See, SEQ.ID.NO.:37 for nucleic acid sequence and SEQ.ID.NO.:38 for deduced amino acid sequence.

t. hRUP27 (Seq. Id. Nos. 39 & 40)

The disclosed human hRUP27 was identified based upon the use of GenBank database information. While searching the database, a cDNA clone with Accession Number AC027643 was identified as a human genomic sequence from chromosome 12. The full length hRUP27 was cloned by PCR using hRUP27 specific primers:

5'-AGTCCACGAACAATGAATCCATTTCATG-3', (SEQ. ID. NO.:79; sense, containing initiation codon)

5'-ATCATGTCTAGACTCATGGTGATCC-3' (SEQ. ID. NO.:80; antisense, 3' of stop codon)

and the human adult brain Marathon-Ready cDNA (Clontech) as template. Advantage cDNA polymerase mix (Clontech) was used for the amplification in a 50 $\mu l$ reaction with 5% DMSO by the following cycle with step 2 to 4 repeated 35 times: 94° C. for 1 minute; 94° C. for 10 seconds; 58° C. for 20 seconds 72° C. for 1 minute 30 seconds and 72° C. for 5 minutes.

A 1.1 kb PCR fragment was isolated from 1% agarose gel and cloned into the pCRII-TOPO vector (Invitrogen) and completely sequenced using the ABI Big Dye Terminator Kit (P.E. Biosystems). See, SEQ.ID.NO.:35 for nucleic acid sequence and SEQ.ID.NO.:36 for deduced amino acid sequence. The sequence of hRUP27 cDNA clone isolated from human brain was determined to match with five unordered segments of AC027643, indicating that the hRUP27 cDNA is composed of 5 exons.

a. hRUP38 (Seq. Id. Nos. 134 & 135)

The disclosed human hRUP38 was identified based upon the use of GenBank database information. While searching the database, a cDNA clone was identified as a human genomic sequence from chromosome 12. The full length hRUP38 was cloned by PCR using hRUP38 specific primers:

5'-GCACTCATGAATCGGCACCA-3', (SEQ. ID. NO.:148; sense, containing initiation codon)

5'-CAGTGACATTACTCGATGCA-3' (SEQ. ID. NO.:149; antisense, 3' of stop codon)

and human genomic DNA (Promega) as template. Advantage cDNA polymerase mix (Clontech) was used for the amplification in a 50 $\mu l$ reaction with 5% DMSO by the following cycle with step 2 to 4 repeated 35 times: 94° C. for 1 minute; 94° C. for 10 seconds; 60° C. for 20 seconds 72° C. for 1 minute 30 seconds and 72° C. for 5 minutes.

A 1.2 kb PCR fragment was isolated from 1% agarose gel and cloned into the pCRII-TOPO vector (Invitrogen) and completely sequenced using the ABI Big Dye Terminator Kit (P.E. Biosystems). See, SEQ.ID.NO.:134 for nucleic acid sequence and SEQ.ID.NO.:135 for deduced amino acid sequence. The sequence of hRUP38 DNA clone isolated from human genomic DNA was determined to match with one genomic sequence on chromosome 12 and is without introns.

B. Endogenous Mouse and Rat GPCRS

1. Identification of Mouse and Rat GPCRs

The mouse and rat orthologs of hRUP25 and the mouse ortholog of hRUP19 have been identified and are disclosed below as determined from genomic sequence. The rat ortholog of hRUP19 has also been identified (PCT Application Number PCT/US02/04397, published as WO 02/83736 on Oct. 24, 2002; said disclosure is hereby incorporated by reference in its entirety) and is provided below.

Evidence to date suggests that there is no mouse or rat ortholog of hRUP38. As the hRUP25 polynucleotide sequence is about 95% identical to hRUP38 polynucleotide sequence, as hRUP25 and hRUP38 are found on the same arm of chromosome 12, and as an hRUP38 ortholog is absent from rodents, one may hypothesize without wishing to be bound by theory that hRUP38 was the product of gene duplication. This event must have happened subsequent to the divergence of human from rodents. Possibly hRUP38 represents a novel antilipolytic regulatory pathway for which there is no counterpart in rodent.

Evidence to date suggests that there may also be no mouse or rat ortholog of hRUP11.

TABLE F

| Disclosed Mouse (m) and Rat (r) GPCRs | Accession Number Identified | Complete DNA Sequence (Base Pairs) | Open Reading Frame (Base Pairs) | Nucleic Acid SEQ. ID. NO. | Amino Acid SEQ. ID. NO. |
|---|---|---|---|---|---|
| mRU25 | AJ300199 | — | 1,083bp | 136 | 137 |
| rRUP25 | None | — | 1,086bp | 138 | 139 |
| mRUP19 | XM_144529 | — | 1,032bp | 150 | 151 |
| rRUP19 | None | — | 1,056bp | 156 | 157 |

2. Full Length Cloning a. mRUP25 (Seq. Id. Nos. 136 & 137)

In order to clone the open reading frame encoding the mouse RUP25 receptor we applied a PCR based cloning strategy. Primers were designed and synthesized based on the start and stop codon sequence of the mouse PUMA-g sequence, published on Genbank, and used on mouse genomic DNA (Promega). The PCR primers were as follows:

```
5'-ATGAGCAAGTCAGACCATTTTCTAGTGATA-3' (SEQ. ID. NO.:140; sense)

5'-TTATCTGGCTTCCACATCTCGTTAA-3'      (SEQ. ID. NO.:141; antisense)
```

Advantage cDNA polymerase mix (Clontech) was used for the amplification with 5% DMSO by the following cycle with step 2 to 4 repeated 35 times: 94° C. for 1 minute; 94° C. for 15 seconds; 56° C. for 20 seconds 72° C. for 1 minute 30 seconds and 72° C. for 5 minutes.

A 1.2 kb PCR fragment was isolated from a 1% agarose gel and cloned into the pCRII-TOPO vector (Invitrogen) and completely sequenced using the ABI Big Dye Terminator Kit (P.E. Biosystems). See, SEQ.ID.NO.:35 for nucleic acid sequence and SEQ.ID.NO.:36 for deduced amino acid sequence.

b. rRUP25 (Seq. Id. Nos. 138 & 139)

The rat RUP25 receptor was cloned in an analogous fashion, however this was done assuming the sequence would be similar to the mouse sequence because there is no previously published rat sequence. Again, we applied a PCR based cloning strategy. Primers were designed and synthesized based on the start and stop codon sequence of the mouse PUMA-g sequence, published on Genbank, and used on rat genomic DNA (Promega). The PCR primers were as follows:

```
5'-ATGAGCAAGTCAGACCATTTTCTAGTGATA-3' (SEQ. ID. NO.:142; sense)

5'-TTATCTGGCTTCCACATCTCGTTAA-3'      (SEQ. ID. NO.:143; antisense)
```

Cloned Pfu polymerase was used for the amplification by the following cycle with step 2 to 4 repeated 35 times: 94° C. for 1 minute; 94° C. for 30sec; 55° C. for 1 min; 72° C. for 2 min; and a final extension at 72° C. for 10 minutes.

A 1.2 kb PCR fragment was isolated from a 1% agarose gel and cloned into the pCRII-TOPO vector (Invitrogen) and 12 clones were completely sequenced using the ABI Big Dye Terminator Kit (P.E. Biosystems).

Example 2

Preparation of Non-Endogenous, Constitutively Activated GPCRS

Those skilled in the art are credited with the ability to select techniques for mutation of a nucleic acid sequence. Presented below are approaches utilized to create non-endogenous versions of several of the human GPCRs disclosed above. The mutations disclosed below are based upon an algorithmic approach whereby the 16$^{th}$ amino acid (located in the IC3 region of the GPCR) from a conserved proline (or an endogenous, conservative substitution therefor) residue (located in the TM6 region of the GPCR, near the TM6/IC3 interface) is mutated, preferably to an alanine, histimine, arginine or lysine amino acid residue, most preferably to a lysine amino acid residue.

1. Transformer Site-Directed™ Mutagenesis

Preparation of non-endogenous human GPCRs may be accomplished on human GPCRs using, inter alia, Transformer Site-Directed™ Mutagenesis Kit (Clontech) according to the manufacturer instructions. Two mutagenesis primers are utilized, most preferably a lysine mutagenesis oligonucleotide that creates the lysine mutation, and a selection marker oligonucleotide. For convenience, the codon mutation to be incorporated into the human GPCR is also noted, in standard form (Table G):

TABLE G

| Receptor Identifier | Codon Mutation |
|---|---|
| hRUP8 | V274K |
| hRUP9 | T249K |
| hRUP10 | R232K |
| hRUP11 | M294K |
| hRUP12 | F220K |
| hRUP16 | A238K |
| hRUP17 | Y215K |
| hRUP18 | L294K |
| hRUP19 | T219K |
| hRUP20 | K248A |
| | K248H |
| | K248R |
| hRUP21 | R240K |
| hRUP22 | Y222K |
| hRUP24 | A245K |
| hRUP25 | I230K |
| hRUP26 | V285K |
| hRUP27 | T248K |

2. QuikChange™ Site-Directed™ Mutagenesis

Preparation of non-endogenous human GPCRs can also be accomplished by using QuikChange™ Site-Directed™ Mutagenesis Kit (Stratagene, according to manufacturer's instructions). Endogenous GPCR is preferably used as a template and two mutagenesis primers utilized, as well as, most preferably, a lysine mutagenesis oligonucleotide and a selection marker oligonucleotide (included in kit). For convenience, the codon mutation incorporated into the novel human GPCR and the respective oligonucleotides are noted, in standard form (Table H):

TABLE H

| Receptor Identifier | Codon Mutation | 5'-3' orientation (sense), (SEQ. ID. NO.) mutation underlined | 5'-3' orientation (antisense) (SEQ. ID. NO.) | Cycle Conditions Min ('), Sec (") Cycles 2–4 repeated 16 times |
|---|---|---|---|---|
| hRUP13 | A268K | GGGGAGGGAAAGCA<br>AAGGTGGTCCTCCTG<br>G (81) | CCAGGAGAACCACC<br>TTTGCTTTCCCTCCC<br>C (82) | 98° for 2'<br>98° for 30"<br>56° C. for 30"<br>72° for 11' 40"<br>72° for 5' |
| hRUP14 | L246K | CAGGAAGGCAAAGA<br>CCACCATCATCATC<br>(85) | GATGATGATGGTGG<br>TCTTTGCCTTCCTG<br>(86) | 98° for 2'<br>98° for 30"<br>55° C. for 30"<br>72° for 11' 40"<br>72° for 5' |
| hRUP15 | A398K | CCAGTGCAAAGCTA<br>AGAAAGTGATCTTC<br>(89) | GAAGATCACTTTCT<br>TAGCTTTGCACTGG<br>(90) | 98° for 2'<br>98° for 30"<br>55° C. for 30"<br>72° for 11' 40"<br>72° for 5' |
| hRUP23 | W275K | GCCGCCACCGCGCC<br>AAGAGGAAGATTGG<br>C (93) | GCCAATCTTCCTCTT<br>GGCGCGGTGGCGGC<br>(94) | 98° for 2'<br>98° for 30"<br>56° C. for 30"<br>72° for 11' 40"<br>72° for 5' |

The non-endogenous human GPCRs were then sequenced and the derived and verified nucleic acid and amino acid sequences are listed in the accompanying "Sequence Listing" appendix to this patent document, as summarized in Table I below:

TABLE I

| Non Endogenous Human GPCR | Nucleic Acid Sequence Listing | Amino Acid Sequence Listing |
|---|---|---|
| hRUP13 | SEQ. ID. NO.: 83 | SEQ. ID. NO.: 84 |
| hRUP14 | SEQ. ID. NO.: 87 | SEQ. ID. NO.: 88 |
| hRUP15 | SEQ. ID. NO.: 91 | SEQ. ID. NO.: 92 |
| hRUP23 | SEQ. ID. NO.: 95 | SEQ. ID. NO. :96 |

Example 3

Receptor Expression

Although a variety of cells are available to the art for the expression of proteins, it is most preferred that mammalian cells be utilized. The primary reason for this is predicated upon practicalities, i.e., utilization of, e.g., yeast cells for the expression of a GPCR, while possible, introduces into the protocol a non-mammalian cell which may not (indeed, in the case of yeast, does not) include the receptor-coupling, genetic-mechanism and secretary pathways that have evolved for mammalian systems—thus, results obtained in non-mammalian cells, while of potential use, are not as preferred as that obtained from mammalian cells. Of the mammalian cells, COS-7, 293 and 293T cells are particularly preferred, although the specific mammalian cell utilized can be predicated upon the particular needs of the artisan.

a. Transient Transfection

On day one, $6\times10^6$/10 cm dish of 293 cells well were plated out. On day two, two reaction tubes were prepared (the proportions to follow for each tube are per plate): tube A was prepared by mixing 4 $\mu$g DNA (e.g., pCMV vector; pCMV vector with receptor cDNA, etc.) in 0.5 ml serum free DMEM (Gibco BRL); tube B was prepared by mixing 24 $\mu$l lipofectamine (Gibco BRL) in 0.5 ml serum free DMEM. Tubes A and B were admixed by inversions (several times), followed by incubation at room temperature for 30–45 min. The admixture is referred to as the "transfection mixture". Plated 293 cells were washed with 1×PBS, followed by addition of 5 ml serum free DMEM. 1 ml of the transfection mixture was added to the cells, followed by incubation for 4hrs at 37° C./5% $CO_2$. The transfection mixture was removed by aspiration, followed by the addition of 10 ml of DMEM/10% Fetal Bovine Serum. Cells were incubated at 37° C./5% $CO_2$. After 48 hr incubation, cells were harvested and utilized for analysis.

b. Stable Cell Lines: Gs Fusion Protein

Approximately 12x10$^6$ 293 cells are plated on a 15 cm tissue culture plate. Grown in DME High Glucose Medium containing ten percent fetal bovine serum and one percent sodium pyruvate, L-glutamine, and antibiotics. Twenty-four hours following plating of 293 cells (or to ~80% confluency), the cells are transfected using 12 μg of DNA. The 12 μg of DNA is combined with 60 μl of lipofectamine and 2 mL of DME High Glucose Medium without serum. The medium is aspirated from the plates and the cells are washed once with medium without serum. The DNA, lipofectamine, and medium mixture are added to the plate along with 10 mL of medium without serum. Following incubation at 37 degrees Celsius for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of 500 μg/mL. The transfected cells now undergo selection for positively transfected cells containing the G418 resistant gene. The medium is replaced every four to five days as selection occurs. During selection, cells are grown to create stable pools, or split for stable clonal selection.

Example 4

Assays for Determination of Constitutive Activity of Non-Endogenous GPCRS

A variety of approaches are available for assessment of constitutive activity of the non-endogenous human GPCRs. The following are illustrative; those of ordinary skill in the art are credited with the ability to determine those techniques that are preferentially beneficial for the needs of the artisan.

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Constitutively activated receptors continue to exchange GDP for GTP. The non-hydrolyzable GTP analog, [$^{35}$S]GTPγS, can be utilized to demonstrate enhanced binding of [$^{35}$S]GTPγS to membranes expressing constitutively activated receptors. The advantage of using [$^{35}$S]GTPγS binding to measure constitutive activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay can, therefore, be used in the direct identification method to screen candidate compounds to known, orphan and constitutively activated G protein-coupled receptors. The assay is generic and has application to drug discovery at all G protein-coupled receptors.

The [$^{35}$S]GTPγS assay was incubated in 20 mM HEPES and between 1 and about 20 mM $MgCl_2$ (this amount can be adjusted for optimization of results, although 20 mM is preferred) pH 7.4, binding buffer with between about 0.3 and about 1.2 nM [$^{35}$S]GTPγS (this amount can be adjusted for optimization of results, although 1.2 is preferred ) and 12.5 to 75 μg membrane protein (e.g, 293 cells expressing the Gs Fusion Protein; this amount can be adjusted for optimization) and 10 μM GDP (this amount can be changed for optimization) for 1 hour. Wheatgerm agglutinin beads (25 μl; Amersham) were then added and the mixture incubated for another 30 minutes at room temperature. The tubes were then centrifuged at 1500×g for 5 minutes at room temperature and then counted in a scintillation counter.

2. Adenylyl Cyclase

A Flash Plate™ Adenylyl Cyclase kit (New England Nuclear; Cat. No. SMP004A) designed for cell-based assays can be modified for use with crude plasma membranes. The Flash Plate wells can contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells were harvested approximately twenty four hours after transient transfection. Media is carefully aspirated off and discarded. 10 ml of PBS is gently added to each dish of cells followed by careful aspiration. 1 ml of Sigma cell dissociation buffer and 3 ml of PBS are added to each plate. Cells were pipetted off the plate and the cell suspension was collected into a 50 ml conical centrifuge tube. Cells were then centrifuged at room temperature at 1,100 rpm for 5 min. The cell pellet was carefully re-suspended into an appropriate volume of PBS (about 3 ml/plate). The cells were then counted using a hemocytometer and additional PBS was added to give the appropriate number of cells (with a final volume of about 50 μl/well).

cAMP standards and Detection Buffer (comprising 1 μCi of tracer [$^{125}$I cAMP (50 μl] to 11 ml Detection Buffer) was prepared and maintained in accordance with the manufacturer's instructions. Assay Buffer was prepared fresh for screening and contained 50 μl of Stimulation Buffer, 3 ul of test compound (12 μM final assay concentration) and 50 μl cells, Assay Buffer was stored on ice until utilized. The assay was initiated by addition of 50 μl of cAMP standards to appropriate wells followed by addition of 50 ul of PBSA to wells H-11 and H12. 50 μl of Stimulation Buffer was added to all wells. DMSO (or selected candidate compounds) was added to appropriate wells using a pin tool capable of dispensing 3 μl of compound solution, with a final assay concentration of 12 μM test compound and 100 μl total assay volume. The cells were then added to the wells and incubated for 60 min at room temperature. 100 μl of Detection Mix containing tracer cAMP was then added to the wells. Plates were then incubated additional 2 hours followed by counting in a Wallac MicroBeta scintillation counter. Values of cAMP/well were then extrapolated from a standard cAMP curve which was contained within each assay plate.

3. Cell-Based cAMP for Gi Coupled Target GPCRs

TSHR is a Gs coupled GPCR that causes the accumulation of cAMP upon activation. TSHR will be constitutively activated by mutating amino acid residue 623 (i.e., changing an alanine residue to an isoleucine residue). A Gi coupled receptor is expected to inhibit adenylyl cyclase, and, therefore, decrease the level of cAMP production, which can make assessment of cAMP levels challenging. An effective technique for measuring the decrease in production of cAMP as an indication of constitutive activation of a Gi coupled receptor can be accomplished by co-transfecting, most preferably, non-endogenous, constitutively activated TSHR (TSHR-A623I) (or an endogenous, constitutively active Gs coupled receptor) as a "signal enhancer" with a Gi linked target GPCR to establish a baseline level of cAMP. Upon creating a non-endogenous version of the Gi coupled receptor, this non-endogenous version of the target GPCR is then co-transfected with the signal enhancer, and it is this material that can be used for screening. We will utilize such approach to effectively generate a signal when a cAMP assay is used; this approach is preferably used in the direct identification of candidate compounds against Gi coupled receptors. It is noted that for a Gi coupled GPCR, when this approach is used, an inverse agonist of the target GPCR will increase the cAMP signal and an agonist will decrease the cAMP signal.

On day one, $2\times10^4$ 293 cells/well will be plated out. On day two, two reaction tubes will be prepared (the proportions to follow for each tube are per plate): tube A will be prepared by mixing 2 μg DNA of each receptor transfected into the mammalian cells, for a total of 4 μg DNA (e.g., pCMV vector; pCMV vector with mutated THSR (TSHR-A623I); TSHR-A623I and GPCR, etc.) in 1.2 ml serum free DMEM (Irvine Scientific, Irvine, Calif.); tube B will be prepared by mixing 120 μl lipofectamine (Gibco BRL) in 1.2 ml serum free DMEM. Tubes A and B will then be admixed by inversions (several times), followed by incubation at room temperature for 30–45 min. The admixture is referred to as the "transfection mixture". Plated 293 cells will be washed with 1×PBS, followed by addition of 10 ml serum free DMEM. 2.4 ml of the transfection mixture will then be added to the cells, followed by incubation for 4 hrs at 37° C./5% $CO_2$. The transfection mixture will then be removed by aspiration, followed by the addition of 25 ml of DMEM/10% Fetal Bovine Serum. Cells will then be incubated at 37° C./5% $CO_2$. After 24 hr incubation, cells will then be harvested and utilized for analysis.

A Flash Plate™ Adenylyl Cyclase kit (New England Nuclear; Cat. No. SMP004A) is designed for cell-based assays, however, can be modified for use with crude plasma membranes depending on the need of the skilled artisan. The Flash Plate wells will contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells will be harvested approximately twenty four hours after transient transfection. Media will be carefully aspirated off and discarded. 10 ml of PBS will be gently added to each dish of cells followed by careful aspiration. 1 ml of Sigma cell dissociation buffer and 3 ml of PBS will be added to each plate. Cells will be pipetted off the plate and the cell suspension will be collected into a 50 ml conical centrifuge tube. Cells will then be centrifuged at room temperature at 1,100 rpm for 5 min. The cell pellet will be carefully re-suspended into an appropriate volume of PBS (about 3 ml/plate). The cells will then be counted using a hemocytometer and additional PBS is added to give the appropriate number of cells (with a final volume of about 50 μl/well).

cAMP standards and Detection Buffer (comprising 1 μCi of tracer [$^{125}$I cAMP (50 μl] to 11 ml Detection Buffer) will be prepared and maintained in accordance with the manufacturer's instructions. Assay Buffer should be prepared fresh for screening and contained 50 μl of Stimulation Buffer, 3 μl of test compound (12 μM final assay concentration) and 50 μl cells, Assay Buffer can be stored on ice until utilized. The assay can be initiated by addition of 50 μl of cAMP standards to appropriate wells followed by addition of 50 μl of PBSA to wells H-11 and H12. Fifty μl of Stimulation Buffer will be added to all wells. Selected compounds (e.g., TSH) will be added to appropriate wells using a pin tool capable of dispensing 3 μl of compound solution, with a final assay concentration of 12 μM test compound and 100 μl total assay volume. The cells will then be added to the wells and incubated for 60 min at room temperature. 100 μl of Detection Mix containing tracer cAMP will then be added to the wells. Plates were then incubated additional 2 hours followed by counting in a Wallac MicroBeta scintillation counter. Values of cAMP/well will then be extrapolated from a standard cAMP curve which is contained within each assay plate.

4. Reporter-Based Assays a. CRE-LUC Reporter Assay (Gs-Associated Receptors)

293 and 293T cells are plated-out on 96 well plates at a density of $2\times10^4$ cells per well and were transfected using Lipofectamine Reagent (BRL) the following day according to manufacturer instructions. A DNA/lipid mixture is prepared for each 6-well transfection as follows: 260 ng of plasmid DNA in 100 μl of DMEM were gently mixed with 2 μl of lipid in 100 μl of DMEM (the 260 ng of plasmid DNA consisted of 200 ng of a 8×CRE-Luc reporter plasmid, 50 ng of pCMV comprising endogenous receptor or non-endogenous receptor or pCMV alone, and 10 ng of a GPRS expression plasmid (GPRS in pcDNA3 (Invitrogen)). The 8×CRE-Luc reporter plasmid was prepared as follows: vector SRIF-β-gal was obtained by cloning the rat somatostatin promoter (−71/+51) at BglV-HindIII site in the pβgal-Basic Vector (Clontech). Eight (8) copies of cAMP response element were obtained by PCR from an adenovirus template AdpCF126CCRE8 (see, 7 *Human Gene Therapy* 1883 (1996)) and cloned into the SRIF-β-gal vector at the Kpn-BglV site, resulting in the 8×CRE-β-gal reporter vector. The 8×CRE-Luc reporter plasmid was generated by replacing the beta-galactosidase gene in the 8×CRE-β-gal reporter vector with the luciferase gene obtained from the pGL3-basic vector (Promega) at the HindIII-BamHI site. Following 30 min. incubation at room temperature, the DNA/lipid mixture was diluted with 400 μl of DMEM and 100 μl of the diluted mixture was added to each well. 100 μl of DMEM with 10% FCS were added to each well after a 4hr incubation in a cell culture incubator. The following day the transfected cells were changed with 200 μl/well of DMEM with 10% FCS. Eight (8) hours later, the wells were changed to 100 μl/well of DMEM without phenol red, after one wash with PBS. Luciferase activity were measured the next day using the LucLite™ reporter gene assay kit (Packard) following manufacturer instructions and read on a 1450 MicroBeta™ scintillation and luminescence counter (Wallac).

b. AP1 Reporter Assay (Gq-Associated Receptors)

A method to detect Gq stimulation depends on the known property of Gq-dependent phospholipase C to cause the activation of genes containing AP1 elements in their promoter. A Pathdetect™ AP-1 cis-Reporting System (Stratagene, Catalogue # 219073) can be utilized following the protocol set forth above with respect to the CREB reporter assay, except that the components of the calcium phosphate precipitate were 410 ng pAPI-Luc, 80 ng pCMV-receptor expression plasmid, and 20 ng CMV-SEAP.

c. SRF-Luc Reporter Assay (Gq-Associated Receptors)

One method to detect Gq stimulation depends on the known property of Gq-dependent phospholipase C to cause the activation of genes containing serum response factors in their promoter. A Pathdetect™ SRF-Luc-Reporting System (Stratagene) can be utilized to assay for Gq coupled activity in, e.g., COS7 cells. Cells are transfected with the plasmid components of the system and the indicated expression plasmid encoding endogenous or non-endogenous GPCR using a Mammalian Transfection™ Kit (Stratagene, Catalogue #200285) according to the manufacturer's instructions. Briefly, 410 ng SRF-Luc, 80 ng pCMV-receptor expression plasmid and 20 ng CMV-SEAP (secreted alkaline phosphatase expression plasmid; alkaline phosphatase activity is measured in the media of transfected cells to control for variations in transfection efficiency between samples) are combined in a calcium phosphate precipitate as per the manufacturer's instructions. Half of the precipitate is equally distributed over 3 wells in a 96-well plate, kept on the cells in a serum free media for 24 hours. The last 5 hours the cells are incubated with 1 $\mu$M Angiotensin, where indicated. Cells are then lysed and assayed for luciferase activity using a Luclite™ Kit (Packard, Cat. # 6016911) and "Trilux 1450 Microbeta" liquid scintillation and luminescence counter (Wallac) as per the manufacturer's instructions. The data can be analyzed using GraphPad Prism™ 2.0a (GraphPad Software Inc.).

d. Intracellular $IP_3$ Accumulation Assay (Gq-Associated Receptors)

On day 1, cells comprising the receptors (endogenous and/or non-endogenous) can be plated onto 24 well plates, usually $1\times10^5$ cells/well (although his umber can be optimized. On day 2 cells can be transfected by firstly mixing 0.25 $\mu$g DNA in 50 $\mu$l serum free DMEM/well and 2 $\mu$l lipofectamine in 50 $\mu$l serum free DMEM/well. The solutions are gently mixed and incubated for 15–30 min at room temperature. Cells are washed with 0.5 ml PBS and 400 $\mu$l of serum free media is mixed with the transfection media and added to the cells. The cells are then incubated for 3–4 hrs at 37° C./5% $CO_2$ and then the transfection media is removed and replaced with 1 ml/well of regular growth media. On day 3 the cells are labeled with $^3$H-myo-inositol. Briefly, the media is removed and the cells are washed with 0.5 ml PBS. Then 0.5 ml inositol-free/serum free media (GMBCO BRL) is added/well with 0.25 $\mu$Ci of $^3$H-myo-inositol/well and the cells are incubated for 16–18 hrs o/n at 37° C./5% $CO_2$. On Day 4 the cells are washed with 0.5 ml PBS and 0.45 ml of assay medium is added containing inositol-free/serum free media 10 $\mu$M pargyline 10 mM lithium chloride or 0.4 ml of assay medium and 50 $\mu$l of 10× ketanserin (ket) to final concentration of 10 $\mu$M. The cells are then incubated for 30 min at 37° C. The cells are then washed with 0.5 ml PBS and 200 $\mu$l of fresh/ice cold stop solution (1M KOH; 18 mM Na-borate; 3.8 mM EDTA) is added/well. The solution is kept on ice for 5–10 min or until cells were lysed and then neutralized by 200 $\mu$l of fresh/ice cold neutralization sol. (7.5% HCL). The lysate is then transferred into 1.5 ml eppendorf tubes and 1 ml of chloroform/methanol (1:2) is added/tube. The solution is vortexed for 15 sec and the upper phase is applied to a Biorad AG1-X8™ anion exchange resin (100–200 mesh). Firstly, the resin is washed with water at 1:1.25 WNV and 0.9 ml of upper phase is loaded onto the column. The column is washed with 10 mls of 5 mM myo-inositol and 10 ml of 5 mM Na-borate/60 mM Na-formate. The inositol tris phosphates are eluted into scintillation vials containing 10 ml of scintillation cocktail with 2 ml of 0.1 M formic acid/1 M ammonium formate. The columns are regenerated by washing with 10 ml of 0.1 M formic acid/3M ammonium formate and rinsed twice with dd $H_2O$ and stored at 4° C. in water.

Exemplary results are presented below in Table J:

TABLE J

Figure 2:
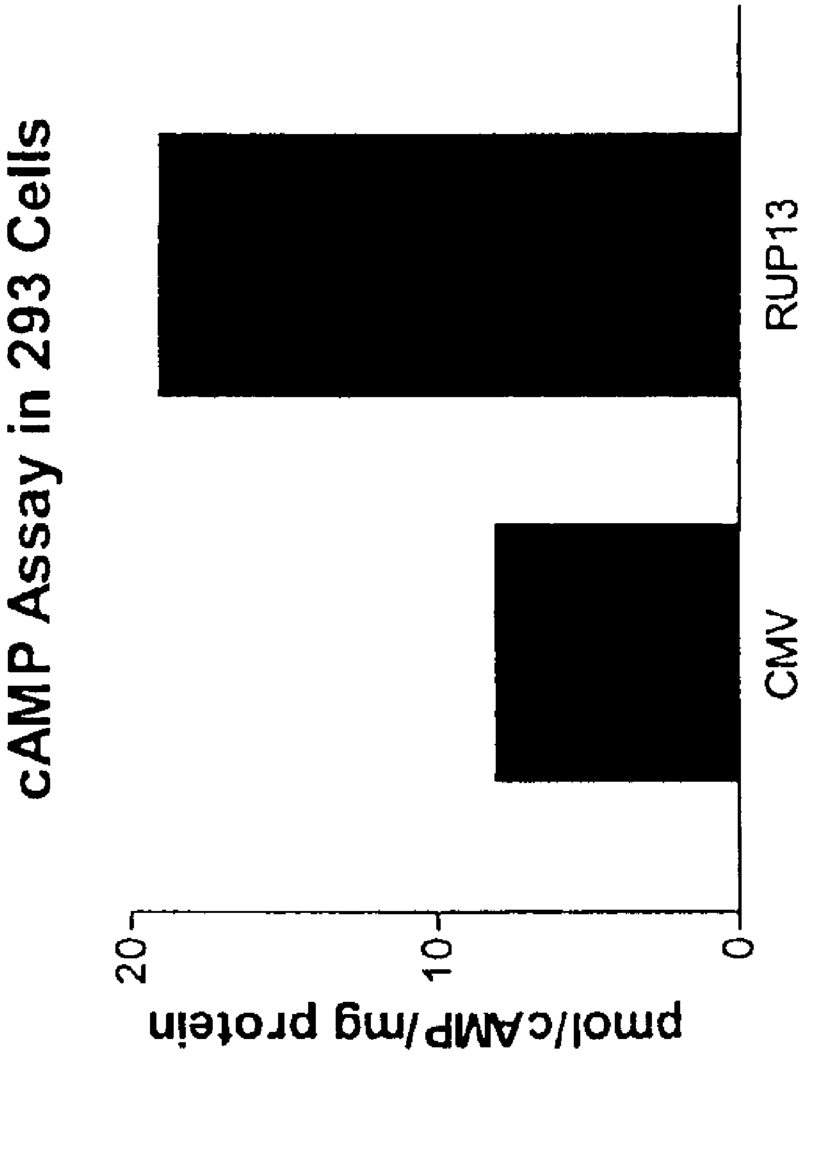
FIG. 2.
Figure 3:
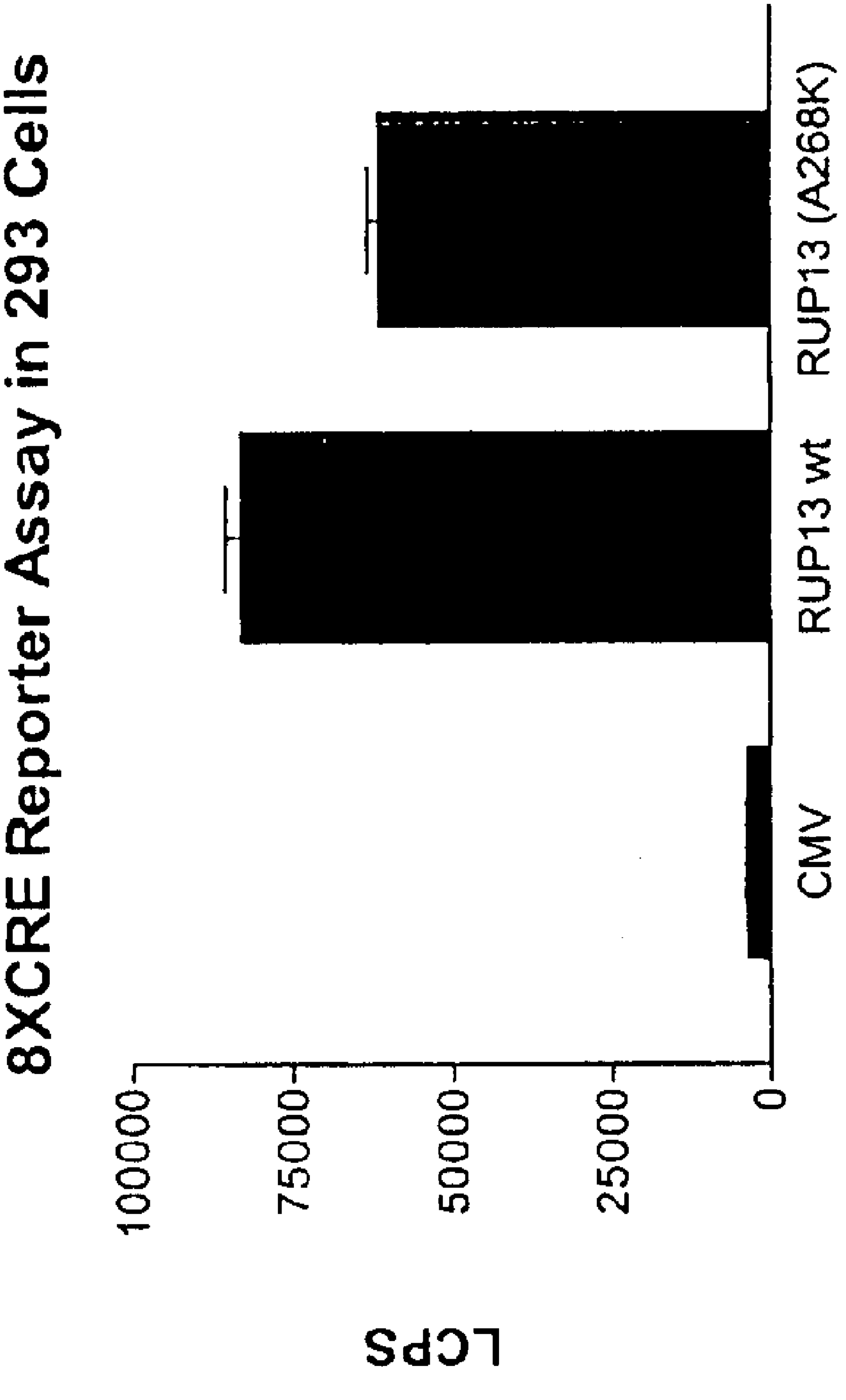
FIG. 3.
Figure 5:
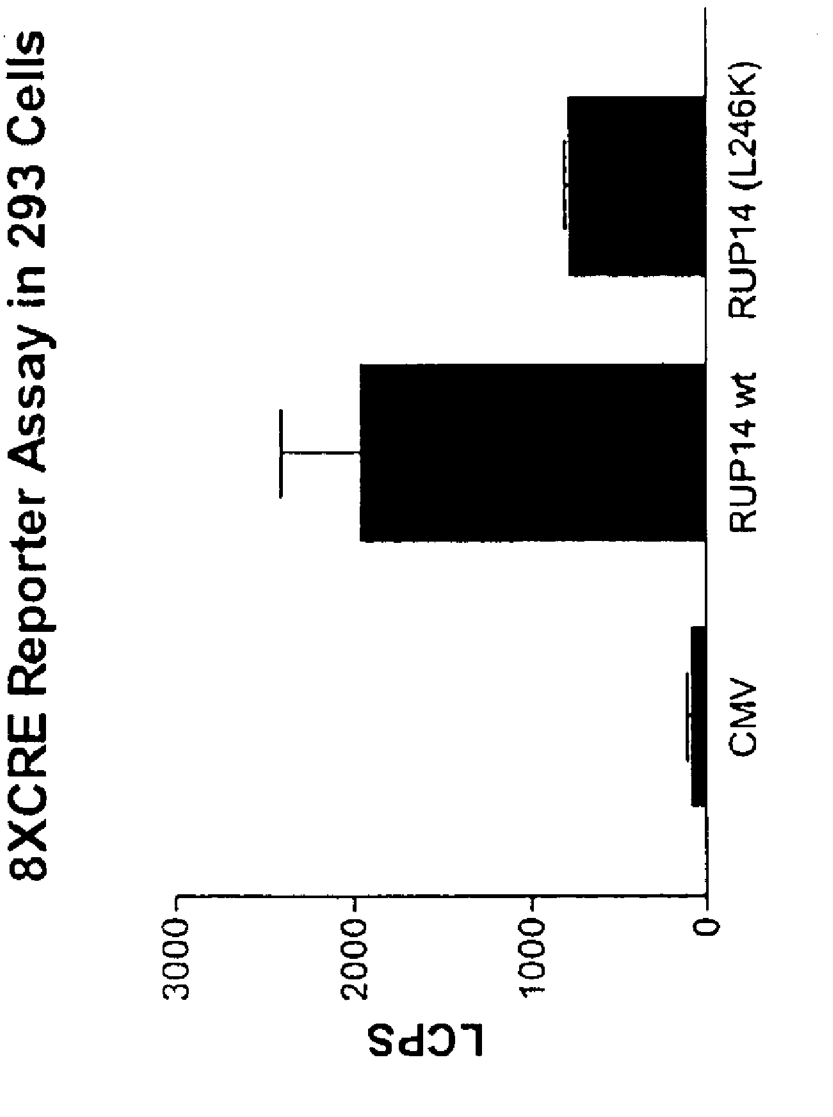
FIG. 5.
Figure 6:
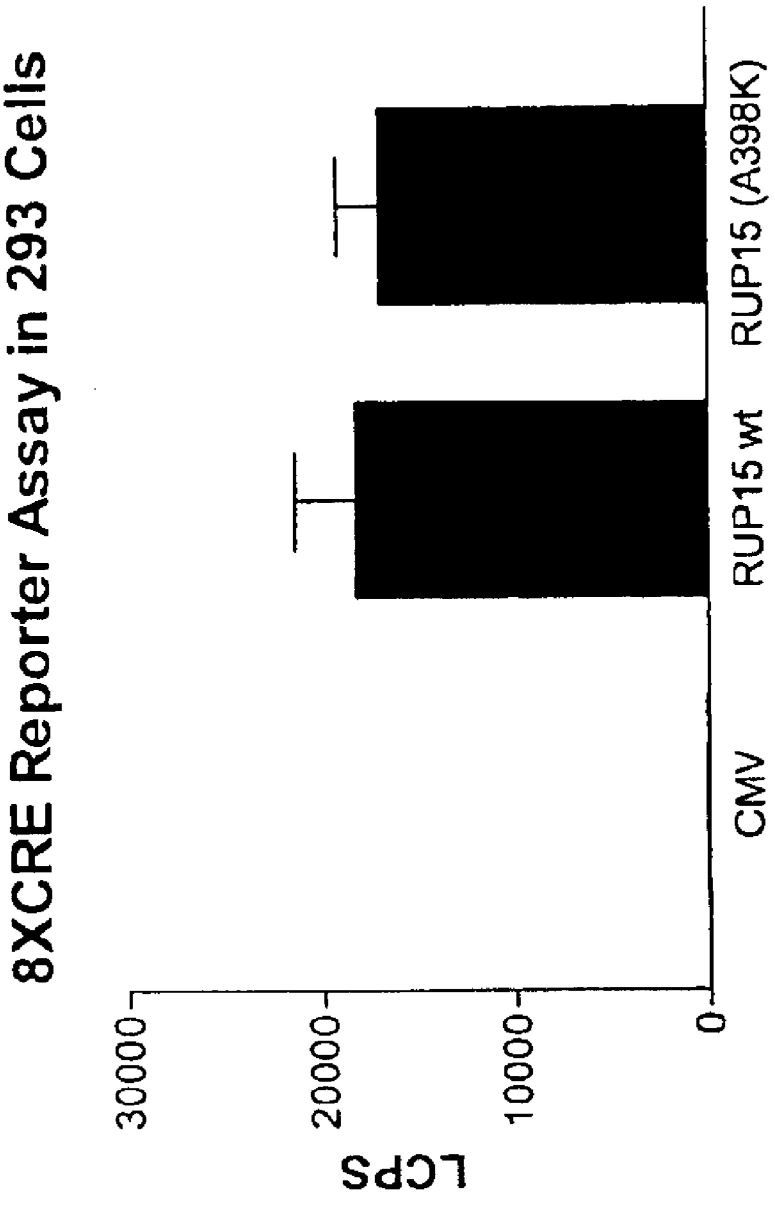
FIG. 6.
Figure 7:
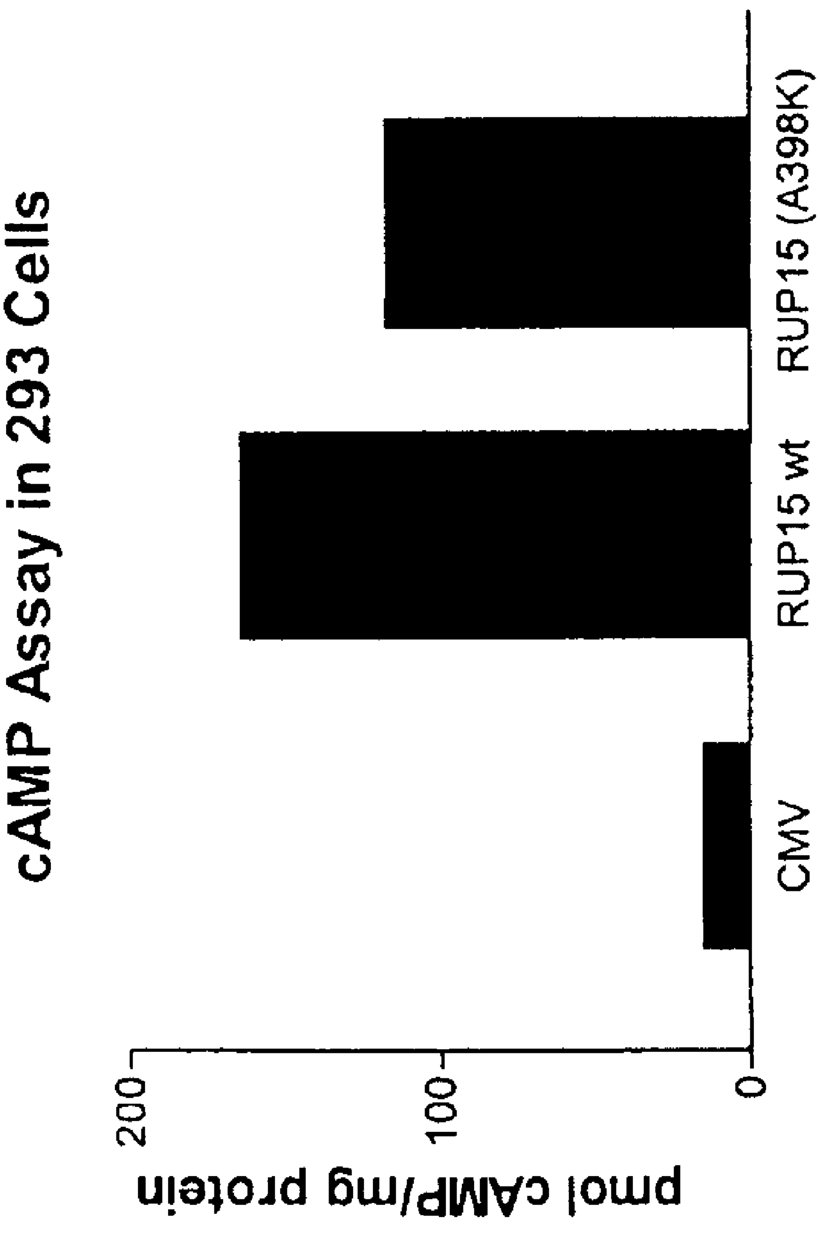
FIG. 7.
Figure 9:
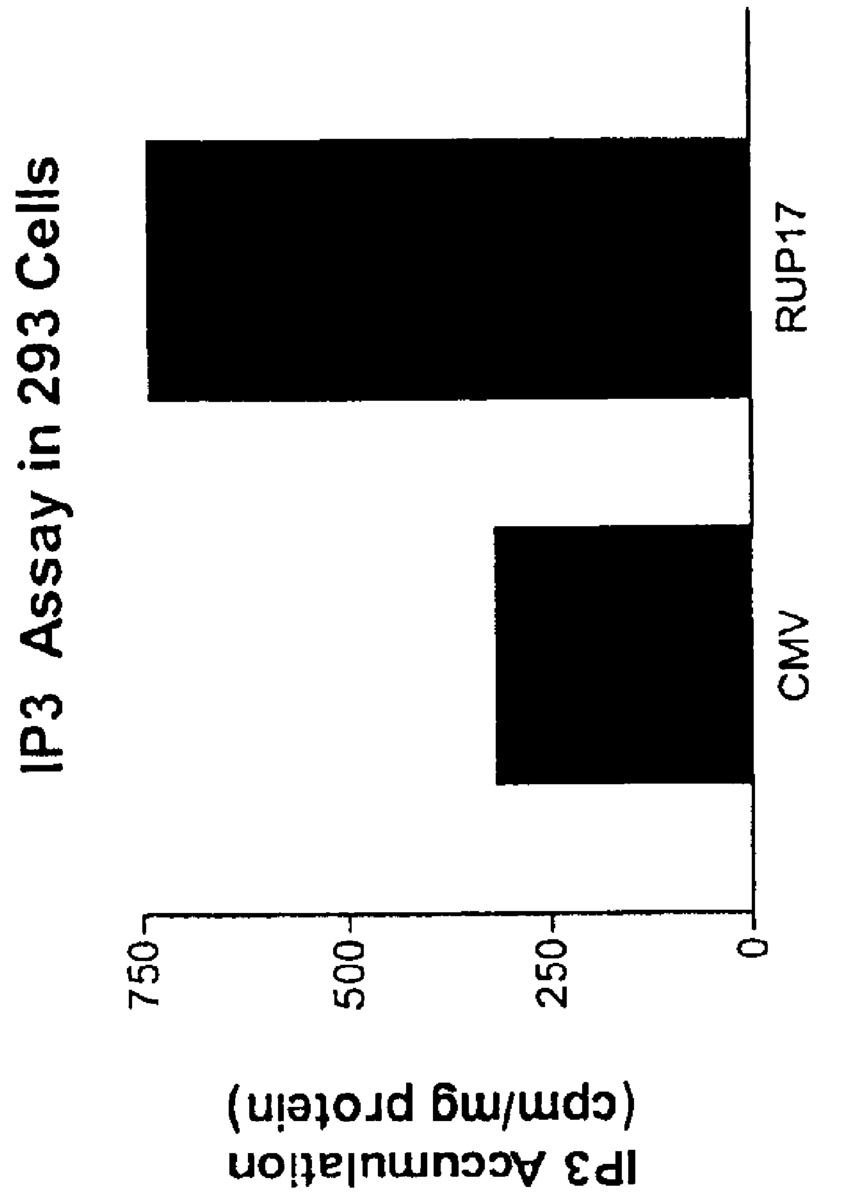
FIG. 9.
Figure 10:
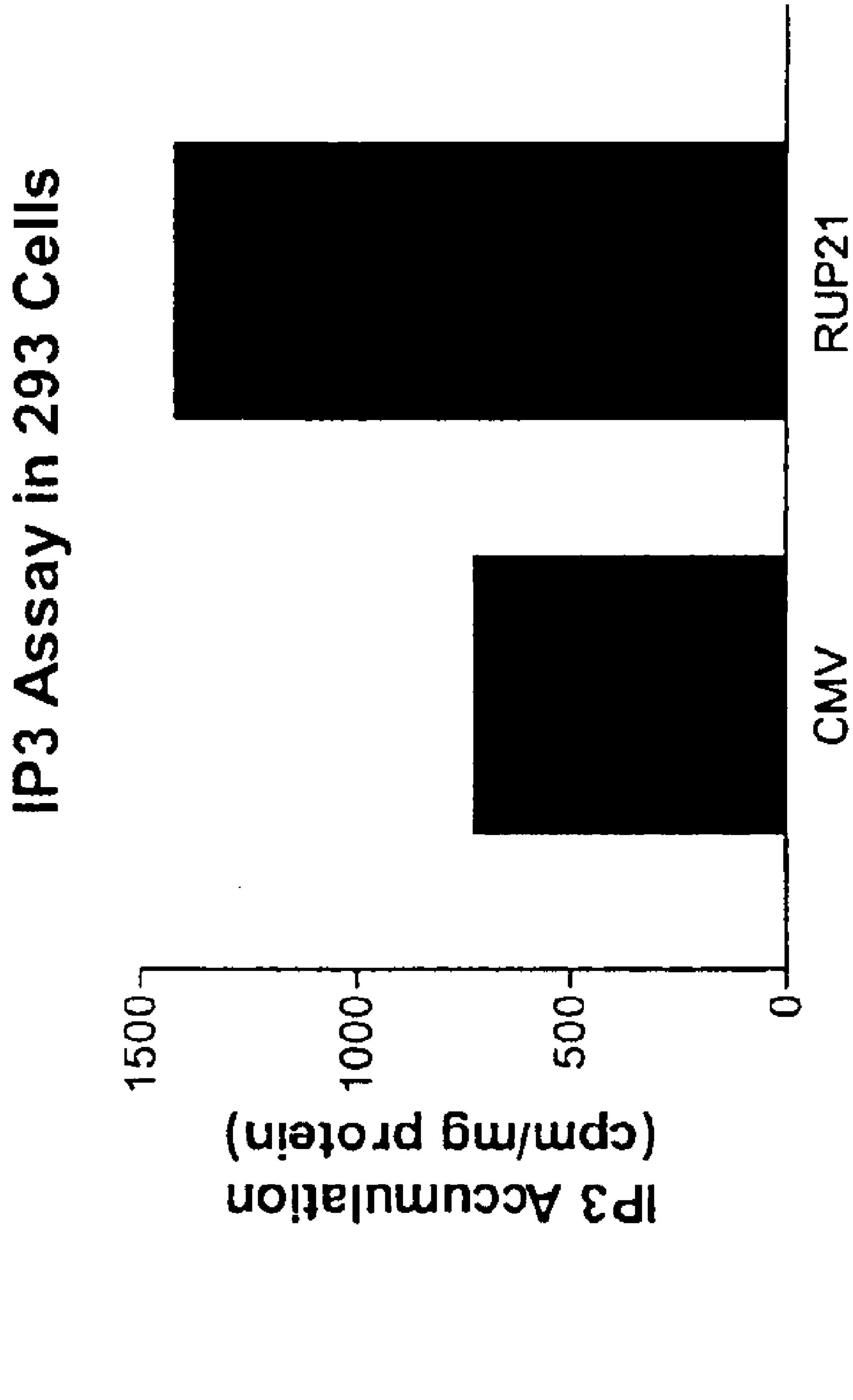
FIG. 10.
Figure 11:
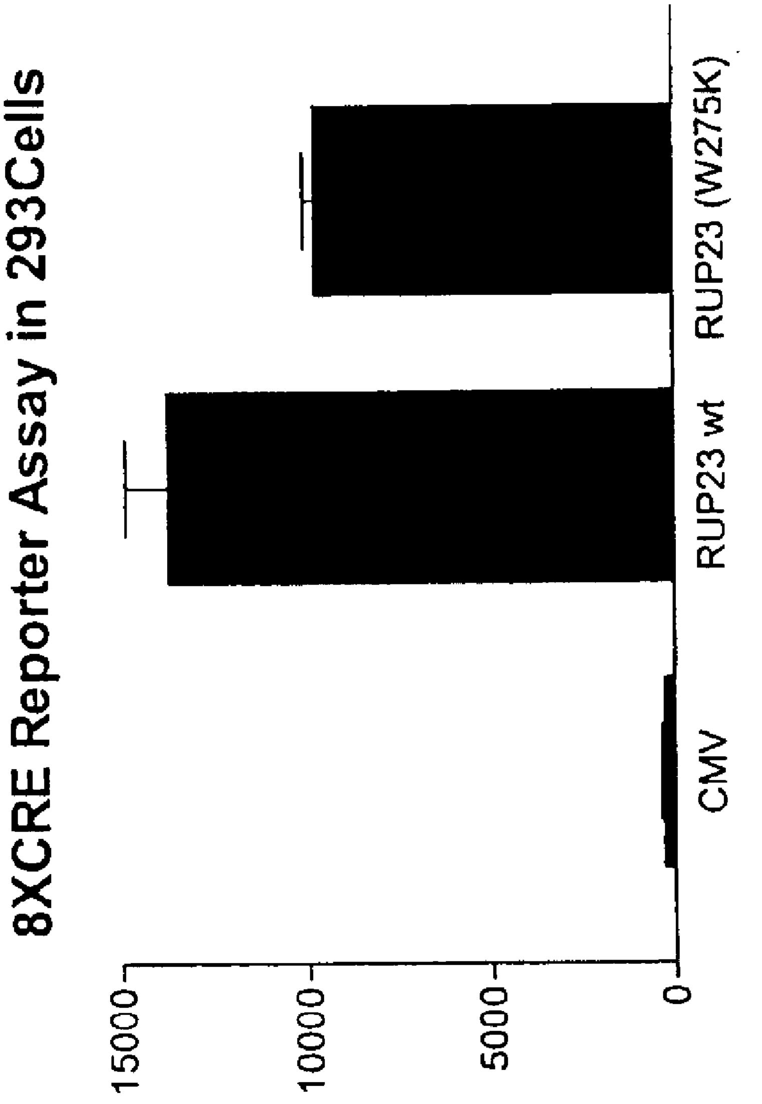
FIG. 11.

| Receptor | Mutation | Assay Utilized (Figure No.) | Signal Generated: CMV | Signal Generated: Endogenous Version (Relative Light Units) | Siganl Generated: Non-Endogenous Version (Relative Light Units) | Difference (↑↓) Between 1. CMV v. Wild-type 2. Wild-type v. Mutant |
|---|---|---|---|---|---|---|
| hRUP12 | N/A | $IP_3$ (FIG. 1) | 317.03 cpm/mg protein | 3463.29 cpm/mg protein | — | 1. 11 Fold ↑ |
| hRUP13 | N/A | cAMP (FIG. 2) | 8.06 pmol/cAMP/mg protein | 19.10 pmol/cAMP/mg protein | — | 1. 24 Fold ↑ |
| | A268K | 8XCRE-LUC (FIG. 3) | 3665.43 LCPS | 83280.17 LPCS | 61713.6 LCPS | 1. 23 Fold ↑ 2. 26% ↓ |
| hRUP14 | L246K | 8XCRE-LUC (FIG. 5) | 86.07 LCPS | 1962.87 LCPS | 789.73 LCPS | 1. 23 Fold ↑ 2. 60% ↓ |
| hRUP15 | A398K | 8XCRE-LUC (FIG. 6) | 86.07 LCPS | 18286.77 LCPS | 17034.83 LCPS | 1. 212 Fold ↑ 2. 1% ↓ |
| | A398K | cAMP (FIG. 7) | 15.00 pmol/cAMP/mg protein | 164.4 pmol/cAMP/mg protein | 117.5 pmol/cAMP/mg protein | 1. 11 Fold ↑ 2. 29% ↓ |
| hRUP17 | N/A | $IP_3$ (FIG. 9) | 317.03 cpm/mg protein | 741.07 cpm/mg protein | — | 1. 2.3 Fold ↑ |
| hRUP21 | N/A | $IP_3$ (FIG. 10) | 730.5 cpm/mg protein | 1421.9 cpm/mg protein | — | 1. 2 Fold ↑ |
| hRUP23 | W275K | 8XCRE-LUC (FIG. 11) | 311.73 pmol/cAMP/mg protein | 13756.00 pmol/cAMP/mg protein | 9756.87 pmol/cAMP/mg protein | 1. 44 Fold ↑ 2. 30% ↓ |

N/A = not applied

Exemplary results of GTPγS assay for detecting constitutive activation, as disclosed in Example 4(1) above, was accomplished utilizing G,:Fusion Protein Constructs on human hRUP13 and hRUP15. Table K below lists the signals generated from this assay and the difference in signals as indicated:

TABLE K

Figure 4:
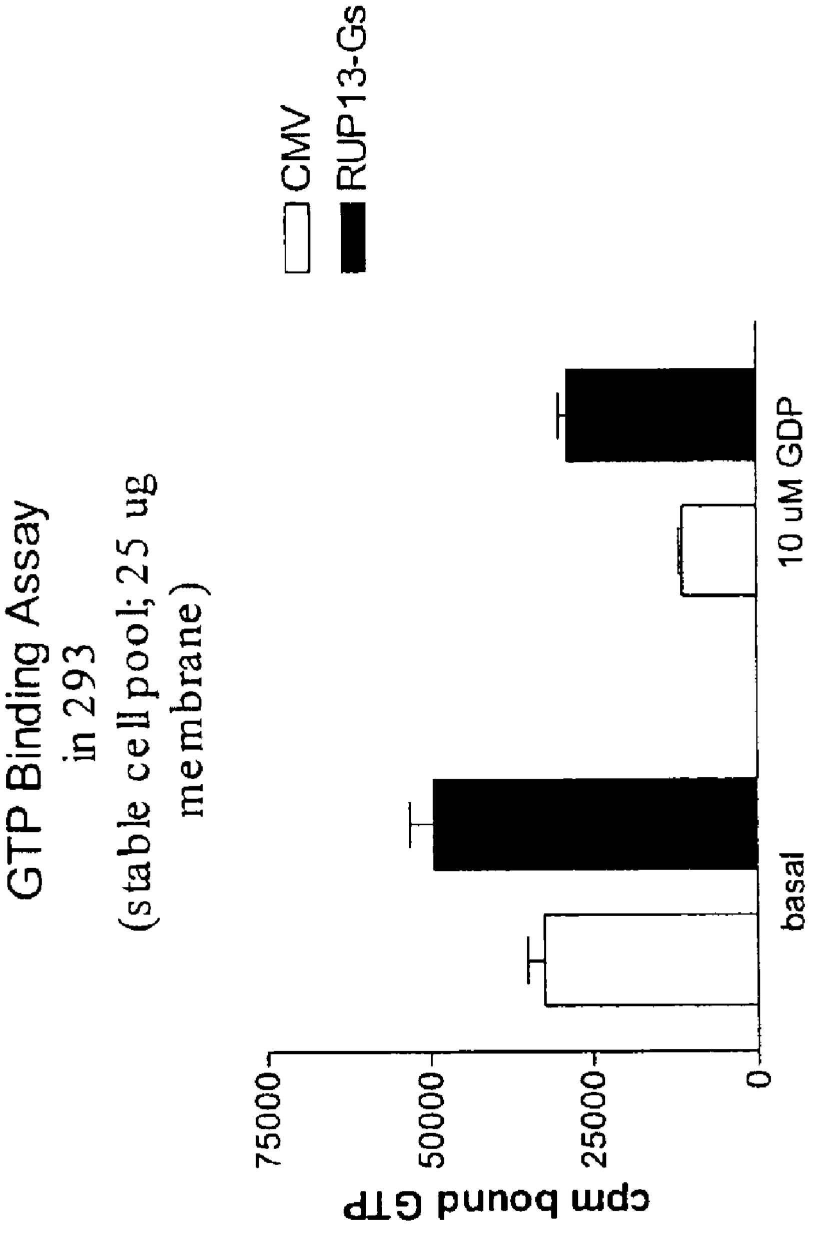
FIG. 4.
Figure 8:
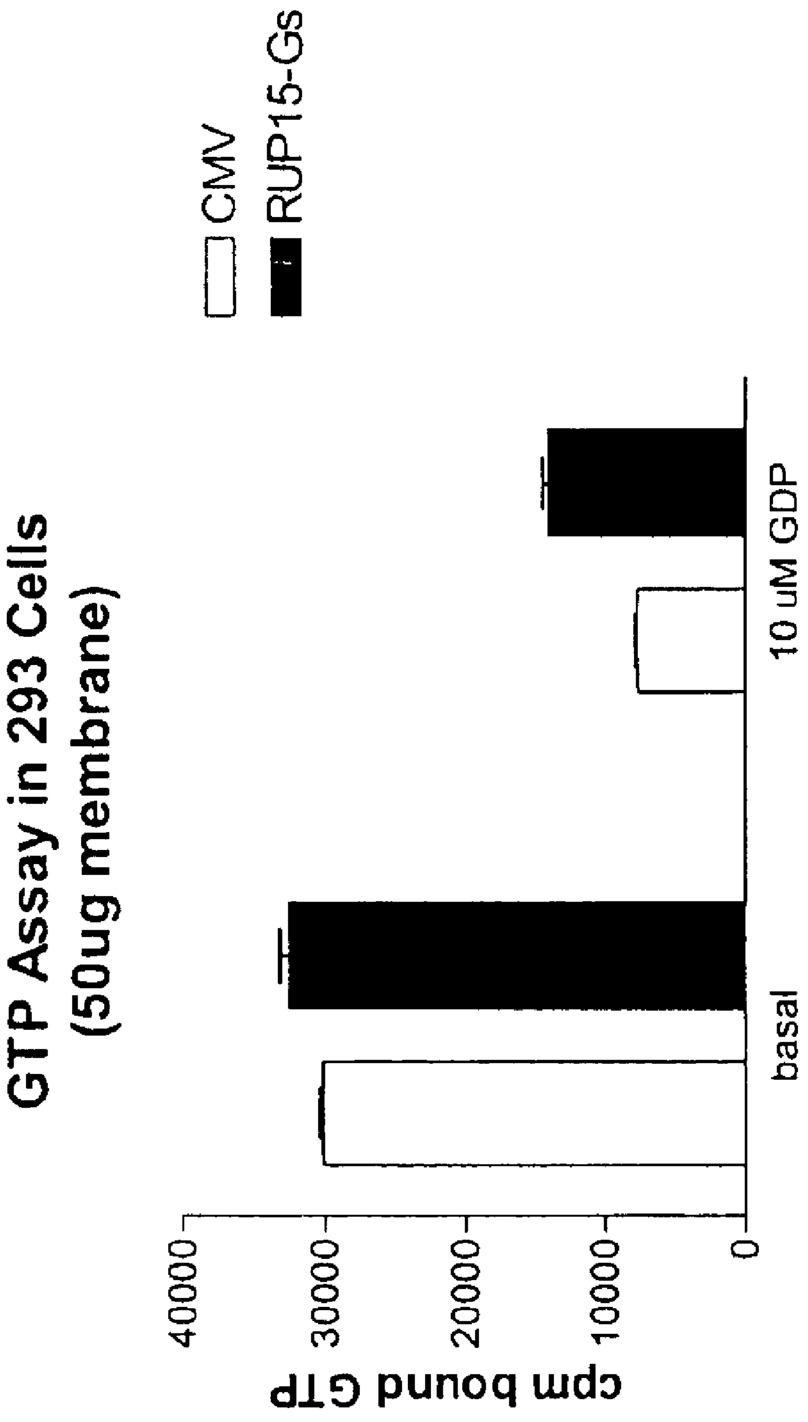
FIG. 8.

| Receptor: Gs Fusion Protein | Assay Utilized | Signal Generated: CMV (cpm bound GTP) | Signal Generated: Fusion Protein (cpm bound GTP) | Signal Generated: CMV + 10 μM GDP (cpm bound GTP) | Signal Generated: Fusion Protein + 10 μM GDP (cpm bound GTP) | Difference Between: 1. CMV v. Fusion Protein 2. CMV + GDP vs. Fusion + GDP 3. Fusion vs. Fusion + GDP (cpm bound GTP) |
|---|---|---|---|---|---|---|
| hRUP13-Gs | GTPγS (FIG. 4) | 32494.0 | 49351.30 | 11148.30 | 28834.67 | 1. 1.5 Fold ↑<br>2. 2.6 Fold ↑<br>3. 42% ↓ |
| hRUP15-Gs | GTPγS (FIG. 8) | 30131.67 | 32493.67 | 7697.00 | 14157.33 | 1. 1. 1 Fold ↑<br>2. 1.8 Fold ↑<br>3. 56% ↓ |

Example 5

Fusion Protein Preparation a. GPCR:Gs Fusion Construct

The design of the constitutively activated GPCR-G protein fusion construct was accomplished as follows: both the 5' and 3' ends of the rat G protein Gsα (long form; Itoh, H. et al., 83 *PNAS* 3776 (1986)) were engineered to include a HindIII (5'-AAGCTT-3') sequence thereon. Following confirmation of the correct sequence (including the flanking HindIII sequences), the entire sequence was shuttled into pcDNA3.1(−) (Invitrogen, cat. no. V795-20) by subcloning using the HindIII restriction site of that vector. The correct orientation for the $G_s\alpha$ sequence was determined after subcloning into pcDNA3.1(−). The modified pcDNA3.1(−) containing the rat $G_s\alpha$ gene at HindIII sequence was then verified; this vector was now available as a "universal" $G_s\alpha$ protein vector. The pcDNA3.1(−) vector contains a variety of well-known restriction sites upstream of the HindIII site, thus beneficially providing the ability to insert, upstream of the Gs protein, the coding sequence of an endogenous, constitutively active GPCR. This same approach can be utilized to create other "universal" G protein vectors, and, of course, other commercially available or proprietary vectors known to the artisan can be utilized—the important criteria is that the sequence for the GPCR be upstream and in-frame with that of the G protein.

hRUP13 couples via Gs. For the following exemplary GPCR Fusion Proteins, fusion to Gsα was accomplished.

A hRUP13-Gsα Fusion Protein construct was made as follows: primers were designed as follows:

```
5'-gatc[TCTAGAAT]GGAGTCCTCACCCATCCCCCAG-3'      (SEQ. ID. NO.:97; sense)

5'-gatc[GATATC]CGTGACTCCAGCCGGGGTGAGGCGGC-3'.   (SEQ. ID. NO.:98; antisense)
```

Nucleotides in lower caps are included as spacers in the restriction sites (designated in brackets) between the G protein and hRUP13. The sense and anti-sense primers included the restriction sites for XbaI and EcoRV, respectively, such that spacers (attributed to the restriction sites) exist between the G protein and hRUP15.

PCR was then utilized to secure the respective receptor sequences for fusion within the Gsα universal vector disclosed above, using the following protocol for each: 100 ng cDNA for hRUP15 was added to separate tubes containing 2 μl of each primer (sense and anti-sense), 3 μL of 10 mM dNTPs, 10 μL of 10×TaqPlus™ Precision buffer, 1 μL of TaqPlus™ Precision polymerase (Stratagene: #600211), and 80 μL of water. Reaction temperatures and cycle times for hRUP15 were as follows with cycle steps 2 through 4 were repeated 35 times: 94° C. for 1 min; 94° C. for 30 seconds; 62° C. for 20 sec; 72° C. 1 min 40 sec; and 72° C. 5 min. PCR product for was run on a 1% agarose gel and then purified (data not shown). The purified product was digested with XbaI and EcoRV and the desired inserts purified and ligated into the Gs universal vector at the respective restriction site. The positive clones was isolated following transformation and determined by restriction enzyme digest; expression using 293 cells was accomplished following the protocol set forth infra. Each positive clone for hRUP15-Gs Fusion Protein was sequenced to verify correctness. (See, SEQ.ID.NO.:99 for nucleic acid sequence and SEQ.ID.NO.:100 for amino acid sequence).

hRUP15 couples via Gs. For the following exemplary GPCR Fusion Proteins, fusion to Gsα was accomplished.

A hRUP15-Gsα Fusion Protein construct was made as follows: primers were designed as follows:

```
5'-TCTAGAATGACGTCCACCTGCACCAACAGC-3'      (SEQ. ID. NO.:101; sense)

5'-gatatcGCAGGAAAAGTAGCAGAATCGTAGGAAG-3'. (SEQ. ID. NO.:102; antisense)
```

Nucleotides in lower caps are included as spacers in the restriction sites between the G protein and hRUP15. The sense and anti-sense primers included the restriction sites for EcoRV and XbaI, respectively, such that spacers (attributed to the restriction sites) exists between the G protein and hRUP15.

PCR was then utilized to secure the respective receptor sequences for fusion within the Gsα universal vector disclosed above, using the following protocol for each: 100 ng cDNA for hRUP15 was added to separate tubes containing 2 μl of each primer (sense and anti-sense), 3 μL of 10 mM dNTPs, 10 μL of 10×TaqPlus™ Precision buffer, 1 μL of TaqPlus™ Precision polymerase (Stratagene: #600211), and 80 μL of water. Reaction temperatures and cycle times for hRUP15 were as follows with cycle steps 2 through 4 were repeated 35 times: 94° C. for 1 min; 94° C. for 30 seconds; 62° C. for 20 sec; 72° C. for 1 min 40 sec; and 72° C. for 5 min The PCR product for was run on a 1% agarose gel and then purified (data not shown). The purified product was digested. The purified product was digested with EcoRV and XbaI and the desired inserts purified and ligated into the Gs universal vector at the respective restriction site. The positive clones were isolated following transformation and determined by restriction enzyme digest; expression using 293 cells was accomplished following the protocol set forth infra. Each positive clone for hRUP15-Gs Fusion Protein was sequenced to verify correctness. (See, SEQ.ID.NO.:103 for nucleic acid sequence and SEQ.ID.NO.:104 for amino acid sequence).

b. Gq(6 Amino Acid Deletion)/Gi Fusion Construct

The design of a Gq (del)/Gi fusion construct can be accomplished as follows: the N-terminal six (6) amino acids (amino acids 2 through 7, having the sequence of TLESIM (SEQ.ID.NO.:129) Gq-subunit will be deleted and the C-terminal five (5) amino acids, having the sequence EYNLV (SEQ.ID.NO.:130) will be replaced with the corresponding amino acids of the $G_{\alpha}i$ Protein, having the sequence DCGLF (SEQ.ID.NO.:131). This fusion construct will be obtained by PCR using the following primers:

```
5'-gatcaagcttcCATGGCGTGCTGCCTGAGCGAGGAG-3'                (SEQ. ID. NO.:132)

and

5'-gatcggatccTTAGAACAGGCCGCAGTCCTTCAGGTTCAGCTGCAGGATGGTG-3' (SEQ. ID. NO.:133)
```

and Plasmid 63313 which contains the mouse $G_{\alpha}q$-wild type version with a hemagglutinin tag as template. Nucleotides in lower caps are included as spacers.

TaqPlus Precision DNA polymerase (Stratagene) will be utilized for the amplification by the following cycles, with steps 2 through 4 repeated 35 times: 95° C. for 2 min; 95° C. for 20 sec; 56° C. for 20 sec; 72° C. for 2 min; and 72° C. for 7 min. The PCR product will be cloned into a pCRII-TOPO vector (Invitrogen) and sequenced using the ABI Big Dye Terminator kit (P.E. Biosystems). Inserts from a TOPO clone containing the sequence of the fusion construct will be shuttled into the expression vector pcDNA3.1 (+) at the HindIII/BamHI site by a 2 step cloning process.

Example 6

Tissue Distribution of the Disclosed Human GPCRs

A. RT-PCR

RT-PCR was applied to confirm the expression and to determine the tissue distribution of several novel human GPCRs. Oligonucleotides utilized were GPCR-specific and the human multiple tissue cDNA panels (MTC, Clontech) as templates. Taq DNA polymerase (Stratagene) were utilized for the amplification in a 40 μl reaction according to the manufacturer's instructions. 20 μl of the reaction will be loaded on a 1.5% agarose gel to analyze the RT-PCR products. Table L below lists the receptors, the cycle conditions and the primers utilized.

Figure 13A:
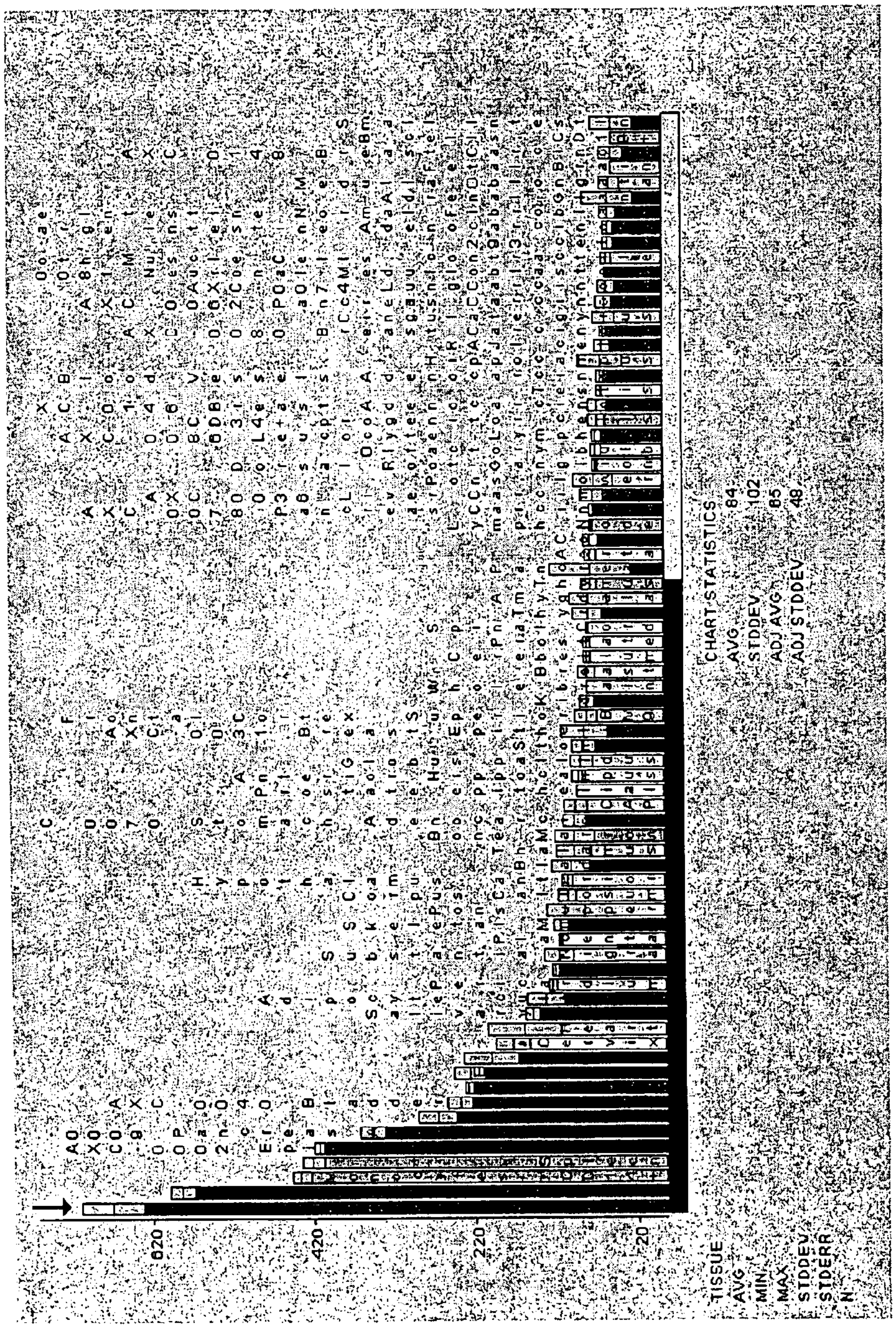
FIGS. 13A–C.
Figure 13B:
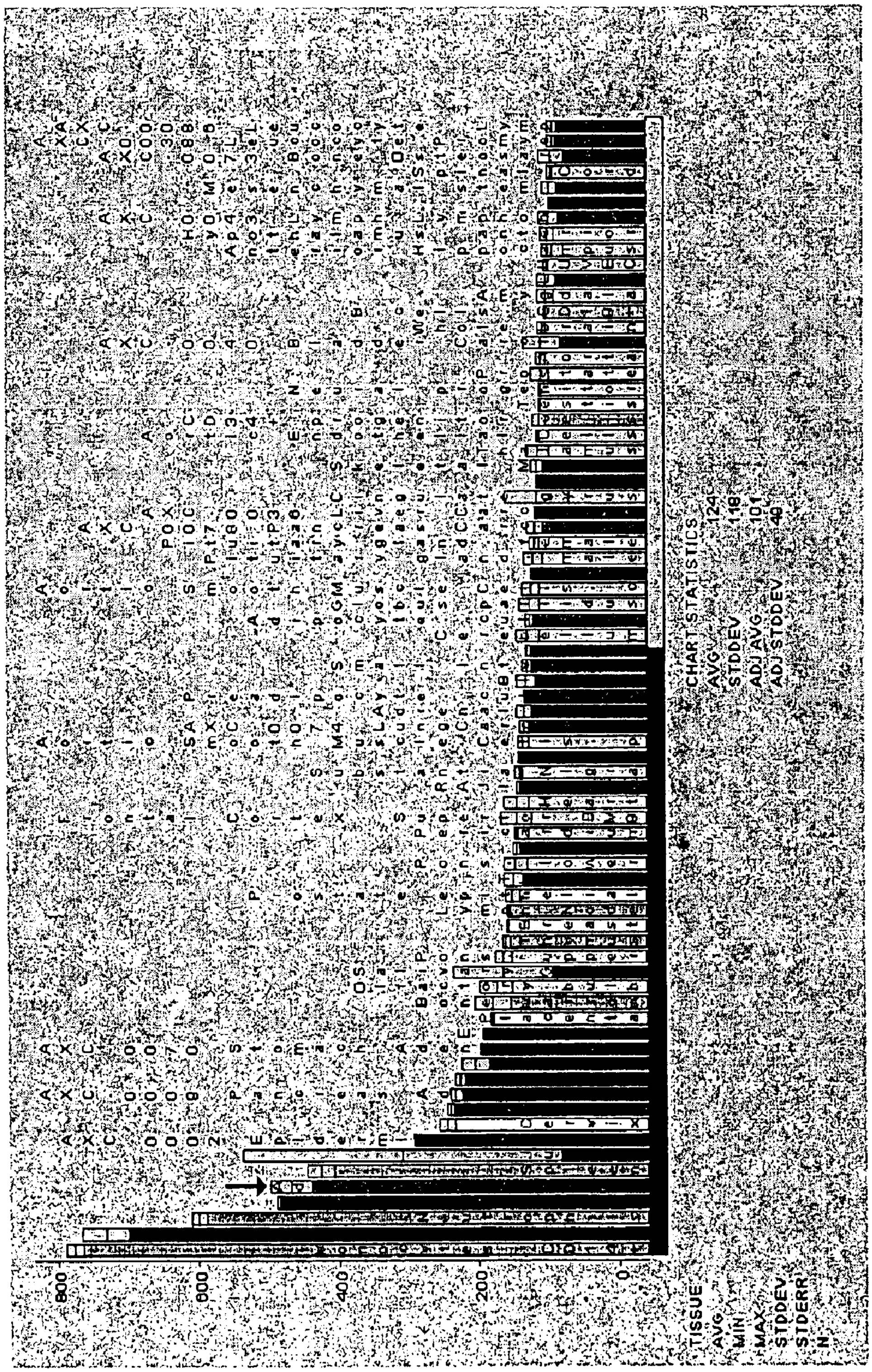
Figure 13C:
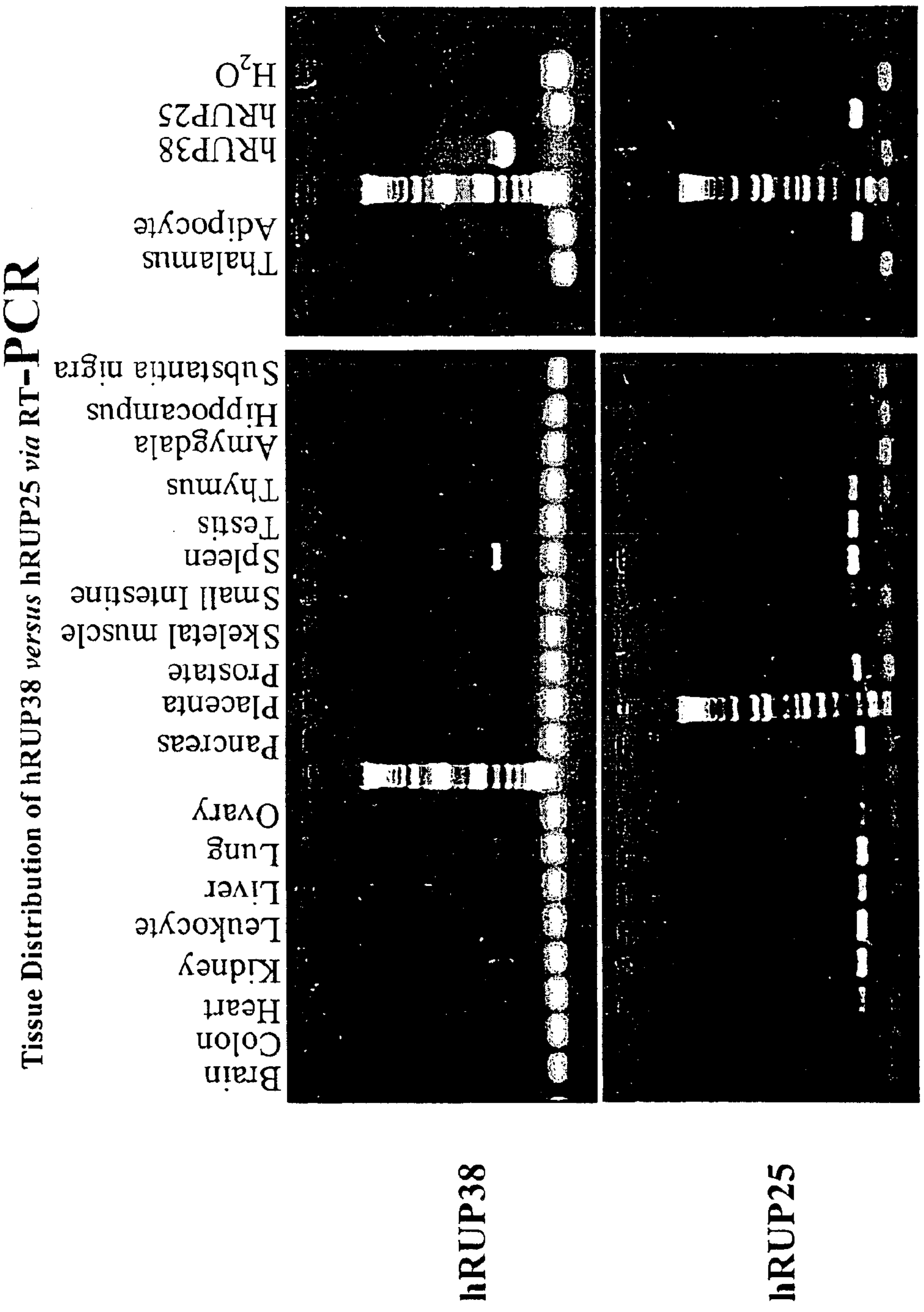
Figure 27:
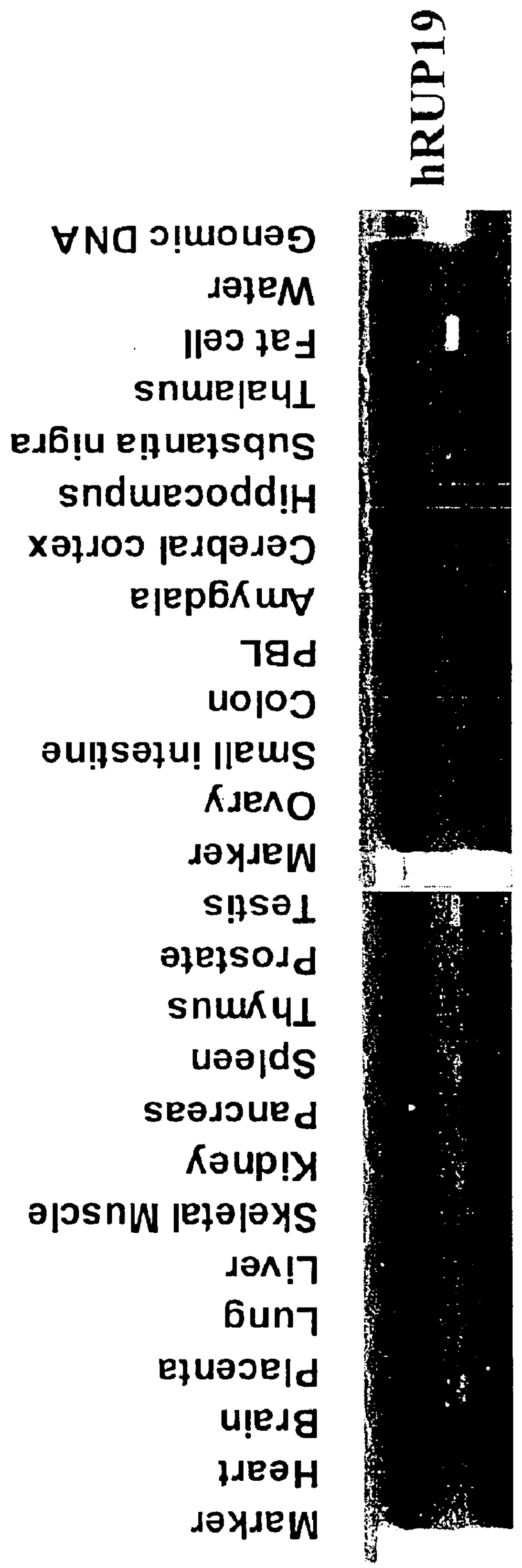
FIG. 27.
Figure 28:
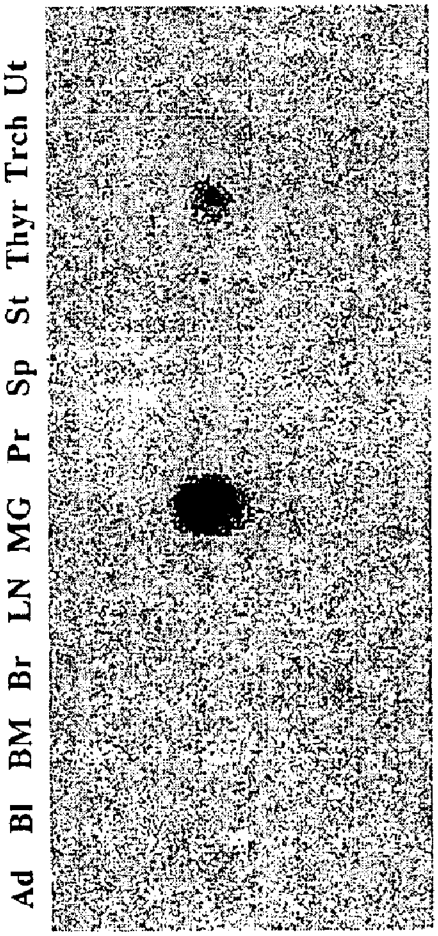
FIG. 28.
Figure 29:
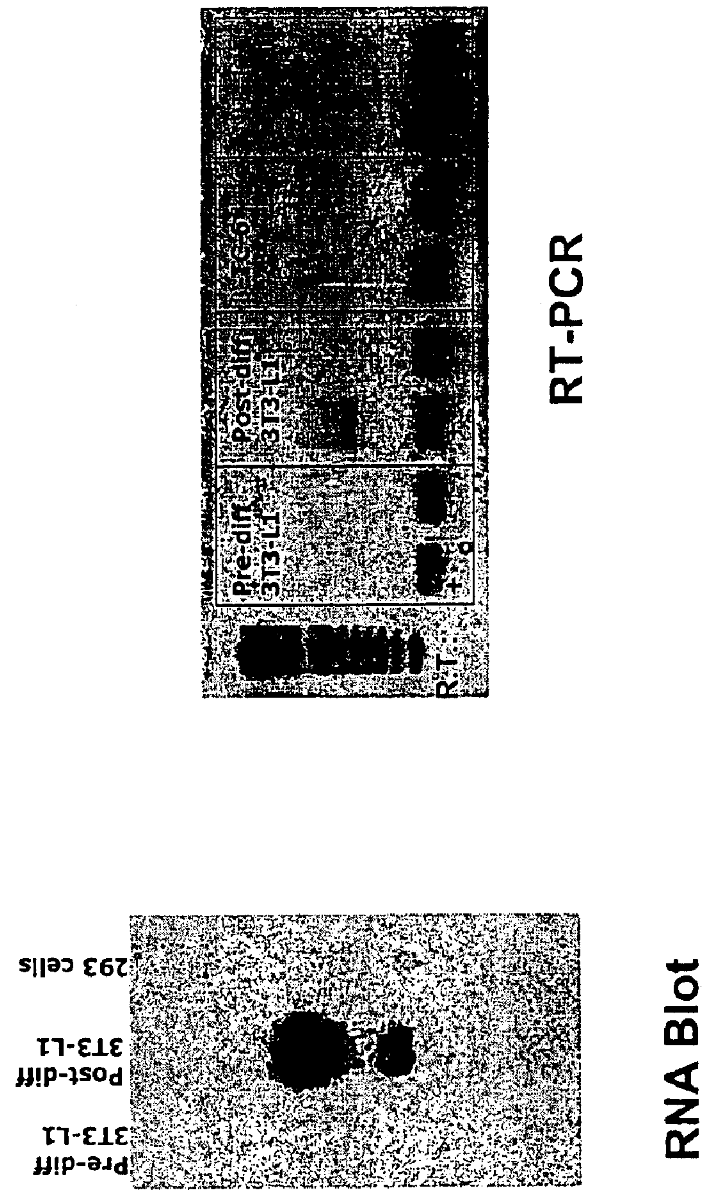
FIG. 29.

By way of illustration, RT-PCR results for hRUP25 and hRUP38 are shown in FIG. 13C. RT-PCR results for hRUP19 are shown in FIG. 27, and RT-PCR results for mRUP19 are shown in FIG. 29. Applicant discloses herein that hRUP25, hRUP38 and hRUP19 are expressed by primary adipocytes and, in the case of hRUP38 and hRUP19, have limited tissue distribution beyond adipose. That hRUP19 has limited tissue distribution is further apparent by Northern blot analysis (FIG. 28).

TABLE L

| Receptor Identifier | Cycle Conditions Min ('), Sec (") Cycles 2–4 repeated 30 times | 5' Primer (SEQ. ID. NO.) | 3' Primer (SEQ. ID. NO.) | DNA Fragment | Tissue Expression |
|---|---|---|---|---|---|
| hRUP10 | 94° for 30"<br>94° for 10"<br>62° C. for 20"<br>72° for 1'<br>72° for 7'<br>*cycles 2–4 repeated 35 times | CATGTATG CCAGCGTC CTGCTCC (105) | GCTATGCCT GAAGCCAG TCTTGTG (106) | 730bp | Kidney, leukocyte, liver, placenta and spleen |
| hRUP11 | 94° for 2'<br>94° for 15"<br>67° C. for 15"<br>72° for 45"<br>72° for 5' | GCACCTGC TCCTGAGC ACCTTCTCC (107) | CACAGCGC TGCAGCCCT GCAGCTGG C (108) | 630bp | Liver, kidney, pancreas, colon, small intestinal, spleen and prostate |
| hRUP12 | 94° for 2'<br>94° for 15"<br>66° C. for 15"<br>72° for 45"<br>72° for 5' | CCAGTGAT GACTCTGT CCAGCCTG (109) | CAGACACTT GGCAGGGA CGAGGTG (110) | 490bp | Brain, colon, heart, kidney, leukocyte, pancreas, prostate, small intestinal, spleen, testis, and thymus |
| hRUP13 | 94° for 1'<br>94° for 15"<br>68° C. for 20"<br>72° for 1' 45"<br>72° for 5' | CTTGTGGTC TACTGCAG CATGTTCC G (111) | CATATCCCT CCGAGTGTC CAGCGGC (112) | 700bp | Placenta and lung |
| hRUP14 | 94° for 1'<br>94° for 15"<br>68° C. for 20"<br>72° for 1' 45"<br>72° for 5' | ATGGATCC TTATCATG GCTTCCTC (113) | CAAGAACA GGTCTCATC TAAGAGCT CC (114) | 700bp | Not yet determined |
| hRUP16 | 94° for 30"<br>94° for 5"<br>69° C. for 15" | CTCTGATG CCATCTGCT GGATTCCT | GTAGTCCAC TGAAAGTC CAGTGATCC | 370bp | Fetal brain, fetal kidney and fetal |

TABLE L-continued

| Receptor Identifier | Cycle Conditions Min ('), Sec (") Cycles 2–4 repeated 30 times | 5' Primer (SEQ. ID. NO.) | 3' Primer (SEQ. ID. NO.) | DNA Fragment | Tissue Expression |
|---|---|---|---|---|---|
| | 72° for 30" | G (115) | (116) | | Skeletal |
| | 72° for 5' | | | | muscle |
| hRUP18 | 94° for 2' | TGGTGGCG | GTTGCGCCT | 330bp | Pancreas |
| | 94° for 15" | ATGGCCAA | TAGCGACA | | |
| | 60° C. for 20" | CAGCGCTC | GATGACC | | |
| | 72° for 1' | (117) | (118) | | |
| | 72° for 5' | | | | |
| hRUP19 | 95° for 4' | GGCCGTGG | AACCGGGT | 492bp | Adipose, |
| | 95° for 1' | CTGATTTCC | CGCCTTCTT | | adipocyte |
| | 60.5° C. for 30" | TCCTTAT | CATCC (153) | | |
| | 72° for 1' | (152) | | | |
| | 72° for 7' | | | | |
| | *cycles 2–4 | | | | |
| | repeated 35 | | | | |
| | times | | | | |
| hRUP21 | 94° for 1' | TCAACCTG | AAGGAGTA | | Kidney, lung |
| | 94° for 15" | TATAGCAG | GCAGAATG | | and testis |
| | 56° C. for 20" | CATCCTC | GTTAGCC | | |
| | 72° for 40" | (119) | (120) | | |
| | *cycles 2–3 | | | | |
| | repeated 30 | | | | |
| | times | | | | |
| hRUP22 | 94° for 30" | GACACCTG | CTGATGGA | | Testis, thymus |
| | 94° for 15" | TCAGCGGT | AGTAGAGG | | and spleen |
| | 69° C. for 20" | CGTGTGTG | CTGTCCATC | | |
| | 72° for 40" | (121) | TC (122) | | |
| | *cycles 2–3 | | | | |
| | repeated 30 | | | | |
| | times | | | | |
| hRUP23 | 94° for 2' | GCGCTGAG | CACGGTGA | 520bp | Placenta |
| | 94° for 15" | CGCAGACC | CGAAGGGC | | |
| | 60° C. for 20" | AGTGGCTG | ACGAGCTC | | |
| | 72° for 1' | (123) | (124) | | |
| | 72° for 5' | | | | |
| hRUP25 | 96° for 2' | CTGATGGA | GCTGAAGC | 297bp | Adipocyte, |
| | 96° for 30" | CAACTATG | TGCTGCACA | | spleen, |

TABLE L-continued

| Receptor Identifier | Cycle Conditions Min ('), Sec (") Cycles 2–4 repeated 30 times | 5' Primer (SEQ. ID. NO.) | 3' Primer (SEQ. ID. NO.) | DNA Fragment | Tissue Expression |
|---|---|---|---|---|---|
| | 55° C. for 1' | TGAGGCGT | AATTTGCAC | | leukocyte, |
| | 72° for 2' | TGG (144) | C (145) | | kidney, lung, |
| | 72° for 10' | | | | testis |
| hRUP26 | 94° for 2' | AGCCATCC | CCAGGTAG | 470bp | Pancreas |
| | 94° for 15" | CTGCCAGG | GTGTGCAG | | |
| | 65° C. for 20" | AAGCATGG | CACAATGG | | |
| | 72° for 1' | (125) | C (126) | | |
| | 72° for 5' | | | | |
| hRUP27 | 94° for 30" | CTGTTCAA | ATCATGTCT | 890bp | Brain |
| | 94° for 10" | CAGGGCTG | AGACTCAT | | |
| | 55° C. for 20" | GTTGGCAA | GGTGATCC | | |
| | 72° for 1' | C (127) | (128) | | |
| | 72° for 3' | | | | |
| | *cycles 2–4 | | | | |
| | repeated 35 | | | | |
| | times | | | | |
| hRUP38 | 96° for 2' | CTACTATGT | CCCTTCTTG | 852bp | Adipocyte, |
| | 96° for 30" | GCGGCGTT | GAATGGTT | | spleen, lung |
| | 55° C. for 1' | CA (146) | ATTT (147) | | |
| | 72° for 2' | | | | |
| | 72° for 10' | | | | |

B. Affymetrix Genechip® Technology

Amino acid sequences were submitted to Affymetrix for the designing and manufacturing of microarray containing oligonucleotides to monitor the expression levels of G protein-coupled receptors (GPCRs) using their GeneChip® Technology. Also present on the microarray were probes for characterized human brain tissues from Harvard Brain Band or obtained from commercially available sources. RNA samples were amplified, labeled, hybridized to the microarray, and data analyzed according to manufacturer's instructions.

Adipose tissues were monitored for the level of gene expression of each of the GPCRs represented on the microarray. GPCRs were determined to be expressed if the expression index was greater than 100 (based upon and according to manufacturer's instructions). The data was analyzed and had indicated that classification of GPCRs with an expression index greater than 100 was reasonable because a number of known GPCRs had previously been reported to be expressed in neuronal tissues with an expression index greater than 100.

Using the GeneChip, Applicant has discovered hRUP25 and hRUP38 to have high levels of expression in adipocytes, consistent with hRUP25 and hRUP38 playing a role in lipolysis (see, Goodman & Gilman's, *The Pharmacological Basis of Therapeutics,* $9^{th}$ Edition, page 235 (1996). See FIGS. 13A and 13B. FIG. 13A is a plot representing the expression level of hRUP25 in various tissues. hRUP25 is highly expressed by primary adipocytes. FIG. 13B is a plot representing the expression level of hRUP38 in various tissues. hRUP38 is highly expressed by primary adipocytes.

This patent document discloses the identification of nicotinic acid as a ligand and agonist of human, mouse and rat RUP25. See, Examples infra. The patent document further discloses that nicotinic acid is not an agonist of hRUP38 or hRUP19. In the case of hRUP38, this was an unexpected result, as hRUP25 and hRUP38 are about 95% identical (Table B), although it is not a result without precedent [see, e.g., Yan M et al. Science (2000) 290:523–7; the disclosure of which is hereby incorporated by reference in its entirety].

Example 7

Protocol: Direct Identification of Inverse Agonists and Agonists

A. [$^{35}$S]GTPγS Assay

Although we have utilized endogenous, constitutively active GPCRs for the direct identification of candidate compounds as, e.g., inverse agonists, for reasons that are not altogether understood, intra-assay variation can become exacerbated. In some embodiments, a GPCR Fusion Protein, as disclosed above, is also utilized with a non-endogenous, constitutively activated GPCR. When such a protein is used, intra-assay variation appears to be substantially stabilized, whereby an effective signal-to-noise ratio is obtained. This has the beneficial result of allowing for a more robust identification of candidate compounds. Thus, in some embodiments it is preferred that for direct identification, a GPCR Fusion Protein be used and that when utilized, the following assay protocols be utilized.

1. Membrane Preparation

In some embodiments membranes comprising the constitutively active orphan GPCR/Fusion Protein of interest and for use in the direct identification of candidate compounds as inverse agonists or agonists are preferably prepared as follows:

a. Materials

"Membrane Scrape Buffer" is comprised of 20 mM HEPES and 10 mM EDTA, pH 7.4; "Membrane Wash Buffer" is comprised of 20 mM HEPES and 0.1 mM EDTA, pH 7.4; "Binding Buffer" is comprised of 20 mM HEPES, 100 mM NaCl, and 10 mM $MgCl_2$, pH 7.4 b. Procedure

All materials will be kept on ice throughout the procedure. Firstly, the media will be aspirated from a confluent monolayer of cells, followed by rinse with 10 ml cold PBS, followed by aspiration. Thereafter, 5 ml of Membrane Scrape Buffer will be added to scrape cells; this will be followed by transfer of cellular extract into 50 ml centrifuge tubes (centrifuged at 20,000 rpm for 17 minutes at 4° C.). Thereafter, the supernatant will be aspirated and the pellet will be resuspended in 30 ml Membrane Wash Buffer followed by centrifuge at 20,000 rpm for 17 minutes at 4° C. The supernatant will then be aspirated and the pellet resuspended in Binding Buffer. This will then be homogenized using a Brinkman Polytron™ homogenizer (15–20 second bursts until the all material is in suspension). This is referred to herein as "Membrane Protein".

2. Bradford Protein Assay

Following the homogenization, protein concentration of the membranes will be determined using the Bradford Protein Assay (protein can be diluted to about 1.5 mg/ml, aliquoted and frozen (−80° C.) for later use; when frozen, protocol for use will be as follows: on the day of the assay, frozen Membrane Protein is thawed at room temperature, followed by vortex and then homogenized with a Polytron at about 12×1,000 rpm for about 5–10 seconds; it was noted that for multiple preparations, the homogenizor should be thoroughly cleaned between homogenization of different preparations).

a. Materials

Binding Buffer (as per above); Bradford Dye Reagent; Bradford Protein Standard will be utilized, following manufacturer instructions (Biorad, cat. no. 500-0006).

b. Procedure

Duplicate tubes will be prepared, one including the membrane, and one as a control "blank". Each contained 800 $\mu$l Binding Buffer. Thereafter, 10 $\mu$l of Bradford Protein Standard (1 mg/ml) will be added to each tube, and 10 $\mu$l of membrane Protein will then be added to just one tube (not the blank). Thereafter, 200 $\mu$l of Bradford Dye Reagent will be added to each tube, followed by vortex of each. After five (5) minutes, the tubes will be re-vortexed and the material therein will be transferred to cuvettes. The cuvettes will then be read using a CECIL 3041 spectrophotometer, at wavelength 595.

3. Direct Identification Assay a. Materials

GDP Buffer consisted of 37.5 ml Binding Buffer and 2 mg GDP (Sigma, cat. no. G-7127), followed by a series of dilutions in Binding Buffer to obtain 0.2 $\mu$M GDP (final concentration of GDP in each well was 0.1 $\mu$M GDP); each well comprising a candidate compound, has a final volume of 200 $\mu$l consisting of 100 $\mu$l GDP Buffer (final concentration, 0.1 $\mu$M GDP), 50 $\mu$l Membrane Protein in Binding Buffer, and 50 $\mu$l [$^{35}$S]GTPγS (0.6 nM) in Binding Buffer (2.5 $\mu$l [$^{35}$S]GTPγS per 10 ml Binding Buffer).

b. Procedure

Candidate compounds will be preferably screened using a 96-well plate format (these can be frozen at −80° C.). Membrane Protein (or membranes with expression vector excluding the GPCR Fusion Protein, as control), will be homogenized briefly until in suspension. Protein concentration will then be determined using the Bradford Protein Assay set forth above. Membrane Protein (and control) will then be diluted to 0.25 mg/ml in Binding Buffer (final assay concentration, 12.5 $\mu$g/well). Thereafter, 100 $\mu$l GDP Buffer was added to each well of a Wallac Scintistrip™ (Wallac). A 5ul pin-tool will then be used to transfer 5 $\mu$l of a candidate compound into such well (i.e., 5 $\mu$l in total assay volume of 200 $\mu$l is a 1:40 ratio such that the final screening concentration of the candidate compound is 10 $\mu$M). Again, to avoid contamination, after each transfer step the pin tool should be rinsed in three reservoirs comprising water (1×), ethanol (1×) and water (2×)—excess liquid should be shaken from the tool after each rinse and dried with paper and kimwipes. Thereafter, 50 $\mu$l of Membrane Protein will be added to each well (a control well comprising membranes without the GPCR Fusion Protein was also utilized), and pre-incubated for 5–10 minutes at room temperature. Thereafter, 50 $\mu$l of [$^{35}$S]GTPγS (0.6 nM) in Binding Buffer will be added to each well, followed by incubation on a shaker for 60 minutes at room temperature (again, in this example, plates were covered with foil). The assay will then be stopped by spinning of the plates at 4000 RPM for 15 minutes at 22° C. The plates will then be aspirated with an 8 channel manifold and sealed with plate covers. The plates will then be read on a Wallac 1450 using setting "Prot. #37" (as per manufacturer instructions).

B. Cyclic AMP Assay

Another assay approach to directly identified candidate compound was accomplished by utilizing a cyclase-based assay. In addition to direct identification, this assay approach can be utilized as an independent approach to provide confirmation of the results from the [$^{35}$S]GTPγS approach as set forth above.

A modified Flash Plate™ Adenylyl Cyclase kit (New England Nuclear; Cat. No. SMP004A) was preferably utilized for direct identification of candidate compounds as inverse agonists and agonists to constitutively activated orphan GPCRs in accordance with the following protocol.

Transfected cells were harvested approximately three days after transfection. Membranes were prepared by homogenization of suspended cells in buffer containing 20 mM HEPES, pH 7.4 and 10 mM $MgCl_2$. Homogenization was performed on ice using a Brinkman Polytron™ for approximately 10 seconds. The resulting homogenate is centrifuged at 49,000×g for 15 minutes at 4° C. The resulting pellet was then resuspended in buffer containing 20 mM HEPES, pH 7.4 and 0.1 mM EDTA, homogenized for 10 seconds, followed by centrifugation at 49,000×g for 15 minutes at 4° C. The resulting pellet was then stored at −80° C. until utilized. On the day of direct identification screening, the membrane pellet was slowly thawed at room temperature, resuspended in buffer containing 20 mM HEPES, pH 7.4 and 10 mM $MgCl_2$, to yield a final protein concentration of 0.60 mg/ml (the resuspended membranes are placed on ice until use).

cAMP standards and Detection Buffer (comprising 2 $\mu$Ci of tracer [$^{125}$I cAMP (100 $\mu$l] to 11 ml Detection Buffer) were prepared and maintained in accordance with the manufacturer's instructions. Assay Buffer was prepared fresh for screening and contained 20 mM HEPES, pH 7.4, 10 mM $MgCl_2$, 20 mM phospocreatine (Sigma), 0.1 units/ml creatine phosphokinase (Sigma), 50 $\mu$M GTP (Sigma), and 0.2 mM ATP (Sigma); Assay Buffer was then stored on ice until utilized.

Candidate compounds identified as per above (if frozen, thawed at room temperature) were added, preferably, to 96-well plate wells (3 $\mu$l/well; 12 $\mu$M final assay concentration), together with 40 $\mu$l Membrane Protein (30 $\mu$g/well) and 50 $\mu$l of Assay Buffer. This admixture was then incubated for 30 minutes at room temperature, with gentle shaking.

Following the incubation, 100 $\mu$l of Detection Buffer was added to each well, followed by incubation for 2–24 hours. Plates were then counted in a Wallac MicroBeta™ plate reader using "Prot. #31" (as per manufacturer instructions).

Figure 12:
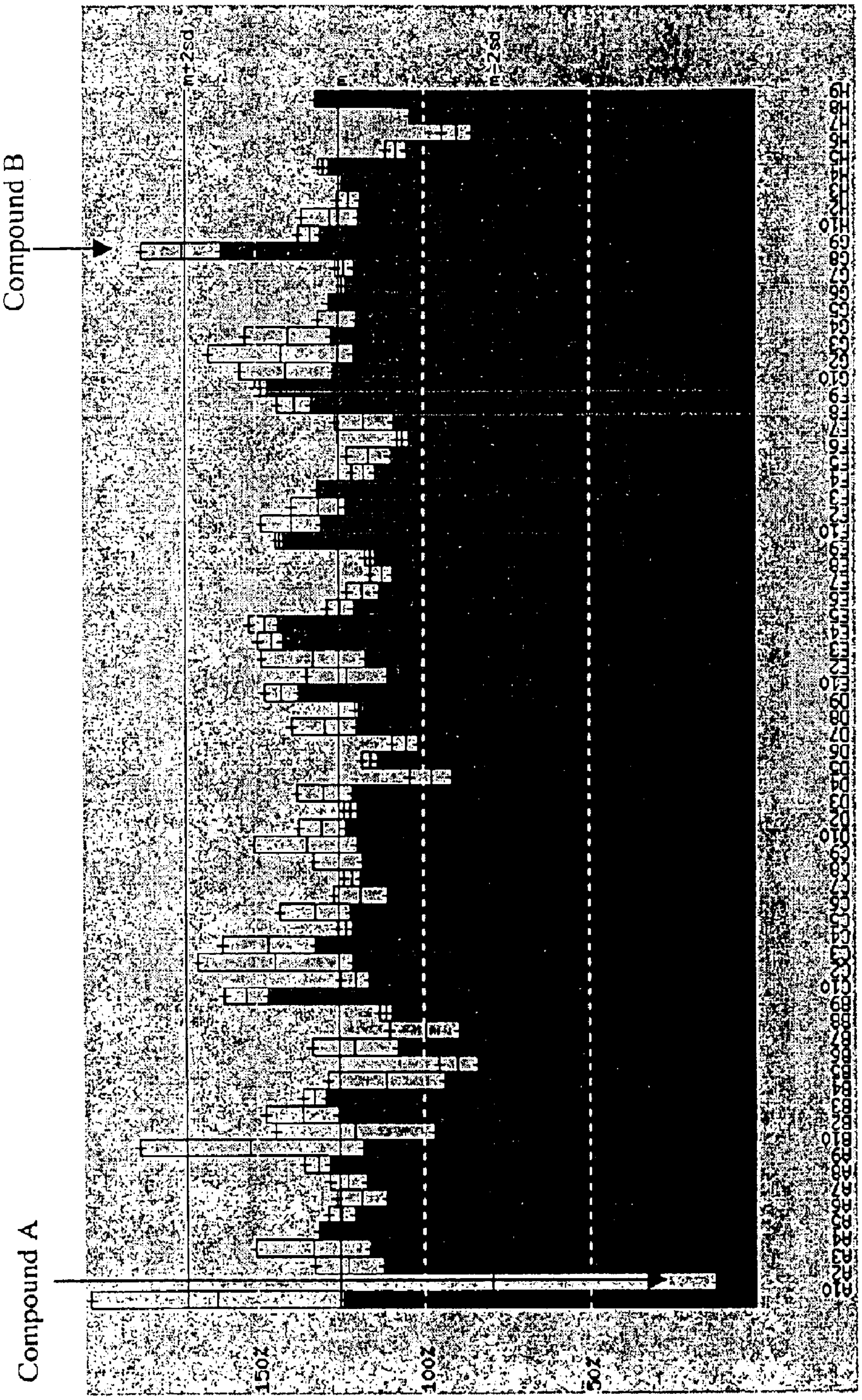
FIG. 12.

A representative screening assay plate (96 well format) result is presented in FIG. 12. Each bar represents the results for a different compound in each well, plus hRUP13-Gsα Fusion Protein construct, as prepared in Example 5(a) above. The representative results presented in FIG. 12 also provide standard deviations based upon the mean results of each plate ("m") and the mean plus two arbitrary preference for selection of inverse agonists as "leads" from the primary screen involves selection of candidate compounds that that reduce the per cent response by at least the mean plate response, minus two standard deviations. Conversely, an arbitrary preference for selection of agonists as "leads" from the primary screen involves selection of candidate compounds that increase the per cent response by at least the mean plate response, plus the two standard deviations. Based upon these selection processes, the candidate compounds in the following wells were directly identified as putative inverse agonist (Compound A) and agonist (Compound B) to hRUP13 in wells A2 and G9, respectively. See, FIG. 12. It is noted for clarity: these compounds have been directly identified without any knowledge of the endogenous ligand for this GPCR. By focusing on assay techniques that are based upon receptor function, and not compound binding affinity, we are able to ascertain compounds that are able to reduce the functional activity of this receptor (Compound A) as well as increase the functional activity of the receptor (Compound B). Based upon the location of these receptors in, for example, lung tissue (see, for example, hRUP13 and hRUP21 in Example 6), pharmaceutical agents can be developed for potential therapeutic treatment of lung cancer.

Example 8

Melanophore Technology

Melanophores are skin cells found in lower vertebrates. They contain pigmented organelles termed melanosomes. Melanophores are able to redistribute these melanosomes along a microtubule network upon G-protein coupled receptor (GPCR) activation. The result of this pigment movement is an apparent lightening or darkening of the cells. In melanophores, the decreased levels of intracellular cAMP that result from activation of a Gi-coupled receptor cause melanosomes to migrate to the center of the cell, resulting in a dramatic lightening in color. If cAMP levels are then raised, following activation of a Gs-coupled receptor, the melanosomes are re-dispersed and the cells appear dark again. The increased levels of diacylglycerol that result from activation of Gq-coupled receptors can also induce this re-dispersion. In addition, the technology is also suited to the study of certain receptor tyrosine kinases. The response of the melanophores takes place within minutes of receptor activation and results in a simple, robust color change. The response can be easily detected using a conventional absorbance microplate reader or a modest video imaging system. Unlike other skin cells, the melanophores derive from the neural crest and appear to express a full complement of signaling proteins. In particular, the cells express an extremely wide range of G-proteins and so are able to functionally express almost all GPCRs.

Melanophores can be utilized to identify compounds, including natural ligands, against GPCRs. This method can be conducted by introducing test cells of a pigment cell line capable of dispersing or aggregating their pigment in response to a specific stimulus and expressing an exogenous clone coding for the GCPR. A stimulant, e.g., melatonin, sets an initial state of pigment disposition wherein the pigment is aggregated within the test cells if activation of the GPCR induces pigment dispersion. However, stimulating the cell with a stimulant to set an initial state of pigment disposition wherein the pigment is dispersed if activation of the GPCR induces pigment aggregation. The test cells are then contacted with chemical compounds, and it is determined whether the pigment disposition in the cells changed from the initial state of pigment disposition. Dispersion of pigments cells due to the candidate compound, including but not limited to a ligand, coupling to the GPCR will appear dark on a petri dish, while aggregation of pigments cells will appear light.

Materials and methods will be followed according to the disclosure of U.S. Pat. Nos. 5,462,856 and 6,051,386. These patent disclosures are hereby incorporated by reference in their entirety.

Figure 14B:
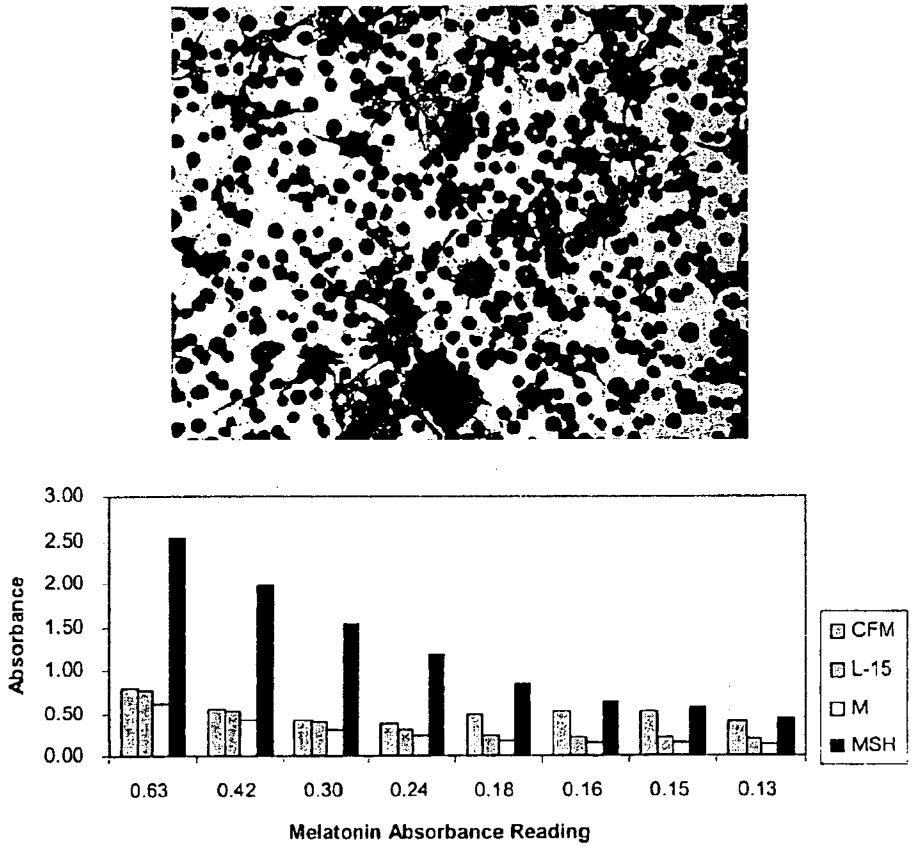
Figure 30:
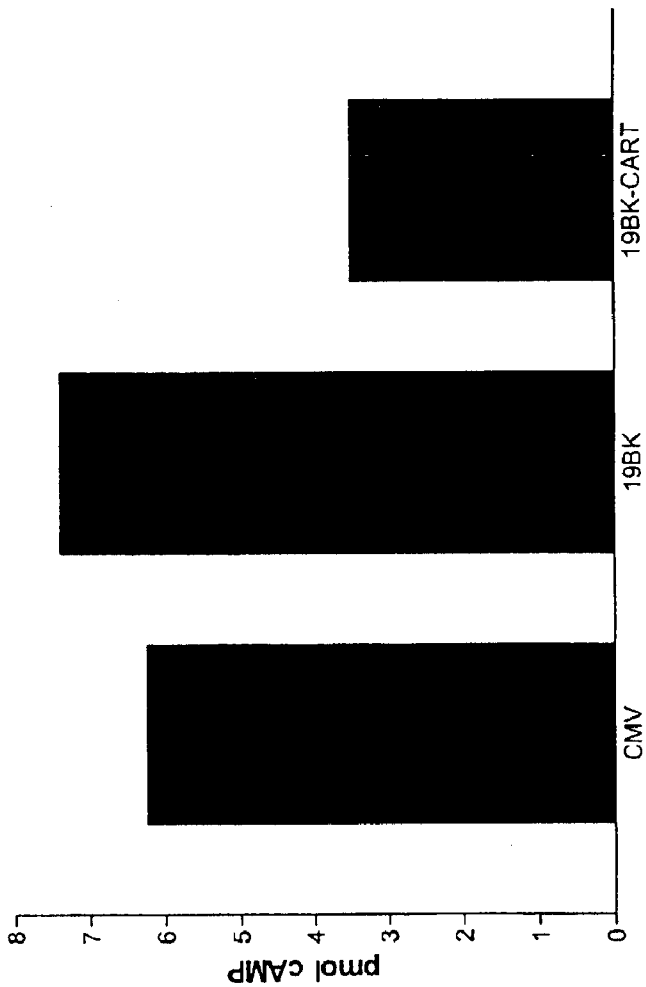
FIG. 30.
Figure 31:
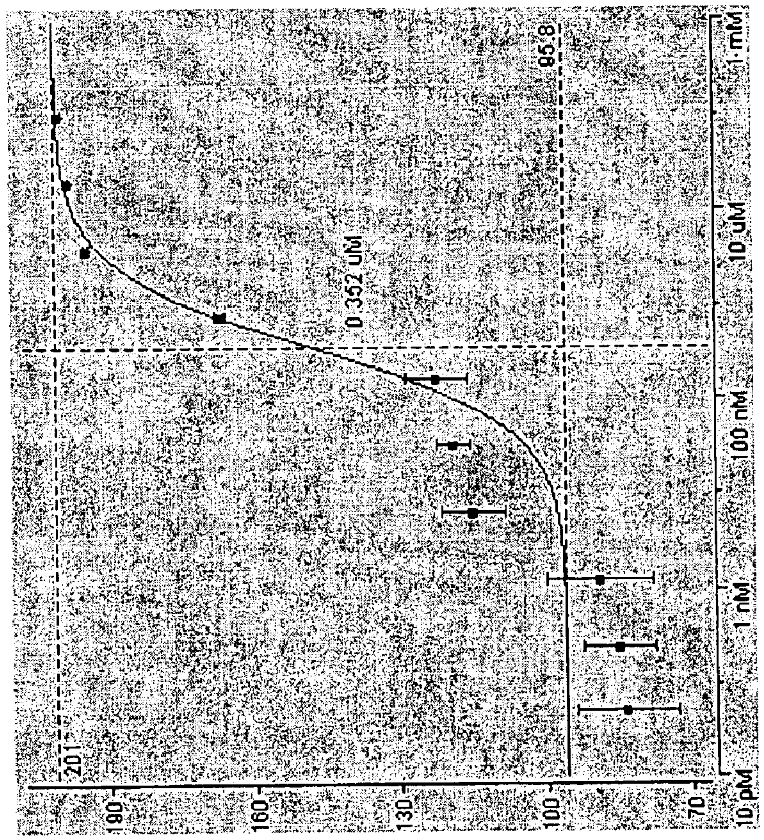
FIG. 31.

Melanophores were transfected by electroporation with plasmids coding for the GPCRs, for example hRUP25, hRUP38, hRUP11 and hRUP19. Pre-screening of the GPCRs in melanophores was performed in the absence of nicotinic acid following the protocol below to determine the G protein coupling. This pre-screen evidenced that hRUP25 (FIG. 14A), hRUP38 (FIG. 14B) and hRUP19 (FIG. 14C) are strongly Gi-coupled. hRUP11 is also strongly Gi-coupled (not shown). Consistent with hRUP19 being Gi-coupled, CART-activated hRUP19 inhibits cAMP production in membranes of transfected 293 cells (FIG. 30).

The cells were plated in 96-well plates (one receptor per plate). 48 hours post-transfection, half of the cells on each plate were treated with 10 nM melatonin. Melatonin activates an endogenous Gi-coupled receptor in the melanophores and causes them to aggregate their pigment. The remaining half of the cells were transferred to serum-free medium 0.7× L-15 (Gibco). After one hour, the cells in serum-free media remained in a pigment-dispersed state while the melatonin-treated cells were in a pigment-aggregated state. At this point, the cells were treated with a dose response of nicotinic acid (Sigma). If the plated GPCRs bound to nicotinic acid, the melanophores would be expected to undergo a color change in response to the compound. If the receptor were either a Gs or Gq coupled receptor, then the melatonin-aggregated melanophores would undergo pigment dispersion. In contrast, if the receptor was a Gi-coupled receptor, then the pigment-dispersed cells would be expected to undergo a dose-dependent pigment aggregation.

Melanophores transfected with hRUP25 were treated with nicotinic acid. Upon this treatment, the cells underwent pigment aggregation in a dose-dependent manner. hRUP25-expressing cells that were pre-aggregated with melatonin did not disperse upon nicotinic acid treatment, which is consistent with the receptor being a Gi-coupled receptor. See, FIG. 15 and infra.

Figure 15A:
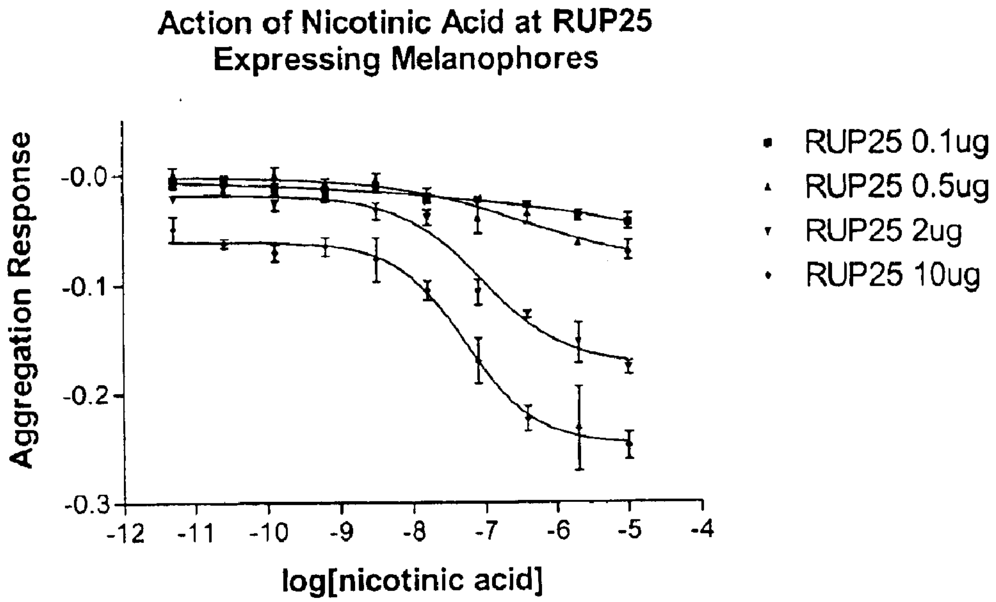
FIGS. 15A–B.

To confirm and extend these results, melanophores were transfected with a range of hRUP25 DNA from 0 to 10 μg. As controls, melanophores were also transfected with 10 μg of $\alpha_{2A}$ Adrenergic receptor (a known Gi-coupled receptor) and salmon sperm DNA (Gibco), as a mock transfection. On day 3, the cells were again incubated for 1 hour in serum-free L-15 medium (Gibco) and remained in a pigment-dispersed state. The cells were then treated with a dose response of nicotinic acid. See, FIG. 15A. FIG. 15A depicts the aggregation response of nicotinic acid at melanophores transfected with various ranges of hRUP25. At 10 μg of hRUP25, the $EC_{50}$ for nicotinic acid is about 54 nM. Stated differently, at very low concentrations, nicotinic acid evidences binding to hRUP25.

Figure 15B:
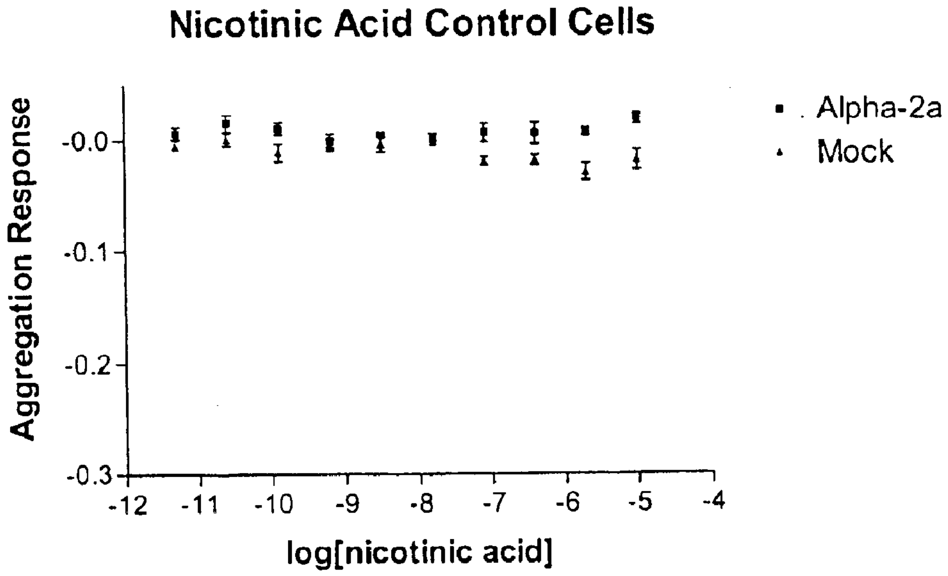

Reference is now made to FIG. 15B. In FIG. 15B, both the mock transfected and $\alpha_{2A}$ transfected cells did not respond to nicotinic acid. This data evidences that nicotinic acid binds specifically to the Gi-coupled receptor hRUP25.

The data show that the greater the amount of hRUP25 plasmid DNA transfected, the greater the magnitude of the observed aggregation response. Collectively these data indicate that hRUP25: 1) is a Gi-coupled receptor that 2) binds to nicotinic acid.

As set forth herein, nicotinic acid is a ligand for, and agonist of, human, mouse and rat RUP25. It is further shown that hRUP38, hRUP11, hRUP19, and human, mouse and rat RUP25 are Gi-coupled. Additionally, hRUP38, human and mouse RUP19, hRUP11, and human, mouse, and rat RUP25 may be used in methods described herein to identify antagonists, agonists, inverse agonists, partial agonists, allosteric enhancers, and negative allosteric modulators. As discussed supra, methods of modifying nicotinic acid receptor activity in adipocytes using a modulator of the receptor are set forth. Preferably, the modulator is an agonist.

Example 9

Figure 16:
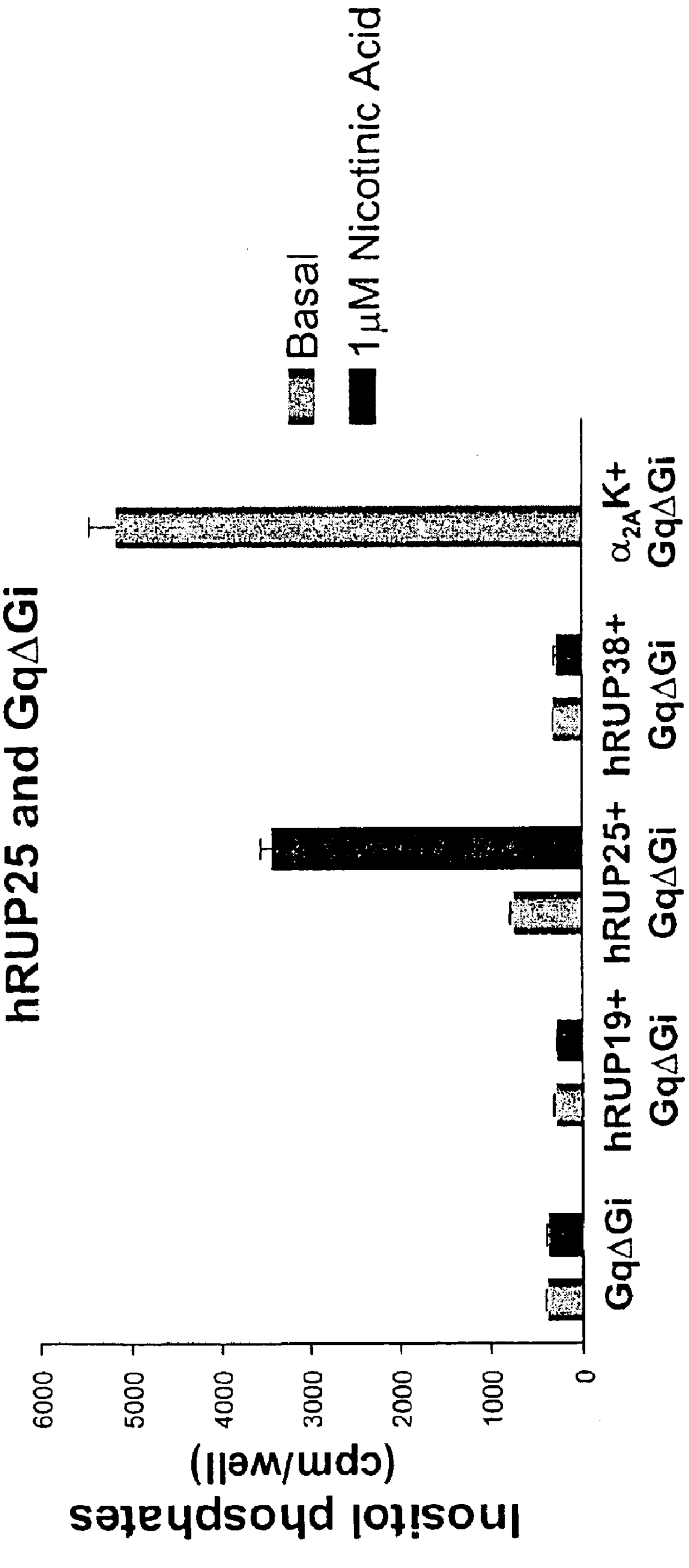
FIG. 16.

Nicotinic Acid Induced-Inositol Phosphates Accumulation in 293 Cells Co-Expressing hRUP and GqΔGi FIG. 16 illustrates the nicotinic acid induced-inositol phosphates (IPs) accumulation in HEK293 cells co-expressing hRUP25 and the chimeric Gaq-subunit in which the last five amino acids have been replaced with the corresponding amino acids of Gal (GqΔGi). This construct has been shown to convert the signaling of a Gi-coupled receptor to the Gq pathway (i.e. accumulation of inositol phosphates) in response to receptor activation. Cells transfected with GqΔGi plus either empty plasmid or the constitutively activated $\alpha_{2A}$AR ($\alpha_{2A}$K) are non-responsive to nicotinic acid and served as controls for the IP assay. Cells transfected with GqΔGi plus either hRUP19 or hRUP38 are also unresponsive to nicotinic acid, indicating that nicotinic acid is not an agonist for either hRUP19 or hRUP38.

Example 10

Figure 17:
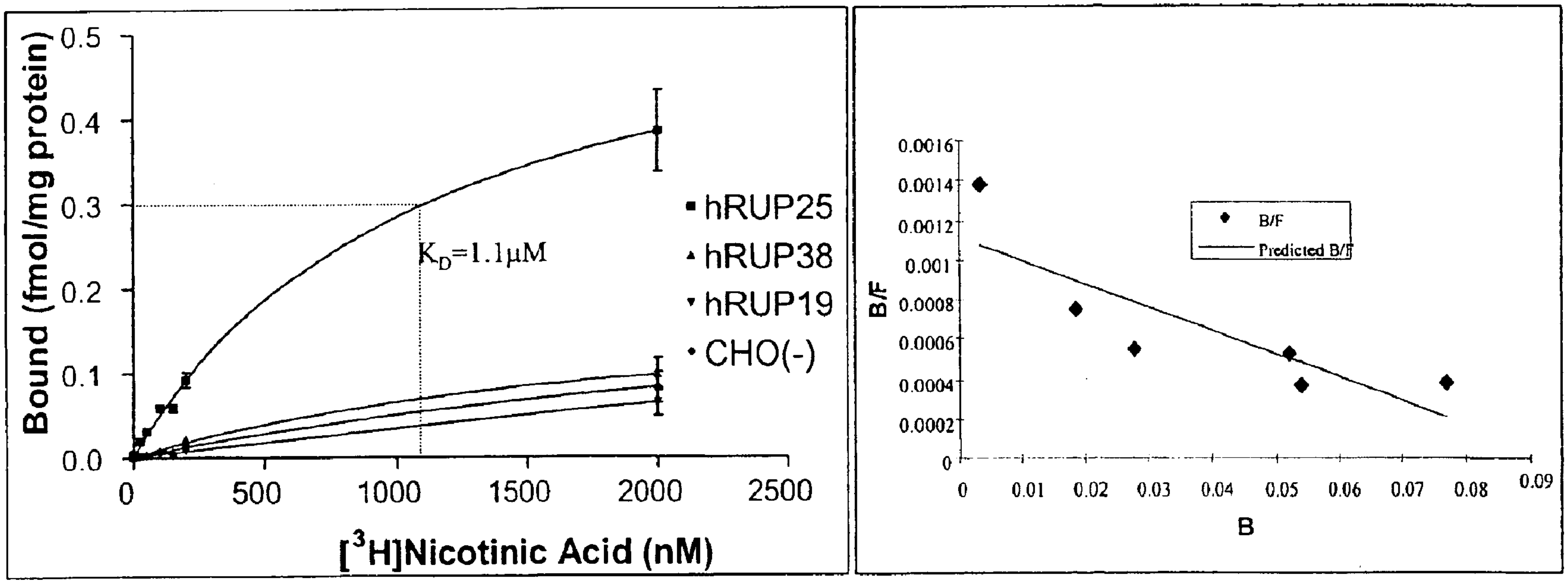
FIG. 17.

Saturation Binding of [$^3$ H] Nicotinic Acid to Membranes from Cells Expressing Either hRUP25, hRUP38, hRUP19 or Vector Alone FIG. 17 shows the results from saturation binding of [3H] nicotinic acid to membranes from cells expressing either hRUP25, hRUP38, hRUP19 or vector alone [CHO(—)]. Only hRUP25 was found to bind nicotinic acid in a specific and high-affinity manner.

Example 11

Nicotinic Acid and (−)-Nicotine Induced-Inhibition of Forskolin Stimulated cAMP Accumulation in hRUP25-CHO Cell Stable Line #46

Figure 18A:
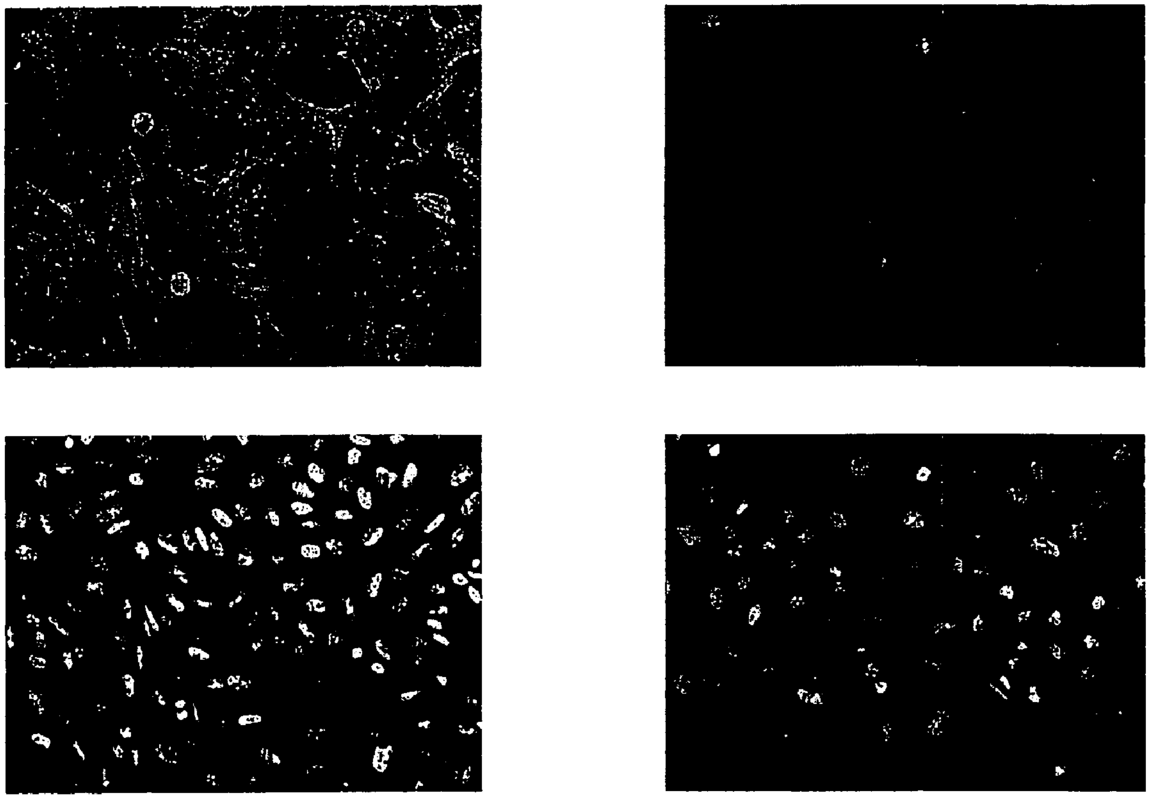
FIGS. 18A–B.

FIG. 18A is a set of immunofluorescent photomicrographs illustrating the expression of hemaglutinin(HA)-tagged hRUP25 in a stably transfected line of CHO cells (top; clone #46). No significant labeling is detected in mock stably-transfected CHO cells (Mock). The lower panels identify the nuclear (DAPI) staining of cells in the same field.

Figure 18B:
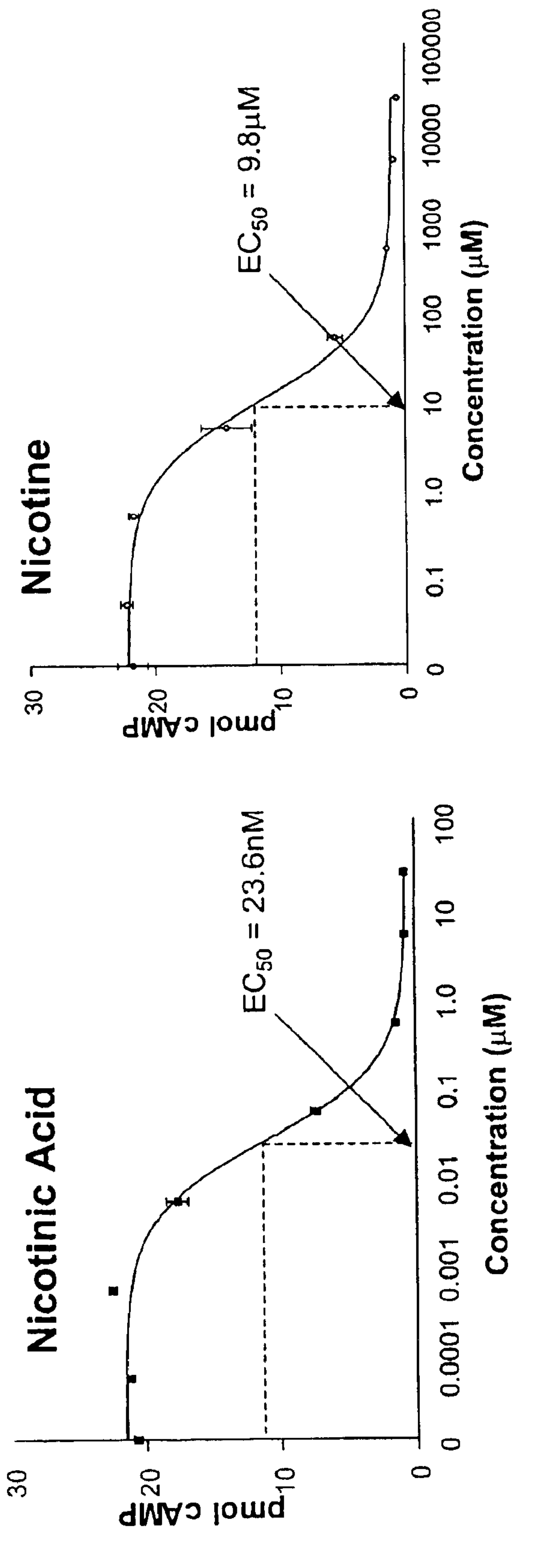

FIG. 18B illustrates nicotinic acid and (−)-nicotine induced-inhibition of forskolin stimulated cAMP accumulation in hRUP25-CHO cell stable line #46 (described in preceding paragraph). The $EC_{50}$ for nicotinic acid is 23.6 nM and that for (−)-nicotine is 9.8 μM.

Figure 19:
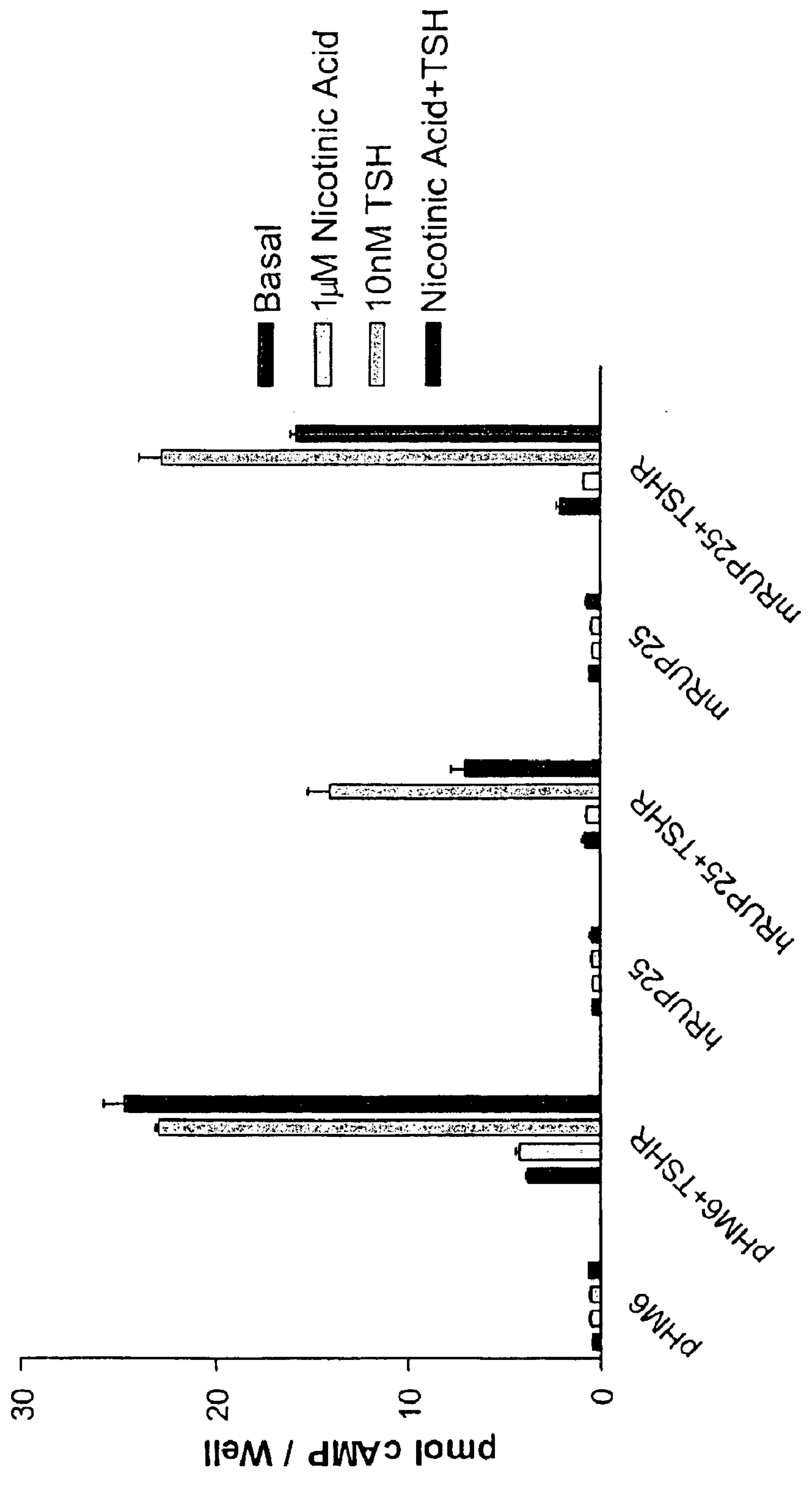
FIG. 19.

Example 12 hRUP25 and mRUP25 Inhibit TSHR Induced-cAMP Accumulation Following Activation by Nicotinic Acid FIG. 19 indicates that, in response to nicotinic acid, both hRUP25 and the mouse ortholog mRUP25 can inhibit TSHR stimulated cAMP production (in the presence and absence of TSH).

Figure 20:
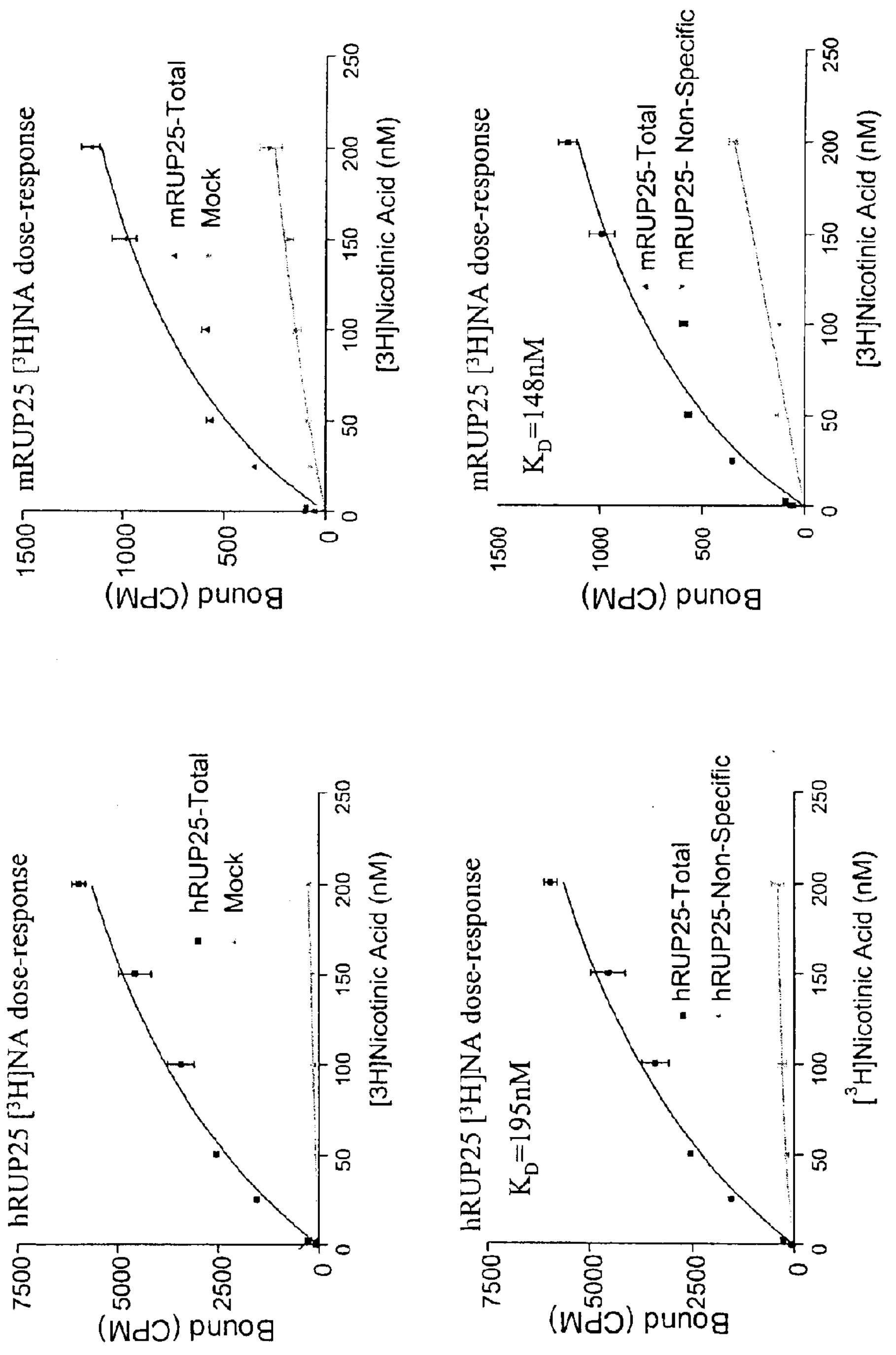
FIG. 20.

Example 13 hRUP25 and mRUP25 Bind to Nicotinic Acid Specifically and with High Affinity FIG. 20 shows the saturation binding curves of [$^3$H] nicotinic acid ([$^3$H]NA) to membranes prepared from HEK293 cells transiently expressing either hRUP25 or mRUP25. Note the significant binding of [3H]NA relative to either that found in membranes derived from mock transfected cells or in the presence of an excess of non-labeled nicotinic acid (200 μM).

Radioligand binding was done as follows. Media was removed from cells grown in culture [either stably or transiently transfected with negative control (empty plasmid) or with the individual receptors hRUP25, mRUP25, rRUP25, hRUP38, hRUP11 or hRUP19] and cells were scraped and homogenized in buffer containing 15 mM HEPES, 5 mM EDTA, 5 mM EGTA, plus protease inhibitors (leupeptin, PMSF and pepstatin). Membranes were harvested following centrifugation at 30,000×g, 4° C. for 30 min. Membranes were then resuspended and re-homogenized in CHAPS binding buffer (50 mM Tris-HCl and 0.02% CHAPS, pH 7.4). Aliquots were taken for protein analysis via the Bradford protein assay and normalized such that each binding reaction contained the same amount of membrane protein (25–50 μg). 50 nM [$^3$ H]nicotinic acid was added to each sample and either buffer (for total samples) or a desired amount of non-labeled compound (at the same volumes and in the same diluent) was added and the reactions were left at room temperature gently shaking for 1 hr. Free ligand was separated from bound ligand via rapid filtration onto a filter. Appropriate scintilant was added to each sample and counted in an appropriate scintillation counter. Data was analyzed using Excel and PrismGraph. In some cases radioligand binding was performed using a scintillation proximity assay (SPA) in which case the samples did not require filtration or the addition of scintilant.

Example 14

The Rank Order of Potency of Compounds on HRUP25 Closely Matches that of the Pharmacologically Defined Nicotinic Acid Receptor FIG. 21 is a table comparing the rank order of potency of various compounds on hRUP25 and the pharmacologically defined nicotinic acid receptor. The potencies at hRUP25 derived both by a functional analysis measuring the inhibition of forskolin induced cAMP production and competitive radioligand binding assays, closely match the order of potencies of the pharmacologically defined nicotinic acid receptor.

Example 15

Figure 22A:
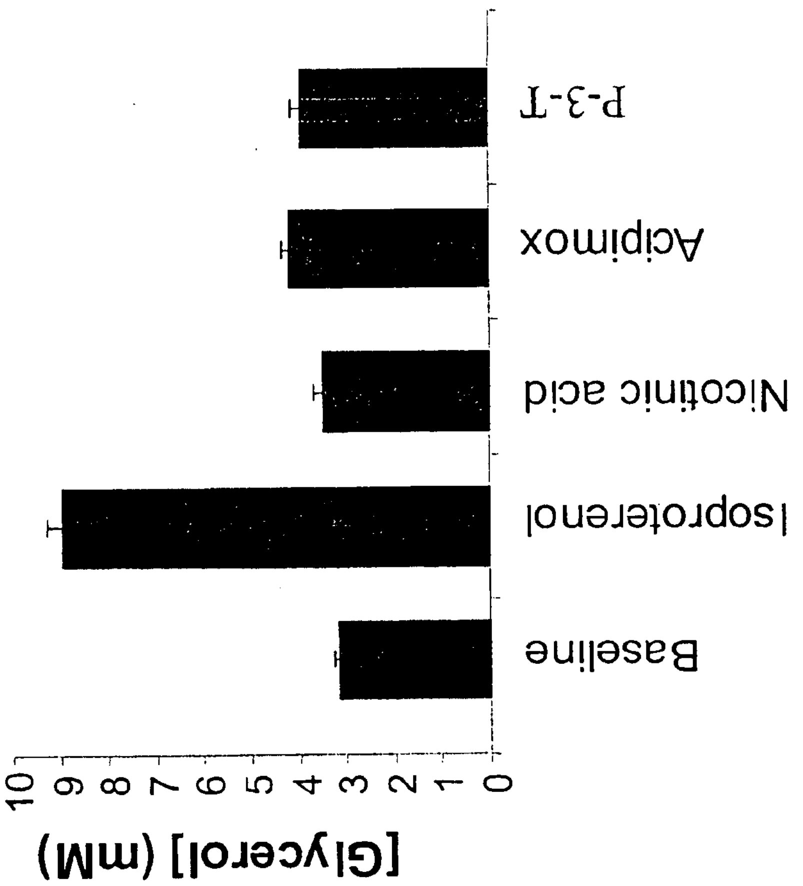
FIGS. 22A–B.

Nicotinic Acid and Related Compounds Inhibit Isoproterenol Induced Lipolysis in Rat Epidiymal Fat Derived Adipocytes FIG. 22A depicts nicotinic acid and related compounds inhibiting isoproterenol induced lipolysis in rat epididymal fat derived adipocytes at a concentration of 10 μM. P-3-T represents 3-tetrazole-5-pyridine.

Figure 22B:
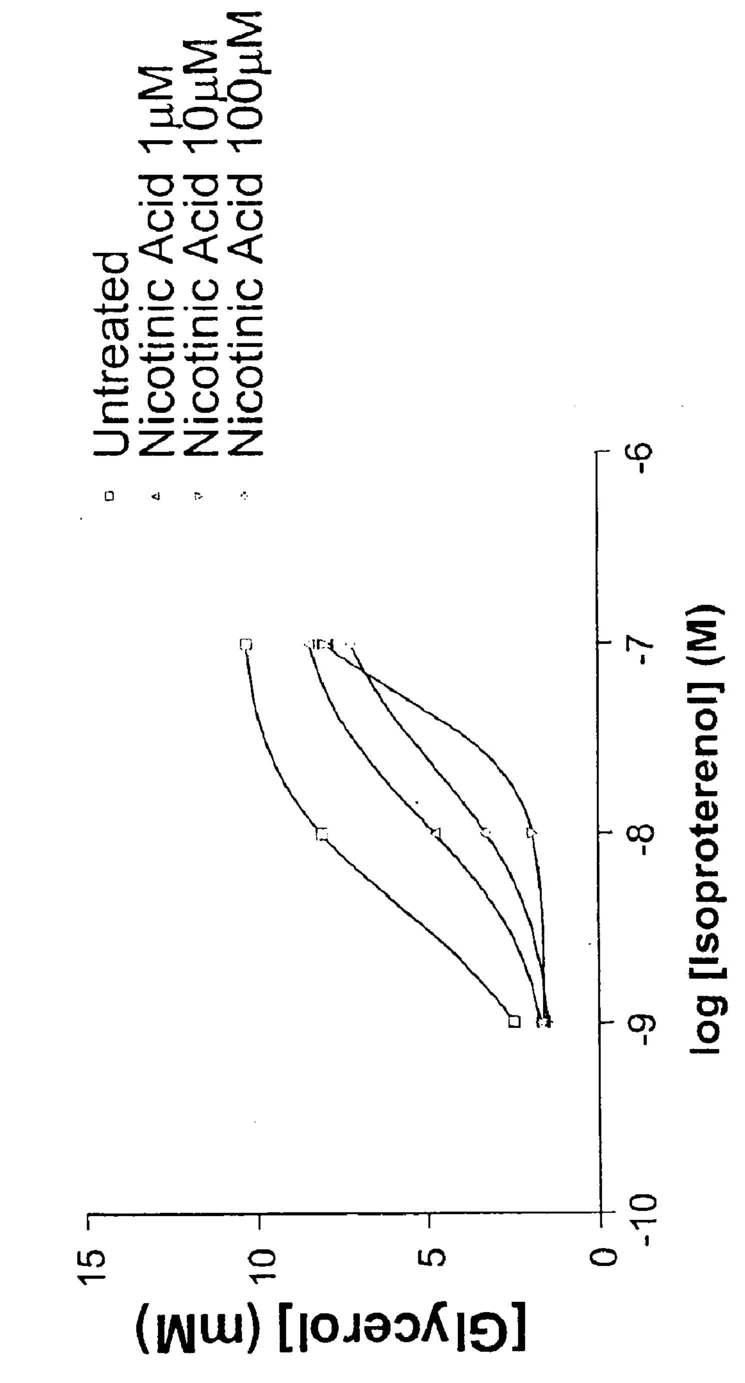

FIG. 22B illustrates a nicotinic acid dose-dependent inhibition of isoproterenol induced-lipolysis in rat epididymal fat derived adipocytes. Note the rightward shift in the dose-response curves with increasing concentrations of nicotinic acid.

Lipolysis assays were done following the isolation of adipocytes from rat or human. The source of fat from rats was the epididymal fat and from humans was either subcutaneous or omental. Cells were isolated following collagenase digestion and floatation. An elevation of intracellular cAMP levels and concomitant activation of lipolysis via hormone sensitive lipase was accomplished using isoproterenol, forskolin, 3-isobutyl-1-methyl-xanthine (IBMX) or a combination thereof at concentrations and times determined empirically and depending on the source of tissue. Lipolysis was allowed to continue for the desired time in the presence or absence of drug (e.g. nicotinic acid, P-3-T, etc). Data was analyzed using Excel and PrismGraph.

To show that a modulator of hRUP19 behaves similarly, an analogous assay is set up using said modulator of hRUP19. Preferred said modulator is an agonist.

To show that a modulator of hRUP38 behaves similarly, an analogous assay is set up using said modulator of hRUP38, wherein the rat is transgenic for hRUP38. Preferred said modulator is an agonist.

To show that a modulator of hRUP11 behaves similarly, an analogous assay is set up using said modulator of hRUP11, wherein the rat is transgenic for hRUP11. Preferred said modulator is an agonist.

Example 16

Figure 23:
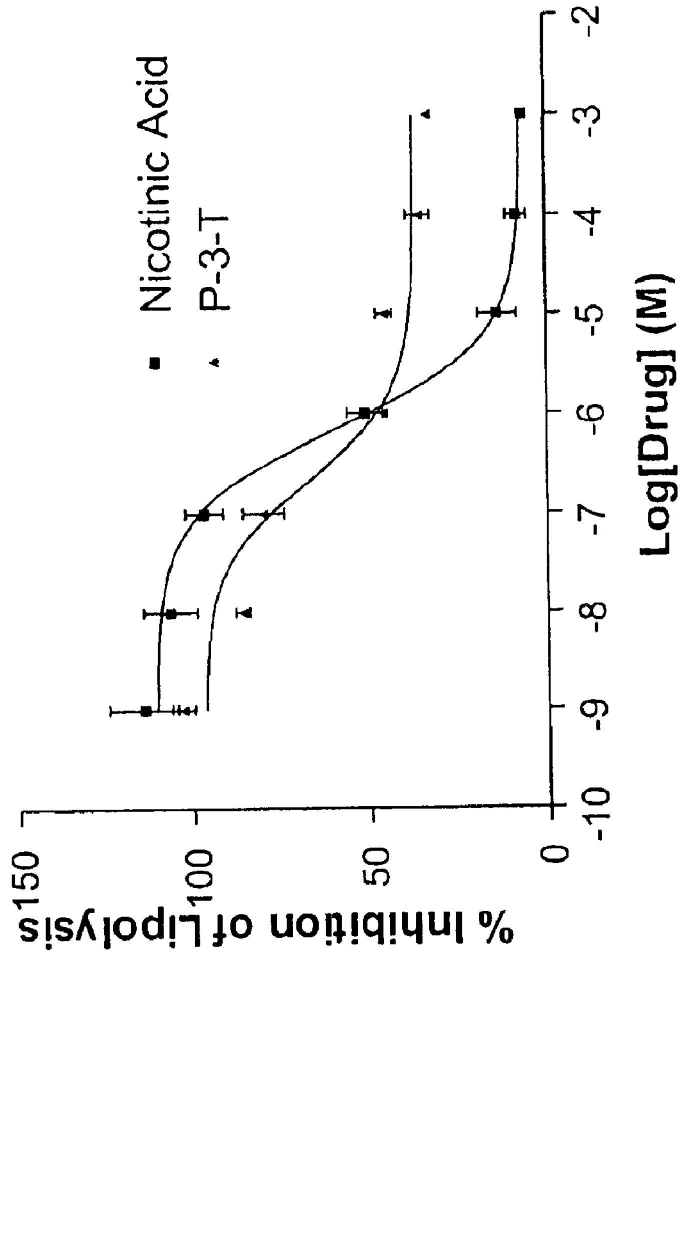
FIG. 23.

Dose-Dependent Inhibition of Isoproterenol Induced-Lipolysis in Human, Subcutaneous-Derived, Primary Adipocytes Via Nicotinic Acid and P-3-T FIG. 23 illustrates the ability of both nicotinic acid and the related compound P-3-T (3-tetrazole-5-pyridine) to inhibit isoproterenol induced lipolysis in adipocyte primary cultures derived from human subcutaneous fat in a dose-dependant manner. The $EC_{50}$ value for nicotinic acid and P-3-T were 716 nM and 218 nM respectively. (Also see Example 15, supra.)

Example 17

Screening Data for Nicotinic Acid and 1-Isopropyl-1H-Benzotriazole-5-Carboxylic Acid in cAMP Assays FIG. 24 presents screening data via adenylyl cyclase assay for hRUP38. Note that nicotinic acid does not activate inhibition of forskolin stimulated cAMP hRUP38-expressing CHO cells whereas 1-Isopropyl-1H-benzotriazole-5-carboxylic acid does. 1-Isopropyl-1H-benzotriazole-5-carboxylic acid has no effect on CHO cells expressing either hRUP25 or hRUP19.

Example 18

Figure 25:
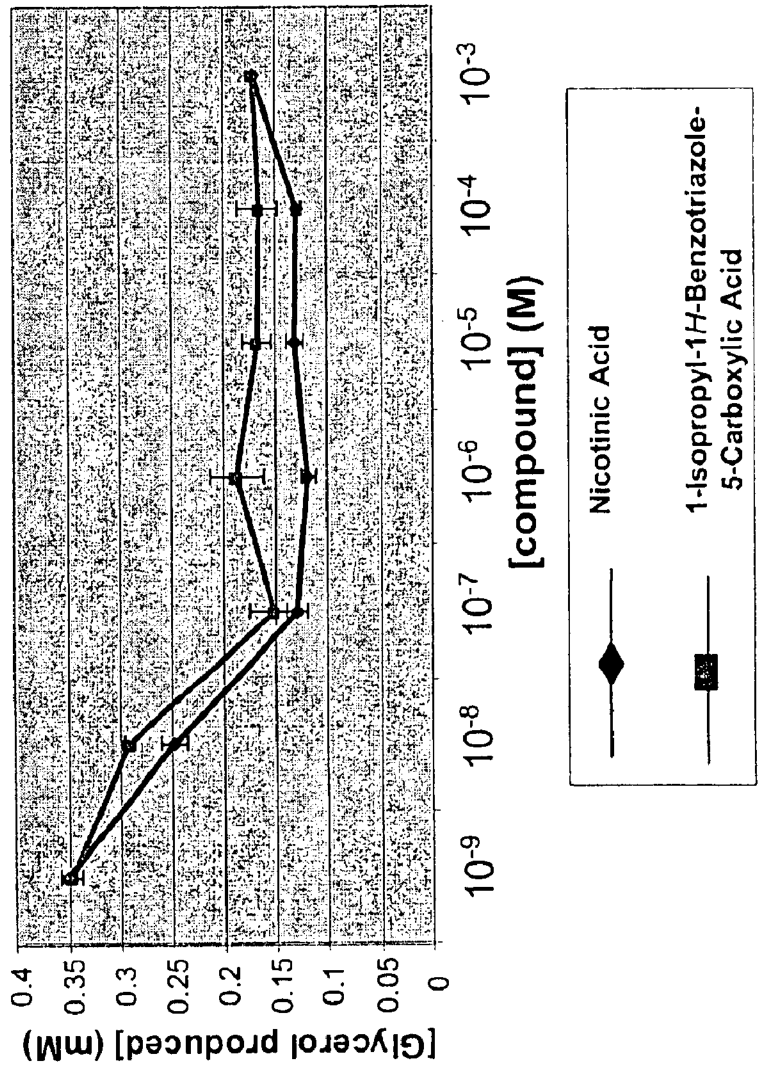
FIG. 25. Nicotinic acid and 1-Isopropyl-1H-benzotriazole-5-carboxylic acid were separately dose-dependently applied to isoproterenol stimulated (100 nM) primary human adipocytes.

Inhibition of Isoproterenol Stimulated Lipolysis in Human Subcutaneous Adipocytes Nicotinic acid (an agonist of hRUP25) and 1-Isopropyl-1H-benzotriazole-5-carboxylic acid (an agonist of hRUP38; see Example 17, supra) were separately dose-dependently applied to isoproterenol (100 nM) stimulated primary human adipocytes. FIG. 25 illustrates the ability of 1-Isopropyl-1H-benzotriazole-5-carboxylic acid to inhibit isoproterenol stimulated lipolysis in adipocyte primary cultures derived from human subcutaneous fat in a dose-dependent manner comparable to that of nicotinic acid.

To show that a modulator of hRUP19 behaves similarly, an analogous assay is set up using said modulator of hRUP19. Preferred said modulator is an agonist.

To show that a modulator of hRUP11 behaves similarly, an analogous assay is set up using said modulator of hRUP11. Preferred said modulator is an agonist.

Example 19

Inhibition of Forskolin Stimulated cAMP Accumulation in hRUP38-CHO Stable Cell Line by 3-(Bromo-2-Ethoxy-Phenyl)-Acrylic Acid FIG. 26 presents screening data via adenylyl cyclase assay for hRUP38. Note that 3-(5-Bromo-2-ethoxy-phenyl)-acrylic acid activates inhibition of forskolin stimulated cAMP in hRUP38-expressing CHO cells but has no effect on CHO cells expressing either hRUP25 or hRUP19. The $EC_{50}$ for 3-(5-Bromo-2-ethoxy-phenyl)-acrylic acid is 1.17 μM. (Also see the legend to Example 11, supra, for details directed to stable CHO transfectants.)

Example 20

RT-PCR Indicates that hRUP19 is Selectively Expressed in Human Fat Cells

FIG. 27 presents an RT-PCR analysis of hRUP19 expression using a panel of human tissues. The analysis indicates that hRUP19 is selectively expressed in fat cells. Low expression is also evident in testis, placenta, kidney and spleen.

Oligonucleotides used for PCR had the following sequences: 5'-GGCCGTGGCTGATTTCCTCCTTAT-3' (SEQ. ID. NO.:152; forward primer) and 5'-AACCGGGTCGCCTTCTTCATCC-3' (SEQ. ID. NO.:153; reverse primer). Commercially available human multiple tissue cDNA panels were used as templates [Clontech, MTC panels Human I (#K1420-1) and Human II (K-1421-1), and human fat cell cDNA (#7128-1)]. 1 ng cDNA was used per PCR amplification. PCR was performed using Platinum PCR SuperMix (Life Technologies, Inc.); according to manufacturer instructions. The following cycles were used: 95° C. for 4 min; 95° C. for 1 min; 60.5° C. for 30 sec, 72° C. for 1 min, and 72° C. for 7 min; cycles 2 through 4 were repeated 35 times. The resulting PCR reactions (15 μl) were loaded on a 1.5% agarose gel to analyze the RT-PCR products, and a specific 492 base-pair DNA fragment representing hRUP19 was specifically amplified from cDNA of fat cell origin. Low expression was also evident in testis, placenta, kidney, and spleen.

Example 21

Northern Blot Analysis of hRUP19 Expression in Selected Tissues

FIG. 28 presents a Northern blot analysis of hRUP19 expression using a panel of human tissues. The analysis indicates that hRUP19 is strongly expressed in mammary gland, probably due to fat cell-specific expression of hRUP19. Ad, adrenal gland; Bl, bladder, BM, bone marrow; Br, brain (whole); LN, lymph node; MG, mammary gland; Pr, prostate; Sp, spinal cord; St, stomach; Thyr, thyroid; Trch, trachea; Ut, uterus.

A pre-made blot containing Poly A+ RNA from 12 human tissues was purchased from Clontech (Human 12-Lane II, Cat. # 7784-1). hRUP19 cDNA probe encompassing the coding region was generated by PCR using a plasmid containing hRUP19 cDNA as template. The blot was pre-hybridized with 20 ml Clontech ExpressHyb solution (Cat. # 8015-2) for 30 minutes in a hybridization oven at 65° C., according to the manufacturer's directions. 25 ng of a random primer-labeled, hRUP19 cDNA probe was added to the prehybridization solution, and the incubation was continued for an additional 2 hr. The membrane was then washed according to the manufacturer's directions (Cat. # 8015-2) and exposed to film for autoradiography over a period of two days. Ad, adrenal gland; Bl, bladder, BM, bone marrow; Br, brain (whole); LN, lymph node; MG, mammary gland; Pr, prostate; Sp, spinal cord; St, stomach; Thyr, thyroid; Trch, trachea; Ut, uterus.

Example 22

RUP19 Expression is Induced During Adipocyte Differentiation: Characterization of mRUP19 Expression in Mouse 3T3 Pre-Adiocytes and AND Adipocytes FIG. 29 presents an analysis of RUP19 mRNA expression as a function of adipocyte differentiation. The analysis indicates that RUP19 mRNA expression is induced during adipocyte differentiation.

3T3 pre-adipocytes were cultured in DMEM containing 10% bovine calf serum. These cells were induced to differentiate into an adipocyte phenotype using a standard protocol [Haraguchi K et al (1996) Biochem Biophys Res Comm 223:193–198; the disclosure of which is hereby incorporated by reference in its entirety]. Briefly, 1 day after confluence, cells were treated with DMEM containing 10% FBS, 10 μg/ml insulin, 0.2 μg/ml dexamethasone, and 0.5 mM isobutylmethylxanthine. After 3 days, the cells were shifted to media supplemented with 10 μg/ml insulin and 10% FBS, and 2 days later, the cells were shifted to media containing 10% FBS alone. After an additional 48 hrs, total RNA was isolated from undifferentiated or differentiated cells using RNAzol according to the manufacturer's directions. Separate populations of undifferentiated and differentiated cells were subjected to staining with Oil Red, to confirm the induction of an adipocyte phenotype with this protocol.

Northern blot analysis. 10 ug of total RNA from 293 cells, 3T3 preadipocytes and 3T3 adipocytes was subjected to electrophoresis on a 1% agarose/formaldehyde gel and transferred to a nylon membrane using standard protocols. The blot was hybridized to a 361 bp mRUP19 cDNA probe and exposed to film as described in FIG. 28. The mRUP19 cDNA probe corresponds to nucleotides 5–365 of SEQ. ID. NO.:150.

RT-PCR analysis. To detect mRUP19 mRNA by RT-PCR, the following primers were used: 5'-ACTGTGGTGGCTGTGGATAGGTA-3' (SEQ. ID. NO.:154; forward primer) and 5'-GCAGATTGTGAGCTTGGCGTAGAA-3' (SEQ. ID. NO.:155; reverse primer). These are predicted to generate an mRUP19 product of 567 bp. The cDNA templates were prepared using a RETROscript™ First Strand Synthesis Kit for RT-PCR (Ambion, Inc., Cat. # 1710), according to the manufacturer's directions, except that duplicate reactions were done for each input RNA, and in one of these, reverse transcriptase was excluded from the reaction. 3 ul of each reaction was used for PCR. The reaction conditions for the PCR were as follows: 1 cycle @ 94° C./5 min., 25 cycles (94° C./30 sec, 59° C./30 sec, 72° C./1 min, and 1 cycle @ 72° C./5 min. The reactions were then analyzed on a 1% agarose gel. Pre-diff 3T3-L1, mouse 3T3 pre-adipocytes; Post-diff 3T3-L1, differentiated 3T3 adipocytes; β-TC-6, a mouse insulin-producing cell line; NIT-1, a mouse insulin-producing cell line.

Example 23

Cart-Activated hRUP19 Inhibits cAMP Production in Membranes of Transfected 293 Cells FIG. 30 presents a CART analysis of signal transduction by hRUP19. The analysis indicates that CART-activated hRUP19 inhibits cAMP production in membranes of transfected 293 cells.

Membranes were prepared as follows. 15 ug of the following expression plasmids were each introduced into 293 cells (one 15 cm dish per transfection) using Lipofectamine Reagent (Invitrogen, #18324-020) according to the manufacturer's instructions: pCMV-MCS (empty CMV expression plasmid), pCMV-hRUP19, pCMV-hRUP19-CART (same as pCMV-hRUP19, except that codon 219 has been converted from threonine to lysine). After 48 hours, a crude membrane preparation was prepared using standard protocols. Briefly, cells were washed with ice cold PBS, removed from the plate by scraping in the presence of a hypotonic Tris/EDTA buffer, fragmented using a pre-chilled dounce homogenizer, spun at low speed to pellet nuclei and intact cells, and finally, the supernatant is subjected to centrifugation at 20,000 rpm in a Beckman Avanti J-20 centrifuge. The membrane pellet is then resuspended at a protein concentration of 1 mg/ml for use in a membrane cyclase assay. The membrane cyclase assay was carried out as per the manufacturer's recommendation using an Adenylyl Cyclase Activation FlashPlate Assay Kit (Perkin Elmer Life Sciences, Inc., #SMP004B).

Example 24

Summary: hRUP25, mRUP25, rRUP25, hRUP38, hRUP19, mRUP19, rRUP19, and hRUP11

TABLE M

| Disclosed Nicotinic Acid Receptor Sub-Family GPCRs | Expression by Adipocytes or Adipose | Gi-Coupled (Lowers the Level of Intracellular cAMP) | Shown to Inhibit Intracellular Lipolysis | Agonist |
|---|---|---|---|---|
| hRUP25 | yes | yes | yes | nicotinic acid; (—)-nicotine; see FIG. 21; |

TABLE M-continued

| Disclosed Nicotinic Acid Receptor Sub-Family GPCRs | Expression by Adipocytes or Adipose | Gi-Coupled (Lowers the Level of Intracellular cAMP) | Shown to Inhibit Intracellular Lipolysis | Agonist |
|---|---|---|---|---|
| | | | | (5-hydroxy-1-methyl-3-propyl-1H-pyrazol-4-yl)-pyridin-3-yl-methanone |
| mRUP25 | yes | yes | n.d. | nicotinic acid |
| rRUP25 | yes | yes | yes | nicotinic acid |
| hRUP38 | yes | yes | yes | 1-Isopropyl-1H-benzotriazole-5-carboxylic acid; 3-(5-Bromo-2-ethoxy-phenyl)-acrylic acid |
| hRUP11 | n.d. | yes | n.d. | n.d. |
| hRUP19 | yes | yes | n.d. | n.d. |
| mRUP19 | yes | n.d. | n.d. | n.d. |
| rRUP19 | n.d. | n.d. | n.d. | n.d. |

n.d.: not displayed

Example 25

Rodent Diabetes Models

Rodent models of type 2 diabetes associated with obesity and insulin resistance have been developed. Genetic models such as db/db and ob/ob [see Diabetes (1982) 31:1–6] in mice and fa/fa in zucker rats have been developed for understanding the pathophysiology of disease and for testing candidate therapeutic compounds [Diabetes (1983) 32:830–838; Annu Rep Sankyo Res Lab (1994) 46:1–57]. The homozygous animals, C57 BL/KsJ-db/db mice developed by Jackson Laboratory are obese, hyperglycemic, hyperinsulinemic and insulin resistant [J Clin Invest (1990) 85:962–967], whereas heterozygotes are lean and normoglycemic. In the db/db model, mice progressively develop insulinopenia with age, a feature commonly observed in late stages of human type 2 diabetes when sugar levels are insufficiently controlled. Since this model resembles that of human type 2 diabetes, the compounds of the present invention are tested for activities including, but not limited to, lowering of plasma glucose and triglycerides. Zucker (fa/fa) rats are severely obese, hyperinsulinemic, and insulin resistant {Coleman, Diabetes (1982) 31:1; E Shafrir in Diabetes Mellitus, H Rifkin and D Porte, Jr, Eds [Elsevier Science Publishing Co, New York, ed. 4, (1990), pp. 299–340]}, and the fa/fa mutation may be the rat equivalent of the murine db mutation [Friedman et al, Cell (1992) 69:217–220; Truett et al, Proc Natl Acad Sci USA (1991) 88:7806]. Tubby (tub/tub) mice are characterized by obesity, moderate insulin resistance and hyperinsulinemia without significant hyperglycemia [Coleman et al, Heredity (1990) 81:424].

The present invention encompasses the use of compounds of the invention for reducing the insulin resistance and hyperglycemia in any or all of the above rodent diabetes models, in humans with type 2 diabetes or other preferred metabolic-related disorders or disorders of lipid metabolism described previously, or in models based on other mammals. Plasma glucose and insulin levels will be tested, as well as other factors including, but not limited to, plasma free fatty acids and triglycerides.

In Vivo Assay for Anti-Hyperglycemic Activity of Compounds of the Invention Genetically altered obese diabetic mice (db/db) (male, 7–9 weeks old) are housed (7–9 mice/cage) under standard laboratory conditions at 22° C. and 50% relative humidity, and maintained on a diet of Purina rodent chow and water ad libitum. Prior to treatment, blood is collected from the tail vein of each animal and blood glucose concentrations are determined using One Touch Basic Glucose Monitor System (Lifescan). Mice that have plasma glucose levels between 250 to 500 mg/dl are used. Each treatment group consists of seven mice that are distributed so that the mean glucose levels are equivalent in each group at the start of the study. db/db mice are dosed by micro-osmotic pumps, inserted using isoflurane anesthesia, to provide compounds of the invention, saline, or an irrelevant compound to the mice subcutaneously (s.c.). Blood is sampled from the tail vein at intervals thereafter and analyzed for blood glucose concentrations. Significant differences between groups (comparing compounds of the invention to saline-treated) are evaluated using Student t-test.

The foregoing is provided by way of illustration and not limitation. Other illustrative rodent models for type 2 diabetes have been described [Moller D E, Nature (2001) 414:821–7 and references therein; and Reed M J et al., Diabetes, Obesity and Metabolism (1999) 1:75–86 and reference therein; the disclosure of each of which is hereby incorporated by reference in its entirety].

Example 26

Mouse Atherosclerosis Model

Adiponectin-deficient mice generated through knocking out the adiponectin gene have been shown to be predisposed to atherosclerosis and to be insulin resistant. The mice are also a suitable model for ischemic heart disease [Matsuda, M et al. J Biol Chem (2002) July, and references cited therein, the disclosures of which are incorporated herein by reference in their entirety].

Adiponectin knockout mice are housed (7–9 mice/cage) under standard laboratory conditions at 22° C. and 50% relative humidity. The mice are dosed by micro-osmotic pumps, inserted using isoflurane anesthesia, to provide compounds of the invention, saline, or an irrelevant compound to the mice subcutaneously (s.c.). Neointimal thickening and ischemic heart disease are determined for different groups of mice sacrificed at different time intervals. Significant differences between groups (comparing compounds of the invention to saline-treated) are evaluated using Student t-test.

The foregoing mouse model of atherosclerosis is provided by way of illustration and not limitation. By way of further example, Apolipoprotein E-deficient mice have also been shown to be predisposed to atherosclerosis [Plump A S et al., Cell (1992) 71:343–353; the disclosure of which is hereby incorporated by reference in its entirety].

A preferred model is that of diet-induced atherosclerosis in C57BL/6J mice, an inbred strain known to be susceptible to diet-induced atherosclerotic lesion formation. This model is well known to those persons of ordinary skill in the art [Kamada N et al., J Atheroscler Thromb (2001) 8:1–6; Garber D W et al., J Lipid Res (2001) 42:545–52; Smith J D et al., J Intern Med (1997) 242:99–109; the disclosure of each of which is hereby incorporated by reference in its entirety].

Example 27

Transgenic Mouse/Rat hRUP38

The present invention also provides methods and compositions for the generation of mice and rats that express hRUP38 recombinant human antilipolytic GPCR polyeptide of the invention.

Methods of making transgenic animals such as mice and rats are well known to those of ordinary skill in the art, and any such method can be used in the present invention. Briefly, transgenic mammals can be produced, e.g., by transfecting a pluripotential stem cell such as an ES cell with a polynucleotide encoding hRUP38 polypeptide of the invention. Successfully transformed ES cells can then be introduced into an early stage embryo that is then implanted into the uterus of a mammal of the same species. In certain cases, the transformed ("transgenic") cells will comprise part of the germ line of the resulting animal and adult animals comprising the transgenic cells in the germ line can then be mated to other animals, thereby eventually producing a population of transgenic animals that have the transgene in each of their cells and that can stably transmit the transgene to each of their offspring. Other methods of introducing the polynucleotide can be used, for example introducing the polynucleotide encoding hRUP38 polypeptide of the invention into a fertilized egg or early stage embryo via microinjection. Alternatively, the transgene may be introduced into an animal by infection of zygotes with a retrovirus containing the transgene [Jaenisch, R, Proc Natl Acad Sci USA (1976) 73:1260–4]. Methods of making transgenic mammals are described, e.g., in Wall et al., J Cell Biochem (1992) 49:113–20; Hogan et al., in Manipulating the Mouse Embryo. A Laboratory Manual. (1986) Cold Spring Harbor Laboratory Press, Cold Spring Harbor, N.Y.; in WO 91/08216; or in U.S. Pat. No. 4,736, 866; all of which disclosures are hereby incorporated by reference in their entirety.

In preferred embodiments, expression of said gene is placed under the control of an essentially adipocyte specific promoter. In further preferred embodiments, said essentially adipocyte specific promoter is adiponectin gene promoter [Das, K et al., Biochem Biophys Res Commun (2001) 280:1120–9; Barth, N et al., Diabetologia (2002) 45:1425–1433; the disclosures of which are hereby incorporated by reference in its entirety]. In other further preferred embodiments, said essentially adipocyte specific promoter is resistin gene promoter [Hartman, H B et al. J Biol Chem (2002) 277:19754–61, which disclosure is hereby incorporated by reference in its entirety]. In other preferred embodiments, said essentially adipocyte specific promoter is aP2 [Felmer, R et al., J Endocrinol (2002) 175:487–498; the disclosure of which is hereby incorporated by reference in its entirety]. In other further preferred embodiments, expression of said gene is kept under the control of its endogenous promoter.

hRUP11

The present invention also provides methods and compositions for the generation of mice and rats that express hRUP11 recombinant human antilipolytic GPCR polyeptide of the invention.

Methods of making transgenic animals such as mice and rats are well known to those of ordinary skill in the art, and any such method can be used in the present invention. Briefly, transgenic mammals can be produced, e.g., by transfecting a pluripotential stem cell such as an ES cell with a polynucleotide encoding hRUP11 polypeptide of the invention. Successfully transformed ES cells can then be introduced into an early stage embryo that is then implanted into the uterus of a mammal of the same species. In certain cases, the transformed ("transgenic") cells will comprise part of the germ line of the resulting animal and adult animals comprising the transgenic cells in the germ line can then be mated to other animals, thereby eventually producing a population of transgenic animals that have the transgene in each of their cells and that can stably transmit the transgene to each of their offspring. Other methods of introducing the polynucleotide can be used, for example introducing the polynucleotide encoding hRUP11 polypeptide of the invention into a fertilized egg or early stage embryo via microinjection. Alternatively, the transgene may be introduced into an animal by infection of zygotes with a retrovirus containing the transgene [Jaenisch, R, Proc Natl Acad Sci USA (1976) 73:1260–4]. Methods of making transgenic mammals are described, e.g., in Wall et al., J Cell Biochem (1992) 49:113–20; Hogan et al., in Manipulating the Mouse Embryo. A Laboratory Manual. (1986) Cold Spring Harbor Laboratory Press, Cold Spring Harbor, N.Y.; in WO 91/08216; or in U.S. Pat. No. 4,736,866; all of which disclosures are hereby incorporated by reference in their entirety.

In preferred embodiments, expression of said gene is placed under the control of an adipocyte specific promoter. In further preferred embodiments, said adipocyte specific promoter is adiponectin gene promoter [Das, K et al., Biochem Biophys Res Commun (2001) 280:1120–9; Barth, N et al., Diabetologia (2002) 45:1425–1433; the disclosures of which are hereby incorporated by reference in its entirety]. In other further preferred embodiments, said adipocyte specific promoter is resistin gene promoter [Hartman, H B et al. J Biol Chem (2002) 277:19754–61, which disclosure is hereby incorporated by reference in its entirety]. In other preferred embodiments, said adipocyte specific promoter is aP2 [Felmer, R et al., J Endocrinol (2002) 175:487–498; the disclosure of which is hereby incorporated by reference in its entirety]. In other further preferred embodiments, expression of said gene is kept under the control of its endogenous promoter.

Example 28

Knockout Mouse/Rat

Mouse

RUP25

A preferred DNA construct will comprise, from 5'-end to 3'-end: (a) a first nucleotide sequence that is comprised in the mRUP25 genomic sequence; (b) a nucleotide sequence comprising a positive selection marker, such as the marker for neomycin resistance (neo); and (c) a second nucleotide sequence that is comprised in the mRUP25 genomic sequence and is located on the genome downstream of the first mRUP25 nucleotide sequence (a). mRUP25 genomic sequence will be isolated using methods well known to those of ordinary skill in the art (Maniatis T et al., *Molecular Cloning: A Laboratory Manual* (1989) Cold Spring Harbor Laboratory; the disclosure of which is hereby incorporated by reference in its entirety).

In preferred embodiments, this DNA construct also comprises a negative selection marker located upstream the nucleotide sequence (a) or downstream the nucleotide sequence (c). Preferably, the negative selection marker comprises the thymidine kinase (tk) gene [Thomas et al., Cell (1986) 44:419–28], the hygromycin beta gene [Te Riele et al., Nature (1990) 348:649–51], the hprt gene [Van der Lugt et al., Gene (1991) 105:263–7; Reid et al., Proc Natl Acad Sci USA (1990) 87:4299–4303] or the Diptheria toxin A fragment (Dt-A) gene [Nada et al., Cell (1993) 73:1125–35; Yagi et al., Proc Natl Acad Sci USA (1990) 87:9918–9922], which disclosures are hereby incorporated by reference in their entireties. Preferably, the positive selection marker is located within an mRUP25 exon sequence so as to interrupt the sequence encoding an mRUP25 polypeptide. These replacement vectors are described, for example, by Thomas et al., Cell (1986) 44:419–28; Thomas et al., Cell (1987) 51:503–12; Mansour et al., Nature (1988) 336:348–52; Koller et al., Annu Rev Immunol (1992) 10:705–30; and U.S. Pat. No. 5,631,153; which disclosures are hereby incorporated by reference in their entireties.

The first and second nucleotide sequences (a) and (c) may be indifferently located within an mRUP25 regulatory sequence, an intronic sequence, an exon sequence or a sequence containing both regulatory and/or intronic and/or exon sequences. The size of the nucleotide sequences (a) and (c) ranges from 1 to 50 kb, preferably from 1 to 10 kb, more preferably from 2 to 6 kb, and most preferably from 2 to 4 kb.

Methods of making a knockout mouse are well known to those of ordinary skill in the art and have been used to successfully inactivate a wide range of genes.

RUP19

A preferred DNA construct will comprise, from 5'-end to 3'-end: (a) a first nucleotide sequence that is comprised in the mRUP19 genomic sequence; (b) a nucleotide sequence comprising a positive selection marker, such as the marker for neomycin resistance (neo); and (c) a second nucleotide sequence that is comprised in the mRUP19 genomic sequence and is located on the genome downstream of the first mRUP19 nucleotide sequence (a). mRUP19 genomic sequence will be isolated using methods well known to those of ordinary skill in the art (Maniatis T et al., *Molecular Cloning: A Laboratory Manual* (1989) Cold Spring Harbor Laboratory; the disclosure of which is hereby incorporated by reference in its entirety).

In preferred embodiments, this DNA construct also comprises a negative selection marker located upstream the nucleotide sequence (a) or downstream the nucleotide sequence (c). Preferably, the negative selection marker comprises the thymidine kinase (tk) gene [Thomas et al., Cell (1986) 44:419–28], the hygromycin beta gene [Te Riele et al., Nature (1990) 348:649–51], the hprt gene [Van der Lugt et al., Gene (1991) 105:263–7; Reid et al., Proc Natl Acad Sci USA (1990) 87:4299–4303] or the Diptheria toxin A fragment (Dt-A) gene [Nada et al., Cell (1993) 73:1125–35; Yagi et al., Proc Natl Acad Sci USA (1990) 87:9918–9922], which disclosures are hereby incorporated by reference in their entireties. Preferably, the positive selection marker is located within an mRUP19 exon sequence so as to interrupt the sequence encoding an mRUP19 polypeptide. These replacement vectors are described, for example, by Thomas et al., Cell (1986) 44:419–28; Thomas et al., Cell (1987) 51:503–12; Mansour et al., Nature (1988) 336:348–52; Koller et al., Annu Rev Immunol (1992) 10:705–30; and U.S. Pat. No. 5,631,153; which disclosures are hereby incorporated by reference in their entireties.

The first and second nucleotide sequences (a) and (c) may be indifferently located within an mRUP19 regulatory sequence, an intronic sequence, an exon sequence or a sequence containing both regulatory and/or intronic and/or exon sequences. The size of the nucleotide sequences (a) and (c) ranges from 1 to 50 kb, preferably from 1 to 10 kb, more preferably from 2 to 6 kb, and most preferably from 2 to 4 kb.

Methods of making a knockout mouse are well known to those of ordinary skill in the art and have been used to successfully inactivate a wide range of genes.

Rat

RUP25

Gene targeting technology for the rat is less robust than that for the mouse and is an area of active interest. One approach will be to inactivate rRUP25 gene in rat embryonic stem cell (ESC)-like cells and then inject cells with inactivated rRUP25 gene into rat blastocysts generated after fusion of two-cell embryos [Krivokharchenko et al., Mol Reprod Dev (2002) 61:460–5].

An alternative approach will be to inactivate rRUP25 gene in rat ESC-like cells and then transfer the nucleus of the rat ESC-like cells having inactivated rRUP25 gene into enucleated oocytes [Sato K et al., Hum Cell (2001) 14:301–4; Wakayama and Yanagimachi, Semin Cell Dev Biol (1999) 10:253–8; Hochedlinger and Jaenisch, Nature (2002) 415:1035–8; Yanagimachi, Mol Cell Endocrinol (2002) 187:241–8; the disclosures of which are incorporated herein by reference in their entireties].

rRUP25 genomic sequence can be isolated using methods well known to those of ordinary skill in the art (Maniatis T et al., *Molecular Cloning: A Laboratory Manual* (1989) Cold Spring Harbor Laboratory; the disclosure of which is hereby incorporated by reference in its entirety).

RUP19

Gene targeting technology for the rat is less robust than that for the mouse and is an area of active interest. One approach will be to inactivate rRUP19 gene in rat embryonic stem cell (ESC)-like cells and then inject cells with inactivated rRUP19 gene into rat blastocysts generated after fusion of two-cell embryos [Krivokharchenko et al., Mol Reprod Dev (2002) 61:460–5].

An alternative approach will be to inactivate rRUP19 gene in rat ESC-like cells and then transfer the nucleus of the rat ESC-like cells having inactivated rRUP25 gene into enucleated oocytes [Sato K et al., Hum Cell (2001) 14:301–4; Wakayama and Yanagimachi, Semin Cell Dev Biol (1999) 10:253–8; Hochedlinger and Jaenisch, Nature (2002) 415:1035–8; Yanagimachi, Mol Cell Endocrinol (2002) 187:241–8; the disclosures of which are incorporated herein by reference in their entireties].

rRUP19 genomic sequence can be isolated using methods well known to those of ordinary skill in the art (Maniatis T et al., *Molecular Cloning: A Laboratory Manual* (1989) Cold Spring Harbor Laboratory; the disclosure of which is hereby incorporated by reference in its entirety).

Cre-loxP System

These new DNA constructs make use of the site specific recombination system of the P1 phage. The P1 phage possesses a recombinase called Cre that interacts with a 34 base pair loxP site. The loxP site is composed of two palindormic sequences of 13 bp separated by an 8 bp conserved sequence [Hoess R H et al, Nucleic Acids Res (1986) 14:2287–300; which disclosure is hereby incorporated by reference in its entirety]. The recombination by the Cre enzyme between two loxP sites having an identical orientation leads to the deletion of the DNA fragment.

The Cre-loxP system used in combination with a homologous recombination technique has been first described by Gu et al. [Gu H et al., Cell (1993) 73:1155–64; Gu H et al., Science (1994) 265:103–6; which disclosures are hereby incorporated by reference in their entirety]. Briefly, a nucleotide sequence of interest to be inserted in a targeted location of the genome harbors at least two loxP sites in the same orientation and located at the respective ends of a nucleotide sequence to be excised from the recombinant genome. The excision event requires the presence of the recombinase (Cre) enzyme within the nucleus of the recombinant cell host. The recombinase enzyme may be brought at the desired time either by (a) incubating the recombinant cell hosts in a culture medium containing this enzyme, by injecting the Cre enzyme directly into the desired cell, such as by lipofection of the enzyme into the cells, such as described by Baubonis et al. [Baubonis W and Sauer B, Nucleic Acids Res (1993) 21:2025–9; which disclosure is hereby incorporated by reference in its entirety]; (b) transfecting the cell host with a vector comprising the Cre Coding sequence operably linked to a promoter functional in the recombinant cell host, which promoter being optionally inducible, said vector being introduced in the recombinant cell host, such as described by Gu et al. [Gu H et al., Cell (1993) 73:1155–64; which disclosure is hereby incorporated by reference in its entirety] and Sauer et al. [Sauer B and Henderson N, Proc Natl Acad Sci USA (1988) 85:5166–70; which disclosure is hereby incorporated by reference in its entirety]; (c) introducing into the genome of the cell host a polynucleotide comprising the Cre coding sequence operably linked to a promoter functional in the recombinant cell host, which promoter is optionally inducible, and said polynucleotide being inserted in the genome of the cell host either by a random insertion event or an homologous recombination event, such as described by Gu et al. [Gu H et al., Science (1994) 265:103–6; which disclosure is hereby incorporated by reference in its entirety].

Vectors and methods using the Cre-loxP system are described by Zou et al. (1994), which disclosure is hereby incorporated by reference in its entirety.

In preferred embodiments of the invention, Cre is introduced into the genome of the cell host by strategy (c) above, wherein said promoter is essentially adipocyte specific and leads to essentially adipocyte specific knockout of (loxP-flanked) mRUP25 or mRUP19 in the mouse or rRUP25 or rRUP19 in the rat. In some embodiments, said essentially adipocyte specific promoter is adiponectin gene promoter [Das, K et al., Biochem Biophys Res Commun. (2001) 280:1120–9; Barth, N et al., Diabetologia (2002) 45:1425–1433; the disclosures of which are hereby incorporated by reference in its entirety]. In some embodiments, said essentially adipocyte specific promoter is resistin gene promoter [Hartman, H B et al. J Biol Chem (2002) 277:19754–61, which disclosure is hereby incorporated by reference in its entirety]. In some embodiments, said essentially adipocyte specific promoter is a P2 [Felmer, R et al., J Endocrinol (2002) 175:487–498; the disclosure of which is hereby incorporated by reference in its entirety]. Methods of constructing a lineage-specific knockout are well known to persons of ordinary skill in the art, as illustrated but not intended to be limited by: Kuhn R and Torres R M, Methods Mol Biol (2002) 180:175–204; Sauer B, Methods (1998) 14:381–92; Gutstein D E et al., Circulation Research (2001) 88:333; Minamino T et al., Circulation Research (2001) 88:587; and Bex A et al., J Urol (2002) 168:2641–2644; the disclosure of each of which is hereby incorporated by reference in its entirety.

Example 29

Fluorometric Imaging Plate Reader (FLIPR) Assay for the Measurement of Intracellular Calcium Concentration Target Receptor (experimental) and pCMV (negative control) stably transfected cells from respective clonal lines are seeded into poly-D-lysine pretreated 96-well plates (Becton-Dickinson, #356640) at $5.5\times10^4$ cells/well with complete culture medium (DMEM with 10% FBS, 2 mM L-glutamine, 1 mM sodium pyruvate) for assay the next day. To prepare Fluo4-AM (Molecular Probe, #F14202) incubation buffer stock, 1 mg Fluo4-AM is dissolved in 467 μl DMSO and 467 μl Pluoronic acid (Molecular Probe, #P3000) to give a 1 mM stock solution that can be stored at −20° C. for a month. Fluo4-AM is a fluorescent calcium indicator dye.

Candidate compounds are prepared in wash buffer (1× HBSS/2.5 mM Probenicid/20 mM HEPES at pH 7.4).

At the time of assay, culture medium is removed from the wells and the cells are loaded with 100 μl of 4 μM Fluo4-AM/2.5 mM Probenicid (Sigma, #P8761)/20 mM HEPES/complete medium at pH 7.4. Incubation at 37° C./5% $CO_2$ is allowed to proceed for 60 min.

After the 1 hr incubation, the Fluo4-AM incubation buffer is removed and the cells are washed 2× with 100 μl wash buffer. In each well is left 100 μl wash buffer. The plate is returned to the incubator at 37° C./5% $CO_2$ for 60 min.

FLIPR (Fluorometric Imaging Plate Reader; Molecular Device) is programmed to add 50 μl candidate compound on the $30^{th}$ second and to record transient changes in intracellular calcium concentration ([$Ca^{2+}$]) evoked by the candidate compound for another 150 seconds. Total fluorescence change counts are used to determine agonist activity using the FLIPR software. The instrument software normalizes the fluorescent reading to give equivalent initial readings at zero.

In some embodiments, the cells comprising Target Receptor further comprise promiscuous G alpha 15/16 or the chimeric Gq/Gi alpha unit.

Although the foregoing provides a FLIPR assay for agonist activity using stably transfected cells, a person of ordinary skill in the art would readily be able to modify the assay in order to characterize antagonist activity. Said person of ordinary skill in the art would also readily appreciate that, alternatively, transiently transfected cells could be used.

Example 30

In vivo Pig Model of HDL-Cholesterol and Atherosclerosis.

The utility of a modulator of the present invention as a medical agent in the prevention or treatment of a high total cholesterol/HDL-cholesterol ratio and conditions relating thereto is demonstrated, without limitation, by the activity of the modulator in lowering the ratio of total cholesterol to HDL-cholesterol, in elevating HDL-cholesterol, or in protection from atherosclerosis in an in vivo pig model. Pigs are used as an animal model because they reflect human physiology, especially lipid metabolism, more closely than most other animal models. An illustrative in vivo pig model not intended to be limiting is presented here.

Yorkshire albino pigs (body weight 25.5±4 kg) are fed a saturated fatty acid rich and cholesterol rich (SFA-CHO) diet during 50 days (1 kg chow 35 $kg^{-1}$ pig weight), composed of standard chow supplemented with 2% cholesterol and 20% beef tallow [Royo T et al., *European Journal of Clinical Investigation* (2000) 30:843–52; which disclosure is hereby incorporated by reference in its entirety].

Saturated to unsaturated fatty acid ratio is modified from 0.6 in normal pig chow to 1.12 in the SFA-CHO diet. Animals are divided into two groups, one group (n=8) fed with the SFA-CHO diet and treated with placebo and one group (n=8) fed with the SFA-CHO diet and treated with the modulator (3.0 mg $kg^{-1}$). Control animals are fed a standard chow for a period of 50 days. Blood samples are collected at baseline (2 days after the reception of the animals), and 50 days after the initiation of the diet. Blood lipids are analyzed. The animals are sacrificed and necropsied.

Alternatively, the foregoing analysis comprises a plurality of groups each treated with a different dose of the modulator. Preferred said doses are selected from the group consisting of: 0.1 mg $kg^{-1}$, 0.3 mg $kg^{-1}$, 1.0 mg $kg^{-1}$, 3.0 mg $kg^{-1}$, 10 mg $kg^{-1}$, 30 mg $kg^{-1}$ and 100 mg $kg^{-1}$. Alternatively, the foregoing analysis is carried out at a plurality of timepoints. Preferred said timepoints are selected from the group consisting of 10 weeks, 20 weeks, 30 weeks, 40 weeks, and 50 weeks.

HDL-Cholesterol

Blood is collected in trisodium citrate (3.8%, 1:10). Plasma is obtained after centrifugation (1200 g 15 min) and immediately processed. Total cholesterol, HDL-cholesterol, and LDL-cholesterol are measured using the automatic analyzer Kodak Ektachem DT System (Eastman Kodak Company, Rochester, N.Y., USA). Samples with value parameters above the range are diluted with the solution supplied by the manufacturer and then re-analyzed. The total cholesterol/HDL-cholesterol ratio is determined. Comparison is made of the level of HDL-cholesterol between groups. Comparison is made of the total cholesterol/HDL-cholesterol ratio between groups.

Elevation of HDL-cholesterol or reduction of the total cholesterol/HDL-cholesterol ratio on administration of the modulator is taken as indicative of the modulator having the aforesaid utility.

Atherosclerosis

The thoracic and abdominal aortas are removed intact, opened longitudinally along the ventral surface, and fixed in neutral-buffered formalin after excision of samples from standard sites in the thoracic and abdominal aorta for histological examination and lipid composition and synthesis studies. After fixation, the whole aortas are stained with Sudan IV and pinned out flat, and digital images are obtained with a TV camera connected to a computerized image analysis system (Image Pro Plus; Media Cybernetics, Silver Spring, Md.) to determine the percentage of aortic surface involved with atherosclerotic lesions [Gerrity R G et al, *Diabetes* (2001) 50:1654–65; Cornhill J F et al, *Arteriosclerosis, Thrombosis, and Vascular Biology* (1985) 5:415–26; which disclosures are hereby incorporated by reference in their entirety]. Comparison is made between groups of the percentage of aortic surface involved with atherosclerotic lesions.

Reduction of the percentage of aortic surface involved with atherosclerotic lesions on administration of the modulator is taken as indicative of the modulator having the aforesaid utility.

Plasma Free Fatty Acids

It would be readily apparent to anyone of ordinary skill in the art that the foregoing in vivo pig model is easily modified in order to address, without limitation, the activity of the modulator in lowering plasma free fatty acids.

Example 31

Measurement of Plasma Free Fatty Acids (FFA) in Rats Administered Niacin.

Figure 32:
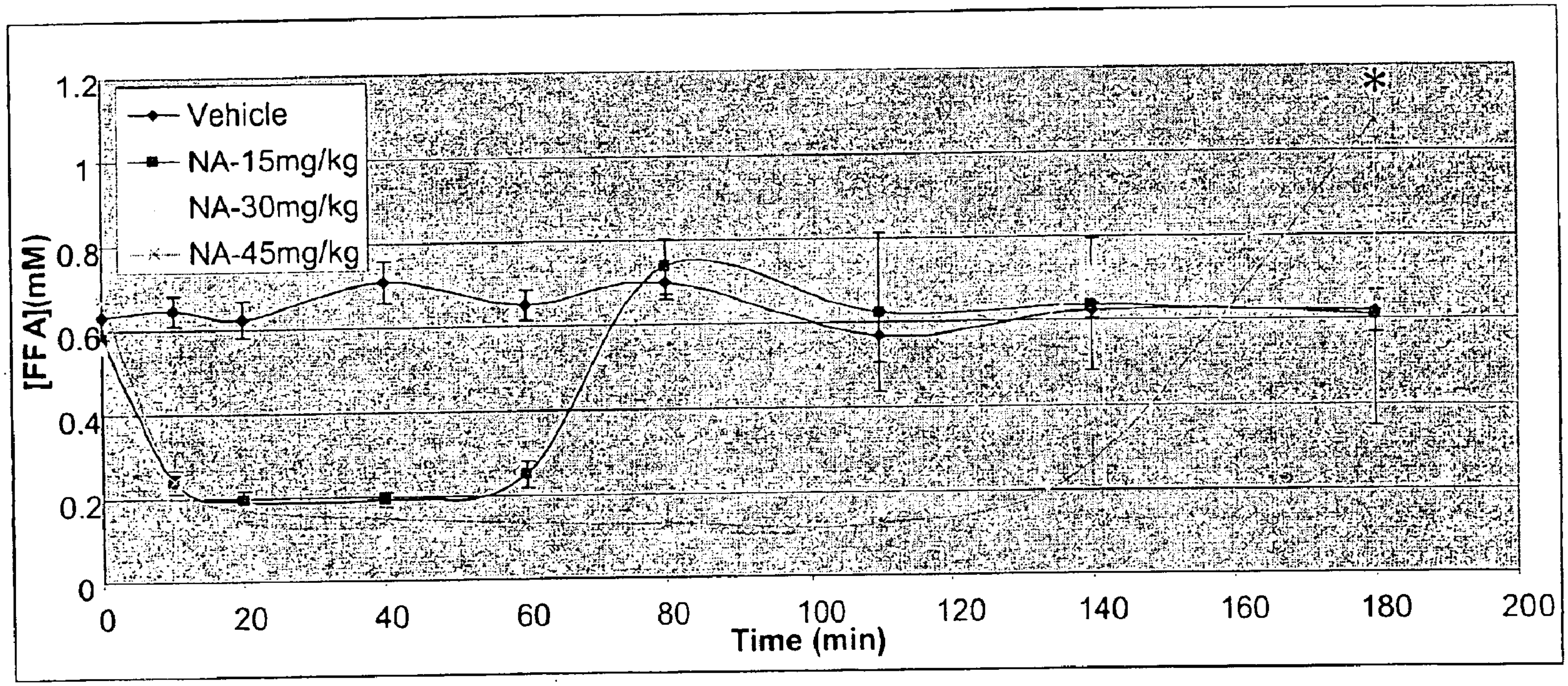
FIG. 32.

Catheters were surgically implanted into the jugular veins of male Sprague Dawley rats. The following day rats were deprived of food and approximately 16 hours later were given interperitoneal (IP) injections of either vehicle, or niacin [NA] at 15 mg/kg, 30 mg/kg or 45 mg/kg body weight. Blood was drawn (~200 ml) at the indicated time points and plasma was isolated following centrifugation. Plasma FFA were then measured via the NEFA C kit according to manufacturer specifications (Wako Chemicals USA, Inc). All three concentrations of niacin significantly decrease plasma FFA levels. [See, FIG. 32.] * Indicates a statistical increase in plasma FFA versus vehicle control indicating a rebound effect in the 45 mg/kg niacin treated rats at 3 hr (i.e., plasma FFA levels go beyond basal levels following inhibition).

By way of illustration and not limitation, said rat model has utility as an in vivo animal model for modulators of RUP25 provided by the invention. By way of illustration and not limitation, said rat model also has utility as an in vivo animal model for modulators of RUP19 provided by the invention. By way of illustration and not limitation, hRUP38 and hRUP11 transgenic rats provided by the invention have utility as in vivo animal models for modulators of hRUP38 and hRUP11 provided by the invention.

To show that a modulator of hRUP25 other than niacin behaves similarly, an analogous assay is set up using said modulator of hRUP25. Preferred said modulator is an agonist.

To show that a modulator of hRUP38 behaves similarly, an analogous assay is set up using said modulator of hRUP38, wherein the rat is transgenic for hRUP38. Preferred said modulator is an agonist.

To show that a modulator of hRUP19 behaves similarly, an analogous assay is set up using said modulator of hRUP19. Preferred said modulator is an agonist.

To show that a modulator of hRUP11 behaves similarly, an analogous assay is set up using said modulator of hRUP11, wherein the rat is transgenic for hRUP11. Preferred said modulator is an agonist.

Example 32

Preparation of Non-Endogenous, Enhanced-for-Agonist [EFA-] GPCRS

Constitutive activity of a GPCR reduces the available window for identification of an agonist of the GPCR, where said window is taken here to be the the difference in assay readout between the GPCR in the absence of agonist and the GPCR in the presence of a known agonist. A mutant of a constitutively active GPCR that is less constitutively active but comparably or more responsive to said known agonist [Enhanced-for-Agonist GPCR; EFA-GPCR] would have novel utility for the identification of modulators of said GPCR, particularly agonists.

EFA-GPCR is disclosed herewith as a mutant GPCR polypeptide that consists of 1, 2, 3, 4, or 5 amino acid substitutions, deletions, or insertions relative to the amino acid sequence of an endogenous GPCR polypeptide having constitutive activity, wherein the agonist screening window of the mutant GPCR is expanded by greater than 20%, greater than 25%, greater than 30%, greater than 31%, greater than 32%, greater than 33%, greater than 34%, greater than 35%, greater than 36%, greater than 37%, greater than 38%, greater than 39%, or greater than 40% relative to that of said endogenous GPCR.

As the GPCRs of the invention are constitutively active to a significant degree, an EFA version of said GPCRs would have novel utility in screening for modulators of said GPCRs, particularly agonists.

Herewith Applicant discloses EFA-hRUP25 "hRUP25-S91" polynucleotide of SEQ. ID. NO:158 and the encoded polypeptide of SEQ. ID. NO.:159. EFA-hRUP25 polypeptide "hRUP25-S91" differs from endogenous hRUP25 polypeptide of SEQ. ID. NO.:36 through substitution of the tryptophan at amino acid position 91 with serine. Mutagenesis was performed using QuickChange Site-Directed Mutagenesis Kit (Stratagene) according to the manufacturer's instructions. The mutagenesis primers had the following sequences:

```
Sense primer:
CTATGTGAGGCGTTCAGACTGGAAGTTTG;   (SEQ. ID. NO.:160

Antisense primer:
CAAACTTCCAGTCTGAACGCCTCACATAG.   (SEQ. ID. NO.:161
```

Figure 33:
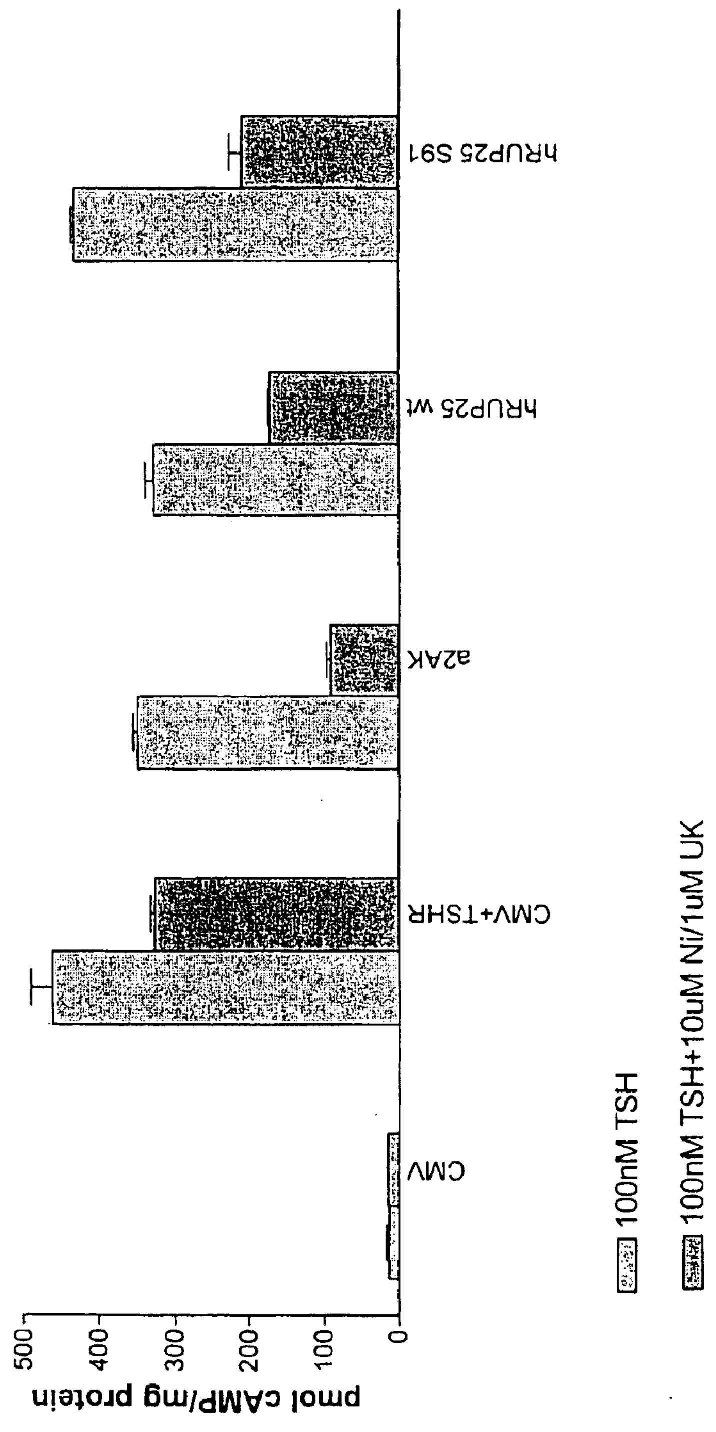
FIG. 33.

Activity of EFA-hRUP25 "hRUP25-S91" polypeptide is presented in FIG. 33. The window for agonist screening is 44% larger for EFA-hRUP25 (433–210 pmol cAMP/mg protein) relative to that of endogenous hRUP25 (329–174 pmol cAMP/mg protein). {[(433–210=223)/(329–174=155)]=1.44≡144%.}

The invention relates in part to an isolated EFA-hRUP25 polypeptide comprising the amino acid sequence of SEQ. ID. NO.:159 and to isolated polynucleotide encoding said EFA-hRUP25 polypeptide. A preferred EFA-hRUP25 polynucleotide has the nucleotide sequence of SEQ. ID. NO.:158.

The invention further relates in part to isolated EFA-hRUP25 polypeptide comprising an amino acid sequence consisting of 1, 2, 3, or 4 amino acid substitutions, deletions, or insertions relative to the amino acid sequence of SEQ. ID. NO.:36 in addition to the substitution of serine for tryptophan at amino acid position 91, as well as to isolated polynucleotide encoding said EFA-hRUP25 polypeptide.

The invention also relates in part to a method of using a polypeptide comprising an EFA-hRUP25 amino acid sequence to identify a modulator of EFA-hRUP25. The invention also relates to a method of using a polypeptide comprising an EFA-hRUP25 amino acid sequence to identify a modulator of lipolysis. Preferred said modulator of EFA-hRUP25 is an agonist.

Other embodiments encompass EFA-mRUP25 and EFA-rRUP25 polypeptide and polynucleotide. Also preferred is a method of using EFA-mRUP25 or EFA-rRUP25 to identify a modulator of EFA-mRUP25 or EFA-rRUP25. Also preferred is a method of using EFA-mRUP25 or EFA-rRUP25 to identify a modulator of lipolysis. Preferred said modulator of EFA-mRUP25 or EFA-rRUP25 is an agonist.

Other embodiments encompass EFA-RUP38 polypeptide and polynucleotide. Also preferred is a method of using EFA-RUP38 to identify a modulator of EFA-RUP38. Also preferred is a method of using EFA-RUP38 to identify a modulator of lipolysis. Preferred said modulator of EFA-RUP38 is an agonist.

Other embodiments encompass EFA-hRUP19 polypeptide and polynucleotide. Also preferred is a method of using EFA-hRUP19 to identify a modulator of EFA-hRUP19. Also preferred is a method of using EFA-hRUP19 to identify a modulator of lipolysis. Preferred said modulator of EFA-hRUP19 is an agonist.

Other embodiments encompass EFA-mRUP19 and EFA-rRUP19 polypeptide and polynucleotide. Also preferred is a method of using EFA-mRUP19 or EFA-rRUP19 to identify a modulator of EFA-mRUP19 or EFA-rRUP19. Also preferred is a method of using EFA-mRUP19 or EFA-rRUP19 to identify a modulator of lipolysis. Preferred said modulator of EFA-mRUP19 or EFA-rRUP19 is an agonist.

Other embodiments encompass EFA-RUP11 polypeptide and polynucleotide. Also preferred is a method of using EFA-RUP11 to identify a modulator of EFA-RUP11. Also preferred is a method of using EFA-RUP11 to identify a modulator of lipolysis. Preferred said modulator of RUP11 is an agonist.

The invention also provides for a method of making an EFA mutant of an endogenous GPCR polypeptide having constitutive activity, comprising the steps of:

(a) introducing 1, 2, 3, 4, or 5 substitutions, insertions, or deletions into the amino acid sequence of the endogenous GPCR polypeptide;

(b) measuring the activity of the mutant GPCR of (a) in the absence of agonist and in the presence of a known agonist;

(c) measuring the activity of the endogenous GPCR in the absence of agonist and in the presence of said known agonist; and (d) comparing (b) and (c);

wherein a determination that the agonist screening window of (b) is greater than 20%, greater than 25% greater than 30%, greater than 31%, greater than 32%, greater than 33%, greater than 34%, greater than 35%, greater than 36%, greater than 37%, greater than 38%, greater than 39%, or greater than 40% than that of (c) identifies the mutant resulting from (a) to be an EFA mutant of the endogenous GPCR.

In some embodiments, the agonist screening window of (b) is greater than 20% than that of (c).

In some preferred embodiments, said known agonist is nicotinic acid.

Methods of carrying out site-specific mutagenesis are well known to those of ordinary skill in the art. [See, e.g, in Maniatis T et al., *Molecular Cloning: A Laboratory Manual* (1989) Cold Spring Harbor Laboratory; the disclosure of which is hereby incorporated by reference in its entirety]. Many commercial kits for carrying out site-specific mutagenesis are well known to those of ordinary skill in the art and are readily available. Those skilled in the art are credited with the ability to select techniques for mutation of a nucleic acid sequence.

Example 33

Oral Bioavailability

Based upon the in vivo data developed, as for example by way of illustration and not limitation data through the rat model of Example 31 supra, oral bioavailability of a modulator of the invention is determined. The modulator is administered by oral gavage at doses ranging from 0.1 mg $kg^{-1}$ to 100 mg $kg^{-1}$. Oral administration of the modulator is shown to reduce the level of plasma free fatty acids. The effect of the modulator is shown to be dose-dependent and comparable to the effect after intraperitoneal administration. The dose of modulator required to achieve half-maximal reduction of plasma free fatty acids through oral administration is compared to the dose of modulator required to achieve half-maximal reduction of plasma free fatty acids through intraperitoneal administration. By way of illustration, if said oral dose is twice said intraperitoneal dose, then the oral bioavailability of the modulator is taken to be 50%. More generally, if said oral dose is θ mg $kg^{-1}$ and said intraperitoneal dose is ρ mg $kg^{-1}$, then the oral availability of the modulator as a percentage is taken to be $[(\rho/\theta)\times 100]$.

It is readily envisioned that the reference route of administration may be other than intraperitoneal. In some embodiments, said reference route of administration is intravenous.

It would be readily apparent to anyone of ordinary skill in the art that the aforesaid determination could be modified to utilize a different in vivo animal model other than normal Sprague Dawley rats. It would also be readily apparent to anyone of ordinary skill in the art that the bioactivity readout in the aforesaid determination could be a parameter other than plasma free fatty acids.

Alternative, physicochemico analytical approaches for assessing oral bioavailability are well known to those of ordinary skill in the art [see, e.g., without limitation: Wong P C et al., Cardiovasc Drug Rev (2002) 20:137–52; and Buchan P et al., Headache (2002) Suppl 2:S54–62; the disclosure of each of which is hereby incorporated by reference in its entirety]. By way of further illustration and not limitation, said alternative analytical approaches may comprise liquid chromatography-tandem mass spectrometry [Chavez-Eng C M et al., J ChromatogrB Analyt Technol Biomed Life Sci (2002) 767:117–29; Jetter A et al., Clin Pharmacol Ther (2002) 71:21–9; Zimmerman J J et al., J Clin Pharmacol (1999) 39:1155–61; and Barrish A et al., Rapid Commun Mass Spectrom (1996) 10:1033–7; the disclosure of each of which is hereby incorporated by reference in its entirety].

What is claimed is:

1. A method of identifying whether a candidate compound is a modulator of a nicotinic acid GPCR, said GPCR comprising the amino acid sequence of SEQ ID NO:36 comprising the steps of:

(a) contacting the candidate compound with the nicotinic acid GPCR; and (b) determining whether the receptor functionality is modulated in a manner consistent with Gi coupling to said receptor; and wherein a modulation in receptor functionality consistent with said Gi coupling is indicative of the candidate compound being a modulator of said nicotinic acid GPCR and wherein said modulation in receptor functionality consistent with said Gi coupling is specific to said nicotinic acid GPCR.

2. The method of claim 1 wherein said GPCR is expressed by a host cell comprising an expression vector encoding said GPCR.

3. A method of identifying whether a candidate compound is a modulator of lipolysis, comprising the steps of:

(a) contacting the candidate compound with a GPCR comprising the amino acid sequence of SEQ ID NO:36; and (b) determining whether the receptor functionality is modulated in a manner consistent with Gi coupling to said receptor; and wherein a modulation in receptor functionality consistent with said Gi coupling is indicative of the candidate compound being a modulator of lipolysis and wherein said modulation in receptor functionality consistent with said Gi coupling is specific to said GPCR comprising the amino acid sequence of SEQ ID NO:36.

4. The method of claim 3 wherein said GPCR is expressed by a host cell comprising an expression vector encoding said GPCR.

* * * * *